United States Patent
Shirai et al.

(10) Patent No.: US 7,183,306 B2
(45) Date of Patent: Feb. 27, 2007

(54) PYRAZOLE DERIVATIVES

(75) Inventors: Fumiyuki Shirai, Osaka (JP); Hidenori Azami, Osaka (JP); Natsuko Kayakiri, Osaka (JP); Kazuo Okumura, Osaka (JP); Katsuya Nakamura, Osaka (JP)

(73) Assignee: Astellas Pharma Inc., Tokyo (JP)

( * ) Notice: Subject to any disclaimer, the term of this patent is extended or adjusted under 35 U.S.C. 154(b) by 163 days.

(21) Appl. No.: 10/706,999

(22) Filed: Nov. 14, 2003

(65) Prior Publication Data

US 2004/0116475 A1 Jun. 17, 2004

(30) Foreign Application Priority Data

| Dec. 2, 2002 | (AU) | ............................. 2002953019 |
| Dec. 30, 2002 | (AU) | ............................. 2002953602 |
| Apr. 29, 2003 | (AU) | ............................. 2003902015 |

(51) Int. Cl.
   C07D 231/12 (2006.01)
   A61K 31/415 (2006.01)

(52) U.S. Cl. .................. 514/406; 514/407; 548/366.1; 548/369.7; 548/370.1; 548/371.4; 548/371.7; 548/372.5; 548/374.1; 548/375.1; 548/376.1; 548/377.1

(58) Field of Classification Search ................ 514/406, 514/407; 548/366.1, 369.7, 370.1, 371.4, 548/371.7, 372.5, 374.1, 375.1, 376.1, 377.1
   See application file for complete search history.

(56) References Cited

U.S. PATENT DOCUMENTS

| 4,826,868 | A | 5/1989 | Wachter et al. |
| 5,051,518 | A | 9/1991 | Murray et al. |
| 5,134,142 | A | 7/1992 | Matsuo et al. |
| 5,164,381 | A | 11/1992 | Wachter et al. |
| 5,298,521 | A | 3/1994 | Ferro |
| 5,550,147 | A | 8/1996 | Matsuo et al. |
| 5,670,533 | A | 9/1997 | Matsuo et al. |
| 6,506,747 | B1 | 1/2003 | Betageri et al. |
| 2003/0162824 | A1 | 8/2003 | Krul |
| 2005/0277678 | A1 | 12/2005 | Lohray et al. |

FOREIGN PATENT DOCUMENTS

| CN | 11631339 | 8/2004 |
| EP | 1 104 759 | 6/2001 |
| WO | WO 96/14302 | 5/1996 |
| WO | WO 98/57910 | 12/1998 |
| WO | WO 00/18741 | 4/2000 |
| WO | WO 00/66562 | 11/2000 |
| WO | WO 01/81332 | 11/2001 |
| WO | WO 02/055502 | 7/2002 |
| WO | WO 03/040110 | 5/2003 |
| WO | WO 2004/050632 | 6/2004 |

OTHER PUBLICATIONS

D.E. Griswold, et al., "Constitutive Cyclooxygenase (COX-1) and Inducible Cyclooxygenase (COX-2): Rationale for Selective Inhibition and Progress to Date", Medicinal Research Reviews, vol. 16, No. 2, 1996, pp. 181-206.

K.N. Zelenin, et al., "", Chemistry of Heterocyclic Compounds, vol. 38, No. 6, 2002, pp. 668-676.

G.W. Kauffman, et al., "QSAR and $k$-Nearest Neighbor Classification Analysis of Selective Cyclooxygenase-2 Inhibitors Using Topologically-Based Numerical Descriptors", J. Chem. Inf. Comput. Sci., vol. 41, 2001, pp. 1553-1560.

P. Chavatte, et al., "Three-Dimensional Quantitative Structure-Activity Relationships of Cyclo-oxygenase-2 (COX-2) Inhibitors: A Comparative Molecular Field Analysis", J. Med. Chem., vol. 44, 2001, pp. 3223-3230.

X. Wang, et al., "Practical Synthesis of 1,3-diaryl-5-alkylpyrazoles By A Highly Regioselective N-arylation of 3,5-disubstituted Pyrazoles with 4-fluoronitrobenzene", Tetrahedron Letters, vol. 41, 2000, pp. 5321-5324.

K. Tsuji, et al., "Studies on Anti-Inflammatory Agents. V.[1)]" Synthesis and Pharmcological Properties of 3-(Difluoromethyl)-1-(4-methoxyphenyl)-5-[4-(methylsulfinyl)phenyl]pyrazole and Related Compounds, Chem. Pharm. Bull., vol. 45, No. 9, 1997, pp. 1475-1481.

(Continued)

Primary Examiner—Patricia L. Morris
(74) Attorney, Agent, or Firm—Oblon, Spivak, McClelland, Maier & Neustadt, P.C.

(57) ABSTRACT

A compound of the formula (I):

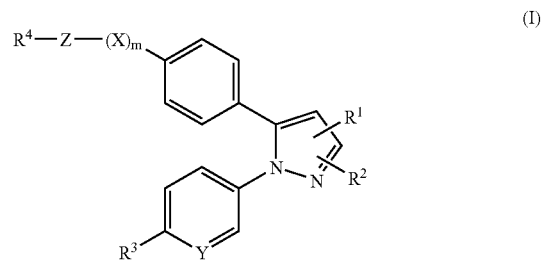

wherein $R^1$ is hydrogen or lower alkyl;
   $R^2$ is lower alkyl, etc.;
   $R^3$ is lower alkoxy, etc.;
   $R^4$ is hydroxy, etc.;
   X is O, S, etc.;
   Y is CH or N;
   Z is lower alkylene or lower alkenylene; and
   m is 0 or 1;
or salts thereof, which are useful as a medicament.

6 Claims, No Drawings

OTHER PUBLICATIONS

K. Tsuji, et al., "Studies on Anti-Inflammatory Agents. V.[1]" Synthesis and Pharmacological Properties of 1,5-Diarylpyrazoles and Related Derivatives, Chem. Pharm. Bull., vol. 45, No. 6, 1997, pp. 987-995.

T.D. Penning, et al., "Synthesis and Biological Evaluation of the 1,5-Diarylpyrazole Class of Cyclooxygenase-2 Inhibitors: Identification of 4[5-(4-Methylphenyl)-3-(trifluoromethyl)-1H-pyrazol-1-yl]benzenesulfonamide (SC-58635, Celecoxib)", J. Med. Chem., vol. 40, 1997, pp. 1347-1365.

W. Murrary, et al., "Synthesis of 3-(1,5-Diphenyl-3-pyrazolyl)aryl Propanoates", J. Heterocyclic Chem., vol. 27, 1990, pp. 1933-1940.

W. Murrary, et al., "A Simple Regioselective Synthesis of Ethyl 1,5-Diarylpyrazole-3-Carboxylates", J. Heterocyclic Chem., vol. 26, 1989, pp. 1389-1392.

M. Mihalic, et al., "Synthesis of the New Indole Derivatives Related to Indomethacin", Groatica Chemica ACTA, vol. 51, No. 1, 1978, pp. 81-92.

K. Zelenin, et al., "5-Hydroxy-4,5-Dihydropyrazoles", Tetrahedron, vol. 51, No. 41, 1995, pp. 11251-11256.

G. Menozzi, et al., "4-Substituted 1,5-Diarylpyrazole, Analogues of Celecoxib: Synthesis and Preliminary Evaluation of Biological Properties", Farmaco, vol. 58, 2003, pp. 795-808.

A. Alberola, et al., "Scope and Limitations in the Regioselective Synthesis of 1,3,5-Trisubstituted Pyrazoles from β-Amino Enones and Hydrazine Derivatives. $^{13}$C-Chemical Shift Prediction Rules for 1,3,5-Trisubstituted Pyrazoles", Heterocycles, vol. 55, No. 2, 2001, pp. 331-351.

B. Stanovnik, et al., "Product Class 1: Pyrazoles", Science of Synthesis, vol. 12, 2002, pp. 15-225.

PYRAZOLE DERIVATIVES

TECHNICAL FIELD

This invention relates to pyrazole compounds having pharmacological activity, to a process for their production and to a pharmaceutical composition containing the same.

BACKGROUND ART

The presence of two cyclooxygenase isoenzymes, cyclooxygenase-I (COX-I) and cyclooxygenase-II (COX-II) is known (Proc. Nat. Acad. Sci. USA 88, 2692–2696 (1991)).

Traditional non steroidal anti-inflammatory compounds (NSAIDs) have inhibiting activities of both COX-I and COX-II (J. Biol. Chem., 268, 6610–6614 (1993), etc). The therapeutic use thereof involves undesired effects on the gastrointestinal tract, such as bleeding, erosions, gastric and intestinal ulcers, etc.

It was reported that selective inhibition of COX-II shows anti-inflammatory and analgesic activities comparable with conventional NSAIDs but with a lower incidence of some gastrointestinal undesired effects (Pro. Nat. Acad. Sci. USA, 91, 3228–3232(1994)). Accordingly, various selective COX-II inhibitors have been prepared. However, it was reported that those "selective COX-II inhibitor" show some side-effects on kidney and/or insufficient efficacy on acute pains.

Further, some compounds such as SC-560, mofezolac, etc, which have certain selective inhibiting activity against COX-I. WO98/57910 shows some compounds having such activity. However, their selectivity of inhibiting COX-I does not seem to be enough to use them as a clinically acceptable and satisfactory analgesic agent due to their gastrointestinal disorders.

WO02/055502 shows some pyridine derivatives having cyclooxygenase inhibiting activity, particularly cyclooxygenase-I inhibiting activity. Further, WO03/040110 shows some triazole derivatives having cyclooxygenase inhibiting activity, particularly cyclooxygenase-I inhibiting activity. And WO99/51580 shows some triazole derivatives having an inhibiting activity of cytokine production.

DISCLOSURE OF INVENTION

This invention relates to pyrazole compounds, which have pharmacological activity such as cyclooxygenase (hereinafter described as COX) inhibiting activity, to a process for their production, to a pharmaceutical composition containing the same and to a use thereof.

Accordingly, one object of this invention is to provide the pyrazole compounds, which have a COX inhibiting activity.

Another object of this invention is to provide a process for production of the pyrazole compounds.

A further object of this invention is to provide a pharmaceutical composition containing, as active ingredients, the pyrazole compounds.

Still further object of this invention is to provide a use of the pyrazole compounds for manufacturing a medicament for treating or preventing various diseases.

The new pyrazole compounds of this invention can be represented by the following general formula (I):

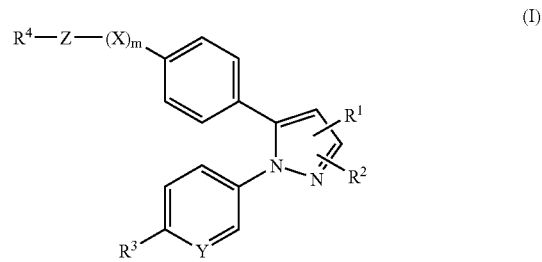

wherein $R^1$ is hydrogen or lower alkyl;

$R^2$ is lower alkyl optionally substituted with halogen, hydroxy, lower alkoxyimino or lower alkoxy; lower alkenyl; cycloalkyl; cyano; lower alkanoyl; cycloalkylcarbonyl; N,N-di(lower)alkylcarbamoyl; carbamoyl; N-lower alkoxy-N-lower alkylcarbamoyl; amino; di(lower)alkylamino; lower alkoxycarbonylamino; N,N-di(lower)alkylcarbamoylamino; N-(N,N-di(lower)alkylcarbamoyl)-N-lower alkylamino; halogen; hydroxy; carboxy; lower alkoxycarbonyl; aroyl; heterocycliccarbonyl; heterocyclic group; lower alkylsulfonyl; lower alkoxy optionally substituted with lower alkoxy, N,N-di(lower)alkylcarbamoyl or halogen; cycloalkyloxy; lower alkylthio; or lower alkylsufinyl;

$R^3$ is lower alkyl optionally substituted with amino, carbamoylamino or lower alkylsulfonylamino; halogen; cyano; hydroxy; lower alkanoyloxy; lower alkylenedioxy; lower alkoxy optionally substituted with aryl, hydroxy, cyano, amino, lower alkoxycarbonylamino, lower alkylsulfonylamino or carbamoylamino; nitro; amino; hetrocyclic group; lower alkylthio; lower alkylsulfinyl; or lower alkylsufonyl;

$R^4$ is hydrogen; cyano; amino optionally substituted with phthaloyl or lower alkyl; aryl; heterocyclic group; lower alkoxy; hydroxy; lower alkylsulfonyloxy; lower alkanoyloxy; lower alkyl substituted with tritylamino and lower alkoxycarbonyl, amino and lower alkoxycarbonyl, amino and carboxy, amino and carbamoyl, or amino and hydroxy; N-lower alkoxycarbonyl-N-lower alkylamino; lower alkanoyl optionally substituted with halogen; carboxy; lower alkylsulfonyl; sulfo; lower alkylsilyloxy; lower alkoxycarbonyl; sulfamoyl optionally substituted with lower alkyl; carbamoyl optionally substituted with lower alkyl; lower alkylthio; lower alkylsulfinyl; carbamoyloxy; thioureido; or a group of the formula:

$R^5$—G—J— in which G is —CO— or —SO$_2$—;

J is —N(R$^6$)—

(wherein $R^6$ is hydrogen or lower alkyl); and $R^5$ is amino optionally substituted with lower alkoxycarbonyl or lower alkyl; lower alkyl optionally substituted with hydroxy, lower alkoxycarbonylamino, lower alkanoyloxy, amino or halogen; lower alkoxy; hydrogen; heterocyclic group; or aryl;

X is O, S, SO or SO$_2$;

Y is CH or N;

Z is lower alkylene or lower alkenylene; and m is 0 or 1;

provided that when R⁴ is hydrogen;

then R³ is lower alkyl substituted with amino, carbamoylamino or lower alkylsulfonylamino; or lower alkoxy substituted with aryl, hydroxy, cyano, amino, lower alkoxycarbonylamino, lower alkylsulfonylamino or carbamoylamino;

or salts thereof.

The object compound (I) of the present invention can be prepared by the following processes.

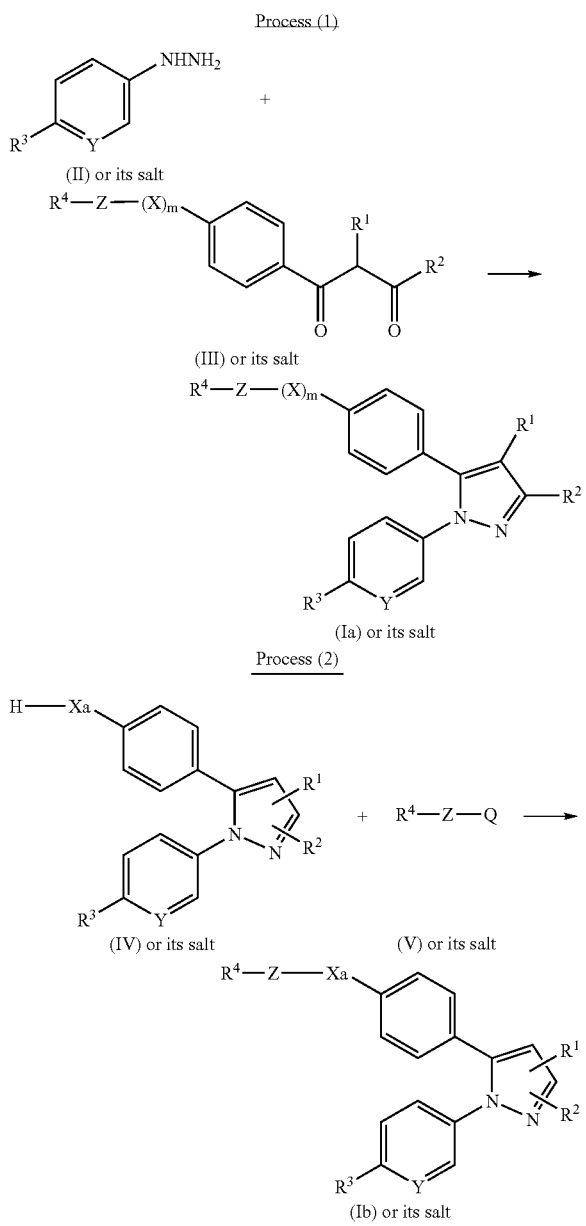

In the above processes, R¹, R², R³, R⁴, X, Y, Z and m are each as defined above, Xa is O or S, and Q is hyroxy or an acid residue.

The compounds of formula (I) may contain one or more asymmetric centers and thus they can exist as enantiomers or diastereoisomers. This invention includes both mixtures and separate individual isomers.

The compounds of the formula (I) may also exist in tautomeric forms and the invention includes both mixtures and separate individual tautomers.

The compounds of the formula (I) and its salts can be in a form of a solvate, which is included within the scope of the present invention. The solvate preferably include a hydrate and an ethanolate.

Also included in the scope of invention are radiolabelled derivatives of compounds of formula (I) which are suitable for biological studies.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

So, the "lower alkyl" and lower alkyl moiety in the terms "lower alkylthio", "lower aklylsufinyl", "lower alkylsulfonyl" and "lower alkylsulfonylamino" means a straight or branched chain aliphatic hydrocarbon, such as methyl, ethyl, propyl, isopropyl, butyl, isobutyl, tert-butyl, pentyl, isoamyl, hexyl, and the like, and it is preferably ($C_1$–$C_4$)alkyl, more preferably ($C_1$–$C_2$)alkyl, most preferably methyl.

The "halogen" may include a fluorine atom, a chlorine atom, a bromine atom and an iodine atom, and it is preferably a fluorine atom or a chlorine atom, more preferably a chlorine atom.

The "lower alkyl substituted with halogen" means a monovalent group in which the above lower alkyl is substituted by one or more (more preferably 1 to 5, most preferably 1 to 3) above halogen atom(s), such as fluoromethyl, chloromethyl, difluoromethyl, dichloro-methyl, dibromomethyl, trifluoromethyl, trichloromethyl, fluoroethyl, chloroethyl, 2,2,2-trifluoroethyl, 2,2,2-trichloroethyl, 2,2,3,3,3-pentafluoroethyl, fluoropropyl, fluorobutyl, fluorohexyl, or the like, and it is preferably ($C_1$–$C_4$)alkyl substituted with halogen, more preferably ($C_1$–$C_2$) alkyl substituted with halogen, more preferably ($C_1$–$C_2$)alkyl substituted with fluorine, more preferably methyl substituted with fluorine, most preferably difluoromethyl or trifluoromethyl.

The "lower alkyl substituted with hydroxy" means a monovalent group in which the above lower alkyl is substituted by a OH group, such as hydroxymethyl, hydroxyethyl, hydroxypropyl, 1-hydroxyisopropyl, 2-hydroxyisopropyl, hydroxybutyl, hydroxyisobutyl, hydroxy-tert-butyl, hydroxyhexyl, or the like, and it is preferably ($C_1$–$C_4$)alkyl substituted with hydroxy, more preferably ($C_1$–$C_3$)alkyl substituted with hydroxy.

The "lower alkenyl" means a straight or branched chain aliphatic hydrocarbon having more than one double bond between two carbon atom, such as ethenyl, propenyl, isopropenyl, butenyl, isobutenyl, pentenyl, hexenyl, and the like, and it is preferably ($C_2$–$C_4$)alkenyl, more preferably ($C_2$–$C_3$)alkenyl.

The "lower alkoxy" means a straight or branched chain aliphatic hydrocarbon oxy group, such as methoxy, ethoxy, propoxy, isopropoxy, butoxy, isobutoxy, tert-butoxy, pentoxy, hexoxy, or the like, and it is preferably ($C_1$–$C_4$)alkoxy, more preferably ($C_1$–$C_2$)alkoxy, most preferably methoxy.

The "cycloalkyl" and cycloalky moiety in the terms "cycloalkylcarbonyl" and "cycloalkyloxy" means $C_3$–$C_{10}$ cycloalkyl group, such as cyclopropyl, cyclobutyl, cyclopentyl, cyclohexyl, cycloheptyl, norbornyl, adamantyl, and the like, and it is preferably $C_3$–$C_6$ cycloalkyl, more preferably $C_3$–$C_5$ cycloalkyl, most preferably cyclopropyl or cyclopentyl.

The "di(lower)alkylamino" means a amino group substituted by the same or different above (lower)alkyl groups, such as dimethylamino, diethylamino, dipropylamino, diisopropylamino, dibutylamino, diisobutylamino, dipentylamino, dihexylamino, ethylmethylamino, methylpropylamino, butylmethylamino, ethylpropylamino, butylethylamino, or the like, and it is preferably [di($C_1$–$C_4$)alkyl]amino, more preferably [di($C_1$–$C_4$)alkyl]amino, most preferably dimethylamino.

The "lower alkoxycarbonyl" and lower alkoxycarbonyl moiety in the term "lower alkoxycarbonylamino" means a —$CO_2$—[(lower)alkyl] group, such as methoxycarbonyl, ethoxycarbonyl, propoxycarbonyl, isopropoxycarbonyl, butoxycarbonyl, isobutoxycarbonyl, tert-butoxycarbonyl, pentoxycarbonyl, hexoxycarbonyl, and the like, and it is preferably [($C_1$–C4)alkoxy]carbonyl, more preferably ethoxycarbonyl or tert-butoxycarbonyl.

The "lower alkanoyl" means carbonyl group which is substituted by hydrogen or the above (lower)alkyl groups, such as formyl, acetyl, propanoyl, butanoyl, 2-methylpropanoyl, pentanoyl, 2,2-dimethylpropanoyl, hexanoyl, or the like, and it is preferably ($C_1$–$C_5$)alkanoyl, more preferably ($C_2$–$C_3$)alkanoyl, most preferably acetyl.

The "cycloalkylcarbonyl" means a carbonyl group substituted with cycloalkyl group mentioned above, such as cyclopropylcarbonyl, cyclobutylcarbonyl, cyclopentylcarbonyl, cyclohexylcarbonyl, cycloheptylcarbonyl, norbornylcarbonyl, adamantylcarbonyl, and the like, and it is preferably [($C_3$–$C_6$) cycloalkyl]carbonyl, more preferably [($C_3$–$C_5$) cycloalkyl]carbonyl, most preferably cyclopropylcarbonyl.

The "N,N-di(lower)alkylcarbamoyl" and N,N-di(lower)alkylcarbamoyl moiety in the term "N,N-di(lower)alkylcarbamoylamino" means a carbamonyl group substituted with the same or different lower alkyl groups mentioned above, such as dimethylcarbamoyl, diethylcarbamoyl, dipropylcarbamoyl, diisopropylcarbamoyl, dibutylcarbamoyl, diisobutylcarbamoyl, dipentylcarbamoyl, dihexylcarbamoyl, ethylmethylcarbamoyl, methylpropylcarbamoyl, butylmethylcarbamoyl, ethylpropylcarbamoyl, butylethylcarbamoyl, and the like, and it is preferably [di($C_1$–$C_4$)alkyl]carbamoyl, more preferably [di($C_1$–$C_2$)alkyl]carbamoyl, most preferably dimethycarbamoyl or ethylmethylcarbamoyl.

The "lower alkoxy substituted with halogen" means a monovalent group in which the above lower alkoxy is substituted by one or more (more preferably 1 to 5, most preferably 1 to 3) above halogen atom(s), such as fluoromethoxy, chloromethoxy, difluoromethoxy, dichloromethoxy, dibromomethoxy, trifluoromethoxy, trichloromethoxy, fluoroethoxy, chloroethoxy, 2,2-difluoroethoxy, 2,2-dichloroethoxy, 2,2,2-trifluoroethoxy, 2,2,2-trichloroethoxy, 2,2,3,3,3-pentafluoroethoxy, fluoropropoxy, fluorobutoxy, fluorohexyloxy, or the like, and it is preferably ($C_1$–$C_4$) alkoxy substituted with halogen, more preferably ($C_1$–$C_2$) alkoxy substituted with halogen, more preferably ($C_1$–$C_2$) alkoxy substituted with fluorine, more preferably ethoxy substituted with fluorine, most preferably 2,2-difluoroethoxy.

The "lower alkyl substituted with amino" means a monovalent group in which the above lower alkyl is substituted by a amino group, such as aminomethyl, 2-aminoethyl, aminopropyl, 1-aminoisopropyl, 2-aminoisopropyl, aminobutyl, aminoisobutyl, amino-tert-butyl, aminohexyl, or the like, and it is preferably ($C_1$–$C_4$)alkyl substituted with amino, more preferably ($C_1$–$C_2$)alkyl substituted with amino.

The "lower alkyl substituted with carbamoylamino" means a monovalent group in which the above (lower)alkyl is substituted by a carbamoylamino group (urea group), such as carbamoylaminomethyl, 2-(carbamoylamino)ethyl, carbamoylaminopropyl, 1-(carbamoylamino)isopropyl, 2-(carbamoylamino)isopropyl, carbamoylaminobutyl, carbamoylaminoisobutyl, carbamoylamino-tert-butyl, carbamoylaminohexyl, or the like, and it is preferably ($C_1$–$C_4$)alkyl substituted with carbamoylamino, more preferably ($C_1$–$C_2$)alkyl substituted with carbamoylamino.

The "aryl" and ar moiety in the term "aroyl" means an aromatic hydrocarbon group, such as phenyl, naphtyl, indenyl, or the like, and it is preferably ($C_6$–$C_{10}$)aryl, more preferably phenyl.

The "aroyl" means a carbonyl group substituted with aryl group mentioned above, such as benzoyl, naphthoyl, or the like, and it is preferably benzoyol.

The "lower alkanoyloxy" means a monovalent group in which oxygen atom is substituted with lower alkanoyl group mentioned above, such as formyl, acetyl, propanoyl, butanoyl, 2-methylpropanoyl, pentanoyl, 2,2-dimethylpropanoyl, hexanoyl, or the like, and it is preferably [($C_1$–$C_4$)alkanoyl]oxy, more preferably [($C_1$–$C_2$)alkanoyl]oxy, most preferably acetoxy.

The "lower alkylene" means a straight or branched chain aliphatic hydrocarbon divalent group, such as methylene, ethylene, 1-methylethylene, 2-methylethylene, propylene, methylpropylene, butylene, pentylene, hexylene, and the like, and it is preferably ($C_1$–$C_4$) alkylene, more preferably ($C_1$–$C_2$)alkylene.

The "lower alkylenedioxy" means —O—[(lower)alkylene]—O— group. That is, in this case, $R^3$ is divalent group and is also substituted at the next carbon atom. This group may be exemplified by methylenedioxy, ethylenedioxy, methylethylenedioxy, propylenedioxy, and the like, and it is preferably [($C_1$–$C_4$)alkylene]dioxy, more preferably [($C_1$–$C_2$) alkylene]dioxy, most preferably methylenedioxy.

The "lower alkoxy substituted with aryl" means a monovalent group in which the above lower alkoxy is substituted by aryl group mentioned above.

The "lower alkoxy substituted with hydroxy" means a monovalent group in which the above lower alkoxy is substituted by hydroxy.

The "lower alkoxy substituted with cyano" means a monovalent group in which the above (lower)alkoxy is substituted by a cyano group, such as cyanomethoxy, cyanoethoxy, cyanopropoxy, cyanobutoxy, and the like, and it is preferably (C1–C4) alkoxy substituted with cyano, more preferably (C1–C2)alkoxy substituted with cyano, most preferably cyanomethoxy.

The "lower alkoxy substituted with amino" means a monovalent group in which the above lower alkoxy is substituted with amino.

The "lower alkoxy" substituted with lower alkoxycarbonylamino means a lower alkoxy substituted with amino group mentioned above substituted with lower alkoxycarbonyl group mentioned above.

The "lower alkoxy" substituted with lower alkylsulfonylamino means a monovalent group in which the above lower alkoxy is substituted with lower alkylsulfonylamino group mentioned above.

The "lower alkoxy substituted with carbamoylamino" means a monovalent group in which the above lower alkoxy is substituted by a (carbamoyl)amino (urea) group, such as

[(carbamoyl)amino]methoxy, [(carbamoyl)amino]ethoxy, [(carbamoyl)amino]propoxy, [(carbamoyl)amino]cyanobutoxy, and the like, and it is preferably (C1–C4)alkoxy substituted with [(carbamoyl)amino], more preferably ($C_1$–$C_2$)alkoxy substituted with [(carbamoyl)amino], most preferably carbamoylaminomethoxy.

The "lower alkokycarbonylamino" means an amino group substituted with lower alkokycarbonyl group mentioned above.

The "lower alkylsulfonylamino" means a sulfonylamino group substituted with lower alkyl group mentioned above.

Suitable "heterocyclic group" may be one containing at least one hetero atom selected from nitrogen, sulfur and oxygen atom, and may include saturated or unsaturated, monocyclic or polycyclic heterocyclic group, and preferable heterocyclic group may be N-containing heterocyclic group such as unsaturated 3 to 6-membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g. 4H-1,2,4-triazolyl, 1H-1,2,3-triazolyl, 2H-1,2,3-triazolyl, etc.], tetrazolyl [e.g. 1H-tetrazolyl, 2H-tetrazolyl, etc.], etc.;

saturated 3 to 7-membered heteromonocyclic group containing 1 to 4 nitrogen atoms [e.g. pyrrolidinyl, imidazolidinyl, piperidyl, piperazinyl, homopiperazinyl, etc.];

unsaturated condensed heterocyclic group containing 1 to 5 nitrogen atoms, for example, indolyl, isoindolyl, indolizinyl, benzimidazolyl, quinolyl, isoquinolyl, imidazopyridyl, indazolyl, benzotriazolyl, tetrazolopyridazinyl [e.g. tetrazolo[1,5-b]pyridazinyl, etc.], quioxalinyl, etc.;

unsaturated 3 to 6-membered heteromonocyclic group containing an oxygen atom, for example, pyranyl, furyl, etc.;

saturated 3 to 6-membered heteromonocyclic group containing an oxygen atom, for example, 1H-tetrahydropyranyl, tetrahydrofuranyl, etc.;

unsaturated 3 to 6-membered heteromonocyclic group containing 1 to 2 sulfur atoms, for example, thienyl, etc.;

unsaturated 3 to 6-membered heteromonocyclic group containing 1 to 2 oxygen atoms and 1 to 3 nitrogen atoms, for example, oxazolyl, isoxazolyl, oxadiazolyl [e.g. 1,2,4-oxadiazolyl, 1,3,4-oxadiazolyl, 1,2,5-oxadiazolyl, etc.], oxazolinyl [e.g. 2-oxazolinyl, etc.], etc.;

saturated 3 to 6-membered heteromonocyclic group containing 1 to 2 oxygen atoms and 1 to 3 nitrogen atoms [e.g. morpholinyl, etc.];

unsaturated condensed heterocyclic group containing 1 to 2 oxygen atoms and 1 to 3 nitrogen atoms [e.g. benzofurazanyl, benzoxazolyl, benzoxadiazolyl, etc.];

unsaturated 3 to 6-membered heteromonocyclic group containing 1 to 2 sulfur atoms and 1 to 3 nitrogen atoms, for example, thiazolyl, thiadiazolyl [e.g. 1,2,4-thiadiazolyl, 1,3,4-thiadiazolyl, 1,2,5-thiadiazolyl, etc.], etc.;

saturated 3 to 6-membered heteromonocyclic group containing 1 to 2 sulfur atoms and 1 to 3 nitrogen atoms [e.g. thiazolidinyl, etc.];

unsaturated condensed heterocyclic group containing 1 to 2 sulfur atoms and 1 to 3 nitrogen atoms [e.g. benzothiazolyl, benzothiadiazolyl, etc.];

unsaturated condensed heterocyclic group containing 1 to 2 oxygen atoms [e.g. benzofuranyl, benzodioxolyl, chromanyl, etc.] and the like.

Said "heterocyclic group" may be substituted with lower alkyl as exemplified above or oxo, in which preferable one is pieridyl, pyrrolyl, 3-metyl-1,2,4-oxadiazol-5-yl, isoindole-1,3-dione-2-yl or 1-methyl-1H-imidazolyl.

The heterocyclic moiety in the term "heterocycliccarbonyl" means heterocyclic group mentioned above and, it is preferably piperidyl.

The "lower alkylsulfonyloxy" means a sulfonyloxy group substituted with lower alkyl group mentioned above.

The "lower alkanoyl substituted with halogen" means a lower alkanoyl group mentioned above substituted with halogen mentioned above, such as trifluoroacetyl, and the like.

The "lower alkylsilyloxy" means silyloxy group substituted by the same or different above (lower)alkyl groups, such as trimethylsilyloxy, triethylsilyloxy, tert-butyldimethylsilyloxy, or the like, and it is preferably tert-butyldimethylsilyloxy.

The "acid residue" means halogen (e.g. fluoro, chloro, bromo, iodo), arenesulfonyloxy (e.g. benzenesulfonyloxy, tosyloxy, etc.), alkanesulfonyloxy (e.g. mesyloxy, ethanesulfonyloxy, etc.), and the like.

Preferred compound (I) is one having hydrogen for $R^1$; lower alkyl optionally substituted with halogen; cycloalkyl; halogen; or lower alkoxy optionally substituted with halogen for $R^2$; lower alkoxy for $R^3$; $R^5$—G—J— (wherein —CO— or —$SO_2$— for G, —NH— for J, amino or lower alkyl for $R^5$) for $R^4$; O for X; CH or N for Y; lower alkylene for Z; and 0 or 1 for m.

Suitable salts of the compounds (I) are pharmaceutically acceptable conventional non-toxic salts and include a metal salt such as an alkali metal salt (e.g., sodium salt, potassium salt, etc.) and an alkaline earth metal salt (e.g., calcium salt, magnesium salt, etc.), an ammonium salt, an organic base salt (e.g., trimethylamine salt, triethylamine salt, pyridine salt, picoline salt, dicyclohexylamine salt, etc.), an organic acid salt (e.g., acetate, maleate, tartrate, methanesulfonate, benzenesulfonate, formate, toluenesulfonate, trifluoroacetate, etc.), an inorganic acid salt (e.g., hydrochloride, hydrobromide, sulfate, phosphate, etc.), a salt with an amino acid (e.g., arginine, aspartic acid, glutamic acid, etc.), or the like.

The processes for preparing the object compounds are explained in detail in the following.

Process (1)

The object compound (Ia) or its salt can be prepared by reacting a compound (II) or its salt with a compound (III) or its salt in the acidic condition, for example, by using acetic acid.

Suitable salts of the compounds (Ia) and (III) may be the same as those exemplified for the compound (I).

Suitable salt of the compound (II) may be acid addition salt exemplified for the compound (I).

The reaction is carried out in a conventional solvent such as water, an alcohol (e.g. methanol, ethanol, propanol, isopropanol, etc.), tetrahydrofuran, dioxane, etc. or a mixture of thereof.

The reaction temperature is not critical and the reaction is usually carried out under cooling to heating.

According to the starting material, the heterocyclic ring is formed but not to form pyrazole ring. In this case, the dehydration process is need to form pyrazole ring.

The hydration process is carried out under the higher temperature.

Process (2)

The object compound (Ib) or its salt can be prepared by reacting a compound (IV) or its salt with a compound (V) or its salt.

Suitable salts of the compounds (Ia), (IV) and (V) may be the same as those exemplified for the compound (I).

When the compound (V) having halogen for Q is used in this reaction, the reaction is preferably carried out in the presence of a base such as alkali metal (e.g. sodium, potassium, etc.), an alkaline earth metal (e.g. magnesium, calcium, etc. ), the hydride or hydroxide or carbonate or bicarbonate thereof.

When the compound (V) having hydroxy for Q is used in this reaction, the reaction is preferably carried out in the presence of diethyl azodicarboxylate and triphenylphosphine.

The reaction is usually carried out in a conventional solvent which does not adversely influence the reaction such as water, dioxane, a alcohol (e.g. methanol, ethanol, etc.), acetonitrile, tetrahydrofuran, acetic acid, N,N-dimethylformamide, or a mixture thereof.

The reaction temperature is not critical and the reaction can be carried out under cooling to heating.

In order to illustrate the usefulness of the object compounds (I), the pharmacological test data of the com pounds (I) are shown in the following.

[A] Analgesic Activity

Effect on Adjuvant Arthritis in Rats:

(i) Test Method

Analgesic activity of a single dose of agents in arthritic rats was studied.

Arthritis was induced by injection of 0.5 mg of Mycobacterium tuberculosis (Difco Laboratories, Detroit, Mich.) in 50 μl of liquid paraffin into the right hind footpad of Lewis rats aged 7 weeks. Arthritic rats were randomized and grouped (n=10) for drug treatment based on pain threshold of left hind paws and body weight on day 22.

Drugs (Test compounds) were administered and the pain threshold was measured 2 hrs after drug administration. The intensity of hyperalgesia was assessed by the method of Randall-Selitto. The mechanical pain threshold of the left hind paw (uninjected hind paw) was determined by compressing the ankle joint with a balance pressure apparatus (Ugo Basile Co. Ltd., Varese, Italy). The threshold pressure of rats squeaking or struggling was expressed in grams. The threshold pressure of rats treated with drugs was compared with that of non-treated rats. A dose showing the ratio of 1.5 is considered to be the effective dose.

(ii) Test Results

| Test compound (Example No.) | Dose (mg/kg) | The coefficient of analgesic |
|---|---|---|
| 23 | 3.2 | >1.5 |
| 28 | 3.2 | >1.5 |
| 61 | 3.2 | >1.5 |
| 181 | 3.2 | >=1.5 |
| 240 | 3.2 | >=1.5 |
| 248 | 3.2 | >=1.5 |
| 250 | 3.2 | >=1.5 |
| 254 | 3.2 | >=1.5 |
| 267 | 3.2 | >=1.5 |

[B] Inhibiting Activity Against COX-I and COX-II (Whole Blood Assay)

(i) Test Metho:

Whole Blood Assay for COX-I

Fresh blood was collected by syringe without anticoagulants from volunteers with consent. The subjects had no apparent inflammatory conditions and had not taken any medication for at least 7 days prior to blood collection.

500 μl Aliquots of human whole blood were immediately incubated with 2 μl of either dimethyl sulfoxide vehicle or a test compound at final concentrations for 1 hr at 37° C. to allow the blood to clot. Appropriate treatments (no incubation) were used as blanks. At the end of the incubation, 5 μl of 250 mM Indomethacin was added to stop the reaction. The blood was centrifuged at 6000×g for 5 min at 4° C. to obtain serum. A 100 μl aliquot of serum was mixed with 400 μl methanol for protein precipitation. The supernatant was obtained by centrifuging at 6000×g for 5 min at 4° C. and was assayed for $TXB_2$ using an enzyme immunoassay kit according to the manufacturer's procedure. For a test compound, the results were expressed as percent inhibition of thromboxane $B_2$($TXB_2$) production relative to control incubations containing dimethyl sulfoxide vehicle.

The data were analyzed by that a test compound at the indicated concentrations was changed log value and was applied simple linear regression. $IC_{50}$ value was calculated by least squares method.

Whole Blood Assay for COX-II

Fresh blood was collected in heparinized tubes by syringe from volunteers with consent. The subjects had no apparent inflammatory conditions and had not taken any medication for at least 7 days prior to blood collection.

500 μl aliquots of human whole blood were incubated with either 2 μl dimethyl sulfoxide vehicle or 2 μl of a test compound at final concentrations for 15 min at 37° C. This was followed by incubation of the blood with 10 μl of 5 mg/ml lipopolysaccharide for 24 hrs at 37° C. for induction of COX-II. Appropriate PBS treatments (no LPS) were used as blanks. At the end of the incubation, the blood was centrifuged at 6000×g for 5 min at 4° C. to obtain plasma. A 100 μl aliquot of plasma was mixed with 400 μl methanol for protein precipitation. The supernatant was obtained by centrifuging at 6000×g for 5 min at 4° C. and was assayed for prostaglandin $E_2$ ($PGE_2$) using a radioimmunoassay kit after conversion of $PGE_2$ to its methyl oximate derivative according to the manufacturer's procedure.

For a test compound, the results were expressed as percent inhibition of $PGE_2$ production relative to control incubations containing dimethyl sulfoxide vehicle. The data were analyzed by that a test compound at the indicated concentrations was changed log value and was applied simple linear regression. $IC_{50}$ value was calculated by least squares method.

(ii) Test Results:

| Test Compound (Example No.) | COX-I IC50 (μM) | COX-II IC50 (μM) |
|---|---|---|
| 23 | <0.01 | >0.1 |
| 28 | <0.01 | >0.1 |
| 61 | <0.01 | >0.1 |
| 181 | <0.01 | >0.1 |
| 240 | <0.01 | >0.1 |
| 248 | <0.01 | >0.1 |
| 250 | <0.01 | >0.1 |
| 254 | <0.01 | >0.1 |
| 267 | <0.01 | >0.1 |

It appeared, from the above-mentioned Test Results, that the compound (I) or pharmaceutically acceptable salts thereof of the present invention have an inhibiting activity against COX, particularly a selective inhibiting activity against COX-I.

[C] Inhibiting Activity on Aggregation of Platelet (i) Methods

Preparation of Platelet-rich Plasma

Blood from healthy human volunteers was collected into plastic vessels containing 3.8% sodium citrate (1/10 volume). The subject had no taken any compounds for at least 7 days prior to blood collection. Platelet-rich plasma was obtained from the supernatant fraction of blood after centrifugation at 1200 rpm. for 10 min. Platelet-poor plasma was obtained by centrifugation of the remaining blood at 3000 rpm for 10 min.

Measurement of Platelet Aggregation

Platelet aggregation was measured according to the turbidimetric method with an aggregometer (Hema Tracer) In the cuvette, platelet-rich plasma was pre-incubated for 2 min at 37° C. after the addition of compounds or vehicle. In order to quantify the inhibitory effects of each compound, the maximum increase in light transmission was determined from the aggregation curve for 7 min after the addition of agonist. We used collagen as agonist of platelet aggregation in this study. The final concentration of collagen was 0.5 μg/mL. The effect of each compound was expressed as percentage inhibition agonist-induced platelet aggregation compared with vehicle treatment. Data are presented as the mean ± S.E.M. for six experiments. The $IC_{50}$ value was obtained by linear regression, and is expressed as the compound concentration required to produce 50% inhibition of agonist-induced platelet aggregation in comparison to vehicle treatment.

It appeared, from the above-mentioned Test Result, that the compound (I) or pharmaceutically acceptable salts thereof of the present invention have an inhibiting activity against platelet aggregation. Therefore, the compound (I) or pharmaceutically acceptable salts thereof are useful for preventing or treating disorders induced by platelet aggregation, such as thrombosis.

Additionally, it was further confirmed that the compounds (I) of the present invention lack undesired side-effects of non-selective NSAIDs, such as gastrointestinal disorders, bleeding, renal toxicity, cardiovascular affection, etc.

As shown above, the object compound (I) or pharmaceutically acceptable salts thereof of this invention possesses COX inhibiting activity and possesses strong anti-inflammatory, antipyretic, analgesic, antithrombotic, anti-cancer activities, and so on.

The object compound (I) and pharmaceutically acceptable salt thereof, therefore, are useful for treating and/or preventing COX mediated diseases, inflammatory conditions, various pains, collagen diseases, autoimmune diseases, various immunological diseases, thrombosis, cancer and neurodegenerative diseases in human beings or animals by using administered systemically or topically.

More particularly, the object compound (I) and pharmaceutically acceptable salts thereof are useful for treating and/or preventing inflammation and acute or chronic pain in joint and muscle [e.g. rheumatoid arthritis, rheumatoid spondylitis, osteoarthritis, gouty arthritis, juvenile arthritis, scapulohumeral periarthritis, cervical syndrome, etc.]; lumbago; inflammatory skin condition [e.g. sunburn, burns, eczema, dermatitis, etc.]; inflammatory eye condition [e.g. conjunctivitis, etc.]; lung disorder in which inflammation is involved [e.g. asthma, bronchitis, pigeon fancier's disease, farmer's lung, etc.]; condition of the gastrointestinal tract associated with inflammation [e.g. aphthous ulcer, Chrohn's disease, atopic gastritis, gastritis varioloid, ulcerative colitis, coeliac disease, regional ileitis, irritable bowel syndrome, etc.]; gingivitis; menorrhalgia; inflammation, pain and tumescence after operation or injury [pain after odontectomy, etc.]; pyrexia, pain and other conditions associated with inflammation, particularly those in which lipoxygenase and cyclooxygenase products are a factor, systemic lupus erythematosus, scleroderma, polymyositis, tendinitis, bursitis, periarteritis nodose, rheumatic fever, Sjogren's syndrome, Behcet disease, thyroiditis, type I diabetes, nephrotic syndrome, aplastic anemia, myasthenia gravis, uveitis contact dermatitis, psoriasis, Kawasaki disease, sarcoidosis, Hodgkin's disease, Alzheimers disease, or the like.

Additionally, the object compound (I) or a salt thereof is expected to be useful as therapeutical and/or preventive agents for cardiovascular or cerebrovascular diseases, the diseases caused by hyperglycemia and hyperlipemia.

The object compound (I) and a salt thereof can be used for prophylactic and therapeutic treatment of arterial thrombosis, arterial sclerosis, ischemic heart diseases [e.g. angina pectoris (e.g. stable angina pectoris, unstable angina pectoris including imminent infarction, etc.), myocardial infarction (e.g. acute myocardial infarction, etc.), coronary thrombosis, etc.], ischemic brain diseases [e.g. cerebral infarction (e.g. acute cerebral thrombosis, etc.), cerebral thrombosis (e.g. cerebral embolism, etc.), transient cerebral ischemia (e.g. transient ischemic attack, etc.), cerebrovascular spasm after cerebral hemorrhage (e.g. cerebrovascular spasm after subarachnoid hemorrhage, etc.), etc.], pulmonary vascular diseases (e.g. pulmonary thrombosis, pulmonary embolism etc.), peripheral circulatory disorder [e.g. arteriosclerosis obliterans, thromboangiitis obliterans (i.e. Buerger's disease), Raynaud's disease, complication of diabetes mellitus (e.g. diabetic angiopathy, diabetic neuropathy, etc.), phiebothrombosis (e.g. deep vein thrombosis, etc.), etc.], complication of tumors (e.g. compression thrombosis), abortion [e.g. placental thrombosis, etc.], restenosis and reocclusion [e.g. restenosis and/or reocclusion after percutaneous transluminal coronary angioplasty (PTCA), restenosis and reocclusion after the administration of thrombolytic drug (e.g. tissueplasminogen activator (TPA), etc.)], thrombus formation in case of vascular surgery, valve replacement, extracorporeal circulation [e.g. surgery (e.g. open heart surgery, pump-oxygenator, etc.) hemodialysis, etc.] or transplantation, disseminated intravascular coagulation (DIC), thrombotic thrombocytopenia, essential thrombocytosis, inflammation (e.g. nephritis, etc.), immunediseases, atrophicthrombosis, creeping thrombosis, dilation thrombosis, jumping thrombosis, mural thrombosis, etc.

The object compound (I) and a salt thereof can be used for the adjuvant therapy with thrombolytic drug (e.g. TPA, etc.) or anticoagulant (e.g. heparin, etc.).

And, the compound (I) is also useful for inhibition of thrombosis during extra corporeal circulation such as dialysis.

Particularly, the following diseases are exemplified: pains caused by or associated with rheumatoid arthritis, osteoarthritis, lumbar rheumatism, rheumatoid spondylitis, gouty arthritis, juvenile arthritis, etc; lumbago; cervico-omo-brachial syndrome; scapulohumeral periarthritis; pain and tumescence after operation or injury; etc.

And on the commercial package comprising the pharmaceutical composition mentioned above, the matter, which states above mentioned effects, may be written.

For therapeutic purpose, the compound (I) and a pharmaceutically acceptable salt thereof of the present invention can be used in a form of pharmaceutical preparation containing said compounds as an active ingredient, in admixture with a pharmaceutically acceptable carrier such as an organic or inorganic solid or liquid excipient suitable for oral, parenteral or external administration. The pharmaceutical preparations may be capsules, tablets, dragees, granules, inhalant, suppositories, solution, lotion, suspension, emulsion, ointment, gel, cream, or the like. If desired, there may be included in these preparations, auxiliary substances, stabilizing agents, wetting or emulsifying agents, buffers and other commonly used additives.

For therapeutic purpose, the analgesic agent of the present invention can be used in a form of pharmaceutical preparation suitable for oral, parenteral or external administration. The pharmaceutical preparations may be capsules, tablets, dragees, granules, inhalant, suppositories, solution, lotion, suspension, emulsion, ointment, gel, or the like.

Particularly, the analgesic agent of this invention is useful for treating or preventing acute or chronic pains associated with acute or chronic inflammations in human beings or animals by using administered systemically or topically.

While the dosage of therapeutically effective amount of the compound (I) will vary depending upon the age and condition of each individual patient, an average single dose of about 0.01 mg, 0.1 mg, 1 mg, 10 mg, 50 mg, 100 mg, 250 mg, 500 mg and 1000 mg of the compound (I) may be effective for treating the above-mentioned diseases. In general, amounts between 0.01 mg/body and about 1,000 mg/body may be administered per day.

In the above and subsequent description of the present specification, the following abbreviations and acronyms mean ones as shown in the following table.

| Abbreviations and Acronyms | Full Name |
| --- | --- |
| AcOEt or EtOAc | ethyl acetate |
| AcOH | acetic acid |
| BuOH, t-BuOH, etc. | butanol, t-butyl alcohol, etc. |
| DME | 1,2-dimethoxyethane |
| DMF | N,N-dimethylformamide |
| DMSO | dimethyl sulfoxide |
| Et3N | triethylamine |
| EtOH | ethanol |
| IPE | diisopropyl ether |
| MeOH | methanol |
| PrOH, i-PrOH or IPA, etc. | propanol, isopropyl alcohol, etc. |
| TFA | trifluoroacetic acid |
| THF | tetrahydrofuran |
| EDCI or WSCD | 1-ethyl-3-[3'-(dimethylamino)propyl]carbodiimide |
| HOBt or HOBT | 1-hydroxybenztriazole |
| Pd/C | palladium on carbon |
| MCBA or mCPBA or mcpba | 3-Chloroperoxybenzoic acid |
| deg | ° C. = degree centigrade |
| min | minute(s) |
| hr or h | hour(s) |
| conc. | concentrated |
| aq | aqueous (ex. aq NaHCO3 solution) |

The following Examples and Preparations are given only for the purpose of illustrating the present invention in more detail.

EXAMPLE 1-1

(1E)-1-[4-(Methoxymethoxy)phenyl]-4-methyl-1-penten-3-one

1M Sodium hydroxide aqueous solution (5.4 ml) was added to a solution of 4-mehoxymethoxybenzaldehyde (4.52 g) and 3-methyl-2-butanone (4.69 g) in ethanol (27 ml), and the mixture was stirred at room temperature overnight.

The mixture partitioned between ethyl acetate andwater. The organic layer was washed with water, saturated aqueous sodium chloride solution, dried over magnesium sulfate, and concentrated in vacuo. The residue was purified by silica gel chromatography eluted with 10% ethyl acetate/n-hexane to give the title compound (4.03 g, 63.2%) as an oil.

1H NMR (CDCl$_3$): δ 1.18 (6H, d, J=6.7 Hz), 2.92 (1H, m), 3.48 (3H, s), 5.21 (2H, s), 6.71 (1H, d, J=16.0 Hz), 7.05 (2H, d, J=8.8 Hz), 7.51 (2H, d, J=8.8 Hz), 7.58 (1H, d, J=16.0 Hz).

MS (ESI+): m/z 257 (M+Na).

EXAMPLE 1-2

(1S, 2R)- and (1R, 2S)-1,2-epoxy-1-[4-(methoxymethoxy)-phenyl]-4-methyl-3-pentanone 30% H$_2$O$_2$ (1.7 ml) and 3M sodium hydroxide aqueous solution (1.7 ml) was added to a solution of (1E)-1-[4-(methoxymethoxy)phenyl]-4-methyl-1-penten-3-one obtained by Example 1-1 (2.00 g) in ethanol:acetone=3:1 (34 ml). The mixture was stirred at room temperature overnight.

The mixture was concentrated in vacuo, and partitioned between ethyl acetate and water. The organic layer was washed with water, saturated aqueous sodium chloride solution, dried over magnesium sulfate, and concentrated in vacuo to give the target compound (2.03 g, 95%) as an oil.

1H NMR (DMSO-d6): δ 1.05 (6H, d, J=6.9 Hz), 2.85 (1H, m), 3.36 (3H, s), 3.93 (1H, d, J=1.9 Hz), 4.00 (1H, d, J=1.9 Hz), 5.20 (2H, s), 7.03 (2H, d, J=8.6 Hz), 7.30 (2H, d, J=8.6 Hz).

MS (ESI): m/z 273 (M+Na).

EXAMPLE 1-3

4-[3-Isopropyl-1-(4-methoxyphenyl)-1H-pyrazol-5-yl]-phenol

A mixture of (1S, 2R)- and (1R, 2S)-1,2-epoxy-1-[4-(methoxymeth-oxy)phenyl]-4-methyl-3-pentanone obtained by Example 1-2 (2.10 g) and 4-methoxyphenylhydrazine hydrochloride (1.76 g) in ethanol:acetic acid=20:1 (20 ml) was stirred at 60° C. for 3 hrs.

The mixture was concentrated in vacuo. To the residue was added ethyl acetate and 1M hydrochloric acid. The whole mixture was treated with activated carbon, and was filtered through a celite pad. The filtrate was partitioned. The organic layer was washed successively with 1M hydrochloric acid, saturated aqueous sodium bicarbonate solution, saturated aqueous sodium chloride solution, dried over magnesium sulfate, and concentrated in vacuo. The residual solid were collected and washed with ethyl acetate to give the target compound (322.2 mg, 12.5%) as a white powder.

1H NMR (CDCl$_3$): δ 1.33 (6H, d, J=7.0 Hz), 3.07 (1H, m), 3.80 (3H, s), 5.18 (1H, s), 6.26 (1H, s), 6.72 (2H, d, J=8.8 Hz), 6.83 (2H, d, J=9.0 Hz), 7.08 (2H, d, J=8.8 Hz), 7.20 (2H, d, J=9.0 Hz).

MS (ESI+): m/z 309 (M+H).

EXAMPLE 2 tert-Butyl 2-{4-[3-isopropyl-1-(4-methoxyphenyl)-1H-pyrazol-5-yl]-phenoxy}ethylcarbamate Diethylazodicarboxylate (259 mg) was added to a mixture of 4-[3-isopropyl-1-(4-methoxyphenyl)-1H-pyrazol-5-yl]phenol obtained by Example 1-3 (305 mg), 2-t-butoxycarbonylaminoethanol (479 mg), and triphenylphosphine (390 mg) in tetrahydrofuran (3 ml). After stirring at room temperature for 7 hrs, diethylazod icarboxylate (17 mg) and triphenylphosphine (26 mg) was added to the reaction mixture.

After stirring at room temperature for 1 hr, the reaction mixture was concentrated in vacuo. The residue was purified by silica gel column chromatography eluted with 30% ethyl acetate/n-hexane to give the target compound (396 mg, 88.5%) as a solid.

1H NMR (CDCl$_3$): δ 1.34 (6H, d, J=7.0 Hz), 1.45 (9H, s), 3.07 (1H, m), 3.48–3.57 (2H, m), 3.80 (3H, s), 3.97–4.03 (2H, m), 4.97 (1H, br-s), 6.26 (1H, s), 6.76–6.87 (4H, m), 7.14 (2H, d, J=8.9 Hz), 7.20 (2H, d, J=9.0 Hz).

EXAMPLE 3

2-{4-[3-Isopropyl-1-(4-methoxyphenyl)-1H-pyrazol-5-yl]-phenoxy}ethanamine hydrochloride 4M Hydrochloric acid/dioxane (2 ml) was added to a solution of tert-butyl 2-{4-[3-isopropyl-1-(4-methoxy-phenyl)-1H-pyrazol-5-yl]-phenoxy}ethylcarbamate obtained by Example 2 (382 mg) in dichloromethane (3 ml) at 0° C.

After stirring at room temperature for 1 hr, the reaction mixture was concentrated in vacuo. The residue was crystallized from a mixture of isopropanol and ethyl acetate to give the target compound (311 mg, 94.7%) as a powder.

1H NMR (DMSO-d6): δ 1.27 (6H, d, J=6.9 Hz), 2.95 (1H, m), 3.14–3.22 (2H, m), 3.76 (3H, s), 4.14–4.20 (2H, m), 6.41 (1H, s), 6.93 (4H, d, J=8.9 Hz), 7.16 (4H, d, J=8.9 Hz), 8.22 (2H, br-s).

MS (ESI+): m/z 352 (M+H).

EXAMPLE 4

N-(2-{4-[3-Isopropyl-1-(4-methoxyphenyl)-1H-pyrazol-5-yl]phenoxy}-ethyl)methanesulfonamide Methanesulfonyl chloride (32.2 mg) was added to a solution of 2-{4-[3-isopropyl-1-(4-methoxyphenyl)-1H-pyrazol-5-yl]phenoxy}ethanamine hydrochloride obtained by Example 3 (90.9 mg) and triethylamine (71.1 mg) in dichloromethane (2 ml). The mixture was stirred at room temperature for 2 hrs.

The mixture was concentrated in vacuo, and the residue was partitioned between ethyl acetate and a mixture of 1M hydrochloric acid and brine. The aqueous layer was reextracted with ethyl acetate. The organic layer was washed with saturated aqueous sodium bicarbonate solution, and saturated aqueous sodium chloride solution, dried over magnesium sulfate, and concentrated in vacuo. The residue was crystallized from a mixture of ethyl acetate and isopropylether to give the target compound (78.0 mg, 77.5%) as a white powder.

MP: 162–163° C.

1H NMR (DMSO-d6): δ 1.26 (6H, d, J=6.9 Hz), 2.94 (3H, s), 2.94 (1H, m), 3.25–3.39 (2H, m), 3.76 (3H, s), 3.98–4.04 (2H, m), 6.40 (1H, s), 6.90 (2H, d, J=8.8 Hz), 6.93 (2H, d, J=8.9 Hz), 7.13 (2H, d, J=8.8 Hz), 7.15 (2H, d, J=8.9 Hz), 7.27 (1H, s).

IR (KBr): 3122, 2966, 2897, 2871, 1614, 1514cm$^{-1}$.

EXAMPLE 5

N-(2-{4-[3-Isopropyl-1-(4-methoxyphenyl)-1H-pyrazol-5-yl]phenoxy}ethyl)urea

Trimethylsilylisocyanate (41.4 mg) was added to a solution of 2-{4-[3-isopropyl-1-(4-methoxyphenyl)-1H-pyrazol-5-yl]phenoxy}ethanamine hydrochloride obtained by Example 3 (93.0 mg) and triethylamine (72.8 mg) in dichloromethane (3 ml) and the mixture was stirred at room temperature for 3 hrs. Trimethylsilylisocyanate (8.3 mg) was added and the mixture was stirred at room temperature for 1.5 hrs. Trimethylsilylisocyanate (13.8 mg) and triethylamine (12.1 mg) was added and the mixture was stirred at room temperature for 1.5 hrs.

The mixture was concentrated in vacuo, and the residue was partitioned between chloroform and a mixture of 1M hydrochloric acid and brine. The aqueous layer was extracted with chloroform. The combined organic layer was washed with saturated aqueous sodium bicarbonate solution and saturated aqueous sodium chloride solution, dried over magnesium sulfate, and concentrated in vacuo. The residue was purified by preparative thin layer silica gel chromatography developed by 10% methanol/chloroform. The separated silica gel was extracted with 10% methanol/chloroform and the solvent was evaporated invacuo. The residue was crystallized from a mixture of ethyl acetate and isopropylether to give the target compound (85.7 mg, 90.6%) as a white powder.

MP: 100–104° C.

1H NMR (DMSO-d6): δ 1.26 (6H, d, J=6.9 Hz), 2.94 (1H, m), 3.27–3.36 (2H, m), 3.76 (3H, s), 3.89–3.96 (2H, m), 5.52 (2H, s), 6.14 (1H, t, J=5.6 Hz), 6.39 (1H, s), 6.89 (2H, d, J=8.7 Hz), 6.93 (2H, d, J=8.9 Hz), 7.12 (2H, d, J=8.7 Hz), 7.15 (2H, d, J=8.9 Hz).

IR (KBr): 3371, 3190, 2964, 2873, 1738, 1684, 1639, 1614, 1543, 1512 cm$^{-1}$.

MS (ESI+): m/z 395 (M+H)

EXAMPLE 6 tert-Butyl 2-{4-[3-(1-hydroxy-1-methylethyl)-1-(4-methoxyphenyl)-1H-pyrazol-5-yl]phenoxy}ethylcarbamate tert-Butyl 2-{4-[3-ethoxycarbonyl-1-(4-methoxy-phenyl)-1-H-pyrazol-5-yl]phenoxy}ethylcarbamate (1.37 g) in tetrahydrofuran (10 ml) was added dropwise to 0.93M solution of methyl magnesium bromide in tetrahydrofuran (16 ml) at 24–27° C. with cooling in a waterbath.

After stirring at room temperature for 1hr, the mixture was poured into a mixture of saturated aqueous ammonium chloride solution and ice. The mixture was extracted with ethyl acetate. The organic layer was washed with saturated aqueous sodium chloride solution, dried over magnesium sulfate, and concentrated in vacuo. The residue was purified by silica gel column chromatography eluted with 70%ethylacetate/n-hexane to give the target compound (1.17 g, 88%) as an amorphous powder.

MS (ESI+): m/z 468 (M+H)

1H NMR (CDCl$_3$): δ 1.45 (9H, s), 1.65 (6H, s), 2.78 (1H, s), 3.48–3.57 (2H, m), 3.81 (3H, s), 3.97–4.03 (2H, m), 4.97 (1H, br), 6.36 (1H, s), 6.78–6.89 (4H, m), 7.13 (2H, d, J=8.7 Hz), 7.21 (2H, d, J=8.9 Hz).

EXAMPLE 7 tert-Butyl 2-{4-[3-isopropenyl-1-(4-methoxyphenyl)-1H-pyrazol-5-yl]phenoxy}ethylcarbamate Methanesulfonyl chloride (367 mg) and triethylamine (649 mg) were added successively to a solution of tert-butyl 2-{4-[3-(1-hydroxy-1-methylethyl)-1-(4-methoxy-phenyl)-1H-pyrazol-5-yl]phenoxy}ethylcarbamate obtained by Example 6 (1.0 g) and N,N-dimethylformamide (91.5 mg) in dichloromethane (10 ml) and the mixture was stirred at room temperature for 2 hrs. Additional methanesulfonyl chloride and triethylamine were added until all starting material was consumed with stirring at the same temperature.

The reaction mixture was partitioned between ethyl acetate and 1M hydrochloric acid, and the organic layer was washed with saturated aqueous sodium bicarbonate solution and saturated aqueous sodium chloride solution, dried over magnesium sulfate, and concentrated in vacuo. The residue was purified by silica gel column chromatography eluted with 30%ethylacetate/n-hexane to give the target compound (900 mg, 93.6%) as an amorphous powder.

1H NMR (CDCl$_3$): δ 1.45 (9H, s), 2.21 (3H, s), 3.48–3.57 (2H, m), 3.81 (3H, s), 3.97–4.03 (2H, m), 4.98 (1H, br-s), 5.12 (1H, br-s), 5.59 (1H, br-s), 6.56 (1H, s), 6.77–6.87 (4H, m), 7.14 (2H, d, J=8.7 Hz), 7.22 (2H, d, J=8.9 Hz).

MS (ESI+): m/z 450 (M+H).

EXAMPLE 8 tert-Butyl 2-{4-[3-isopropyl-1-(4-methoxyphenyl)-1H-pyrazol-5-yl]phenoxy}ethylcarbamate A mixture of 10% Pd-C 50% wet (65 mg) and tert-butyl 2-{4-[3-isopropenyl-1-(4-methoxyphenyl)-1H-pyrazol-5-yl]phenoxy}ethylcarbamate obtained by Example 7 (645 mg) in tetrahydrofuran (2 ml) and methanol (4 ml) was hydrogenated under H$_2$ 1 atm at room temperature for 3 hrs.

The catalyst was removed by filtration. The filtrate and combined washings were concentrated in vacuo. The residue was crystallized from a mixture of ethyl acetate and isopropyl ether to give the target compound (370 mg, 57.1%) as a white powder.

1H NMR (CDCl$_3$): δ 1.34 (6H, d, J=7.0 Hz), 1.45 (9H, s), 3.07 (1H, m), 3.48–3.57 (2H, m), 3.80 (3H, s), 3.97–4.03 (2H, m), 4.97 (1H, br-s), 6.26 (1H, s), 6.76–6.87 (4H, m), 7.14 (2H, d, J=8.9 Hz), 7.20 (2H, d, J=9.0 Hz).

MS (ESI+): m/z 452 (M+H).

EXAMPLE 9 tert-Butyl 2-{4-[3-(1-hydroxy-1-methylethyl)-1-(6-methoxy-3-pyridinyl)-1H-pyrazol-5-yl]phenoxy}ethyl-carbamate.

The title compound (624.4 mg, 42.9%) was prepared as an amorphous powder from tert-butyl 2-{4-[3-(1-hydroxy-1-methylethyl)-1-(6-methoxy-3-pyridinyl)-1H-pyrazol-5-yl]phenoxy}ethylcarbamate in a similar manner to that of Example 6.

1H NMR (CDCl$_3$): δ 1.45 (9H, s), 1.65 (6H, s), 3.49–3.57 (3H, m), 3.93 (3H, s), 3.98–4.04 (2H, m), 4.98 (1H, br), 6.39 (1H, s), 6.72 (1H, d, J=8.8 Hz), 6.83 (2H, d, J=8.8 Hz), 7.15 (2H, d, J=8.8 Hz), 7.54 (1H, dd, J=2.8, 8.8 Hz), 8.07 (1H, d, J=2.8 Hz).

MS (ESI+): 469 (M+H).

EXAMPLE 10 tert-Butyl 2-{4-[3-isopropenyl-1-(6-methoxy-3-pyridinyl)-1H-pyrazol-5-yl]phenoxy}ethylcarbamate The title compound (495 mg, 85.7%) was prepared as an oil from tert-butyl 2-{4-[3-(1-hydroxy-1-methylethyl)-1-(6-methoxy-3-pyridinyl)-1H-pyrazol-5-yl]phenoxy}-ethylcarbamate obtained by Example 9 in a similar manner to that of Example 7.

1H NMR (CDCl$_3$): δ 1.45 (9H, s), 2.20 (3H, s), 3.49–3.57 (2H, m), 3.92 (3H, s), 3.98–4.04 (2H,m), 4.99 (1H, br-s), 5.15 (1H, br-s), 5.60 (1H, br-s), 6.58 (1H, s), 6.72 (1H, d, J=8.8 Hz), 6.83 (2H, d, J=8.7 Hz), 7.15 (2H, d, J=8.7 Hz), 7.55 (1H, dd, J=2.6, 8.8 Hz), 8.09 (1H, d, J=2.6 Hz).

MS (ESI+): m/z 451 (M+H).

EXAMPLE 11 tert-Butyl 2-{4-[3-isopropyl-1-(6-methoxy-3-pyridinyl)-1H-pyrazol-5-yl]phenoxy}ethylcarbamate The title compound (220 mg, quant.) was prepared as an amorphous powder from tert-butyl 2-{4-[3-isopropenyl-1-(6-methoxy-3-pyridinyl)-1H-pyrazol-5-yl]phenoxy}-ethylcarbamate obtained by Example 10 in a similar manner to that of Example 8.

1H NMR (CDCl$_3$): δ 1.34 (6H, d, J=6.8 Hz), 1.45 (9H, s), 3.07 (1H, m), 3.48–3.57 (2H, m), 3.92 (3H, s), 3.98–4.04 (2H, m), 4.98 (1H, br), 6.28 (1H, s), 6.71 (1H, d, J=8.9 Hz), 6.82 (2H, d, J=8.9 Hz), 7.14 (2H, d, J=8.9 Hz), 7.56 (1H, dd, J=2.6, 8.9 Hz), 8.05 (1H, d, J=2.6 Hz).

MS (ESI+): m/z 453 (M+H).

EXAMPLE 12

2-{4-[3-Isopropyl-1-(6-methoxy-3-pyridinyl)-1H-pyrazol-5-yl]phenoxy}ethanamine dihydrochloride The title compound (257 mg, quant.) was prepared as an amorphous powder from tert-butyl 2-{4-[3-isopropyl-1-(6-methoxy-3-pyridinyl)-1H-pyrazol-5-yl]phenoxy}ethyl-carbamate obtained by Example 11 in a similar manner to that of Example 3.

1H NMR (DMSO-d6): δ 1.27 (6H, d, J=6.9 Hz), 2.96 (1H, m), 3.15–3.23 (2H, m), 3.85 (3H, s), 4.15–4.21 (2H, m), 6.47 (1H, s), 6.86 (1H, d, J=8.8 Hz), 6.97 (2H, d, J=8.8 Hz), 7.20 (2H, d, J=8.8 Hz), 7.62 (1H, dd, J=2.7, 8.8 Hz), 8.01 (1H, d, J=2.7 Hz), 8.19 (2H, s).

MS (ESI+): m/z 353 (M+H).

EXAMPLE 13

N-(2-{4-[3-Isopropyl-1-(6-methoxy-3-pyridinyl)-1H-pyrazol-5-yl]phenoxy}ethyl)urea The title compound (49.9 mg, 51.6%) was prepared as a white powder from 2-{4-[3-isopropyl-1-(6-methoxy-3-pyridinyl)-1H-pyrazol-5-yl]phenoxy}ethanamine obtained by Example 12 in a similar manner to that of Example 5.

MP: 106–107° C.

1H NMR (DMSO-d6): δ 1.27 (6H, d, J=6.9 Hz), 2.96 (1H, m), 3.27–3.36 (2H, m), 3.85 (3H, s), 3.94 (2H, t, J=5.5 Hz), 5.52 (2H, s), 6.15 (1H, t, J=5.6 Hz), 6.45 (1H, s), 6.85 (1H, d, J=8.8 Hz), 6.93 (2H, d, J=8.7 Hz), 7.16 (2H, d, J=8.7 Hz), 7.60 (1H, dd, J=2.6, 8.8 Hz), 8.02 (1H, d, J=2.6 Hz).

IR (KBr): 3400, 3390, 3379, 3352, 2960, 1657, 1608, 1547, 1512, 1500 cm$^{-1}$.

MS (ESI+): m/z 396 (M+H).

EXAMPLE 14-1

5-[4-(Benzyloxy)phenyl]-1-(4-methoxyphenyl)-4,5-dihydro-1H-pyrazol-3-amine

Sodium (3.19 g) was added portionwise to ethanol (160 ml) After all sodium was dissolved, 4-methoxyphenylhydrazine hydrochloride (14.5 g) was added in one portion to the solution. The mixture was stirred at room temperature for 10 min. To this mixture was added 3-(4-benzyloxyphenyl)acrylonitrile (16.3 g) in one portion, and the mixture was refluxed for 3 days.

Insoluble matter was filtered off, and the filtrate was concentrated in vacuo. Ethyl acetate and water were added to the residue and the mixture was stirred at room temperature for 1 hr. Precipitates were collected and washed successively with water, ethyl acetate, and air dried to give the target compound (12.57 g, 48.6%) as a powder.

1H NMR (DMSO-d6): δ 2.49 (1H, dd, J=8.3, 16.1 Hz), 3.29 (1H, dd, J=10.2, 16.1 Hz), 3.60 (3H, s), 4.69 (1H, dd, J=8.3, 10.2 Hz), 5.06 (2H, s), 5.62 (2H, s), 6.65 (4H, s), 6.97 (2H, d, J=8.6 Hz), 7.25 (2H, d, J=8.6 Hz), 7.31–7.48 (5H, m).

MS: (ESI+): m/z 374 (M+H).

EXAMPLE 14-2

5-[4-(Benzyloxy)phenyl]-1-(4-methoxyphenyl)-1H-pyrazol-3-amine

MnO$_2$ (3.5 g) was added to a solution of 5-[4-(benzyloxy)phenyl]-1-(4-methoxyphenyl)-4,5-dihydro-1H-pyrazol-3-amine obtained by Example 14-1 (12.54 g). in N,N-dimethylformamide (65 ml) and the mixture was stirred at 60° C. for 2 hrs. MnO$_2$ (5.3 g) was added and the mixture was stirred at 60° C. for 1 hr.

The mixture was filtered through a celite pad and the pad was washed with N,N-dimethylformamide. To the filtrate were added ethyl acetate and water, and the mixture was stirred at room temperature for 1 hr. Precipitates were collected and washed with water and air dried. The obtained powder was suspended in hot isopropylether cooled with stirring, collected and washed with isopropylether to give the target compound (11.70 g, 93.8%) as a powder.

1H NMR (DMSO-d6): δ 3.74 (3H, s), 4.84 (2H, s), 5.08 (2H, s), 5.73 (1H, s), 6.87 (2H, d, J=9.0 Hz), 6.96 (2H, d, J=9.0 Hz), 7.03–7.13 (4H, m), 7.34–7.47 (5H, m).

MS (ESI+): m/z 372 (M+H).

EXAMPLE 15

5-[4-(Benzyloxy)phenyl]-1-(4-methoxyphenyl)-N,N-dimethyl-1H-pyrazol-3-amine

37% Aqueous formamide solution (6 ml) and sodium cyanoborohydride (1.39 g) were added successively to a solution of 5-[4-(benzyloxy)phenyl]-1-(4-methoxyphenyl)-1H-pyrazol-3-amine obtained by Example 14-2 (2.75 g) in methanol 30 ml. The reaction mixture was stirred at room temperature for 3 days, occasionally adding 37% aqueous formamide solution and sodium cyanoborohydride appropriate amount to consume all starting material.

The reaction mixture was concentrated in vacuo, and the residue was partitioned between ethyl acetate and water. The organic layer was washed with saturated aqueous sodium chloride solution, dried over magnesium sulfate, and concentrated in vacuo. The residue was purified by silica gel column chromatography eluted with 20% ethyl acetate/chloroform to give the target compound (0.88 g, 29.8%) as an oil.

1H NMR (DMSO-d6): δ 2.81 (6H, s), 3.75 (3H, s), 5.08 (2H, s), 6.03 (1H, s), 6.90 (2H, d, J=8.9 Hz), 6.97 (2H, d, J=8.8 Hz), 7.06–7.16 (4H, m), 7.32–7.46 (5H, m)

MS (ESI+): m/z 400 (M+H).

EXAMPLE 16

4-[3-(Dimethylamino)-1-(4-methoxyphenyl)-1H-pyrazol-5-yl]phenol

A mixture of 5-[4-(benzyloxy)phenyl]-1-(4-methoxyphenyl) -N,N-dimethyl-1H-pyrazol-3-amine obtained by Example 15 (0.83 g) and 10% Pd-C 50% wet (160 mg) in acetic acid (8 ml) was hydrogenated under H$_2$ 1 atm at room temperature for 10 hrs.

The catalyst was removed by filtration. The filtrate and combined washings were concentrated in vacuo. The residue was purified by silica gel column chromatography eluted with 20% ethyl acetate/chloroform and was crystallized from a mixture of isopropylether and ethyl acetate to give the target compound (455 mg, 70.8%) as a white powder.

1H NMR (DMSO-d6): δ 2.80 (6H, s), 3.74 (3H, s), 5.96 (1H, s), 6.69 (2H, d, J=8.5 Hz), 6.89 (2H, d, J=9.0 Hz), 7.01 (2H, d, J=8.5 Hz), 7.09 (2H, d, J=9.0 Hz), 9.64 (1H, s).

MS (ESI+): m/z 310 (M+H).

EXAMPLE 17 tert-Butyl 2-{4-[3-(dimethylamino)-1-(4-methoxyphenyl)-1H-pyrazol-5-yl]phenoxy}ethylcarbamate The title compound (477.1 mg, 99.7%) was prepared as an oil from 4-[3-(dimethylamino)-1-(4-methoxyphenyl)-1-H-pyrazol-5-yl]phenol obtained by Example 16 in a similar manner to that of Example 2.

1H NMR (CDCl$_3$): δ 1.45 (9H, s), 2.93 (6H, s), 3.48–3.54 (2H, m), 3.79 (3H, s), 3.97–4.03 (2H, m), 4.97 (1H, br), 5.85 (1H, s), 6.79 (2H, d, J=8.7 Hz), 6.81 (2H, d, J=9.0 Hz), 7.10–7.27 (4H, m)

EXAMPLE 18

5-[4-(2-Aminoethoxy)phenyl]-1-(4-methoxyphenyl)-N,N-dimethyl-1-H-pyrazol-3-amine hydrochloride The title compound (454 mg, quant.) was prepared as an amorphous from tert-butyl 2-{4-[3-(dimethylamino)-1-(4-methoxyphenyl)-1H-pyrazol-5-yl]phenoxy}ethyl-carbamate obtained by Example 17 in a similar manner to that of Example 3.

1H NMR (DMSO-d6): δ 2.83 (6H, s), 3.16–3.25 (2H, m), 3.75 (3H, s), 4.13–4.18 (2H, m), 6.06 (1H, s), 6.91 (2H, d, J=9.0 Hz), 6.94 (2H, d, J=8.8 Hz), 7.12 (2H, d, J=9.0 Hz), 7.17 (2H, d, J=8.8 Hz), 8.05 (2H, br-s).

MS (ESI+): m/z 353 (M+H).

EXAMPLE 19

N-(2-{4-[3-(Dimethylamino)-1-(4-methoxyphenyl)-1H-pyrazol-5-yl]phenoxy}ethyl)urea The title compound (116 mg, 55.7%) was prepared as an amorphous from 5-[4-(2-aminoethoxy)phenyl]-1-(4-methoxyphenyl)-N,N-dimethyl-1H-pyrazol-3-amine hydrochloride obtained by Example 18 in a similar manner to that of Example 75 described later.

1H NMR (DMSO-d6): δ 2.81 (6H, s), 3.29–3.34 (2H, m), 3.74 (3H, s), 3.92 (2H, t, J=5.6 Hz), 5.53 (2H, s), 6.03 (1H, s), 6.15 (1H, t, J=5.6 Hz), 6.88–6.92 (4H, m), 7.04–7.14 (4H, m).

IR (neat): 3344, 3330, 3321, 1658, 1651, 1643, 1612, 1579, 1564, 1554, 1529, 1514 $cm^{-1}$.

MS (ESI+): m/z 396 (M+H).

EXAMPLE 20-1

5-[4-(Methoxymethoxy)phenyl]-1-(4-methoxyphenyl)-4,5-dihydro-1H-pyrazol-3-amine

The title compound (4.0 g, 57.8%) was prepared as a powder from 3-(4-methoxymethoxyphenyl)acrylonitrile in a similar manner to that of Example 14-1.

1H NMR (DMSO-d6): δ 2.49 (1H, dd, J=8.3, 16.1 Hz), 3.30 (1H, dd, J=10.3, 16.1 Hz), 3.36 (3H, s), 3.59 (3H, s), 4.70 (1H, dd, J=8.3, 10.3 Hz), 5.16 (2H, s), 5.62 (2H, s), 6.65 (4H, s), 6.97 (2H, d, J=8.6 Hz), 7.25 (2H, d, J=8.6 Hz).

MS (ESI+): m/z 328 (M+H).

EXAMPLE 20-2

5-[4-(Methoxymethoxy)phenyl]-1-(4-methoxyphenyl)-1H-pyrazol-3-amine

The title compound (4.80 g, quant.) was prepared as an oil from 5-[4-(methoxymethoxy)phenyl]-1-(4-methoxy-phenyl)-4,5-dihydro-1H-pyrazol-3-amine obtained by Example 20-1 in a similar manner to that of Example 14-2.

1H NMR (DMSO-d6): δ 3.36 (3H, s), 3.74 (3H, s), 4.85 (2H, s), 5.18 (2H, s), 5.74 (1H, s), 6.88 (2H, d, J=9.0 Hz), 6.96 (2H, d, J=8.8 Hz), 7.02–7.13 (4H, m).

MS (ESI+): m/z 326 (M+H).

EXAMPLE 21

3-Chloro-5-[4-(methoxymethoxy)phenyl]-1-(4-methoxy-phenyl)-1H-pyrazole

A mixture of 5-[4-(methoxymethoxy)phenyl]-1-(4-methoxyphenyl)-1H-pyrazol-3-amine obtained by Example 20-2 (3.79 g), lithium chloride (2.47 g), and copper (II) chloride (3.13 g) in acetonitrile (60 ml) was stirred at room temperature for 10 min. To this mixture was added isoamyl nitrite (2.73 g), and the mixture was stirred at room temperature for 1 hr.

The mixture was partitioned between ethyl acetate and saturated aqueous ammonium chloride solution. The organic layer was washed with saturated aqueous ammonium chloride solution and saturated aqueous sodium chloride solution, dried over magnesium sulfate, and concentrated in vacuo. The residue was purified by silica gel column chromatography eluted with 30% ethyl acetate/n-hexane. The solvent was evaporated in vacuo. The residue was crystallized from a mixture of isopropyl ether and ethyl acetate to give the target compound (2.38 g, 59.3%) as a white powder.

1H NMR (CDCl$_3$): δ 3.48 (3H, s), 3.82 (3H, s), 5.17 (2H, s), 6.36 (1H, s), 6.85 (2H, d, J=9.0 Hz), 6.95 (2H, d, J=8.9 Hz), 7.12 (2H, d, J=8.9 Hz), 7.20 (2H, d, J=9.0 Hz).

MS (ESI+): m/z 345 (M+H).

EXAMPLE 22

4-[3-Chloro-1-(4-methoxyphenyl)-1H-pyrazol-5-yl]phenol

To a solution of 3-chloro-5-[4-(methoxymethoxy)-phenyl]-1-(4-methoxyphenyl)-1H-pyrazole obtained by Example 21 (2.35 g) in tetrahydrofuran (10 ml) and methanol (10 ml) was added 36% hydrochloric acid (0.34 ml). The reaction mixture was stirred at room temperature for 1 hr, at 50° C. for 1.5 hrs, and at 60° C. for 1.5 hrs.

The mixture was partitioned between ethyl acetate and water. The organic layer was washed with saturated aqueous sodium chloride solution, dried over magnesium sulfate, and concentrated in vacuo. The residue solid was collected and washed with a mixture of isopropylether and n-hexane to give the target compound (1.99 g, 97.1%) as a white powder.

1H NMR (DMSO-d6): δ 3.78 (3H, s), 6.62 (1H, s), 6.71 (2H, d, J=8.7 Hz), 6.96 (2H, d, J=9.0 Hz), 7.03 (2H, d, J=8.7 Hz), 7.19 (2H, d, J=9.0 Hz), 9.80 (1H, s).

200 MHz 1H NMR (CDCl$_3$): δ 3.82 (3H, s), 5.24 (1H, s), 6.35 (1H, s), 6.75 (2H, d, J=8.6 Hz), 6.84 (2H, d, J=9.0 Hz), 7.07 (2H, d, J=8.6 Hz), 7.18 (2H, d, J=9.0 Hz).

MS (ESI+): m/z 301 (M+H).

EXAMPLE 23

2-{4-[3-Chloro-1-(4-methoxyphenyl)-1H-pyrazol-5-yl]-phenoxy}ethanol

Sodium hydride 60% dispersion in mineral oil (31.1 mg) was added to a solution of 4- [3-chloro-1-(4-methoxyphenyl)-1H-pyrazol-5-yl]phenol obtained by Example 22 (180 mg) in N,N-dimethylformamide (2 ml) under cooling in an ice bath. The reaction mixture was stirred at room temperature for 1 hr. To the reaction mixture was added a solution of 2-bromoethyl tert-butyl (dimethyl)silyl ether (258 mg) in N,N-dimethylformamide (2 ml).

After stirring at room temperature overnight, the mixture was poured into ice water. The mixture was extracted with ethyl acetate. The organic layer was washed with water and saturated aqueous sodium chloride solution, dried over magnesium sulfate, and concentrated in vacuo. The residue was dissolved in ethanol (3.6 ml). To this solution was added 36% aqueous hydrochloric acid (0.3 ml). After stirring at room temperature for 3 hrs, the mixture was concentrated in vacuo. The residue was partitioned between ethyl acetate and saturated aqueous sodium bicarbonate solution. The organic layer was washed with saturated aqueous sodium chloride solution, dried over magnesium sulfate, and concentrated in vacuo. The residue was purified by preparative thin layer silica gel chromatography developed by 70% ethyl acetate/n-hexane. The separate silica gel was extracted with 10% methanol/chloroform and the solvent was evaporated in vacuo. The residue was crystallized from a mixture of isopropylether and ethyl acetate to give the target compound (136.4 mg, 66.1%) as a white powder.

MP : 114.7–115.5° C.

1H NMR (DMSO-d6): δ 3.64–3.73 (2H, m), 3.77 (3H, s), 3.97 (2H, t, J=4.9 Hz), 4.86 (1H, t, J=5.4 Hz), 6.68 (1H, s), 6.91 (2H, d, J=8.9 Hz), 6.96 (2H, d, J=8.9 Hz), 7.15 (2H, d, J=8.9 Hz), 7.20 (2H, d, J=8.9 Hz).

IR (KBr): 3521, 1610, 1518cm$^{-1}$.

MS (ESI+): m/z 345 (M+H).

EXAMPLE 24 tert-Butyl 2-{4-[3-chloro-1-(4-methoxyphenyl)-1H-pyrazol-5-yl]phenoxy}ethylcarbamate The title compound (329.5 mg, 22.3%) was prepared as an amorphous from 4-[3-chloro-1-(4-methoxyphenyl)-1H-pyrazol-5-yl]phenol obtained by Example 22 in a similar manner to that of Example 73 described later.

1H NMR (CDCl$_3$): δ 145 (9H, s), 3.48–3.57 (2H, m), 3.81 (3H, s), 4.00 (2H, t, J=5.1 Hz), 4.96 (1H, br), 6.35 (1H, s), 6.81 (2H, d, J=8.8 Hz), 6.84 (2H, d, J=8.9 Hz), 7.12 (2H, d, J=8.8 Hz), 7.18 (2H, d, J=8.9 Hz).

MS (ESI+): m/z 444 (M+H).

EXAMPLE 25 tert-Butyl 2-{4-[3-chloro-1-(4-methoxyphenyl)-1H-pyrazol-5-yl]phenoxy}ethylcarbamate The title compound (1.31 g, 97.8%) was prepared from 4-[3-chloro-1-(4-methoxyphenyl)-1H-pyrazol-5-yl]phenol obtained by Example 22 in a similar manner to that of Example 2.

MS (ESI+): m/z 444 (M+H).

EXAMPLE 26

2-{4-[3-Chloro-1-(4-methoxyphenyl)-1H-pyrazol-5-yl]-phenoxy}ethanamine hydrochloride The title compound (605.2 mg, 85.4%) was prepared as a white powder from tert-butyl 2-{4-[3-chloro-1-(4-methoxyphenyl)-1H-pyrazol-5-yl]phenoxy}ethylcarbamate obtained by Example 25 in a similar manner to that of Example 3.

1H NMR (DMSO-d6): δ 3.14–3.23 (2H, m), 3.78 (3H, s), 4.14–4.20 (2H, m), 6.70 (1H, s), 6.96 (2H, d, J=8.8 Hz), 6.97 (2H, d, J=8.9 Hz), 7.19 (2H, d, J=8.8 Hz), 7.21 (2H, d, J=8.9 Hz), 8.19 (2H, br-s).

MS (ESI+): m/z 344 (M+H).

EXAMPLE 27

N-(2-{4-[3-chloro-1-(4-methoxyphenyl)-1H-pyrazol-5-yl]-phenoxy}ethyl)methanesulfonamide The title compound (137.8 mg, 82.8%) was prepared as a white powder from 2-{4-[3-chloro-1-(4-methoxyphenyl)-1H-pyrazol-5-yl]phenoxy}ethanamine hydrochloride obtained by Example 26 in a similar manner to that of Example 4.

MP: 117–119° C.

1H NMR (DMSO-d6): δ 2.94 (3H, s), 3.27–3.34 (2H, m), 3.76 (3H, s), 4.02 (2H, t, J=5.5 Hz), 6.69 (1H, s), 6.90–7.01 (4H, m), 7.14–7.25 (4H, m), 7.28 (1H, t, J=5.7 Hz).

IR (KBr): 1612, 1516cm$^{-1}$.

MS (ESI+): m/z 422 (M+H).

EXAMPLE 28

N-(2-{4-[3-Chloro-1-(4-methoxyphenyl)-1H-pyrazol-5-yl]-phenoxy}ethyl)urea

The title compound (174.6 mg, 85.8%) was prepared as a white powder from 2-{4-[3-chloro-1-(4-methoxyphenyl)-1H-pyrazol-5-yl]phenoxy}ethanamine hydrochloride obtained by Example 26 in a similar manner to that of Example 75 described later.

MP: 144.8–145.4° C.

1H NMR (DMSO-d6): δ 3.27–3.34 (2H, m), 3.77 (3H, s), 3.93 (2H, t, J=5.5 Hz), 5.52 (2H, s), 6.15 (1H, t, J=5.7 Hz), 6.68 (1H, s), 6.92 (2H, d, J=9.0 Hz), 6.97 (2H, d, J=9.0 Hz), 7.15 (2H, d, J=9.0 Hz), 7.20 (2H, d, J=9.0 Hz).

IR (ATR): 3423, 3402, 3203, 3143, 3010, 2976, 2943, 2885, 1651, 1610, 1583, 1516 cm$^{-1}$.

MS (ESI+): m/z 387 (M+H).

EXAMPLE 29-1

5-[4-(Methoxymethoxy)phenyl]-1-(6-methoxy-3-pyridinyl)-4,5-dihydro-1H-pyrazol-3-amine The title compound (1.63 g, 41.2%) was prepared as a powder from 3-(4-methoxymethoxyphenyl)acrylonitrile and 2-methoxy-5-pyridinylhydrazine dihydrochloride in a similar manner to that of Example 14-1.

H NMR (DMSO-d6): δ 2.48–2.60 (1H, dd, overlapping), 3.23–3.34 (1H, dd, overlapping), 3.36 (3H, s), 3.68 (3H, s), 4.75 (1H, dd, J=8.6, 10.0 Hz), 5.16 (2H, s), 5.77 (2H, s), 6.56 (1H, d, J=8.8 Hz), 6.98 (2H, d, J=8.6 Hz), 7.15 (1H, dd, J=2.8, 8.8 Hz), 7.27 (2H, d, J=8.6 Hz), 7.49 (1H, d, J=2.8 Hz)

MS (ESI+): m/z 329 (M+H).

EXAMPLE 29-2

5-[4-(Methoxymethoxy)phenyl]-1-(6-methoxy-3-pyridinyl)-1H-pyrazol-3-amine

The title compound (1.77 g, quant.) was prepared as an oil from 5-[4-(methoxymethoxy)phenyl]-1-(6-methoxy-3-pyridinyl)-4,5-dihydro-1H-pyrazol-3-amine obtained by Example 29-1 in a similar manner to that of Example 14-2.

1H NMR (DMSO-d6): δ 3.37(3H, s), 3.83(3H, s), 4.97 (2H, s), 5.19(2H, s), 5.78(1H, s), 6.81(1H, d, J=8.9 Hz), 6.99(2H, d, J=8.8 Hz), 7.15(2H, d, J=8.8 Hz), 7.51(1H, dd, J=2.7, 8.9 Hz), 7.92(1H, d, J=2.7 Hz)

MS (ESI+): m/z 327 (M+H).

EXAMPLE 30

5-{3-Chloro-5-[4-(methoxymethoxy)phenyl]-1H-pyrazol-1-yl}-2-methoxypyridine

The title compound (981.7 mg, 57.9%) was prepared as a powder from 5-[4-(methoxymethoxy)phenyl]-1(6-methoxy-3-pyridinyl)-1H-pyrazol-3-amine obtained by Example 29-2 in a similar manner to that of Example 21.

1H NMR (CDCl$_3$): δ 3.48(3H, s), 3.93(3H, s), 5.18(2H, s), 6.39(1H, s), 6.74(1H, d, J=8.8 Hz), 6.99(2H, d, J=8.8 Hz), 7.13(2H, d, J=8.8 Hz), 7.55(1H, dd, J=2.7, 8.8 Hz), 8.05 (1H, d, J=2.7 Hz).

MS (ESI+): m/z 346 (M+H).

EXAMPLE 31

4-[3-Chloro-1-(6-methoxy-3-pyridinyl)-1H-pyrazol-5-yl]-phenol

The title compound (2.15 g, 80.5%) was prepared as a white powder from 5-{3-chloro-5-[4-(methoxymethoxy)-phenyl]-1H-pyrazol-1-yl}-2-methoxypyridine obtained by Example 30 in a similar manner to that of Example 22.

1H NMR (DMSO-d6): δ 3.87(3H, s), 6.68(1H, s), 6.74 (2H, d, J=8.6 Hz), 6.89(1H, d, J=8.8 Hz), 7.07(2H, d, J=8.6 Hz), 7.65(1H, dd, J=2.7, 8.8 Hz), 8.09(1H, d, J=2.7 Hz), 9.86 (1H, br-s).

MS (ESI+): m/z 302 (M+H).

EXAMPLE 32

2-{4-[3-Chloro-1-(6-methoxy-3-pyridinyl)-1H-pyrazol-5-yl]phenoxy}ethanol

The title compound (140.9 mg, 86%) was prepared as a white powder from 4-[3-chloro-1-(6-methoxy-3-pyridinyl)-1H-pyrazol-5-yl]phenol obtained by Example 31 in a similar manner to that of Example 23.

MP: 136.5–138.2° C.

1H NMR (DMSO-d6): δ 3.65–3.74(2H, m), 3.87(3H, s), 3.9 8(2H, t, J=4.9 Hz), 4.87(1H, t, J=5.5 Hz), 6.74(1H, s), 6. 86–6.98(3H, m), 7.19(2H, d, J=8.8 Hz), 7.67(1H, dd, J=2.8, 8.8 Hz), 8.10(1H, d, J=2.8 Hz).

IR (KBr): 3369, 2960, 1610, 1502cm$^{-1}$.

MS (ESI+): m/z 346 (M+H).

EXAMPLE 33 tert-Butyl 2-{4-[3-chloro-1-(6-methoxy-3-pyridinyl)-1H-prazol-5-yl]phenoxy}ethylcarbamate The title compound (964 mg, 93.4%) was prepared as a white solid from 4-[3-chloro-1-(6-methoxy-3-pyridinyl)-1H-pyrazol-5-yl]phenol obtained by Example 31 in a similar manner to that of Example 2.

1H NMR (DMSO-d6): δ 1.37(9H, s), 3.22–3.33(2H, m), 3.8 7(3H, s), 3.95(2H, t, J=5.7 Hz), 6.74(1H, s), 6.86–7.04(4 H, m), 7.19(2H, d, J=8.7 Hz), 7.67(1H, dd, J=2.7, 8.8 Hz), 8.11(1H, d, J=2.7 Hz).

MS (ESI+): m/z 445 (M+H).

EXAMPLE 34

2-{4-[3-Chloro-1-(6-methoxy-3-pyridinyl)-1H-pyrazol-5-yl]phenoxy}-ethanamine dihydrochloride The title compound (842 mg, 98.6%) was prepared as an amorphous from tert-butyl 2-{4-[3-chloro-1-(6-methoxy-3-pyridinyl)-1H-pyrazol-5-yl]phenoxylethy}carbamate obtained by Example 33 in a similar manner to that of Example 3.

1H NMR (DMSO-d6): δ 3.15–3.24(2H, m), 3.87(3H, s), 4.1 9(2H, t, J=4.9 Hz), 6.76(1H, s), 6.90(1H, d, J=8.8 Hz), 6. 99(2H, d, J=8.8 Hz), 7.23(2H, d, J=8.8 Hz), 7.68(1H, d, J=2.7, 8.8 Hz), 8.10(1H, d, J=2.7 Hz), 8.20(2H, br-s).

MS (ESI+): m/z 345 (M+H).

EXAMPLE 35

N-(2-{4-[3-Chloro-1-(6-methoxy-3-pyridinyl)-1H-pyrazol-5-yl]phenoxy}ethyl)urea The title compound (119.5 mg, 62.4%) was prepared as a white powder from 2-{4-[3-chloro-1-(6-methoxy-3-pyridinyl)-1H-pyrazol-5-yl]phenoxy}ethanamine dihydrochloride obtained by Example 34 in a similar manner to that of Example 75 described later.

MP: 155.6–157.9° C.

1H NMR (DMSO-d6): δ 3.27–3.34(2H, m), 3.87(3H, s), 3.9 4(2H, t, J=5.5 Hz), 5.53(2H, s), 6.15(1H, t, J=5.5 Hz), 6. 75(1H, s), 6.89(1H, d, J=8.8 Hz), 6.95(2H, d, J=8.8 Hz), 7. 19(2H, d, J=8.8 Hz), 7.66(1H, dd, J=2.7, 8.8 Hz), 8.11(1H, d, J=2.7 Hz).

IR (KBr): 3425, 3415, 3319, 1657, 1610, 1591, 1581, 1574, 1500 cm$^{-1}$.

EXAMPLE 36

5-[4-(Benzyloxy)phenyl]-3-isopropoxy-1-(4-methoxy-phenyl)-1H-pyrazole

A mixture of 5-[4-(benzyloxy)phenyl]-3-hydroxy-1-(4-methoxyphenyl)-1H-pyrazol (2.4 g), 2-iodopropane (5.4 8 g), and potassium carbonate (2.67 g) in N,N-dimethylformamide (10 ml) was stirred at 100° C. for 3 hrs.

The reaction mixture was poured into ice water and the mixture was extracted with ethyl acetate. The organic layer was washed with water and saturated aqueous sodium chloride solution, dried over magnesium sulfate, and concentrated in vacuo. The residue was purified by silica gel column chromatography eluted with 20% ethyl acetate/n-hexane and the solvent was evaporated in vacuo. The residue was recrystallized from a mixture of ethyl acetate and n-hexane to give the target compound (2.14 g, 80.1%) asawhite powder.

1H NMR (DMSO-d6): δ 1.31(6H, d, J=6.1 Hz), 3.76(3H, s), 4.75(1H,m), 5.08(2H, s), 6.00(1H, s), 6.92(2H, d, J=9.0 Hz), 6.97(2H, d, J=8.9 Hz), 7.10–7.16(4H, m), 7.34–7.43 (5H, m)

MS (ESI+): m/z 415 (M+H).

EXAMPLE 37

4-[3-Isopropoxy-1-(4-methoxyphenyl)-1H-pyrazol-5-yl]-phenol

To a solution of ammonium formate (954 mg) in water (2 ml) were added ethanol (10 ml), a solution of 5-[4-(benzyloxy)phenyl]-3-isopropoxy-1-(4-methoxyphenyl)-1H-pyrazole obtained by Example 36 (2.09 g) in tetrahydrofuran (10 ml), and 10% palladium on carbon 50% wet (200 mg) successively. The mixture was refluxed for 1 hr.

The catalyst was removed by filtration and washed with ethyl acetate. The filtrate and combined washings were concentrated in vacuo. Ethyl acetate and water were added to the residue. Precipitates were collected and washed with water and ethyl acetate to give the first crop of the target compound (419 mg) as a white powder. The filtrate was partitioned, and the organic layer was saturated aqueous sodium chloride solution, dried over magnesium sulfate, and concentrated in vacuo. The residue crystals were collected and washed with isopropylether to give the second crop of the target compound (1.19 g, 72.5%) as a white powder.

1H NMR (DMSO-d6): δ 1.31(6H, d, J=6.2 Hz), 3.75(3H, s), 4.75(1H, m), 5.93(1H, s), 6.70(2H, d, J=8.6 Hz), 6.91 (2H, d, J=9.0 Hz), 7.01(2H, d, J=8.6 Hz), 7.11(2H, d, J=9.0 Hz), 9.70(1H, s).
MS (ESI+): m/z 325(M+H).

EXAMPLE 38

2-{4-[3-Isopropoxy-1-(4-methoxyphenyl)-1H-pyrazol-5-yl]phenoxy}ethanol

The title compound (147.3 mg, 88.2%) was prepared as an oil from 4-[3-isopropoxy-1-(4-methoxyphenyl)-1H-pyrazol-5-yl]phenol obtained by Example 37 in a similar manner to that of Example 23.

1H NMR (CDCl$_3$): 1.40(6H, d, J=6.2 Hz), 2.02(1H, t, J=5. 8 Hz), 3.79(3H, s), 3.94–4.00(2H, m), 4.04–4.10(2H, m), 4. 87(1H, m), 5.85(1H, s), 6.81(2H, d, J=9.0 Hz), 6.82(2H, d, J=8.9 Hz), 7.10–7.21(4H, m).
IR (neat): 3400, 3369, 2974, 2933, 1612, 1514cm$^{-1}$.
MS (ESI+): m/z 369 (M+H).

EXAMPLE 39 tert-Butyl 2-{4-[3-isopropoxy-1-(4-methoxyphenyl)-1H-pyrazol-5-yl]phenoxy}ethylcarbamate The title compound (520 mg, 72.2%) was prepared as a white powder from 4-[3-isopropoxy-1-(4-methoxyphenyl)-1H-pyrazol-5-yl]phenol obtained by Example 37 in a similar manner to that of Example 2.

1H NMR (DMSO-d6): δ 1.31(6H, d, J=6.2 Hz), 1.37(9H, s), 3.22–3.31(2H, m), 3.75(3H, s), 3.90–3.97(2H, m), 4.76 (1H, m), 5.99(1H, s), 6.86–6.96(4H, m), 7.01(1H, t, J=5.6 Hz), 7.09–7.15(4H, m).
MS (ESI+): m/z 467 (M+H).

EXAMPLE 40

2-{4-[3-Isopropoxy-1-(4-methoxyphenyl)-1H-pyrazol-5-yl]phenoxy}ethanamine hydrochloride The title compound (557 mg, quant.) was prepared as an amorphous from tert-butyl 2-{4-[3-isopropoxy-1-(4-methoxyphenyl)-1H-pyrazol-5-yl]phenoxy}ethylcarbamate obtained by Example 39 in a similar manner to that of Example 3.

1H NMR (DMSO-d6): δ 1.31(6H, d, J=6.1 Hz), 3.12–3.28(2H, m), 3.76(3H, s), 4.00–4.18(2H, m), 4.76(1H, m), 6.01(1H, s), 6.92(2H, d, J=9.0 Hz), 6.94(2H, d, J=8.7 Hz), 7.10–7. 19(4H, m), 8.06(2H, br-s).
MS (ESI+): m/z 368 (M+H).

EXAMPLE 41

N-(2-{4-[3-Isopropoxy-1-(4-methoxyphenyl)-1H-pyrazol-5-yl]phenoxy}ethyl)methanesulfonamide The title compound (125 mg, 79.8%) was prepared as a white powder from 2-{4-[3-isopropoxy-1-(4-methoxy-phenyl)-1H-pyrazol-5-yl]phenoxy}ethanamine hydrochloride obtained by Example 40 in a similar manner to that of Example 4.
MP: 167.9–168.0° C.
1H NMR (DMSO-d6): δ 1.31(6H, d, J=6.1 Hz), 2.94(3H, s), 3.27–3.36 (2H, m), 3.75(3H, s), 3.98–4.05(2H, m)), 4.76(1H, m), 6.0 0(1H, s), 6.88–6.94(4H, m), 7.12(2H, d, J=9.0 Hz), 7.14(2 H, d, J=8.9 Hz), 7.29(1H, t, J=5.8 Hz).
IR (KBr): 3132, 2979, 2939, 1612, 1556, 1518cm$^{-1}$.
MS (ESI+): m/z 446 (M+H).

EXAMPLE 42

N-(2-{4-[3-Isopropoxy-1-(4-methoxyphenyl)-1H-pyrazol-5-yl]phenoxy}ethyl)urea

The title compound (76.3 mg, 50.1%) was prepared as a white powder from 2-{4-[3-isopropoxy-1-(4-methoxy-phenyl)-1H-pyrazol-5-yl]phenoxy}ethanamine hydrochlorid e obtained by Example 40 in a similar manner to that of Example 75 described later.
MP: 139–140° C.
1H NMR (DMSO-d6): δ 1.31(6H, d, J=6.1 Hz), 3.27–3.35(2H, m), 3.75(3H, s), 3.89–3.96(2H, m), 4.76(1H, m), 5.53(2H, s), 6.00(1H, s), 6.15(1H, t, J=5.7 Hz), 6.90(2H, d, J=8. 9 Hz), 6.92(2H, d, J=9.0 Hz), 7.08–7.15(4H, m).
IR (KBr): 3388, 3350, 3332, 1658, 1612, 1579, 1562, 1554, 1518 cm$^{-1}$.
MS (ESI+): m/z 411 (M+H).

EXAMPLE 43

5-[4-(Benzyloxy)phenyl]-1-(6-methoxy-3-pyridinyl)-1H-pyrazol-3-ol

To a solution of 3-(4-benzyloxyphenyl)propiolic acid (1 g) and 1-hydroxybenzotriazole hydrate (643 mg) in N-methylpyrrolidone (10 ml) was added WSCD-HCl (912 mg) and the mixture was stirred at room temperature for 10 min. In another flask, diisopropylethylamine (2.31 g) was added to a suspension of 5-hydrazino-2-methoxypyridine dihydrochloride (1.26 g) in N-methylpyrrolidone (4 ml) and stirred at room temperature until all 5-hydrazino-2-methoxypyridine dihydrochloride was dissolved. Thus obtained hydrazine solution was added to the reaction flask and the mixture was stirred at room temperature for 1.5 hrs.

The mixture was partitioned between ethyl acetate and 0.1M hydrochloric acid, and the aqueous layer was reextracted withethyl acetate. The combinedorganic layers werewashed with saturated aqueous sodium bicarbonate solution and saturated aqueous sodium chloride solution, dried over magnesium sulfate, and concentratedin vacuo. The residue was dissolved in dichloroethane (15 ml) and tetrakis (triphenylphosphine) palladium(0) (45.8 mg) was added. The mixture was refluxed for 1 hr and then concentrated in vacuo. The residue was crystallized from ethyl acetate to give the target compound (739 mg, 49.9%) as a powder.

1H NMR (DMSO-d6): δ 3.84(3H, s), 5.10(2H, s), 5.87 (1H, s), 6.83(1H, d, J=8.7 Hz), 7.00(2H, d, J=8.7 Hz), 7.16(2H, d, J=8.7 Hz), 7.29–7.48(5H, m), 7.54(1H, dd, J=2.6, 8.7 Hz), 7.97(1H, d, J=2.6 Hz), 10.13(1H, s).
MS (ESI+): m/z (M+H).

EXAMPLE 44

5-{5-[4-(Benzyloxy)phenyl]-3-isopropoxy-1H-pyrazol-1-yl}-2-methoxypyridine

The title compound (1.33 g, quant.) was prepared as a powder from 5-[4-(benzyloxy)phenyl]-1-(6-methoxy-3-pyridinyl)-1H-pyrazol-3-ol obtained by Example 43 in a similar manner to that of Example 36.

EXAMPLE 45

4-[3-Isopropoxy-1-(6-methoxy-3-pyridinyl)-1H-pyrazol-5-yl]phenol

The title compound (442.5 mg, 54.9%) was prepared as a powder from 5-{5-[4-(benzyloxy)phenyl]-3-isopropoxy-1H-pyrazol-1-yl}-2-methoxypyridine obtained by Example 44 in a similar manner to that of Example 37.

1H NMR (CDCl$_3$): δ 1.40(6H, d, J=6.2 Hz), 3.91(3H, s), 4. 84(1H, m), 5.80(1H, s), 5.87(1H, s), 6.71(1H, d, J=8.8 Hz), 6.75(2H, d, J=8.6 Hz), 7.08(2H, d, J=8.6 Hz), 7.55(1H, dd, J=2.7, 8.8 Hz), 8.00(1H, d, J=2.7 Hz).

MS (ESI+): m/z 326 (M+H).

EXAMPLE 46

2-{4-[3-Isopropoxy-1-(6-methoxy-3-pyridinyl)-1H-pyrazol-5-yl]phenoxy}ethanol

The title compound (94.6 mg, 52.2%) was prepared as a white powder from 4-[3-isopropoxy-1-(6-methoxy-3-pyridinyl)-1H-pyrazol-5-yl]phenol obtained by Example 45 in a similar manner to that of Example 23.

MP 74–75° C.

1H NMR (CDCl$_3$): δ 1.40(6H, d, J=6.1 Hz), 1.99(1H, t, J=6. 1 Hz), 3.91(3H, s), 3.94–4.00(2H, m), 4.05–4.11(2H, m), 4. 86(1H, m), 5.88(1H, s), 6.69(1H, d, J=8.7 Hz), 6.85(2H, d, J=8.7 Hz), 7.15(2H, d, J=8.7 Hz), 7.51(1H, dd, J=2.7, 8.7 Hz), 8.03(1H, d, J=2.7 Hz).

IR (KBr): 3350, 1612, 1512, 1500cm$^{-1}$.

MS (ESI+): m/z 370 (M+H).

EXAMPLE 47 tert-Butyl 2-{4-[3-isopropoxy-1-(6-methoxy-3-pyridinyl)-1H-pyrazol-5-yl]phenoxy}ethylcarbamate The title compound (515.3 mg, 87.6%) was prepared as a powder from 4-[3-isopropoxy-1-(6-methoxy-3-pyridinyl)-1H-pyrazol-5-yl]phenol obtained by Example 45 in a similar manner to that of Example 2.

1H NMR (DMSO-d6): δ 1.32(6H, d, J=6.2 Hz), 1.37(9H, s), 3.22–3.34(2H, m), 3.84(3H, s), 3.92(2H, t, J=5.7 Hz), 4.77(1H, m), 6.06(1H, s), 6.84(1H, d, J=8.8 Hz), 6.91(2H, d, J=8.8 Hz), 7.01(1H, t, J=5.5 Hz), 7.16(2H, d, J=8.8 Hz), 7. 58(1H, dd, J=2.7, 8.8 Hz), 7.99(1H, d, J=2.7 Hz).

EXAMPLE 48

2-{4-[3-Isopropoxy-1-(6-methoxy-3-pyridinyl)-1H-pyrazol-5-yl]phenoxy}ethanamine dihydrochloride The title compound (531 mg, quant.) was prepared as an amorphous from tert-butyl 2-{4-[3-isopropoxy-1-(6-methoxy-3-pyridinyl)-1H-pyrazol-5-yl]phenoxy}ethyl-carbamate obtained by Example 47 in a similar manner to that of Example 3.

1H NMR (DMSO-d6): δ 1.32(6H, d, J=6.1 Hz), 3.15–3.24(2H, m), 3.84(3H, s), 4.19(2H, t, J=4.9 Hz), 4.77 (1H, m), 6.0 7(1H, s), 6.85(1H, d, J=8.8 Hz), 6.97(2H, d, J=8.8 Hz), 7. 21(2H, d, J=8.8 Hz), 7.60(1H, dd, J=2.7, 8.8 Hz), 7.99(1H, d, J=2.7 Hz), 8.22(2H, br-s).

MS (ESI+): m/z 369 (M+H).

EXAMPLE 49

N-(2-{4-[3-Isopropoxy-1-(6-methoxy-3-pyridinyl)-1H-pyrazol-5-yl]phenoxy}ethyl)urea The title compound (81.4 mg, 60.2%) was prepared as a white powder from 2-{4-[3-isopropoxy-1-(6-methoxy-3-pyridinyl)-1H-pyrazol-5-yl]phenoxy}ethanamine dihydrochloride obtained by Example 48 in a similar manner to that of Example 75 described later.

MP: 120° C.

1H NMR (DMSO-d6): δ 1.32(6H, d, J=6.2 Hz), 3.27–3.36(2H, m), 3.84(3H, s), 3.94(2H, t, J=5.5 Hz), 4.77 (1H, m), 5.5 2(2H, s), 6.06(1H, s), 6.15(1H, t, J=5.6 Hz), 6.84(1H, d, J=8.8 Hz), 6.93(2H, d, J=8.8 Hz), 7.17(2H, d, J=8.8 Hz), 7. 58(1H, dd, J=2.7, 8.8 Hz), 7.99(1H, d, J=2.7 Hz).

IR (KBr): 3400, 3330, 1658, 1612, 1514, 1500cm$^{-1}$.

MS (ESI+): m/z 412 (M+H).

EXAMPLE 50

N-(2-{4-[3-Isopropoxy-1-(6-methoxy-3-pyridinyl)-1H-pyrazol-5-yl]phenoxy}ethyl)methanesulfonamide The title compound (94.4 mg, 58.4%) was prepared from 2-{4-[3-isopropoxy-1-(6-methoxy-3-pyridinyl)-1H-pyrazol-5-yl]phenoxy}ethanamine dihydrochloride obtained by Example 48 in a similar manner to that of Example 4.

MP: 121.0–121.6° C.

1H NMR (DMSO-d6): δ 1.32(6H, d, J=6.1 Hz), 2.94(3H, s), 3.29–3.34(2H, m), 3.84(3H, s), 4.00–4.06(2H, m), 4.77 (1H, m), 6.06(1H, s), 6.85(1H, d, J=8.7 Hz), 6.94(2H, d, J=8. 8 Hz), 7.18(2H, d, J=8.8 Hz), 7.28(1H, br-s), 7.58(1H, dd, J=2.7, 8.7 Hz), 7.99(1H, d, J=2.7 Hz).

IR (KBr): 3242, 1612, 1514, 1502cm$^{-1}$.

MS (ESI+) m/z 447 (M+H).

EXAMPLE 51

2-{4-[1-(4-Chlorophenyl)-3-(trifluoromethyl)-1H-pyrazol-5-yl]phenyl}ethyl methanesulfonate To a solution of 2-{4-[1-(4-chlorophenyl)-3-(trifluoromethyl)-1H-pyrazol-5-yl]phenyl}ethanol (2.72 g) and triethylamine (1.55 ml) in dichloromethane (30 ml) was added dropwise methanesulfonyl chloride (0.86 ml) under ice-cooling. The reaction mixture was allowed to warm to room temperature and stirred for 1 hr.

The reaction mixture was quenched with water. The organic layer was separated and washed with 1N hydrochloric acid and water, dried over sodium sulfate, filtered and evaporated under reduced pressure to give the target compound (3.25 g, 98.5%).

1 HNMR (CDCl$_3$): δ 2.929( 3H, s), 3.072(2H, t, J=6.7 Hz), 4.427(2H, t, J=6.7 Hz), 6.739(1H, ), 7.175(2H, d, J=8.4 Hz), 7.234(2H, d, J=8.4 Hz), 7.253(2H, d, J=8.9 Hz), 7.344 (2H, d, J=8.8 Hz).

MS (ESI+): m/z 467 (M+Na).

EXAMPLE 52

2-(2-{4-[1-(4-Chlorophenyl)-3-(trifluoromethyl)-1H-pyrazol-5-yl]phenyl}ethyl)-1H-isoindole-1,3(2H)-dione A mixture of 2-{4-[1-(4-chlorophenyl)-3-(trifluoromethyl)-1H-pyrazol-5-yl]phenyl}ethyl methanesulfonate obtained by Example 51 (3.2 g) and Potassium phthalimide (1.6 g) was stirred at 80° C. for 5 hrs.

After cooling, the mixture was diluted with water and ethyl acetate. The aqueous layer was separated and extracted with ethyl acetate (twice). The combined organic layer was washed with water (twice) and brine, dried over magnesium sulfate, filtered and evaporated under reduced pressure to give the target compound (1.55 g, 43.5%) as a powder.

1H NMR (CDCl$_3$): δ 1.59(3H, s ), 3.02(2H, t, J=7.3 Hz), 3. 94(2H, t, J=7.3 Hz), 6.71(1H, s), 7.11(2H, d, J=8.2 Hz), 7. 21(2H, d, J=7.6 Hz), 7.24(2H, d, J=8.4 Hz), 7.32(2H, d, J=8.9 Hz), 7.70–7.86(4H, m).

MS (ESI+): m/z 518 (M+Na).

EXAMPLE 53

2-{4-[1-(4-Chlorophenyl)-3-(trifluoromethyl)-1H-pyrazol-5-yl]phenyl}ethanamine

A mixture of 2-(2-{4-[1-(4-chlorophenyl)-3-(trifluoromethyl)-1H-pyrazol-5-yl]phenyl}ethyl)-1H-isoindole-1,3(2H)-dione obtained by Example 52 (1.5 g) and hydrazine (2.93 ml) in acetonitrile (30 ml) was stirred at 60° C. for 5 hrs.

After cooling, the mixture was filtered and washed with acetonitrile. The filtrate was evaporated under reduced pressure to give the target compound (1.1 g, quant.) as an oil.

1H NMR (CDCl$_3$): δ 3.09(2H, dd, J=5.6 Hz, 9.3 Hz), 3.24(2H, dd, J=5.6 Hz, 8.6 Hz), 5.47(2H, s), 6.69(1H, s), 7.12(1H, d, J=8.2 Hz), 7.21(1H, d, J=8.2 Hz), 7.22(1H, d, J=8.9 Hz), 7.32(1H, d, J=8.9 Hz).

MS (ESI+): m/z 366 (M+1).

EXAMPLE 54

N-(2-{4-[1-(4-Chlorophenyl)-3-(trifluoromethyl)-1H-pyrazol-5-yl]phenyl}ethyl)methanesulfonamide To a solution of 2-{4-[1-(4-chlorophenyl)-3-(trifluoromethyl)-1H-pyrazol-5-yl]phenyl}ethanamine obtained by Example 53 (400 mg) and triethylamine (0.46 ml) in dichloromethane (20 ml) was added dropwise methanesulfonyl chloride (0.25 ml) at room temperature.

After stirring for 1 hr, the reaction mixture was quenched with 1N hydrochloric acid. The aqueous layer was separated and extracted twice with chloroform. The combined organic layer was washed with 1N hydrochloric acid, sodium hydrogencarbonate solution, water, dried over sodium sulfate, filtered and evaporated under reduced pressure. The residue was column chromatographed on silica gel (chloroform/methanol=4:1) to give the target compound (166 mg, 34.2%) as an oil.

1H NMR (CDCl$_3$): δ 2.899(3H, s), 2.904(2H, t, J=6.9 Hz), 3. 417(2H, dt, J=6.7,6.8 Hz), 4.272(1H, t, J=6.1 Hz), 6.737 (1H, s), 7.178(2H, d, J=8.4 Hz), 7.21(2H, d, J=8.4 Hz), 7. 255(2H, d, J=8.8 Hz), 7.35(2H, d, J=8.8 Hz).

IR (Film): 3346, 1657, 1597, 1552, 1496, 1471, 1236, 1163, 1136, 1092, 978, 835, 756 cm$^{-1}$.

MS (ESI−): 442 (M−1).

EXAMPLE 55

N-(2-{4-[1-(4-Chlorophenyl)-3-(trifluoromethyl)-1H-pyrazol-5-yl]phenyl}ethyl)urea To a solution of 2-{4-[1-(4-chlorophenyl)-3-(trifluoromethyl)-1H-pyrazol-5-yl]phenyl}ethanamine obtained by Example 53 (300 mg) and triethylamine (0.57 ml) in dichloromethane (10 ml) was added dropwise trimethylsilyl isocyanate (0.555 ml) at room temperature.

After stirring overnight, the reaction mixture was quenched with 1N hydrochloric acid. Aqueous layer was separated and extracted twice with chloroform. The combined organic layer was washed with 1N hydrochloric acid, sodiumhydrogencarbonate solution, water, dried over sodium sulfate, filtered and evaporated under reduced pressure. The residue was column chromatographed on silica gel (chloroform/methanol=4:1) to give the target compound (205 mg, 61.1%) as an amorphous.

1H NMR (CDCl$_3$): δ 2.83(2H, t, J=7 Hz), 3.43(2H, dt, J=6.6 Hz, 6.8 Hz), 4.41(2H, s), 4.61(1H, t, J=5.4 Hz), 6.72(1H, s), 7.16(4H, s), 7.25(2H, d, J=8.8 Hz), 7.34(2H, d, J=8.8 Hz).

IR (Film): 3346, 1657, 1597, 1552, 1496, 1471, 1448, 1375, 1271, 1236, 1163, 1136, 1092, 978, 835, 756 cm$^{-1}$.

MS (ESI+): m/z 431 (M+Na).

EXAMPLE 56

4-[1-(4-Methoxyphenyl)-3-(trifluoromethyl)-1H-pyrazol-5-yl]benzonitrile

A mixture of 4-(4,4,4-trifluoro-3-oxobutanoyl)-benzonitrile (1.0 g), 4-methoxyphenylhydrazine hydrochloride (760 mg), and sodium acetate (357 mg) in acetic acid (10 ml) was stirred at 80° C. for 4 hrs.

After cooling, the reaction mixture was poured into water and ethyl acetate. The aqueous layer was extracted twice with ethyl acetate. Combined organic layers were washed with saturated sodium hydrogencarbonate solution (twice), water and brine, dried over sodium sulfate, and evaporated under reduced pressure to give crude product. The crude product was column chromatographed on silica gel (50 ml, n-hexane:ethyl acetate=5:1–4:1) and triturate with petroleum ether to give the target compound (553 mg, 38.8%).

1H NMR (CDCl$_3$): δ 3.84(3H, s), 6.82(1H, s), 6.9(2H, d, J=9 Hz), 7.2(2H, d, J=9 Hz), 7.33(2H, d, J=8.6 Hz), 7.62 (2H, d, J=8.6 Hz).

IR (Film): 2229, 1610, 1512, 1468, 1240, 1161, 1132, 839 cm$^{-1}$.

MS (ESI+): m/z 366 (M+Na).

EXAMPLE 57

4-[1-(4-Methoxyphenyl)-3-(trifluoromethyl)-1H-pyrazol-5-yl]benzyl-amine hydrochloride A mixture of 4-[1-(4-methoxyphenyl)-3-(trifluoromethyl)-1H-pyrazol-5-yl]benzonitrile obtained by Example 56 (430 mg), Pd/C (100 mg) and 1N hydrochloric acid (1.3 ml) in methanol (43 ml) was stirred under Hydrogen atmosphere for 5 hrs.

The reaction mixture was filtered with paper filter, and filtrate was evaporated. After dissolving in methanol, the solution was filtered with membrane filter. The filtrate was evaporated to give the target compound (450 mg, 93.6%) as crystals.

1H NMR (CDCl$_3$): δ 3.79(3H, s), 4.04(2H, br-s), 6.69 (1H, s), 6.85(2H, d, J=8.9 Hz), 7.13(2H, d, J=8.9 Hz), 7.24(2H, d, J=9 Hz), 7.42(2H, d, J=9 Hz).
IR (Film): 2964, 1512, 1468, 1238, 1161, 1130, 976, 837 cm$^{-1}$.
MS (ESI+): m/z 331 (M—Cl—NH$_3$).

EXAMPLE 58

N-{4-[1-(4-Methoxyphenyl)-3-(trifluoromethyl)-1H-pyrazol-5-yl]benzyl}methanesulfonamide To a solution of 4-[1-(4-methoxyphenyl)-3-(trifluoromethyl)-1H-pyrazol-5-yl]benzylamine hydrochloride obtained by Example 57 (100 mg) and triethylamine (0.073 ml) in chloroform (10 ml) was added dropwise methanesulfonyl chloride (0.04 ml) at room temperature.

After stirring for 1 hr, the reaction mixture was partitioned between chloroform and water. The organic layer was washed with water, sodium bicarbonate solution, brine, dried over magnesium sulfate, filtered and evaporated under reduced pressure to give the target compound (90 mg, 81.2%) as an oil.

1H NMR (CDCl$_3$): δ 2.93(3H, s), 3.82(3H, s), 4.32(2H, d, J=6.2 Hz), 4.71(1H, t, J=6.2 Hz), 6.73(1H, s), 6.86(2H, d, J=9 Hz), 7.21(2H, d, J=9 Hz), 7.21(2H, d, J=8.3 Hz), 7.31 (2H, d, J=8.3 Hz).
IR (Film): 3282, 1514, 1321, 1240, 1151, 974, 837cm$^{-1}$.
MASS (ESI+): m/z 426 (M+1).

EXAMPLE 59

4-[3-(Difluoromethyl)-1-(4-methoxyphenyl)-1H-pyrazol-5-yl]benzonitrile

The title compound (4.5 g, 20.6%) was prepared from 4-(4,4-difluoro-3-oxobutanoyl)benzonitrile in a similar manner to that of Example 56.

1H NMR (CDCl$_3$): δ 3.84(3H, s), 6.77(1H, t, J=54.9 Hz), 6. 8(1H, s), 6.9(2H, d, J=9 Hz), 7.19(2H, d, J=9 Hz), 7.33(2H, d, J=8.6 Hz), 7.61(2H, d, J=8.6 Hz).
MS (ESI+): m/z 348 (M+Na).

EXAMPLE 60

1-{4-[3-(Difluoromethyl)-1-(4-methoxyphenyl)-1H-pyrazol-5-yl]phenyl}methanamine hydrochloride The title compound (510 mg, 45.4%) was prepared from 4-[3-(difluoromethyl)-1-(4-methoxyphenyl)-1H-pyrazol-5-yl]benzonitrile obtained by Example 59 in a similar manner to that of Example 57.

1H NMR (DMSO-d6): δ 3.35(3H, s), 3.79(2H, s), 7.1(1H, t, J=54.5 Hz), 6.95(1H, s), 6.99(2H, d, J=8.8 Hz), 7.26(2H, d, J=8.8 Hz), 7.3(2H, d, J=8.3 Hz), 7.49(2H, d, J=8.3 Hz).
MS (ESI−): m/z 365 (M—HCl).

EXAMPLE 61

N-{4-[3-(Difluoromethyl)-1-(4-methoxyphenyl)-1H-pyrazol-5-yl]benzyl}methanesulfonamide The title compound (146 mg, 65.5%) was prepared from 1-{4-[3-(difluoromethyl)-1-(4-methoxyphenyl)-1H-pyrazol-5-yl]phenyl}methanamine hydrochloride obtained by Example 60 in a similar manner to that of Example 58.

1H NMR (CDCl$_3$): δ 2.90(3H, s), 3.82(3H, s), 4.31(2H, d, J=6.2 Hz), 4.73(1H, t, J=6.2 Hz), 6.72(1H, s), 6.77(1H, t, J=55 Hz), 6.86(2H, d, J=9 Hz), 7.19(2H, d, J=9 Hz), 7.22(2 H, d, J=8.4 Hz), 7.30(2H, d, J=8.4 Hz).
IR (film): 3143, 1518, 1508, 1452, 1325, 1244, 1151, 1074, 1022, 972, 843, 793 cm$^{-1}$.
MS (ESI−): m/z 406 (M−1).

EXAMPLE 62

N-{4-[3-(Difluoromethyl)-1-(4-methoxyphenyl)-1H-pyrazol-5-yl]benzyl}urea

To a solution of 1-{4-[3-(difluoromethyl)-1-(4-methoxyphenyl)-1H-pyrazol-5-yl]phenyl}methanamine hydrochloride obtained by Example 60 (100 mg) in dichloromethane (1 ml) was added dropwise triethylamine (0.163 ml) and trimethylsilyl isocyanate (0.01 ml) at room temperature.

The mixture was stirred at room temperature overnight and quenched by adding saturated sodium hydrogencarbonate solution (0.5 ml). The mixture was filtered by Chemelute. The elution was evaporated and purified by preparative thin layer chromatography (0.5 mm, 10% methanol/chloroform) to give solid. The solid was added ethyl acetate and n-hexane, and the precipitate was collected by filtration to give the target compound(160 mg, 62.9%).

1HNMR (CDCl$_3$): δ 3.82(3H, s), 4.35(2H, d, J=6 Hz), 4.46(2H, br-s), 4.99(1H, t, J=6 Hz), 6.69(1H, s), 6.76(1H, t, J=55.1 Hz), 6.86(2H, d, J=9 Hz), 7.14–7.21(6H, m).
MS (ESI+) m/z 395 (M+Na).
IR (film): 1657, 1608, 1593, 1550, 15120, 1510, 1467, 1338, 1252, 1171, 1088, 1030, 837, 796 cm$^{-1}$.

EXAMPLE 63

4-[1-(4-Methylphenyl)-3-(trifluoromethyl)-1H-pyrazol-5-yl]benzonitrile

The title compound (942 mg, 86.8%) was prepared from 4-(4,4,4-trifluoro-3-oxobutanoyl)benzonitrile in a similar manner to that of Example 56.

1H NMR (CDCl$_3$): δ 2.39(3H, s), 6.82(1H, s), 7.15(2H, d, J=8.9 Hz), 7.21(2H, d, J=8.8 Hz), 7.33(2H, d, J=8.3 Hz), 7. 62(2H, d, J=8.3 Hz).
MS (ESI+): m/z 328 (M+1).

EXAMPLE 64

1-{4-[1-(4-Methylphenyl)-3-(trifluoromethyl)-1H-pyrazol-5-yl]phenyl}methanamine hydrochloride The title compound (414 mg, 92.1%) was prepared from 4-[1-(4-methylphenyl)-3-(trifluoromethyl)-1H-pyrazol-5-yl]benzonitrile obtained by Example 63 in a similar manner to that of Example 57.

1H NMR (DMSO-d6): δ 2.35(3H, d, J=4.2 Hz), 3.35(2H, s), 7.17(1H, s), 7.17–7.29(4H, m), 7.32(2H, d, J=8.1 Hz), 7.5 1(2H, d, J=8.2 Hz).
MS (ESI+): m/z 332 (M+1).

EXAMPLE 65

N-{4-[1-(4-Methylphenyl)-3-(trifluoromethyl)-1H-pyrazol-5-yl]benzyl}urea

The title compound (81 mg, 31.8%) was prepared from 1-{4-[1-(4-methylphenyl)-3-(trifluoromethyl)-1H-pyrazol -5-yl]phenyl}methanamine hydrochloride obtained by Example 64 in a similar manner to that of Example 62.

1H NMR (CDCl$_3$): δ 2.36(3H, s), 4.35(2H, d, J=5.9 Hz), 4.50(2H, br-s), 5.02(1H, t, J=5.5 Hz), 6.71(1H, s), 7.16(4H, s), 7.20(4H, d, J=5.7 Hz).

IR (film): 3344, 1658, 1600, 1552, 1518, 1236, 1159, 1134cm$^{-1}$.

MS (ESI+): m/z 397 (M+Na).

EXAMPLE 66

4-[5-(4-Methylphenyl)-3-(trifluoromethyl)-1H-pyrazol-1-yl]benzonitrile

The title compound (1.05 g, 73.8%) was prepared from 4-methyl-1-(4,4,4-trifluoro-3-oxobutanoyl)benzene in a similar manner to that of Example 69 described later.

MP: 125.0–125.5° C.

1H NMR (CDCl3): δ 2.39(3H, s), 6.74( 1H, s), 7.10(2H, d, J=8.1 Hz), 7.19(2H, d, J=8.2 Hz), 7.45(2H, d, J=8.7 Hz), 7.65 (2H, d, J=8.7 Hz).

MASS (ESI+): m/z 350 (M+Na).

EXAMPLE 67

1-{4-[5-(4-Methylphenyl)-3-(trifluoromethyl)-1H-pyrazol-1-yl]phenyl}methanamine hydrochloride The title compound (830 mg, 92.3%) was prepared from 4-[5-(4-methylphenyl)-3-(trifluoromethyl)-1H-pyrazol-1-yl]benzonitrile obtained by Example 66 in a similar manner to that of Example 70 described later.

1H NMR (DMSO-d6): δ 2.30(3H, d, J=2.3 Hz), 4.07(2H, s), 7.15(1H, s), 7.15(2H, d, J=9.0 Hz), 7.21(2H, d, J=8.9 Hz), 7.39(2H, d, J=8.5 Hz), 7.58(2H, d, J=8.5 Hz).

MS (ESI+): m/z 332 (M+1).

EXAMPLE 68

N-{4-[5-(4-Methylphenyl)-3-(trifluoromethyl)-1H-pyrazol-1-yl]benzyl}urea

The title compound (65 mg, 31.9%) was prepared from 1-{4-[5-(4-methylphenyl)-3-(trifluoromethyl)-1H-pyrazol-1-yl]phenyl }methanamine hydrochlorideobtained by Example 67 in a similar manner to that of Example 72 described later.

1H NMR (CDCl$_3$) δ 2.34(3H, s), 4.34(2H, d, J=5.8 Hz), 4.56(2H, br-s), 5.23(1H, t, J=5.8 Hz), 6.71(1H, s), 7.07(2H, d, J=8.7 Hz), 7.13(2H, d, J=8..7 Hz), 7.24(4H, s).

IR (film): 3344, 1658, 1604, 1552, 1234, 1159, 1134cm$^{-1}$.

MS (ESI+): 397 (M+Na).

EXAMPLE 69

4-[5-(4-Methoxyphenyl)-3-(trifluoromethyl)-1H-pyrazol-1-yl]benzonitrile

A mixture of 4-methoxy-1-(4,4,4-trifluoro-3-oxobutanoyl)benzene (1.0 g), 4-methoxyphenylhydrazine hydrochloride (758 mg) and sodium acetate (367 mg) in acetic acid (5 ml) was stirred overnight at room temperature.

After then, the reaction mixture was poured into water and ethyl acetate. The aqueous layer was extracted twice with ethyl acetate. Combined organic layers were washed with water, saturated sodiumhydrogencarbonate (twice) and brine, dried over sodium sulfate, and evaporated under reduced pressure to give crude product. The crude product was column chromatographed on silica gel (50 ml, n-hexane:ethyl acetate=10:1–5:1) to give the target compound (930 mg, 66.7%).

1H NMR (CDCl$_3$): δ 3.84(3H, s), 6.72(1H, s), 6.9(2H, d, J=8.9 Hz), 7.14(2H, d, J=8.9 Hz), 7.46(2H, d, J=8.7 Hz), 7.66(2H, d, J=8.7 Hz).

MS (ESI+): m/z 366 (M+Na).

EXAMPLE 70

4-[5-(4-Methoxyphenyl)-3-(trifluoromethyl)-1H-pyrazol-1-yl]benzylamine hydrochloride A mixture of 4-[5-(4-methoxyphenyl)-3-(trifluoro-methyl)-1H-pyrazol-1-yl]benzonitrile obtained by Example 69 (400 mg) and 50% wet pd/C (400 mg) in ethanol (10 ml) and 1N hydrochloric acid (1.2 ml) was stirred under hydrogen atmosphere for 8 hrs.

The mixture was filtered and filtrate was evaporated under reduced pressure. The residue was washed with isopropyl ether to give the target compound (400 mg, 89.4%) as a powder.

1H NMR (CDCl$_3$): δ 3.36(s, 3H), 3.76(d, J=2.4, 2 Hz), 6.94(d, J=8.7, 2 Hz), 7.12(s, 1H), 7.23(d, J=8.7, 2 Hz), 7.39 (d, J=8.4, 2 Hz), 7.59(d, J=8.4, 2 Hz).

MS (ESI+): m/z 348 (M+1).

EXAMPLE 71

N-{4-[5-(4-Methoxyphenyl)-3-(trifluoromethyl)-1H-pyrazol-1-yl]benzyl}methanesulfonamide To a solution of 4-[5-(4-methoxyphenyl)-3-(trifluoromethyl)-1H-pyrazol-1-yl]benzylamine hydrochloride obtained by Example 70 (150 mg) and triethylamine (0.1 ml) in dichloromethane (10 ml) was added dropwise methanesulfonyl chloride (0.06 ml) under ice cooling.

After stirring for 1 hr, the reaction mixture was quenched and partitioned between chloroform and water. The aqueous layer was extracted with chloroform. The combined organic layer was washed with water, 1N hydrochloric acid, saturated sodium hydrogencarbonate solution and brine, dried over magnesium sulfate, filtered and evaporated under reduced pressure. The residue was chromatographed by high performanced thin layer chromatography to give the target compound (67 mg, 40.3%).

1H NMR (CDCl$_3$): δ 2.91(3H, s), 3.82(s, 3H), 4.35(2H, d, J=6.1 Hz), 4.69(1H, t, J=6.1 Hz), 6.69(1H, s), 6.84(2H, d, J=8.6 Hz), 7.13(2H, d, J=8.6 Hz), 7.32(2H, d, J=9 Hz), 7.37 (2H, d, J=9 Hz).

IR (film) 3207, 1479, 1456, 1323, 1252, 1234, 1146, 1122, 984, 968, 962, 841, 802 cm$^{-1}$.

MS (ESI+): m/z 448 (M+Na).

EXAMPLE 72

N-{4-[5-(4-Methoxyphenyl)-3-(trifluoromethyl)-1H-pyrazol-1-yl]benzyl}urea

To a solution of 4-[5-(4-methoxyphenyl)-3-(trifluoromethyl)-1H-pyrazol-1-yl]benzylamine hydrochloride obtained by Example 70 (150 mg) in water (8 ml) and ethanol (4 ml) was added sodium cyanate (100 mg) under ice cooling.

After stirring for 3 hrs, the reaction mixture was partitioned between chloroform and water. The aqueous layer was extracted with chloroform. The combined organic layer was washed with water and brine, dried over magnesium sulfate, filtered and evaporated under reduced pressure. The residue was chromatographed by high performanced thin layer chromatography to give the target compound (105 mg, 69%).

1H NMR (CDCl$_3$): δ 3.80(3H, s), 4.35(2H, d, J=5.9 Hz), 4. 53(2H, br-s), 5.171(1H, t, J=5.7 Hz), 6.68(1H, s), 6.84(2 H, d, J=8.7 Hz), 7.12(2H, d, J=8.7 Hz), 7.25(4H, s).

MS (ESI+): m/z 413 (M+Na).

EXAMPLE 73 tert-Butyl 2-{4-[1-(4-methoxyphenyl)-3-(trifluoromethyl)-1H-pyrazol-5-yl]phenoxy}ethylcarbamate To solution of 4-[1-(4-methoxyphenyl)-3-trifluoro-methyl-1H-pyrazol-5-yl]phenol (500 g) in N,N-dimethyl-formamide (1.5 L) was added sodium hydride (dispersion in mineral oil, 77.8 g) over 25 min under ice cooling. The mixture was warmed to room temperature over 10 min and then stirred at room temperature for 30 min. A solution of 2-tert-butoxycabonylaminoethyl bromide (469 g)(prepared by reacting di-ter-butyl dicarbonate with 2-bromoethylamine hydrobromide) reaction in N,N-dimethylformamide (300 ml) was added to the mixture over 10 min at 25–28° C., and the whole mixture was stirred at 60° C. for 6 hrs.

After allowed to stand overnight, the mixture was poured into a mixture of water (4.5 L) and toluene (3 L). The organic layer was separated, and the aqueous layer was extracted with toluene (1.5 L). The combined organic layers were washed with water (1.5 L×3) and brine (1.5 L), dried over magnesium sulfate, filtered and evaporated to give the oil (1.02 kg). The oil was purified with silica gel column chromatography [5 L, n-hexane (10 L), 50% ethyl acetate/n-hexane (30 L)] to give the target compound (680 g, 95%) as a pale yellow oil.

MP: 104.7–105.1° C.

1HNMR (CDCl$_3$): δ 1.45(3H, s), 3.53(2H, dt, J=4 Hz), 3.82 (3H, s), 4.01(2H, t, J=4 Hz), 6.67(1H, s), 6.83(2H, d, J=8 Hz), 6.8 7(2H, d, J=8 Hz), 7.13(2H, d, J=8 Hz), 7.23(2H, d, J=8 Hz).

EXAMPLE 74

2-{4-[1-(4-Methoxyphenyl)-3-(trifluoromethyl)-1H-pyrazol-5-yl]phenoxy}ethanamine hydrochloride To a solution of hydrogen chloride in ethyl acetate (4N, 1.0L) was added powdered tert-Butyl 2-{4-[1-(4-methoxyphenyl)-3-(trifluoromethyl)-1H-pyrazol-5-yl]-phenoxy}ethylcarbamate obtained by Example 73 (500 g) at 5° C. over 20 min.

After stirring at the same temperature for 30 min and then at room temperature for 1 hr, the mixture was evaporated to give oil (543.12 g). The oil was dissolved in toluene (1.5 L). And then, n-hexane (200 ml) and the target compound (as seeds for crystallization) were added to the solution. The mixture was stirred at room temperature overnight. And the precipitate was filtered, washed with toluene (500 ml×2) and isopropylether (650 ml), and dried to give the target compound (420.5 g, 97%) as a white powder.

MP: 166.8–168.0° C.

1HNMR (DMSO-d6): δ 3.185(2H, t, J=5 Hz), 3.8(3H, s), 4. 215(2H, t, J=5 Hz), 6.96–7.05(4H, m), 7.1(1H, s), 7.22–7. 33(4H, m).

EXAMPLE 75

N-(2-{4-[1-(4-Methoxyphenyl)-3-(trifluoromethyl)-1H-pyrazol-5-yl]phenoxy}ethyl)urea 2-{4-[1-(4-Methoxyphenyl)-3-(trifluoromethyl)-1H-pyrazol-5-yl]phenoxy}ethanamine hydrochloride obtained by Example 74 (400 g) and sodium acetate (159 g) was dissolved in a mixture of N,N-dimethylformamide (1.4 L) and water (0.52 L) at 50° C. A solution of potassium cyanate (157 g) in water (520 ml) was added dropwise to the solution over 15 min at 38–40° C. The whole solution was stirred at 50° C. for 2 hrs.

The solution was filtered and washed with N,N-dimethylformamide (0.68 L) at the same temperature. The filtrate was cooled to room temperature, and then water (0.4 L) and the target compound (A04 type crystal) was added as seeds for crystallization to the filtrate, and the mixture was stirred at room temperature for 30 min. Then water (2.76 L) was added dropwise to the mixture over 30 min, and the mixture was stirred at room temperature for 30 min. The precipitate was filtered, washed with water (0.8 L×3), and dried under reduced pressure at 45° C. overnight to give the target compound (A04 type crystals, 442.01 g) as a white powder.

1HNMR (CDCl$_3$): δ 3.555(2H, dt, J=5, 6 Hz), 3.81(3H, 3), 3.995(2H, t, J=5 Hz), 4.67(2H, s), 5.37(1H, t, J=6 Hz), 6.66(1H, br-s), 6.79(2H, d, J=8 Hz), 6.845(2H, d, J=6 Hz), 7.11(2H, d, J=8 Hz), 7.19(2H, d, J=8 Hz).

1HNMR (DMSO-d6): δ 3.28–3.36 (2H, m), 3.79 (3H, s), 3.945(2H, t, J=5 Hz), 5.54(2H, br-s), 6.165(1H, t, J=5 Hz), 6.92–7.08(5H, m), 7.2(2H, d, J=8 Hz), 7.28(2H, d, J=8 Hz).

EXAMPLE 76

2-Hydroxy-N-{4-[1-(4-methoxyphenyl)-3-(trifluoromethyl) -1H-pyrazol-5-yl]benzyl}acetamide To a solution of 4-[1-(4-methoxyphenyl)-3-(trifluoromethyl)-1H-pyrazol-5-yl]benzylamine hydrochloride obtained by Example 57 (46.5 mg) in dichloromethane (1.5 ml) was added diisopropylethylamine (135 μL) and acetoxyacetylchloride (41.6 μL) at 0° C.

After stirring at room temperature for 3 hrs, the mixture was quenched with water. The whole mixture was extracted with ethyl acetate. The organic layer was washed with brine, dried over magnesium sulfate, filtered and evaporated to give oil (67 mg). The oil was dissolved in methanol (1.5 ml). Potassiumcarbonate (55 mg) was added to the solution. After stirring at room temperature for 3 hrs, the mixture was filtered and evaporated to give oil which was purified with preparative thin layer chromatography (0.5 mm×2, 10% methanol/chloroform) to give colorless oil (42.5 mg). The oil was crystallized from a mixture of ethyl acetate, diisopropylether, and n-hexane with stirring at room temperature. The precipitate was filtered and dried to give the target compound (33.9 mg, 64.8%) as a white powder.

1HNMR (CDCl$_3$): δ 2.32(1H, t, J=5.2 Hz), 3.83(3H, s), 4.2 0(2H, d, J=5.2 Hz), 4.51(2H, d, J=6.1 Hz), 6.72(1H, s), 6. 87(2H, d, J=8.9 Hz), 7.16–7.24(6H, m).

MS (ESI+): 428.2(M+Na).

EXAMPLE 77

2-Hydroxy-N-(2-{4-[1-(4-methoxyphenyl)-3-(trifluoro-methyl)-1H-pyrazol-5-yl]phenyl}ethyl)ethanesulfonamide To a solution of 2-{4-[1-(4-methoxyphenyl)-3-(trifluoromethyl)-1H-pyrazol-5-yl]phenyl}ethanamine hydrochloride and triethylamine in chloroform was added methanesulfonyl chloride at room temperature.

After stirring for 1 hr, the reaction mixture was poured into water and chloroform. The aqueous layer was separated and extracted with chloroform. The combined organic layer was washed with water and brine, dried over sodium sulfate, filtered and evaporated under reduced pressure. The residue was column chromatographed on silica gel and crystallized to give the target compound (27.7 mg, 23.5%).

1HNMR (CDCl$_3$): δ 2.78–2.91(2H, m), 3.16(2H, t, J=5.1 Hz), 3.32–3.43(2H,m), 3.82(3H, s), 3.96(2H,t,J=5.1 Hz), 4.65(1H, t,J=6.2 Hz), 6.72(1H, s), 6.87(2H, d, J=9.0 Hz), 7.12–7.27(6H, m).

MS(LC, ESI+), 470.21(MH+), 511.17(MHMeCN).

EXAMPLE 78-1 tert-Butyl 2-(4-acetylphenoxy)ethylcarbamate

To a solution of 4-hydroxyacetophenone (10 g) and 2-tert-butoxycarbonylaminoethylbromide (24.7 g) in N,N-dimethylformamide (50 ml) was added potassium iodide (12.2 g) and potassium carbonate (15.2 g).

After stirring at 50° C. overnight, the mixture was quenched with water and extracted with ethyl acetate (3 times). The combined organic layers were washed with 1N sodium hydroxide aqueous solution (2 times) and brine, dried over magnesium sulfate, and evaporated to give oil. The oil was purified with silica gel column chromatography [500 ml, 20% ethyl acetate/n-hexane (1000 ml), 30% ethyl acetate/n-hexane (1000 ml)] to give the target compound (19.89 g, 96.9%) as a white solid.

1HNMR(CDCl$_3$): δ 1.46(9H, s), 2.56(3H, s), 3.52–3.60 (2H, m), 4.09(2H, t, J=5.1 Hz), 6.93(2H, d, J=8.9 Hz), 7.93(2H, d, J=8.9 Hz).

MS (ESI+): 280.09(MH+).

EXAMPLE 78-2 tert-Butyl 2-[4-(4,4,4-trifluoro-3-oxobutanoyl)-phenoxy]ethylcarbamate

A mixture of tert-butyl 2-(4-acetylphenoxy)ethyl-carbamate obtained by Example 78-1 (15 g), trifluoroacetic acid (8.95 ml), and sodium ethoxide (8.77 g) in ethanol (45 ml) was stirred at 70° C. for 2.5 hrs.

The mixture was poured into a mixture of aqueous hydrogen chloride solution (1N) and ethyl acetate. The whole mixture was extracted with ethyl acetate (2 times). The organic layer was separated, washed with saturated sodium hydrogencarbonate and brine, dried over magnesium sulfate, and evaporated to give oil (25 g). The oil was purified with silica gel column chromatography [500 ml, 30% ethyl acetate/n-hexane (1000 ml)] to give oil. The oil was dissolved in ethyl acetate (5 ml) under heating by water bath. n-Hexane (100 ml) was added to the solution, and the solution was cooled to room temperature over 30 min under stirring. And n-hexane (100 ml) was added to the mixture.

The precipitate was filtered and dried to give the target compound (15.956 g, 79.2%) as an orange powder.

1HNMR (CDCl$_3$) δ 3.40–3.70(2H, m), 4.00–4.20(2H, m), 5.00(1H, br-s), 6.50(1H, s), 6.98(2H, d, J=8.6 Hz), 7.93(2H, d, J=8.6 Hz).

EXAMPLE 78-3 tert-Butyl 2-{4-[1-(4-methoxyphenyl)-3-(trifluoromethyl)-1H-pyrazol-5-yl]phenoxy}ethylcarbamate To a suspension of 4-methoxyaniline (100 mg) in a mixture of acetic acid (2 ml) and concentrated hydrogen chloride (0.4 ml) was added dropwise a solution of sodium nitrite (61.6 mg) in water (0.1 ml) over 5 min at 3° C., and the mixture was stirred at 3° C. for 1 hr. To the mixture was added dropwise a solution of tin chloride (641 mg) in concentrated hydrogen chloride (0.3 ml) at 0° C. over 10 min, and then the mixture was stirred at 0° C. for 1 hr. Acetic acid (5 ml) was added dropwise to the mixture at between –20 and –10° C. over 2 min, and then the mixture was quenched with a solution of sodium hydroxide (336 mg) in water (2.24 ml) at –10° C. over 2 min and warmed to room temperature to give a solution containing 4-methoxyphenylhydrazine hydrochloride.

A solution of tert-butyl 2-[4-(4,4,4-trifluoro-3-oxobutanoyl)-phenoxy]ethylcarbamate obtained by Example 78-2 (305 mg) was added to the former solution at –10° C., and then the mixture was stirred at room temperature for 3 hrs. The mixture was poured into a mixture of saturated sodium hydrogen carbonate aqueous solution (150 ml) and ethyl acetate (100 ml), and adjusted pH to basic by sodium hydrogencarbonate powder.

The organic layer was separated and the aqueous layer was extracted with ethyl acetate (50 ml×2). The combined organic layers were washed with saturated sodium hydrogen carbonate aqueous solution and brine, dried over magnesium sulfate, filtered, and evaporated to give oil (450 mg). The oil was purified with silica gel column chromatography [35 ml, 15% ethyl acetate/n-hexane (800 ml)] to give an oil. (343.2 mg, 88.5%). The oil was dissolved in isopropylether (2 ml), and then n-hexane (6 ml) was added to the solution. The whole mixture was stirred at room temperature for 1 hr. And then the precipitate was filtered, washed with n-hexane (10 ml), and dried under reduced pressure for 2 hrs to give the target compound (280.6 mg, 72.4%) as a white powder.

1HNMR (CDCl$_3$) data was identical to authentic sample.

1HNMR (CDCl$_3$): δ 1.45(3H, s), 3.53(2H, dt, J=4.4 Hz), 3.82(3H, s), 4.01(2H, t, J=4 Hz), 6.67(1H, s), 6.83(2H, d, J=8 Hz), 6.87(2H, d, J=8 Hz), 7.13(2H, d, J=8 Hz), 7.23(2H, d, J=8 Hz).

EXAMPLE 79-1

1-[4-(Benzyloxy)phenyl]hydrazine hydrochloride

To the suspension of 4-benzyloxyaniline (10 g) in concentrated hydrogen chloride (100 ml) was added dropwise a solution of sodium nitrite (3.2 g) in water (10 ml) over 10min at between –15 and –10° C., and then the mixture was stirred at 3° C. for 1 hr. To the mixture was added dropwise a solution of tin chloride (33.5 g) in concentrated hydrogen chloride (80 ml) at between –20 and –10° C. over 30 min, and then the mixture stirred at 0° C. for 1 hr.

After cooling to −20° C., the precipitate was filtered, washed with water (25 ml), ethanol (25 ml) and ether (50 ml), and dried to give the target compound (10.637 g, 100%) as a pale brown powder.

1HNMR(DMSO-d6): δ 5.05(2H, s), 6.93–7.03(4H, m), 7.46–7.28(4H, m).

EXAMPLE 79-2

2-{4-[1-(4-Benzyloxyphenyl)-3-(trifluoromethyl)-1H-pyrazol-5-yl]phenoxyl}ethanamine hydrochloride The title compound (12.9 g, 87.5%) was prepared from 1-[4-(benzyloxy)phenyl]hydrazine hydrochloride obtained by Example 79-1 and tert-butyl 2-[4-(4,4,4-trifluoro-3-oxobutanoyl)phenoxy]ethylcarbamate obtained by Example 78-2 in a similar manner to that of Example 78-3.

1HNMR (DMSO-d6): δ 3.10–3.30(2H, m), 4.19(2H, t, J=6.3 Hz), 5.14(2H, s), 6.98(2H, d, J=8.7 Hz), 7.09(1H, s), 7.09(2H, d, J=8.9 Hz), 7.49–7.22(9H, m).

EXAMPLE 80

N-(2-{4-[1-[4-(Benzyloxy)phenyl]-3-(trifluoromethyl)-1H-pyrazol-5-yl]phenoxy}ethyl)urea The title compound (10.57 g, 84.3%) was prepared from 2-{4-[1-(4-benzyloxyphenyl)-3-(trifluoromethyl)-1H-pyrazol-5-yl]phenoxyl}-ethanamine hydrochloride obtained by Example 79-2 in a similar manner to that of Example 75.

1HNMR (CDCl$_3$): δ 3.57(2H, td, J=5.7, 5.0 Hz), 4.01(2H, t, J=5.0 Hz), 4.57(1H,br-s), 5.06(2H,s), 5.20(1H, t, J=5.7 Hz), 6.66(1H, s), 6.80(2H, d, J=8.7 Hz), 6.93(2H, d, J=9.0 Hz), 7.12(2H, d, J=8.7 Hz), 7.21(2H, d, J=9.0 Hz), 7.35–7.42(5H, m).

EXAMPLE 81

N-(2-{4-[1-(4-Hydroxyphenyl)-3-(trifluoromethyl)-1H-pyrazol-5-yl]-phenoxy}ethyl)urea To a solution of N-(2-{4-[1-[4-(benzyloxy)phenyl]-3-(trifluoromethyl)-1H-pyrazol-5-yl]phenoxy}ethyl)urea obtained by Example 80 (10.33 g) in methanol (100 ml) was added palladium on carbon (10% wet, 2 g), and the mixture was stirred vigorously at room temperature under hydrogen atmosphere for 3 hrs. The whole mixture was filtered and evaporated to give oil (8.23 g). The oil was purified with silica gel column chromatography [250 ml, 3% methanol/chloroform (500 ml), 5% methanol/chloroform (500 ml), and 10% methanol/chloroform (500 ml)] to give the target compound (8.07 g, 95.4%) as an oil.

1HNMR (DMSO-d6): δ 3.28–3.33(2H, m), 3.94(2H, t, J=5.5 Hz), 5.52(2H, br-s), 6.14(1H, br-t, J=5.7 Hz), 6.80(2H, d, J=8.7 Hz), 6.93(2H, d, J=8.9 Hz), 7.05(1H, s), 7.14(2H, d, J=8.7 Hz), 7.19(2H, d, J=8.9 Hz).

MS (ESI+): 407.10(MH+).

EXAMPLE 82

4-[5-(4-{2-[(Aminocarbonyl)amino]ethoxy}phenyl)-3-(trifluoromethyl)-1H-pyrazol-1-yl]phenyl acetate To a mixture of N-(2-{4-[1-(4-hydroxyphenyl)-3-(trifluoromethyl)-1H-pyrazol-5-yl]phenoxy}ethyl)urea obtained by Example 81 (148.5 mg) in dichloromethane (1.5 ml) was added pyridine (163 μL) and acetic anhydride (45 μL), and the mixture was stirred at room temperature for 1 hr and stirred under reflux for 3 hrs.

After evaporation, the mixture was purified with preparative thin layer chromatography (1.0 mm, 10% methanol/chloroform) to give oil. The oil was crystallized from a mixture of dichloromethane and isopropylether at room temperature to give the target compound (138.6 mg, 84.6%) as a white powder.

1HNMR (CDCl$_3$): δ 2.30(3H, s), 3.59(2H, td, J=5.5, 4.9Hz), 4.04(2H, t, J=4.9 Hz), 4.51(2H, br-s), 5.22(1H, br-t, J=5.5 Hz), 6.69(1H, s), 6.84(2H, d, J=8.7 Hz), 7.10(2H, d, J=8.8 Hz), 7.14(2H, d, J=8.7 Hz), 7.31(2H, d, J=8.9 Hz).

MS(LC, ESI+): 449.24(MH$^+$), (ESI−) 492.5(M−H+HCO$_2^-$)

EXAMPLE 83-1

1-(1,3-Benzodioxol-5-yl)hydrazine hydrochloride

The title compound (1.811 g, quant.) was prepared from 3,4-(methylenedioxy)aniline in a similar manner to that of Example 79-1.

1HNMR (DMSO-d6): δ 5.94(2H, s), 6.53(1H, dd, J=2.2 8.2 Hz), 6.80(1H, s), 6.83(1H, d, J=8.2 Hz).

MS(LS, ESI+): 153.9(MH+) 193.99(MH+CH$_3$CN).

EXAMPLE 83-2 tert-Butyl 2-{4-[1-(1,3-benzodioxol-5-yl)-3-(trifluoro-methyl)-1H-pyrazol-5-yl]phenoxy}ethylcarbamate The title compound (371.3 mg, 56.7%) was prepared from tert-butyl 2-[4-(4,4,4-trifluoro-3-oxobutanoyl)-phenoxy]ethylcarbamate obtained by Example 78-2 and 1-(1,3-benzodioxol-5-yl)hydrazine hydrochloride obtained by Example 83-1 in a similar manner to that of Example 78-3.

NMR (CDCl$_3$) MA12.048: δ 1.75(9H, s), 3.45–3.60(2H, m), 4.02(2H, t, J=5.1 Hz), 6.02(2H, s), 6.66–6.88(1H, m), 7.1 6(2H, d, J=8.8 Hz).

MS(LC, ESI+): 492.22 (MH+), 533.26 (MHMeCN+).

EXAMPLE 84

2-{4-[1-(1,3-Benzodioxol-5-yl)-3-(trifluoromethyl)-1H-pyrazol-5-yl]phenoxy}ethanamine The title compound (181.2 mg, 61.5%) was prepared from tert-butyl 2-{4-[1-(1,3-benzodioxol-5-yl)-3-(trifluoromethyl)-1H-pyrazol-5-yl]phenoxy}ethylcarbamate obtained by Example 83-2 in a similar manner to that of Example 74.

1HNMR (CDCl$_3$): δ 1.75(9H, s), 3.45–3.60(2H, m), 4.02 (2H, t, J=5.1 Hz), 6.02(2H, s), 6.66–6.88(1H, m), 7.16(2H, d, J=8.8 Hz)

MS (LC, ESI+): 392.09(MH+), 433.16(MHMeCN+).

EXAMPLE 85

N-(2-{4-[1-(1,3-Benzodioxol-5-yl)-3-(trifluoromethyl)-1H-pyrazol-5-yl]phenoxy}ethyl)urea The title compound (181.2 mg, 90.1%) was prepared from 2-{4-[1-(1,3-benzodioxol-5-yl)-3-(trifluoro-methyl)-1H-pyrazol-5-yl]phenoxy}ethanamine obtained by Example 84 in a similar manner to that of Example 75.

1HNMR (CDCl$_3$): δ 3.6(2H, td, J=5.0, 5.0 Hz), 4.045(2H, t, J=5 Hz), 4.5(2H, br-s), 5.095(1H, br-t, J=5 Hz), 6.01(2H, s), 6.66(1H, s), 6.75–6.86(3H, m), 6.84(2H, d, J=8 Hz), 7.16(2H, d, J=8 Hz).

MS (LC, ESI+): 435.08(MH+).

EXAMPLE 86 tert-Butyl 2-({4-[1-(4-methoxyphenyl)-3-(trifluoromethyl)-1H-pyrazol-5-yl]benzyl}amino)-2-oxoethyl-carbamate A mixture of 4-[1-(4-methoxyphenyl)-3-(trifluoro-methyl)-1H-pyrazol-5-yl]benzylamine hydrochloride obtained by Example 57, N-tert-butoxycarbonyl-glycine, WSCD and 1-hydroxybenzotriazole hydrate in triethylamine and dichloromethane was stirred at room temperature.

After stirring for 15 hrs, the reaction mixture was poured onto water and chloroform. The aqueous layer was separated and extracted with chloroform. The combined organic layer was washed with water and brine, dried over sodium sulfate, filtered and evaporated under reduced pressure. The residue was column chromatographed on silica gel and crystallized to give the target compound (93.5 mg, 88.9%).

1HNMR (CDCl$_3$): δ 1.43(9H, s), 3.82(3H, s), 3.82–3.85 (2H, m), 4.475(2H, d, J=6 Hz), 6.71(1H, s), 6.87(2H, d, J=8 Hz), 7.14–7.26(6H, m).

MS (ESI+): 505(MH+).

EXAMPLE 87

2-Amino-N-{4-[1-(4-methoxyphenyl)-3-(trifluoromethyl)-1H-pyrazol-5-yl]benzyl}acetamide hydrochloride The title compound (62.3 mg, 82.9%) was prepared from tert-butyl 2-({4-[1-(4-methoxyphenyl)-3-(trifluoro-methyl)-1H-pyrazol-5-yl]benzyl}amino)-2-oxoethyl-carbamate obtained by Example 86 in a similar manner to that of Example 74.

1HNMR (DMSO-d6): δ 3.61(2H, s), 3.79(3H, s), 4.345 (2H, d, J=6 Hz), 7.005(2H, d, J=10 Hz), 7.15(1H, s), 7.22–7.32 (6H, m), 8.09(2H, br-s), 8.93(1H, br-t, J=6 Hz).

MS (ESI+): 405.33 (free, MH+).

EXAMPLE 88

N-{4-[1-(4-Methoxyphenyl)-3-(trifluoromethyl)-1H-pyrazol-5-yl]benzyl}acetamide

To a solution of 4- [1- (4-methoxyphenyl) -3- (trifluoromethyl)-1H-pyrazol-5-yl]benzylamine hydrochloride obtained by Example 57 and triethylamine in dichloromethane was added dropwise acetyl chloride at 0° C.

After stirring at room temperature for 1 hr, the mixture was quenched with saturated sodium hydrogen carbonate aqueous solution and extracted with ethyl acetate (3 times). The combined organic layers were washed with 1N hydrochloric acid, water, and brine, dried over magnesium sulfate, and evaporated to give oil, which was purified with silica gel column chromatography (eluted with 50% ethyl acetate/n-hexane) to give oil. The oil was crystallized from a mixture of ethyl acetate and n-hexane at 50° C. to give the target compound (52.2 mg, 69.3%) as a solid.

1HNMR (CDCl$_3$) 6 2.04(3H, s), 3.83(3H, s), 4.435(2H, d, J=6 Hz), 6.71(1H, s), 6.87(2H, d, J=8 Hz), 7.15–7.26(6H, m)

IR (KBr): 1647cm$^{-1}$.

MS (ESI+): 412.1(M+Na).

EXAMPLE 89

N-(2-{4-[1-(4-Methoxyphenyl)-3-(trifluoromethyl)-1H-pyrazol-5-yl]-phenyl}ethyl)-1-methyl-1H-imidazole-4-sulfonamide The title compound (72 mg, 70.8%) was prepared from 2-{4-[1-(4-methoxyphenyl)-3-(trifluoromethyl)-1H-pyrazol-5-yl]phenyl}ethanamine hydrochloride in a similar manner to that of Example 77.

1HNMR (CDCl$_3$): δ 2.83(2H, t, J=8 Hz), 3.26(2H, dt, J=6H z), 3.75(3H, s), 3.83(3H, s), 5.005(1H, t, J=6 Hz), 6.7(1 H, s), 6.88(2H, d, J=8 Hz), 7.13(4H, s), 7.22(2H, d, J=8H z), 7.45–7.47(2H, m).

MS (ESI+): 528.1 (MNa+).

EXAMPLE 90

N-((1R)-2-{4-[1-(4-methoxyphenyl)-3-(trifluoromethyl)-1H-pyrazol-5-yl]phenoxy}-1-methylethyl)urea To a solution of (1R)-2-{4-[1-(4-methoxyphenyl)-3-(trifluoromethyl)-1-H-pyrazol-5-yl]phenoxy}-1-methyl-ethanamine hydrochloride in dichloromethane was added triethylamine and trimethylsilyl isocyanate at 0° C.

After stirring for 5 hrs, the mixture was quenched with water and extracted with dichloromethane. The combined organic layers were washed with brine, dried over magnesium sulfate, and evaporated under reduced pressure to give oil, which was purified with preparative thin layer chromatography (1 mm, ethyl acetate) to give oil. The oil was crystallized from a mixture of isopropyl ether, ethyl acetate, and n-hexane to give the target compound as a white solid (22.8 mg, 88.1%).

1HNMR (CDCl$_3$): δ 6 1.29(3H, d, J=8 Hz), 3.82(3H, s), 3.87–3.94(2H, m), 4.07–4.19(1H, m), 4.51(2H, s), 4.87(1H, d, J=8 Hz), 6.67(1H, s), 6.8–6.89(4H, m), 7.12(2H, d, J=8 Hz), 7.215(2H, d, J=10 Hz).

MS (ESI+): 435.3 (MH+), 476.3(MH+MeCN).

EXAMPLE 91

N-(2-{4-[1-(6-Methoxy-3-pyridinyl)-3-(trifluoromethyl)-1H-pyrazol-5-yl]phenoxy}ethyl)methanesulfonamide The title compound (130 mg, 71.8%) was prepared from 2-{4-[1-(6-methoxy-3-pyridinyl)-3-(trifluoromethyl)-1H-pyrazol-5-yl]phenoxy}ethanamine dihydrochloride in a similar manner to that of Example 77.

1HNMR (CDCl$_3$): δ 3.03(3H, s), 3.555(2H, dt, J=5, 5 Hz), 3.94(3H, s), 4.115(2H, t, J=5 Hz), 4.785(1H, br-t, J=5 Hz), 6.71(1H, s), 6.76(1H, d, J=8 Hz), 6.85(2H, d, J=8 Hz), 7. 16(2H, d, J=8 Hz), 7.555(2H, dd, J=8, 2 Hz), 8.085(1H, d, J=2 Hz).

MS (ESI+): 479.1 (M+Na)+.

EXAMPLE 92

4-[5-(4-Methoxyphenyl)-3-(trifluoromethyl)-1H-pyrazol-1-yl]phenol

A mixture of 4-methoxy-1-(4,4,4-trifluoro-3-oxo-butanoyl)benzene (5.0 g) and p-hydroxyphenyl hydrazine hydrochloride (3.59 g) in acetic acid (30 ml) was stirred at room temperature.

After stirring for 15 hrs, toluene and water was added. The aqueous layer was separated and extracted twice with toluene. The combined organic layer was washed with water (twice) and brine, dried over sodium sulfate, filtered and evaporated under reduced pressure. The residue was column chromatographed on silica gel to give the target compound (4.88 g, 71.9%) as crystals.

1H NMR (CDCl$_3$): δ 3.80(3H, s), 6.68(1H, s), 6.72(2H, d, J=8.8 Hz), 6.83(2H, d, J=8.8 Hz), 7.12(2H, d, J=8.8 Hz), 7.13(2H, d, J=8.8 Hz).

MS (ESI+): m/z 357 (M+Na).

EXAMPLE 93

2-{4-[5-(4-Methoxyphenyl)-3-(trifluoromethyl)-1H-pyrazol-1-yl]phenoxy}ethanol A suspension of 4-[5-(4-methoxyphenyl)-3-(tri-fluoromethyl)-1H-pyrazol-1-yl]phenol obtained by Example 92 (500 mg), potassium carbonate (1.24 g), potassium iodide (1.49 g), and 2-chloro-1-ethanol (0.60 ml) was stirred at 80° C. for 5 hrs.

After cooling, the reaction mixture was poured into water. The mixture was extracted twice with ethyl acetate, washed with water and brine, dried over sodium sulfate, filtered and evaporated under reduced pressure. The residue was column chromatographed on silica gel to give the target compound (545 mg, 96.4%).

1H NMR (CDCl$_3$): δ 2.03(1H, t, J=5.8 Hz), 3.81(3H, s), 3. 94–4.01(2H, m), 4.09(2H, dd, J=3.5,4.6 Hz), 4.52(3H, s), 6.68(1H, s), 6.84(2H, d, J=8.9 Hz), 6.89(2H, d, J=9 Hz), 7.13(2H, d, J=8.9 Hz), 7.24(2H, d, J=9 Hz).

MASS (ESI+): m/z 401 (M+Na).

EXAMPLE 94

{4-[5-(4-Methoxyphenyl)-3-(trifluoromethyl)-1H-pyrazol-1-yl]phenoxy}acetonitrile A suspension of 4-[5-(4-methoxyphenyl)-3-(tri-fluoromethyl)-1H-pyrazol-1-yl]phenol obtained by Example 92 (2.0 g), potassium carbonate (992 mg), potassium iodide (993 mg), and chloroacetonitrile (0.57 ml) was stirred at 80° C. for 4 hrs.

After cooling, the reaction mixture was poured into water. The mixture was extracted twice with ethyl acetate, washed with water and brine, dried over sodium sulfate, filtered and evaporated under reduced pressure. The residue was column chromatographed on silica gel to give the target compound (1.75 g, 78.3%) as an oil.

1H NMR (CDCl$_3$): δ 3.81(3H, s), 4.79(2H, s), 6.69(1H, s), 6.86(2H, d, J=8.8 Hz), 6.96(2H, d, J=9 Hz), 7.14(2H, d, J =8.8 Hz), 7.31(2H, d, J=9 Hz).

MS (APCI+): m/z 374 (M+1).

EXAMPLE 95 tert-Butyl 2-{4-[5-(4-methoxyphenyl)-3-(trifluoromethyl)-1H-pyrazol-1-yl]phenoxy}ethylcarbamate The title compound (420 mg, 21%) was prepared from 4-[5-(4-methoxyphenyl)-3-(trifluoromethyl)-1H-pyrazol-1-yl]phenol obtained by Example 92 in a similar manner to that of Example 73.

1H NMR (CDCl$_3$): δ 1.46(9H, s), 3.501–3.58(2H, m), 4.02 (2H, t, J=5.1 Hz), 4.99(1H, br-s), 6.67(1H, s), 6.84(2H, d, J=8.9 Hz), 6.85(2H, d, J=9 Hz), 7.13(2H, d, J=8.9 Hz), 7. 23(2H, d, J=9 Hz).

MS (ESI+): m/z 500 (M+Na).

EXAMPLE 96

2-{4-[5-(4-Methoxyphenyl)-3-(trifluoromethyl)-1H-pyrazol-1-yl]phenoxy}ethanamine hydrochloride The title compound (0.35 g, 96.2%) was prepared from tert-butyl 2-{4-[5-(4-methoxyphenyl)-3-(trifluoro-methyl)-1H-pyrazol-1-yl]phenoxy}ethylcarbamate obtained by Example 95 in a similar manner to that of Example 74.

1H NMR (CDCl$_3$+CD$_3$OD): δ 3.2–3.5(4H, m), 3.81(3H, s), 4. 2–4.35(2H, m), 6.70(1H, s), 6.84(2H, d, J=8.6 Hz), 6.95(2 H, d, J=8.6 Hz), 7.13(2H, d, J=8.6 Hz), 7.25(2H, d, J=8.6 Hz).

MS (ESI+): m/z 378 (M-Cl).

EXAMPLE 97

N-(2-{4-[5-(4-Methoxyphenyl)-3-(trifluoromethyl)-1H-pyrazol-1-yl]phenoxy}ethyl)methanesulfonamide To a solution of 2-{4-[5-(4-methoxyphenyl)-3-(trifluoromethyl)-1-H-pyrazol-1-yl]phenoxy}ethanamine hydrochloride obtained by Example 96 (100 mg) in dichloromethane (5 ml) and triethylamine (0.1 ml) was added dropwise methanesulfonyl chloride (38 µl) at room temperature.

After stirring for 2 hrs, the reaction mixture was partitioned between chloroform and water. The aqueous layer was extracted with chloroform. The combined organic layer was washed with water and brine, dried over magnesium sulfate, filtered and evaporated under reduced pressure. The residue was purified with high performanced thin layer chromatography to give the target compound (35 mg, 31.8%) as crystals.

1H NMR (CDCl$_3$): δ 3.03(3H, s), 3.56(2H, dt, J=5,5.7 Hz), 3.81(3H, s), 4.11(2H, t, J=5 Hz), 4.82(1H, t, J=5.7 Hz), 6.68(1H, s), 6.85(2H, d, J=7.9 Hz), 6.85(2H, d, J=8.7 Hz), 7.13(2H, d, J=8.7 Hz), 7.24(2H, d, J=7.9 Hz).

MS (ESI+): m/z 478 (M+Na).

EXAMPLE 98

N-(2-{4-[5-(4-Methoxyphenyl)-3-(trifluoromethyl)-1H-pyrazol-1-yl]-phenoxy}ethyl)urea To a solution of 2-{4-[5-(4-methoxyphenyl)-3-(tri-fluoromethyl)-1H-pyrazol-1-yl]phenoxy}ethanamine hydrochloride obtained by Example 96 (200 mg) in water (10 ml) and ethanol (5 ml) was added sodium cyanate (314 mg) at room temperature.

After stirring for 15 hrs, the reaction mixture was partitioned between ethyl acetate and water. The aqueous layer was extracted with ethyl acetate. The combined organic layer was washed with water, dried over sodium sulfate, filtered and evaporated under reduced pressure. The residue was column chromatography by high performanced thin layer chromatography (chloroform:methanol=8:1) to give the target compound (0.148 g, 72.8%).

1HNMR (CDCl₃): δ 3.60(2H, dt, J=5.6, 5.0 Hz), 3.81(3H, s), 4.04(2H, t, J=5.0Hz), 4.50(2H, br-s), 5.12(1H, t, J=5.6 Hz), 6.68(1H, s), 6.84(2H, d, J=8.8 Hz), 6.85(2H, d, J=8.9 Hz), 7.13(2H, d, J=8.8 Hz), 7.22(2H, d, J=8.9 Hz).

MS (ESI+): m/z 443 (M+Na).

EXAMPLE 99

N-(2-{4-[3-(Difluoromethyl)-1-(4-methoxyphenyl)-1H-pyrazol-5-yl]phenyl}ethyl)-2-hydroxyethanesulfonamide To a solution of 2-(2-{4-[1-(4-methoxyphenyl)-3-difluoromethyl-1H-pyrazol-5-yl]phenyl}ethyl)-1H-isoindole-1,3(2H)-dione in acetonitrile was added hydrazine monohydrate.

After stirring at 60° C. overnight, the mixture was filtered. And the filtrate was evaporated to give 2-{4-[1-(4-methoxyphenyl)-3-(difluoromethyl)-1H-pyrazol-5-yl]phenyl}ethanamine as an orange oil.

To a solution of the oil and triethylamine in chloroform was added 2-hydroxyethanesulfonyl chloride at room temperature.

After stirring for 1 hr, the reaction mixture was poured onto water and chloroform. The aqueous layer was separated and extracted with chloroform. The combined organic layer was washed with water and brine, dried over sodium sulfate, filtered and evaporated under reduced pressure. The residue was column chromatographed on silica gel and crystalized to give the target compound (220 mg, 76.1%).

1H NMR (CDCl₃): δ 2.875(2H, t, J=7 Hz), 2.91–3.19(2H, m), 3.395(2H, dt, J=6 Hz), 3.83(3H, s), 3.985(2H, t, J=5 Hz), 4.44(1H, br-t, J=6 Hz), 6.7(1H, s), 6.765(1H, t, J=55 Hz), 6.875(2H, d, J=10 Hz), 7.12(6H, s).

MS (ESI+): 452.19(MH+).

Preparation 1

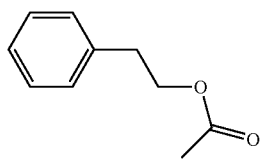

To a suspension of AlCl3 (45.9 g) was added dropwise acetyl chloride (13.4 ml) (About 5° C.), and then I (25.7 g) mentioned above under ice-cooling (5–10° C.). After stirring for 8 hours, the reaction mixture was poured onto ice-water. The organic layer was separated and washed with water (twice) and 1NHCl, sat.NaHCO3 and brine, dried over MgSO4, filtered and evaporated under reduced pressure to give crude product. The product was distilled under reduced pressure to give 105.8 g (84%) of the following compound (P0001)

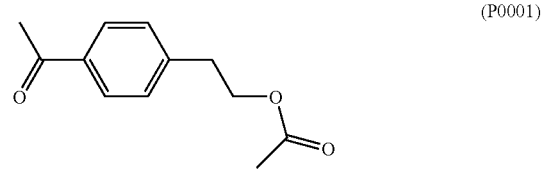

TLC Check: Ninhydrin/UV
b.p. 1>91–117° C./0.7 mmHg. E111271-1 12.6 g
2>117° C./0.7 mmHg. E111271-2 105.8 g Preparation 2

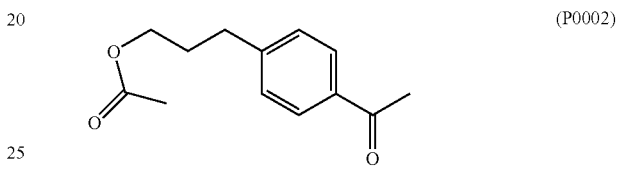

The above compound P0002 was prepared in a similar manner to that of P0001.

Mass (API-ES positive): 243 (M+Na)+

200MHz 1H NMR (CDCl3, d): 1.91–2.05(2H, m), 2.06 (3H, s), 2.59(3H, s), 2.76(2H, t, J=7.7 Hz), 4.09(2H, t, J=6.5 Hz), 7.28(2H, d, J=8.2 Hz), 7.90(2H, d, J=8.2 Hz)

Preparation 3

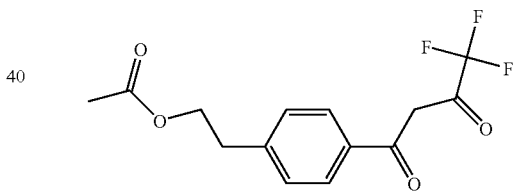

60% Sodium hydride 427 mg was added to a solution of the compound P0001 (2 g) and ethyl trifluoroacetate 2.6 ml in DMF 10 ml portionwise (in three portions) under ice bath cooling. The reaction mixture was stirred at same temperature for 45 minutes. Then ice bath was replaced to water bath. The temperature of reaction mixture was raised to 24.5° C., then slowly fall down to 22° C. over 1 hour. The mixture was stirred at r.t. for 1 hour, then poured into a mixture of 1M HCl 12 ml and ice 40 ml. The whole mixture was extracted with AcOEt 20 ml. The organic layer was washed with H2O 30 ml, saturated aqueous sodium chloride solution, dried over magnesium sulfate, concentrated in vacuo. The residue was purified by silica gel column chromatography eluted with toluene. Obtained crystals were washed with chilled n-hexane 10 ml and petroleum ether 5 ml by decantation to give a compound P0003 as white crystals. mp. 87–88° C.

Mass (API-ES negative) 301(M−H)+

200 MHz 1H NMR (DMSO-d6, d) 3.00(2H, t, J=6.7 Hz), 4.27(2H, t, J=6.7 Hz), 6.99(1H, s), 7.48(2H, d, J=8.3 Hz), 8.08(2H, d, J=8.3 Hz)

Preparation 4

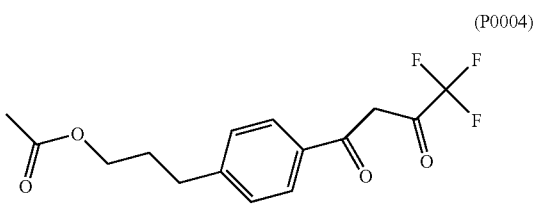
(P0004)

P0004 was prepared in a similar manner to that of P0003 as shown in Preparation 3.
Mass (API-ES negative): 315 (M–H)+
NMR JA24.112
200 MHz 1H NMR (CDCl3, d): 1.92–2.06 (2H, m), 2.06 (3H, s), 2.74–2.82 (2H, m), 4.10 (2H, t, J=6.5 Hz), 6.55 (1H, s), 7.33 (2H, d, J=8.3 Hz), 7.89 (2H, d, J=8.3 Hz)

Preparation 5

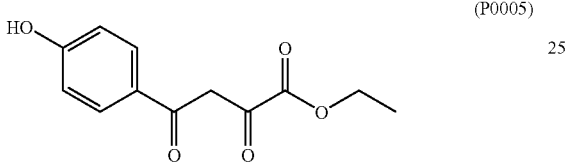
(P0005)

P0005 was prepared in a similar manner to that of P0003 as shown in Preparation 3.
yellow crystals
Mass (API-ES positive): 259 (M+Na)+
400 MHz 1H NMR (CDCl3, d): 1.41 (3H, t, J=7.1 Hz), 4.40 (2H, q, J=7.1 Hz), 6.93 (2H, d, J=8.9 Hz), 7.02 (1H, s), 7.96 (2H, d, J=8.9 Hz)

Preparation 6

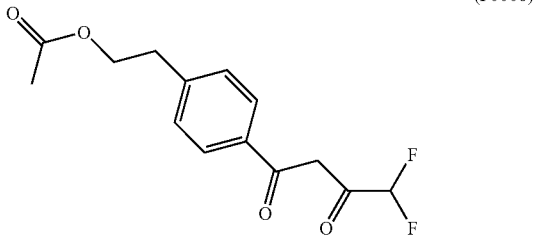
(P0006)

P0006 was obtained according to a similar manner to that of P0003. (PREPARATION 3)

Preparation 7

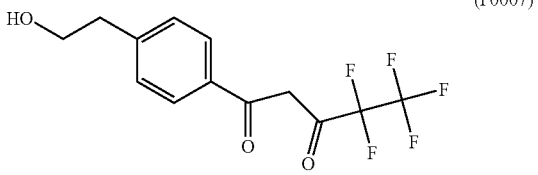
(P0007)

60% Sodium hydride 233 mg was added to a solution of P0001 1 g and ethyl pentafluoropropionate 0.93 ml in three portions under ice bath cooling. The reaction mixture was stirred at 24–27° C. with cooling in a water bath for several hours, then poured into a mixture of ice and 1M HCl 50 ml. The whole mixture was extracted with AcOEt twice. The combined organic layer was washed with saturated aqueous sodium chloride solution, dried over magnesium sulfate, and concentrated in vacuo to give P0007 1.94 g as an oil.
Mass (API-ES negative): 309 (M–H)+
200 MHz 1H NMR (CDCl3, d): 2.90–3.05 (2H, m), 3.85–4.00 (2H, m), 6.62 (1H, s), 7.39 (2H, d, J=8.3 Hz), 7.92 (2H, d, J=8.3 Hz)

Preparation 8

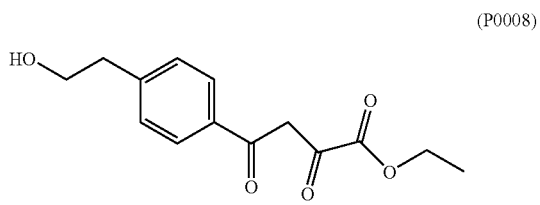
(P0008)

20% solution of sodium ethoxide in EtOH 18 ml was added dropwise to a solution of P0001 (4.00 g) and diethyl oxalate 5.95 g in DMF 12 ml at 4–6° C. After stirring at same temperature for 1 hour, the reaction mixture was poured into a mixture of ice-water 100 ml and conc.HCl 5 ml, and extracted with AcOEt. The organic layer was washed successively with 1M HCl, H2O, and saturated aqueous sodium chloride solution, dried over magnesium sulfate, treated with activated carbon, then filtered through a SiO2 (20 ml) pad. The pad was washed with AcOEt. The filtrate and combined washings were concentrated in vacuo to give P0008 (6.05 g) as an oil.
Mass (API-ES positive): 287 (M+Na)+, (API-ES negative) 263 (M–H)+
200 MHz 1H NMR (CDCl3, d): 1.42 (3H, t, J=7.1 Hz), 2.96 (2H, t, J=6.5 Hz), 3.93 (2H, t, J=6.5 Hz), 4.40 (2H, q, J=7.1 Hz), 7.06 (1H, s), 7.38 (2H, d, J=8.3 Hz), 7.96 (2H, d, J=8.3 Hz)

Preparation 9

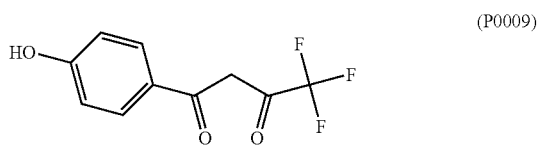
(P0009)

To a solution of 4-Hydroxybenzophenone (160 g), Ethyl trifluoroacetate (182 ml), and ethanol (11 ml) in N,N-dimethylformamide (670 ml) was added portionwise sodium hydride (suspension in mineral oil, 103 g) over 15 minutes at 0~35° C. The mixture was stirring at room temperature for 2 hours, and then at 35~40° C. for 3 hours. The mixture was poured into a mixture of ice and concentrated hydrogen chloride (320 ml) (aqueous layer total 4 L) and diisopropyl ether (2 L). The aqueous layer was separated and extracted with diisopropyl ether (500 ml×2). The combined organic layers were washed with water (500 ml×4) and brine, dried over magnesium sulfate, and evaporated to give 415 g of solid. The solid was dissolved in diisopropyl ether (200 ml)

at 65° C. The solution was added dropwise hexane (1.5 L) under stirring at room temperature. After stirring at room temperature for 1 hour, The suspension was filtered and dried under reduced pressure to give solid (first crop, 109.53 g, 40%). The mother liquid evaporated and similarly treated diisopropyl ether (20 ml) and hexane (250 ml) to give second crop (71.11 g, 26%). P0009 (first corp and second corp total, 66.2%).

NMR (CDCl3); 5.65 (1H, brs), 6.50 (1H, s), 6.94 (2H, d, J=8.8 Hz), 7.91 (2H, d, J=8.8 Hz).

MS (ESI+), 255.1 (M+Na)+.

Preparation 10

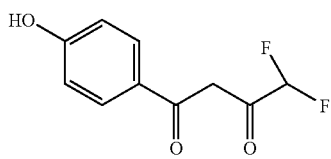
(P0010)

This compound was obtained according to a similar manner to that of P0009 (S0203744) as a powder (56.195 g, 102%).

NMR (CDCl3); 6.01 (1H, t, J=54 Hz), 6.49 (1H, s), 6.92 (2H, d, J=8.8 Hz), 7.90 (2H, d, J=8.8 Hz).

MS (ESI−), 213.3 (M−H)+

Preparation 11

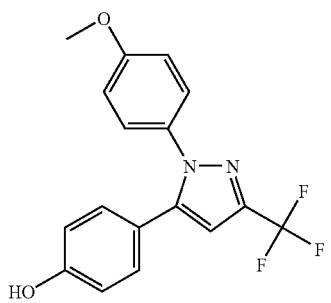
(P0011)

A mixture of P0009 (100 g), 4-Methoxyphenylhydrazine hydrochloride (82.4 g), and sodium acetate (42.6 g) in acetic acid (550 ml) was stirring at 70° C. for 3 hours. After cooling to room temperature, the mixture was poured into water (4 L) and stirred at room temperature for 1 hour. The precipitate was filtered, washed with water (250 ml×3) and Hex (500 ml×2), and dried at room temperature overnight to give powder (157.86 g). The powder was purified by recrystallization from ethyl acetate and hexane to give P0011 as a powder 121.34G (77%).

NMR (CDCl3); 3.82 (3H, s), 5.08 (1H, brs), 6.67 (1H,s), 6.77 (2H, d, J=8.6 Hz), 6.87 (2H, d, J=9.0 Hz), 7.09 (2H, d, J=8.6 Hz), 7.23 (2H, d, J=9.0 Hz).

MS (ESI+); 357.1 (M+Na)+.

Preparation 12

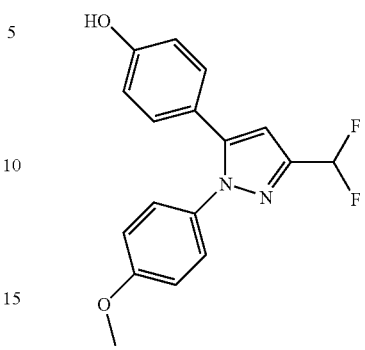
(P0012)

This compound was obtained according to a similar manner to that of P0011 as a solid (3.2028 g, 72%).

NMR (DMSO-d6); 3.88 (3H, s), 6.74 (2H, d, J=8.6 Hz), 6.82 (1H, s), 6.90 (1H, d, J=8.6 Hz), 7.10 (2H, d, J=8.6 Hz), 7.09 (1H, t, J=55 Hz), 7.68 (1H, dd, J=8.6, 2.7 Hz), 8.12 (1H, d, J=2.7 Hz).

MS (ESI+); 316.1 (M−H)+, 633.3 (2M−H).

Preparation 13

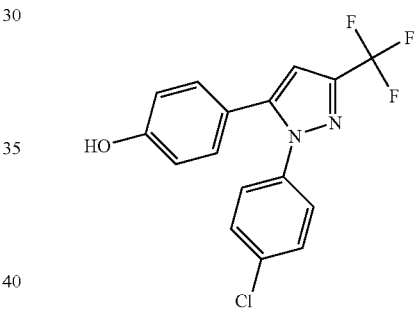
(P0013)

This compound was obtained according to a similar manner to that of P0011.

Preparation 14

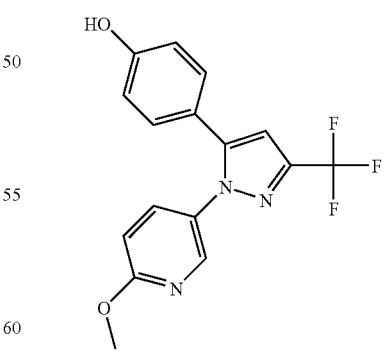

To a solution of 4-methoxyphenylhydrazine hydrochloride (3.43 g) in water (7.7 ml) was added a solution of P0009 in acetic acid (50 ml). The mixture was then allowed to stand at room temperature overnight. The mixture was poured into water (500 ml) and stirred at room temperature for 1 hour.

The precipitate was filtered, washed with water (100 ml), and dried at room temperature to give P0014 as a brown solid (3.26 g, 90%).

NMR (DMSO-d6); 3.88 (3H, s), 6.75 (2H, d, J=8.6 Hz), 6.92 (1H, d, J=8.5 Hz), 7.06–7.15 (3H, m), 7.73 (1H, dd, J=8.5, 2.8 Hz), 8.16 (1H, d, J=2.8 Hz), 9.86 (1H, s, OH).

MS (ESI-); 334.1 (M-H)+, 669.2 (2M-1)+.

Preparation 15

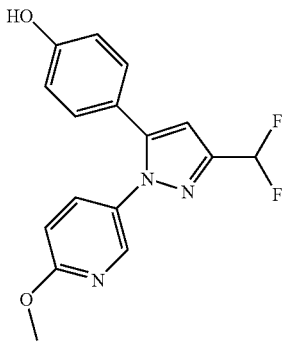

This compound was obtained according to a similar manner to that of P0014 as a pale brown powder (13.58 g, 91.7%).

NMR (DMSO-d6); 3.94 (3H, s), 6.67 (1H, s), 6.75 (1H, t, J=55 Hz), 6.73–6.80 (3H, m), 7.09 (2H, d, J=8.6 Hz), 7.57 (1H, dd, J=8.6, 2.6 Hz), 8.07 (1H, d, J=2.6 Hz).

MS (ESI-); 316.1 (M-H), 633.3 (2M-H).

Preparation 16

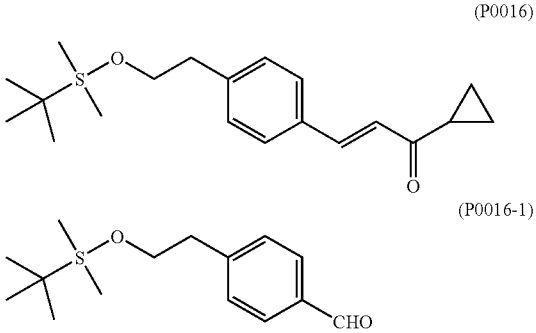

(P0016)

(P0016-1)

1M NaOH 1 ml was added to a solution of P0016-1 (reported in W09427973) 1.31 g and in EtOH5 ml and the mixture was stirred at amibient temperature overnight. The mixture partitioned between AcOEt and H2O. The organic layer was washed with H2O, saturated aqueous sodium chloride solution, dried over magnesium sulfate, and concentrated in vacuo. The residue was purified by silica gel column chromatography eluted with AcOEt/n-hexane to give P0016 (900 mg) as an oil. Mass (ESI+): 331 (M+H)+

200 MHz 1H NMR (DMSO-d6, d): −0.05 (6H, s), 0.82 (9H, s), 0.94 (4H, d, J=6.0 Hz), 2.38–2.52 (1H, m), 2.78 (2H, t, J=6.6 Hz), 3.79 (2H, t, J=6.6Hz), 7.01 (1H, d, J=16.2 Hz), 7.29 (2H, d, J=8.1 Hz), 7.65 (2H, d, J=8.1 Hz), 7.65 (1H, d, J=16.2 Hz)

Preparation 17

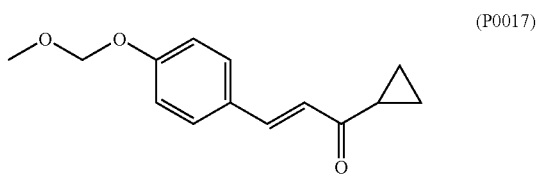

(P0017)

P0017 6.41 g was prepared in a similar manner to that of P0016.

Mass (API-ES positive): 255 (M+Na)+

200 MHz 1H NMR (CDCl3, d) 0.90–1.01 (2H, m), 1.11–1.20 (2H, m), 2.22 (1H, m), 3.49 (3H, s), 5.21 (2H, s), 6.78 (1H, d, J=16.0 Hz), 7.05 (2H, d, J=8.7 Hz), 7.52 (2H, d, J=8.7 Hz), 7.58 (1H, d, J=16.0 Hz)

Preparation 18

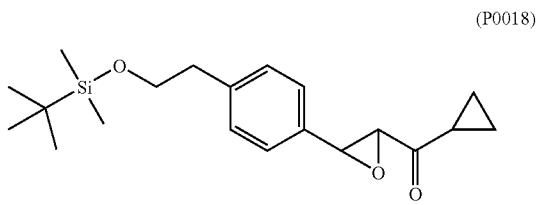

(P0018)

30% H2O2 0.64 ml and 3M NaOH 0.64 ml was added to a 0.25 M solution of P0016 1.03 g in EtOH:acetone=3:1. The mixture was stirred at ambient temperature overnight. The mixture was concentrated in vacuo, and partitioned between AcOEt and H2O. The organic layer was washed with H2O, saturated aqueous sodium chloride solution, dried over magnesium sulfate, and concentrated in vacuo to give P0018 (792 mg) as an oil.

Mass (ESI+): 347 (M+H)+

200 MHz 1H NMR (DMSO-d6, d): −0.05 (6H, s), 0.82 (9H, s), 0.92–1.04 (4H, m), 2.24 (1H, m), 2.75 (2H, t, J=6.7 Hz), 3.76 (2H, t, J=6.7 Hz), 3.86 (1H, d, J=1.9 Hz), 4.19 (1H, d, J=1.9 Hz), 7.24 (2H, d, J=8.4 Hz), 7.30 (2H, d, J=8.4 Hz)

Preparation 19

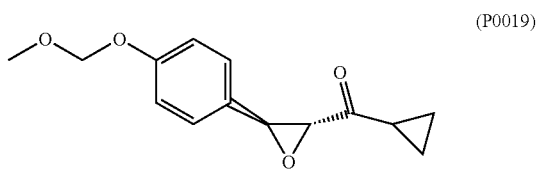

(P0019)

P0019 1.082 g was prepared from P0017 1.0 g in a similar manner to that of P0018.

Mass (API-ES positive): 271 (M+Na)+

200 MHz 1H NMR (DMSO-d6, d): 0.90–1.04 (4H, m), 2.24 (1H, m), 3.37 (3H, s), 3.88 (1H, d, J=1.9 Hz), 4.17 (1H, d, J=1.9 Hz), 5.20 (2H, s), 7.03 (2H, d, J=8.7 Hz), 7.32 (2H, d, J=8.7 Hz)

200 MHz 1H NMR (CDCl3, d): 0.90–1.07 (2H, m), 1.12–1.26 (2H, m), 2.18 (1H, m), 3.48 (3H, s), 3.58 (1H, d, J=1.9 Hz), 4.05 (1H, d, J=1.9 Hz), 5.18 (2H, s), 7.04 (2H, d, J=8.7 Hz), 7.23 (2H, d, J=8.7 Hz)

Preparation 20

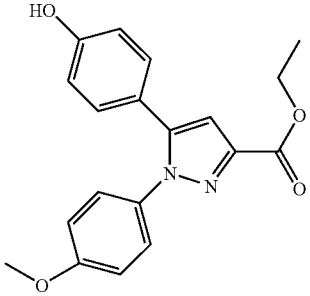
(P0020)

P0005 17.00 g was dissolved in warm EtOH 68 ml and AcOH 170 ml at 70° C. To this solution was added P0005, suspended in H2O 20 ml, in one portion. The mixture was stirred at 70° C. for 1.5 hours and then poured into a mixture of ice 500 ml and conc.HCl 10 ml. Diisopropyl ether 100 ml was added and the mixture was stirred at ambient temperature for 20 minutes. The precipitates were collected and washed successively with 1M HCl, H2O, and diisopropylether. This was air dried overnight to give P0020 21.28 g was a pale yellow powder.

Mass (ESI+): 339 (M+H)+

400 MHz 1H NMR (CDCl3, d): 1.41 (3H, t, J=7.1 Hz), 3.82 (3H, s), 4.44 (2H, q, J=7.1 Hz), 6.76 (2H, d, J=8.7 Hz), 6.85 (2H, d, J=9.0 Hz), 6.96 (1H, s), 7.08 (2H, d, J=8.7 Hz), 7.24 (2H, d, J=9.0 Hz)

Preparation 21

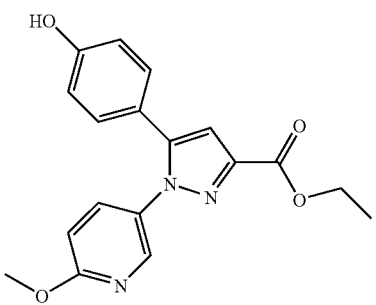
(P0021)

P0021 was prepared from P0005 in a similar manner to that of P0020. white powder Mass (ESI+): 340 (M+H)+

200 MHz 1H NMR (DMSO-d6, d): 1.31 (3H, t, J=7.1 Hz), 3.88 (3H, s), 4.32 (2H, q, J=7.1 Hz), 6.74 (2H, d, J=8.6 Hz), 6.92 (1H, d, J=8.8 Hz), 7.00 (1H, s), 7.09 (2H, d, J=8.6 Hz), 7.71 (1H, dd, J=8.8, 2.7 Hz), 8.13 (1H, d, J=2.7 Hz), 9.82 (1H, s)

Preparation 22

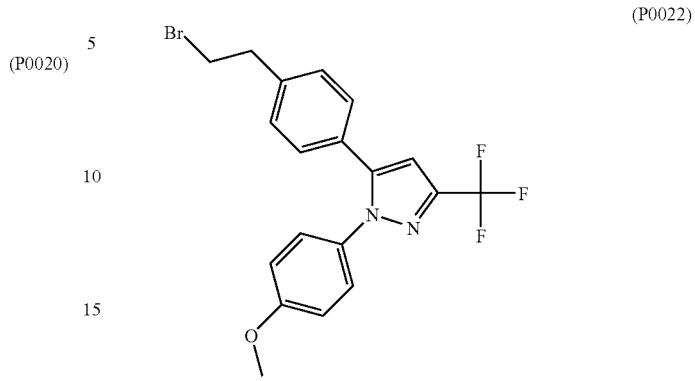
(P0022)

A solution of triphenylphosphine 831 mg in THF 5 ml was added dropwise to a solution of E0118 521.8 mg and carbon tetrabromide 1.15 g in THF 5 ml at ambient temperature. The reacion mixture was stirred at ambient temperaturer for 1 hour. Carbon tetrabromide 573 mg and triphenylphosphine 415 mg were added in one portion and stirred for further 1 hour. Unsoluble matter was filtered off and washed with THF. The filtrate and combined washings were concentrated in vacuo. The residue was purified by silica gel column chromatography eluted with AcOEt/n-hexane=5%, then 25% to give P0022 647.2 mg as pale yellow wax. mp. 60–70° C.

Mass (API-ES positive): 425,427 (M+H)+, 447,449 (M+Na)+

200 MHz 1H NMR (CDCl3, d): 3.12–3.19 (2H, m), 3.52–3.60 (2H, m), 3.82 (3H, s), 6.72 (1H, s), 6.87 (2H, d, J=9.0 Hz), 7.16–7.30 (6H, m)

Preparation 23

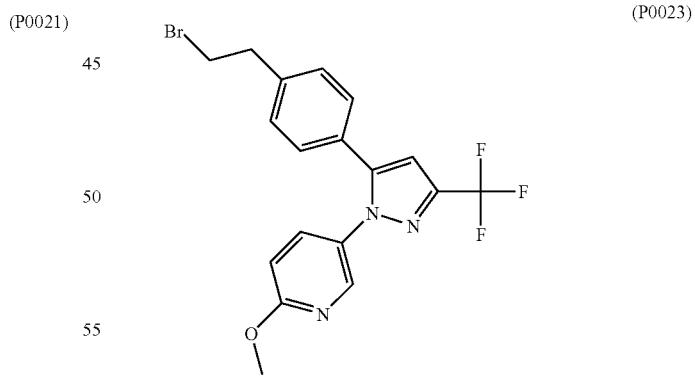
(P0023)

P0023 was prepared in a similar manner to that of P0022. colorless oil

Mass (API-ES positive): 448,450 (M+Na)+

400 MHz 1H NMR (DMSO-d6, d): 3.14 (2H, t, J=7.2 Hz), 3.74 (2H, t, J=7.2 Hz), 3.88 (3H, s), 6.92 (1H, d, J=8.8 Hz), 7.20 (1H, s), 7.27 (2H, d, J=8.4 Hz), 7.32 (2H, d, J=8.4 Hz), 7.76 (1H, dd, J=2.7, 8.8 Hz), 8.19 (1H, d, J=2.7 Hz),

Preparation 24

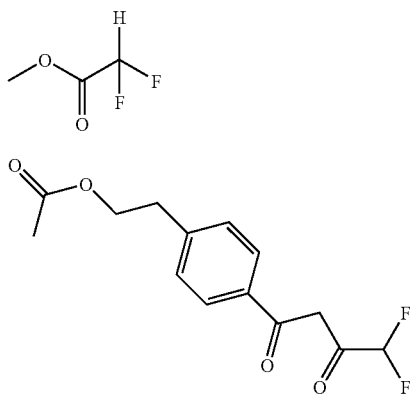

To a solution of P0001 (20.0 g) and P0024-0 (53.4 g) in DMF (200 ml) was added portionwise NaH (4.27 g) under ice-cooling. The reaction mixture was warmed at room temperature and the temperature was kept under 40° C. After stirring for 5 hours, the reaction mixture was poured onto ice-cooled dilHCl and extracted twise with ethylacetate. The combined organic layer was washed with water (twice) and brine, dried over MgSO4, filtered and evaporated under reduced pressure. The residue was column chromatographed on silica gel (500 ml, Hex:EtOAc) to give 12.12 g of P0024 as crystal.

mp: 52.6–53.6° C.

EXAMPLE 100

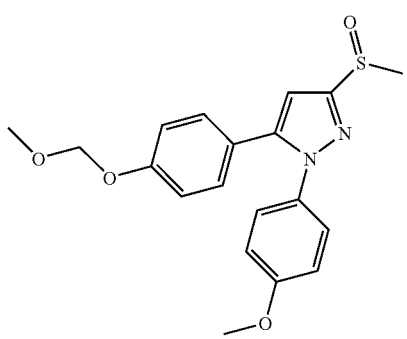

To a solution of 4-hydroxybenzophenone (4.16 g) and chloromethyl methyl ether (2.46 g) in N,N-dimethylacetoamide (15 ml) was added portionwise sodium hydride (suspension in mineral oil (60%), 1.22 g) over 15 minutes at 0° C. The mixture was stirred for 30 minutes at ambient temperature. To the reaction mixture was added 2-propanole (0.5 ml), carbon disulfide (2.56 g) and portionwise sodium hydride (suspension in mineral oil (60%), 2.50 g) over 15 minutes at 25° C. The mixture was stirred at ambient temperature for 1.5 hours, diluted with toluene (20 ml) and poured into a mixture of ice and concentrated hydrogen chloride (8 ml) (aqueous layer total 68 ml). The resultant mixture was extracted with ethyl acetate, washed with brine, dried over magnesium sulfate, and evaporated. To the mixture of the resultant residue and sodium hydrogen carbonate (13 g) in ethyl acetate (30 ml) and water (20 ml) was added portionwise the solution of iodine (3.88 g) and sodium iodide (8.0 g) in water at 0° C. To the mixture was added portionwise 4-Methoxyphenylhydrazine hydrochloride (3.80 g) at 0° C. under nitrogen. The mixture was stirred at ambient temperature for 3 hours and the organic layer was seperated, washed with water and brine, dried over magnesium sulfate, and evaporated. To the solution of the residue in ethyl acetate (30 ml) was added methyl iodide (4.0 ml) and triethylamine (10 ml) at 0° C. The mixture was stirred for 30 minutes at ambient temperature, washed with water and aqueous potassium carbonate, dried over magnesium sulfate, and evaporated. The residue was column chromatographed on silica gel (80 g), eluting with a mixture of ethyl acetate and toluene (1:20) to give 7.56 g of 5-[4-(methoxymethoxy)-phenyl]-1-(4-methoxyphenyl)-3-(methylthio)-1H-pyrazole.

To the solution of methyl sulfide (7.56 g) in dichloromethane (30 ml) was added a solution of m-chloroperbenzoic acid (80%, 4.4 g) in dichloromethane (15 ml) at 0° C., and the mixture was stirred at 0° C. for 1 hour. The mixture was washed with aqueous potassium carbonate, dried over magnesium sulfate, and evaporated. The residue was column chromatographed on silica gel (80 g), eluting with ethyl acetate to give 5.43 g of 5-[4-(methoxymethoxy)phenyl]-1-(4-methoxyphenyl)-3-(methylsulfinyl)-1H-pyrazole (E0100).

mp. 136.9–137.3° C.

Mass; 373 (M+1)

IR(KBr); 1054 cm−1

NMR (CDCl3, δ); 3.00 (H, s), 3.48 (H, s), 3.83 (H, s), 5.17 (H, s), 6.88 (H, d, J=9.0 Hz), 6.92 (H, s), 6.97 (H, d, J=8.8 Hz), 7.14 (H, d, J=8.8 Hz), 7.22 (H, d, J=9.0 Hz),

EXAMPLE 101

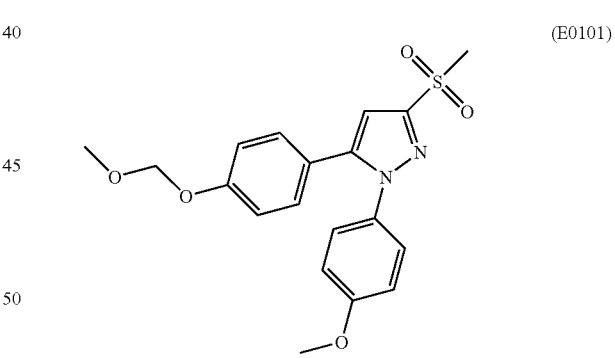

To the solution of 5-[4-(methoxymethoxy)phenyl]-1-(4-methoxyphenyl)-3-(methylsulfinyl)-1H-pyrazole (7.56 g) in dichloromethane (20 ml) was added m-chloroperbenzoic acid (60%, 3.76 g) at 0° C., and the mixture was stirred at 0° C. for 3 hour. The mixture was washed with aqueous sodium hydrogen carbonate, dried over magnesium sulfate, and evaporated. The residue was purified by recrystallization with toluene to give 5.07 g of 5-[4-(methoxymethoxy) phenyl]-1-(4-methoxyphenyl)-3-(methylsulfonyl)-1H-pyrazole(E0101).

mp. 128.0–128.1° C.

Mass; 389 (M+1)

IR (KBr); 1300cm−1

NMR (CDCl3, δ); 3.29 (3H, s), 3.48 (3H, s), 3.83 (3H, s), 5.17 (2H, s), 6.88 (2H, d, J=9.0 Hz), 6.93 (1H, s), 6.98 (2H, d, J=8.8 Hz), 7.13 (2H, d, J=8.8 Hz), 7.24 (2H, d, J=9.0 Hz),

Preparation 25

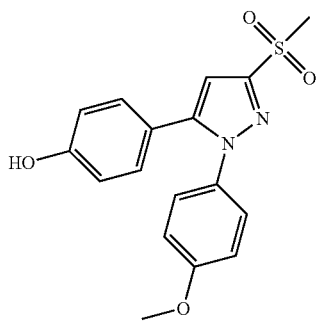
(P0024)

To the solution of 5-[4-(methoxymethoxy)phenyl]-1-(4-methoxyphenyl)-3-(methylsulfonyl)-1H-pyrazole (0.93 g) in a mixture of tetrahydrofuran (10 ml) and isopropyl alcohol (5 ml) was added hydrogen chloride aqueous solution (20%, 8 ml) at ambient temperature. The solution was stirred for 3 hours, extracted with ethyl acetate, washed with brine, dried over magnesium sulfate, and evaporated to give 0.82 g of 4-[1-(4-methoxyphenyl)-3-(methylsulfonyl)-1H-pyrazol-5-yl]phenol (P0025).

Mass; 345 (M+1)

NMR (DMSO-d6, δ); 3.32 (3H, s), 3.79 (3H, s), 6.73 (2H, d, J=8.6 Hz), 7.01 (2H, d, J=8.9 Hz), 7.05 (1H, s), 7.08 (2H, d, J=8.6 Hz), 7.27 (2H, d, J=8.9 Hz), 9.84 (1H, s),

Preparation 26

(P0026-0)

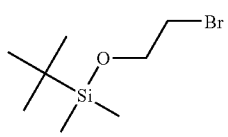
(P0026)

To a solution of P0026-0 (5.0 g) and imidazole (3.3 g) in DMF (40 ml) was added portionwise TBDMSCl (6.69 g) at room temperature. After stirring overnight, water and hexane was added. The aqueous layer was separated and extracted twice with hexane. The combined organic layer was washed with water (twice) and brine, dried over MgSO4, filtered and evaporated under reduced pressure to give 9.49 g (98.3%) of P0026.

IR (film): 2952.5, 2935.1, 1467.6, 1255.4, 1124.3, 1097.3, 838.9, 777.2 cm−1.

Preparation 27

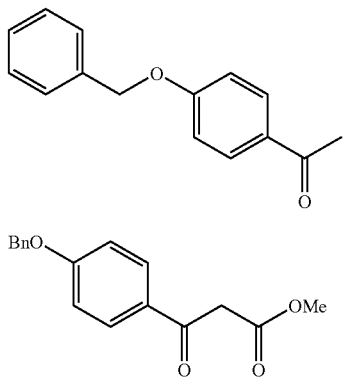
(P0027-0)

(P0027)

To a solution of P0027-0 (10 g) and dimethylcarbonate 5.97 g in DMF was added sodium methoxide 4.77 g. The mixture was stirred at ambient temperature for 2 hours. The mixture was poured into water with 8 ml of conc. HCl, and extracted with AcOEt. The organic layer was dried over magnesium sulfate, and concentrated in vacuo. The residue was purified by silica gel column chromatography to give orange solid. Which was recrystallized from MeOH to give P0027 as white crystals.

NMR (200 MHz, CDCl3) 3.75 (3H, s), 3.96 (2H, s), 5.14 (2H, s), 7.02 (2H, d, J=8.9 Hz), 7.34–7.45 (5H, m), 7.93 (2H, d, J=8.9 Hz)

Mass ESI 285 (M+H)+ (file platform 7366-1)

Preparation 28

(P0028)

To a solution of triphenylphosphin oxide 294 mg in 1,2-dichloroethane 3 ml was added trifluoromethanesulfonic anhydride 198 mg dropwise under cooling in an ice bath. The mixture was stirred at same temperature for 15 minutes, when white precipitates were came out. To this mixture was added P0027 (300 mg) in 1,2-dichloroethane 2 ml dropwise, followed by addition of Et3N 214 mg. The mixture was refluxed for 2 hours. The mixture was allowed to cool to ambient temperature and was washed with H2O, sat.aq NaCl, dried over MgSO4, concentrated in vacuo. The residue was purified by silica gel column chromatography eluted with AcOEt/n-hexane=5%, and 10%. The residue was crystallized from IPE to give P0028 (166 mg) as a white powder.

Mass (ESI+): 289 (M+Na)+

200 MHz 1H NMR (DMSO-d6, d): 3.76 (3H, s), 5.18 (2H, s), 7.11 (2H, d, J=8.8 Hz), 7.33–7.48 (5H, m), 7.62 (2H, d, J=8.8 Hz)

Preparation 29

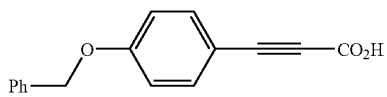
(P0029)

Solid KOH 124 mg was dissolved in EtOH 5 ml at 50° C. To this solution was added P0028 (196 mg). After stirring at same temperature for 2 hours, the reaction mixture was allowed to cool to ambient temperature. The mixture was partitioned between 1M HCl and CHCl3. The aqueous layer was reextracted with CHCl3. The combined organic layers were dried over MgSO4, evaporated in vacuo. The residual crystals were collected and washed with IPE to give 1st crop of P0029 (87 mg) as a white powder. The mother liqour was concentrated in vacuo and the residual crystals were collected and washed with n-hexane to give 2nd crop of P0029 (39 mg) as a slightly reddish powder.

Mass (ESI-): 251 (M-H)+
200 MHz 1H NMR (CDCl3, d): 5.10 (3H, s), 6.97 (2H, d, J=8.9 Hz), 7.34–7.43 (5H, m), 7.56 (2H, d, J=8.9 Hz)

Preparation 30

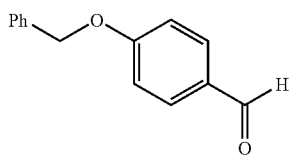
(P0030-0)

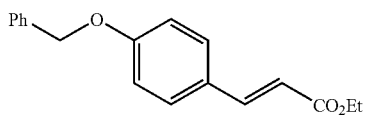
(P0030)

To a solution of P0030-0 (2 g) and triethylphosphonoacetate 2.32 g in DMF 20 ml was added 60% NaH 490 mg in two portions with cooling on ice bath. The mixture was stirred at same temperature for 1 hour, and then poured into ice water containing NH4Cl. The mixture was stirred for a while, and white precipitates were collected and washed with water and 10% aqueous IPA to give P0030.

200 MHz 1H NMR (CDCl3, d): 1.33 (3H, t, J=7.2 Hz), 4.25 (2H, q, J=7.2 Hz), 5.10 (2H, s), 6.31 (1H, d, J=16.0 Hz), 6.97 (2H, d, J=8.7 Hz), 7.32–7.50 (7H, m), 7.64 (1H, d, J=16.0 Hz)

Preparation 31

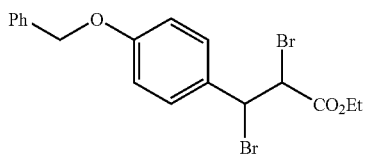
(P0031)

To a solution of P0030 (2.79 g) in CH2Cl2 28 ml was added bromine 1.66 g dropwise under ice bath cooling. The mixture was stirred at same temperature for 30 minutes. The reaction mixture was poured into 5% aqueous solution of Na2S2O3, and partitioned. The organic layer was washed with sat.aq NaHCO3, sat.aqNaCl, dried over MgSO4, concentrated in vacuo. The residual crystals were collected and washed with n-hexane to give P0031 (3.07 g) as a pale yellow powder.

200 MHz 1H NMR (CDCl3, d): 1.38 (3H, t, J=7.2 Hz), 4.35 (2H, q, J=7.2 Hz), 4.81 (1H, d, J=11.8 Hz), 5.07 (2H, s), 5.35 (1H, d, J=11.8 Hz), 6.98 (2H, d, J=8.7 Hz), 7.34 (2H, d, J=8.7 Hz), 7.32–7.45 (5H, m)

Preparation 32

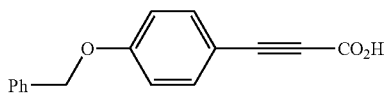
(P0032)

85% solid KOH 1.73 g was dissolved in 95% aqueous EtOH 20 ml at 50° C. P0031 (3.05 g) was added in one portion and the mixture was refluxed for 9 hours. To this mixture was added a solution of 85% KOH 0.32 g dissolved in 95% aqueous EtOH 10 ml and refluxed for 5 hours. The mixture was cooled in an ice bath, precipitates were collected and washed with EtOH. The crystals were suspended in AcOEt and H2O, cooled in an ice bath, acidified by 3M HCl and 1M HCl. The mixture was partitioned and the organic layer was washed with H2O, dried over MgSO4, concentrated in vacuo. The residual solid was collected and washed with IPE-n-hexane to give P0032 (0.67 g) as a white powder.

200 MHz 1H NMR (CDCl3, d): 5.10 (3H, s), 6.97 (2H, d, J=8.9 Hz), 7.34–7.43 (5H, m), 7.56 (2H, d, J=8.9 Hz)

EXAMPLE 102

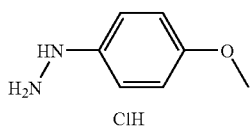
(E0102-0)

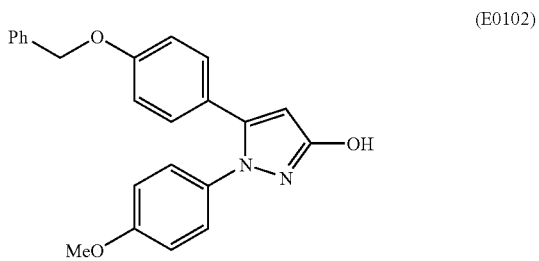
(E0102)

To a solution of P0032 (99.9 mg) and HOBT 64.2 mg in N-methylpyrrolidone 1 ml was added WSCD.HCl 91.1 mg and the mixture was stirred at ambient temperature for 20 minutes. In another flask, diisopropylethylamine 76.8 mg was added to a suspension of E0102-0 (83.0 mg) in N-methylpyrrolidone 1 ml and stirred at ambient temperature until all E0102-0 was dissolved. The solution of E0102-0 was added to the reaction flask and the mixture was stirred at ambient temperature for 1 hour. The mixture was partitioned between AcOEt and H2O, washed with sat.aqNaHCO3, sat.aqNaCl, dried over MgSO4, and concentrated in vacuo. The residue was dissolved in CH2Cl2 3 ml, and stirred at ambient temperature for 24 hours. The mixture was concentrated in vacuo. The residual crystals were suspended in hot AcOEt, cooled with stirring, collected and washed with AcOEt to give E0102 (90.9 mg) as a white powder.

Mass (ESI+): 373 (M+H)+

200 MHz1H NMR (DMSO-d6, d): 3.75 (3H, s), 5.08 (2H, s), 5.81 (1H, s), 6.90 (2H, d, J=9.0 Hz), 6.96 (2H, d, J=9.0 Hz), 7.10 (2H, d, J=9.0 Hz), 7.12 (2H, d, J=9.0 Hz), 7.32–7.47 (5H, m), 10.00 (1H, s)

EXAMPLE 103

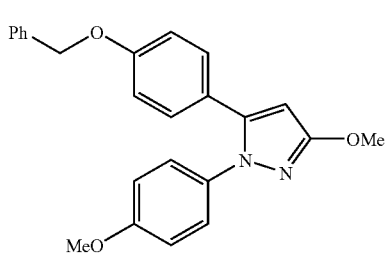
(E0103)

To a suspension of E0102 (20.9 mg) and K2CO3 23.3 mg in DMSO 0.5 ml was added dimethylsulfate 10.6 mg and the mixture was stirred at ambient temperature for 1 hour. The mixture was partitioned between AcOEt and H2O, and the organic layer was washed with sat.aqNaCl, dried over MgSO4, concentrated in vacuo. The residue was purified by preparative thin layer chromatography developed with AcOEt/n-hexane=25%. The obtained crystals were crystallized from IPE to give E0103 (12.0 mg) as white crystals.

Mass (ESI+): 387 (M+H)+

200 MHz1H NMR (DMSO-d6, d): 3.76 (3H, s), 3.83 (3H, s), 5.08 (2H, s), 6.04 (1H, s), 6.92 (2H, d, J=9.0 Hz), 6.97 (2H, d, J=9.0 Hz), 7.11–7.17 (4H, m), 7.30–7.50 (5H, m)

200 MHz1HNMR (CDCl3, d):3.80 (3H, s), 3.97 (3H, s), 5.04 (2H, s), 5.88 (1H, s), 6.82 (2H, d, J=9.0 Hz), 6.88 (2H, d, J=8.9 Hz), 7.11–7.21 (4H, m), 7.34–7.43 (5H, m)

EXAMPLE 104

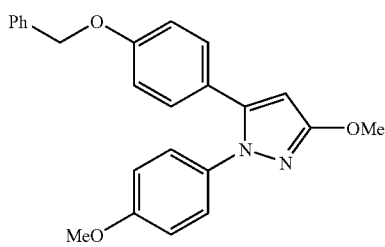
(E0104)

To suspension of E0102 (818 mg) and K2C03 911 mg in DMF 6 ml was added dimethylcarbonate 0.56 ml. The mixture was stirred at 120° C. for 2 hours. Additional dimethylcarbonate 1 ml was added and stirred at 120° C. for 8 hours. The mixture was partitioned between AcOEt and H2O, and the aq layer was reextracted with AcOEt. The combined organic layers were washed with sat.aqNaCl, dried over MgSO4, concentrated in vacuo. The residue was purified by silica gel column chromatography eluted with AcOEt/n-hexane=30%. The residue was crystallized from AcOEt 2.5 ml and n-hexane 5 ml to give E0104 (583 mg) as white crystals.

200 MHz1H NMR (DMSO-d6, d): 3.76 (3H, s), 3.83 (3H, s), 5.08 (2H, s), 6.04 (1H, s), 6.92 (2H, d, J=9.0 Hz), 6.97 (2H, d, J=9.0 Hz), 7.11–7.17 (4H, m), 7.30–7.50 (5H, m)

200 MHz1H NMR (CDCl3, d):3.80 (3H, s), 3.97 (3H, s), 5.04 (2H, s), 5.88 (1H, s), 6.82 (2H, d, J=9.0 Hz), 6.88 (2H, d, J=8.9 Hz), 7.11–7.21 (4H, m), 7.34–7.43 (5H, m)

Preparation 33

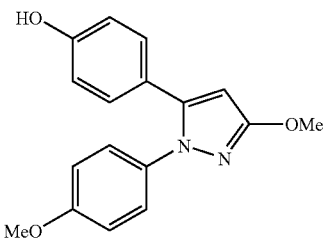
(P0033)

A mixture of 10% Pd-C 50% wet 50 mg and E0104 (261 mg) in AcOEt 2 ml and MeOH 2 ml was hydrogenated under H2 1 atm at ambient temperature for 1 day. The additional 10% Pd-C 50% wet 50 mg was added and the mixture was hydrogenated under H2 3.5 atm at ambient temperature for 3 hours. The catalyst was filtered off and the filtrate and combined washings were concentrated in vacuo. The residue was dissolved in AcOEt, dried over MgSO4, and concentrated in vacuo. The residue was crystallized from AcOEt-n-hexane to give P0033 (146 mg) as a white powder.

Mass (ESI+): 297 (M+H)+

200 MHz 1H NMR (DMSO-d6, d): 3.75 (3H, s), 3.83 (3H, s), 5.98 (1H, s), 6.70 (2H, d, J=8.6 Hz), 6.91 (2H, d, J=8.9 Hz), 7.01 (2H, d, J=8.6 Hz), 7.12 (2H, d, J=8.9 Hz), 9.69 (1H, s)

Preparation 34

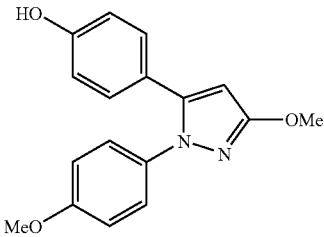
(P0034)

To a solution of ammmonium formate 455 mg in H2O 1 ml was added EtOH 6 ml, E0104 (558 mg), THF 1 ml, and 10% Pd-C 50% wet 60 mg successively. The mixture was refluxed for 1 hour. The catalyst was removed by filtration. The filtrate and combined washings were concentrated in vacuo. The residue was partitioned between AcOEt and H2O, and the organic layer was washed with sat.aqNaCl, dried over MgSO4, concentrated in vacuo. The residual crystals were recrystallized from AcOEt 3 ml and n-hexane 3 ml to give P0034 (335 mg) as white crystals.

Mass (ESI+): 297 (M+H)+

EXAMPLE 105

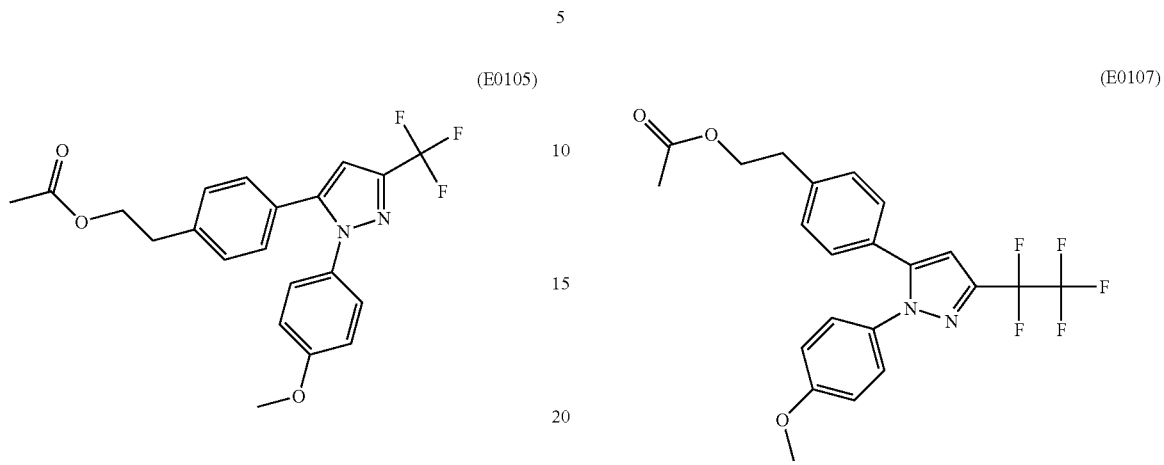
(E0105)

A mixture of P0003 (2.9 g) and 4-methoxyphenylhydrazine (1.68 g) in acetic acid (30 ml) was stirred at room temperature for 15 hours. After addition of water, the mixture was extracted twice with toluene. The combined organic layer was washed with water (twice), sat.NaHCO3, water and brine, dried over MgSO4, filtered and evaporated under reduced pressure. The residue was column chromatographed on silica gel (Hex/EtOAc=8:1–4:1) to give 2.2 g (57%) of E0105 as an oil.

IR (film): 1737.6, 1511.9, 1240.0, 1159.0, 1130.1 cm−1.

EXAMPLE 106

(E0106)

E0106 was prepared from P0004 in a similar manner to that of E0105.

Mass (ESI+): 420 (M+H)+

200 MHz 1H NMR (DMSO-d6, d): 1.79–1.94 (2H, m), 1.98 (3H, s), 2.60–2.68 (2H, m), 3.88 (3H, s), 3.98 (2H, t, J=6.5 Hz), 6.92 (1H, d, J=8.9 Hz), 7.18 (1H, s), 7.24 (4H, s), 7.75 (1H, dd, J=2.7, 8.9 Hz), 8.48 (1H, d, J=2.7 Hz)

EXAMPLE 107

(E0107)

E0107 (175.7 mg) was prepared from P0007 (590 mg) and 4-methoxyphenylhydrazine hydrochloride (332 mg) in a similar manner to that of E0105.

Mass (ESI+): 455 (M+H)+

200 MHz 1H NMR (DMSO-d6, d): 1.96 (3H, s), 2.88 (2H, t, J=6.8 Hz), 3.79 (3H, s), 4.20 (2H, t, J=6.8 Hz), 6.99 (2H, d, J=8.9 Hz), 7.15 (1H, s), 7.17–7.30 (6H, m)

EXAMPLE 108

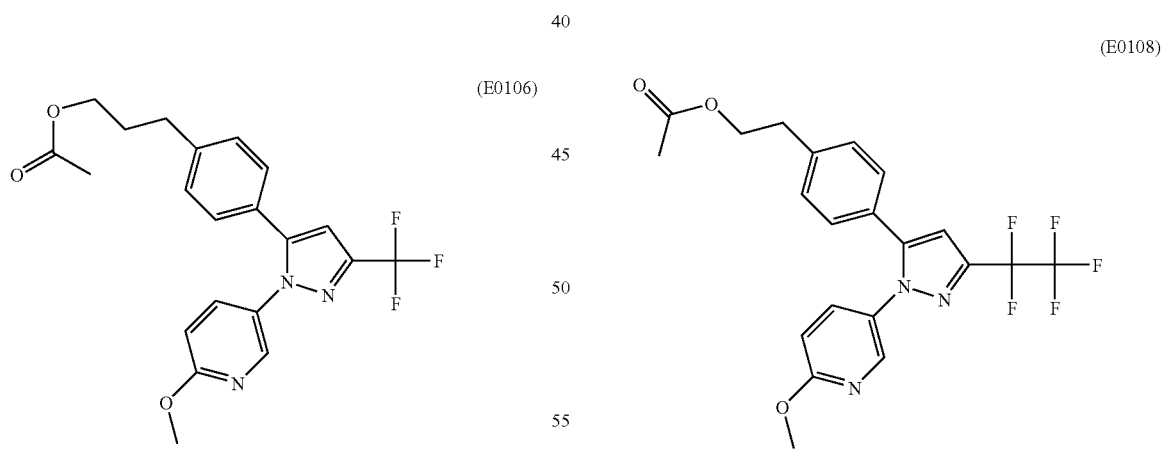
(E0108)

E0108 was prepared from P0007 in a similar manner to that of E0105.

Mass (API-ES positive): 456 (M+H)+, 478 (M+Na)+

200 MHz 1H NMR (DMSO-d6, d): 1.96 (3H, s), 2.89 (2H, t, J=6.8 Hz), 3.88 (3H, s), 4.21 (2H, t, J=6.8 Hz), 6.92 (1H, d, J=8.8 Hz), 7.15–7.35 (4H, m), 7.21 (1H, s), 7.76 (1H, dd, J=2.7, 8.8 Hz), 8.17 (1H, d, J=2.7 Hz)

EXAMPLE 109

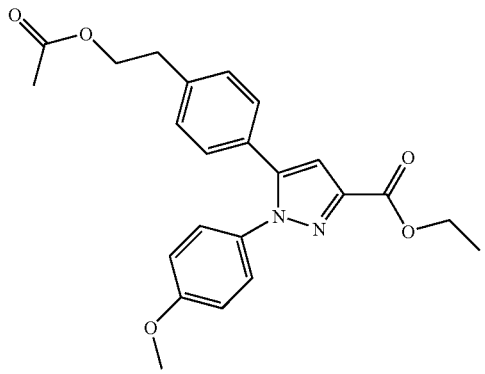
(E0109)

E0109 was prepared in a similar manner to that of E0105.
Mass (ESI+) 409 (M+H)+, 431 (M+Na)+
NMR: SE20.059 200 MHz 1H NMR (DMSO-d6, d): 1.31 (3H, t, J=7.1 Hz), 1.96 (3H, s), 2.87 (2H, t, J=6.8 Hz), 3.79 (3H, s), 4.20 (2H, t, J=6.8 Hz), 4.32 (2H, q, J=7.1 Hz), 6.99 (2H, d, J=9.0 Hz), 7.08 (1H, s), 7.16–7.28 (6H, m)

EXAMPLE 110

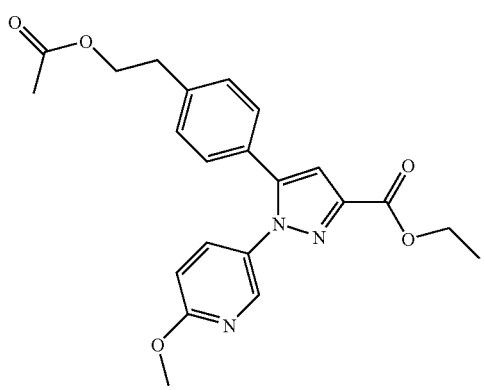
(E0110)

E0110 was prepared in a similar manner to that of E0105.
Mass (ESI+): 410 (M+H)+
200 MHz1H MNR (DMSO-d6, d): 1.32 (3H, t, J=7.1 Hz), 1.96 (3H, s), 2.89 (2H, t, J=6.8 Hz), 3.88 (3H, s), 4.21 (2H, t, J=6.8 Hz), 4.33 (2H, q, J=7.1 Hz), 6.92 (1H, d, J=8.8 Hz), 7.12 (1H, s), 7.19–7.32 (4H, m), 7.73 (1H, dd, J=2.7, 8.8 Hz), 8.14 (1H, d, J=2.7 Hz)

EXAMPLE 111

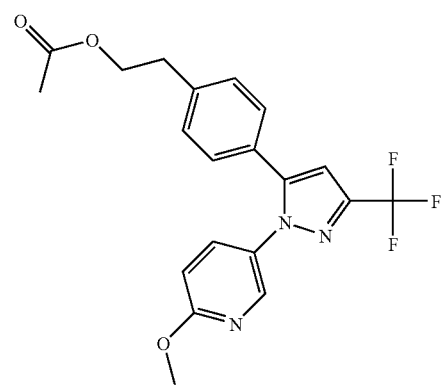
(E0111)

E0111 was prepared in a similar manner to that of E0105.
Mass (API-ES positive): 406 (M+H)+, 428 (M+Na)+
200 MHz 1H NMR (DMSO-d6, d) 1.96 (3H, s), 2.89 (2H, t, J=6.7 Hz), 3.88 (3H, s), 4.21 (2H, t, J=6.7 Hz), 6.92 (1H, d, J=8.8 Hz), 7.20 (1H, s), 7.24 (2H, d, J=8.7 Hz), 7.30 (2H, d, J=8.7 Hz), 7.76 (1H, dd, J=2.7, 8.8 Hz), 8.18 (1H, d, J=2.7 Hz)

EXAMPLE 112

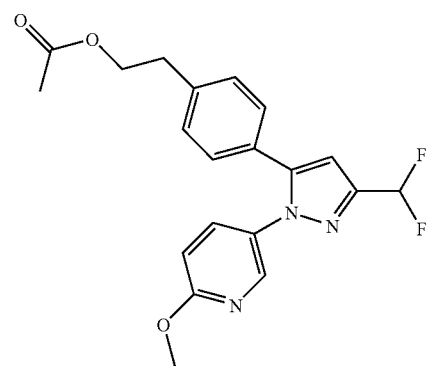
(E0112)

E0112 was obtained according to a similar manner to that of E0105.

EXAMPLE 113

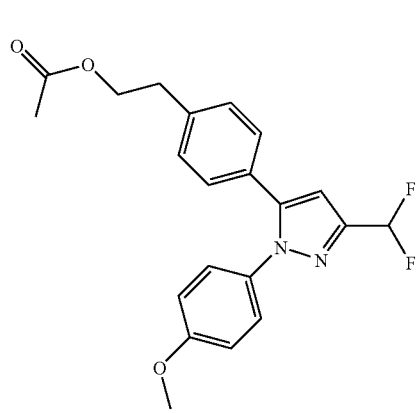

E0113 was obtained according to a similar manner to that of E0105.

EXAMPLE 114

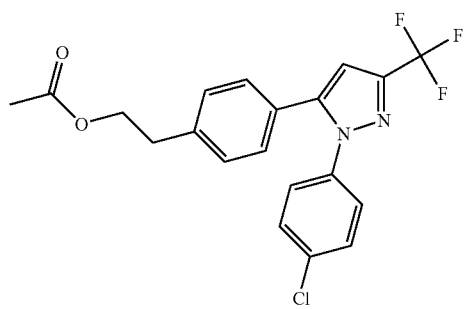

E0114 was obtained according to a similar manner to that of E0105.

EXAMPLE 115

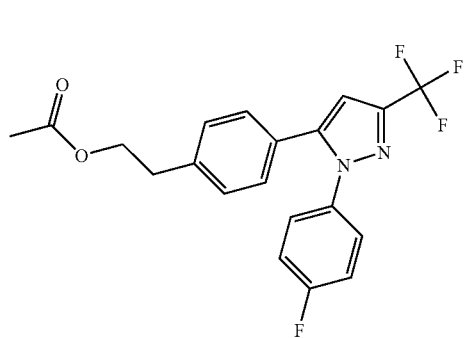

E0115 was obtained according to a similar manner to that of E0105.

EXAMPLE 116

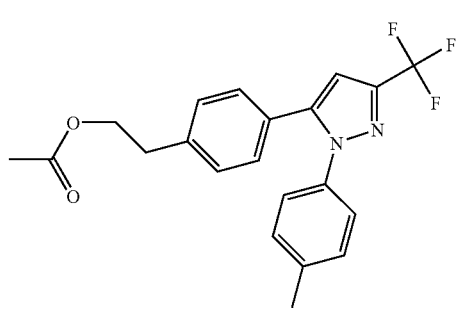

E0116 was obtained according to a similar manner to that of E0105.

EXAMPLE 117

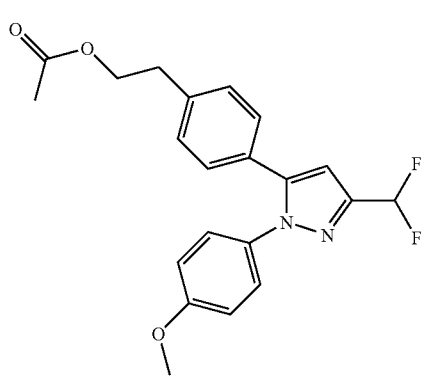

E0117 was obtained according to a similar manner to that of E0105.

EXAMPLE 118

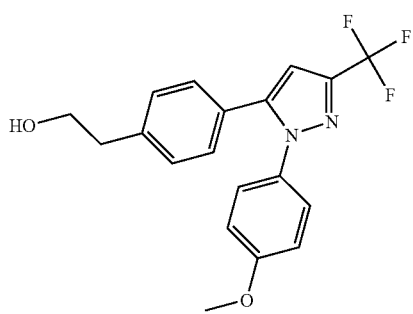

A mixture of E0105 (2.0 g) and 1N NaOH (15 ml) in THF (40 ml) was stirred at room temperature for 5 hours. After the reaction was completed, the mixture was neutralized with 1N HCl (15 ml), extracted twice with ethylacetate, washed with 1N HCl, sat.NaHCO3, and brine, dried over NA2SO4, filtered and evaporated under reduced pressure.

The residue was column chromatographed on silica gel (H/EA =2:1–1:1) to give 1.14 g (64%) of E0118 as a crystal.

mp: 103–104° C.

IR (film): 3396.0, 1513.9, 1467.6, 1238.1, 1160.9, 1132.0 cm−1.

EXAMPLE 119

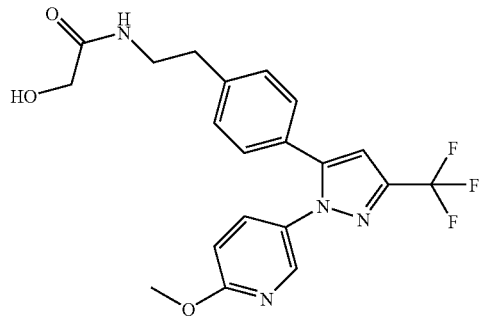

(E0119)

E0119 was prepared from E0217 in a similar manner to that of E0118.

IR (neat): 3359, 3332, 3325, 1658, 1651, 1624, 1614, 1545, 1533, 1500 cm−1

Mass (ESI+): 421 (M+H)+

200 MHz1H MNR (DMSO-d6, d): 2.71–2.79 (2H, m), 3.28–3.39 (2H, m), 3.76 (2H, brs), 3.88 (3H, s), 5.47 (1H, br), 6.92 (1H, d, J=8.9 Hz), 7.18 (1H, s), 7.24 (4H, s), 7.74 (1H, dd, J=2.7, 8.9 Hz), 7.80 (1H, t, J=5.9 Hz), 8.19 (1H, d, J=2.7 Hz)

EXAMPLE 120

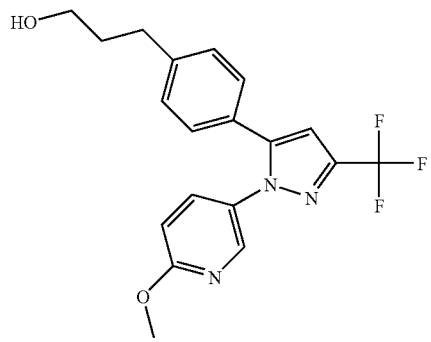

(E0120)

E0120 was prepared-from E0002 in a similar manner to that of E0118.

IR (neat): 3433, 3423, 3398, 3367, 2945, 1612, 1500 cm−1

Mass (ESI+): 378 (M+H)+

200 MHz 1H NMR (DMSO-d6, d): 1.62–1.77 (2H, m), 2.57–3.65 (2H, m), 3.34–3.44 (2H, m), 3.88 (3H, s), 4.48 (1H, t, J=5.1 Hz), 6.92 (1H, d, J=8.9 Hz), 7.17 (1H, s), 7.23 (4H, s), 7.76 (1H, dd, J=8.9, 2.8 Hz), 8.18 (1H, d, J=2.8 Hz)

EXAMPLE 121

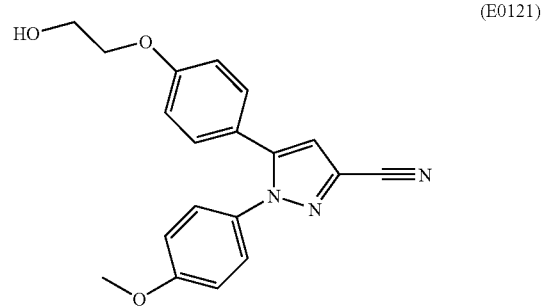

(E0121)

E0121 was prepared from E0268 in a similar manner to that of E0118.

White Powder mp. 91–92° C.

IR (KBr): 3491, 3471, 3437, 2941, 2239, 1610, 1508 cm−1

Mass (ESI+): 336 (M+H)+

200 MHz 1H NMR (DMSO-d6, d) 3.65–3.73 (2H, m), 3.79 (3H, s), 3.95–4.05 (2H, m), 4.87 (1H, t, J=5.4 Hz), 6.93 (2H, d, J=8.8 Hz), 7.00 (2H, d, J=9.0 Hz), 7.16 (2H, d, J=8.8 Hz), 7.28 (2H, d, J=9.0 Hz), 7.32 (1H, s)

EXAMPLE 122

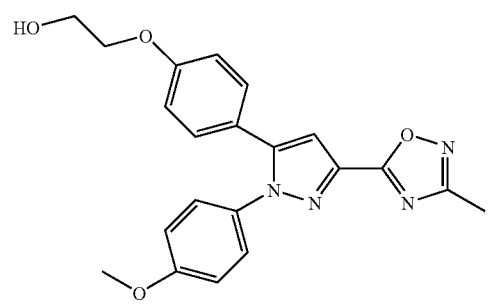

(E0122)

E0122 was prepared from E0353 in a similar manner to that of E0118.

White Powder mp. 158–159° C.

IR (KBr): 3399, 2955, 1707, 1693, 1647, 1614, 1566, 1547, 1529, 1512 cm−1

Mass (ESI+): 393 (M+H)+

200 MHz 1H NMR (DMSO-d6, d): 2.44 (3H, s), 3.66–3.74 (2H, m), 3.80 (3H,s),3.96–4.02 (2H,m), 4.88 (1H, t, J=5.4 Hz), 6.94 (2H, d, J=8.7 Hz), 7.02 (2H, d, J=8.9 Hz), 7.22 (2H, d, J=8.7 Hz), 7.26 (1H, s), 7.31 (2H, d, J=8.9 Hz)

EXAMPLE 123

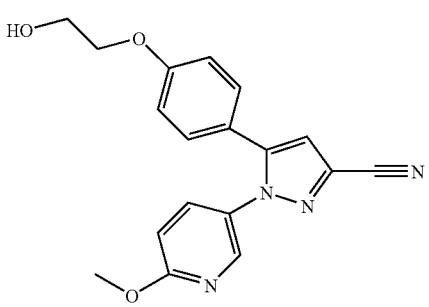

(E0123)

E0123 was prepared from E0358 in a similar manner to that of E0118.
White Powder
mp. 105–107° C.
IR (KBr): 3529, 3437, 2956, 1610, 1570, 1547, 1529 cm−1
Mass (ESI+): 337 (M+H)+
200 MHz 1H NMR (DMSO-d6, d): 3.65–3.73 (2H, m), 3.88 (3H, s), 3.96–4.02 (2H, m), 4.87 (1H, t, J=5.3 Hz), 6.93 (1H, d, J=8.8 Hz), 6.96 (2H, d, J=8.7 Hz), 7.21 (2H, d, J=8.7 Hz), 7.35 (1H, s), 7.73 (1H, dd, J=2.7, 8.8 Hz), 8.20 (1H, d, J=2.7 Hz)

EXAMPLE 124

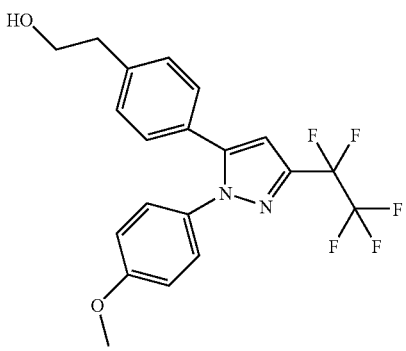

(E0124)

E0124 was prepared from E0107 in a similar manner to that of E0118.
White Powder
mp. 97–98° C.
IR (KBr): 3427, 2960, 1608, 1516 cm−1
Mass (ESI+): 413 (M+H)+ 200 MHz 1H NMR (DMSO-d6, d): 2.71 (2H, t, J=6.9 Hz), 3.54–3.65 (2H, m), 3.79 (3H, s), 4.64 (1H, t, J=5.1 Hz), 7.00 (2H, d, J=9.0 Hz), 7.12 (1H, s), 7.15–7.33 (4H, m), 7.29 (2H, d, J=9.0 Hz)

EXAMPLE 125

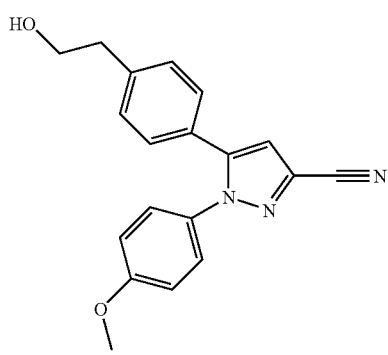

(E0125)

E0125 was prepared in a similar manner to that of E0118.
IR (neat): 3435, 3425, 3406, 3398, 3367, 1691, 1658, 1647, 1614, 1547, 1512 cm−1
Mass (ESI+): 320 (M+H)+, 361 (M+CH3CN+H)+
200 MHz 1H NMR (DMSO-d6, d) 2.71 (2H, t, J=6.8 Hz), 3.54–3.64 (2H, m), 3.79 (3H, s), 4.64 (1H, t, J=5.2 Hz), 7.00 (2H, d, J=8.9 Hz), 7.15 (2H, d, J=8.3 Hz), 7.23 (2H, d, J=8.3 Hz), 7.29 (2H, d, J=8.9 Hz), 7.34 (1H, s)

EXAMPLE 126

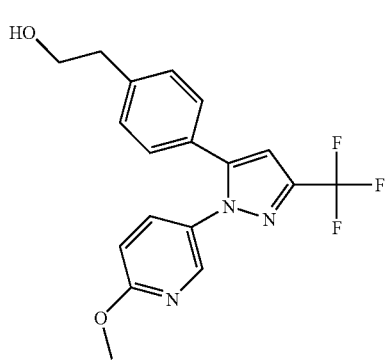

(E0126)

E0126 was prepared from E0111 in a similar manner to that of E0118.
White Powder
mp. 89–92° C.
IR (KBr): 3481, 2947, 1608, 1496 cm−1
Mass (ESI+): 364 (M+H)+
200 MHz 1H NMR (DMSO-d6, d): 2.72 (2H, t, J=6.8 Hz), 3.55–3.65 (2H, m), 3.88 (3H, s), 4.65 (1H, t, J=5.2 Hz), 6.92 (1H, d, J=8.8 Hz), 7.16 (1H, s), 7.19–7.28 (4H, m), 7.77 (1H, dd, J=2.6, 8.8 Hz), 8.19 (1H, d, J=2.6 Hz)

EXAMPLE 127

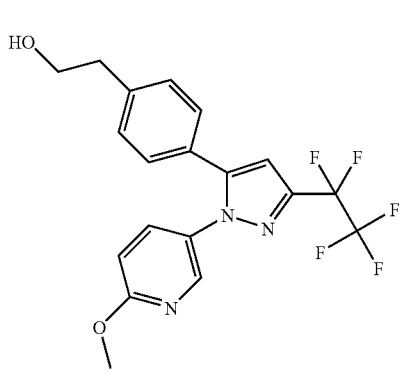

E0127 was prepared from E0108 in a similar manner to that of E0118.

IR (neat): 3400, 2951, 1610, 1502 cm−1

Mass (API-ES positive): 414 (M+H)+, 436 (M+Na)+

200 MHz 1H NMR (DMSO-d6, d): 2.72 (2H, t, J=6.9 Hz), 3.51–3.65 (2H, m), 3.88 (3H, s), 4.65 (1H, t, J=5.1 Hz), 6.93 (1H, d, J=8.8 Hz), 7.15–7.35 (4H, m), 7.18 (1H, s), 7.77 (1H, dd, J=2.7,8.8 Hz), 8.18 (1H, d, J=2.7 Hz)

EXAMPLE 128

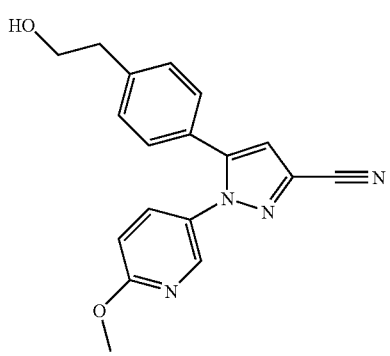

E0128 104.4 mg was prepared in a similar manner to that of E0118.

IR (neat): 3433, 3423, 3398, 2947, 2873, 2243, 1608 cm−1

Mass (ESI+): 321 (M+H)+

200 MHz 1H NMR (DMSO-d6, d): 2.72 (2H, t, J=6.8 Hz), 3.55–3.65 (2H, m), 3.88 (3H, s), 4.65 (1H, t, J=5.1 Hz), 6.93 (1H, d, J=8.8 Hz), 7.19 (2H, d, J=8.4 Hz), 7.26 (2H, d, J=8.4 Hz), 7.38 (1H, s), 7.76 (1H, dd, J=2.7, 8.8 Hz), 8.21 (1H, d, J=2.7 Hz)

EXAMPLE 129

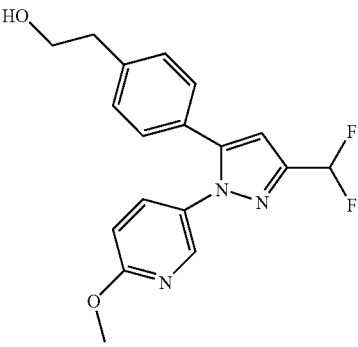

E0129 was obtained according to a similar manner to that of E0118.

EXAMPLE 130

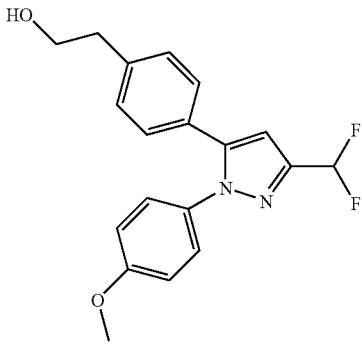

E0130 was obtained according to a similar manner to that of E0118.

EXAMPLE 131

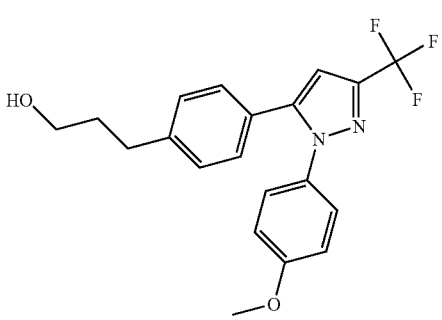

E0131 was obtained according to a similar manner to that of E0118.

EXAMPLE 132

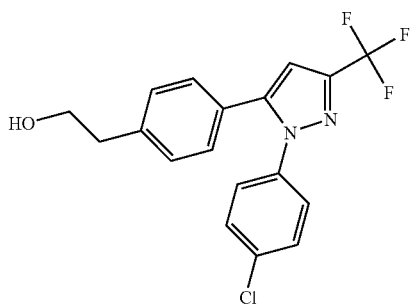
(E0132)

E0132 was obtained according to a similar manner to that of E0118.

IR (film): 3392.2, 1494.6, 1236.2, 1160.9, 1133.9, 1095.4, 975.8, 833.1 cm−1.

EXAMPLE 133

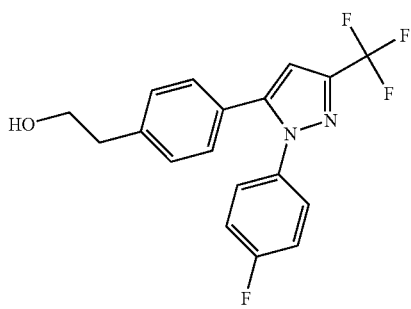
(E0133)

E0133 was obtained according to a similar manner to that of E0118.

IR (film): 3374.8, 1511.9, 1471.4, 1274.7, 1232.3, 1160.9, 1133.9, 977.7, 842.7, 811.9 cm−1.

mp: 82–83 °C.

EXAMPLE 134

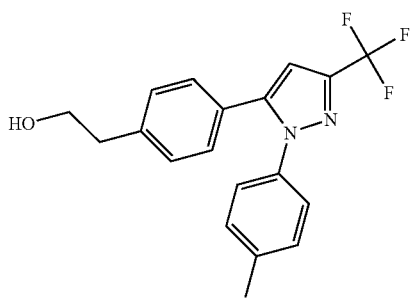
(E0134)

E0134 was obtained according to a similar manner to that of E0118.

IR (film): 3386.4, 1511.9, 1471.4, 1236.2, 1159.0, 1132.0, 1047.2, 975.8, 817.7 cm−1.

EXAMPLE 135

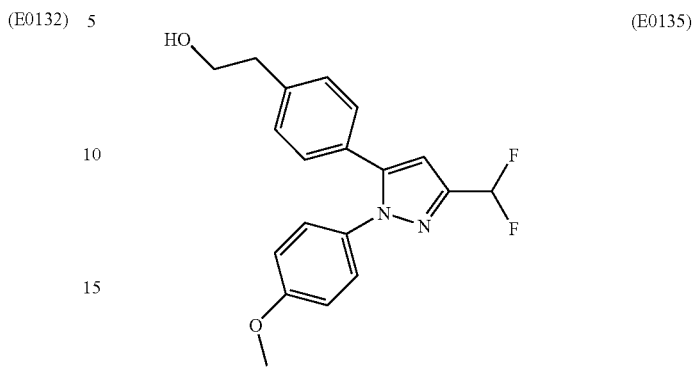
(E0135)

E0135 was obtained according to a similar manner to that of E0118.

IR (film): 3399.9, 1610.3, 1513.9, 1459.9, 1251.6, 1172.5, 1083.8, 1033.7, 836.9, 802.2 cm−1. (FS7081)

EXAMPLE 136

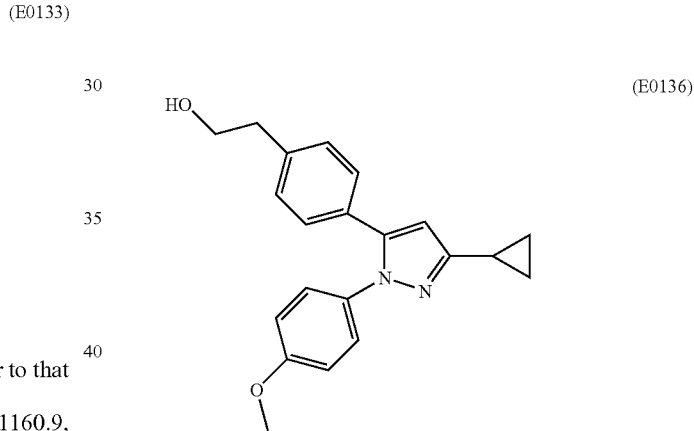
(E0136)

P0018 (277mg) and 4-methoxyphenylhydrazine hydrochloride (209 mg) in EtOH:AcOH=20:1 6 ml was refluxed for 2 hours. The mixture was partitioned between AcOEt and H2O. The organic layer was washed successively with 1M HCl, saturated aqueous sodium bicarbonate solution, and saturated aqueous sodium chloride solution, dried over magnesium sulfate, and concentrated in vacuo. The residue was purified by silica gel column chromatography eluted with AcOEt/n-hexane=30%, 40%, 50%. The pure fraction was collected and concentrated in vacuo. The residue was crystallized from AcOEt/n-hexane to give E0136 (95.6 mg) as a white powder.

mp. 111–112° C.

IR (KBr): 3325, 2931, 1707, 1693, 1685, 1658, 1647, 1564, 1549, 1514 cm−1

Mass (ESI+): 335 (M+H)+

200 MHz 1H NMR (DMSO-d6, d): 0.69–0.77 (2H, m), 0.86–0.96 (2H, m), 1.93 (1H, m), 2.69 (2H, t, J=6.9 Hz), 3.53–3.64 (2H, m), 3.76 (3H, s), 4.64 (1H, t, J=5.2 Hz), 6.28 (1H, s), 6.92 (2H, d, J=9.0 Hz), 7.05–7.19 (6H, m)

EXAMPLE 137

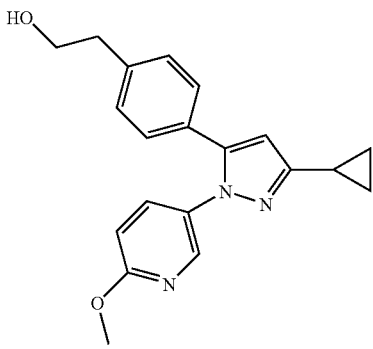
(E0137)

E0137 was prepared from P0018 498.5 mg in a similar manner to that of E0136.

Preparation 34

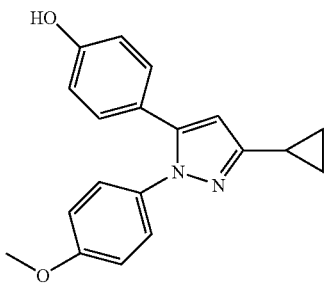
(P0034)

P0034 was prepared in a similar manner to that of E0137.
White Powder
Mass (ESI+): 306 (M+H)+
200 MHz 1H NMR (DMSO-d6, d): 0.67–0.76 (2H, m), 0.84–0.94 (2H, m), 1.91 (1H, m), 3.76 (3H, s), 6.18 (1H, s), 6.68 (2H, d, J=8.7 Hz), 6.91 (2H, d, J=9.0 Hz), 6.98 (2H, d, J=8.7 Hz), 7.12 (2H, d, J=9.0 Hz), 9.63 (1H, s)

EXAMPLE 138

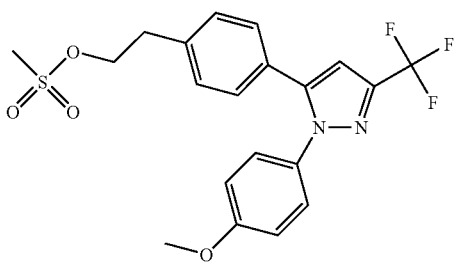
(E0138)

To a solution of E0118 (1.0 g) and Et3N (0.6 ml) in CH2Cl2 (20 ml) was added dropwise methanesulfonyl chloride (0.26 ml) under ice-cooling. After stirring for 1 hour, the reaction mixture was quenched with water and extracted with CHCl3. The organic layer was washed with water, dried over Na2SO4, filtered and evaporated to give 1.2 g (99%) of crude E0138 as an off-white solid.

IR (film): 1513.9, 1469.5, 1351.9, 1240.0, 1166.7, 1130.1, 971.9, 835.0, 804.2 cm−1.

EXAMPLE 139

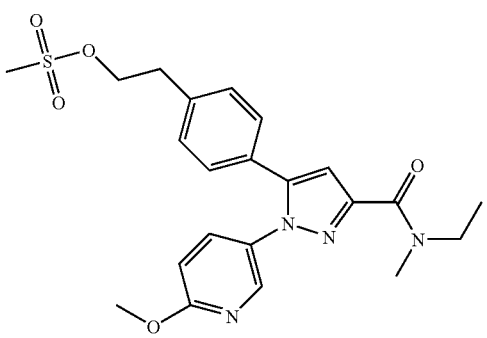
(E0139)

E0139 was prepared in a similar manner to that of E00138.

Mass (ESI+): 459 (M+H)+

200 MHz 1H NMR (DMSO-d6, d) 1.09–1.23 (3H, m), 2.98, 3.29 (3H, s), 3.01 (2H, t, J=6.6 Hz), 3.09 (3H, s), 3.43–3.77 (2H, m), 3.87 (3H, s), 4.42 (2H, t, J=6.6 Hz), 6.88–6.92 (2H, m), 7.25 (2H, d, J=8..3 Hz), 7.33 (2H, d, J=8.3 Hz), 7.65–7.73 (1H, m), 8.15 (1H, d, J=2.6 Hz)

EXAMPLE 140

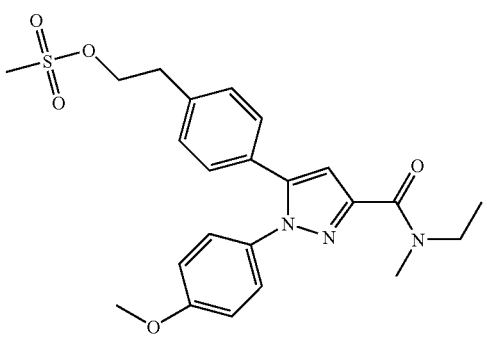
(E0140)

E0140 was prepared in a similar manner to that of E0138.
Mass (APCI+): 458 (M+H)+
200 MHz1H MNR (DMSO-d6, d): 1.05–1.25 (3H,m), 2.96–3.03 (2H, m), 2.98, 3.29 (3H, s), 3.08 (3H, s), 3.40–3.85 (2H, m), 3.78 (3H, s), 4.42 (2H, t, J=6.6 Hz), 6.86, 6.88 (1H, s), 6.98 (2H, d, J=8.9 Hz), 7.18–7.32 (6H, m)

EXAMPLE 141

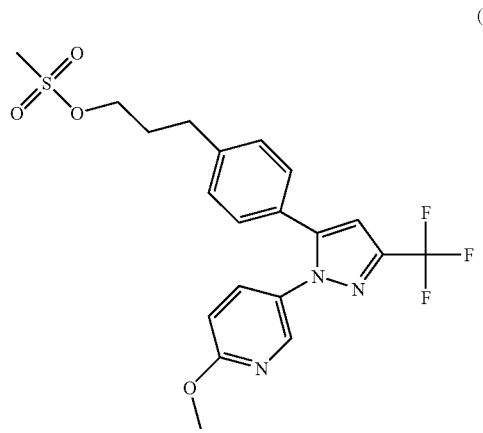
(E0141)

E0141 was prepared in a similar manner to that of E0138.
Mass (ESI+): 456 (M+H)+
200 MHz1H MNR (DMSO-d6, d): 1.89–2.04 (2H, m), 2.52–2.73 (2H, m), 3.16 (3H, s), 3.88 (3H, s), 4.19 (2H, t, J=6.3 Hz), 6.92 (1H, d, J=8.9 Hz), 7.18 (1H, s), 7.21–7.31 (4H, m), 7.76 (1H, dd, J=2.6, 8.9 Hz), 8.19 (1H, d, J=2.6 Hz)

EXAMPLE 142

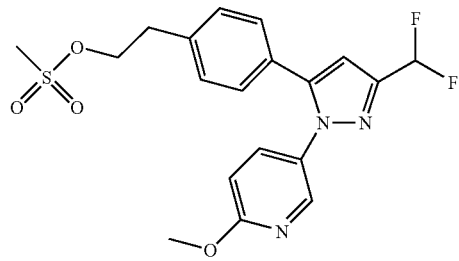
(E0142)

E0142 was obtained according to a similar manner to that of E0138.

EXAMPLE 143

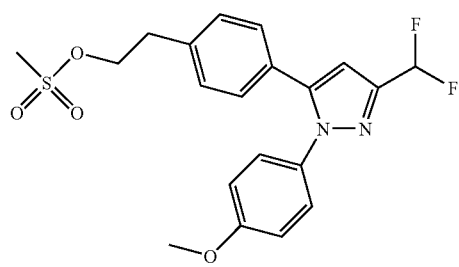
(E0143)

E0143 was obtained according to a similar manner to that of E0138.

EXAMPLE 144

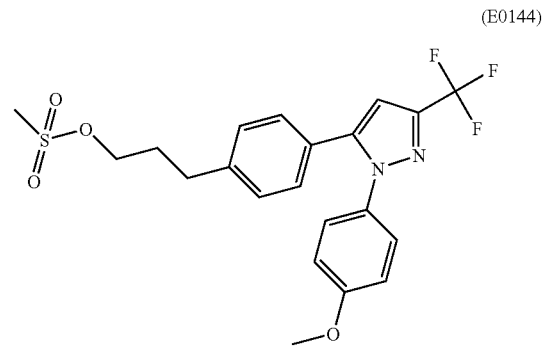
(E0144)

This compound was obtained according to a similar manner to that of E0138.

EXAMPLE 145

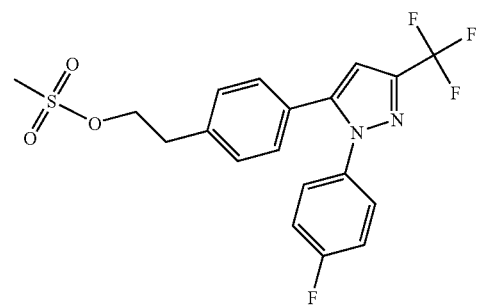
(E0145)

This compound was obtained according to a similar manner to that of E0138.

EXAMPLE 146

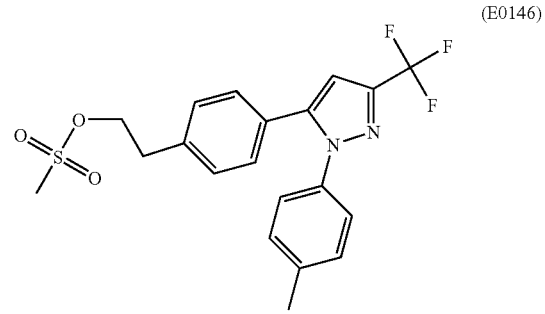
(E0146)

This compound was obtained according to a similar manner to that of E0138.

EXAMPLE 147

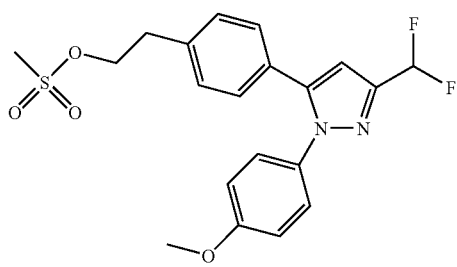

This compound was obtained according to a similar manner to that of E0138.

EXAMPLE 148

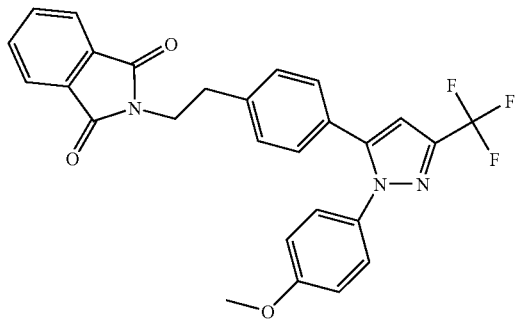

A mixture of E0138 (900 mg) and potassium phthalimide (454 mg) in DMF (18 ml) was stirred at 60° C. for 3.0 hours. After addition of water, the reaction mixture was extracted with EtOAc and washed twice with water and with brine. The organic layer was dried over Na2SO4, filtered and evaporated under reduced pressure. The residue was column chromatographed on silica gel (50 ml) to give 930 mg (93%) of E0148 as a powder.

IR (film): 1772.3, 1712.5, 1240.0, 1160.9, 1130.1 cm−1.

EXAMPLE 149

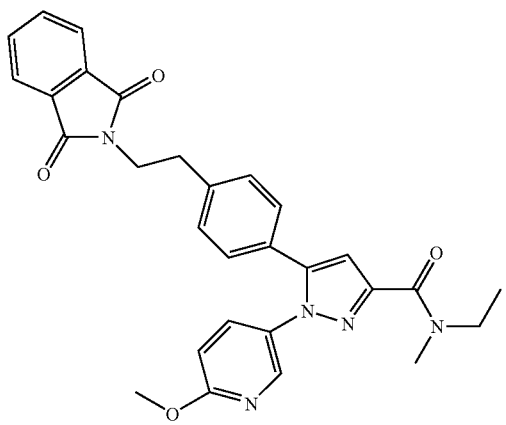

E0149 was prepared from E0139 in a similar manner to that of E0148.

Amorphous Powder

Mass (ESI+): 510 (M+H)+

200 MHz 1H NMR (DMSO-d6, d) 1.08–1.22 (3H, m), 2.89–2.98 (2H, m), 2.98, 3.27 (3H, s), 3.48, 3.70 (2H, q, J=7.1, 6.9 Hz), 3.82 (2H, t, J=7.3 Hz), 3.88 (3H, s), 6.83–6.88 (2H, m), 7.23 (2H, d, J=8.7 Hz), 7.18 (2H, d, J=8.7 Hz), 7.53–7.63 (1H, m), 7.79–7.89 (4H, m), 8.15 (1H, d, J=2.6 Hz)

EXAMPLE 150

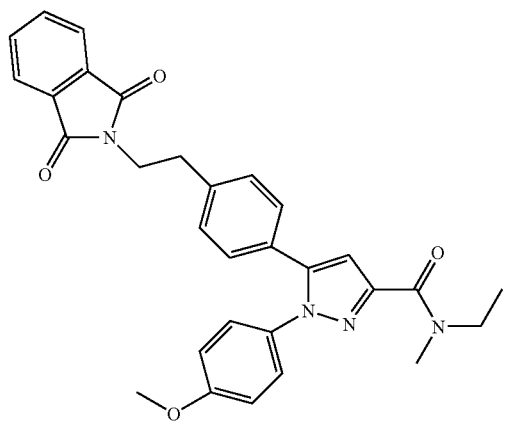

E0150 was prepared from E0140 in a similar manner to that of E0148.

Amorphous Powder

Mass (ESI+): 509 (M+H)+

200 MHz 1H NMR (DMSO-d6, d): 1.12, 1.18 (3H, t, J=7.0, 7.1 Hz), 2.92 (2H, t, J=7.0 Hz), 2.97, 3.28 (3H, s), 3.47, 3.71 (2H, q, J=7.1, 7.0 Hz), 3.78 (3H, s), 3.81 (2H, t, J=7.0 Hz), 6.82, 6.84 (1H, s), 6.94 (2H, d, J=9.0 Hz), 7.11–7.20 (6H, m), 7.79–7.89 (4H, m)

EXAMPLE 151

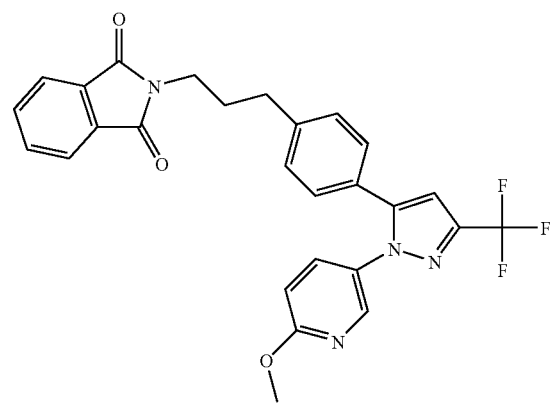

E0151 was prepared from E0038 in a similar manner to that of E0148.

Mass (ESI+): 507 (M+H)+

200 MHz1H NMR (DMSO-d6, d): 1.82–1.97 (2H, m), 2.59–2.67 (2H, m), 3.60 (2H, t, J=7.0 Hz), 3.88 (3H, s), 6.91 (1H, d, J=8.8 Hz), 7.14 (1H, s), 7.20 (2H, d, J=8.5 Hz), 7.26 (2H, d, J=8.5 Hz), 7.73 (1H, dd, J=8.8, 2.8 Hz), 7.78–7.89 (4H, m), 8.17 (1H, d, J=2.8 Hz)

EXAMPLE 152

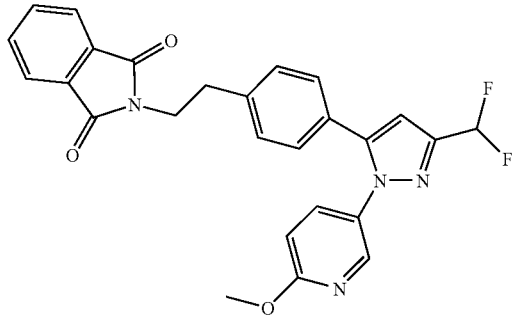
(E0152)

This compound was obtained according to a similar manner to that of E0148.

EXAMPLE 153

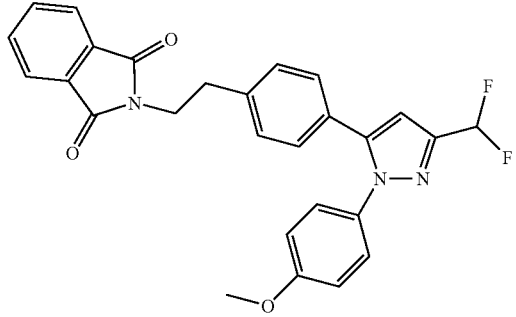
(E0153)

This compound was obtained according to a similar manner to that of E0148.

EXAMPLE 154

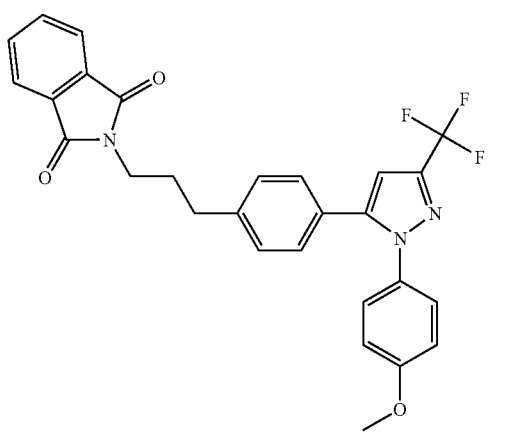
(E0154)

This compound was obtained according to a similar manner to that of E0148.

EXAMPLE 155

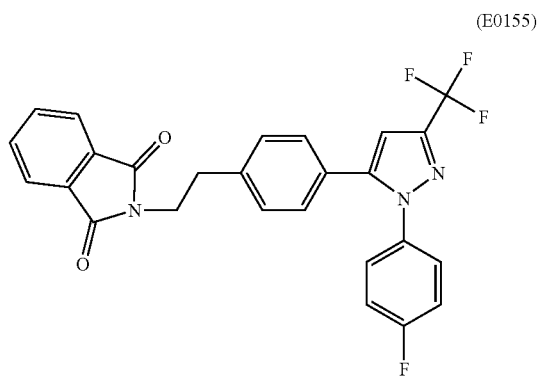
(E0155)

This compound was obtained according to a similar manner to that of E0148.

EXAMPLE 156

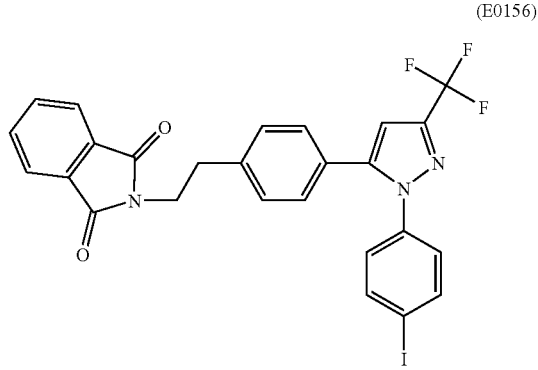
(E0156)

This compound was obtained according to a similar manner to that of E0148.

EXAMPLE 157

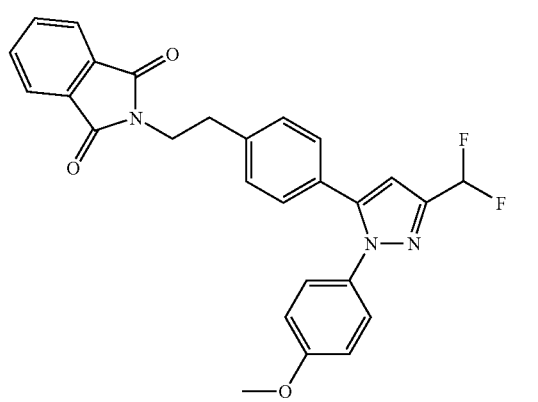
(E0157)

This compound was obtained according to a similar manner to that of E0148.

EXAMPLE 158

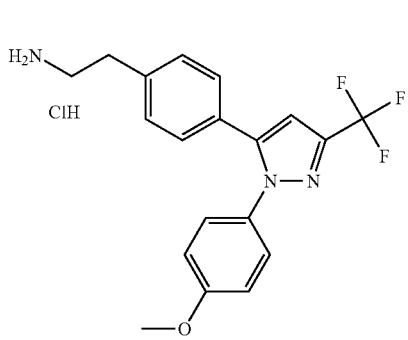

(E0158)

To a solution of E0148 (800 mg) in CH3CN (10 ml) was added hydrazine hydroxide (87 ul) at room temperature. After stirring for 1 hour, the reaction mixture was filtered and evaporated. After addition of dichloromethane, the mixture was stirred for an hour, filtered and evaporated. The residue was treated with 4NHCl/EtOAc to give 518 mg (80%) of E0158.

IR (Film); 3403.74, 1610.27, 1511.92, 1467.56, 1238.08, 1160.94, 1130.08, 1027.87, 975.80, 836.96, 806.10 cm−1.

EXAMPLE 159

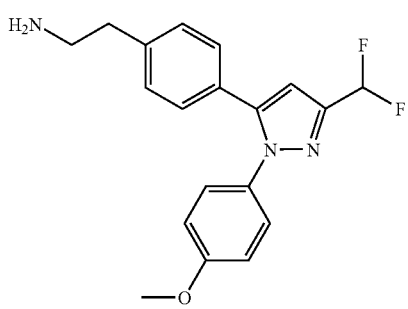

(E0159)

This compound was obtained according to a similar manner to that of E0158.

EXAMPLE 160

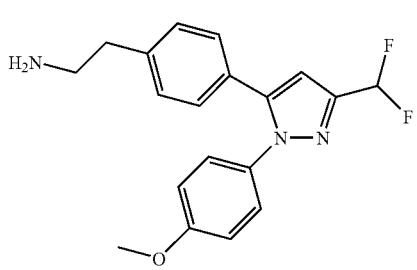

(E0160)

This compound was obtained according to a similar manner to that of E0158.

EXAMPLE 161

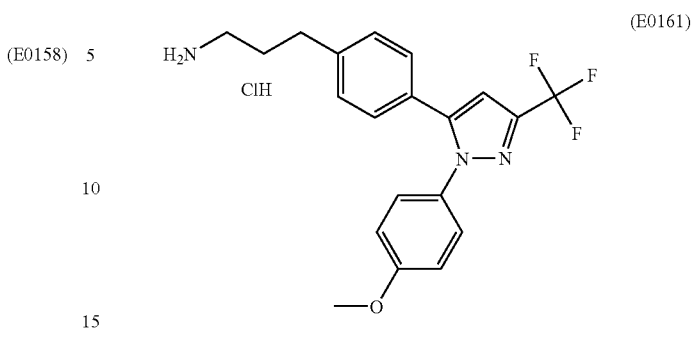

(E0161)

This compound was obtained according to a similar manner to that of E00158.

IR (film): 3428.8, 1511.9, 1467.6, 1238.1, 1160.9, 1132.0 cm−1.

EXAMPLE 162

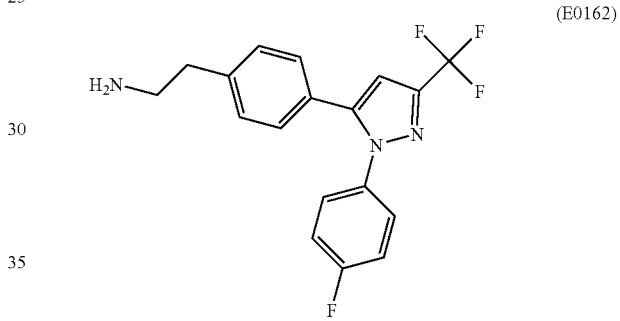

(E0162)

This compound was obtained according to a similar manner to that of E0158.

IR (film): 3371.0, 1511.9, 1471.4, 1272.8, 1230.4, 1160.9, 1133.9, 975.8, 842.7, 810.0 cm−1.

EXAMPLE 163

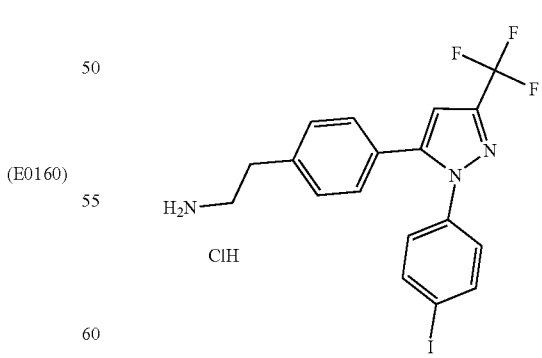

(E0163)

This compound was obtained according to a similar manner to that of E0158.

mp: 163.1–165.1° C.

IR (film): 2973.7, 1511.9, 1471.4, 1236.2, 1159.0, 1133.9 cm−1.

EXAMPLE 164

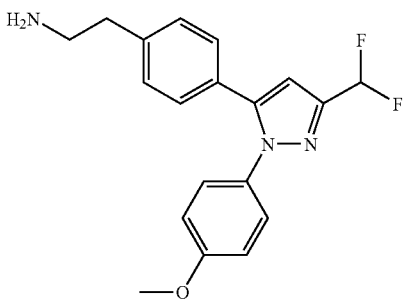

(E0164)

This compound was obtained according to a similar manner to that of E0158.

IR(film): 3369.0, 1604.5, 1513.9, 1459.9, 1251.6, 1172.5, 1083.8, 1029.8, 837.0, 800.3 cm-1.

EXAMPLE 165

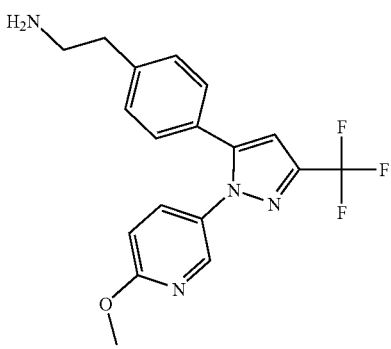

(E0165)

To a solution of E0395 (1.08 g) in acetonitril (15 ml) was added hydrazine monohydrate (0.53 ml). After stirring at 60° C. overnight, the mixture was filtered. And the filtrate was evaporated to give E0165 as an orange oil (814 mg, 102%).

NMR (CDCl3), 2.76 (2H, t, J=6.5 Hz), 2.98 (2H, t, J=6.5 Hz), 3.94 (3H, s), 6.73 (1H, s), 6.76 (1H, d, J=8.9 Hz), 7.22–7.12 (4H, m), 7.57 (1H, dd, J=8.9, 2.7 Hz), 8.09 (1H, d, J=2.7 Hz).

MS (ESI+); 363.3 (MH+).

EXAMPLE 166

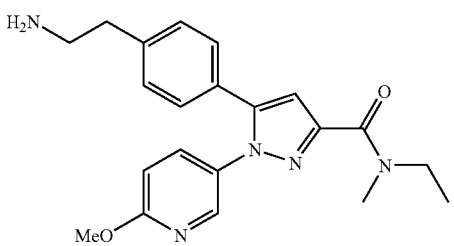

(E0166)

E0166 was prepared from E0046 in a similar manner to that of E0165.

Mass (ESI+): 380 (M+H)+

200 MHz 1H NMR (DMSO-d6, d) 1.91–1.23 (3H, m), 2.59–2.79 (4H, m), 2.98, 3.28 (3H, s), 3.48, 3.71 (2H, q, J=7.2, 7.0 Hz), 3.87 (3H, s), 6.86–6.93 (2H, m), 7.16–7.26 (4H, m), 7.64–7.73 (1H, m), 8.15 (1H, d, J=2.5 Hz)

EXAMPLE 167

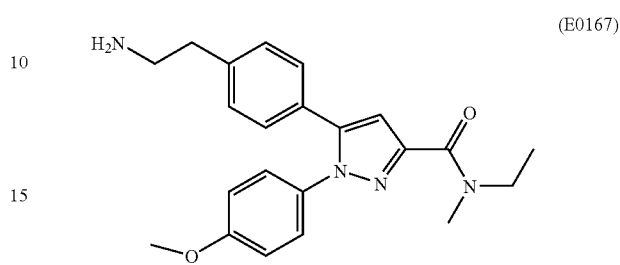

(E0167)

E0167 was prepared from E0150 in a similar manner to that of E0165.

Mass (ESI+): 379 (M+H)+200 MHz 1H NMR (DMSO-d6, d): 1.08–1.22(3H, m), 2.57–2.78(4H, m), 2.97,3.29(3H, s), 3.48,3.72(2H, q, J=7.2,7.0 Hz), 3.78(3H, s), 6.83,6.85 (1H, s), 6.98(2H, d, J=8.9 Hz), 7.06–7.26(6H, m)

EXAMPLE 168

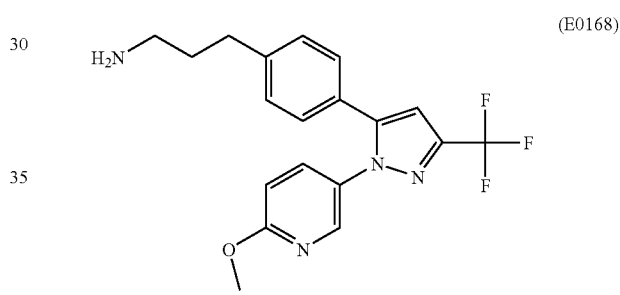

(E0168)

E0168 was prepared from E0048 in a similar manner to that of E0165.

Mass (ESI+): 377 (M+H)+200 MHz1HNMR (DMSO-d6, d): 1.54–1.69(2H,m), 2.49–2.64(4H, m), 3.88(3H, s), 6.92 (1H, d, J=8.7 Hz), 7.17(1H, s), 7.22(4H, s), 7.75(1H, dd, J=8.7,2.6 Hz), 8.18(1H, d, J=2.6 Hz)

EXAMPLE 169

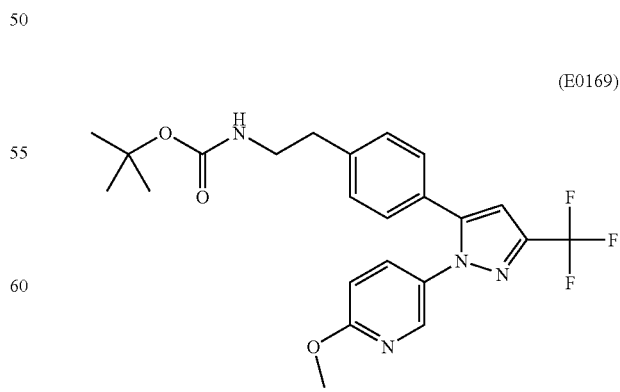

(E0169)

To a solution of E0165 (180 mg) in tetrahydrofuran (2 ml) was added triethylamine (0.242 ml) and t-butoxycarbonyl anhydride (325 mg) at room temperature. After stirring at room temperature overnight, the mixture was quenched with water and extracted with ethyl acetate (x3). The organic layer was washed with hydrogen chloride aqueous solution (1N), saturated sodium hydrogen carbonate aqueous solution, and brine, dried over magnesium sulfate, and evaporated to give oil, which was purified with column chromatography (SiO2 25 ml, 20% ethyl acetate/hexane) to give E0169 as an oil (224 mg, 97.5%).

NMR (CDC13); 1.35(9H, s), 2.69(2H, t, J=7.7 Hz), 3.09–3.19(2H,m),3.88(3H,s), 6.91(1H,d,J=8.8 Hz),7.17(1H, s), 7.18–7.27(4H, m), 7.75(1H, dd, J=8.8, 2.7 Hz), 8.19(1H, d, J=2.7 Hz).

MS (ESI+); 485.2(M+Na).

EXAMPLE 170

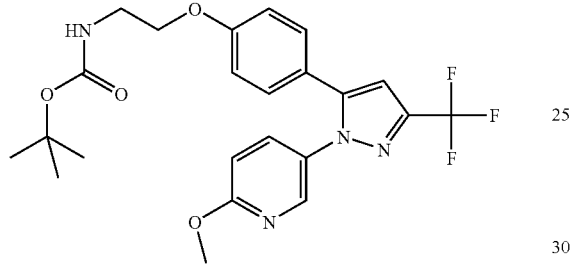
(E0170)

This compound was obtained according to a similar manner to that of E0169.

NMR (CDC13), 1.45(9H, s), 3.49–3.57(2H, m), 3.82(3H, s), 4.01(2H, t, J=5.1 Hz), 6.67(1H, s), 6.82(2H, d, J=8.7 Hz), 6.87(2H, d, J=9.0 Hz), 7.13(2H, d, J=8.7 Hz), 7.22(2H, d, J=9.0 Hz).

MS (ESI+), 500.2(M+Na).

EXAMPLE 171

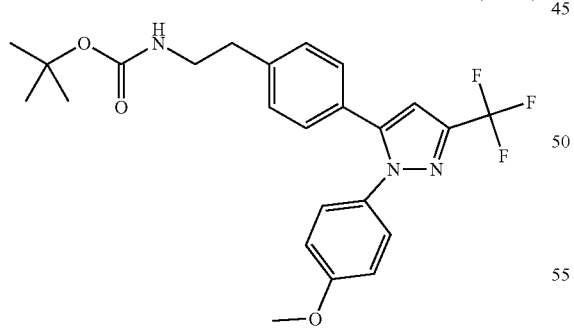
(E0171)

A mixture of E0158 (650 mg), Boc2O (428 mg) and 1NNaOH (3.3 ml) in THF (20 ml) was stirred at room temperature for 15 hours. Water and EtOAc was added and the aqueous layer was separated and extracted with EtOAc. The combined organic layer was washed with sat NaHCO3, water and brine, dried over NA2SO4, filtered and evaporated under reduced pressure. The residue was column chromatographed on silica gel (Hex/EtOAc) to give 700mg (93%) of E0171 as an oil.

EXAMPLE 172

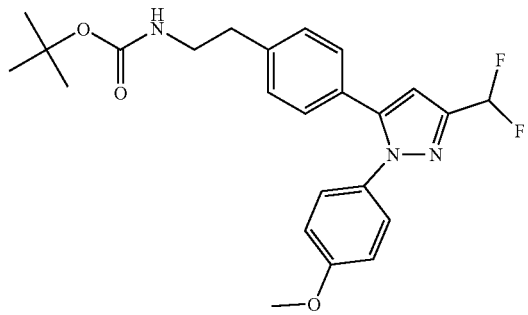
(E0172)

This compound was obtained according to a similar manner to that of E0171.

EXAMPLE 173

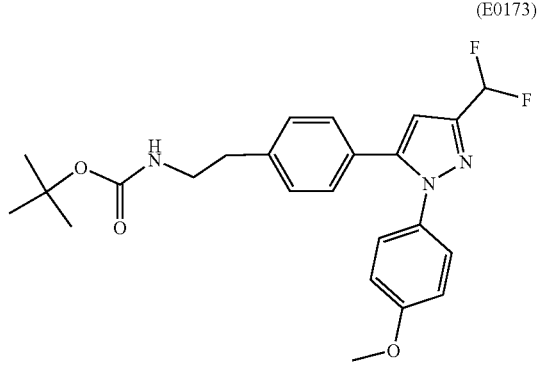
(E0173)

This compound was obtained according to a similar manner to that of E0171.

EXAMPLE 174

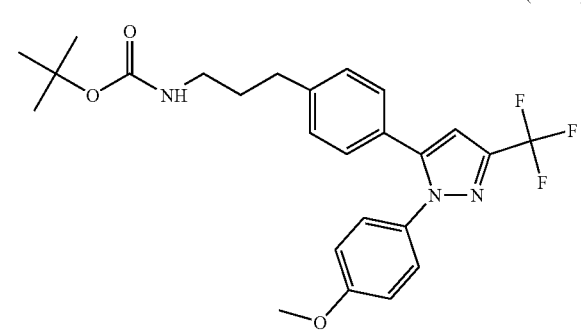
(E0174)

This compound was obtained according to a similar manner to that of E0171.

IR (film): 1702.8, 1513.9, 1241.9, 1164.8, 1132.0cm−1.

EXAMPLE 175

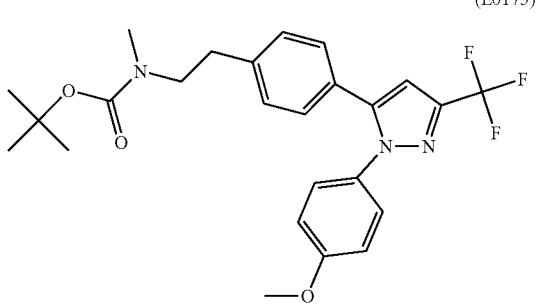
(E0175)

To a solution of E0171 (200 mg) and MeI (0.14 ml) in THF (20 ml) was added portionwise NaH (35 mg) at room temperature.

Then the reaction mixture was heated at 70° C. for 1 hour. Almost no reaction.

MeI (0.3 ml) and NaH (40 mg) was added, and DMF was added.

The mixture was stirred at 70° C. for 12 hours, and then cooled, quenched with water. The aqueous layer was extracted twice with EtOAc. The combined organic layer was washed with water and brine, dried over MgSO4, filtered and evaporated. The residue was column chromatographed on silica gel to give 151 mg (73%) of E0175 as an oil.

EXAMPLE 176

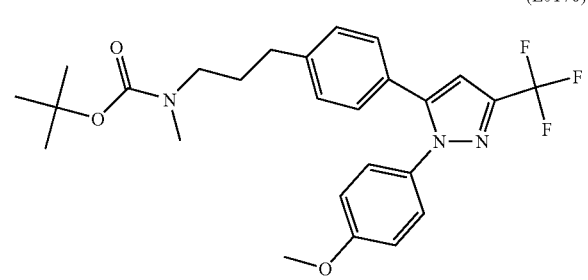
(E0176)

This compound was obtained according to a similar manner to that of E0175.

EXAMPLE 177

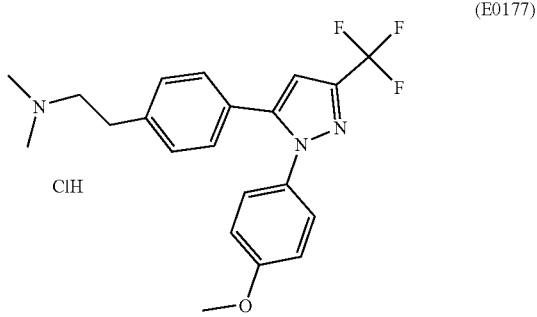
(E0177)

To a mixture of E0158 (150 mg) and HCHO (46 ul) in Et3N (53 ul) and CH3CN (5 ml) was added portionwise NaBH(OAc)2 (240 mg) at room temperature. After stirring for 15 hours, the mixture was quenched with water and extracted three times with EtOAc. The combined organic layer was washed with water and brine, dried over Na2SO4, filtered and evaporated under reduced pressure. The residue was column chromatographed on silica gel (CHCl3/MeOH) and treated with 4NHCl/dioxane to give 108 mg (70%) of E0177.

EXAMPLE 178

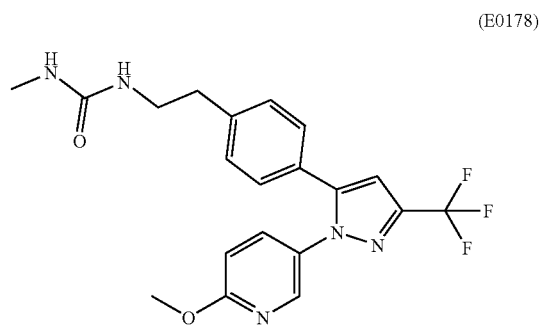
(E0178)

Methylisocyanate 36.2 mg was added to a solution of E0165 (199.3 mg) and triethylamine 48.6 mg in CH2Cl2 2 ml under ice bath cooling. The reaction mixture was stirred at same temperature for 1 hour and concentrated in vacuo. The residue was partitioned between AcOEt and 1M HCl. The organic layer was washed with saturated aqueous sodium bicarbonate solution and saturated aqueous sodium chloride solution, dried over magnesium sulfate, and concentrated in vacuo. The residue was recrystallized from AcOEt-n-hexane. Obtained powder was dissolved in CHCl3 and further purified by preparative thin layer silica gel chromatography developed by MeOH/CHCl3=10%. The separated silica gel was extracted with 10% MeOH/CHCl3 and the solvent was evaporated in vacuo. The residual solid was collected and washed with diisopropyl ether to give E0178 (101.3 mg) as a white powder.

mp. 149° C.

IR (KBr): 3348, 2947, 2885, 1626, 1583, 1529, 1500cm−1

Mass (ESI+): 420 (M+H)+

200 MHz 1H NMR (DMSO-d6, d): 2.49–2.53(3H, overlapping), 2.64–2.72(2H, m), 3.15–3.26(2H, m), 3.88(3H, s), 5.72(1H, q, J=4.5 Hz), 5.89(1H, t, J=5.7 Hz), 6.92(1H, d, J=8.8 Hz), 7.17(1H, s), 7.24(4H, s), 7.76(1H, dd, J=2.7, 8.8 Hz), 8.19(1H, d, J=2.7 Hz)

EXAMPLE 179

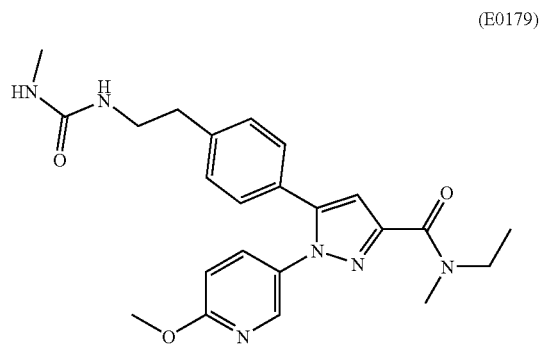
(E0179)

E0179 80.7 mg was prepared from E0166 in a similar manner to that of E0178.

Amorphous Powder

IR (neat): 3350, 2950, 2930, 1707, 1691, 1674, 1645, 1641, 1622, 1614, 1566, 1549, 1533, 1510 cm−1

Mass (ESI+): 437 (M+H)+

200 MHz1HNMR(DMSO-d6,d): 1.09–1.23(3H,m), 2.49–2.54(3H, overlapping), 2.67(2H, t, J=7.2 Hz), 2.98, 3.28(3H, s), 3.15–3.28(2H, m), 3.48,3.71(2H, q, J=6.8,6.9 Hz), 3.88(3H, s), 5.73(1H, q, J=4.6 Hz), 5.90(1H, t, J=5.6 Hz), 6.86–6.93(2H, m), 7.22(4H, s), 7.64–7.73(1H, m), 8.15(1H, d, J=2.6 Hz)

EXAMPLE 180

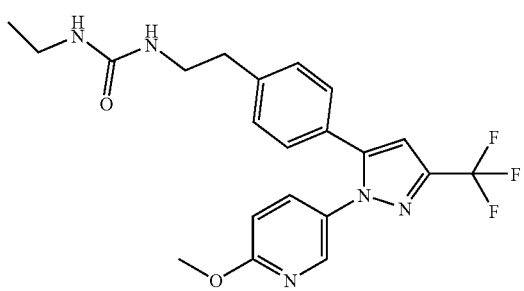
(E0180)

E0180 was prepared from E0294 in a similar manner to that of E0178.

White Powder mp. 155–157° C.

IR (KBr): 3336, 2968, 1707, 1693, 1674, 1621, 1576, 1533cm−1

Mass (ESI+): (M+H)+

200 MHz 1H NMR (DMSO-d6, d): 0.96(3H, t, J=7.1 Hz), 2.64–2.72(2H, m), 2.91–3.05(2H, m), 3.15–3.26(2H, m), 3.88(3H,s),5.76–5.84(2H,m), 6.92(1H,d,J=8.8 Hz),7.17(1H, s), 7.24(4H, s), 7.76(1H, dd, J=8.8,2.7 Hz), 8.19(1H, d, J=2.7 Hz)

EXAMPLE 181

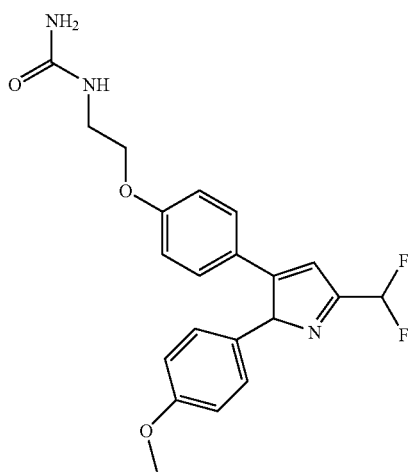
(E0181)

This compound was obtained according to a similar manner to that of E0178.

IR (film): 3343.9, 1658.5, 1608.3, 1513.9, 1457.9, 1249.6, 1029.8, 836.9 cm−1.

EXAMPLE 182

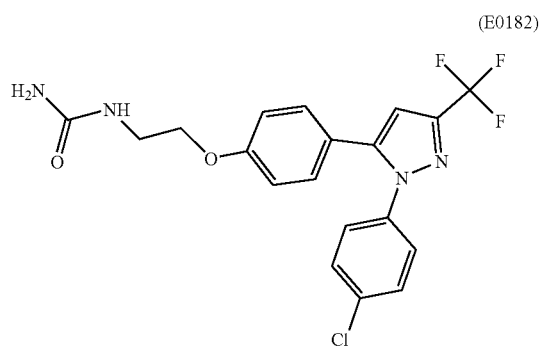
(E0182)

This compound was obtained according to a similar manner to that of E0178.

IR (Film): 1659.0, 1608.8, 1554.8, 1485.4, 1470.0, 1240.4, 1165.1, 1134.3, 1097.6, 835.3 cm−1.

EXAMPLE 183

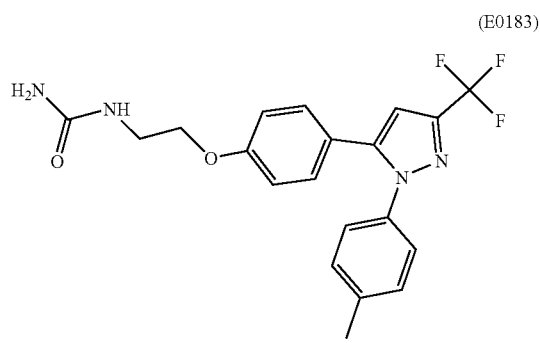
(E0183)

This compound was obtained according to a similar manner to that of E0178.

IR (film): 3249.8, 1658.5, 1608.3, 1554.3, 1469.5, 1240.0, 1164.8, 1133.9, 1097.3, 975.8, 835.0 cm−1.

EXAMPLE 184

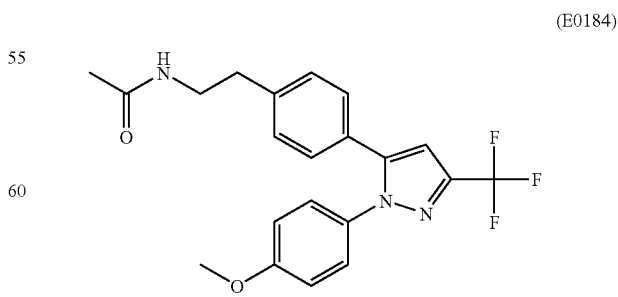
(E0184)

AcCl 23.3 mg was added to E0158 (107.4 mg) and triethylamine 68.3 mg in CH2Cl2 2 ml with cooling in an ice bath. After stirring at same temperature for 1hour, the reaction mixture was concentrated in vacuo. The residue was partitioned between AcOEt and 1M HCl. The organic layer was washed with saturated aqueous sodium bicarbonate solution and saturated aqueous sodium chloride solution, dried over magnesium sulfate, and concentrated in vacuo. The residual solid were collected and washed with diisopropyl ether to give E0184 (84 mg) as a white powder.

mp. 79–80° C.

IR (KBr): 3307, 3221, 3093, 2964, 1689, 1639, 1554, 1514cm−1

Mass (ESI+): 404 (M+H)+

200 MHz 1H NMR (DMSO-d6, d): 1.76(3H, s), 2.65–2.73(2H, m), 3.18–3.31(2H,m),3.79(3H,s), 6.99(2H,d,=J=8.9 Hz),7.12(1H, s), 7.20(4H, s), 7.28(2H, d, J=8.9 Hz), 7.92(1H, t, J=5.4 Hz)

EXAMPLE 185

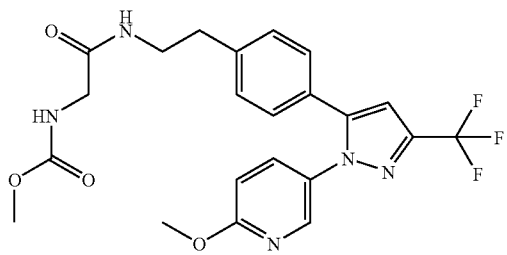

(E0185)

E0185 (143.4 mg) was prepared from E0232 (155.3 mg), methyl chloroformate 35.8 mg, and triethylamine 105 mg in a similar manner to that of E0184.

Amorphous Powder

IR (neat): 3319, 2954, 1718, 1711, 1668, 1660, 1612, 1545, 1533, 1500 cm−1

Mass (ESI+): 178 (M+H)+

200 MHz1HNMR (DMSO-d6, d): 2.67–2.75(2H, m), 3.22–3.33(2H, m), 3.50–3.60(2H, overlapping), 3.53(3H, s), 3.88(3H, s), 6.92(1H, d, J=8.8 Hz), 7.18(1H, s), 7.24(4H, s), 7.28(1H, t, J=6 Hz), 7.75(1H, dd, J=2.7,8.8 Hz), 7.94(1H, t, J=5.6 Hz), 8.19(1H, d, J=2.7 Hz)

EXAMPLE 186

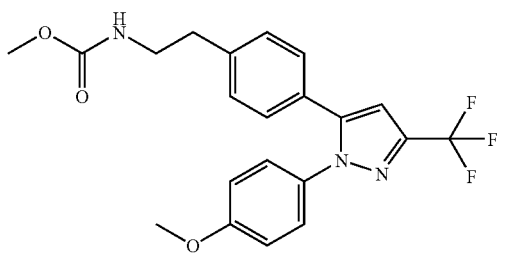

(E0186)

E0186 (59.3 mg) was prepared from E0158 (96.2 mg), methyl chloroformate 25.1 mg and triethylamine 61.2 mg in a similar manner to that of E0184.

mp. 78–80° C.

IR (KBr): 3352, 1739, 1695, 1658, 1647, 1549, 1514cm−1

Mass (ESI+): 420 (M+H)+

200 MHz1HNMR (DMSO-d6, d): 2.66–2.74(2H,m), 3.14–3.25(2H, m), 3.49(3H,s), 3.79(3H,s), 6.99(2H,d,J=8.9 Hz),7.12(1H, s), 7.12–7.32(1H, m), 7.20(4H, s), 7.28(2H, d, J=8.9 Hz)

EXAMPLE 187

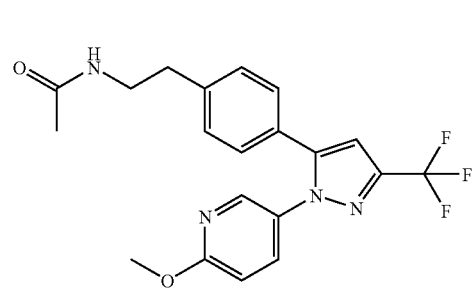

(E0187)

E0187 (63.4 mg) was prepared from E0165 (113.6 mg), acetyl chloride 29.5 mg, and triethylamine 41.2 mg in a similar manner to that of E0184.

White Powder mp.97–98° C.

IR (KBr): 3311, 2956, 1674, 1641, 1543, 1500cm−1

Mass (ESI+): 405 (M+H)+

200 MHz 1H NMR (DMSO-d6, d): 1.76(3H, s), 2.66–2.74(2H, m), 3.19–3.30(2H,m),3.88(3H,s), 6.92(1H,d, J=8.8 Hz),7.18(1H, s), 7.24(4H, s), 7.75(1H, dd, J=8.8,2.6 Hz), 7.92(1H, t, J=5.3 Hz), 8.19(1H, d, J=2.6 Hz)

EXAMPLE 188

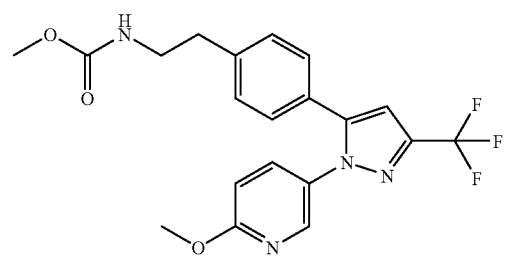

(E0188)

E0188 was prepared from E0165 in a similar manner to that of E0184.

IR (neat): 3338, 3020, 2951, 1716, 1610, 1527, 1500cm−1

Mass (ESI+): 421 (M+H)+

200 MHz1HNMR (DMSO-d6, d):2.67–2.75(2H, m), 3.14–3.25(2H, m), 3.49(3H, s), 3.88(3H, s), 6.92(1H, d, J=8.9 Hz), 7.15–7.35(5H, m), 7.18(1H, s), 7.75(1H, dd, J=2.7,8.9 Hz), 8.19(1H, d, J=2.7 Hz)

EXAMPLE 189

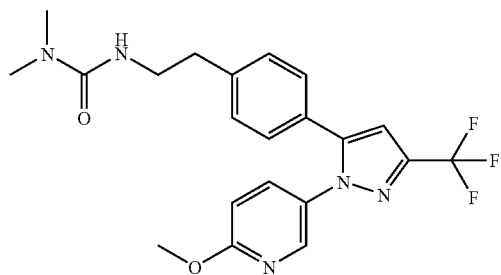
(E0189)

E0189 was prepared from E0294 in a similar manner to that of E0184.

IR (neat): 3352, 2939, 1691, 1639, 1533, 1500cm−1
Mass (ESI+): 434 (M+H)+
200 MHz 1H NMR (DMSO-d6, d): 2.67–2.74(2H, m), 2.74(6H, s), 3.15–3.26(2H,m),3.88(3H,s), 6.34(1H,t,J=5.4 Hz), 6.92(1H, d, J=8.9 Hz), 7.17(1H, s), 7.23(4H, s), 7.75 (1H, dd, J=8.9,2.7 Hz), 8.19(1H, d, J=2.7 Hz)

EXAMPLE 190

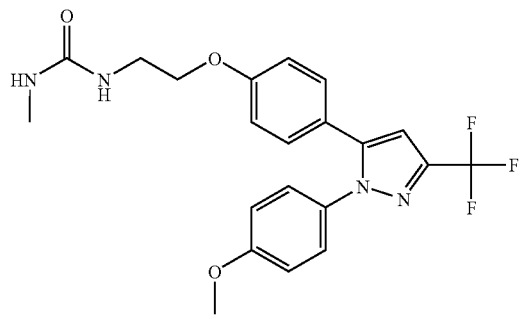
(E0190)

This compound was obtained according to a similar manner to that of E0189.

NMR (CDC13);2.78(3H,d, J=5.0 Hz), 3.56–3.64(2H,m), 3.82(3H, s), 4.03(2H, t, J=5.1 Hz), 4.2–4.4(1H, m, NH), 4.6–4.9(1H, m, NH), 6.67(1H, s), 6.80–6.91(4H, m), 7.13 (2H, d, J=8.8 Hz), 7.22(2H, d, J=9.0 Hz).
MS (ESI+). 457.1(M+Na).
IR (NBr), 1627.6cm−1

EXAMPLE 191

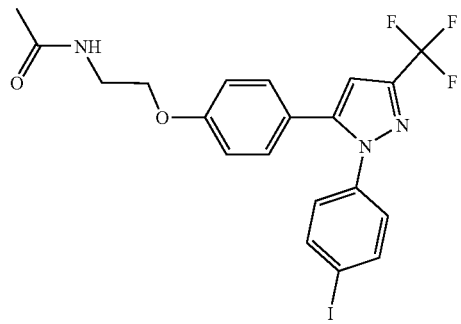
(E0191)

This compound was obtained according to a similar manner to that of E0184.

IR (film): 3299.6, 1658.5, 1550.5, 1515.8, 1467.6, 1240.0, 1164.8, 1132.0, 975.8, 829.2, 755.9 cm−1.

EXAMPLE 192

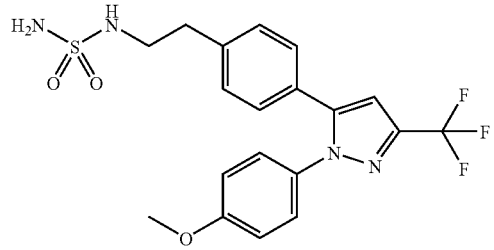
(E0192)

E0158 (250 mg) was suspended in AcOEt 5 ml and was partitioned between AcOEt and saturated aqueous sodium bicarbonate solution. The organic layer was washed with aqueous sodium chloride solution, dried over magnesium sulfate, and concentrated in vacuo. The residue was dissolved in dimethoxyethane 5 ml, sulfamide 181 mg was added and refluxed for 2days. The reaction mixture was concentrated in vacuo, and the residue was purified by silica gel column chromatography eluted with MeOH/ CHC13=1%, 2%, then 3%. Obtained amorphous powder was crystallized from EtOH-diisopropyl ether to give E0192 153 mg as a white powder.

mp. 127–128° C.
IR (KBr): 3357, 1707, 1693, 1647, 1564, 1549, 1529, 1514cm−1
Mass (ESI+): 441 (M+H)+
400 MHz1HNMR(DMSO-d6,d):2.76–2.80(2H,m), 3.06–3.11(2H, m), 3.79(3H,s), 6.53(2H, s), 6.53–6.61(1H, broad),7.00(2H, d, J=8.9 Hz), 7.12(1H, s), 7.21(2H, d, J=8.5 Hz), 7.24(2H, d, J=8.5 Hz), 7.29(2H, d, J=8.9 Hz)

EXAMPLE 193

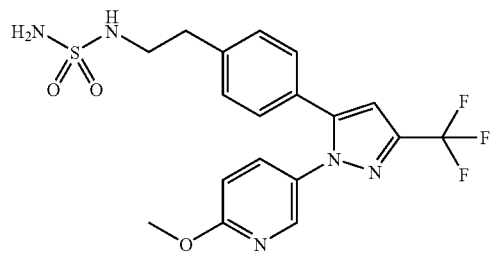
(E0193)

E0193 was prepared from E0294 in a similar manner to that of E0192.

White Powder
mp.114–115° C.
IR (KBr): 3489, 3469, 3458, 3435, 3425, 3398, 3363, 3280, 1647, 1500 cm−1
Mass (ESI+): 442 (M+H)+
200 MHz 1HNMR (DMSO-d6, d): 2.75–2.83(2H, m)), 3.00–3.20(2H, m), 3.88(3H, s), 6.45–6.67(3H, m), 6.92(1H, d, J=8.7 Hz), 7.18(1H, s), 7.21–7.31(4H, m), 7.76(1H, dd, J=2.6,8.7 Hz), 8.19(1H, d, J=2.6 Hz)

EXAMPLE 194

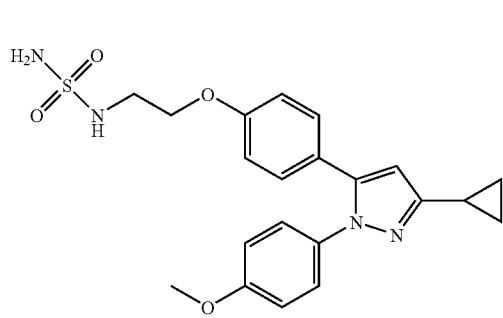

E0194 was prepared from E0322 in a similar manner to that of E0192.
White Powder
mp. 142–143° C.
IR (KBr): 3415, 3323, 3111, 3093, 3010, 2962, 1614, 1516cm−1
Mass (ESI+): 429 (M+H)+
200 MHz 1HNMR(DMSO-d6, d): 0.68–0.76(2H,m), 0.85–0.95(2H, m), 1.92(1H,m), 3.15–3.31(2H,m), 3.76(3H, s), 4.00–4.07(2H, m), 6.25(1H, 1), 6.60(2H,brs), 6.72(1H, brs), 6.86–6.96(4H, m), 7.10(2H, d, J=8.7 Hz), 7.13(2H, d, J=8.9 Hz)

EXAMPLE 195

(E0195)

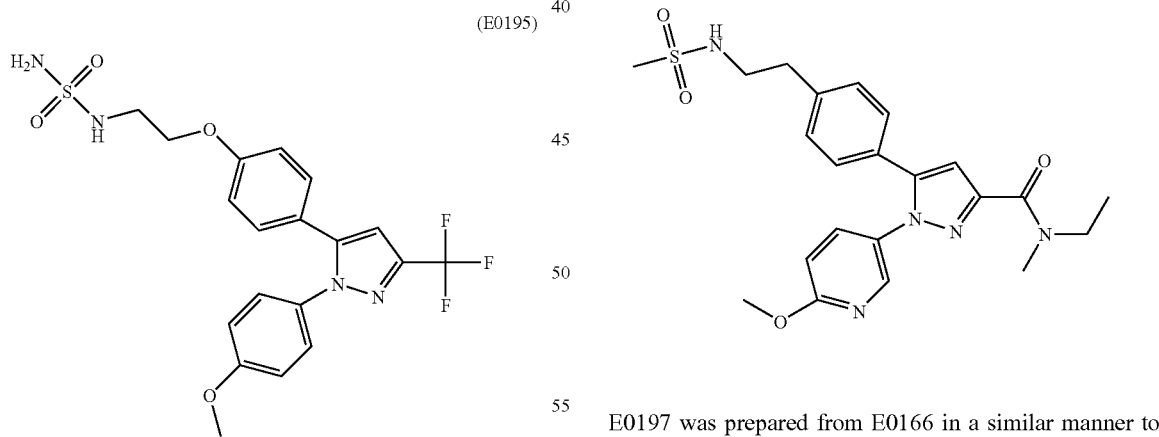

This compound was obtained according to a similar manner to that of E0192.
NMR (CDC13), 3.50–3.59(2H,m), 3.82(3H, s), 4.14(2H, t, J=4.9 Hz), 6.68(1H, s), 6.80–6.90(4H, m), 7.15(2H, d, J=8.8 Hz), 7.22(2H, d, J=9.0 Hz).
IR (KBr); 1612, 1552cm−1.
MS (ESI+), 479.1(M+Na).

EXAMPLE 196

(E0196)

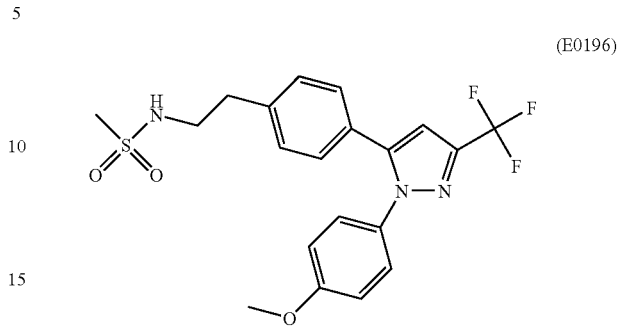

To a solution of E0158 (100 mg) and Et3N (53 ul) in CHC13 (10 ml) was added MsCl (29 ul) at room temperature. After stirring for 1 hour, the reaction mixture was poured onto water and CHC13. The aqueous layer was separated and extracted with CHC13. The combined organic layer was washed with water and brine, dried over Na2SO4, filtered and evaporated under reduced pressure. The residue was column chromatographed on silica gel (50 ml) and crystalized to give 75 mg (68%) of E0196 as a powder.
IR (film): 3284.2, 1513.9, 1319.1, 1240.0, 1151.3, 973.9cm−1.

EXAMPLE 197

(E0197)

E0197 was prepared from E0166 in a similar manner to that of E0196.
mp.137–138° C.
IR (KBr): 3222, 1691, 1684, 1658, 1645, 1610, 1566, 1547, 1531 cm−1
Mass (ESI+): 458 (M+H)+
200 MHz 1H NMR (DMSO-d6, d) 1.09–1.22(3H, m), 2.73–2.81(2H, m), 2.80(3H, s), 2.98,3.28(3H, s), 3.09–3.30 (2H, m), 3.48,3.71(2H, q, J=7.0,6.8 Hz),3.87(3H, s), 6.88–6.93(2H,m),7.10(1H,brs), 7.22(2H, d, J=8.5 Hz), 7.28 (2H, d, J=8.5 Hz), 7.64–7.73(1H, m), 8.15(1H, d, J=2.5 Hz)

EXAMPLE 198

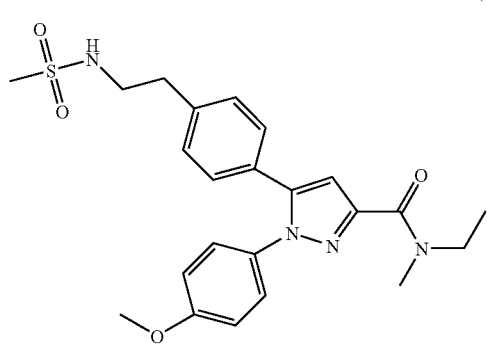
(E0198)

E0198 was prepared from E0167 in a similar manner to that of E0196.

mp.162–163° C.

IR (KBr): 3224, 1610, 1547, 1512cm−1

Mass (ESI+): 457 (M+H)+

200 MHz 1H NMR (DMSO-d6, d): 1.08–1.22(3H, m), 2.76(2H, t, J=7.2 Hz), 2.80(3H, s), 2.98,3.29(3H, s), 3.12–3.23(2H, m), 3.48,3.73(2H, q, J=7.2,6.9 Hz), 3.78(3H, s), 6.84,6.87(1H, s), 6.98(2H, d, J=9.0 Hz), 7.09(1H, t, J=5.7 Hz), 7.16–7.26(6H, m)

EXAMPLE 199

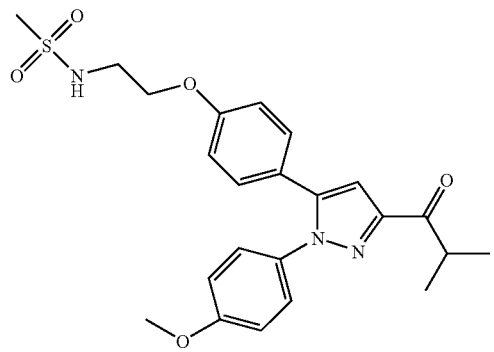
(E0199)

E0199 was prepared from E0234 in a similar manner to that of E0196.

White Powder, mp. 155° C.

IR (KBr): 3265, 2974, 2937, 1682, 1612, 1512cm−1

Mass (ESI+): 458 (M+H)+

200 MHz 1HNMR (DMSO-d6, d): 1.15(6H, d, J=6.8 Hz), 2.94(3H, s), 3.27–3.36(2H, m), 3.68(1H, m), 3.79(3H, s), 4.03(2H, t, J=5.5 Hz), 6.93(2H, d, J=8.8 Hz), 6.98(1H, s), 7.00(2H, d, J=8.9 Hz), 7.19(2H, d, J=8.8 Hz), 7.28(2H, d, J=8.9 Hz), 7.17–7.30(1H, overlapping)

EXAMPLE 200

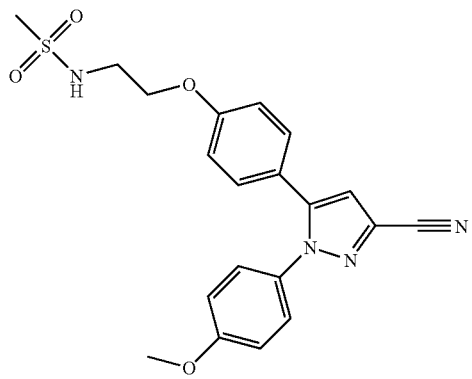
(E0200)

E0200 was prepared from E0235 in a similar manner to that of E0196.

White Powder mp. 149–153° C.

IR (KBr): 3321, 1693, 1658, 1647, 1610, 1547, 1510cm−1

Mass (ESI+): 413 (M+H)+

200 MHz 1HNMR (DMSO-d6, d): 2.93(3H, s), 3.27–3.35 (2H, m), 3.79(3H, s), 4.03(2H, t, J=5.5 Hz), 6.95(2H, d, J=8.7 Hz), 7.01(2H, d, J=9.0 Hz), 7.18(2H, d, J=8.7 Hz), 7.28(2H, d, J=9.0 Hz), 7.31(1H, s), 7.15–7.31(1H, overlapping)

EXAMPLE 201

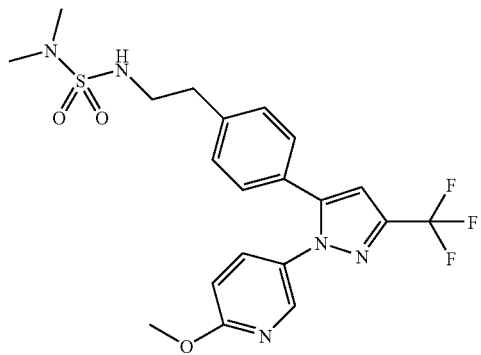
(E0201)

E0201 was prepared from E0294 in a similar manner to that of E0196.

IR (neat): 3298, 2952, 2885, 1612, 1566, 1547, 1529cm−1

Mass (ESI+): 470 (M+H)+

200 MHz 1HNMR (DMSO-d6, d): 2.56(6H, s), 2.71–2.79 (2H, m), 3.07–3.17(2H, m), 3.88(3H, s), 6.92(1H, d, J=8.7 Hz), 7.18(1H, s), 7.19–7.30(5H, m), 7.77(1H, dd, J=8.7,2.6 Hz), 8.18(1H, d, J=2.6 Hz)

EXAMPLE 202

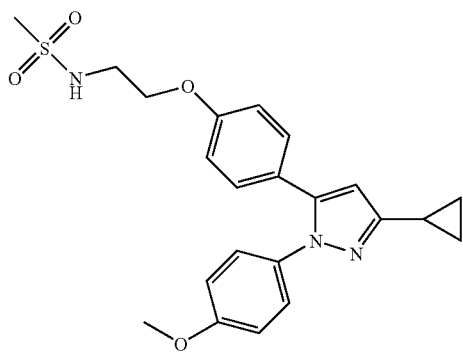
(E0202)

E0202 was prepared from E0322 in a similar manner to that of E0196.

White Powder mp. 166–168° C.

IR (KBr): 3093, 2964, 2873, 2854, 1614, 1516cm-1

Mass (ESI+): 428 (M+H)+

200 MHz1HNMR (DMSO-d6, d): 0.68–0.76(2H, m), 0.85–0.95(2H, m), 1.92(1H, m), 2.93(3H, s), 3.27–3.36(2H, m), 3.76(3H, s), 3.98–4.04(2H, m), 6.25(1H, s), 6.90(2H, d, J=8.7 Hz), 6.92(2H, d, J=8.9 Hz), 7.11(2H, d, J=8.7 Hz), 7.13(2H, d, J=8.9 Hz), 7.27(1H, t, J=5.8 Hz)

EXAMPLE 203

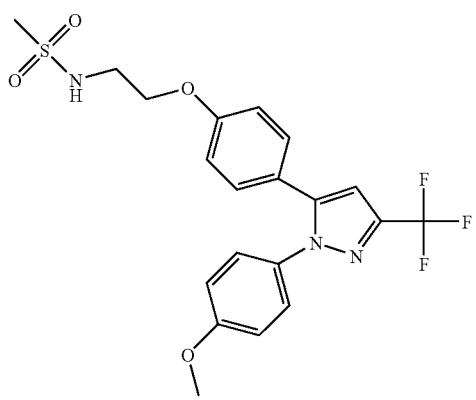
(E0203)

This compound was obtained according to a similar manner to that of E00196.

MS (ESI+); 454.1(MH+).

IR (KBr); 1612.2, 1515.8cm-1.

NMR (CDCl3), 3.03(3H, s), 3.51–3.59(2H, m), 3.82(3H, s), 4.10(2H, t, J=4.9 Hz), 6.68(1H, s), 6.82(1H, d, J=8.7 Hz), 6.88(1H, d, J=8.9 Hz), 7.15(1H, d, J=8.7 Hz), 7.22(1H, d, J=8.9 Hz).

EXAMPLE 204

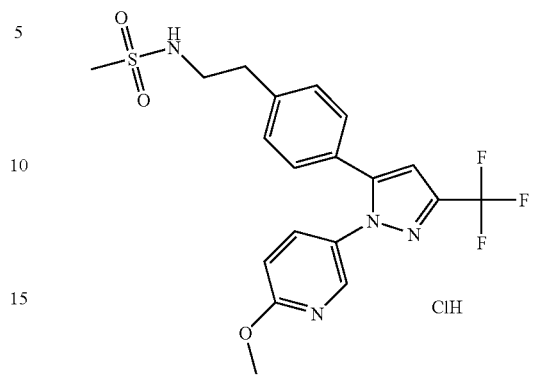
(E0204)

This compound was obtained according to a similar manner to that of E0196.

NMR (DMSO-d6); 2.80(3H, s), 2.73–2.84(2H,m), 3.13–3.22(2H, m), 3.88(3H, s), 6.92(1H, d, J=9.0 Hz), 7.08–7.13(1H, m), 7.19(1H, s), 7.22–7.33(4H, m), 7.76(1H, dd, J=9.0, 2.6 Hz), 8.19(1H, d, J=2.6 Hz).

MS (ESI+),463.1(M+Na).

IR (KBr), 3136, 1614, 1554, 1144cm-1.

EXAMPLE 205

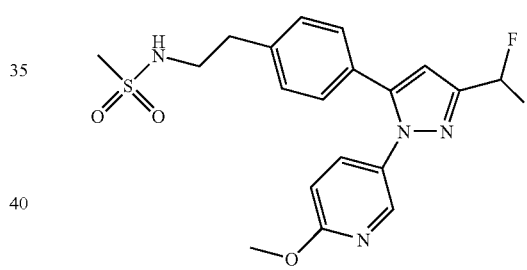
(E0205)

This compound was obtained according to a similar manner to that of E0196.

EXAMPLE 206

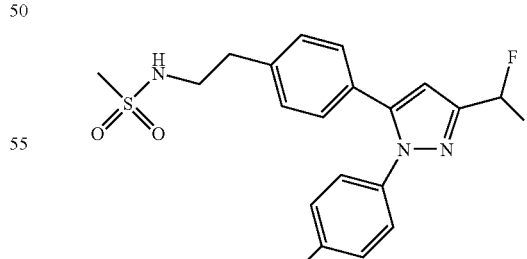
(E0206)

This compound was obtained according to a similar manner to that of E0196.

mp: 134.2–134.5° C.

IR (film): 3284.2, 1610.3, 1513.9, 1457.9, 1321.0, 1251.6, 1151.3, 1083.8, 1031.7, 838.9, 802.2, 757.9 cm-1.

EXAMPLE 207

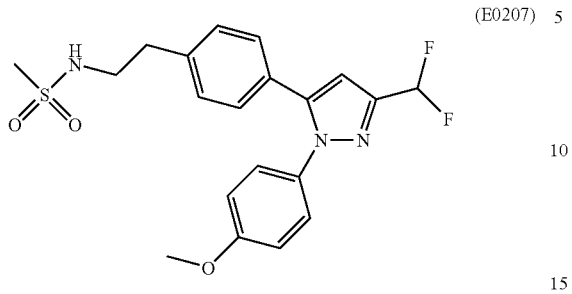
(E0207)

This compound was obtained according to a similar manner to that of E00196.

IR (film): 3286.11, 1606.41, 1513.85, 1457.92, 1319.07, 1251.58, 1153.22, 1081.87, 1029.80, 836.955 cm−1.

EXAMPLE 208

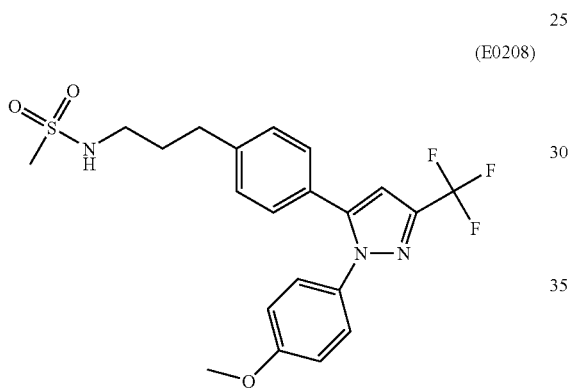
(E0208)

This compound was obtained according to a similar manner to that of E0196.

IR (film): 3284.2, 1513.9, 1317.1, 1240.0, 1153.2 cm−1.

EXAMPLE 209

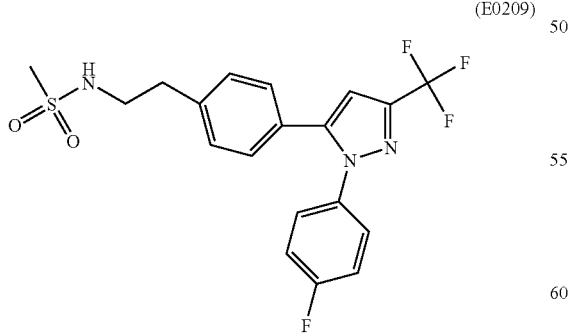
(E0209)

This compound was obtained according to a similar manner to that of E0196.

IR (film): 3286.1, 1511.9, 1321.0, 1230.4, 1155.2, 975.8, 842.7, 756.0 cm−1.

EXAMPLE 210

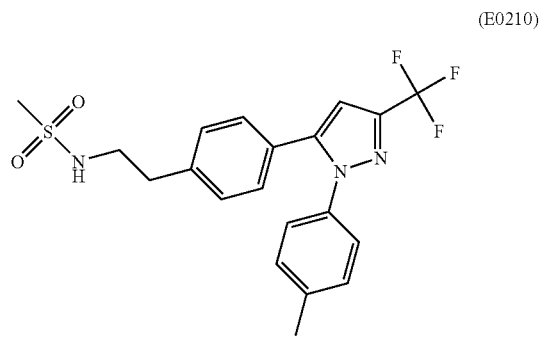
(E0210)

This compound was obtained according to a similar manner to that of E0196.

IR (film): 3284.2, 1511.9, 1469.5, 1321.0, 1236.2, 1153.2, 975.8, 821.5, 756.0 cm−1.

EXAMPLE 211

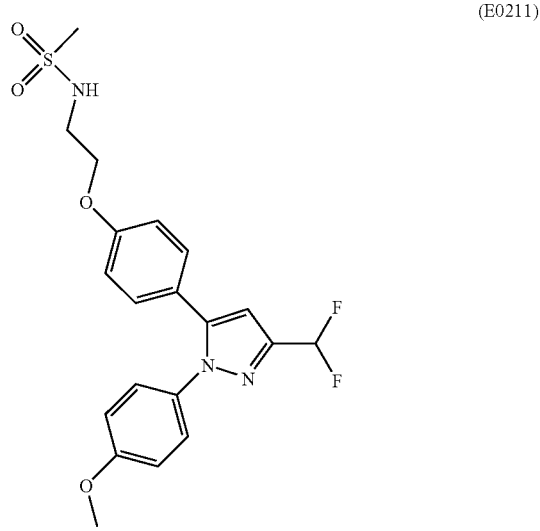
(E0211)

This compound was obtained according to a similar manner to that of E0196.

IR (film): 3289.9, 1612.2, 1513.9, 1322.9, 1251.6, 1155.1, 1085.7, 1029.8, 975.8, 836.9, 796.4 cm−1.

EXAMPLE 212

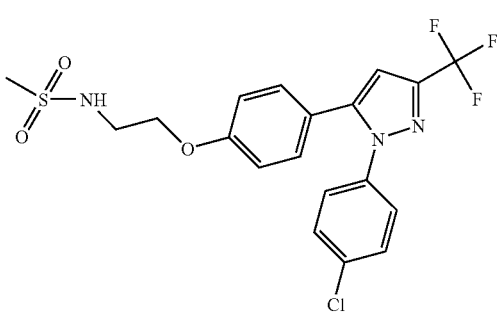
(E0212)

This compound was obtained according to a similar manner to that of E0196.

IR (film): 3266.8, 1612.2, 1469.5, 1321.0, 1240.0, 1153.2, 1097.3, 975.8, 835.0 cm−1.

EXAMPLE 213

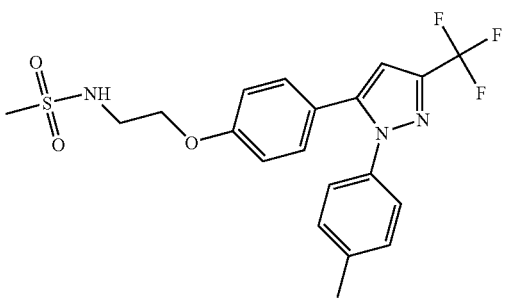
(E0213)

This compound was obtained according to a similar manner to that of E0196.

IR (film): 3288.0, 1612.2, 1322.9, 1240.0, 1153.2, 975.8, 946.9 cm−1.

EXAMPLE 214

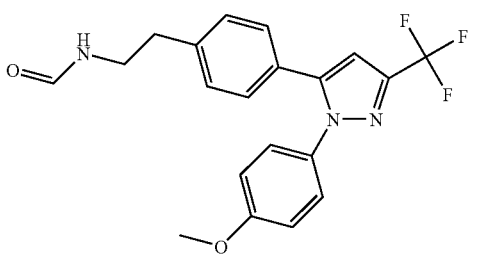
(E0214)

A mixture of E0158 (180 mg), formic acid (38 ul), and WSCD (155 mg) in Et3N (0.3 ml) and THF (5 ml) was stirred at room temperature for 1 hour. After addition of water and EtOAc, the aqueous layer was separated and extracted twice with EtOAc. The combined organic layer was washed with 1NHCl, sat.NaHCO3, water and brine, dried over Na2SO4, filtered and evaporated under reduced pressure. The residue was column chromatographed on silica gel (Hex/EtOAc=2:1) to give 136 mg (70%) of E0214 as a powder.

IR (film): 1670.1, 1513.9, 1238.1, 1160.9, 1130.1 cm−1.

EXAMPLE 215

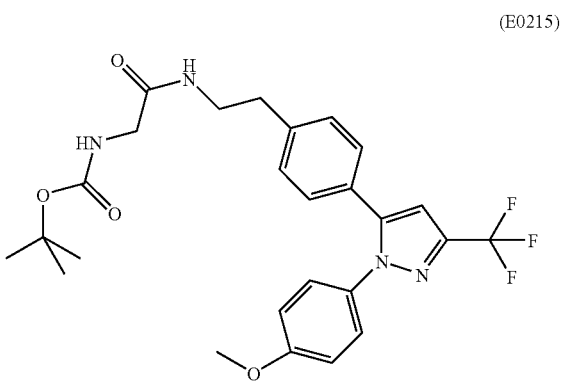
(E0215)

A mixture of E0158 (250 mg), BocGly (132 mg), WSCD (127 mg) and HOBt (110 mg) in Et3N (114 ul) and CH2Cl2 (30 ml) was stirred at room temperature. After stirring for 15 hour, the reaction mixture was poured onto water and CHCl3. The aqueous layer was separated and extracted with CHCl3. The combined organic layer was washed with water and brine, dried over Na2SO4, filtered and evaporated under reduced pressure. The residue was column chromatographed on silica gel (50 ml) and crystalized to give 325 mg (99%) of E0215 as an oil.

EXAMPLE 216

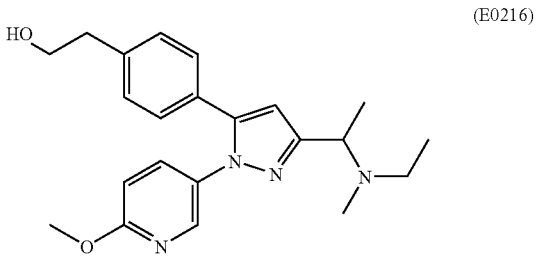
(E0216)

E0216 was prepared in a similar manner to that of E0215. oil

IR (neat): 3431, 3421, 3404, 3400, 2939, 1614, 1570, 1547 cm−1

Mass (ESI+): 381 (M+H)+

200 MHz 1H NMR (DMSO-d6, d) 1.09–1.23 (3H, m), 2.72 (2H, t, J=6.9 Hz), 2.98, 3.29 (3H, s), 3.42–3.77 (4H, m), 3.88 (3H, s), 6.86–6.93 (2H, m), 7.19 (2H, d, J=8.5 Hz), 7.24 (2H, d, J=8.5 Hz), 7.65–7.74 (1H, m), 8.15 (1H, d, J=2.6 Hz)

EXAMPLE 217

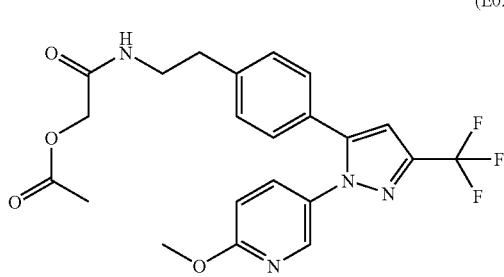
(E0217)

E0217 was prepared from E0294 and acetoxyacetic acid in a similar manner to that of E0215.

oil

Mass (ESI+): 463 (M+H)+

200 MHz 1H NMR (DMSO-d6, d): 2.07 (3H, s), 2.69–2.77 (2H, m), 3.24–3.33 (2H, m), 3.88 (3H, s), 4.40 (2H, s), 6.92 (1H, d, J=8.7 Hz), 7.18 (1H, s), 7.24 (4H, s), 7.75 (1H, dd, J=2.7, 8.7 Hz), 8.10 (1H, t, J=5.6 Hz), 8.19 (1H, d, J=2.7 Hz)

EXAMPLE 218

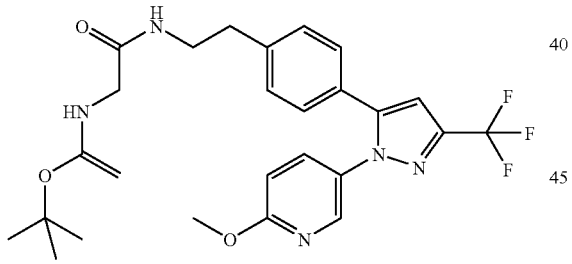
(E0218)

E0218 was prepared from E0294 and N-tert-butoxycarbonyl glycine in a similar manner to that of E0215 using N-methylmorpholine 55.8 mg instead of triethylamine.

Amorphous Powder

IR (neat): 3315, 1707, 1693, 1684, 1676, 1658, 1649, 1624, 1614, 1564, 1547, 1533, 1510, 1500 cm−1

Mass (ESI+): 520 (M+H)+

200 MHz 1H NMR (DMSO-d6, d): 1.37 (9H, s), 2.67–2.75 (2H, m), 3.22–3.33 (2H, m), 3.47 (2H, d, J=6.0 Hz), 3.88 (3H, s), 6.80–7.00 (1H, overlapping), 6.92 (1H, d, J=8.8 Hz), 7.17 (1H, s), 7.24 (4H, s), 7.75 (1H, dd, J=8.8, 2.7 Hz), 7.86 (1H, t, J=5.6 Hz), 8.19 (1H, d, J=2.7 Hz)

EXAMPLE 219

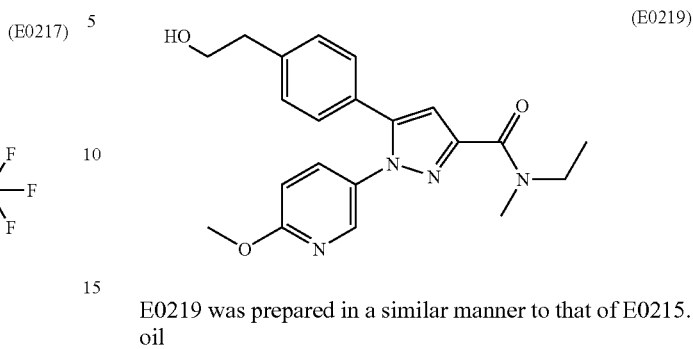
(E0219)

E0219 was prepared in a similar manner to that of E0215.

oil

IR (KBr): 3329, 3313, 3303, 1620, 1564, 1547, 1512 cm−1

Mass (ESI+): 380 (M+H)+

200 MHz 1H NMR (DMSO-d6, d): 1.08–1.22 (3H, m), 2.71 (2H, t, J=6.9 Hz), 2.97, 3.29 (3H, s), 3.42–3.78 (4H, m), 3.78 (3H, s), 4.65 (1H, t, J=5.1 Hz), 6.82, 6.85 (1H, s), 6.98 (2H, d, J=8.9 Hz), 7.12–7.27 (6H, m)

EXAMPLE 220

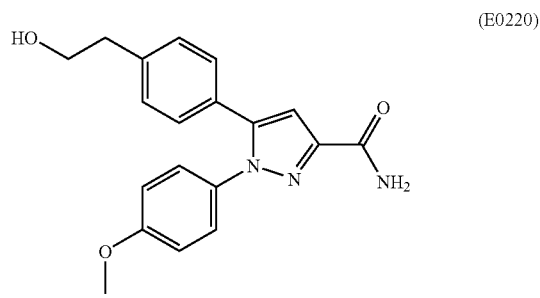
(E0220)

E0220 was prepared in a similar manner to that of E0215.

EXAMPLE 221

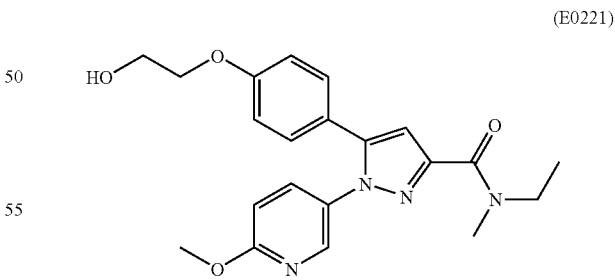
(E0221)

E0221 was prepared in a similar manner to that of E0215.

White Powder mp. 95–101° C.

IR (KBr): 3421, 1693, 1647, 1603, 1566, 1549, 1516 cm−1

Mass (ESI+): 396 (M+H)+

200 MHz 1H NMR (DMSO-d6,d): 1.08–1.22 (3H,m), 2.97, 3.29 (3H, s), 3.42–3.74 (4H, m), 3.78 (3H, s), 3.95–4.00 (2H, m), 4.86 (1H, t, J=5.4 Hz), 6.78, 6.81 (1H, s), 6.91 (2H, d, J=8.8 Hz), 6.98 (2H, d, J=8.8 Hz), 7.16 (2H, d, J=8.8 Hz), 7.23 (2H, d, J=8.8 Hz)

EXAMPLE 222

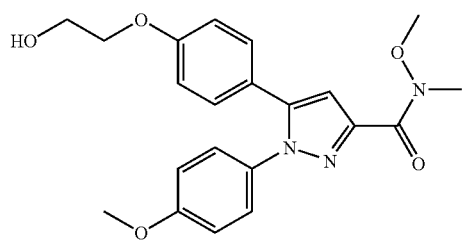
(E0222)

E0222 was prepared in a similar manner to that of E0215.
White Powder
Mass (ESI+): 398 (M+H)+
200 MHz 1H NMR (DMSO-d6, d): 3.38 (3H, s), 3.65–3.74 (2H, m), 3.77 (3H,s), 3.78 (3H, s), 3.95–4.01 (2H,m), 4.87 (1H, t, J=5.4 Hz), 6.89 (1H, s), 6.92 (2H, d, J=8.8 Hz), 6.99 (2H, s, J=8.9 Hz), 7.17 (2H, d, J=8.8 Hz), 7.24 (2H, d, J=8.9 Hz)

EXAMPLE 223

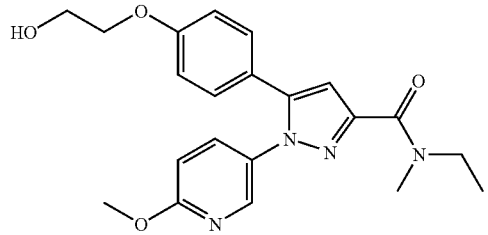
(E0223)

E0223 was prepared in a similar manner to that of E0215.
White Powder
mp. 110–111° C.
IR (KBr): 3425, 2979, 2945, 1606, 1570, 1549 cm−1
Mass (ESI+): 397 (M+H)+
200 MHz 1H NMR (DMSO-d6, d): 1.09–1.23 (3H, m), 2.98,3.28 (3H, s), 3.42–3.73 (4H, m), 3.87 (3H, s), 3.96–4.02 (2H, m), 4.87 (1H, t, J=5.3 Hz), 6.82–6.97 (4H, m), 7.21 (2H, d, J=8.7 Hz), 7.63–7.72 (1H, m), 8.14 (1H, d, J=2.6 Hz)

EXAMPLE 224

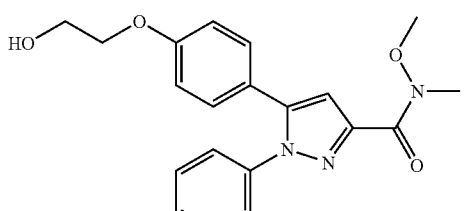
(E0224)

E0224 was prepared in a similar manner to that of E0215.
White Powder
Mass (ESI+): 399 (M+H)+
200 MHz 1H NMR (DMSO-d6, d): 3.37 (3H, s), 3.66–3.74 (2H, m), 3.77 (3H, s), 3.88 (3H, s), 3.96–4.02 (2H, m), 4.87 (1H, t, J=5.5 Hz), 6.88–6.97 (4H, m), 7.21 (2H, d, J=8.7 Hz), 7.69 (1H, dd, J=2.7, 8.8 Hz), 8.16 (1H, d, J=2.7 Hz)

EXAMPLE 225

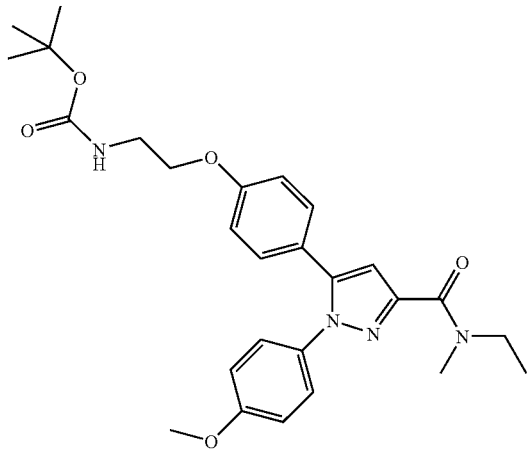
(E0225)

E0225 was prepared in a similar manner to that of E0215.
White Powder
Mass (ESI+): 495 (M+H)+
400 MHz 1H NMR (DMSO-d6, d): 1.12, 1.18 (3H, t, J=7.0 Hz), 1.37 (9H, s), 2.97,3.29 (3H, s), 3.24–3.28 (2H, m), 3.48,3.45 (2H, q, J=7.0 Hz), 3.78 (3H, s), 3.95 (2H, t, J=5.7 Hz), 6.78,6.81 (1H, s), 6.91 (2H, d, J=8.8 Hz), 6.98 (2H, d, J=8.8 Hz), 7.00 (1H, overlapping), 7.16 (2H, d, J=8.8 Hz), 7.23 (2H, d, J=8.9 Hz)

EXAMPLE 226

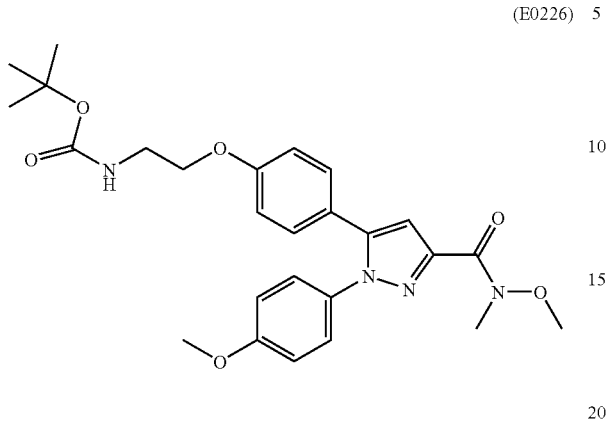
(E0226)

E0226 was prepared in a similar manner to that of E0215.
White Powder
Mass (ESI+): 497 (M+H)+
400 MHz 1H NMR (DMSO-d6, d): 1.37 (9H, s), 3.25–3.29 (2H, m), 3.37 (3H, brs), 3.76 (3H, s), 3.78 (3H, s), 3.95 (2H, t, J=5.7 Hz), 6.88 (1H, s), 6.91 (2H, d, J=8.8 Hz), 6.99 (2H, d, J=8.9 Hz), 6.97–7.00 (1H, br), 7.17 (2H, d, J=8.8 Hz), 7.24 (2H, d, J=8.9 Hz)

EXAMPLE 227

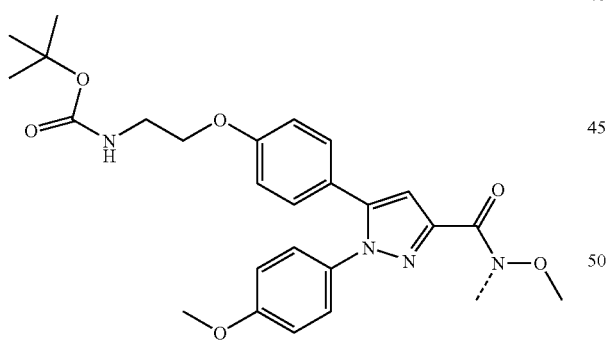
(E0227)

E0227 was prepared in a similar manner to that of E0215.
White Powder
Mass (ESI+): 498 (M+H)+
200 MHz 1H NMR (DMSO-d6, d): 1.37 (9H, s), 3.22–3.33 (2H, m), 3.37 (3H, s), 3.77 (3H, s), 3.88 (3H, s), 3.93–3.99 (2H, m), 6.88–7.05 (5H, m), 7.22 (2H, d, J=8.6 Hz), 7.69 (1H, dd, J=2.7, 8.8 Hz), 8.16 (1H, d, J=2.7 Hz)

EXAMPLE 228

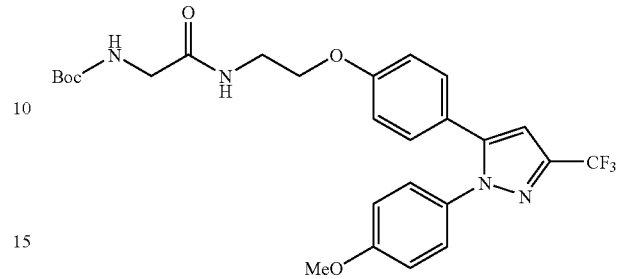
(E0228)

This compound was obtained according to a similar manner to that of E0215 as an oil (371.9 mg, 96%).
NMR (CDCl3); 1.43 (9H, s), 3.65–3.73 (2H, m), 3.79–3.82 (2H, m), 3.82 (3H, s), 4.03 (2H, t, J=5.2 Hz), 6.67 (1H, s), 6.79–6.89 (4H, m), 7.14 (2H, d, J=8.7 Hz), 7.22 (2H, d, J=9.0 Hz).
MS (ESI+); 557.2 (M+Na).

EXAMPLE 229

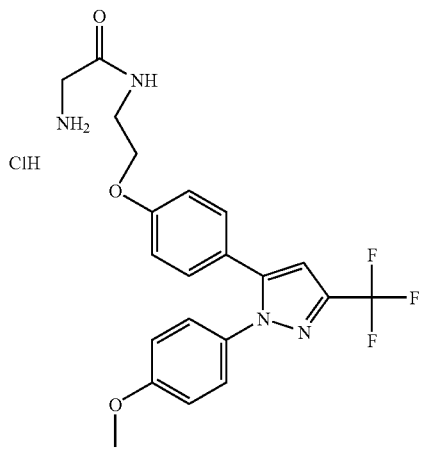
(E0229)

This compound was obtained according to a similar manner to that of E0289 as a white powder.
NMR (DMSO-d6), 3.49–3.63 (4H, m), 3.79 (3H, s), 4.03 (2H, t, J=4.8 Hz), 6.92–7.08 (5H, m), 7.21 (2H, d, J=8.7 Hz), 7.28 (2H, d, J=8.9 Hz).
MS (ESI−), 433.2 (M−H).
IR (KBr); 1683 cm−1

EXAMPLE 230

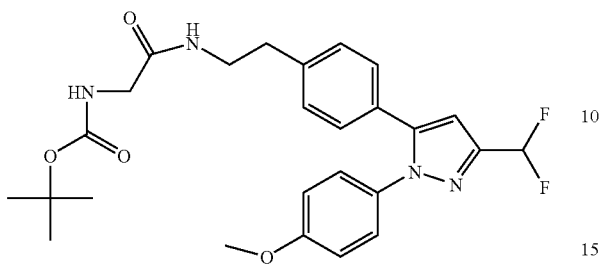

This compound was obtained according to a similar manner to that of E0215.

IR (film): 3320.82, 1706.69, 1668.12, 1515.77, 1249.65, 1168.65, 1031.73 cm−1.

EXAMPLE 231

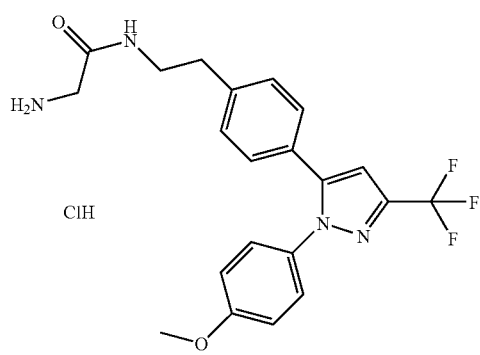

A mixture of E0215 (300 mg) and 4NHCl in dioxane (5.8 ml) was stirred at room temperature for 1.0 hour. After then, the reaction mixture was evaporated under reduced pressure to give 260 mg (99%) of E0231 as an amorphous.

IR (film): 3226.3, 1679.7, 1513.9, 1251.6, 1083.8, 1029.8, 837.0 cm−1.

EXAMPLE 232

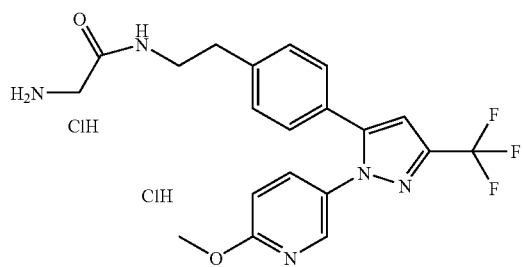

E0232 was prepared in a similar manner to that of E0231. White Powder

IR (KBr): 3458, 3435, 3404, 3244, 3078, 3026, 1671, 1614, 1579, 1566, 1554, 1500 cm-1

Mass (ESI+): 420 (M+H)+

200 MHz 1H NMR (DMSO-d6, d): 2.71–2.79 (2H, m), 3.30–3.41 (2H, m), 3.44–3.54 (2H, m), 3.88 (3H, s), 6.93 (1H, d, J=8.7 Hz), 7.22 (1H, s), 7.22–7.33 (4H, m), 7.77 (1H, dd, J=2.7, 8.7 Hz), 8.10 (2H, br), 8.19 (1H, d, J=2.7 Hz), 8.55 (1H, t, J=5.4 Hz)

EXAMPLE 233

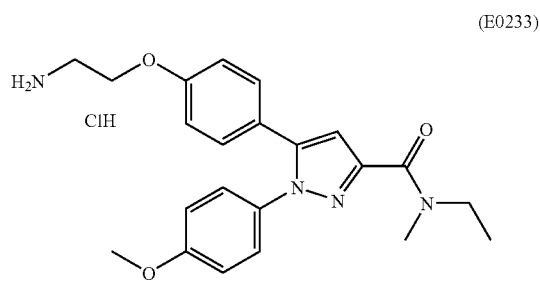

E0233 was prepared in a similar manner to that of E0231. White Powder mp. 207–209° C.

IR (KBr) :2966, 2933, 2871, 2750, 1606, 1566, 1549, 1512 cm-1

Mass (ESI+): 395 (M+H)+

200 MHz 1H NMR (DMSO-d6, d): 1.08–1.22 (3H, m), 2.97,3.29 (3H, s), 3.17–3.22 (2H, m), 3.40–3.80 (2H, m), 3.78 (3H, s), 4.14–4.20 (2H, m), 6.80,6.83 (1H, s), 6.94–7.01 (4H, m), 7.18–7.26 (4H, m), 8.13 (2H, brs)

EXAMPLE 234

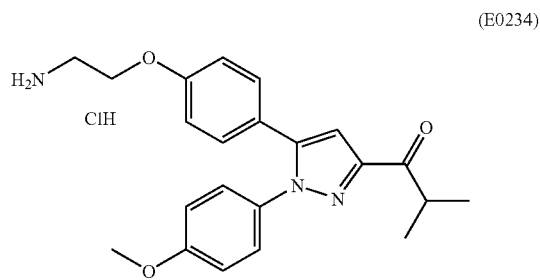

E0234 was prepared in a similar manner to that of E0231. White Powder mp. 129–142° C.

IR (KBr): 3471, 3437, 2968, 2933, 1674, 1639, 1631, 1612, 1545, 1512 cm-1

Mass (ESI+): 380 (M+H)+

200 MHz 1H NMR (DMSO-d6, d): 1.15 (6H, d, J=6.9 Hz), 3.16–3.22 (2H, m), 3.68 (1H, m), 3.79 (3H, s), 4.15–4.20 (2H, m), 6.94–7.05 (5H, m), 7.22 (2H, d, J=8.8 Hz), 7.29 (2H, d, J=8.9 Hz), 8.15 (2H, brs)

EXAMPLE 235

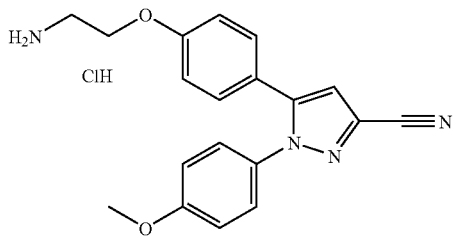
(E0235)

E0235 was prepared and in a similar manner to that of E0231.
White Powder
mp. 186–189° C.
IR (KBr): 3209, 3136, 2968, 2873, 1647, 1610, 1547, 1512 cm−1
Mass (ESI+): 335 (M+H)+
200 bMHz 1H NMR (DMSO-d6, d): 3.19 (2H, t, J=4.9 Hz), 3.79 (3H, s), 4.18 (2H, t, J=4.9 Hz), 6.96–7.05 (4H, m), 7.21 (2H, d, J=8.8 Hz), 7.29 (2H, d, J=9.0 Hz), 7.32 (1H, s), 8.16 (2H, brs)

EXAMPLE 236

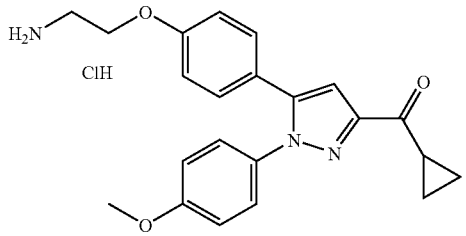
(E0236)

E0236 was prepared in a similar manner to that of E0231.
White Powder
Mass (ESI+): 378 (M+H)+
200 MHz 1H NMR (DMSO-d6, d): 1.04 (4H, d, J=6.1 Hz), 3.04 (1H, m), 3.14–3.22 (2H, m), 3.80 (3H, s), 4.15–4.21 (2H, m), 6.93–7.05 (5H, m), 7.23 (2H, d, J=8.6 Hz), 7.31 (2H, d, J=8.9 Hz), 8.15 (2H, brs)

EXAMPLE 237

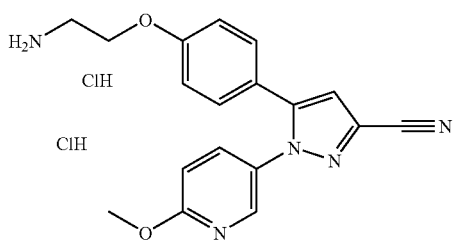
(E0237)

E0237 was prepared in a similar manner to that of E0231.
Amorphous Powder
IR (KBr): 3433, 3425, 3404, 3043, 3028, 3022, 2962, 1658, 1612 cm−1
Mass (ESI+): 336 (M+H)+
200 MHz 1H NMR (DMSO-d6, d): 3.15–3.24 (2H, m), 3.88 (3H, s), 4.16–4.22 (2H, m), 6.94 (1H, d, J=8.8 Hz), 7.01 (2H, d, J=8.7 Hz), 7.25 (2H, d, J=8.7 Hz), 7.36 (1H, s), 7.75 (1H, dd, J=2.6, 8.8 Hz), 8.10–8.30 (2H, br), 8.20 (1H, d, J=2.6 Hz)

EXAMPLE 238

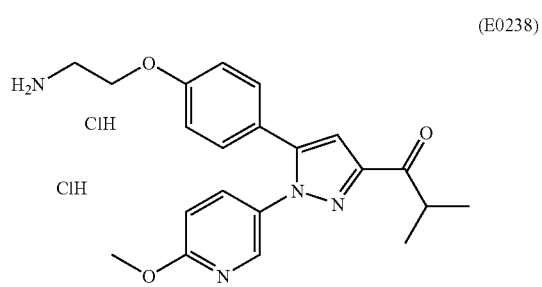
(E0238)

E0238 was prepared in a similar manner to that of E0231.
White Powder
mp. 156–161° C.
IR (KBr): 2970, 1676, 1647, 1612, 1550, 1500 cm−1
Mass (ESI+): 381 (M+H)+
200 MHz 1H NMR (DMSO-d6, d): 1.16 (6H, d, J=6.9 Hz), 3.15–3.24 (2H, m), 3.68 (1H, m), 3.88 (3H, s), 4.16–4.22 (2H, m), 6.91–7.06 (4H, m), 7.26 (2H, d, J=8.7 Hz), 7.75 (1H, dd, J=2.7, 8.9 Hz), 8.18 (1H, d, J=2.7 Hz), 8.22 (2H, brs)

EXAMPLE 239

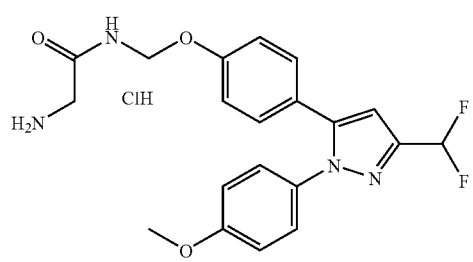
(E0239)

This compound was obtained according to a similar manner to that of E0231.
IR (film): 3220.5, 1679.7, 1513.9, 1461.8, 1251.6, 1081.9, 1029.8, 837.0, 800.3 cm−1.

EXAMPLE 240

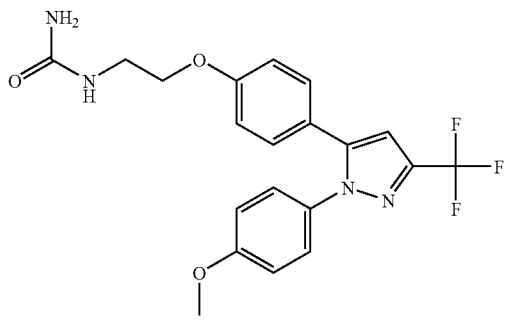
(E0240)

To a solution of E0267 (75.2 mg) in dichloromethane (1 ml) was added triethylamine (30.4 ml) and trimethylsilyl isocyanate (36.9 ml) at 0° C. After stirring for 5 hours, the mixture was quenched with water and extracted with dichloromethane. The combined organic layers were washed with brine, dried over magnesium sulfate, and evaporated under reduced pressure to give oil, which was purified with preparative TLC (1 mm, ethyl acetate) to give oil. The oil was crystallized from a mixture of isopropyl ether, ethyl acetate, and hexane to give E0240 as a white solid (39.1 mg, 51.2%).

NMR (DMSO-d6); 3.27–3.32 (2H, m)), 3.79 (3H, s), 3.94 (2H, t, J=5.6 Hz), 5.52 (2H, brs, NH2), 6.15 (1H, t, J=5.6 Hz, NH), 6.94 (2H, d, J=8.8 Hz), 7.00 (2H, d, J=8.9 Hz), 7.07 (1H, s), 7.20 (2H, d, J=8.8 Hz), 7.28 (2H, d, J=8.9 Hz).

MS (ESI+); 443.2 (M+Na).

IR (KBr), 1685.5, 1656.6 cm−1.

EXAMPLE 241

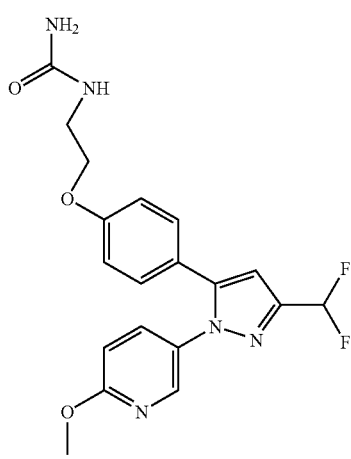
(E0241)

E0241 was prepared from E0194 in a similar manner to that of E0240.

White Powder mp. 139–140° C.

IR (KBr): 3458, 3342, 1691, 1647, 1604, 1572, 1529 cm−1

Mass (ESI+): 404 (M+H)+

200 MHz 1H NMR (DMSO-d6, d): 3.28–3.36 (2H, m), 3.87 (3H, s), 3.92–3.98 (2H, m), 5.52 (2H, brs), 6.15 (1H, t, J=5.5 Hz), 6.88–6.98 (4H, m), 7.10 (1H, t, J=54.4 Hz), 7.22 (2H, d, J=8.7 Hz), 7.69 (1H, dd, J=2.7, 8.8 Hz), 8.14 (1H, d, J=2.7 Hz)

EXAMPLE 242

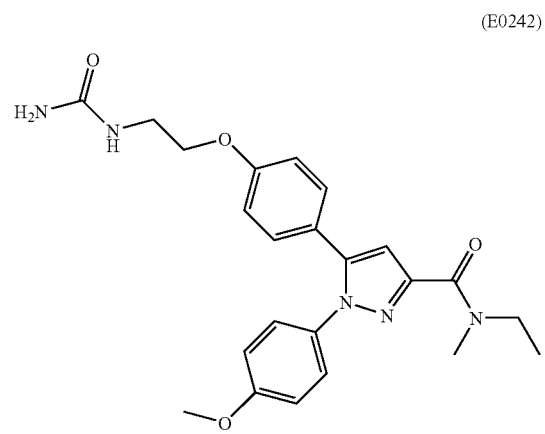
(E0242)

E0242 was prepared in a similar manner to that of E0240.

White Powder mp. 108–113° C.

IR (KBr): 3492, 3435, 3425, 3359, 3298, 1647, 1614, 1564, 1549, 1512 cm−1

Mass (ESI+): 438 (M+H)+

200 MHz 1H NMR (DMSO-d6, d): 1.08–1.22 (3H,m), 2.97, 3.29 (3H, s), 3.20–3.85 (4H, m), 3.78 (3H, s), 3.94 (2H, t, J=5.5 Hz), 5.53 (2H, s), 6.15 (1H, t, J=5.6 Hz), 6.79, 6.81 (1H, s), 6.92 (2H, d, J=8.8 Hz), 6.99 (2H, d, J=8.9 Hz), 7.17 (2H, d, J=8.8 Hz), 7.23 (2H, d, J=8.9 Hz)

EXAMPLE 243

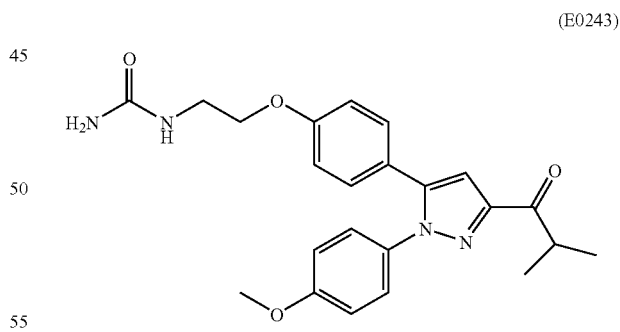
(E0243)

E0243 was prepared from E0234 in a similar manner to that of E0240.

White Powder mp. 144–145° C.

IR (KBr): 3435, 3369, 3176, 2970, 1674, 1612, 1547, 1514 cm−1

Mass (ESI+): 423 (M+H)+

200 MHz 1H NMR (DMSO-d6, d): 1.15 (6H, d, J=6.9 Hz), 3.27–3.36 (2H, m), 3.68 (1H, m), 3.79 (3H, s), 3.90–3.97 (2H, m), 5.53 (2H, s), 6.15 (1H, t, J=5.6 Hz), 6.92

(2H, d, J=8.7 Hz), 6.98 (1H, s), 7.00 (2H, d, J=8.9 Hz), 7.18 (2H, d, J=8.7 Hz), 7.28 (2H, d, J=8.9 Hz)

EXAMPLE 244

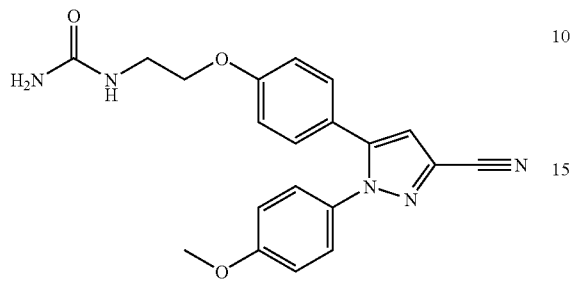
(E0244)

E0244 was prepared from E0235 in a similar manner to that of E0240.
White Powder
mp. 187–190° C.
IR (KBr): 3379, 3201, 1649, 1614, 1579, 1527, 1506 cm−1
Mass (ESI+): 378 (M+H)+
200 MHz 1H NMR (DMSO-d6, d): 3.27–3.34 (2H, m), 3.79 (3H, s), 3.94 (2H, t, J=5.5 Hz), 5.52 (2H, brs), 6.14 (1H, t, J=5.6 Hz), 6.94 (2H, d, J=8.8 Hz), 7.00 (2H, d, J=9.0 Hz), 7.17 (2H, d, J=8.8 Hz), 7.24–7.31 (3H, m)

EXAMPLE 245

(E0245)

E0245 was prepared in a similar manner to that of E0240.
White Powder
mp. 136–137° C.
IR (KBr) :3433, 3342, 3221, 1658, 1612, 1581, 1549, 1512 cm−1
Mass (ESI+): 421 (M+H)+
200 MHz 1H NMR (DMSO-d6, d): 1.04 (4H, d, J=6.2 Hz), 3.03 (1H, m), 3.27–3.36 (2H, m), 3.80 (3H, s), 3.90–3.97 (2H, m), 5.52 (2H, s), 6.14 (1H, t, J=5.6 Hz), 6.93 (2H, d, J=8.8 Hz), 6.97 (1H, s), 7.01 (2H, d, J=8.9 Hz), 7.19 (2H, d, J=8.8 Hz), 7.30 (2H, d, J=8.9 Hz)

EXAMPLE 246

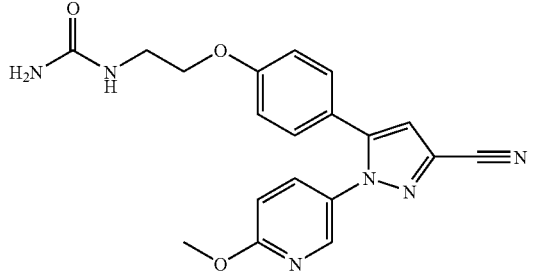
(E0246)

E0246 was prepared in a similar manner to that of E0240.
White Powder
mp. 173–176° C.
IR (KBr): 3473, 3334, 1630, 1624, 1601, 1583 cm−1
Mass (ESI+): 379 (M+H)+
200 MHz 1H NMR (DMSO-d6, d): 3.27–3.36 (2H, m), 3.88 (3H, s), 3.92–3.98 (2H, m), 5.52 (2H, s), 6.14 (1H, t, J=5.7 Hz), 6.93 (1H, d, J=8.8 Hz), 6.97 (2H, d, J=8.8 Hz), 7.21 (2H, d, J=8.8 Hz), 7.35 (1H, s), 7.73 (1H, dd, J=2.7, 8.8 Hz), 8.20 (1H, d, J=2.7 Hz)

EXAMPLE 247

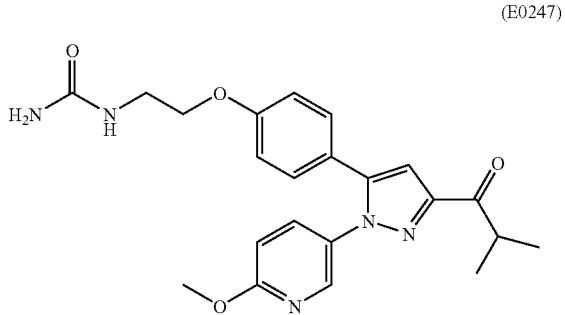
(E0247)

E0247 was prepared in a similar manner to that of E0240.
White Powder
mp. 145–147° C.
IR (KBr) :3367, 3174, 2972, 1689, 1674, 1610, 1566, 1502 cm−1
Mass (ESI+): 424 (M+H)+
200 MHz 1H NMR (DMSO-d6, d): 1.16 (6H, d, J=6.9 Hz), 3.28–3.37 (2H, m), 3.68 (1H, m), 3.88 (3H, s), 3.92–3.98 (2H, m), 5.52 (2H, s), 6.15 (1H, t, J=5.6 Hz), 6.93 (1H, d, J=8.7 Hz), 6.95 (2H, d, J=8.8 Hz), 7.02 (1H, s), 7.22 (2H, d, J=8.8 Hz), 7.73 (1H, dd, J=2.7, 8.7 Hz), 8.19 (1H, d, J=2.7 Hz)]

EXAMPLE 248

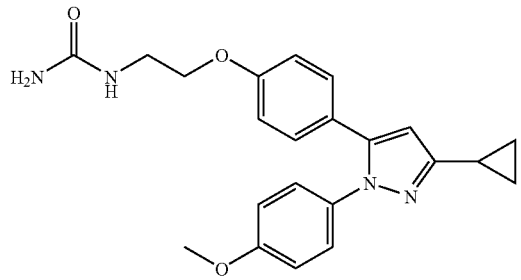
(E0248)

E0248 was prepared in a similar manner to that of E0240.
White Powder
mp. 150.8–151.0° C.
IR (KBr): 3496, 3361, 3294, 1705, 1674, 1647, 1603, 1581, 1568, 1554, 1516 cm−1
Mass (ESI+): 393 (M+H)+
200 MHz 1H NMR (DMSO-d6, d): 0.71–0.77 (2H, m), 0.85–0.92 (2H, m), 1.92 (1H, m), 3.27–3.37 (2H, m), 3.76 (3H, s), 3.92 (2H, t, J=5.5 Hz), 5.51 (2H, s), 6.14 (1H, t, J=5.5 Hz), 6.24 (1H, s), 6.86–6.96 (4H, m), 7.07–7.15 (4H, m)

EXAMPLE 249

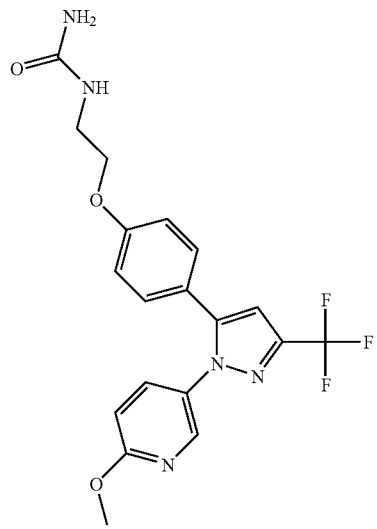
(E0249)

This compound was obtained according to a similar manner to that of E0240 as an amorphous.
NMR (CDCl3), 3.56–3.64 (2H, m), 3.94 (3H, s), 4.04 (2H, t, J=4.9 Hz), 4.50 (2H, brs, NH2), 6.69 (1H, s), 6.76 (1H, d, J=8.8 Hz), 6.84 (2H, d, J=8.8 Hz), 7.12 (2H, d, J=8.8 Hz), 7.58 (1H, dd, J=8.8, 2.8 Hz), 8.05 (1H, d, J=2.8 Hz).
MS (ESI+), 444.1 (M+Na)+. IR(KBr); 1650.8, 1608.3 cm−1.
LCMS (ESI+), 422.27 (MH+).

EXAMPLE 250

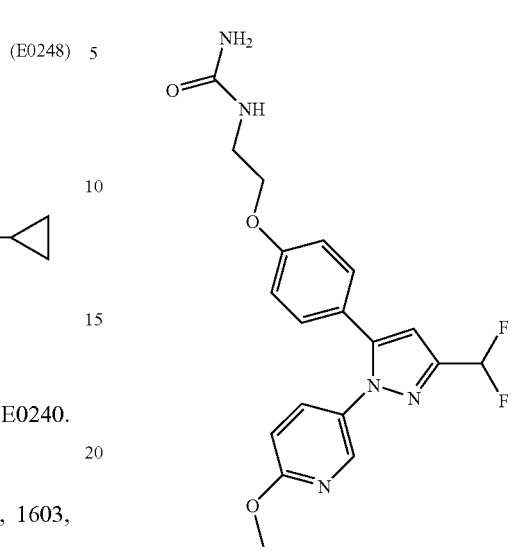
(E0250)

This compound was obtained according to a similar manner to that of E0240 as a white powder.
NMR (CDCl3), 3.55–3.63 (2H, m), 3.93 (3H, s), 4.04 (2H, t, J=5.1 Hz), 4.55 (2H, brs, NH2), 5.23 (1H, brt, J=5.4 Hz, NH), 6.67 (1H, s), 6.75 (1H, t, J=55 Hz), 6.75 (1H, d, J=8.4 Hz), 6.88 (2H, d, J=8.8 Hz), 7.13 (2H, d, J=8.8 Hz), 7.56 (1H, d, J=8.4, 2.9 Hz), 8.04 (1H, d, J=2.9 Hz).
LCMS (ESI+), 404.39 (MH+).
IR (KBr) 1649 cm−1
MP, 141.5–142.1° C.

EXAMPLE 251

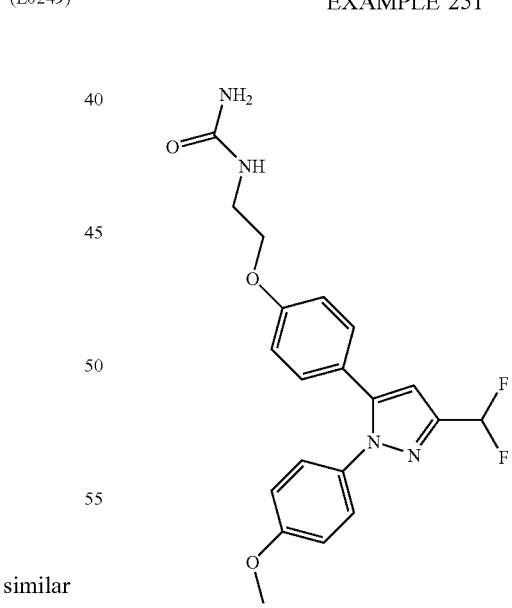
(E0251)

This compound was obtained according to a similar manner to that of E0240 as a powder.
NMR (CDCl3), 3.56–3.64 (2H, m), 3.82 (3H, s), 4.03 (2H, t, J=5.0 Hz), 4.42 (2H, brs), 6.65 (1H, s), 6.76 (1H, t, J=55 Hz), 6.79–6.89 (4H, m), 7.14 (2H, d, J=8.7 Hz), 7.20 (2H, d, J=9.0 Hz).
MS (ESI+), 425 (M+Na)+.

EXAMPLE 252

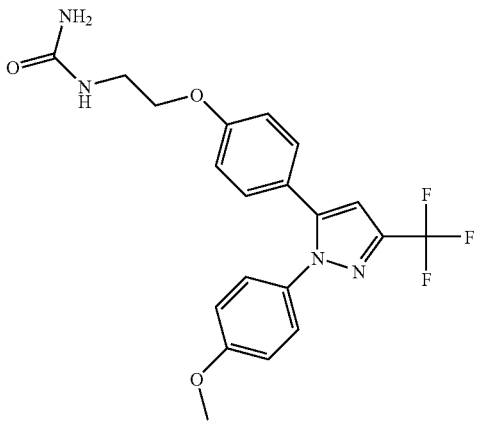

(E0252)

To a solution of E0267 (15.3 g) in ethanol (75 ml) and hydrogen chloride aqueous solution (1N, 220 ml) was added dropwise a solution of sodium cyanate (14.4 g) in water (300 ml) at 45° C. over 5 minutes. After stirring at 45° C. for 4 hours, the mixture was quenched with saturated sodium hydrogen carbonate aqueous solution and extracted with ethyl acetate. The combined organic layers were washed with brine, dried over magnesium sulfate, and evaporated to give powder. The powder was crystallized from ethyl acetate and hexane at room temperature~70° C. to give E0252 as a powder (12.628 g, 81.2%).

The physical data of this compound was identical to previously obtained authentic sample.

EXAMPLE 253

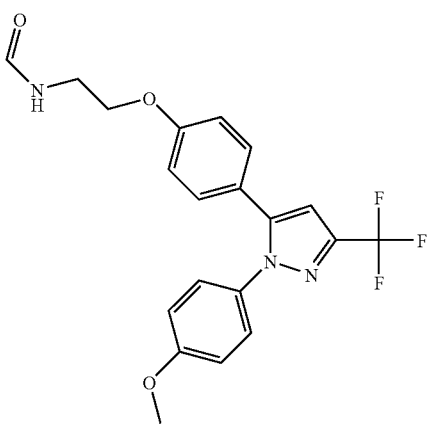

(E0253)

To a solution of E0267 (200 mg) in methanol (1 ml) was added sodium methoxide methanol solution (5.2M, 0.1 ml) at room temperature. After stirring for 20 minutes, the mixture was evaporated to give residue. To the residue was added tetrahydrofuran, and the mixture was filtered and evaporated to give oil. The oil was dissolved in ethyl formate (2 ml) and stirred at room temperature overnight. The mixture was evaporated and purified with preparative TLC (1 mm, 50% ethyl acetate/hexane) to give oil, which was crystallized from isopropyl ether, ethyl acetate, and hexane to give E0253 as a white powder (162.8 mg, 83%).

NMR (CDCl3), 3.68–3.76 (2H, m), 3.82 (3H, s), 4.06 (2H, t, J=5.0 Hz), 6.68 (1H, s), 6.80–6.89 (4H, m), 7.14 (2H, d, J=8.7 Hz), 7.22 (2H, d, J=9.0 Hz), 8.22 (1H, s).

MS (ESI+), 428.2 (M+Na).

IR (KBr), 1660.4, 1614.1 cm−1.

EXAMPLE 254

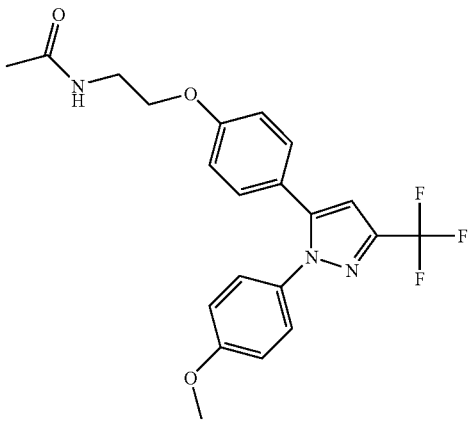

(E0254)

To a solution of E0267 (800 mg) and triethylamine (0.7 ml) in dichloromethane (9 ml) was added dropwise acetyl chloride (0.18 ml) at 0° C. After stirring at room temperature for 1 hour, the mixture was quenched with saturated sodium hydrogen carbonate aqueous solution and extracted with ethyl acetate (×3). The combined organic layers were washed with hydrogen chloride aqueous solution (1N), water, and brine, dried over magnesium sulfate, and evaporated to give oil, which was purified with column chromatography (SiO2 100 ml, eluted with 50% ethyl acetate/hexane) to give oil. The oil was crystallized from a mixture of ethyl acetate and hexane at 50° C. to give E0254 as a solid (768.6 mg, 94.8%).

NMR (CDCl3). 2.01 (3H, s), 3.62–3.70 (2H, m), 3.82 (3H, s), 4.03 (2H, t, J=5.0 Hz), 6.67 (1H, s), 6.80–6.91 (4H, m), 7.14 (2H, d, J=8.7 Hz), 7.22 (2H, d, J=9.0 Hz).

MP; 109.8–110.2° C.

IR (KBr), 1649 cm−1.

MS (ESI+). 442.1 (M+Na).

EXAMPLE 255

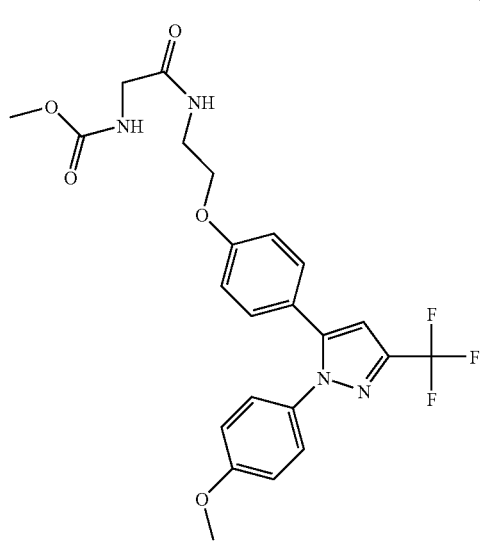
(E0255)

This compound was obtained according to a similar manner to that of E0254 as an oil.

NMR (CDCl3), 3.69 (3H, s), 3.65–3.73 (2H, m), 3.82 (3H, s), 3.86 (2H, d, J=5.9 Hz), 4.04 (2H, t, J=5.1 Hz), 6.67 (1H, s), 6.80–6.89 (4H, m), 7.14 (2H, d, J=8.5 Hz), 7.22 (2H, d, J=8.9 Hz),

MS (ESI+). 515.2 (M+Na).

IR (KBr, 20727-10), 1722.1, 1710.6, 1673.9 cm−1.

EXAMPLE 256

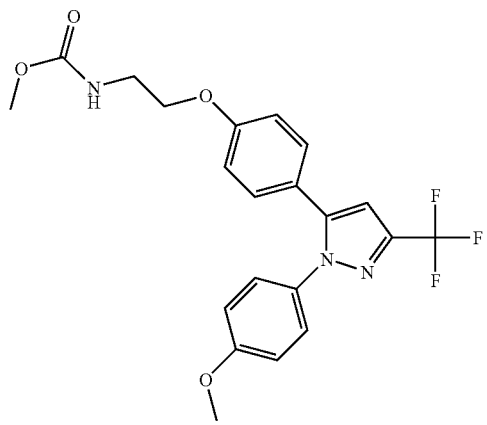
(E0256)

This compound was obtained according to a similar manner to that of E0254 as an oil (82 mg, 78%).

MS (ESI+). 458.2 (M+Na).

IR (Neat), 1699 cm−1.

NMR (CDCl3); 3.54–3.62 (2H, m), 3.69 (3H, s), 3.82 (3H, s), 4.02 (2H, t), 6.67 (1H, s), 6.80–6.89 (4H, m), 7.13 (2H, d, J=8.9 Hz), 7.22 (2H, d, J=9.0 Hz).

EXAMPLE 257

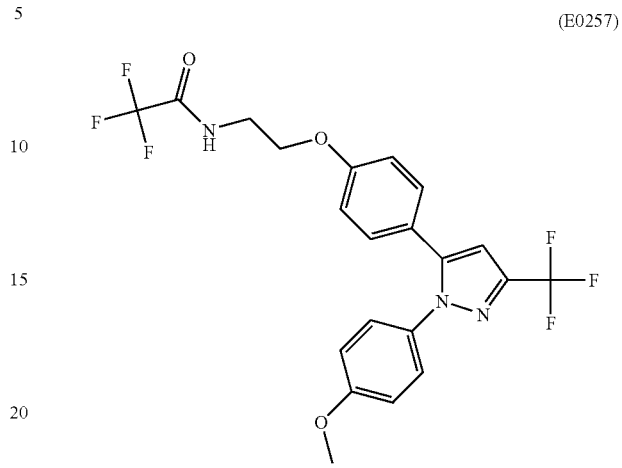
(E0257)

To a solution of E0275 (97.5 mg) and pyridine (0.14 ml) in dichloromethane (1 ml) was added trifluoroacetic anhydride (60.6 ml) at 0° C. After stirring at room temperature overnight, the mixture was quenched with saturated sodium hydrogen carbonate aqueous solution (0.5 ml), filtered with chemelute1001 (Varian), and purified with preparative TLC (1 mm, 50% ethyl acetate/hexane) to give E0257 as a solid (92.5 mg, 76%).

MS (ESI+), 496.1 (M+Na).

IR (KBr), 1705 cm−1.

NMR (CDCl3), 3.75–3.87 (2H, m), 3.82 (3H, s), 4.10 (4.8H, t), 6.68 (1H, s), 6.83 (2H, d, J=8.8 Hz), 6.88 (2H, d, J=8.9 Hz), 7.16 (2H, d, J=8.8 Hz), 7.22 (2H, d, J=8.9 Hz).

EXAMPLE 258

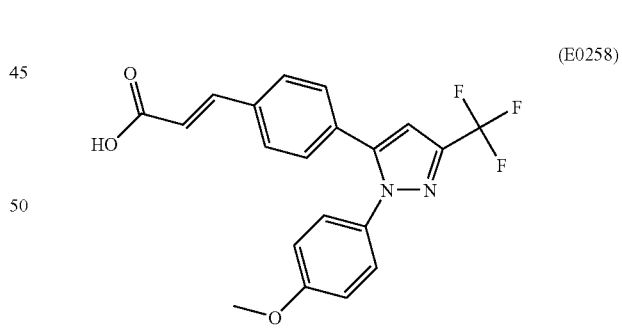
(E0258)

To a solution of E0327 (400 mg) in THF (5 ml) was added dropwise 1N NaOH (2.5 ml) at room temperature. The mixture was stirred overnight, and then quenched with 1N HCl and CHCl3. The organic layer was separated and water layer was extracted twice with CHCl3. The combined organic layer was washed with water and brine, dried over Na2SO4, and evaporated under reduced pressure. The residue was washed with IPE to give 273 mg (70.7%) of E0258.

IR (film): 2971.8, 1683.6, 1629.6, 1515.8, 1315.2, 1230.4, 1159.0, 1132.0, 977.7, 835.0 cm−1.

EXAMPLE 259

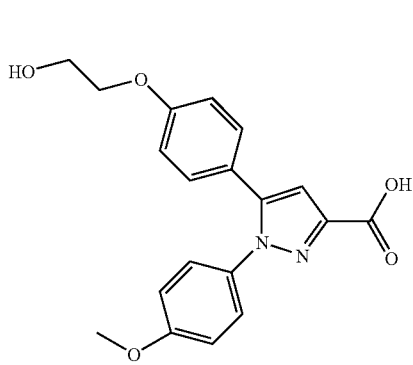

(E0259)

E0259 was prepared in a similar manner to that of E0258.
White Powder
Mass (ESI+): 355 (M+H)+
200 MHz 1H NMR (DMSO-d6, d): 3.63–3.78 (2H, m), 3.79 (3H, s), 3.95–4.00 (2H, m), 4.86 (1H, brs), 6.91 (2H, d, J=8.7 Hz), 6.95 (1H, s), 6.99 (2H, d, J=8.9 Hz), 7.16 (2H, d, J=8.7 Hz), 7.24 (2H, d, J=8.9 Hz), 12.88 (1H, brs)

EXAMPLE 260

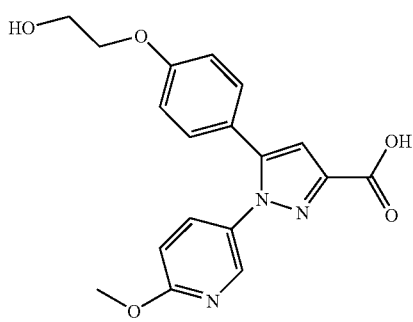

(E0260)

E0260 was prepared in a similar manner to that of E0258.
White Powder
Mass (ESI+): 356 (M+H)+
200 MHz 1H NMR (DMSO-d6, d): 3.69–3.79 (2H, m), 3.88 (3H, s), 3.96–4.02 (2H, m), 4.87 (1H, br), 6.89–7.00 (4H, m), 7.20 (2H, d, J=8.8 Hz), 7.70 (1H, dd, J=2.6, 8.8 Hz), 8.14 (1H, d, J=2.6 Hz), 12.97 (1H, br)

EXAMPLE 261

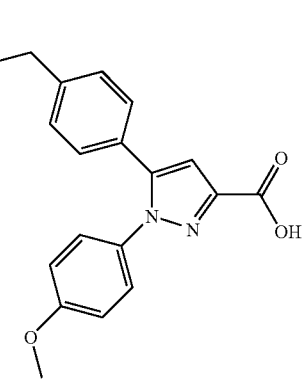

(E0261)

E0261 was prepared from E0109 in a similar manner to that of E0258.
White Powder
Mass (ESI+): 339(M+H)+
200 MHz 1H NMR (DMSO-d6, d): 2.70 (2H, t, J=6.9 Hz), 3.59 (2H, t, J=6.9 Hz), 3.79 (3H, s), 4.64 (1H, brs), 6.96–7.03 (3H, m), 7.12–7.28 (6H, m), 12.90 (1H, br)

EXAMPLE 262

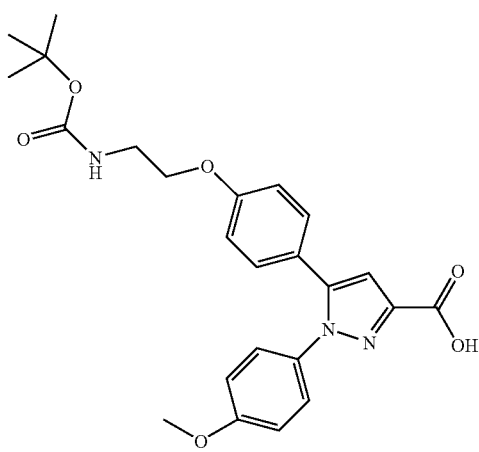

(E0262)

E0262 was prepared in a similar manner to that of E0258.
White Powder
Mass (ESI+): 454 (M+H)+
200 MHz 1H NMR (DMSO-d6, d): 1.37 (9H, s), 3.22–3.32 (2H, mr), 3.79 (3H, s), 3.91–3.98 (2H, m), 6.90 (2H, d, J=8.7 Hz), 6.90–7.03 (1H, overlapping), 6.95 (1H, s), 6.99 (2H, d, J=8.9 Hz), 7.16 (2H, d, J=8.7 Hz), 7.24 (2H, d, J=8.9 Hz)

EXAMPLE 263

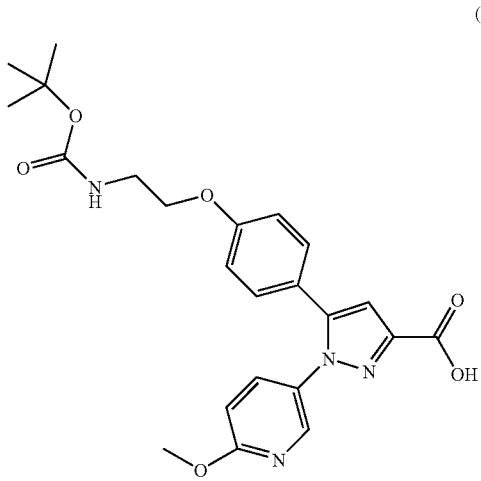

E0263 was prepared in a similar manner to that of E0258.
amorphous powder
Mass (ESI+): 455 (M+H)+
200 MHz 1H NMR (DMSO-d6, d): 1.37 (9H, s), 3.22–3.32 (2H, m), 3.88 (3H, s), 3.93–3.98 (2H, m), 6.89–7.05 (5H, m), 7.20 (2H, d, J=8.7 Hz), 7.70 (1H, dd, J=2.7,8.8 Hz), 8.14 (1H, d, J=2.7 Hz), 12.98 (1H, br)

EXAMPLE 264

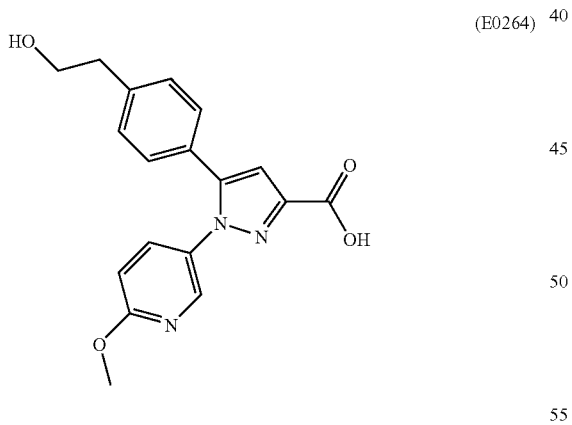

E0264 was prepared from E0006 in a similar manner to that of E0258.
White Powder
Mass (ESI+): 340 (M+H)+
200 MHz 1H NMR (DMSO-d6, d): 2.71 (2H, t, J=6.9 Hz), 3.56–3.64 (2H, m), 3.88 (3H, s), 4.64 (1H, br), 6.92 (1H, d, J=8.8 Hz), 7.03 (1H, s), 7.16–7.28 (4H, m), 7.72 (1H, dd, J=8.8,2.7 Hz), 8.15 (1H, d, J=2.7 Hz), 12.94 (1H, br)

EXAMPLE 265

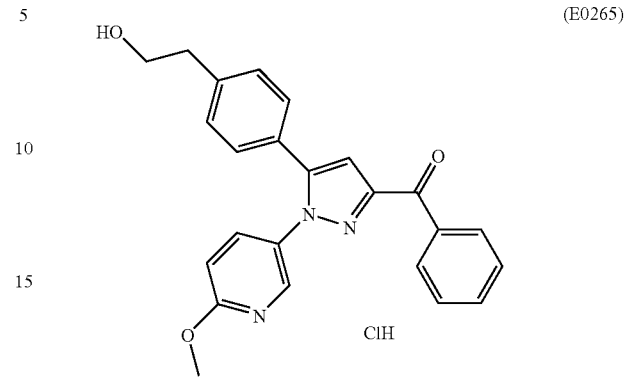

4M HCl/AcOEt 0.4 ml was added to a solution of E0378 (73 mg) in AcOEt 1 ml. The mixture was concentrated and dried in vacuo to give E0265 68.4 mg as an amorphous powder.
IR (neat): 3440, 2960, 1739, 1707, 1691, 1674, 1647, 1624, 1614, 1566, 1549, 1533, 1500 cm−1
Mass (ESI+): 400 (M+H)+
200 MHz 1H NMR (DMSO-d6, d): 2.73 (2H, t, J=6.9Hz), 3.62 (2H, t, J=6.9 Hz), 3.89 (3H, s), 6.94 (1H, d, J=8.8 Hz), 7.19–7.32 (5H, m), 7.52–7.70 (3H, m), 7.80 (1H, dd, J=8.8, 2.7 Hz), 8.22–8.28 (3H, m)

EXAMPLE 266

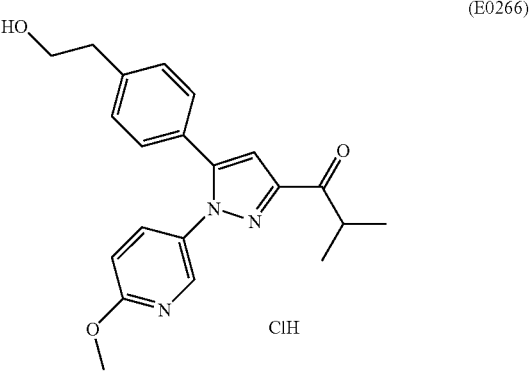

E0266 was prepared in a similar manner to that of E0265.
oil
IR (neat): 3435, 2966, 2935, 1678, 1662, 1649, 1612, 1581, 1566, 1547, 1533, 1500 cm−1
Mass (ESI+): 366 (M+H)+
200 MHz 1H NMR (DMSO-d6, d): 1.16 (6H, d, J=6.9Hz), 2.72 (2H, t, J=6.9 Hz), 3.54–3.75 (3H, m), 3.89 (3H, s), 6.93 (1H, d, J=8.8 Hz), 7.05 (1H, s), 7.13–7.35 (4H, m), 7.76 (1H, dd, J=2.7,8.8 Hz), 8.19 (1H, d, J=2.7 Hz)

EXAMPLE 267

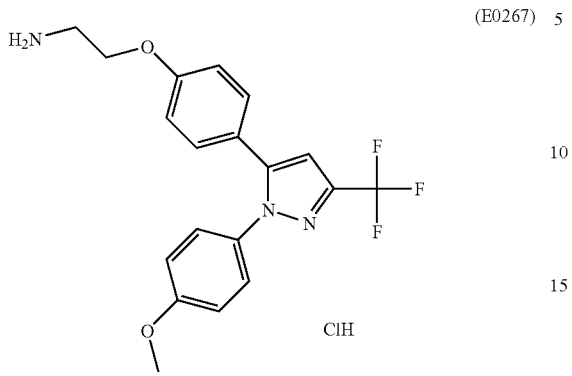
(E0267)

To a solution of E0275 (765 mg) in ethyl acetate (1.9 ml) was added a solution of hydrogen chloride in ethyl acetate (4N, 0.56 ml). The mixture was evaporated to give oil, which was crystallized from diisopropyl ether and ethyl acetate at 65° C. to give E0267 as a solid (766.8 mg, 91.4%).

NMR (CDCl3), 3.30 (2H, t, J=5.0 Hz), 3.79 (3H, s), 4.18 (2H, t, J=5.0 Hz), 6.62 (1H, s), 6.83–6.88 (4H, m), 7.10 (2H, d, J=8.8 Hz), 7.18 (2H, d, J=8.8 Hz).

NMR (DMSO-d6), 3.19 (2H, brs), 3.79 (3H, s), 4.18 (2H, t, J=5.0 Hz), 6.96–7.01 (4H, m), 7.08 (1H, s), 7.23–7.29 (4H, m).

MS(ESI+), 378.3 (MH+, free).

IR (KBr, 20727-2), 1612.2, 1513.9 cm-1.

EXAMPLE 268

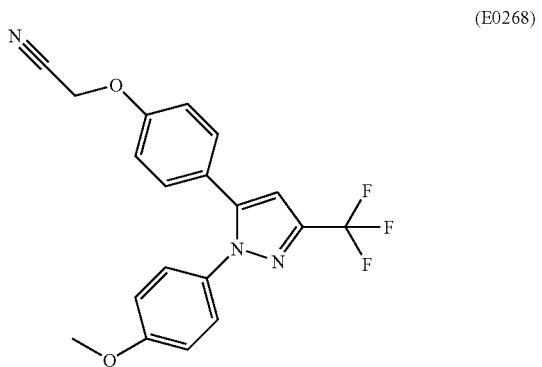
(E0268)

A mixture of P0011 (30 g), chloroacetonitrile (8.52 ml), potassium iodide (4.47 g), and potassium carbonate (14.9 g) in acetone (150 ml) was stirring under reflux at 80° C. for 2.5 hours. After cooling to room temperature, the mixture was quenched with water (600 ml) and extracted with ethyl acetate (300 ml×2, 150 ml). The combined organic layers were washed with brine (300 ml), dried over magnesium sulfate, and evaporated to give solid (36.34 g). The solid was recrysallized from diisopropyl ether (60 ml) and hexane (200 ml) at room temperature to give E0268 as a powder (31.5 g, 94%).

NMR (CDCl3), 3.83 (3H, s), 4.78 (2H, s), 6.70 (1H, s), 6.86–6.97 (4H, m), 7.18–7.24 (4H, m).

IR (KBr), 2051.9 cm-1.

EXAMPLE 269

(E0269)

E0269 was obtained according to a similar manner to that of E0268.

White Powder

Mass (ESI+): 346 (M+H)+

200 MHz 1H NMR (DMSO-d6, d): 0.69–0.77 (2H, m), 0.86–0.96 (2H, m), 1.92 (1H, m), 3.76 (3H, s), 5.16 (2H, s), 6.30 (1H, s), 6.93 (2H, d, J=9.0 Hz), 7.02 (2H, d, J=8.8 Hz), 7.10–7.21 (4H, m)

EXAMPLE 270

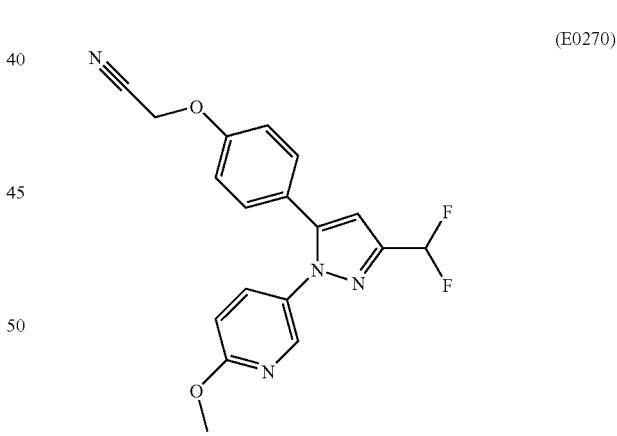
(E0270)

This compound was obtained according to a similar manner to that of E0268 as a powder.

NMR (CDCl3), 3.95 (3H, s), 4.78 (2H, s), 6.71 (1H, s), 6.76 (1H, t, J=55 Hz), 6.76 (1H, d, J=8.4 Hz), 6.96 (2H, d, J=8.9 Hz), 7.23 (2H, d, J=8.9 Hz), 7.53 (1H, dd, J=8.4, 2.6Hz), 8.08 (1H, d, J=2.6 Hz).

MS (ESI+), 379 (M+Na)

EXAMPLE 271

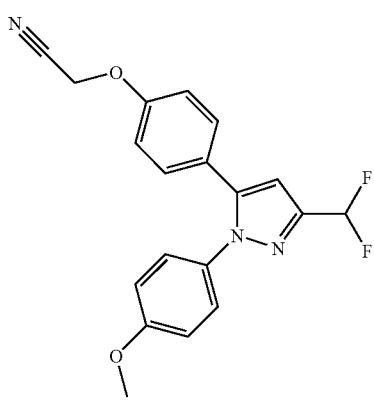

This compound was obtained according to a similar manner to that of E0268.

EXAMPLE 272

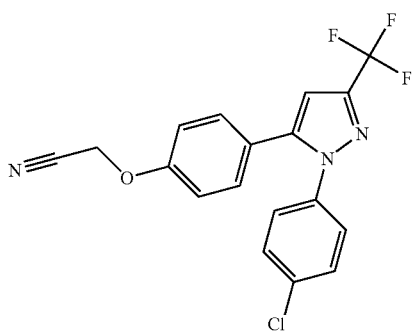

This compound was obtained according to a similar manner to that of E0268.

IR (film): 1612.2, 1482.9, 1234.2, 1162.8, 1132.0, 1095.3, 973.8, 835.0 cm−1.

EXAMPLE 273

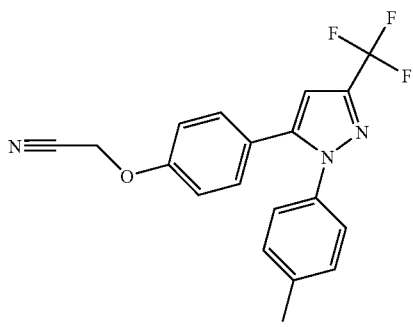

This compound was obtained according to a similar manner to that of E0268.

EXAMPLE 274

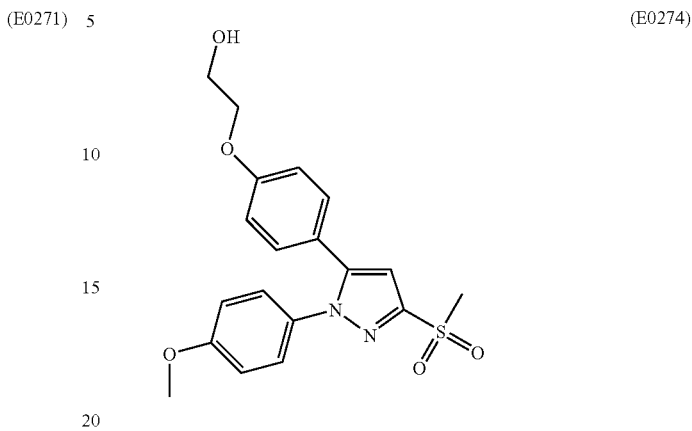

This compound was obtained according to a similar manner to that of E0268.

mp.96–99° C.
Mass;389 (M+1)
NMR (CDC13, δ); 1.98 (1H, t, J=6.1 Hz),3.29 (3H, s),3.83 (3H, s), 3.93–4.01 (2H, m), 4.06–4.11 (2H, m), 6.86 (2H, d, J=8.8 Hz), 6.88 (2H, d, J=9.0 Hz), 6.93 (1H, s), 7.14 (2H, d, J=8.8 Hz), 7.23 (2H, d, J=9.0 Hz)

EXAMPLE 275

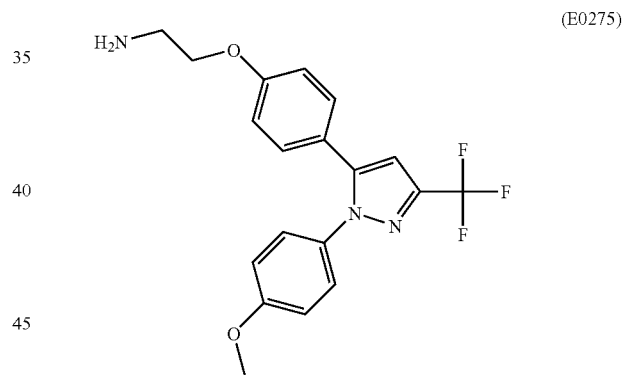

To a suspension of lithium aluminum hydride (250 mg) in ether (14 ml) was added E0268 (1.38 g) in ether (5 ml) and tetrahydrofuran (1 ml) under ice-bath. The mixture was stirred at room temperature for 1 hour. Lithium aluminum hydride (50 mg) was added to the mixture under ice-bath., and then the mixture was stirred at room temperature for 1 hour. The mixture was quenched with water (0.3 ml), sodium hydroxide aqueous solution (15%, 0.3 ml), and water (0.9 ml), and then stirred at room temperature for 30 minutes. Magnesium sulfate and celite was added to the mixture, then the suspension was filtered and washed with ether. The filtrate was evaporated to give 1.307 g of oil. The oil purified with column chromatography (SiO2, 100 ml, eluted with 20% methanol/chloroform (500 ml)) to give E0275 as an oil (1.156 g, 82.9%).

NMR (CDC13), 3.09 (2H, t, J=5.1 Hz), 3.82 (3H, s), 3.99 (2H, t, J=5.1 Hz), 6.67 (1H, s), 6.82–6.89 (4H, m), 7.14 (2H, d, J=8.9 Hz), 7.23 (2H, d, J=9.0 Hz). MS (ESI+), 378 (MH+).

EXAMPLE 276

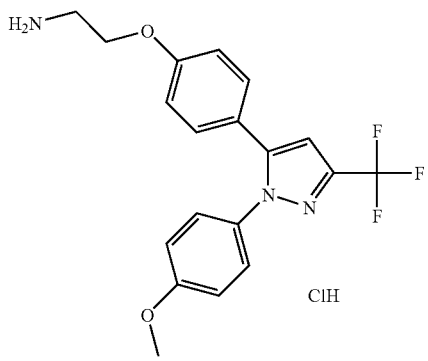

(E0276)

To a solution of E0268 (27.43 g) in tetrahydrofuran (270 ml) was added borane methylsulfide complex (10M, 15 ml) at room temperature. The mixture was stirred at room temperature overnight. Then borane methylsulfide complex (7.5 ml) was added to the mixture. After stirring at room temperature overnight, the mixture was quenched with methanol (100 ml) and evaporated under reduced pressure to give oil. The oil was dissolved in a mixture of tetrahydrofuran (150 ml) and hydrochloric acid (6N, 100 ml), and then stirred at 40 ~50° C. for 1 hour. To the mixture was added dropwise aqueous sodium hydroxide solution (30%, 80 ml), and then sodium hydrogen carbonate, and sodium chloride. The mixture was extracted with ethyl acetate (×4). The organic layer was evaporated to give oil (31.86 g), which was purified with column chromatography (SiO2, 1L, eluted with 20% methanol/dichloromethane and concentrated ammonia/methanol/chloroform (0.025:1:4)) to give oil. A solution of hydrogen chloride in ethyl acetate (4N, 22 ml) was added to the solution of the oil in ethyl acetate (50 ml), and the mixture was evaporated to give E0276 as an amorphous (22.87 g, 69.4%).

EXAMPLE 277

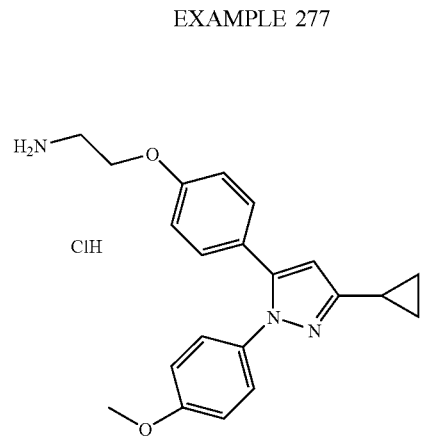

(E0277)

E0277 was prepared in a similar manner to that of E0276.
White Powder
mp. 229–231° C.

IR (KBr): 3084, 2960, 2885, 2800, 2731, 2563, 2519, 2482, 1606, 1576, 1516 cm−1

Mass (ESI+): 350 (M+H)+

200 MHz 1H NMR (DMSO-d6, d): 0.69–0.77 (2H, m), 0.84–0.96 (2H, m), 1.93 (1H, m),3.14–3.22 (2H, m), 3.76 (3H, s), 4.14–4.20 (2H, m), 6.26 (1H, s), 6.94 (4H, d, J=8.8 Hz), 7.14 (4H, d, J=8.8 Hz), 8.21 (2H, brs)

EXAMPLE 278

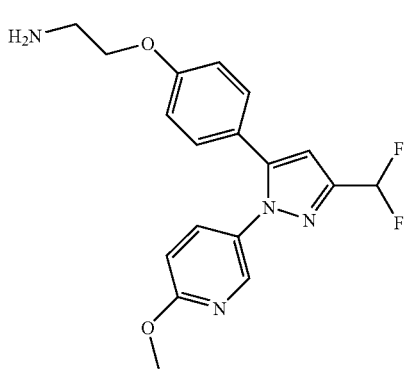

(E0278)

This compound was obtained according to a similar manner to that of E0276 without formation of hydrogen chloride salt (oil).

NMR (CDC13), 3.09 (2H, t, J=5.2 Hz), 3.94 (3H, s), 3.99 (2H, t, J=5.2 Hz), 6.77 (1H, t, J=54.9 Hz), 6.67 (1H, s), 6.74 (2H, d, J=7.5 Hz), 6.87 (2H, d, J=8.9 Hz), 7.15 (2H, d, J=8.7 Hz), 7.55 (1H, dd, J=8.9, 2.8 Hz), 8.09 (1H, d, J=2.8 Hz).

MS (ESI+), 361 (MH+).

EXAMPLE 279

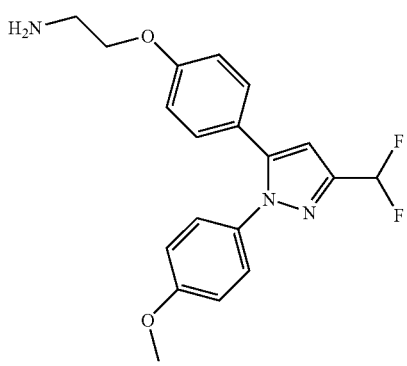

(E0279)

This compound was obtained according to a similar manner to that of E0276.

EXAMPLE 280

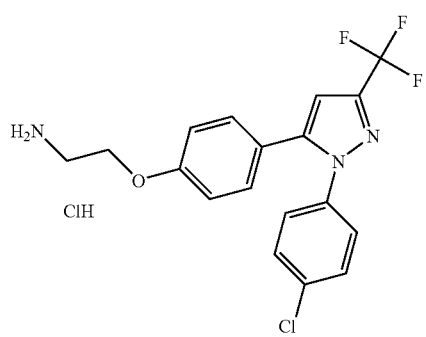
(E0280)

This compound was obtained according to a similar manner to that of E0276.

IR (film): 3423.0, 1612.2, 1469.5, 1240.0, 1164.8, 1132.0, 1095.4, 975.8, 836.9 cm−1.

EXAMPLE 281

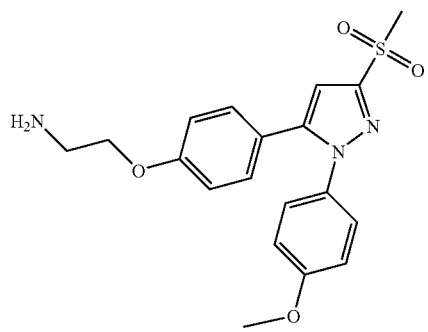
(E0281)

This compound was obtained according to a similar manner to that of E0276.

mp.104–106° C.

Mass;388 (M+1)

IR (KBr);1310 cm−1

NMR (CDCl3,δ);3.09 (2H, t, J=5.1 Hz), 3.29 (3H, s), 3.83 (3H, s), 3.99 (2H, t, J=5.1 Hz), 6.83 (2H, d, J=8.8 Hz), 6.88 (2H, d, J=8.9 Hz), 6.93 (1H, s), 7.13 (2H, d, J=8.8 Hz), 7.24 (2H, d, J=8.9 Hz),

EXAMPLE 282

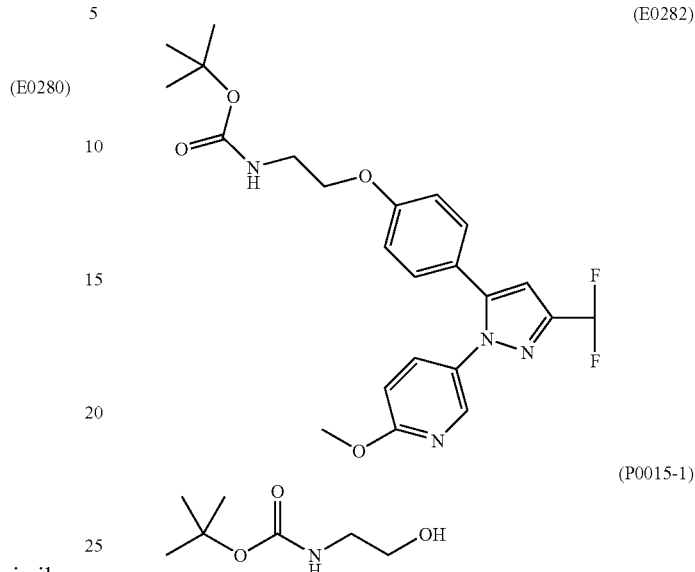
(E0282)

(P0015-1)
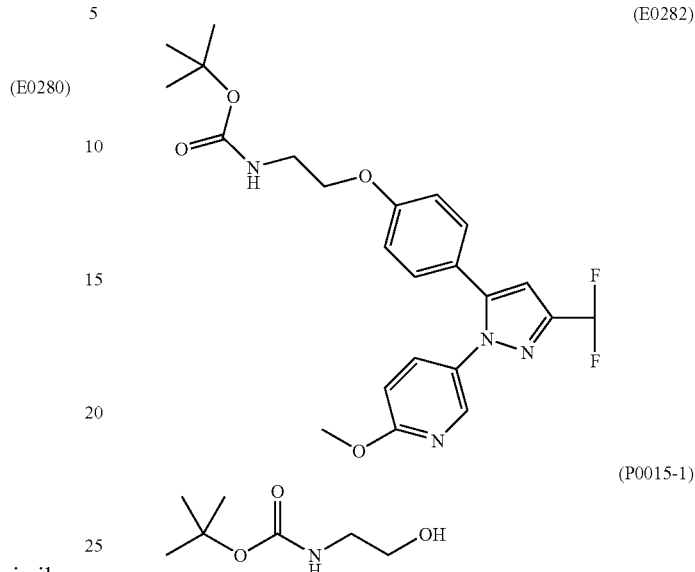

Diethylazodicarboxylate 82.3 mg was added to a solution of P0015 (100 mg), P0015-1 (152 mg), and triphenylphosphine 124 mg in THF 2ml. After stirring at ambient temperature for 5 hours, The reaction mixture was concentrated in vacuo. The residue was purified by silica gel column chromatography eluted with AcOEt/CHCl3=5% viscous oil to give E0282.

Mass (ESI+) 461 (M+H)+

200 MHz 1H NMR (DMSO-d6, d): 1.37 (9H, s), 3.22–3.33 (2H, m), 3.87 (3H, s), 3.93–3.99 (2H, m), 6.88–7.04 (5H, m), 7.10 (1H, t, J=54.4 Hz), 7.21 (2H, d, J=8.7 Hz), 7.69 (1H, dd, J=2.7,8.8 Hz), 8.14 (1H, d, J=2.7 Hz)

EXAMPLE 283

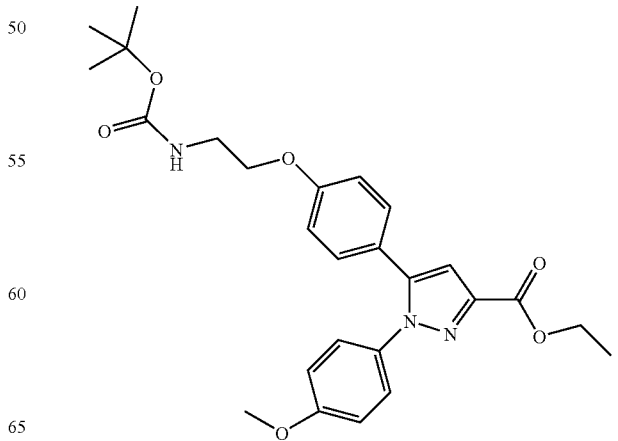
(E0283)

E0283 was prepared from P0020 in a similar manner to that of E0282.
White Powder
Mass (ESI+): 482 (M+H)+
200 MHz 1H NMR (DMSO-d6, d): 1.31 (3H, t, J=7.1 Hz), 1.37 (9H, s), 3.22–3.32 (2H, m),3.79 (3H, s),3.91–3.98 (2H, m), 4.32 (2H, q, J=7.1 Hz), 6.90 (2H, d, J=8.7 Hz),6.95–7.06 (1H, overlapping), 6.99 (2H, d, J=8.9 Hz), 7.01 (1H, s), 7.17 (2H, d, J=8.7 Hz), 7.25 (2H, d, J=8.9 Hz)

EXAMPLE 284

(E0284)

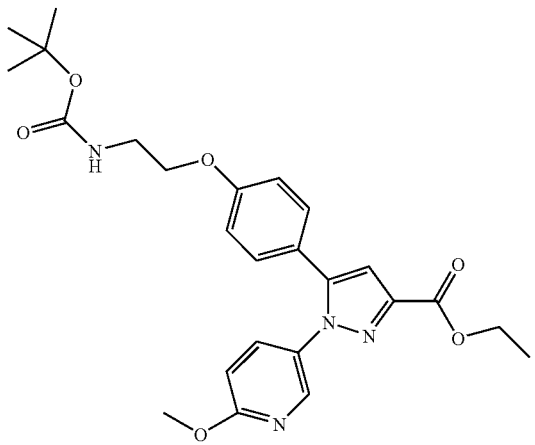

E0284 was prepared in a similar manner to that of E0282.
White Powder
Mass (ESI+): 483 (M+H)+
200 MHz 1H NMR (DMSO-d6, d): 1.31 (3H, t, J=7.1 Hz), 1.37 (9H, s), 3.22–3.33 (2H, m), 3.88 (3H, s), 3.96 (2H, t, J=5.7 Hz), 4.33 (2H,q, J=7.1Hz), 6.89–7.05 (1H, overlapping), 6.92 (1H, d, J=8.9 Hz), 6.93 (2H, d, J=8.7 Hz), 7.05 (1H, s), 7.21 (2H, d, J=8.7 Hz), 7.72 (1H, dd, J=2.7,8.9 Hz), 8.15 (1H, d, J=2.7 Hz)

EXAMPLE 285

(E0285)

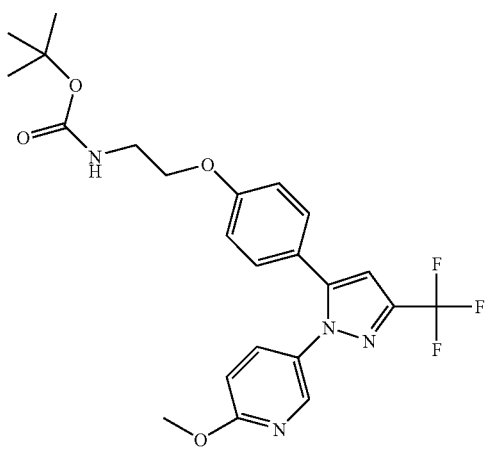

This compound was obtained according to a similar manner to that of E0282 as an oil.
NMR (CDCl3), 1.45 (9H, s), 3.50–3.58 (2H, m), 3.94 (3H, s), 4.02 (2H, t, J=5.1 Hz), 6.70 (1H, s), 6.75 (1H, d, J=8.4 Hz), 6.85 (2H, d, J=8.9 Hz), 7.15 (2H, d, J=8.9 Hz), 7.56 (1H, dd, J=8.4, 2.9 Hz), 8.08 (1H, d, J=2.9 Hz).
MS (ESI+), 501.2 (M+Na).

EXAMPLE 286

(E0286)

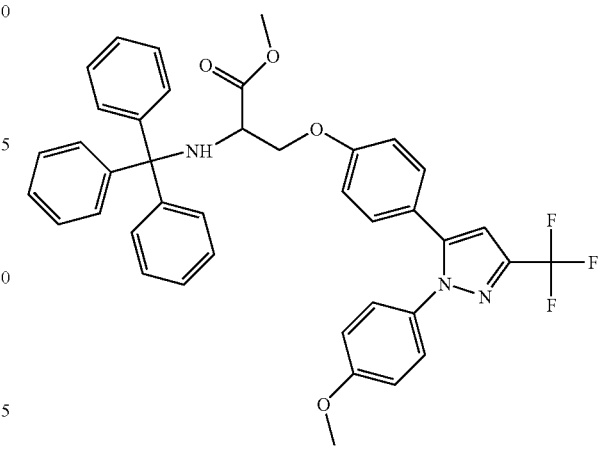

This compound was obtained according to a similar manner to that of E0282 as a powder.
NMR (CDCl3), 2.89 (1H, d, J=10.4 Hz, NH), 3.23 (3H, s), 3.67–3.78 (1H, m), 3.81 (3H, s), 3.99 (1H, dd, J=9.2, 6.4 Hz), 4.22 (1H, dd, J=9.2, 5.0 Hz), 6.67 (1H, s), 6.81 (2H, d, J=8.9 Hz), 6.86 (2H, d, J=6.0Hz), 7.10–7.29 (13H, m), 7.49–7.54 (6H, m).
MS (ESI+), 678.4 (MH+).

EXAMPLE 287

(E0287)

This compound was obtained according to a similar manner to that of E0282 as an oil.
NMR (CDCl3), 1.28 (3H, d, J=6.6 Hz), 1.45 (9H, s), 3.82 (3H, s), 3.92 (2H, d, J=4.1 Hz), 3.90–4.14 (1H, m), 6.67 (1H, s), 6.84 (2H, d, J=8.9 Hz), 6.86 (2H, d, J=9.0 Hz), 7.13 (2H, d, J=8.9 Hz), 7.23 (2H, d, J=9.0 Hz). MS (ESI+), 514.2 (M+Na).

EXAMPLE 288

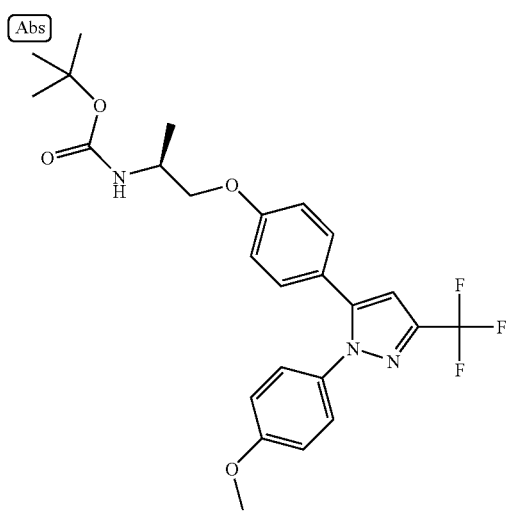

(E0288)

This compound was obtained according to a similar manner to that of E0282 as an oil.

NMR (CDC13), 1.28 (3H, d, J=6.6 Hz), 1.45 (9H, s), 3.82 (3H, s), 3.92 (2H, d, J=4.1 Hz), 3.90–4.14 (1H, m), 6.67 (1H, s), 6.84 (2H, d, J=8.9 Hz), 6.86 (2H, d, J=9.0 Hz), 7.13 (2H, d, J=8.9 Hz), 7.23 (2H, d, J=9.0 Hz).

MS (ESI+), 514.2 (M+Na).

EXAMPLE 289

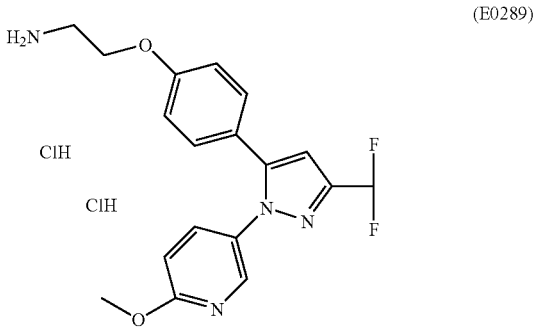

(E0289)

4M HCl/AcOEt 1 ml was added to a solution of E0282 (129 mg) in AcOEt 1 ml, and the mixture was stirred at ambient temperature for 1hour. The supernatant was removed by decantation. The residual oily solid was washed with AcOEt 1 ml by decantation. To the residue was added acetone 2 ml, and oily residual solid became white powder on stirring. This was stirred at ambient temperature for 20 minutes. The precipitates were collected and washed with acetone to give E0289 (91.4 mg) as a white powder.

IR (neat): 2964, 1705, 1668, 1660, 1614, 1581, 1566, 1531, 1512 cm−1

Mass (ESI+): 361 (M+H)+

200 MHz 1H NMR (DMSO-d6, d): 3.11–3.23 (2H, m), 3.87 (3H, s), 4.12–4.28 (2H, m), 6.90–7.02 (4H, m), 7.11 (1H, t, J=54.3Hz), 7.26 (2H, d, J=8.6 Hz), 7.71 (1H, dd, J=2.7,8.8 Hz), 8.14 (1H, d, J=2.7 Hz), 8.24 (2H, brs)

EXAMPLE 290

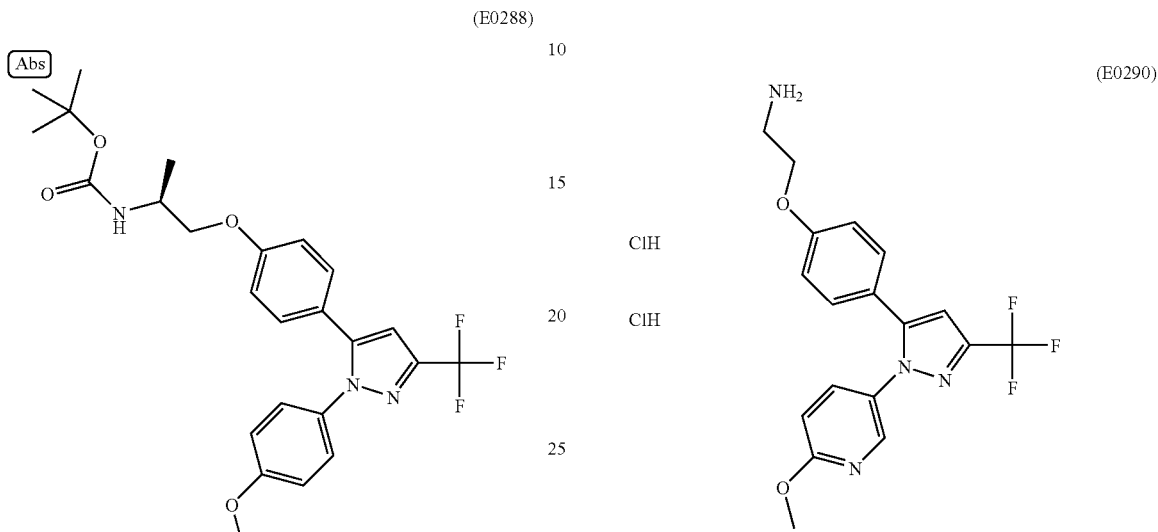

(E0290)

This compound was obtained according to a similar manner to that of E0289 as a white powder.

NMR (DMSO-d6), 3.17–3.21 (2H, m), 3.95 (3H, s), 4.19 (2H, t, J=5.0 Hz), 6.93 (1H, d, J=8.8 Hz), 7.00 (2H, d, J=8.8 Hz), 7.15 (1H, s), 7.28 (2H, d, J=8.8 Hz), 7.76 (1H, dd, J=8.8, 2.6 Hz), 8.18 (1H, d, J=2.6 Hz).

MS (ESI+), 379.1 (MH+).

IR (KBr), 1612.2 cm−1.

EXAMPLE 291

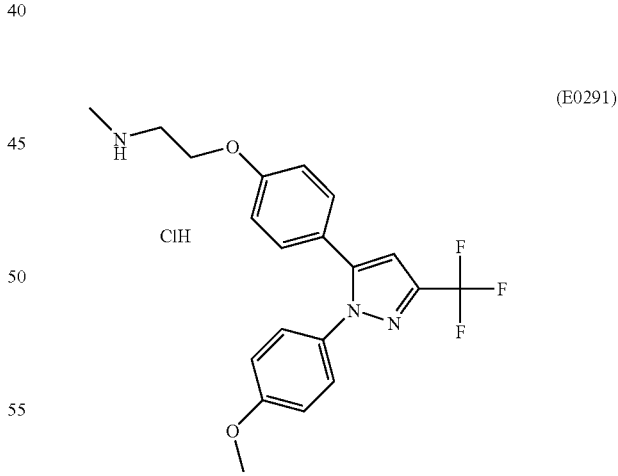

(E0291)

This compound was obtained according to a similar manner to that of E0289 as a white powder.

NMR (DMSO-d6), 2.60 (3H, s), 3.28–3.33 (2H, m), 3.79 (3H, s), 4.25 (2H, t, J=4.7 Hz), 7.04–6.96 (4H, m), 7.09 (1H, s), 7.22–7.31 (4H, m).

MS (ESI−), 426.2 (M+Cl)+.

IR (KBr); 1610.2, 1515.8 cm−1.

MP; 189–189.2° C.

EXAMPLE 292

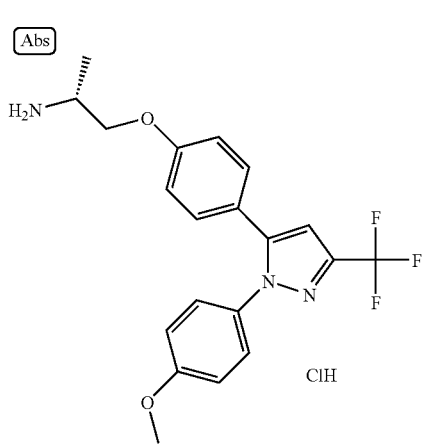

This compound was obtained according to a similar manner to that of E0289 as a white amorphous.

NMR (DEMSO-d6),1.04 (3H, d, J=6.0 Hz), 3.5–3.7 (1H, m), 3.79 (3H, s), 3.98 (1H, dd, J=10.1, 6.9 Hz), 4.11 (1H, dd, J=10.1, 6.5Hz), 6.96–7.04 (4H, m),7.09 (1H, s),7.22–7.31 (4H, m).

MS (ESI+), 392.2 (MH+).

EXAMPLE 293

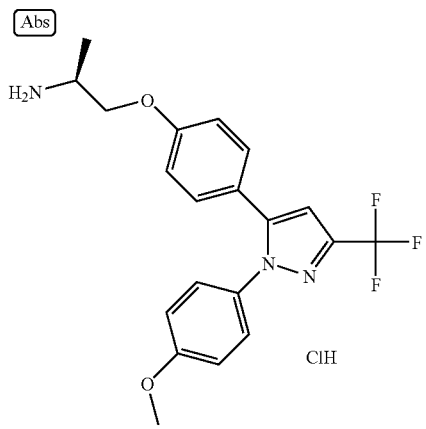

This compound was obtained according to a similar manner to that of E0289 as a white amorphous.

NMR (DEMSO-d6),1.04 (3H, d, J=6.0 Hz), 3.5–3.7 (1H, m), 3.79 (3H, s), 3.98 (1H, dd, J=10.1, 6.9 Hz), 4.11 (1H, dd, J=10.1, 6.5Hz), 6.96–7.04 (4H, m),7.09 (1H, s),7.22–7.31 (4H, m).

MS (ESI+), 392.2 (MH+). IR (Neat) 1612.2 cm−1.

EXAMPLE 294

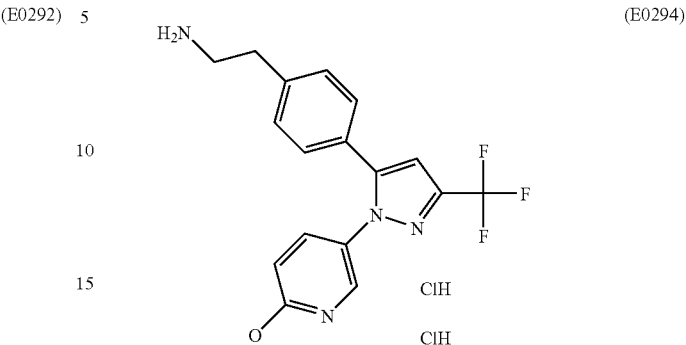

This compound was obtained according to a similar manner to that of E0289 as a white powder.

NMR (DMSO-d6); 2.84–3.20 (4H, m), 3.88 (3H, s), 6.93 (1H, d, J=8.9Hz),7.19 (1H, s),7.30–7.36 (4H, m),7.86 (1H, dd, J=8.9, 2.7 Hz), 8.19 (1H, d, J=2.7 Hz).

MS (ESI+); 363.3 (MH+).

IR (KBr); 1612.2, 1500.3 cm−1.

EXAMPLE 295

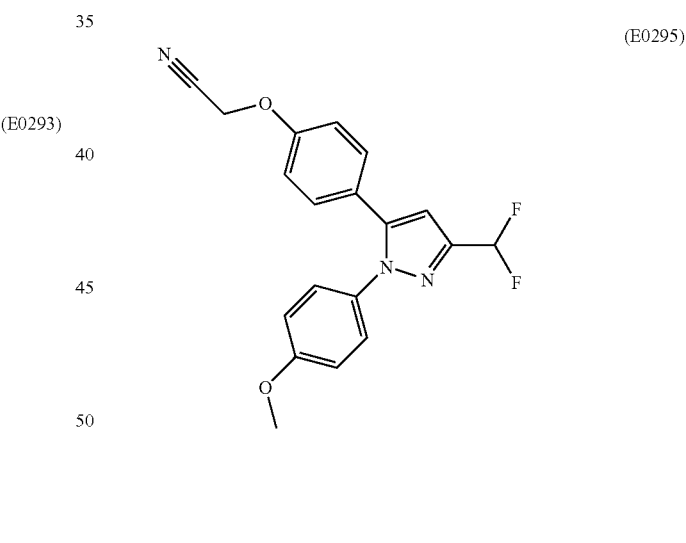

A mixture of P0012 (0.5 g), chloroacetonitrile (0.2 ml), potassium iodide (525 mg), and potassium carbonate (437 mg) in N, N-dimethylformamide (6 ml) was stirring at 75° C. for 6 hours. After cooling to room temperature, the mixture was quenched with water, and extracted with ethyl acetate (×3). The combined organic layers were washed with water (×3) and brine, dried over magnesium sulfate, and evaporated to give E0295 as a solid (631.6 mg, 112%).

NMR (CDC13), 3.83 (3H, s), 4.77 (2H, s),.6.69 (1H, s), 6.76 (1H, t, J=55 Hz), 6.96–6.86 (4H, m), 7.18–7.24 (4H, m).

MS (ESI+), 378.1 (M+Na).

EXAMPLE 296

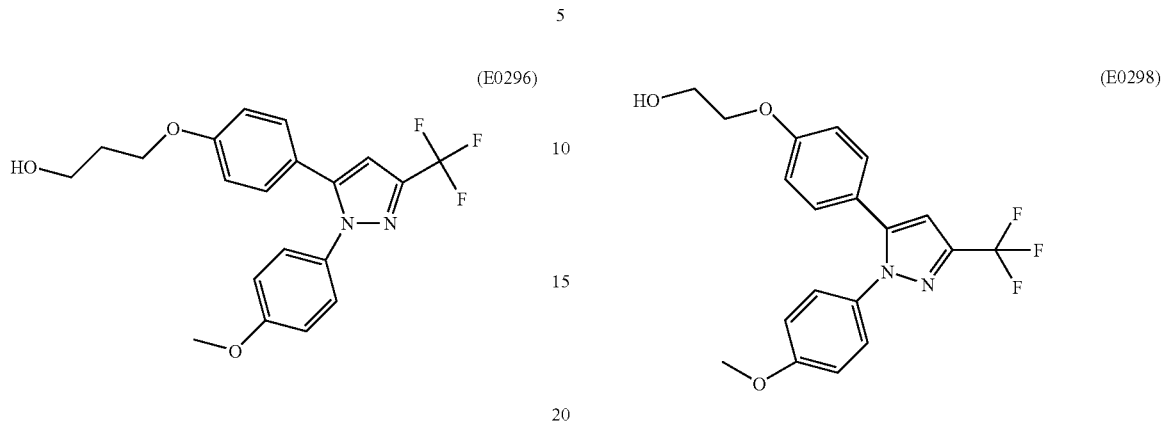

This compound was obtained according to a similar manner to that of E0295 as an oil.

NMR (CDCl3);1.63 (1H, t, J=5.2Hz),1.99–2.11 (2H, m), 3.82 (3H, s), 3.82–3.91 (2H, m), 4.12 (2H, t, J=6.0 Hz), 6.67 (1H, s), 6.84 (2H, d, J=8.8 Hz), 6.87 (2H, d, J=8.9 Hz), 7.13 (2H, d, J=8.8 Hz), 7.32 (2H, d, J=8.9 Hz).

IR (Neat); 1612, 1514 cm−1.

MS (ESI+); 393.1 (MH+), 415.1 (M+Na).

EXAMPLE 297

This compound was obtained according to a similar manner to that of E0205 as an oil.

NMR (CDCl3);3.03 (3H, s), 3.83 (3H, s), 4.97 (2H, s), 6.70 (1H, s), 6.88 (2H, d, J=9.0 Hz), 7.01 (2H, d, J=8.8 Hz), 7.17–7.26 (4H, m).

IR (KBr); 1612.2, 1513.9 cm−1.

MS (ESI+),449.1 (M+Na).

EXAMPLE 298

This compound was obtained according to a similar manner to that of E0295 as a white solid.

NMR (DMSO-d6), 3.65–3.73 (2H, m), 3.79 (3H, s), 3.98 (2H, t, J=4.7 Hz), 4.87 (1H, t, J=5.4 Hz), 6.93 (2H, d, J=8.7 Hz), 7.00 (2H, d, J=8.9 Hz), 7.07 (1H, s), 7.19 (2H, d, J=8.7 Hz), 7.28 (2H, d, J=8.9 Hz).

MS (ESI+), 401.2 (M+Na).

IR (KBr); 1610.3, 1511.9 cm−1.

EXAMPLE 299

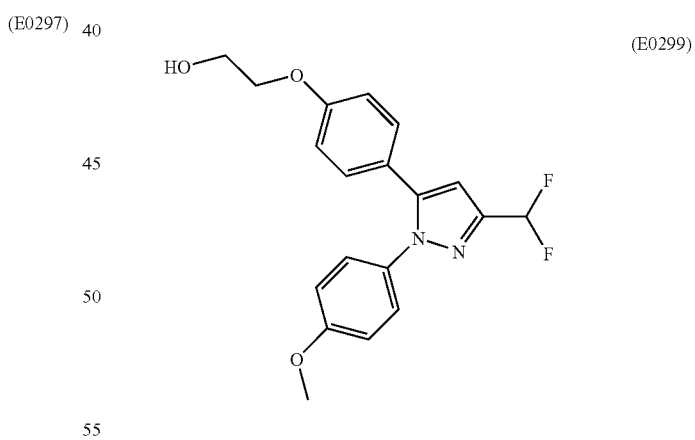

This compound was obtained according to a similar manner to that of E0295 as a white solid.

NMR (CDCl3),2.01 (1H, t, J=6.1Hz),3.82 (3H, s), 3.93–4.10 (4H, m), 6.66 (1H, s), 6.76 (1H, t, J=55.1 Hz), 6.85 (2H, d, J=8.7 Hz), 6.87 (2H, d, J=9.0 Hz), 7.15 (2H, d, J=8.7 Hz), 7.21 (2H, d, J=9.0 Hz).

MS (ESI+) ; 383.2 (M+Na)

IR (KBr); 1610.3, 1513.9, 1454.1 cm−1.

EXAMPLE 300

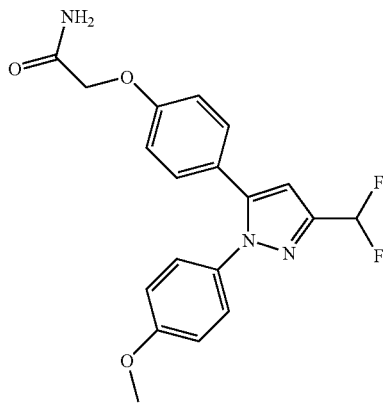
(E0300)

This compound was obtained according to a similar manner to that of E0295 as a white powder.

NMR (DMSO-d6); 3.78 (3H, s), 4.43 (2H, s), 6.80–7.53 (12H, m, NH2),
MS (ESI+);396.3 (M+Na)+.
IR (KBr); 1681.6, 1606.4 cm−1.

EXAMPLE 301

(E0301)

Alkylation of this compound was achieved bya similar manner to that of E0295 to give salt free compound as an oil. Hydrogen chloride salt formation was achieved successively by a similar manner to that of E0172 to give E0301 as a white powder (498.7 mg, 49.6%).

NMR (DMSO-d6), 3.69 (2H, t, J=5.0 Hz), 3.88 (3H, s), 3.99 (2H, t, J=5.0 Hz), 6.92 (1H, d, J=8.7 Hz), 6.96 (2H, d, J=8.8 Hz), 7.13 (1H, s), 7.23 (2H, d, J=88.8 Hz), 7.53 (1H, dd, J=8.7, 2.9 Hz), 8.18 (1H, d, J=2.9 Hz).

MS (ESI+), 402.1 (M+Na)+, (Free).
IR (Neat), 1614, 1552 cm−1.

EXAMPLE 302

(E0302)

This compound was obtained according to a similar manner to that of E0295 as a white solid.

NMR (CDCl3) ; 3.88 (3H- s), 4.45 (2H, s), 6.92 (1H, d, J=8.9 Hz), 6.96 (2H, d, J=8.8 Hz), 7.14 (1H, s), 7.26 (2H, d, J=8.8 Hz), 7.41 (1H, brs, NH2), 7.56 (1H, brs, NH2), 7.76 (1H, dd, J=8.9, 2.5 Hz), 8.18 (1H, d, J=2.5 Hz).

MS (ESI+); 415.1 (M+Na).
IR (KBr); 1693.2, 1608.3 cm−1.

EXAMPLE 303

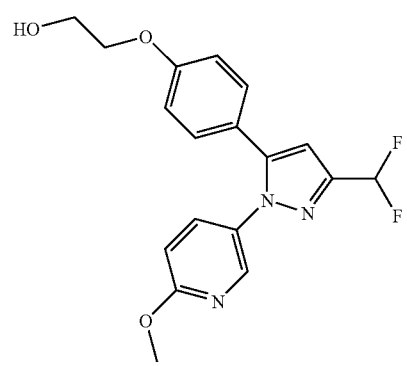
(E0303)

This compound was obtained according to a similar manner to that of E0295 as an oil.

NMR (CDCl3); 3.94 (3H, s), 3.94–4.14 (4H, m), 6.68 (1H, s), 6.74 (1H, d, J=8.7 Hz), 6.86 (1H, t, J=55.0 Hz), 6.88 (2H, d, J=8.9 Hz), 7.16 (2H,-d, J=8.9 Hz), 7.53 (1H, dd, J=2.6, 8.7 Hz), 8.08 (1H, d, J=2.6 Hz).

MS (ESI+); 384.2 (M+Na).
IR (KBr), 1805.1, 1612.2 cm−1.

EXAMPLE 304

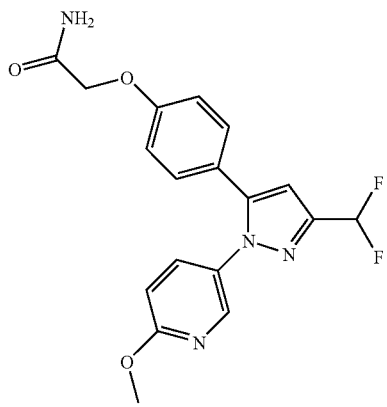
(E0304)

This compound was obtained according to a similar manner to that of E0295 as a white powder.

NMR (DMSO-d6); 3.88 (3H, s), 4.44 (2H, s), 6.98–9.89 (4H, m), 7.10 (1H, t, J=54.3 Hz), 7.24 (2H, d, J=8.8 Hz), 7.39 (1H, brs, NH2), 7.54 (1H, brs, NH2), 7.70 (1H, dd, J=8.9, 2.8 Hz), 8.14 (1H, d, J=2.8 Hz).

MS (ESI−); 373 (M−H)+.

IR (KBr); 1662.3, 1610.3 cm−1.

EXAMPLE 305

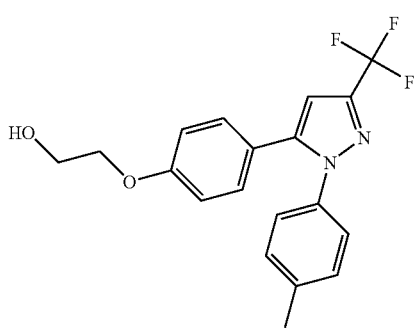
(E0305)

This compound was obtained according to a similar manner to that of E0298.

IR (film): 3388.3, 1494.6, 1236.2, 1160.9, 1133.9, 1095.4, 975.8, 833.1 cm−1.

EXAMPLE 306

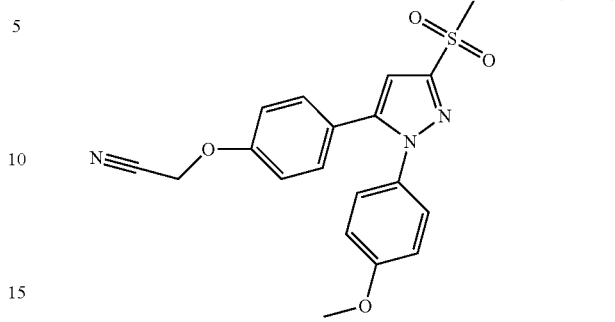
(E0306)

This compound was obtained according to a similar manner to that of E0295.

Mass; 384 (M+1)

EXAMPLE 307

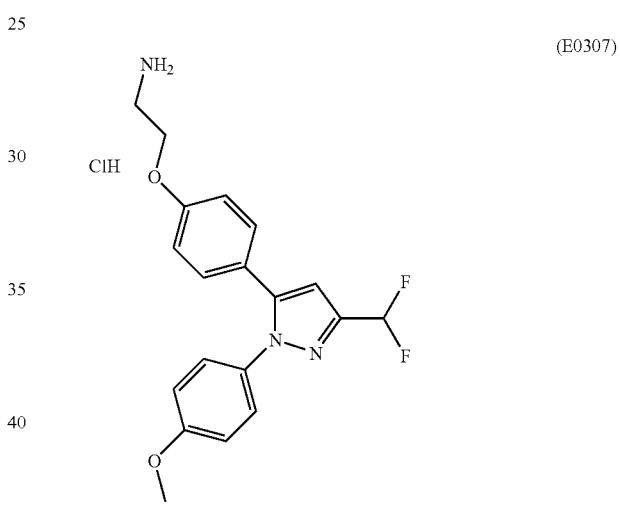
(E0307)

To a suspension of lithium aluminum hydride (250 mg) in ether (5 ml) was added E0295 (630 mg) in tetrahydrofuran (1 ml) under ice-bath. After stirring at room temperature for 1 hour. the mixture was quenched with water (0.125 ml), sodium hydroxideaqueous solution (15%, 0.125 ml), and water (0.375 ml), and then stirred at room temperature for 30 minutes. Magnesium sulfate and celite was added to the mixture, then the suspension was filtered and washed with ether. The filtrate was evaporated to give 0.5 g of oil. The oil was purified with column chromatography (SiO2, 50 ml, eluted with methanol/dichloromethane/concentrated ammonia water (1/10/0.05)) to give oil (300 mg). The oil was dissolved in ethyl acetate and added a solution of hydrogen chloride in ethyl acetate (4N, 1.6 ml). The mixture was evaporated to give oil, which was crystallized from methanol and diisopropyl ether to give E0307 as a powder (300 mg, 42.7%). NMR (DMSO-d6), 3.20 (2H, t, J=4.9 Hz), 3.78 (3H, s), 4.16 (2H, t, J=4.9 Hz), 6.85 (1H, s), 6.94–7.01 (4H, m), 7.08 (1H, t, J=54.6 Hz), 7.20–7.26 (4H, m).

MS (ESI+); 360.3 (MH+, free).

IR (KBr, 20727-7), 1612, 1513.9 cm−1.

EXAMPLE 308

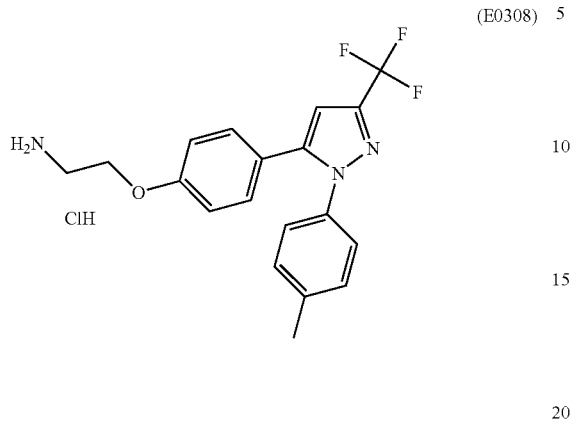
(E0308)

This compound was obtained according to a similar manner to that of E0307.

IR (film): 3401.8, 1610.3, 1511.9, 1469.5, 1240.0, 1162.9, 1130.1, 975.8, 827.3 cm−1.

EXAMPLE 309

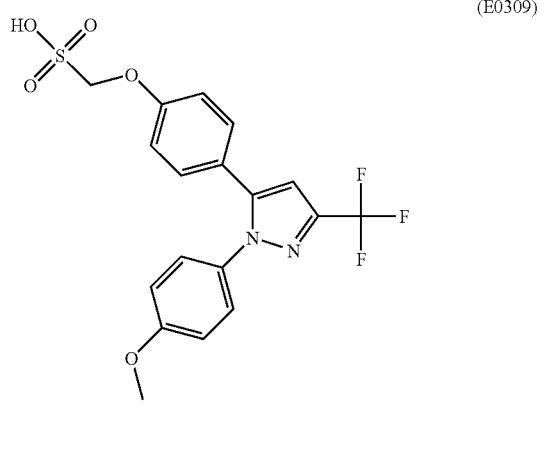
(E0309)

A mixture of P0011 (200 mg), Chloromethylsulfonic acid sodium salt (274 mg), potassium iodide (298 mg), and potassium carbonate (248 mg) in 1-methyl-2-pyrrolidinone (2 ml) was stirring at 150° C. overnight. After cooling to room temperature, the mixture was poured into a mixture of aqueous hydrogen chloride solution (1 N), brine, and ethyl acetate. The aqueous layer was separated and extracted with ethyl acetate (×3). The combined organic layers were dried over magnesium sulfate, and evaporated under reduced pressure to give oil. The oil was purified with column chromatography (SiO2 100 ml, eluted with 15% methanol/dichloromethane) to give E0309 as a brown amorphous (154.3 mg, 60%)

MS (ESI−); 427.1 (M−H).

NMR (DMSO-d6), 3.79 (3H, s), 4.52 (2H, s), 7.00 (2H, d, J=9.0 Hz), 7.01 (2H, d, J=8.9 Hz), 7.07 (1H, s), 7.18 (2H, d, J=9.0 Hz), 7.27 (2H, d, J=8.9 Hz).

EXAMPLE 310

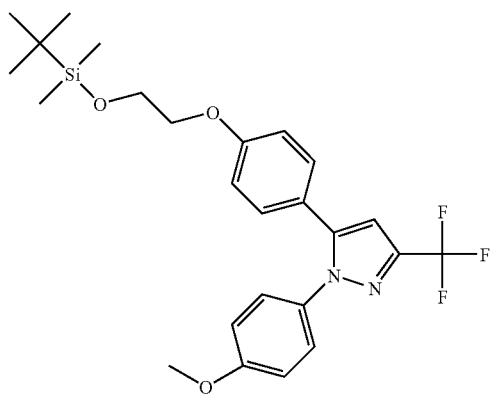
(E0310)

To a solution of P0011 (1.0 g) in DMF (10 ml) under water cooling was added portionwise NaH (60% in Oil, 144 mg) and stirred for 1 hour. After then, III (787 mg) was added and the reaction mixture was stirred at 50° C. for 5 hours. The mixture was quenched with water and extracted twice with EtOAc. The organic layer was washed three times with water and once with brine, dried over MgSO4, filtered and evaporated under reduced pressure. The residue was column chromatographed on silica gel (50 ml) to give 803 mg (55%) of E0310 as a oil.

EXAMPLE 311

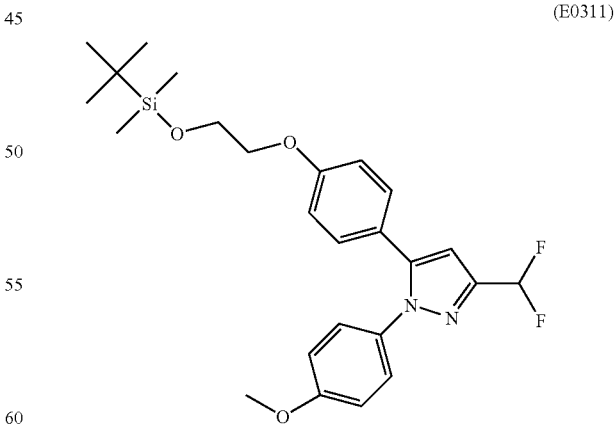
(E0311)

This compound was obtained according to a similar manner to that of E0310.

EXAMPLE 312

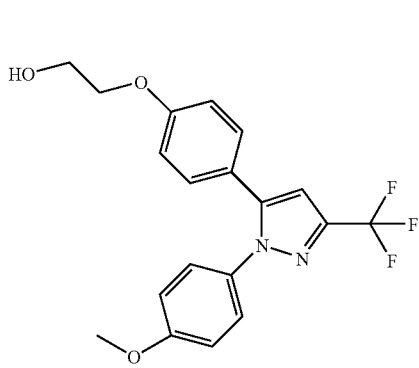
(E0312)

The mixture of E0310 (800 mg) and cHCl (100 ul) in EtOH (10 ml) was stirred at room temperature for 3 hours. After addition of aqueous sodium bicarbonate, the mixture was evaporated, and extracted twice with EtOAc. The organic layer was washed with water and brine, dried over MgSO4, filtered and evaporated under reduced pressure. The residue (710 mg) was column chromatographed on silica gel (50 ml) to give 570 mg (93%) of E0312.

IR (film): 3409.5, 1612.2, 1513.9, 1467.6, 1243.9, 1162.9, 1130.1, 835.0, 835.0 cm−1.

EXAMPLE 313

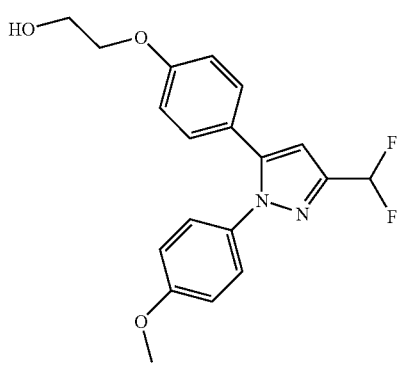
(E0313)

This compound was obtained according to a similar manner to that of E0312.

mp: 122.3–122.5° C.

IR (film): 3399.9, 1612.2, 1513.9, 1456.0, 1251.6, 1174.4, 1083.8, 1033.7, 836.9, 800.3 cm−1.

EXAMPLE 314

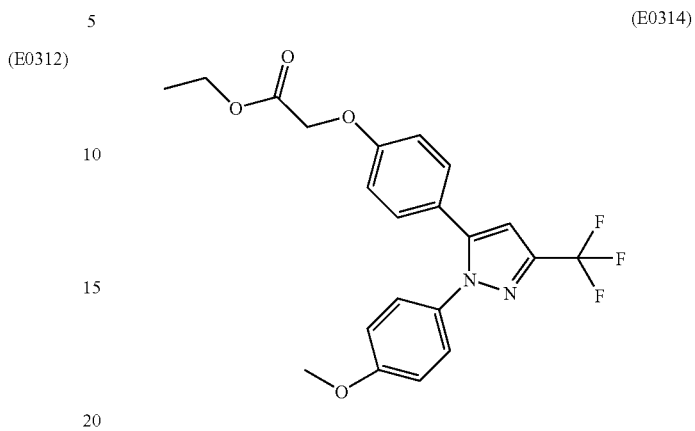
(E0314)

60% Sodium hydride 39.7 mg was added to a solution of P0011 (255 mg) in DMF 1.5 ml. The mixture was stirred at ambient temperature for 1 hour. To this was added ethyl bromoacetate 153 mg. The reaction mixture was stirred at ambient temperature for 1 hour, and then quenched by adding saturated ammonium chloride solution, and whole mixture was extracted with AcOEt. The organic layer was washed with H2O, aqueous sodium chloride solution, dried over magnesium sulfate, and concentrated in vacuo. The residue was purified by silica gel column chromatography eluted with AcOEt/n-hexane=30% to give E0314 (217 mg) as an oil.

Mass (ESI+) 421 (M+H)+

200 MHz 1H NMR (DMSO-d6, d): 1.94 (3H, t, J=7.1 Hz), 3.79 (3H, s), 4.15 (2H, q, J=7.1 Hz), 4.79 (2H, s), 6.92 (2H, d, J=8.8 Hz), 6.99 (2H, d, J=8.9 Hz), 7.09 (1H, s), 7.20 (2H, d, J=8.8 Hz), 7.28 (2H, d, J=8.9 Hz)

EXAMPLE 315

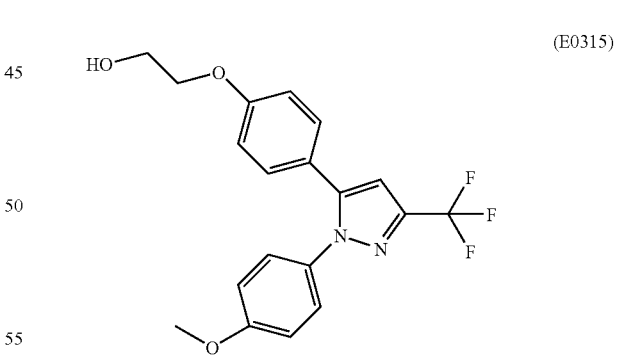
(E0315)

1M solution of diisobutylaluminum hydride in toluene 0.5 ml was added dropwise to a solution of E0314 (98 mg) in THF 3 ml at −50° C. The mixture was stirred at −50° C. for 1 hour, then at 5° C. for 1 hour. Additional 1M solution of diisobutylaluminum hydride in toluene 0.5 ml was added dropwise. After stirring at 5° C. for one more hour, the reaction was quenched by adding 10% aqueous potassium sodium tartaric acid salt, and the mixture was filtered through a celite pad. The filtrate was extracted with AcOEt. The organic layer was washed with saturated aqueous sodium chloride solution, dried over magnesium sulfate, and concentrated in vacuo. The residue was purified by preparative thin layer silica gel chromatography developed by AcOEt/n-hexane=60%. The separated silica gel was extracted with 10% MeOH/CHCl3 and the solvent was evaporated in vacuo to give E0315 (54.5 mg) as an oil, which became solid on standing.

IR (KBr): 3431, 2931, 1612, 1564, 1549, 1512 cm−1
Mass (ESI+): 379 (M+H)+
400 MHz 1H NMR (DMSO-d6, d): 3.67–3.72 (2H, m), 3.79 (3H, s), 3.84–3.99 (2H, m), 4.87 (1H, t, J=5.4 Hz), 6.93 (2H, d, J=8.7 Hz), 7.00 (2H, d, J=8.9 Hz), 7.10 (1H, s), 7.19 (2H, d, J=8.7 Hz), 7.27 (2H, d, J=8.9 Hz)

EXAMPLE 316

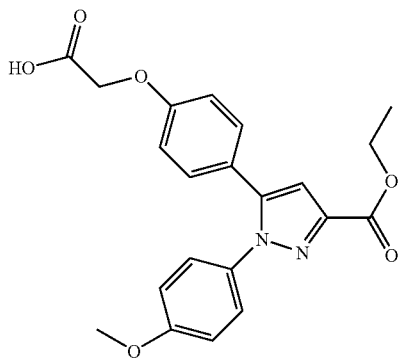

(E0316)

60% Sodium hydride 52 mg was added to a solution of P0020 (200 mg) in DMF 2 ml under ice bath cooling. The mixture was stirred at same temperature for 30 minutes. To this was added bromoacetic acid 90.3 mg. The reaction mixture was stirred at ambient temperature for 2 hours, and then quenched by adding s1M HCl 3 ml. H2O 3 ml and diisopropyl ether 2 ml were added and the mixture was stirred in an ice bath for 30 minutes. The precipitates were collected and washed with H2O and diisopropyl ether to give E0316 (231.2 mg) as a white powder Mass (ESI+): 397 (M+H)+
200 MHz 1H NMR (DMSO-d6, d): 1.31 (3H, t, J=7.1 Hz), 3.79 (3H, s), 4.32 (2H, q, J=7.1 Hz), 4.68 (2H, s), 6.88 (2H, d, J=8.8 Hz), 7.00 (2H, d, J=8.9 Hz), 7.02 (1H, s), 7.18 (2H, d, J=8.8 Hz), 7.26 (2H, d, J=8.9 Hz), 13.05 (1H, brs)

EXAMPLE 317

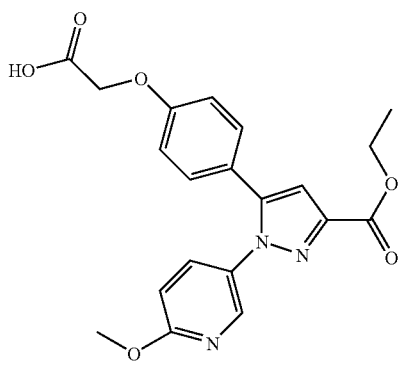

(E0317)

E0317 was prepared in a similar manner to that of E0316.
white powder

Mass (ESI+): 398 (M+H)+
200 MHz 1H NMR (DMSO-d6, d): 1.31 (3H, t, J=7.1 Hz), 3.88 (3H, s), 4.33 (2H, q, J=7.1 Hz), 4.70 (2H, s), 6.92 (2H, d, J=8.8 Hz), 6.89–7.00 (1H, m), 7.06 (1H, s), 7.22 (2H, d, J=8.8 Hz), 7.73 (1H, dd, J=2.8, 8.8 Hz), 8.15 (1H, d, J=2.8 Hz), 13.04(1H, brs)

EXAMPLE 318

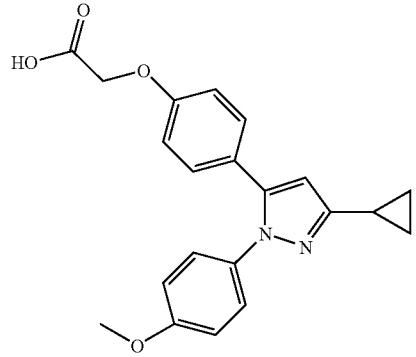

(E0318)

E0318 was obtained according to a similar manner to that of E0316.
oil

Mass (ESI+): 365 (M+H)+
200 MHz 1H NMR (DMSO-d6, d): 0.70–0.93 (4H, m), 1.70–2.00 (1H, m), 3.76 (3H, s), 4.66 (2H, s), 6.25 (1H, s), 6.85 (2H, d, J=8.9 Hz), 6.92 (2H, d, J=9.0 Hz), 7.06–7.16 (4H, m), 13.00 (1H, brs)

EXAMPLE 319

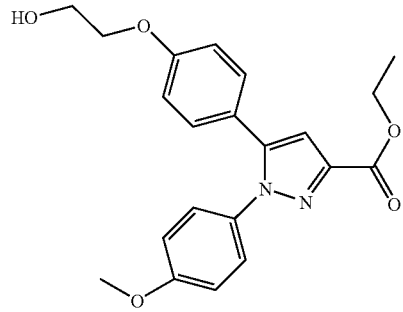

(E0319)

To a suspension of sodium borohydride 19.1 mg in THF 2 ml was added boron trifluoride diethyl etherate 89.5 mg dropwise under ice bath cooling 2.5 eq. The mixture was stirred at same temperature for 30 minutes. E0316 (100 mg) was added in one portion and the mixture was stirred at ambient temperature for 5 hours. 1M HCl 5 ml was added and the mixture was stirred at ambient temperature for 30 minutes. The mixture was extracted with AcOEt. The organic layer was washed with saturated aqueous sodium bicarbonate solution and saturated aqueous sodium chloride solution, dried over magnesium sulfate, and concentrated in vacuo. The residue was crystallized from diisopropyl ether to give E0319 (68.9 mg) as a white powder.

Mass (ESI+): 383 (M+H)+
200 MHz 1H NMR (DMSO-d6, d): 1.31 (3H, t, J=7.1 Hz), 3.65–3.73 (2H, m), 3.79 (3H, s), 3.94–4.00 (2H, m), 4.32

(2H, q, J=7.1 Hz), 4.87 (1H, t, J=5.5 Hz), 6.91 (2H, d, J=8.8 Hz), 6.99 (2H, d, J=8.9 Hz), 7.01 (1H, s), 7.17 (2H, d, J=8.8 Hz), 7.25 (2H, d, J=8.9 Hz)

EXAMPLE 320

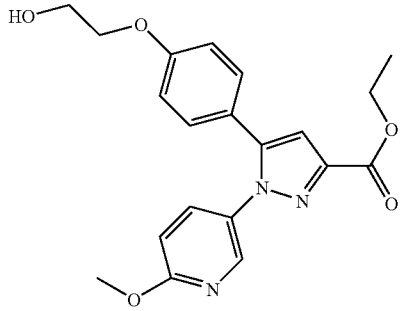
(E0320)

E0320 was prepared in a similar manner to that of E0319.
white powder
Mass (ESI+): 384 (M+H)+
200 MHz 1H NMR (DMSO-d6, d): 1.31 (3H, t, J=7.1 Hz), 3.65–3.74 (2H, m), 3.88 (3H, s), 3.96–4.02 (2H, m), 4.33 (2H, q, J=7.1 Hz), 4.87 (1H, t, J=5.4 Hz), 6.89–6.96 (3H, m), 7.05 (1H, s), 7.21 (2H, d, J=8.7 Hz), 7.72 (1H, dd, J=2.7, 8.8 Hz), 8.14 (1H, d, J=2.7 Hz)

EXAMPLE 321

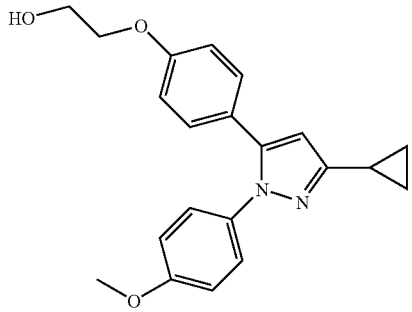
(E0321)

E0321 was prepared in a similar manner to that of E0319.
white powder
mp. 142–144° C.
IR (KBr): 3246, 2924, 1612, 1566, 1547, 1516 cm−1
Mass (ESI+): 351 (M+H)+
200 MHz 1H NMR (DMSO-d6, d): 0.68–0.77 (2H, m), 0.85–0.95 (2H, m), 1.92 (1H, m), 3.64–3.73 (2H, m), 3.76 (3H, s), 3.96 (2H, t, J=4.9 Hz), 4.85 (1H, t, J=5.5 Hz), 6.24 (1H, s), 6.85–6.96 (4H, m), 7.05–7.17 (4H, m)

EXAMPLE 322

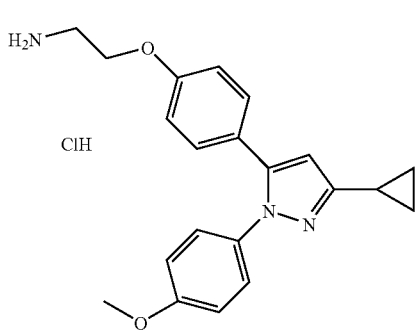
(E0322)

E0322 was prepared in a similar manner to that of E0319.
white powder
mp. 228–231° C.
IR (KBr): 3082, 2958, 2885, 2802, 2733, 2480, 1606, 1572, 1512 cm−1
Mass (ESI+): 350 (M+H)+
200 MHz 1H NMR (DMSO-d6, d): 0.69–0.77 (2H, m), 0.83–0.96 (2H, m), 1.93 (1H,m), 3.14–3.22 (2H, m), 3.76 (3H, s), 4.14–4.20 (2H, m), 6.27 (1H, s), 6.93 (4H, d, J=8.8 Hz), 7.14 (4H, d, J=8.8 Hz), 8.24 (2H, brs)

EXAMPLE 323

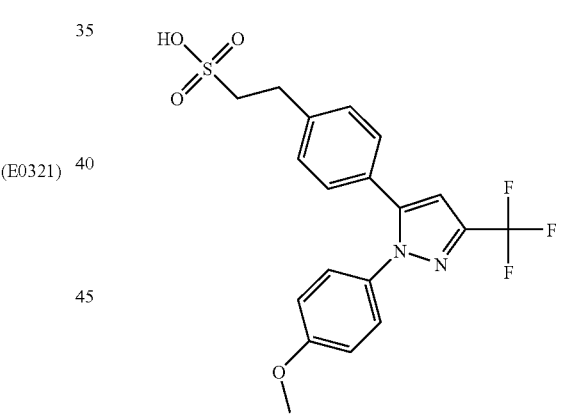
(E0323)

A solution of sodium sulfite 84.2 mg in H2O 1 ml was added to a solution of P0022 (258.1 mg) in EtOH 3 ml and stirred at 70° C. for 2 hours. At which time, white precipitates were appeared and H2O 1 ml was added to dissolve the precipitates. The mixture was stirred at 80° C. overnight to give a clear solution. This was stirred at 80° C. further for 28 hours. The reaction mixture was acidified by 1M HCl 0.7 ml, concentrated and dried under vacuo. The residue was dissolved in CHCl3, dried over magnesium sulfate, all of unsoluble matter was filtered off, and concentrated in vacuo to give E0323 (245 mg) as an amorphous powder.
Mass (API-ES negative) 425 (M−H)+
200 MHz 1H NMR (DMSO-d6, d): 2.61–2.69 (2H, m), 2.78–2.91 (2H, m), 3.79 (3H, s), 7.00 (2H, d, J=8.9 Hz), 7.12 (1H, s), 7.17 (2H, d, J=8.6 Hz), 7.22 (2H, d, J=8.6 Hz), 7.29 (2H, d, J=8.9 Hz)

EXAMPLE 324

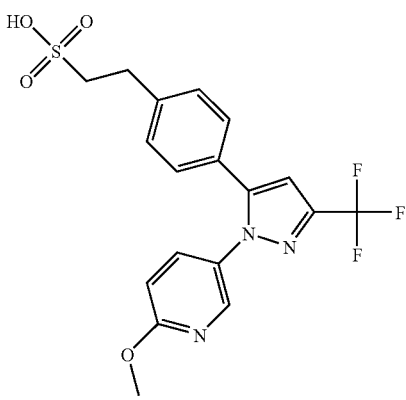

(E0324)

E0324 was prepared from P0023 in a similar manner to that of E0323.

amorphous powder

Mass (API-ES negative): 426 (M−H)+

200 MHz 1H NMR (DMSO-d6, d): 2.61–2.69 (2H, m), 2.83–2.92 (2H, m), 3.88 (3H, s), 6.92 (1H, d, J=8.8Hz), 7.17 (1H, s), 7.23 (4H, s), 7.75 (1H, dd, J=8.8, 2.7 Hz), 8.20 (1H, d, J=2.7 Hz)

EXAMPLE 325

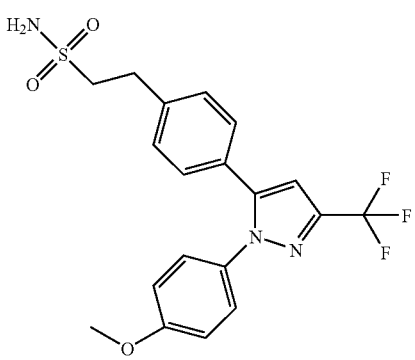

(E0325)

DMF 41 mg was added to a solution of E0319 (239 mg) in thionyl chloride 0.6 ml and the mixture was stirred at 50° C. for 30 minutes. The reaction mixture was concentrated in vacuo. To the residue was added toluene 3 ml, and concentrated in vacuo. The residue was dissolved in THF 10 ml and was added dropwise to a solution of 28% aqoueous ammonium hydroxide solution 0.5 ml and tetrabutylammonium hydrogensulfate 19 mg in THF 4 ml under ice bath cooling. After stirring at ambient temperature for 30 minutes, the reaction mixture was partitioned between AcOEt and aqueous sodium chloride solution. The organic layer was washed with aqueous sodium chloride solution, dried overmagnesium sulfate. The residue was purified by silica gel column chromatography eluted with MeOH/CHCl3=2%, 5%. Pure fraction was collected and concentrated in vacuo. The residual solid was recrystallized from EtOH-diisopropyl ether to give E0325 (72.6 mg) as a white powder.

mp. 131–132° C.

IR (KBr): 3354, 3184, 3126, 1707, 1693, 1676, 1647, 1564, 1549, 1516 cm−1

Mass (ESI+): 426 (M+H)+

200 MHz 1H NMR (DMSO-d6, d): 2.95–3.04 (2H, m), 3.21–3.30 (2H, m), 3.79 (3H, s), 6.87 (2H, s), 7.00 (2H, d, J=8.9 Hz), 7.14 (1H, s), 7.23–7.33 (6H, m)

EXAMPLE 326

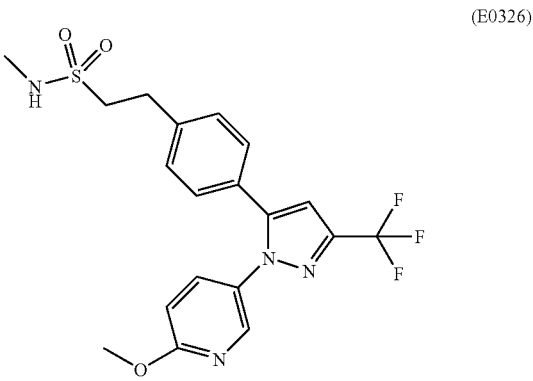

(E0326)

E0326 was prepared in a similar manner to that of E0325.

white powder mp. 139–140° C.

IR (KBr): 3230, 3132, 1610, 1568, 1527, 1500 cm−1

Mass (ESI+) 441 (M+H)+

200 MHz 1H NMR (DMSO-d6, d): 2.58 (3H, s), 2.90–3.00 (2H, m), 3.25–3.33 (2H, m), 3.88 (3H, s), 6.93 (1H, d, J=8.9 Hz), 6.97 (1H, brs), 7.19 (1H, s), 7.26 (2H, d, J=8.3 Hz), 7.34 (2H, d, J=8.3 Hz), 7.77 (1H, dd, J=8.9, 2.8 Hz), 8.19 (1H, d, J=2.8 Hz)

EXAMPLE 327

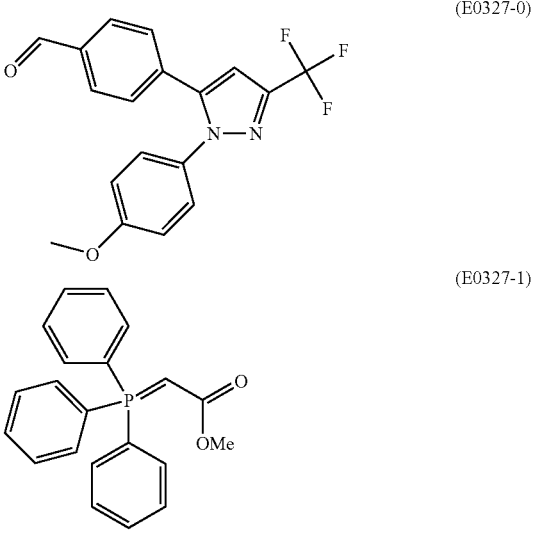

(E0327-0)

(E0327-1)

-continued

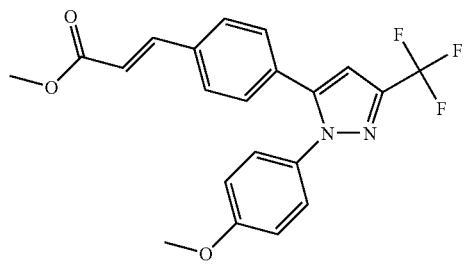

(E0327)

EXAMPLE 329

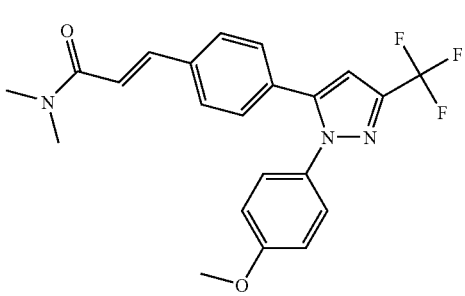

(E0329)

A mixture of E0327-0 (800 mg) and E0327-1, methyl (triphenylphosphoranylidene)-acetate (850 mg) in toluene (10 ml) was stirred under reflux condition for 5 hrs. The mixture was evaporated under reduced pressure and column chromatographed on silica gel (50 ml, Hex:EtOAc=5:1) to give 795 mg (85.5%) of E0327.

IR (film): 1718.3, 1637.3, 1513.9, 1241.9, 1166.7, 1132.0, 977.7, 837.0 cm−1

EXAMPLE 328

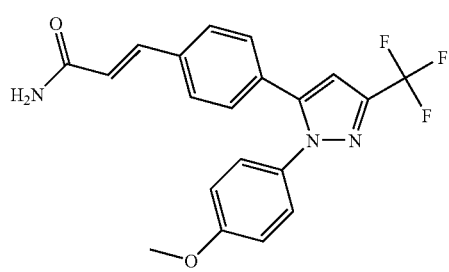

(E0328)

To a suspension of E0258 (180 mg) in toluene (5 ml) was adde thionylchloride (0.17 ml) at room temperature. The reaction mixture was stirred at 100° C. for 5 hours until the mixture become clear solution. After then, the mixture was evaporated under reduced pressure. (become solid) THF was added, and then aqueous NH3 (37%) was added. The mixture was stirred for 1 hour, and quenched with water, and extracted twice with EtOAc. The combined organic layer was washed with sat. NaHCO3, water and brine, dried over Na2SO4, filtered and evaporated under reduced pressure to give 170 mg (95%) of E0328 as a powder.

IR (KBr): 3347.8, 1671.9, 1606.4, 1513.9, 1467.6, 1388.5, 1236.2, 1164.8, 1132.0, 979.7, 837.0 cm−1.

To a suspension of E0258 (200 mg) in toluene (4 ml) was added thionylchloride (0.19 ml) at room temperature. The reaction mixture was stirred at 10° C. for 5 hours until the mixture become clear solution. After then, the mixture was evaporated under reduced pressure. (become solid) THF was added, and then Me2NH (116 mg) was added. The mixture was stirred for 1 hour, and quenched with water, and extracted twice with EtOAc. The combined organic layer was washed with sat.NaHCO3, water and brine, dried over Na2SO4, filtered and evaporated under reduced pressure to give 45 mg (21%) of E0329 as a powder.

Filtrate (58 mg).

mp: 118–120° C.

IR (film): 1650.8, 1608.3, 1511.9, 1469.5, 1240.0, 1159.0, 1133.9 cm−1.

EXAMPLE 330

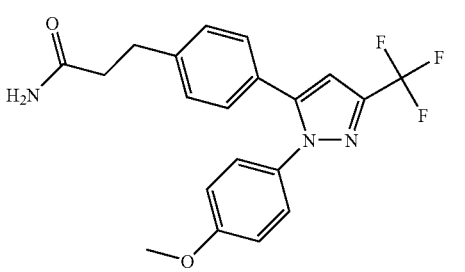

(E0330)

A mixture of E0328 (125 mg) and Pd/C (100 mg) in EtOH (10 m) was stirred under H2 atmosphere for 3.0 hours. After filtration, a filtrate was evaporated under reduced pressure. The residue was dissolved in EtOH and filtered with syringe driven filter, and evaporated to give 85 mg of E0330.

IR (KBr): 3342.0, 1670.0, 1511.9, 1240.0, 1160.9, 1130.1 cm−1.

EXAMPLE 331

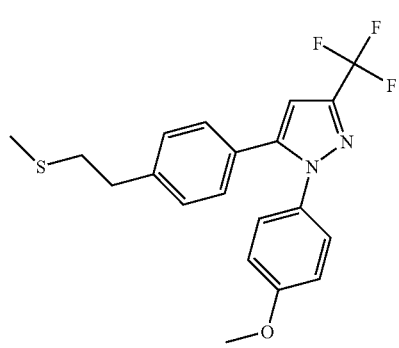

(E0331)

A mixture of E0138 (300 mg) and MeSNa (72 mg) in DMF (6 ml) was heated at 70° C. for 5 hours. After cooling, the reaction mixture was partitioned between EtOAc and water. The aqueous layer was separated and extracted with EtOAc. The combined organic layer was washed with water (twice) and brine, dried over Na2SO4, filtered and evaporated. The residue was column chromatographed on silica gel to give 270 mg (quant) of E0331.

EXAMPLE 332

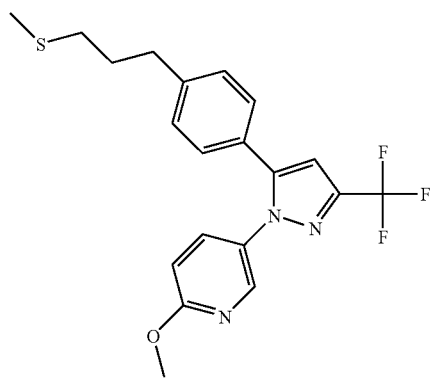

(E0332)

E0332 was prepared from E0141 in a similar manner to that of E0331.
oil
Mass (ESI+): 408 (M+H)+
200 MHz 1H NMR (DMSO-d6, d) 1.73–1.89 (2H, m), 2.03 (3H, s), 2.40–2.52 (2H, m), 2.62–2.70 (2H, m), 3.88 (3H, s), 6.92 (1H, d, J=8.8 Hz), 7.18 (1H, s), 7.24 (4H, s), 7.76 (1H, dd, J=8.8,2.7 Hz), 8.18 (1H, d, J=2.7 Hz)

EXAMPLE 333

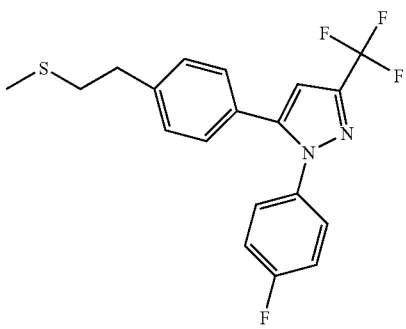

(E0333)

This compound was obtained according to a similar manner to that of E0331.

EXAMPLE 334

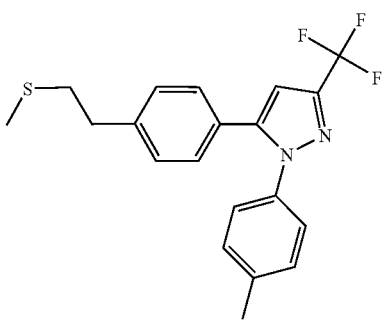

(E0334)

This compound was obtained according to a similar manner to that of E0331.

EXAMPLE 335

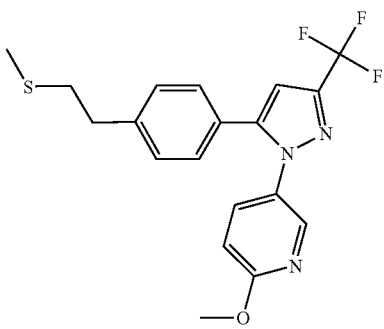

(E0335)

This compound was obtained according to a similar manner to that of E0331

EXAMPLE 336

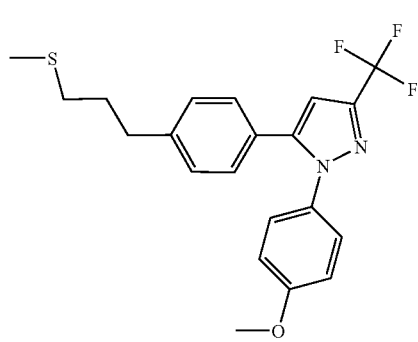
(E0336)

This compound was obtained according to a similar manner to that of E0331.

EXAMPLE 337

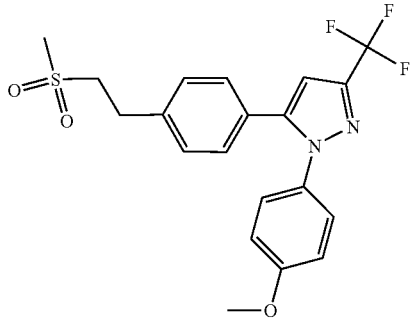
(E0337)

A mixture of E0331 (250 mg) and mcpba (165 mg) in CH2Cl2 was stirred under ice-cooling for 1 hour, and then mcpba (55 mg) was added. After stirring for 1 hour under ice cooling, the reaction mixture was partitioned between CDCl3 and sat.NaHCO3. The organic layer was separated, washed with sat.NaHCO3, water and brine, dried over Na2SO4, filtered and evaporated under reduced pressure. The residue was column chromatographed on silica gel (Hex/EtOAc) to give 141 mg (52%) of E0337.

IR (film): 1511.9, 1303.6, 1240.0, 1130.1 cm−1.
Oxide: FR267958
NMR (CDCl3): 2.599 (s, 3H), 2.85–3.21 (m, 4H), 3.828 (s, 3H), 6.721 (s, 1H), 6.872 (d, J=9.0 Hz, 2H), 7.141 (s, 4H), 7.179 (d, J=9.0 Hz, 2H).
MS: (M+Na)+431.1 (M110092-2)

EXAMPLE 338

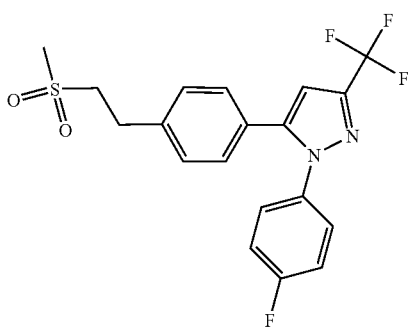
(E0338)

This compound was obtained according to a similar manner to that of E0337.

IR (film): 1511.9, 1469.5, 1311.4, 1282.4, 1236.2, 1126.2, 973.9, 823.5, 759.8 cm−1.

EXAMPLE 339

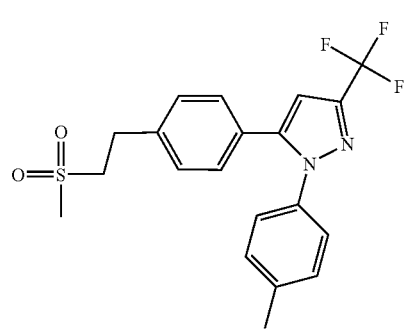
(E0339)

This compound was obtained according to a similar manner to that of E0337.

IR (film): 1511.9, 1469.5, 1311.4, 1282.4, 1236.2, 1128.2, 973.9, 823.5, 759.8 cm−1.

EXAMPLE 340

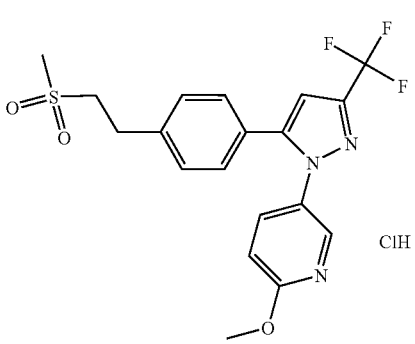
(E0340)

This compound was obtained according to a similar manner to that of E0337.

IR (film): 1673.9, 1616.1, 1498.4, 1477.2, 1467.6, 1390.4, 1307.5, 1290.1, 1240.0, 1160.9, 1132.0, 971.9, 756.0 cm−1.

NMR (CDCl3): 2.76–2.94 (m, 4H), 3.927 (s, 3H), 3.943 (s, 3H), 6.728 (s, 1H), 6.752 (d, J=8.9 Hz, 1H), 7.12–7.26 (m, 4H), 7.46–7.59 (m, 1H), 8.04–8.10 (m, 1H).

MASS (M+Na)+445.1 (FR267958-N)

EXAMPLE 341

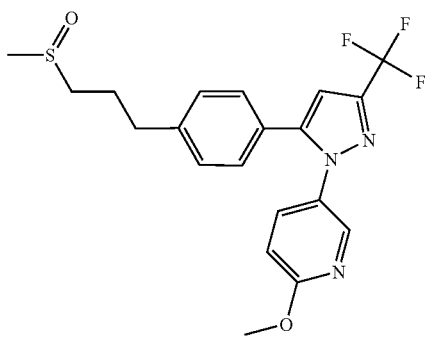
(E0341)

To a solution of E0336 (450 mg) in dichloromethane (45 ml) was added MCPBA (306 mg) at room temperature. After stirring for 1 hour, the reaction mixture was washed with sat.NaHCO3 (twice) and water, dried over Na2SO4, filtered and evaporated under reduced pressure. The residue was column chromatographed on silica gel (50 ml) to give 470 mg of E0341 as an oil.

EXAMPLE 342

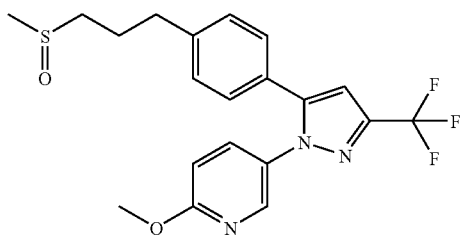
(E0342)

E0342 was prepared in a similar manner to that of E0341. white powder.

mp. 92–93° C.

IR (KBr): 3080, 2952, 1612, 1566, 1547, 1529, 1500 cm−1

Mass (ESI+): 424 (M+H)+

200 MHz 1H NMR (DMSO-d6, d): 1.87–2.00 (2H, m), 2.51 (3H, s), 2.56–2.78 (4H, m), 3.88 (3H, s), 6.92 (1H, d, J=8.9 Hz),7.19 (1H, s), 7.21–7.31 (4H, m), 7.76 (1H, dd, J=2.7,8.9 Hz), 8.19 (1H, d, J=2.7 Hz)

EXAMPLE 343

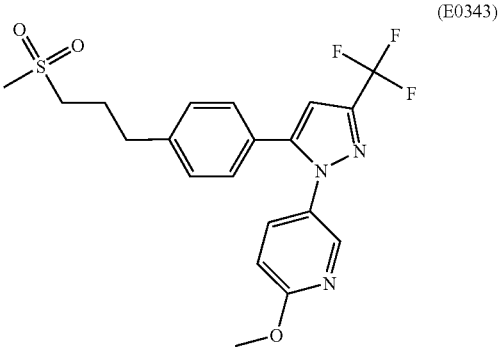
(E0343)

To a solution of E0336 (450 mg) in dichloromethane (45 ml) was added MCPBA (306 mg) at room temperature. After stirring for 1 hour, the reaction mixture was washed with sat.NaHCO3 (twice) and water, dried over Na2SO4, filtered and evaporated under reduced pressure. The residue was column chromatographed on silica gel (50 ml) and recrystalized from EtOH to give 168 mg (44%) of E0343.

EXAMPLE 344

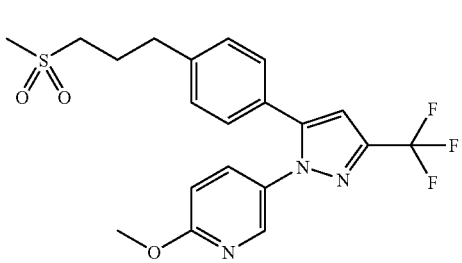
(E0344)

3-Chloroperoxybenzoic acid (407 mg) was added to a solution of E0342 (666.3 mg) in CH2Cl2 6 ml under ice bath cooling. The reaction mixture was stirred at ambient temperature for 1 hour. The mixture was diluted with CHCl3, washed with 1M NaOH, 5% aqueous sodium thiosulfate solution, and saturated aqueous sodium chloride solution, dried over magnesium sulfate, and concentrated in vacuo. The residue was recrystallized from AcOEt-n-hexane to give E0344 (565.2 mg) as a white powder.

mp. 121–122° C.

IR (KBr): 3120, 2954, 1707, 1693, 1647, 1612, 1566, 1547, 1529, 1500 cm−1

Mass (ESI+): 440 (M+H)+

200 MHz 1H NMR (DMSO-d6, d): 1.93–2.06 (2H, m), 2.67–2.75 (2H, m), 2.96 (3H, s), 3.04–3.13 (2H, m), 3.88 (3H, s), 6.92 (1H, d, J=8.8 Hz), 7.19 (1H, s), 7.19–7.31 (4H, m), 7.76 (1H, dd, J=8.8, 2.8 Hz), 8.19 (1H, d, J=2.8 Hz)

EXAMPLE 345

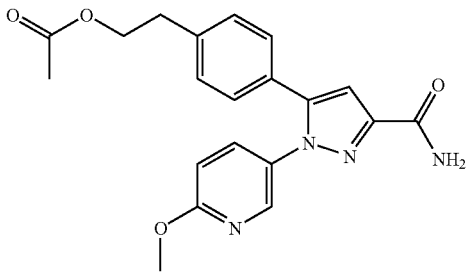
(E0345)

Oxalylchloride 286 mg was added to a suspension of E0363 (0.43 g) in CH2Cl2 3 ml under ice bath cooling. DMF 1 drop was added and the mixture was stirred at same temperature for 1 hour, and then concentrated in vacuo. To the residue, was added toluene and concentrated in vacuo. The residue was dissolved in THF 5 ml and was added to a solution of aqueous ammoniumhydroxide solution 5 ml with under ice bath cooling. The mixture was stirred at same temperature for 1 hour, diluted with AcOEt, washed successively with 1M HCl, saturated aqueous sodium bicarbonate solution, and saturated aqueous sodium chloride solution, dried over magnesium sulfate, and concentrated in vacuo. The residue was purified by silica gel column chromatography eluted with AcOEt/n-hexane=60%. The pure fraction was collected and concentrated in vacuo and the residue was crystallized from diisopropylether to give E0345 (287.8 mg) as a white powder.

Mass (ESI+): 381 (M+H)+

200 MHz 1H NMR (DMSO-d6, d): 1.97 (3H, s), 2.89 (2H, t, J=6.8 Hz), 3.87 (3H, s), 4.21 (2H, t, J=6.8 Hz), 6.91 (1H, d, J=8.8 Hz), 6.98 (1H, s), 7.22 (2H, d, J=8.4 Hz), 7.28 (2H, d, J=8.4 Hz), 7.38 (1H, brs), 7.63–7.75 (1H, brs), 7.72 (1H, dd, J=2.7, 8.8 Hz), 8.16 (1H, d, J=2.7 Hz)

EXAMPLE 346

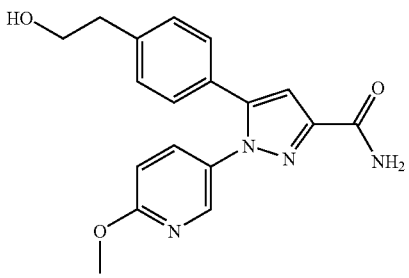
(E0346)

A mixture of E0109 (449.1 mg) and sodium methoxide 238 mg in formamide 5 ml was heated at 70° C. for 5 hours. The mixture was allowed to cool to ambient temperature, and was partitioned between ethyl acetate and H2O. The organic layer was washed with saturated aqueous sodium chloride solution, dried over magnesium sulfate, and concentrated in vacuo. The residue was purified by silica gel column chromatography eluted with CHCl3, then MeOH/CHCl3=2%, 5% to give E0346 (235.7 mg) as a white powder.

Mass (ESI+): 338 (M+H)+

400 MHz 1H NMR (DMSO-d6, d): 2.70 (2H, t, J=6.9 Hz), 3.56–3.62 (2H, m), 3.79 (3H, s), 4.65 (1H, t, J=5.1 Hz), 6.92 (1H, s), 6.99 (2H, d, J=8.9 Hz), 7.15 (2H, d, J=8.3 Hz), 7.20 (2H, d, J=8.3 Hz), 7.27 (2H, d, J=8.9 Hz), 7.33 (1H, s), 7.64 (1H, s)

EXAMPLE 347

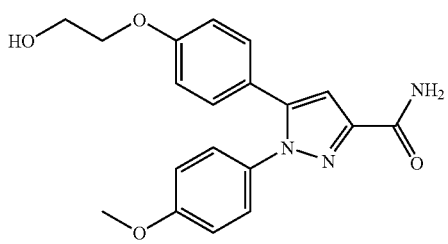
(E0347)

E0347 was prepared in a similar manner to that of E0346.

white powder

Mass (ESI+): 454 (M+H)+

200 MHz 1H NMR (DMSO-d6, d): 3.65–3.73 (2H, m), 3.78 (3H, s), 3.94–4.00 (2H, m), 4.86 (1H, t, J=5.5 Hz), 6.88 (1H, s), 6.91 (2H, d, J=8.8 Hz), 6.99 (2H, d, J=8.9 Hz), 7.16 (2H, d, J=8.8 Hz), 7.26 (2H, d, J=8.9 Hz), 7.32 (1H, s), 7.63 (1H, s)

EXAMPLE 348

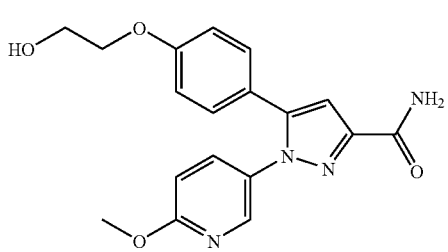
(E0348)

E0348 was prepared in a similar manner to that of E0346.

white powder

Mass (ESI+): 355 (M+H)+

200 MHz 1HNMR (DMSO-d6, d): 3.65–3.74 (2H, m), 3.87 (3H, s), 3.96–4.05 (2H, m), 4.87 (1H, t, J=5.5 Hz), 6.88–6.97 (4H, m), 7.20 (2H, d, J=8.7 Hz), 7.37 (1H, brs), 7.67–7.73 (1H, brs, overlapping), 7.71 (1H, dd, J=2.6, 8.8 Hz), 8.16 (1H, d, J=2.6 Hz)

EXAMPLE 349

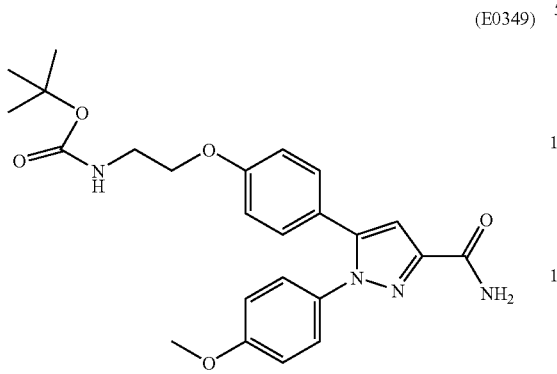
(E0349)

E0349 was prepared in a similar manner to that of E0346.
White Powder
Mass (ESI+): 453 (M+H)+
400 MHz 1HNMR (DMSO-d6, d): 1.37 (9H, s), 3.24–3.29 (2H, m), 3.78 (3H, s), 3.94 (2H, t, J=5.8 Hz), 6.88 (1H, s), 6.90 (2H, d, J=8.8 Hz), 6.99 (2H, d, J=9.0 Hz), 6.97–7.00 (1H, br), 7.16 (2H, d, J=8.8 Hz), 7.25 (2H, d, J=9.0 Hz), 7.32 (1H, brs), 7.62 (1H, brs)

EXAMPLE 350

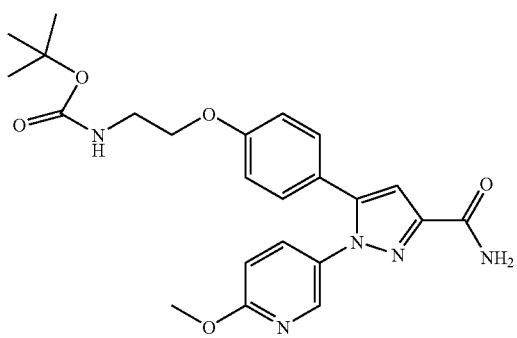
(E0350)

E0350 was prepared in a similar manner to that of E0346.
White Powder
Mass (ESI+): 454 (M+H)+
200 MHz 1H NMR (DMSO-d6, d): 1.37 (9H, s), 3.22–3.33 (2H, m), 3.88 (3H, s), 3.93–3.99 (2H, m), 6.88–7.10 (4H, m), 6.91 (1H, s), 7.20 (2H, d, J=8.7 Hz), 7.36 (1H, brs), 7.68 (1H, brs), 7.71 (1H, dd, J=2.7, 8.8 Hz), 8.16 (1H, d, J=2.7 Hz)

EXAMPLE 351

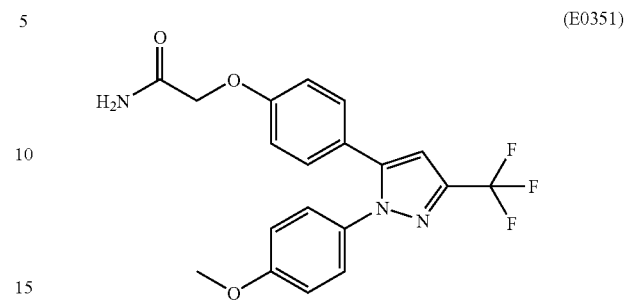
(E0351)

E0351 was prepared in a similar manner to that of E0346.
mp. 168–169° C.
IR (KBr): 3381, 3192, 1705, 1695, 1674, 1643, 1614, 1564, 1549, 1516 cm−1
Mass (ESI+): 392 (M+H)+
400 MHz 1HNMR (DMSO-d6, d): 3.79 (3H, s), 4.43 (2H, s), 6.93 (2H, d, J=8.9 Hz), 7.00 (2H, d, J=9.0 Hz), 7.08 (1H, s), 7.21 (2H, d, J=8.9 Hz), 7.28 (2H, d, J=9.0 Hz), 7.40 (1H, brs), 7.54 (1H, brs)

EXAMPLE 352

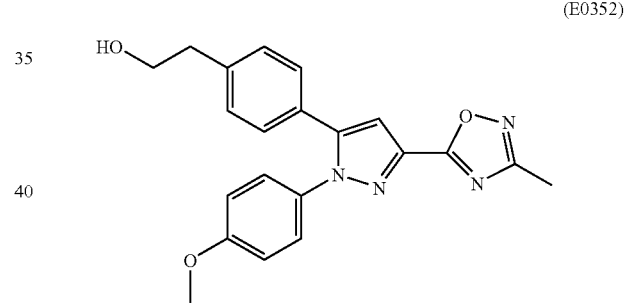
(E0352)

A mixture of E0346 (433.5 mg) and N,N-dimethylacetamide dimethyl acetal 856 mg in toluene 5 ml was heated at 100° C. for 40 minutes. The reaction mixture was concentrated in vacuo. To the residue was added toluene and concentrated in vacuo. The residue was dissolved in toluene 5 ml, hydroxylamine hydrochloride 893 mg and AcOH 3 ml was added and the mixture was heated at 100° C. for 1 hour. The mixture was cooled to ambient temperature, and partitioned between AcOEt and H2O, The organic layer was washed with H2O, saturated aqueous sodium bicarbonate solution, and saturated aqueous sodium chloride solution, dried over magnesium sulfate, and concentrated in vacuo. The residue was purified by silica gel column chromatography eluted with AcOEt/n-hexane=40%, 60%, 80%. The pure fraction was collected and concentrated in vacuo. The residue was crystallized from AcOEt/n-hexane to give E0352 (203 mg) as a white powder.
mp. 148–150° C.
IR (KBr): 3431, 3425, 3406, 1614, 1547, 1510 cm−1
Mass (ESI+): 377 (M+H)+

200 MHz 1H NMR (DMSO-d6, d): 2.44 (3H, s), 2.72 (2H, t, J=6.9 Hz), 3.55–3.65 (2H, m), 3.80 (3H, s), 4.66 (1H, t, J=5.1 Hz), 7.02 (2H, d, J=8.9 Hz), 7.20 (2H, d, J=9.0 Hz), 7.24 (2H, d, J=9.0 Hz), 7.28–7.36 (3H, m)

EXAMPLE 353

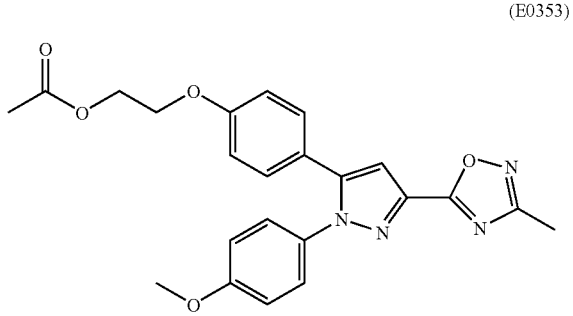
(E0353)

E0353 was prepared in a similar manner to that of E0352.
oil
Mass (ESI+): 435 (M+H)+
200 MHz 1H NMR (DMSO-d6, d): 2.03 (3H, s), 2.44 (3H, s), 3.80 (3H, s), 4.17–4.22 (2H, m), 4.25–4.35 (2H, m), 6.97 (2H, d, J=8.7 Hz), 7.02 (2H, d, J=9.0 Hz), 7.23 (2H, d, J=8.7 Hz), 7.27 (1H, s), 7.31 (2H, d, J=9.0 Hz)

EXAMPLE 354

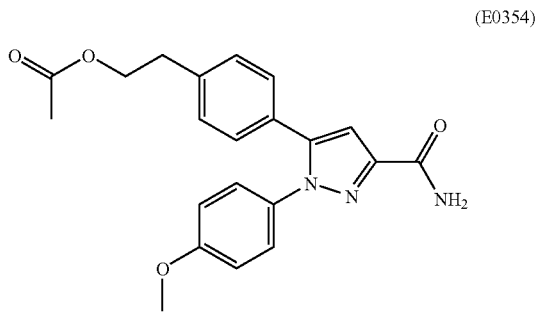
(E0354)

Acetic anhydride 124 mg was added to a solution of E0346 (102.6 mg) and pyridine 241 mg in CH2Cl2 1 ml. The reaction mixture was stirred at ambient temperature for 1 hour. Acetic anhydride 62 mg and pyridine 1 ml was added and stirred at ambient overnight. Acetic anhydride 62 mg was added and stirred at ambient for 4 hours. The mixture was concentrated in vacuo, and the residue was partitioned between ethyl acetate and 1M HCl. The organic layer was washed with saturated aqueous sodium bicarbonate solution and saturated aqueous sodium chloride solution, dried over magnesium sulfate, and concentrated in vacuo. The residual solid was collected and washed with diisopropyl ether to give E0354 (76.3 mg) as a white powder.

Mass (ESI+): 380 (M+H)+
200 MHz 1H NMR (DMSO-d6, d): 1.96 (3H, s), 2.87 (2H, t, J=6.8 Hz), 3.78 (3H, s), 4.20 (2H, t, J=6.8Hz), 6.94 (1H, s), 6.98 (2H, d, J=8.9 Hz), 7.15–7.30 (6H, m), 7.33 (1H, s), 7.64 (1H, s)

EXAMPLE 355

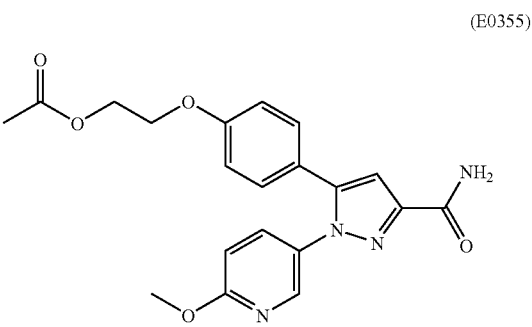
(E0355)

E0355 was prepared in a similar manner to that of E0354.
White Powder
Mass (ESI+): 397 (M+H)+
200 MHz 1H NMR (DMSO-d6, d): 2.03 (3H, s), 3.87 (3H, s), 4.16–4.21 (2H, m), 4.29–4.34 (2H, m), 6.88–6.98 (4H, m), 7.21 (2H, d, J=8.7 Hz), 7.37 (1H, brs), 7.68–7.70 (1H, brs, overlapping), 7.71 (1H, dd, J=2.7, 8.8 Hz), 8.16 (1H, d, J=2.7 Hz)

EXAMPLE 356

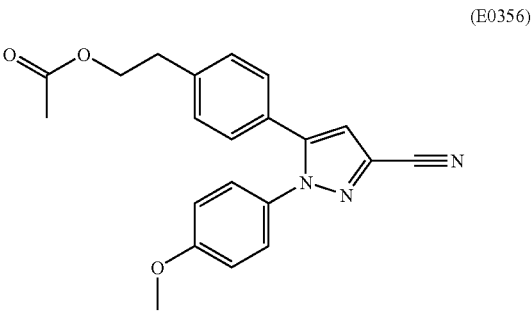
(E0356)

Phosphorus oxychloride 40.4 mg was added to DMF 0.5 ml under ice bath cooling. After stirring at same temperature for 5 minutes, E0354 (50 mg) was added in one portion. The reaction mixture was stirred at same temperature for 1 hour, and quenched by adding aqueous sodium bicarbonate solution. The mixture was extracted with ethyl acetate. The organic layer was washed with H2O, saturated aqueous sodium chloride solution, dried over magnesium sulfate, and concentrated in vacuo to give E0356 (45.0 mg) as an oil.

Mass (ESI+): 403 (M+CH3CN+H)+
Mass (API-ES positive): 362 (M+H)+, 384 (M+Na)+
200 MHz 1H NMR (DMSO-d6, d): 1.96 (3H, s), 2.88 (2H, t, J=6.8 Hz), 3.79 (3H, s), 4.20 (2H, t, J=6.8 Hz), 7.00 (2H, d, J=8.9 Hz), 7.15–7.31 (6H, m), 7.36 (1H, s)

EXAMPLE 357

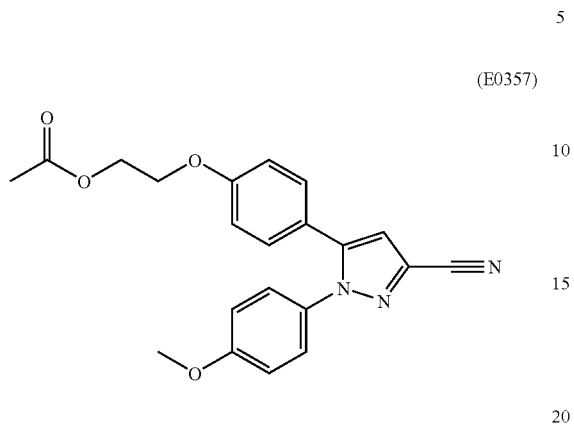
(E0357)

E0357 was prepared in a similar manner to that of E0356.
oil
Mass (ESI+): 378 (M+H)+
200 MHz 1H NMR (DMSO-d6, d): 2.02 (3H, s), 3.79 (3H, s), 4.15–4.21 (2H, m), 4.29–4.34 (2H, m), 6.93–7.04 (4H, m), 7.18 (2H, d, J=8.8 Hz), 7.24–7.31 (3H, m)

EXAMPLE 358

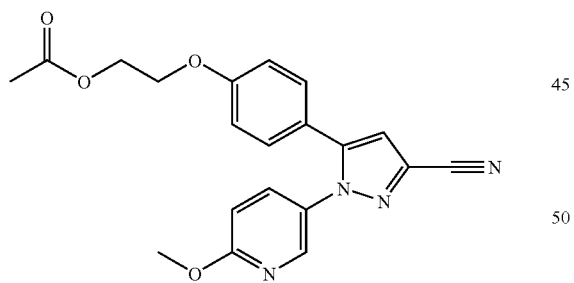
(E0358)

E0358 was prepared in a similar manner to that of E0356.
oil
Mass (ESI+): 379 (M+H)+
200 MHz 1H NMR (DMSO-d6, d): 2.02 (3H, s), 3.88 (3H, s), 4.17–4.21 (2H, m), 4.29–4.34 (2H, m), 6.90–7.03 (3H, m), 7.22 (2H, d, J=8.8 Hz), 7.36 (1H, s), 7.74 (1H, dd, J=2.7, 8.9 Hz), 8.20 (1H, d, J=2.7 Hz)

EXAMPLE 359

(E0359)

E0359 was prepared in a similar manner to that of E0356.
Amorphous Powder
Mass (ESI+): 435 (M+H)+
200 MHz 1H NMR (DMSO-d6, d): 1.37 (9H, s), 3.22–3.32 (2H, m), 3.79 (3H, s), 3.92–3.98 (2H, m), 6.90–7.08 (1H, br, overlapping), 6.92 (2H, d, J=8.8 Hz), 7.00 (2H, d, J=9.0 Hz), 7.16 (2H, d, J=8.8 Hz), 7.28 (2H, d, J=9.0 Hz), 7.30 (1H, s)

EXAMPLE 360

(E0360)

E0360 was prepared in a similar manner to that of E0356.
White Powder
Mass (ESI+): 436 (M+H)+
200 MHz 1H NMR (DMSO-d6, d): 1.37 (9H, s), 3.22–3.32 (2H, m), 3.88 (3H, s), 3.93–3.99 (2H, m), 6.90–7.01 (1H, overlapping), 6.92 (1H, d, J=8.8 Hz), 6.95 (2H, d, J=8.8 Hz), 7.21 (2H, d, J=8.8 Hz), 7.34 (1H, s), 7.73 (1H, d, J=2.7, 8.8 Hz), 8.20 (1H, d, J=2.7 Hz)

EXAMPLE 361

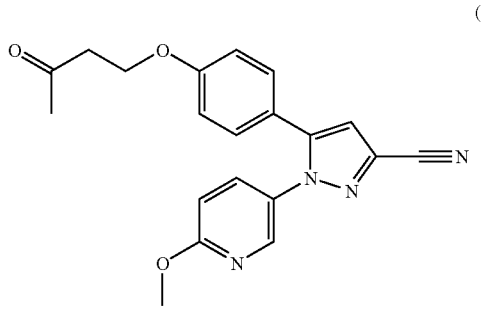
(E0361)

E0361 was prepared from E0345 in a similar manner to that of E0356.

oil

Mass (ESI+): 363 (M+H)+

200 MHz 1H NMR (DMSO-d6, d): 1.96 (3H, s), 2.89 (2H, t, J=6.8 Hz), 3.88 (3H, s), 4.21 (2H, t, J=6.8 Hz), 6.92 (1H, d, J=8.8 Hz), 7.22 (2H, d, J=8.3 Hz), 7.30 (2H, d, J=8.3 Hz), 7.41 (1H, s), 7.75 (1H, dd, J=8.8,2.7 Hz), 8.20 (1H, d, J=2.7 Hz)

EXAMPLE 362

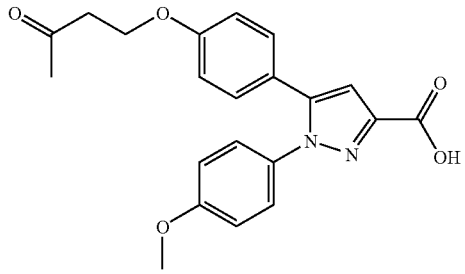
(E0362)

A solution of acetyl chloride 0.28 ml in was added to a solution of E0261 (441.6 mg) in CH2Cl2 4 ml and pyridine 2 ml under ice bath cooling. The reaction mixture was stirred at ambient temperature for 1 hour. Acetyl chloride 0.14 ml was added and stirred at ambient temperature for 1 hour. The reaction was quenched by adding aqueous sodium bicarbonate solution and the mixture was stirred at ambient temperature overnight. The mixture was acidified to pH 2 by 6M HCl and extracted with ethyl acetate. The organic layer was washed with H2O and saturated aqueous sodium chloride solution, dried over magnesium sulfate, and concentrated in vacuo. The residue was crystallized from diisopropyl ether to give E0362 (405.3 mg) as a white powder.

Mass (ESI+): 381 (M+H)+

200 MHz 1H NMR (DMSO-d6, d): 1.96 (3H, s), 2.87 (2H, t, J=6.8 Hz), 3.79 (3H, s), 4.20 (2H, t, J=6.8 Hz), 6.96–7.02 (3H, m), 7.15–7.27 (6H, m), 12.91 (1H, br)

EXAMPLE 363

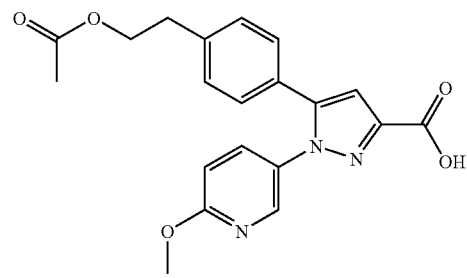
(E0363)

E0363 was prepared in a similar manner to that of E0362.

oil

Mass (ESI+): 382 (M+H)+

200 MHz 1H NMR (DMSO-d6, d): 2.04 (3H, s), 2.94 (2H, t, J=7.0 Hz), 3.95 (3H, s), 4.29 (2H, t, J=7.0 Hz), 6.76 (1H, d, J=8.8 Hz), 7.08 (1H, s), 7.04–7.35 (4H, m), 7.59 (1H, dd, J=2.7, 8.8 Hz), 8.12 (1H, d, J=2.7 Hz)

EXAMPLE 364

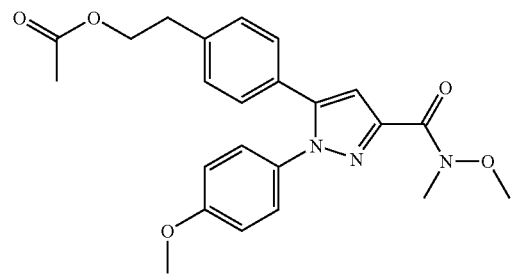
(E0364)

Oxalyl chloride 264 mg was added to a suspension of E0362 (395 mg) in CH2Cl2 5 ml under ice bath cooling. DMF 1 drop was added and the mixture was stirred at ambient temperature for 1 hour.

The mixture was concentrated in vacuo. To the residue was added toluene, and concentrated in vacuo. The residue was dissolved in CH2Cl2 30 ml, cooled in an ice bath, N,O-dimethylhydroxylamine hydrochloride 203 mg and triethylamine 525 mg were added and the mixture was stirred at ambient temperature overnight. The mixture was diluted with AcOEt, washed successively with 1M HCl, aqueous sodium bicarbonate solution, and saturated aqueous sodium chloride solution, dried over magnesium sulfate, and concentrated in vacuo. The residue was purified by silica gel column chromatography eluted with CHCl3, then AcOEt/CHCl3=10%, 20% to give E0364 (418.4 mg) as an oil.

Mass (ESI+): 424 (M+H)+

200 MHz 1H NMR (DMSO-d6, d): 1.97 (3H, s), 2.88 (2H, t, J=6.8 Hz), 3.38 (3H, s), 3.77 (3H, s), 3.78 (3H, s), 4.20 (2H, t, J=6.8 Hz), 6.94–7.03 (3H, m), 7.16–7.27 (6H, m)

EXAMPLE 365

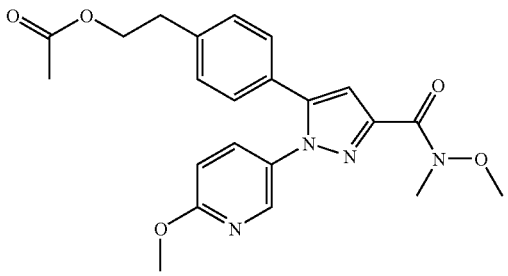
(E0365)

E0365 was prepared from E0363 and N, O-dimethylhydroxylamine hydrochloride in a similar manner to that of E0364.

oil

Mass (ESI+): 425 (M+H)+

200 MHz 1H NMR (DMSO-d6, d): 1.97 (3H, s), 2.89 (2H, t, J=6.8 Hz), 3.37 (3H, s), 3.77 (3H, s), 3.88 (3H, s), 4.21 (2H, t, J=6.8 Hz), 6.91 (1H, d, J=8.8 Hz), 6.98 (1H, s), 7.20–7.33 (4H, m), 7.70 (1H, dd, J=2.8, 8.8 Hz), 8.15 (1H, d, J=2.8 Hz)

EXAMPLE 366

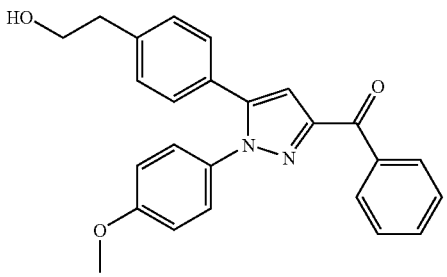
(E0366)

To a solution of 1.0M phenylmagnesium bromide in THF 3.4 ml was added a solution of E0364 (106.5 mg) in THF 2 ml under ice bath cooling. After stirring at same temperature for 1 hour, the mixture was poured into sat.aqNH4Cl, and extracted with AcOEt. The organic layer was washed with saturated aqueous sodium chloride solution, dried over magnesium sulfate, and concentrated invacuo. The residue was purified by silica gel column chromatography eluted with AcOEt/n-hexane=30%, 40%, 50% to give E0366 (107 mg ) as an oil. IR (neat): 3469, 3435, 3425, 3406, 3398, 3369, 2937, 1647, 1606, 1512 cm−1

Mass (ESI+): 399 (M+H)+

200 MHz 1H NMR (DMSO-d6, d): 2.72 (2H, t, J=6.9 Hz), 3.56–3.66 (2H, m), 3.80 (3H, s), 4.65 (1H, t, J=5.1Hz), 7.02 (2H, d, J=8.9 Hz), 7.20 (1H, s), 7.22 (4H, s), 7.34 (2H, d, J=8.9 Hz), 7.52–7.68 (3H, m), 8.25 (2H, d, J=8.5 Hz)

EXAMPLE 367

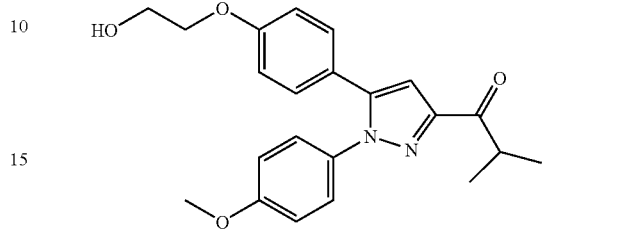
(E0367)

E0367 was prepared in a similar manner to that of E0366.

White Powder mp. 95–96° C.

IR (KBr): 3498, 3476, 2966, 1678, 1649, 1612, 1547, 1512 cm−1

Mass (ESI+): 381 (M+H)+

200 MHz 1H NMR (DMSO-d6, d): 1.15 (6H, d, J=6.8 Hz), 3.61–3.75 (3H, m), 3.79 (3H, s), 3.95–4.00 (2H, m), 4.87 (1H, t, J=5.3 Hz), 6.91 (2H, d, J=8.7 Hz), 6.98 (1H, s), 7.00 (2H, d, J=8.9 Hz), 7.17 (2H, d, J=8.7 Hz), 7.28 (2H, d, J=8.9 Hz)

EXAMPLE 368

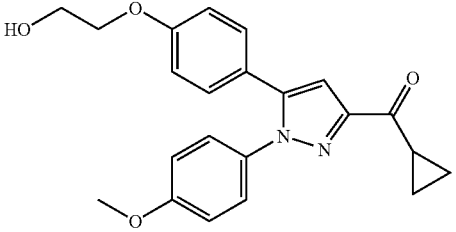
(E0368)

E0368 was prepared in a similar manner to that of E0366.

White Powder mp.132–133° C.

IR (KBr): 3390, 3334, 3288, 1707, 1670, 1612, 1564, 1549, 1512 cm−1

Mass (ESI+): 379 (M+H)+

200 MHz 1HNMR (DMSO-d6, d): 1.04 (4H, d, J=6.2 Hz), 3.03 (1H, m), 3.65–3.73 (2H, m), 3.80 (3H, s), 3.95–4.00 (2H, m), 4.87 (1H, t, J=5.4 Hz), 6.92 (2H, d, J=8.7 Hz), 6.96 (1H, s), 7.01 (2H, d, J=8.9 Hz), 7.18 (2H, d, J=8.7 Hz), 7.31 (2H, d, J=8.9 Hz)

EXAMPLE 369

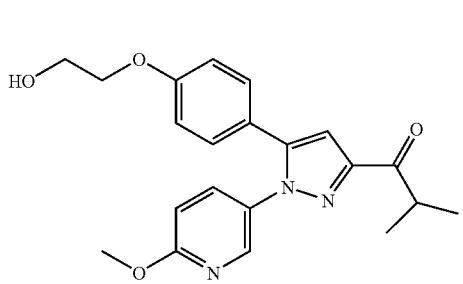

(E0369)

E0369 was prepared in a similar manner to that of E0366.
White Powder
mp. 108–109° C.
IR (KBr): 3440, 2966, 1678, 1610, 1566, 1549, 1533, 1502 cm−1
Mass (ESI+): 382 (M+H)+
200 MHz 1H NMR (DMSO-d6, d): 1.16 (6H, d, J=6.9 Hz), 3.64–3.74 (3H, m), 3.88 (3H, s), 3.96–4.02 (2H, m), 4.87 (1H, t, J=5.4 Hz), 6.93 (1H, d, J=8.9 Hz), 6.94 (2H, d, J=8.7 Hz), 7.02 (1H, s), 7.21 (2H, d, J=8.7 Hz), 7.74 (1H, dd, J=2.7, 8.9 Hz), 8.18 (1H, d, J=2.7 Hz)

EXAMPLE 370

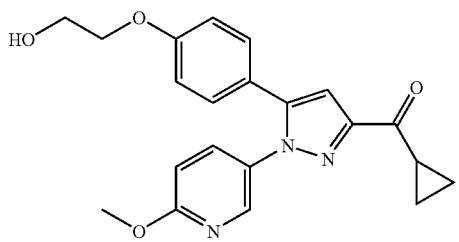

(E0370)

E0370 was prepared in a similar manner to that of E0368.
White Powder
mp. 104–106° C.
IR (KBr): 3367, 2947, 1668, 1610, 1566, 1549, 1531 cm−1
Mass (ESI+): 380 (M+H)+
2500 MHz 1HNMR (DMSO-d6, d): 1.05 (4H, d, J=6.2Hz), 3.04 (1H, m), 3.65–3.73 (2H, m), 3.89 (3H, s), 3.96–4.02 (2H, m), 4.87 (1H, t, J=5.4 Hz), 6.93 (1H, d, J=8.8 Hz), 6.95 (2H, d, J=8.8 Hz), 7.06 (1H, s), 7.22 (2H, d, J=8.8 Hz), 7.76 (1H, dd, J=2.6, 8.8 Hz), 8.21 (1H, d, J=2.6 Hz)

EXAMPLE 371

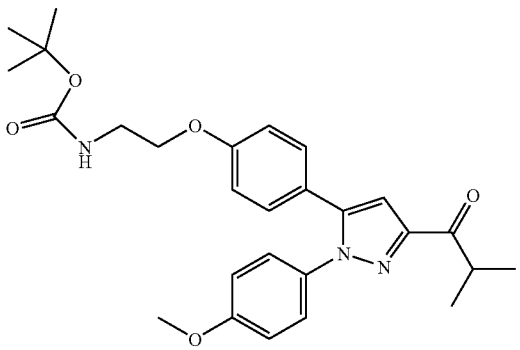

(E0371)

E0371 was prepared in a similar manner to that of E0366.
White Powder
Mass (ESI+): 480 (M+H)+
200 MHz 1H NMR (DMSO-d6, d): 1.15 (6H, d, J=6.9 Hz), 1.37 (9H, s), 3.25–3.33 (2H, m), 3.68 (1H, m), 3.79 (3H, s), 3.91–3.98 (2H, m), 6.90 (2H, d, J=8.7 Hz), 6.90–7.05 (1H, overlapping), 6.97 (1H, s), 7.00 (2H, d, J=8.9 Hz), 7.17 (2H, d, J=8.7 Hz), 7.28 (2H, d, J=8.9 Hz)

EXAMPLE 372

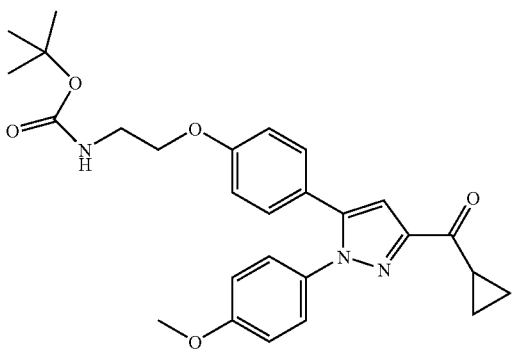

(E0372)

E0372 was prepared in a similar manner to that of E0368.
White Powder
Mass (ESI+): 477 (M+H)+
200 MHz 1H NMR (DMSO-d6, d): 1.04 (4H, d, J=6.2 Hz), 1.37 (9H, s), 3.04 (1H, m), 3.22–3.33 (2H, m), 3.80 (3H, s), 3.95 (2H, t, J=5.7Hz), 6.88–7.03 (1H, overlapping), 6.91 (2H, d, J=8.7 Hz), 6.97 (1H, s), 7.01 (2H, d, J=8.9 Hz), 7.18 (2H, d, J=8.7 Hz), 7.31 (2H, d, J=8.9 Hz)

EXAMPLE 373

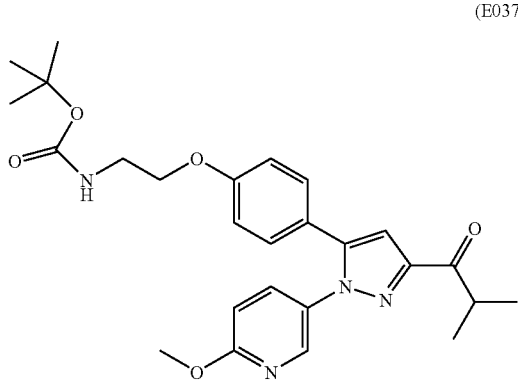
(E0373)

E0373 was prepared in a similar manner to that of E0366.
White Powder
Mass (ESI+): 481 (M+H)+
200 MHz 1HNMR (DMSO-d6, d): 1.16 (6H, d, J=6.9 Hz), 1.37 (9H, s), 3.22–3.32 (2H, m), 3.68 (1H, m), 3.88 (3H, s), 3.93–3.99 (2H, m), 6.90–7.02 (5H, m), 7.22 (2H, d, J=8.7 Hz), 7.73 (1H, dd, J=2.7, 8.8 Hz), 8.18 (1H, d, J=2.7 Hz)

EXAMPLE 374

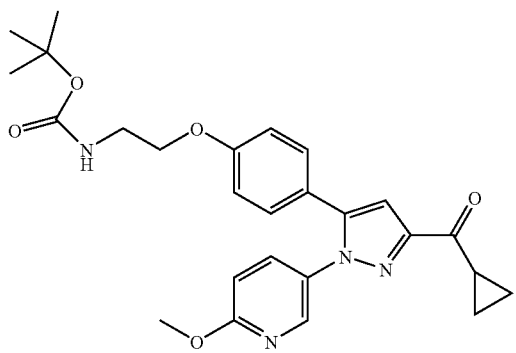
(E0374)

E0374 was prepared in a similar manner to that of E0368.
White Powder
Mass (ESI+): 479 (M+H)+
200 MHz 1HNMR (DMSO-d6, d): 1.05 (4H, d, J=6.2 Hz), 1.37 (9H, s), 3.04 (1H, m), 3.23–3.33 (2H, m), 3.89 (3H, s), 3.93–3.99 (2H, m), 6.89–7.08 (5H, m), 7.22 (2H, d, J=8.7 Hz), 7.76 (1H, dd, J=2.7, 8.8 Hz), 8.21 (1H, d, J=2.7 Hz)

EXAMPLE 375

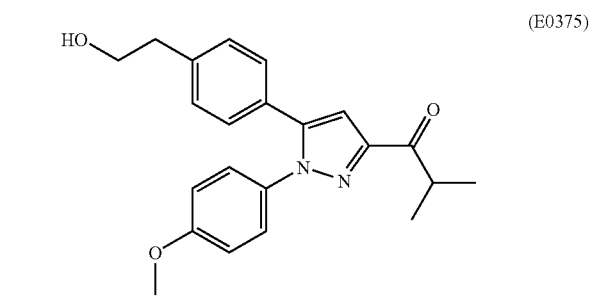
(E0375)

E0375 was prepared from E0364 in a similar manner to that of E0366.
oil
IR (neat): 3487, 3469, 3435, 3408, 3398, 3369, 2966, 2933, 1678, 1512 cm−1
Mass (ESI+): 365 (M+H)+
200 MHz1H NMR (DMSO-d6, d): 1.19 (6H, d, J=7.9 Hz), 2.70 (2H, t, J=6.9 Hz), 3.54–3.75 (3H, m), 3.79 (3H, s), 4.64 (1H, t, J=5.1 Hz), 7.00 (2H, d, J=8.9 Hz), 7.02 (1H, s), 7.16 (2H, d, J=8.6 Hz), 7.21 (2H, d, J=8.6 Hz), 7.29 (2H, d, J=8.9 Hz)

EXAMPLE 376

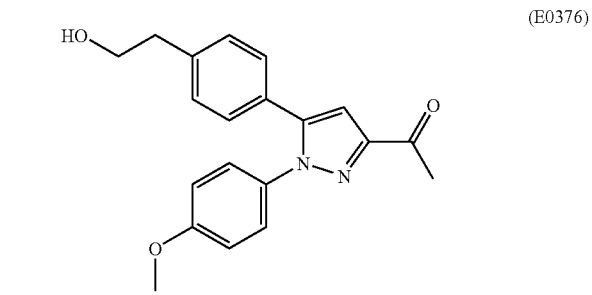
(E0376)

To a solution of 1.0M methylmagnesium bromide in diethyl ether 2.8 ml was added a solution of E0364 (237.6 mg) in THF 4 ml dropwise under ice bath cooling. After stirring at same temperature for 30 minues the mixture was poured into sat.aqNH4Cl, and extracted with AcOEt. The organic layer was washed successively with a mixture of 1M HCl and saturated aqueous sodium chloride solution, saturated aqueous sodium bicarbonate solution, and saturated aqueous sodium chloride solution, dried over magnesium sulfate, and concentrated in vacuo. The residue was dissolved in THF1 ml, 1M NaOH 0.4 ml was added and the mixture was stirred at ambient temperature for several hours. The mixture was neutralized with 1M HCl 0.4 ml, and partitioned between AcOEt and saturated aqueous sodium chloride solution. The organic layer was dried over magnesium sulfate, and concentrated in vacuo. The residue was purified by silica gel column chromatography eluted with AcOEt/n-hexane=50% to give E0376 (139.1 mg) as a white powder.
Mass (ESI+): 337 (M+H)+
200 MHz 1H NMR (DMSO-d6, d): 2.54 (3H, s), 2.70 (2H, t, J=6.9 Hz), 3.55–3.64 (2H, m), 3.80 (3H, s), 4.65 (1H, t, J=5.1 Hz), 7.00 (2H, d, J=8.9 Hz), 7.01 (1H, s), 7.15 (2H, d, J=8.5 Hz), 7.21 (2H, d, J=8.5 Hz), 7.29 (2H, d, J=8.9 Hz)

EXAMPLE 377

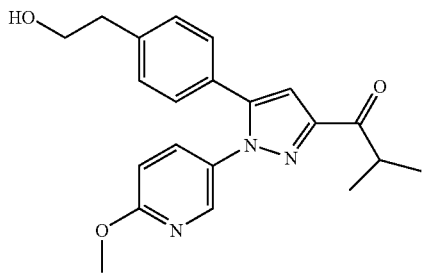

(E0377)

E0377 was prepared in a similar manner to that of E0376.
oil
Mass (ESI+): 366 (M+H)+
200 MHz 1HNMR (DMSO-d6, d): 1.16 (6H, d, J=6.9 Hz), 2.72 (2H, t, J=6.9 Hz), 3.55–3.75 (3H, m), 3.88 (3H, s), 4.65 (1H, t, J=5.1Hz), 6.93 (1H, d, J=8.8Hz), 7.05 (1H, s), 7.17–7.29 (4H, m), 7.76 (1H, dd, J=8.8,2.7 Hz), 8.19 (1H, d, J=2.7 Hz)

EXAMPLE 378

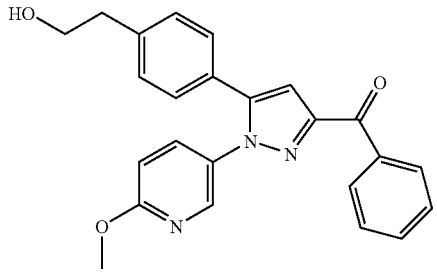

(E0378)

E0378 was prepared in a similar manner to that of E0376.
oil
200 MHz 1H NMR (DMSO-d6, d): 2.73 (2H, t, J=6.9 Hz), 3.57–3.66 (2H, m), 3.89 (3H, s), 4.66 (1H, t, J=5.0Hz), 6.94 (1H, d, J=8.8 Hz), 7.23 (1H, s), 7.15–7.35 (4H, m), 7.52–7.72 (3H, m), 7.80 (1H, dd, J=2.7, 8.8 Hz), 8.23–8.32 (3H, m)

EXAMPLE 379

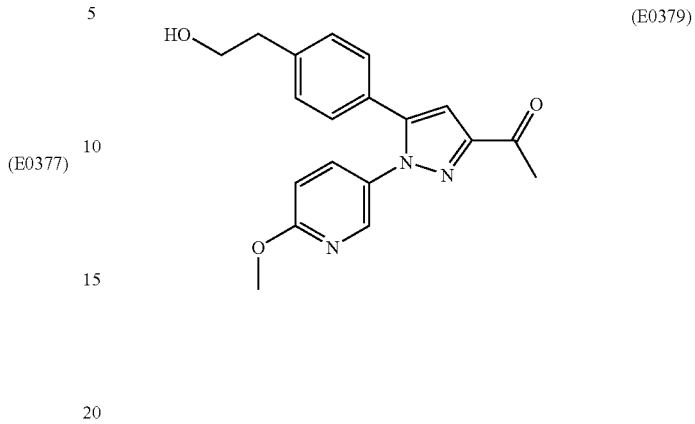

(E0379)

E0379 was prepared in a similar manner to that of E0376.
White Powder
Mass (ESI+): 338 (M+H)+
200 MHz 1H NMR (DMSO-d6, d): 2.55 (3H, s), 2.71 (2H, t, J=6.9 Hz), 3.55–3.65 (2H, m), 3.89 (3H, s), 4.65 (1H, t, J=5.1 Hz), 6.93 (1H, d, J=8.8 Hz), 7.05 (1H, s), 7.19 (2H, d, J=8.6 Hz), 7.24 (2H, d, J=8.6Hz), 7.75 (1H, dd, J=2.7, 8.8 Hz), 8.19 (1H, d, J=2.7 Hz)

EXAMPLE 380

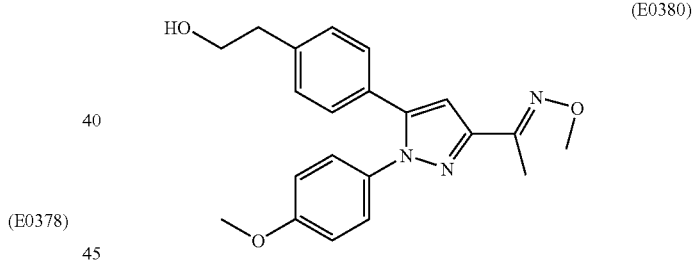

(E0380)

A mixture of E0376 (127 mg), O-methylhydroxylamine hydrochloride 47.3 mg and pyridine in EtOH 3 ml was heated at 60° C. for 1 hour. The mixture was concentrated in vacuo and the residue was purified by silica gel column chromatography eluted with AcOEt/n-hexane=40%. The pure fraction was collected and concentrated invacuo. The residue was crystallized from diisopropyl ether to give E0380 (103.2 mg) as a white powder.
mp. 82–86° C.
IR (KBr): 3359, 3269, 3246, 2939, 1549, 1512 cm−1
Mass (ESI+): 366 (M+H)+
200 MHz 1H NMR (DMSO-d6, d): 2.20 (3H, s), 2.70 (2H, t, J=6.9 Hz), 3.54–3.65 (2H, m), 3.78 (3H, s), 3.92 (3H, s), 4.65 (1H, t, J=5.0 Hz), 6.77 (1H, s), 6.97 (2H, d, J=8.9 Hz), 7.12–7.26 (6H, m)

EXAMPLE 381

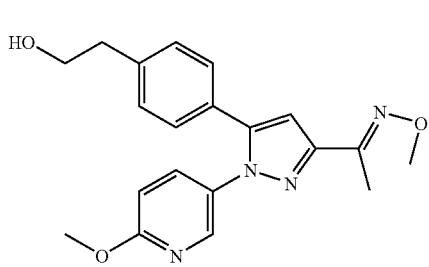
(E0381)

E0381 was prepared in a similar manner to that of E0380.
White Powder
mp.94–95° C.
IR (KBr): 3469, 3433, 3423, 3404, 3400, 3371, 1647, 1549cm−1
Mass (ESI+): 267 (M+H)+
200 MHz 1H NMR (DMSO-d6, d): 2.20 (3H, s), 2.71 (2H, t, J=6.8 Hz), 3.55–3.65 (2H, m), 3.87 (3H, s), 3.92 (3H, s), 4.65 (1H, t, J=5.0 Hz), 6.81 (1H, s), 6.90 (1H, d, J=8.8 Hz), 7.18 (2H, d, J=8.7 Hz), 7.23 (2H, d, J=8.7 Hz), 7.69 (1H, dd, J=8.8,2.7 Hz), 8.11 (1H, d, J=2.7 Hz)

EXAMPLE 382

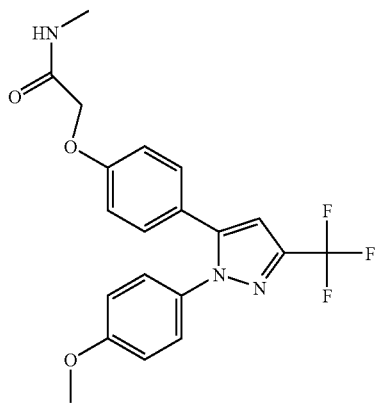
(E0382)

To a solution of E0314 (100 mg) in methanol (21 ml) was added a solution of methyl amine in methanol (40%, 92 ml). After stirring at room temperature overnight, the mixture was evaporated to give oil, which was purified with preparative TLC (1 mm, 60% ethyl acetate/hexane) to give E0382 as an oil (97 mg, 100%).
NMR (CDCl3), 2.92 (3H, d, J=5.0 Hz), 3.83 (3H, s), 4.49 (2H, s), 6.69 (1H, s), 6.82–6.91 (4H, m), 7.14–7.24 (4H, m).
MS (ESI+);428.2 (M+Na).
IR (Neat, 20727-11), 1693.2 cm−1.

EXAMPLE 383

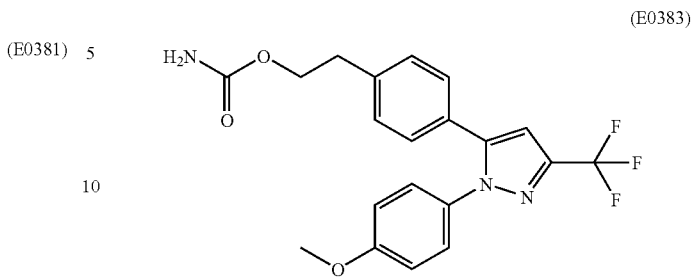
(E0383)

Trichloroacetyl isocyanate 62.4 mg was added to a solution of E0118 100 mg in CH2Cl2 2 ml under ice bath cooling. After stirring at ambient temperature for 3 hours, the reaction mixture was concentrated invacuo. The residue was dissolved in THF 1 ml, MeOH 1 ml, and H2O 1 ml. Potassium carbonate 153 mg was added to the reaction mixture, and stirred at ambient temperature overnight. The reaction mixture was partitioned between AcOEt and H2O. The organic layer was washed with saturated aqueous sodium chloride solution, dried over magnesium sulfate, and concentrated in vacuo. The residual solid was recrystallized from AcOEt-n-hexane to give E0383 84.1 mg as a white powder.
mp. 169–170° C.
IR (KBr): 3435, 3332, 3263, 3209, 1684, 1610, 1516 cm−1
Mass (ESI+): 406 (M+H)+
400 MHz 1H NMR (DMSO-d6, d): 2.84 (2H, t, J=6.8 Hz), 3.79 (3H, s), 4.10 (2H, t, J=6.8 Hz), 6.30–6.70 (2H, br), 7.00 (2H, d, J=9.0 Hz), 7.14 (1H, s), 7.21 (2H, d, J=8.4 Hz), 7.26 (2H, d, J=8.4 Hz), 7.29 (2H, d, J=9.0 Hz)

EXAMPLE 384

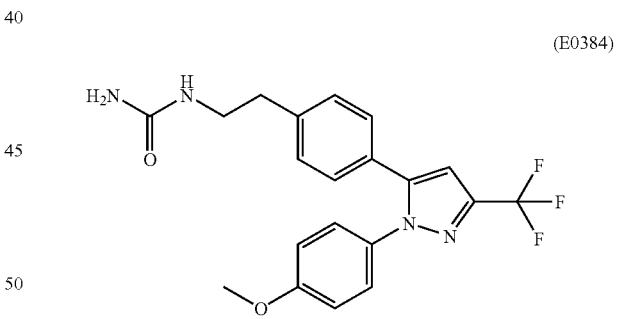
(E0384)

Trimethylsilyl isocyanate 42.7 mg was added to a solution of E0158 98.2 mg and triethylamine 30 mg in CH2Cl2 1 ml under ice bath cooling. The reaction mixture was stirred at same temperature for 1 hour and concentrated in vacuo. The residue was purified by preparative thin layer silica gel chromatography developed by MeOH/CHCl3=10%. The separated silica gel was extracted with 10% MeOH/CHCl3, filtered, and the solvent was evaporated in vacuo. The residue was crystallized from ethylacetate-diisopropyl ehter to give E0384 (59.7 mg) as a white powder.
mp.157–158° C.
IR (KBr): 3406, 3357, 3330, 3209, 1704, 1662, 1614, 1529, 1520 cm−1
Mass (ESI+): 405 (M+H)+

200 MHz 1H NMR (DMSO-d6, d) NO06.067:2.62–2.70 (2H, m), 3.13–3.24 (2H, m), 3.79 (3H, s), 5.42 (2H, s), 5.93 (1H, t, J=5.4 Hz), 7.00 (2H, d, J=8.8Hz), 7.12 (1H, s), 7.21 (4H, s), 7.29 (2H, d, J=8.8 Hz)

EXAMPLE 385

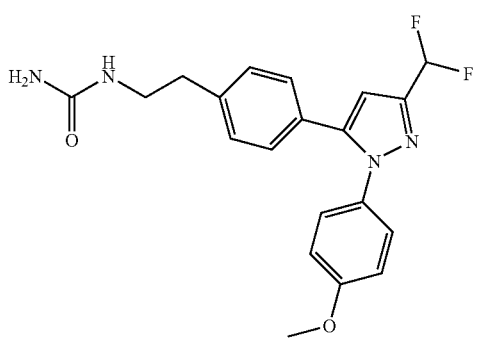
(E0385)

This compound was obtained according to a similar manner to that of E0384.

IR (film): 3343.9, 1656.6, 1604.5, 1550.5, 1515.8, 1457.9, 1342.2, 1251.6, 1029.8 cm−1.

EXAMPLE 386

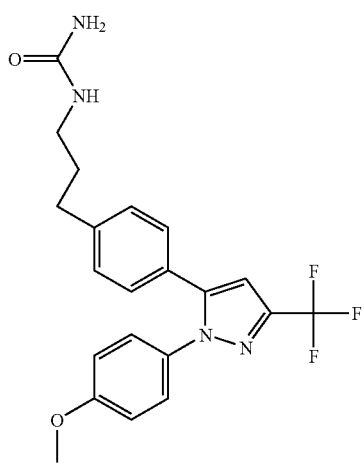
(E0386)

This compound was obtained according to a similar manner to that of E0384.

IR (film): 3345.9, 1654.6, 1604.5, 1556.3, 1513.9, 1465.6, 1240.0, 1160.9, 1132.0 cm−1.

EXAMPLE 387

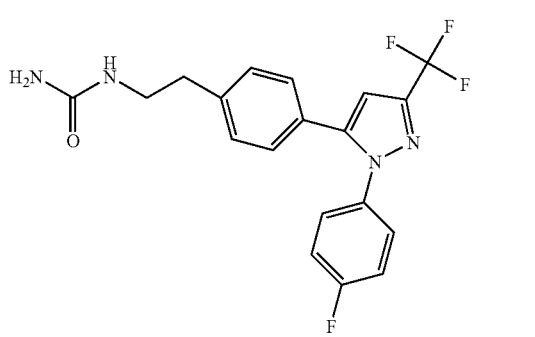
(E0387)

This compound was obtained according to a similar manner to that of E0384.

IR (film): 3345.9, 1658.5, 1602.6, 1552.4, 1236.2, 1159.0, 1133.9 cm−1.

EXAMPLE 388

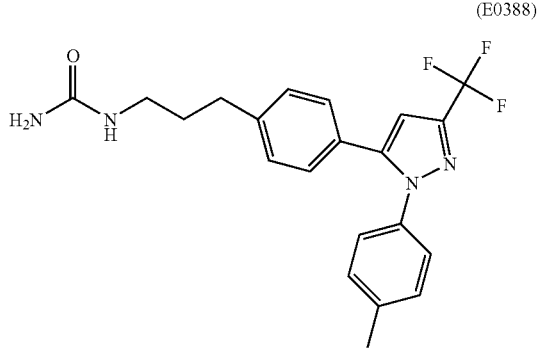
(E0388)

This compound was obtained according to a similar manner to that of E0384.

IR (film): 3345.9, 1658.5, 1602.6, 1552.4, 1517.7, 1236.2, 1159.0, 1133.9 cm−1.

EXAMPLE 389

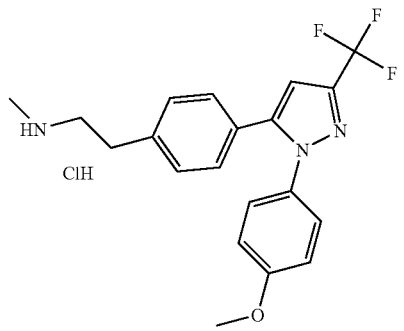
(E0389)

A mixture of E0175 (150 mg) and 6 ml of 4N HCl/dioxane was stirred at room temperature. After 2 hours, the reaction mixture was evaporated under reduced pressure to give 128 mg (quant.) of E0389 as an oil.

IR (film): 3403.7, 1513.9, 1467.6, 1241.9, 1162.9, 1130.1 cm−1.

EXAMPLE 390

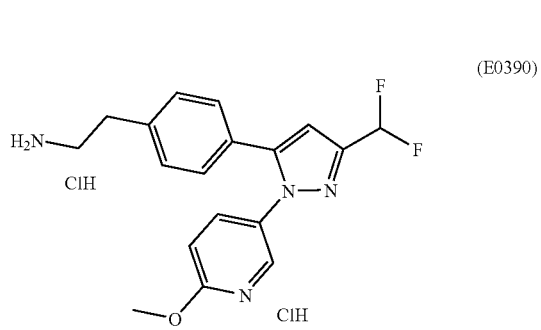
(E0390)

This compound was obtained according to a similar manner to that of E0389.

IR (film): 3428.8, 1662.34, 1612.2, 1500.4, 1461.8, 1390.4, 1292.1, 1166.7, 1087.7, 1029.8 cm−1.

EXAMPLE 391

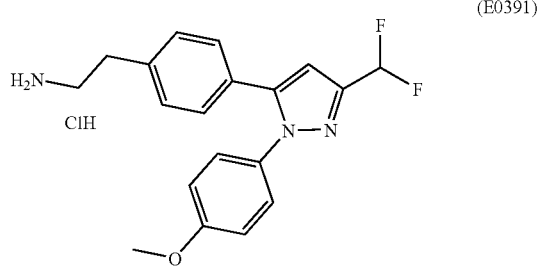
(E0391)

This compound was obtained according to a similar manner to that of E0389.

IR (film): 3403.74, 2965.98, 1610.27, 1513.85, 1461.78, 1251.58, 1170.58, 1085.73, 1029.80, 836.955, 800.314 cm−1.

EXAMPLE 392

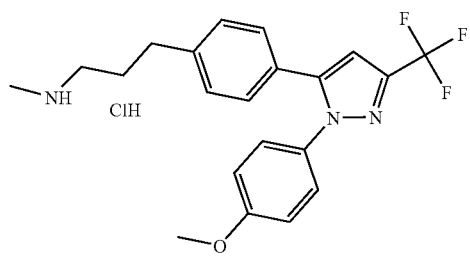
(E0392)

This compound was obtained according to a similar manner to that of E0389.

IR (film): 3432.7, 1511.9, 1467.6, 1240.0, 1160.9, 1130.1 cm−1.

EXAMPLE 393

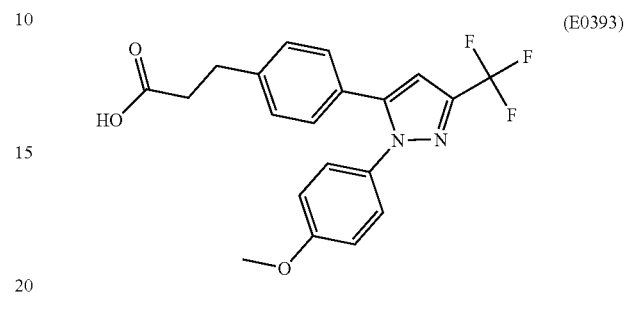
(E0393)

A mixture of E0258 (100 mg) and Pd/C (100 mg) in EtOH (10 m) was stirred under H2 atmosphere for 3.0 hours. After filtration, a filtrate was evaporated under reduced pressure. The residue was dissolved in EtOH and filtered with syringe driven filter, and evaporated to give 93 mg (93%) of E0393.

IR (film): 3019.9, 1704.8, 1513.9, 1303.6, 1238.1, 1133.9 cm−1.

EXAMPLE 394

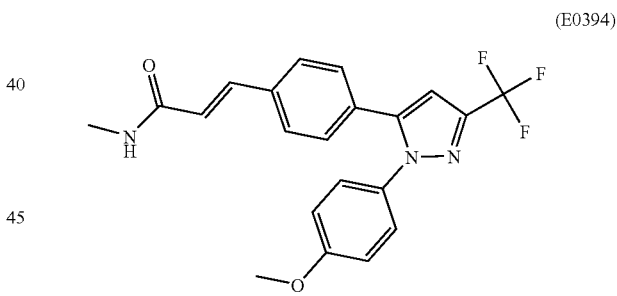
(E0394)

T a suspension of E0258 (200 mg) in toluene (4 ml) was added thionylchloride (0.19 ml) at room temperature. The reaction mixture was stirred at 100° C. for 5 hours until the mixture become clear solution. After then, the mixture was evaporated under reduced pressure. (become solid) THF was added, and then aqueous MeNH2 (37%) was added. The mixture was stirred for 1 hour, and quenched with water, and extracted twice with EtOAc. The combined organic layer was washed with sat.NaHCO3, water and brine, dried over Na2SO4, filtered and evaporated under reduced pressure to give 63 mg (31%) of E0394 as a powder.

mp: 155–157° C.

IR (film) 3297.7, 1662.3, 1617.9, 1513.9, 1236.2, 1162.9, 1133.9 cm−1

EXAMPLE 395

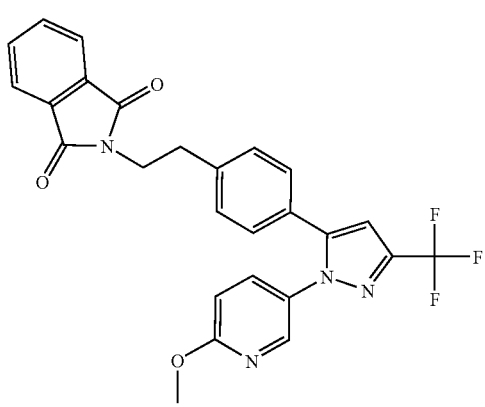
(E0395)

A suspension of E0399 (1.8 g) and potassium phtalimido (1.13 g) in N,N-dimethylformamide (6.6 ml) was stirred at 80° C. for 3 hours. The mixture was added water (700 ml) and extracted with a mixture of ethyl acetate and hexane (2:1) (×4). The combined organic layers were washed with aqueous sodium hydroxide (1N) (×2) and brine, dried over magnesium sulfate, and evaporated to give oil, which was purified with column chromatography (SiO2 100 ml, eluted with 30% ethyl acetate/hexane) to give oil (1.83 g, 91.1%). Ethanol (15 ml) was added to the oil, then the mixture was stirred at room temperature for 10 minutes. The precipitate was filtered, washed with ethanol (3 ml), and dried under reduced pressure to give E0395 as a white solid (1.16 g, 58%).

NMR (CDCl3), 3.00 (2H, t, J=7.6 Hz), 3.93 (2H, t, J=7.6 Hz), 3.94 (3H, s), 6.73 (1H, s), 6.73 (1H, d, J=8.7 Hz), 7.13–7.26 (4H, m), 7.49 (1H, dd, J=8.7, 2.5 Hz), 7.70–7.86 (4H, m), 8.10 (1H, d, J=2.5 Hz).

MS (ESI+), 515 (M+Na).

EXAMPLE 396

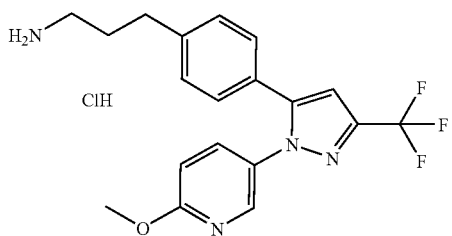
(E0396)

6M HCl 0.045 ml was added to a solution of E0168 (101.5 mg) in AcOEt 1 ml and EtOH 1 ml. The mixture was concentrated and dried in vacuo to give E0396 (94.8 mg) as an amorphous powder.

IR (neat): 3433, 3020, 2956, 1668, 1658, 1612, 1572, 1543, 1500 cm−1

Mass (ESI+): 377 (M+H)+

200 MHz 1H NMR (DMSO-d6, d): 1.76–1.92 (2H, m), 2.52–2.81 (4H, m), 3.88 (3H, s), 6.93 (1H, d, J=8.9 Hz), 7.19 (1H, s), 7.26 (4H, s), 7.76 (1H, dd, J=8.9, 2.7 Hz), 8.19 (1H, d, J=2.7 Hz)

EXAMPLE 397

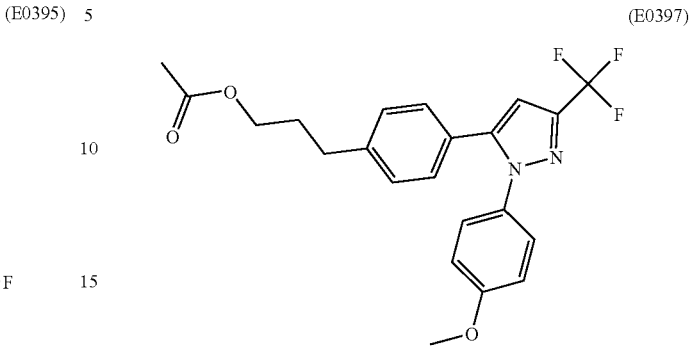
(E0397)

To a mixture of P0002 (5.0 g) and CF3COOEt (3.5 ml) in DMF (30 ml) was added NaH (1.1 g) under ice-cooling. The reaction mixture was allowed to warm to room temperature, and stirred under 40° C. for 1 hour. The reaction mixture was extracted twice with EtOAc. The organic layer was washed with water and brine, dried over MgSO4, filtered and evaporated under reduced pressure. The residue, sodium acetate (2.23 g) and 4-methoxyphenylhydrazine (3.96 g) in acetic acid (20 ml) was stirred at room temperature for 15 hours. The mixture was extracted twice with ethyl acetate. The combined organic layer was washed with water (twice), sat.NaHCO3, water and brine, dried over MgSO4, filtered and evaporated under reduced pressure. The residue was column chromatographed on silica gel (Hex/EtOAc =8:1–4:1) to give 2.58 g (36%) of E0397 as an oil.

EXAMPLE 398

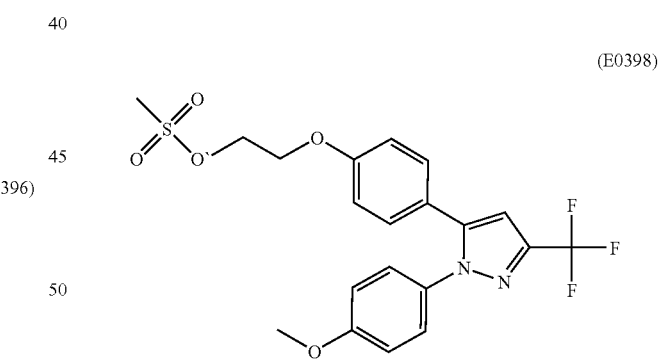
(E0398)

To a solution of E0312 (326.7 mg) in ethyl acetate (3 ml) was added methanesulfonyl chloride (86.9 ml) and triethylamine (0.181 ml) at 0° C. After stirring for 40 minutes at 0° C., the mixture was quenched with water and extracted with ethyl acetate (×3). The combined organic layers were washed with water and brine, dried over sodium sulfate, and evaporated under reduced pressure to give E0398 as an oil (351.3 mg, 89%).

NMR (CDC13); 3.09 (3H, s), 3.82 (3H, s), 4.22–4.26 (2H, m), 4.52–4.59 (2H, m), 6.68 (1H, s), 6.75 (2H, d, J=8.7 Hz), 6.87 (2H, d, J=8.9 Hz), 7.16 (2H, d, J=8.7 Hz), 7.22 (2H, d, J=8.9 Hz).

EXAMPLE 399

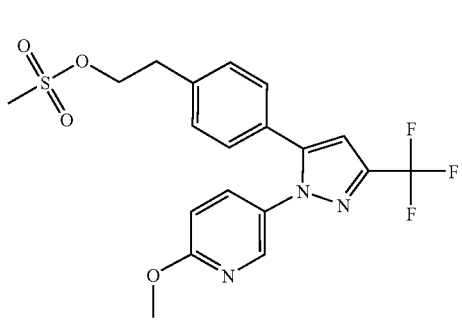
(E0399)

This compound was obtained according to a similar manner to that of E0398 as a pale yellow oil (1.82 g, 98.6%).

NMR (CDCl3), 2.91 (3H, s), 3.07 (2H, t, J=6.8 Hz), 3.94 (3H, s), 4.43 (2H, t, J=6.8 Hz), 6.75 (1H, s), 6.78 (1H, d, J=8.2 Hz), 7.17–7.26 (4H, m), 7.58 (1H, dd, J=9.0, 2.9 Hz), 8.05 (1H, d, J=2.8 Hz).

MS (ESI+), 442.1 (MH+), 464.0 (M+Na).

EXAMPLE 400

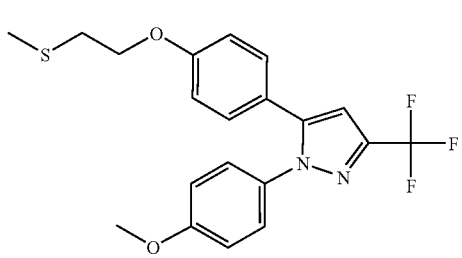
(E0400)

A suspension of E0398 (351.3 mg) and sodium thiomethoxide (162 mg) in N,N-dimethylformamide (3 ml) was stirred at 60° C. for 3.5 hours. The mixture was quenched with water and extracted with ethyl acetate (×3). The combined organic layers were washed with water and brine, dried over magnesium sulfate, and evaporated to give oil. The oil was purified with column chromatography (SiO2 50 ml, eluted with 10% ethyl acetate/hexane) to give E0400 as an oil (236.7 mg, 75.3%).

NMR (CDCl3); 2.24 (3H, s), 2.88 (2H, t, J=6.6 Hz), 3.82 (3H, s), 4.15 (2H, t, J=6.6 Hz), 6.67 (1H, s), 6.83 (2H, d, J=8.8 Hz), 6.88 (2H, d, J=9.0 Hz), 7.13 (2H, d, J=8.8 Hz), 7.23 (2H, d, J=9.0 Hz).

MS (ESI+); 431 (M+Na).

EXAMPLE 401

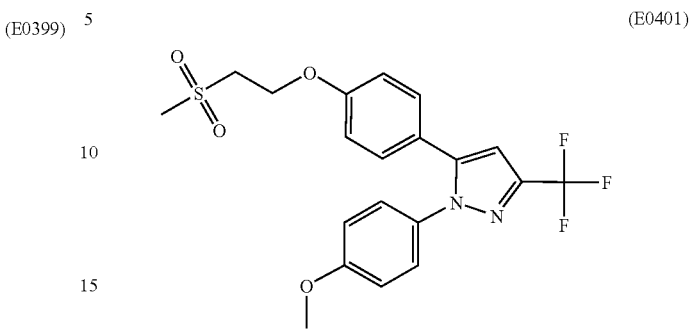
(E0401)

To a solution of E0400 (103.5 mg) in dichloromethane (1 ml) was added m-chloroperbenzoic acid (134 mg) at room temperature. After stirring at room temperature for 1 hour, the mixture was added saturated sodium hydrogen sulfate aqueous solution (0.5 ml) and sodium thiosulfate pentahydrate (100 mg), and stirred for 30 minutes at room temperature. The mixture was filtered by Chemelut 1001 (Varian) and evaporated to give oil, which was purified with preparative TLC (1 mm, 50% ethyl acetate/hexane) to give E0401 as an amorphous (105.9 mg, 94.9%).

NMR (CDCl3); 3.07 (3H, s), 3.45 (2H, t, J=5.3 Hz), 4.44 (2H, t, J=5.3 Hz), 3.83 (3H, s), 6.69 (1H, s), 6.69–6.90 (4H, m), 7.15–7.26 (4H, m).

MS (ESI+); 463.1 (M+Na)+. IR (KBr, 20727-8), 1612.2, 1515.8 cm−1.

EXAMPLE 402

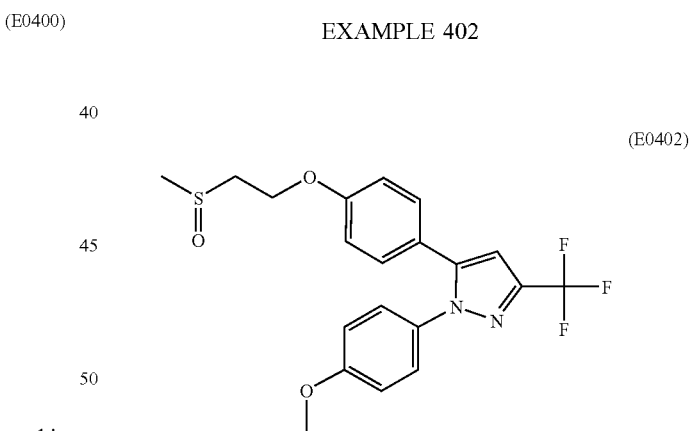
(E0402)

To a solution of E0400 (104.8 mg) in dichloromethane (1ml) was added m-chloroperbenzoic acid (44.7 mg) at 0° C., and the mixture was stirred at 0° C. for 1 hour. Then m-chloroperbenzoic acid (35 mg) was added to the mixture. After stirring at 0° C. for 30 minutes, the mixture was quenched with saturated sodium hydrogen sulfate aqueous solution (0.5 ml) and sodium thiosulfate pentahydrate (100 mg), and stirred for 30 minutes at room temperature. The mixture was filtered by Chemelut 1001 (Varian) and evaporated to give oil, which was purified with preparative TLC (1 mm, ethyl acetate) to give 2 fractions of E0401 (TLC upper) as an amorphous (40.7 mg, 37.4%) and E0402 (TLC lower) as a powder (60 mg, 55%).

NMR (CDCl3); 2.70 (3H, s), 2.99–3.27 (2H, m), 3.83 (3H, s), 4.40–4.46 (2H, m), 6.68 (1H, s), 6.84–6.90 (4H, m), 7.15 (2H, d, J=8.7 Hz), 7.22 (2H, d, J=9.0 Hz).

MS (ESI+); 447.1 (M+Na).

IR (KBr); 1612.2, 1513.9 cm–1.

EXAMPLE 403

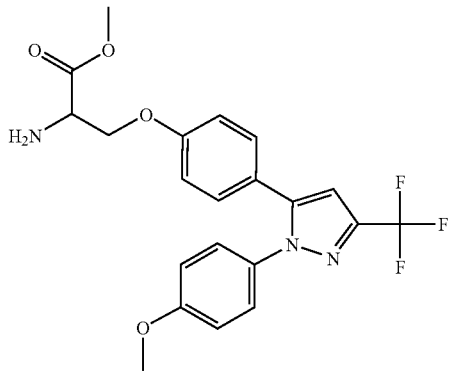

(E0403)

To a solution of E0286 (500 mg) in dichloromethane (1.5 ml) was added successively anisol (0.5 ml) and triflutoroacetic acid (1 ml). After stirring at room temperature for 2 hours, the mixture was quenched with saturated sodium hydrogen carbonate aqueous solution and extracted with ethyl acetate (×3). The organic layers were dried over magnesium sulfate and evaporated to give oil, which was purified with column chromatography (SiO2 50 ml, eluted with ethyl acetate) to give E0403 as an oil (302.5 mg, 94.2%).

NMR (CDCl3), 3.77 (3H, s), 3.80 (3H, s), 3.80–3.87 (1H, m), 4.21–4.28 (2H, m), 6.67 (1H, s), 6.80–6.89 (4H, m), 7.13 (2H, d, J=8.7 Hz), 7.22 (2H, d, J=8.9 Hz). MS (ESI+), 436.1 (MH+).

EXAMPLE 404

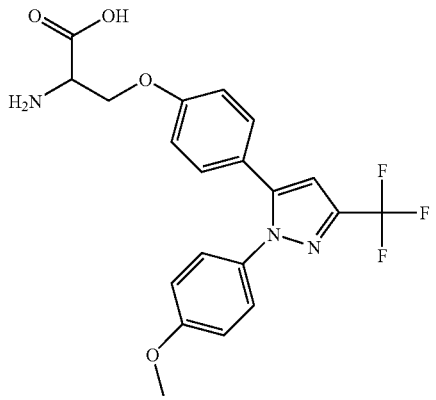

(E0404)

A solution of E0403 (104.6 mg) in methanol (3 ml) and sodium hydroxide aqueous solution (1N, 2 ml) was stirred at room temperature for 3 hours. The mixture was evaporated, and methanol was added to the residue and evaporated to give white powder, which was purified with preparative TLC (1 mm, 20% methanol/chloroform) to give E0404 as a powder (29.9 mg, 29.5%).

NMR (DMSO-d6), 3.50–3.54 (1H, m), 3.79 (3H, s), 4.13–4.30 (2H, m), 6.91–7.07 (5H, m), 7.21 (2H, d, J=8.7 Hz), 7.27 (2H, d, J=8.9 Hz).

MS (ESI-). 420.4 (M–H).

IR (KBr), 1641, 1616cm–1.

EXAMPLE 405

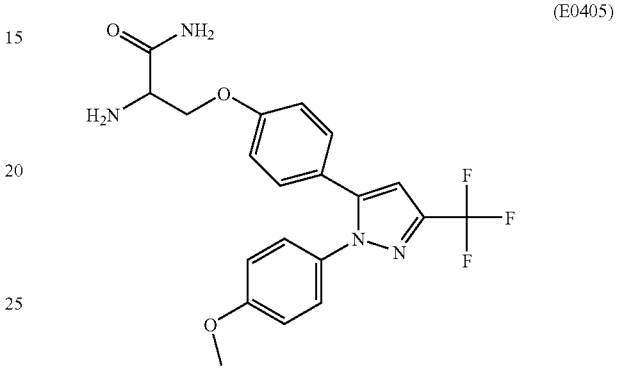

(E0405)

To a solution of E0403 (106.6 mg) in methanol (2 ml) was added concentrated ammonia solution (1 ml). After stirring at room temperature overnight, the mixture was evaporated to give solid, which was purified with preparative TLC (1 mm, 20% methanol/chloroform) to give E0405 as a solid (58.2 mg, 56.5%).

NMR (CDCl3), 3.75–3.82 (1H, m), 3.82 (3H, s), 4.15–4.29 (2H, m), 6.67 (1H, s), 6.83–6.91 (4H, m), 7.14 (2H, d, J=6.7 Hz), 7.22 (2H, d, J=9.0 Hz).

MS (ESI+). 421.4 (MH+), 462.4 (MHMeCN)+.

IR (KBr), 1658 cm–1.

EXAMPLE 406

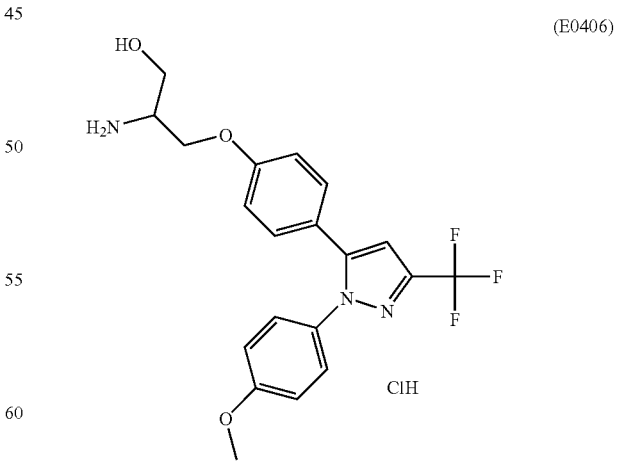

(E0406)

To a solution of E0403 (87.5 mg) in tetrahydrofuran (1 ml) was added lithium aluminum hydride (30.5 mg) at room temperature. After stirring at room temperature for 2 hours, the mixture was quenched with water (30 ml), sodium hydroxide aqueous solution (15%, 30 ml), and water (90 ml), and then stirred at room temperature for 30minutes. Magnesium sulfate and celite was added to the mixture, then the suspension was filtered and washed with tetrahydrofuran.

The filtrate was evaporated to give oil, which was purified with preparative TLC (0.5 mm, 20% methanol/chloroform) to give oil.

To a solution of the oil in ethyl acetate was added a solution of hydrogen chloride in ethyl acetate (4N, 0.5 ml), and then the mixture was evaporated to give E0406 as an oil (43.5 mg, 49%).

NMR (CDCl3), 3.64–4.13 (5H, m), 3.76 (3H, s), 6.60 (1H, s), 6.73–6.85 (4H, m), 7.07 (2H, d, J=8.5 Hz), 7.16 (2H, d, J=8.9 Hz).

MS (ESI+), 408.1 (MH+) (Free). IR (Neat, 20727-5), 1614.1 cm−1.

EXAMPLE 407

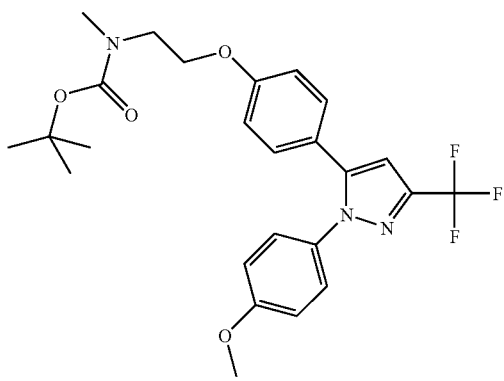

(E0407)

To a suspension of sodium hydride (34.8 mg) interahydrofuran (2 ml) was added a solution of E0347 (208 mg) in tetrahydrofuran (1 ml) at 0□, and then the mixture was stirred at room temperature for 20 minutes. Then iodomethane (54.2 ml) was added to the mixture. After stirring at room temperature overnight, the mixture was quenched with water, extracted with ethyl acetate (×3). The combined organic layers were washed with water (×3) and brine, dried over magnesium sulfate, and evaporated under reduced pressure to give oil, which was purified with preparative TLC (1 mm, 30% ethyl acetate/hexane) to give E0407 as an oil (160 mg, 74.7%).

NMR (CDCl3), 1.45 (9H, s), 2.97 (3H, s), 3.59 (2H, t, J=5.5 Hz), 3.82 (3H, s), 4.0–4.15 (2H, m), 6.67 (1H, s), 6.80–6.91 (4H, m), 7.13 (2H, d, J=8.8 Hz), 7.23 (2H, d, J=9.0 Hz).

MS (ESI+). 514.2 (M+Na).

EXAMPLE 408

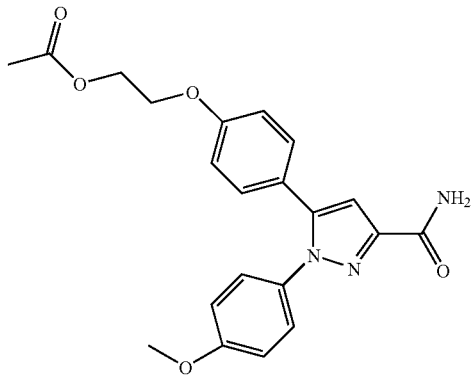

(E0408)

AcCl 0.31 ml was added to a suspension of E0347 (1.29 g) and Et3N 0.66 ml in CH2Cl2 10 ml under ice bath cooling. The mixture was stirred at ambient temperature for 2 hours. AcCl 0.31 ml and Et3N 0.66 ml was added and stirred at ambient temperature for 3 hours. To this mixture was added H2O and stirred at ambient temperature for a while. White precipitates were appeared, which was collected and washed with H2O and diisopropyl ether to give E0408 (879.3 mg) as a white powder.

Mass (ESI+): 396 (M+H)+

200 MHz 1H NMR (DMSO-d6, d): 2.03 (3H, s), 3.78 (3H, s), 4.15–4.19 (2H, m), 4.29–4.33 (2H, m), 6.89 (1H, s), 6.93 (2H, d, J=8.8 Hz), 6.98 (2H, d, J=8.9 Hz), 7.17 (2H, d, J=8.8 Hz), 7.26 (2H, d, J=8.9 Hz), 7.32 (1H, s), 7.63 (1H, s)

EXAMPLE 409

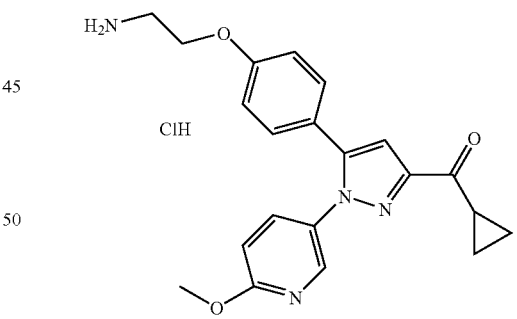

(E0409)

To a solution of E0374 (61.4 mg) in CH2Cl2 2 ml was added trimethylsilyl trifluoromethanesulfonate 85.6 mg at 0° C., followed by an addition of triethylamine 39 mg. The mixture was stirred at 0° C. for 30 minutes, and partitioned between AcOEt and H2O. The organic layer was washed with saturated aqueous sodium chloride solution, dried over magnesium sulfate, and concentrated invacuo. The residue was purified by preparative thin layer silica gel chromatography developed by 28% NH3aq: MeOH: CHCl3=1:10:100. The separated silica gel was extracted with 28% NH3aq: MeOH: CHCl3=1:10:100 and the solvent was evaporated in vacuo. The residue was dried under vacuo and then dissolved in EtOH 3 ml. To this solution was added 1M HCl 0.0892 ml and concentrated in vacuo. The residue was dried under vacuo to give E0409 (37 mg) as an amorphous powder.

IR (KBr): 2958, 1668, 1662, 1612, 1581, 1568, 1549, 1531, 1500 cm−1 Mass (ESI+): 379 (M+H)+

200 MHz 1H NMR 1.05 (4H, d, J=6.2 Hz), 3.04 (1H, m), 3.15–3.24 (2H, m), 3.89 (3H, s), 4.16–4.22 (2H, m), 6.94 (1H, d, J=8.8 Hz), 7.00 (2H, d, J=8.7 Hz), 7.02 (1H, s), 7.27 (2H, d, J=8.7 Hz), 7.78 (1H, dd, J=2.7, 8.8 Hz), 8.14 (2H, brs), 8.21 (1H, d, J=2.7 Hz)

EXAMPLE 410

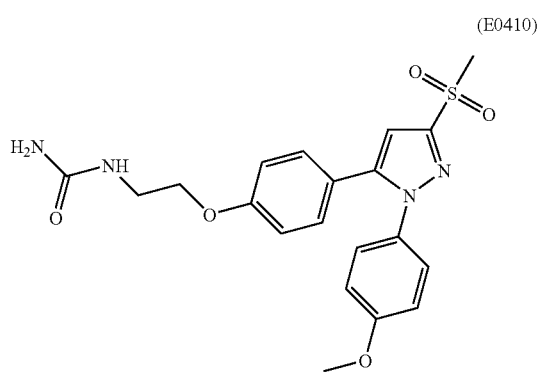

(E0410)

To a solution of 2-{4-[1-(4-methoxyphenyl)-3-(methyl-sulfonyl)-1H-pyrazol -5-yl]phenoxy}ethanamine (133 mg, 0.342 mmol) in methylene chloride (5 ml) was added trimethylsilyl isocyanate (118 mg, 1.03 mmol) and triethylamine (1.39 mg, 1.37 mmol) at ambient temperature and stirred for two days. The reaction mixture was washed with water and brine, dried over magnesium sulfate, filtered and evaporated. Purification by column chromatography (silica gel, methylene chloride/methanol=20/1) followed by recrystallization from ethylacetate gave 102 mg (69%) of E0410 as white crystals.

mp. 165–167° C.

Mass; 431 (M+1)

IR (KBr); 1650, 1310CM−1

NMR (DMSO-d6, δ); 3.32 (2H, q, J=5.5Hz), 3.33 (3H, s), 3.79 (3H, s), 3.94 (2H, t, J=5.5 Hz), 5.52 (2H, s), 6.14 (1H, t, J=5.5 Hz), 6.94 (2H, d, J=8.7 Hz), 7.01 (2H, d, J=8.9 Hz), 7.11 (1H, s), 7.20 (2H, d, J=8.7 Hz), 7.28 (2H, d, J=8.9 Hz),

EXAMPLE 411

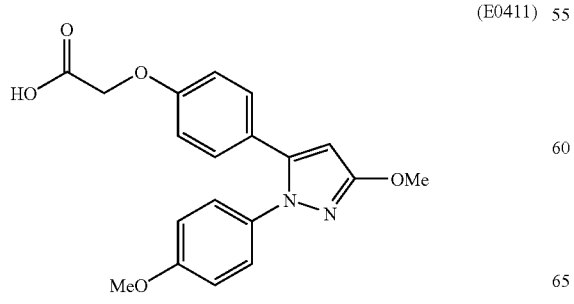

(E0411)

A solution of P0034 64 mg in DMF 1 ml was added 60% NaH 11.4 mg at 4° C. and the mixture was stirred at same temperature for 30 minutes. To the mixture was added bromoacetic acid 33 mg and the mixture was stirred at ambient temperature for 2 hours. The reaction was quenched by adding 1M HCl 2 ml, and the mixture was extracted with AcOEt. The organic layer was washed with H2O, sat. aqNaCl, dried over MgSO4, concentrated in vacuo to give E0411 (73 mg) as crystals.

Mass (ESI+): 355 (M+H)+ 200 MHz 1H NMR (DMSO-d6, d): 3.79 (3H, s), 3.96 (3H, s), 4.63 (2H, s), 5.88 (1H, s), 6.82 (4H, d, J=9.0 Hz), 7.14 (2H, d, J=9.0 Hz), 7.17 (2H, d, J=9.0 Hz)

EXAMPLE 412

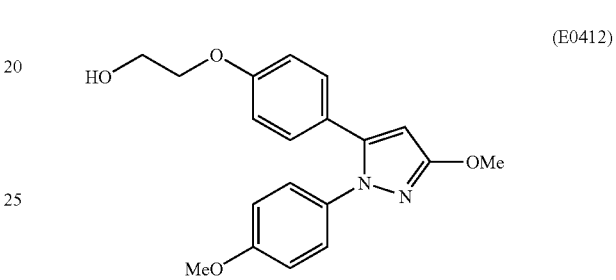

(E0412)

Boron trifluoride diethyl etherate 137 mg was added to a suspension of sodium borohydride 29.3 mg in THF 3 ml with cooling in an ice bath, and the mixture was stirred at same temperature for 30 minutes. To the reaction mixture was added E0411 (137 mg) in THF 3 ml in one portion and the mixture was stirred at ambient temperature for 4 hours. The reaction was quenched by adding ice water containing 1M HCl 1 ml, and the mixture was stirred at ambient temperature for 1 hour. The mixture was extracted with AcOEt for 2 times, the combined organic layers were washed with sat. aqNaHCO3, sat.aqNaCl, dried over MgSO4, evaporated in vacuo. The residue was purified by preparative thin layer chromatography developed with AcOEt/n-hexane=50%. The residue was crystallized from IPE to give E0412 (79.2 mg) as a white powder.

mp. 107–109° C.

IR (KBr): 3334, 2935, 1693, 1612, 1564, 1520cm−1

Mass (ESI+): 341 (M+H)+

200 MHz 1H NMR (DMSO-d6, d): 2.02 (1H, t, J=6.1 Hz), 3.80 (3H, s), 3.91–3.99 (2H, m), 3.97 (3H, s), 4.04–4.09 (2H, m), 5.88 (1H, s), 6.82 (4H, d, J=9.0 Hz), 7.14 (2H, d, J=9.0 Hz), 7.17 (2H, d, J=9.0 Hz)

EXAMPLE 413

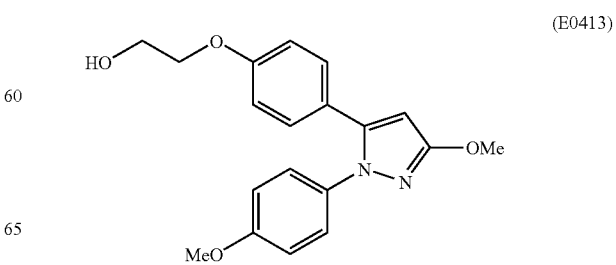

(E0413)

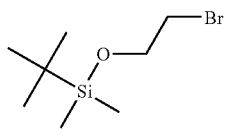

(E0413-0)

To a solution of P0034 (237 mg) in DMF 2 ml was added 60% NaH 41.6 mg with cooling in an ice bath, and the mixture was stirred at ambient temperature for 1 hour. To the mixture was added E0413-0 (287 mg) in DMF 1 ml and the mixture was stirred at ambient temperature for 13 hours, and at 60° C. for 3 hours. The reaction was quenched by adding sat.NH4Claq, and the mixture was extracted with AcOEt. The organic layer was washed with H2O, sat.aqNaCl, dried over MgSO4, concentrated in vacuo. The residue was dissolved in EtOH 4 ml, and conc. HCl 40 μL was added. After stirring at ambient temperature for 2 hours, the mixture was concentrated in vacuo. The residue was partitioned between AcOEt and sat.aqNaHCO3, and the organic layer was washed with sat.aqNaCl, dried over MgSO4, concentrated in vacuo. The residue was purified by silica gel column chromatography eluted with AcOEt/n-hexane=40%, 60%. The residue was crystallized from AcOEt 1 ml and IPE2 ml. The obtained crystals were recrystallized from AcOEt 0.7 ml and IPE1.5 ml to give E0413 (196.9 mg) as white crystals.

mp. 114.9–116 (115)° C.

Mass (ESI+): 341 (M+H)+

200 MHz 1H NMR (DMSO-d6, d): 3.65–3.73 (2H, m), 3.75 (3H, s), 3.83 (3H, s), 3.94–3.99 (2H, m), 4.86 (1H, t, J=5.4 Hz), 6.04 (1H, s), 6.87–6.96 (4H, m), 7.10–7.16 (4H, m)

EXAMPLE 414

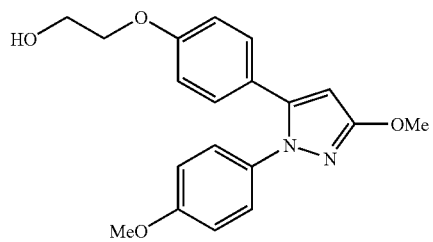

(E0414)

To a solution of P0034 (100 mg) in DMF 1 ml was added 60% NaH 17.5 mg with cooling in an ice bath. The mixture was stirred at ambient temperature for 1 hour. The mixture was cooled to 0° C. To the mixture was added 2-bromoethyl acetate 113 mg and the mixture was stirred at ambient temperature for 24 hours. The reaction was quenched by adding sat.NH4Claq, and the mixture was extracted with AcOEt. The organic layer was washed with H2O, sat.aqNaCl, dried over MgSO4, concentrated in vacuo. The residue was dissolved in THF 0.9 ml and MeOH 0.9 ml. To this solution was added 1M NaOH 0.4 ml.

The mixture was stirred at ambient temperature for 1 hour. The mixture was partitioned between AcOEt and H2O, and the aqueous layer was reexracted with AcOEt. The combined organic layers were washed with sat.aqNaCl, dried over MgSO4, concentrated in vacuo. The residue was crystallized from AcOEt 0.3 ml-IPE 0.9 ml to give E0414 (82.4 mg) as white crystals.

Mass (ESI+): 341 (M+H)+

Preparation 35

To a solution of N'-[5-[4-(benzyloxy)phenyl]-1-(4-methoxy-phenyl)-1H-pyrazol-3-yl]-N,N-dimethylurea (1.19 g) in EtOH (10 ml) and THF (10 ml) were added a solution of ammonium formate (509 mg) in H2O (2 ml) and 10% Pd-C 50% wet (150 mg). The mixture was refluxed for 1 hour. The catalyst was filtered off through a celite pad and the pad was washed with EtOH. The filtrate and combined washings were concentrated in vacuo. To the residue were added AcOEt and H2O. White precipitates were appeared and collected and washed with H2O and IPE successively to give N'-[5-(4-hydroxyphenyl)-1-(4-methoxyphenyl)-1H-pyrazol-3-yl]-N,N-dimethylurea (555 mg) as a white powder.

Mass (ESI+): 353 (M+H)+

200 MHz 1H NMR (DMSO-d6, d): 2.91 (6H, s), 3.76 (3H, s), 6.57 (1H, s), 6.71 (2H, d, J=8.6 Hz), 6.93 (2H, d, J=9.0 Hz), 7.01 (2H, d, J=8.6 Hz), 7.14 (2H, d, J=9.0 Hz), 8.99 (1H, s), 9.68 (1H, s)

The following compound(s) was(were) obtained in a similar manner to that of Preparation 35.

Preparation 36

N-[5-(4-hydroxyphenyl)-1-(4-methoxyphenyl)-1H-pyrazol-3-yl]-N,N', N'-trimethylurea White Powder Mass (ESI+): 367 (M+H)+

200 MHz 1H NMR (DMSO-d6, d)

2.78 (6H, s), 3.11 (3H, s), 3.76 (3H, s), 6.19 (1H, s), 6.70 (2H, d, J=8.6 Hz), 6.93 (2H, d, J=9.0 Hz), 7.03 (2H, d, J=8.6 Hz), 7.15 (2H, d, J=9.0 Hz), 9.72 (1H, s)

Preparation 37

4-[3-ethoxy-1-(4-methoxyphenyl)-1H-pyrazol-5-yl]phenol

White Powder

Mass (ESI+): 311 (M+H)+

200 MHz 1H NMR (DMSO-d6, d): 1.32 (3H, t, J=7.0 Hz), 3.75 (3H, s), 4.16 (2H, q, J=7.0 Hz), 5.96 (1H, s), 6.70 (2H, d, J=8.6 Hz), 6.91 (2H, d, J=8.9 Hz), 7.01 (2H, d, J=8.6 Hz), 7.11 (2H, d, J=8.9 Hz), 9.74 (1H, brs)

Preparation 38

4-[3-isobutoxy-1-(4-methoxyphenyl)-1H-pyrazol-5-yl]-phenol

White Powder

Mass (ESI+): 339 (M+H)+

200 MHz 1H NMR (CDCl3, d): 1.02 (6H, d, J=6.6 Hz), 2.10 (1H, m), 3.79 (3H, s), 3.98 (6.6H, d, J=2 Hz), 538 (1H, s), 5.87 (1H, s), 6.72 (2H, d, J=8.6 Hz), 6.81 (2H, d, J=9.0 Hz), 7.07 (2H, d, J=8.6 Hz), 7.16 (2H, d, J=9.0 Hz)

Preparation 39

4-[3-(2-methoxyethoxy)-1-(4-methoxyphenyl)-1H-pyrazol-5-yl]phenol

White Powder
Mass (ESI+): 341 (M+H)+
200 MHz 1H NMR (DMSO-d6, d): 3.30 (3H, s), 3.62–3.67 (2H, m), 3.75 (3H, s), 4.21–4.26 (2H, m), 5.98 (1H, s), 6.70 (2H, d, J=8.6 Hz), 6.91 (2H, d, J=9.0 Hz), 7.01 (2H, d, J=8.6 Hz), 7.12 (2H, d, J=9.0 Hz), 9.69 (1H, s)

Preparation 40

4-[3-(2-ethoxyethoxy)-1-(4-methoxyphenyl)-1H-pyrazol-5-yl]phenol

White Powder
Mass (ESI+): 355 (M+H)+
200 MHz 1H NMR (DMSO-d6, d): 1.13 (3H, t, J=7.0 Hz), 3.49 (2H, q, J=7.0 Hz), 3.65–3.71 (2H, m), 3.75 (3H, s), 4.20–4.25 (2H, m), 5.99 (1H, s), 6.70 (2H, d, J=8.6 Hz), 6.91 (2H, d, J=9.0 Hz), 7.01 (2H, d, J=8.6 Hz), 7.12 (2H, d, J=9.0 Hz), 9.72 (1H, s)

Preparation 41

2-{[5-(4-hydroxyphenyl)-1-(4-methoxyphenyl)-1H-pyrazol-3-yl]oxy}-N,N-dimethylacetamide White Powder
Mass (ESI+): 368 (M+H)+
200 MHz 1H NMR (DMSO-d6, d): 2.84 (3H, s), 2.97 (3H, s), 3.75 (3H, s), 4.87 (2H, s), 6.01 (1H, s), 6.70 (2H, d, J=8.6 Hz), 6.92 (2H, d, J=9.0 Hz), 7.01 (2H, d, J=8.6 Hz), 7.10 (2H, d, J=9.0 Hz), 9.71 (1H, s)

Preparation 42

4-[3-methoxy-1-(6-methoxy-3-pyridinyl)-1H-pyrazol-5-yl]phenol

White Powder
MS (ESI+): m/z 298 (M+H)+
200 MHz 1H NMR (DMSO-d6, d): 3.84 (6H, s), 6.05 (1H, s), 6.73 (2H, d, J=8.6 Hz), 6.85 (1H, d, J=8.8 Hz), 7.05 (2H, d, J=8.6 Hz), 7.59 (1H, dd, J=8.8, 2.7 Hz), 7.98 (1H, d, J=2.7 Hz), 9.77 (1H, s)

Preparation 43
4-[3-ethoxy-1-(6-methoxy-3-pyridinyl)-1H-pyrazol-5-yl]phenol
White Powder
MS (ESI+): m/z 312 (M+H)+
200 MHz 1HNMR (DMSO-d6, d): 1.33 (3H, t, J=7.0 Hz), 3.84 (3H, s), 4.18 (2H, q, J=7.0 Hz), 6.03 (1H, s), 6.73 (2H, d, J=8.6 Hz), 6.84 (1H, d, J=8.7 Hz), 7.05 (2H, d, J=8.6 Hz), 7.57 (1H, dd, J=2.6, 8.7 Hz), 7.97 (1H, d, J=2.6 Hz), 9.76 (1H, s)

Preparation 44

4-[1-(4-methoxyphenyl)-4-methyl-3-(trifluoromethyl)-1H-pyrazol-5-yl]phenol

MASS (ESI+): m/z=371.2 (M+Na).
1HNMR (400 MHz, CDCl3): 2.15 (3H, s), 3.78 (3H, s), 6.79 (2H, d, J=8.9 Hz ), 6.8 (2H, d, J=8.6 Hz ), 7.01 (2H, d, J=8.6 Hz ), 7.13 (2H, d, J=8.9 Hz ).

Preparation 45

4-[3-cyclopropyl-1-(6-methoxy-3-pyridinyl)-1H-pyrazol-5-yl]phenol

White Powder
MS(ESI+): m/z 308 (M+H)
1HNMR (200 MHz, CDCl3) 0.76–0.85 (2H, m), 0.93–1.06 (2H, m), 1.97–2.08 (1H, m), 3.91 (3H, s), 6.08 (1H, s), 6.15 (1H, s), 6.68–6.76 (3H, m), 7.04 (2H, d, J=8.6 Hz ), 7.56 (1H, dd, J=2.7, 6.2 Hz), 8.02 (1H, d, J=2.7 Hz Preparation 46

4-[3-(cyclopentyloxy)-1-(6-methoxy-3-pyridinyl)-1H-pyrazol-5-yl]phenol

White Powder
MS (ESI+): m/z 352 (M+H)
1HNMR (200 MHz, DMSOd6): 1.09–2.41 (8H, m), 3.84 (3H, s), 4.92–5 (1H, m), 6.01 (1H, s), 6.73 (2H, d, J=8.6 Hz), 6.84 (1H, d, J=8.8 Hz ), 7.05 (2H, d, J=8.6 Hz ), 7.57 (1H, dd, J=2.7, 8.8 Hz), 7.97 (1H, d, J=2.7 Hz ), 9.76 (1H, brs)

Preparation 47

4-[1-(4-methoxyphenyl)-3-(2,2,2-trifluoroethoxy)-1H-pyrazol-5-yl]phenol

White Powder
MS (ESI+): m/z 365 (M+H)
1HNMR (200 MHz, DMSOd6): 3.76 (3H, s), 4.8 (1H, d, J=9 Hz ), 4.89 (1H, d, J=9 Hz ), 6.15 (1H, s), 6.71 (2H, d, J=8.6 Hz), 6.93 (2H, d, J=8.9 Hz), 7.03 (2H, d, J=8.6 Hz), 7.14 (2H, d, J=8.9 Hz), 9.74 (1H, brs)

Preparation 48

4-[3-(2,2-difluoroethoxy)-1-(4-methoxyphenyl)-1H-pyrazol-5-yl]phenol

White Powder
MS (ESI+): m/z 347 (M+H)
1HNMR (200 MHz, DMSOd6): 3.76 (3H, s), 4.43 (2H, dt, J=3.5, 14.9 Hz), 6.08 (1H, s), 6.40 (1H, tt, J=3.5, 54.6 Hz), 6.71 (2H, d, J=8.6 Hz), 6.92 (2H, d, J=9.0 Hz), 7.02 (2H, d, J=8.6 Hz), 7.14 (2H, d, J=9.0 Hz)

Preparation 49

4-[1-(6-methoxy-3-pyridinyl)-3-(2,2,2-trifluoroethoxy)-1H-pyrazol-5-yl]phenol

White Powder
MS (ESI+): m/z 366 (M+H)
1HNMR (200 MHz, CDCl3): 3.92 (3H, s), 4.61 (1H, d, J=8.5 Hz), 4.69 (1H, d, J=8.5 Hz), 5.39 (1H, brs), 5.97 (1H, s), 6.72 (1H, d, J=8.9 Hz), 6.76 (2H, d, J=8.5 Hz), 7.09 (2H, d, J=8.5 Hz), 7.51 (1H, dd, J=2.7, 8.9 Hz), 8.01 (1H, d, J=2.7 Hz)

Preparation 50

4-[3-(2,2-difluoroethoxy)-1-(6-methoxy-3-pyridinyl)-1H-pyrazol-5-yl]phenol

White Powder
MS (ESI+): m/z 348 (M+H)
1HNMR (200 MHz, CDCl3): 3.92 (3H, s), 4.46 (2H, dt, J=4.2, 13.5 Hz), 5.42 (1H, brs), 5.93 (1H, s), 6.16 (1H, tt, J=4.2, 55.4 Hz), 6.72 (1H, d, J=8.7 Hz), 6.76 (2H, d, J=8.6 Hz), 7.09 (2H, d, J=8.6 Hz), 7.51 (1H, dd, J=2.7, 8.7 Hz), 8.01 (1H, d, J=2.7 Hz)

Preparation 51

4-[1-(4-methoxyphenyl)-4-methyl-1H-pyrazol-5-yl] phenol

White Powder
MS (ESI+): m/z 281 (M+H)
200 MHz 1HNMR (DMSO-d6, d): 2.00 (3H, s), 3.74 (3H, s), 6.74 (2H, d, J=8.5 Hz), 6.88 (2H, d, J=9.0 Hz), 6.96 (2H, d, J=8.5 Hz), 7.09 (2H, d, J=9.0 Hz), 7.53 (1H, s), 9.66 (1H, s)

Preparation 52

4-[1-(6-methoxy-3-pyridinyl)-4-methyl-1H-pyrazol-5-yl]phenol

White Powder
MS (ESI+): m/z 282 (M+H)
1HNMR (200 MHz, DMSOd6): 2.01 (3H, s), 3.83 (3H, s), 6.75–6.85 (3H, m), 7.01 (2H, d, J=8.6 Hz), 7.53 (1H, dd, J=2.7, 8.8 Hz), 7.6 (1H, s), 7.96 (1H, d, J=2.7 Hz), 9.73 (1H, brs)

Preparation 53

To a solution of 4'-benzyloxypropiophenone (6.0 g) in THF (120 ml) at −60° C. was added 38 ml of 1N lithium bis(trimethylsilyl)amide (LiHMDS), and the mixture was stirred at under −60° C. for 45 mins. 1-(Trifluoroacetyl)-imidazole (3.4 ml) was added and the mixture was stirred at −60° C. for 1 hour and at 0° C. for 30 min. The raction mixture was quenched with 0.5N HCl, the mixture was poured into EtOAc and water, and the EtOAc layer was separated, washed with brine, died over MgSO4, and concentrated to give 1-[4-(benzyloxy)phenyl]-4,4,4-trifluoro-2-methyl-1,3-butanedione.

MASS (ESI+): m/z=359.2 (m+Na).
1HNMR (400 MHz, CDCl3): 1.36 (1H, d, J=7.2 Hz), 1.52 (2H, d, J=7 Hz), 5.16 (2H, s), 7.02–7.08 (2H, m), 7.37–7.44 (5H, m), 7.92–7.98 (2H, m).

Preparation 54

To a mixture of 4-(methylthio)aniline (6.3 g) and conc.HCl (45 ml) was added dropwise NaNO2 (3.6 g) in water (18 ml) under ice-cooling. After stirring for 30 min., SnC1H2O (28.6 g) in conc.HCl (24 ml) was added under ice cooling over 1 hour. After stirring for 1 hour, filtrate, washed with conc.HCl and water, and dried to give 14.1 g of [4-(methylthio)phenyl]hydrazine hydrochloride as a solid.

MASS (ESI+): m/z=139.3 (M-NH2+1).
1HNMR (400 MHz, DMSOd6): 2.42 (3H, s), 3.75 (2H, b.s), 6.97 (2H, d, J=8.7 Hz), 7.24 (2H, d, J=8.7 Hz), 10.24 (1H, b.s).

Preparation 55

A mixture of 4-hydroxypropiophenone (20 g), benzyl chloride (16.1 ml), K2CO3 (12.9 g) and KI (2.21 g) in EtOH (80 ml) and H2O (1 ml) was stirred under reflux condition for 4 hours. The reaction mixture was cooled and filtered. Appeared crystal was dissovled with EtOAc and water. Organic layer was separated and washed with water and brine, dried over MgSO4 and filtered. Filtrate was evaporated under reduced pressure to give 30.0 g (94%) of 1-[4-(benzyloxy)phenyl]-1-propanone as a crystal.

MASS (ESI+): m/z=263.2 (M+Na).
1HNMR (400 MHz, CDCl3): 1.21 (3H, t, J=7.3 Hz), 2.95 (2H, q, J=7.3 Hz), 5.13 (2H, s), 7 (2H, d, J=8.9 Hz), 7.34–7.45 (5H, m), 7.95 (2H, d, J=8.9 Hz).

Preparation 56

1M NaOH (4.8 ml) was added to a solution of 4-benzyloxybenzaldehyde (5 g) and cyclopropyl methyl ketone (3.96 g) in EtOH (24 ml) and the mixture was stirred at ambient temperature overnight. The reaction mixture was diluted with H2O and EtOH. The mixture was stirred at ambient temperature for 20 minutes. Pale yellow crystals were collected and washed with H2O and 50% aqueous EtOH to give (2E)-3-[4-(benzyloxy)phenyl]-1-cyclopropyl-2-propen-1-one (6.29 g).

Pale yellow crystals
MS (ESI+): m/z 301 (M+Na)
1HNMR (200 MHz, CDCl3): 0.9–1.00 (2H, m), 1.11–1.19 (2H, m), 2.16–2.29 (1H, m), 5.11 (2H, s), 6.77 (1H, d, J=16.1 Hz), 6.99 (2H, d, J=8.8 Hz), 7.32–7.46 (4H, m), 7.52 (2H, d, J=8.8 Hz), 7.58 (2H, d, J=16.1 Hz)

Preparation 57

(2E)-3-[4-(Benzyloxy)phenyl]-1-cyclopropyl-2-propen-1-one (6.25 g) was suspended in EtOH (67.5 ml), acetone (22.5 ml) To this mixture was added hydrogen peroxide 30% aqueous solution (4.5 ml), and 3M NaOH (4.5 ml), and the mixture was stirred at ambient temperature for 1 day. The mixture was diluted with H2O. White precipitates were collected and washed with H2O, and air dried to give {(2R,3S)-3-[4-(benzyloxy)phenyl]-2-oxiranyl}(cyclopropyl)methanone (6.27 g).

Powder
MS (ESI+): m/z 317 (M+Na)
1HNMR (200 MHz, DMSOd6): 0.96–1.07 (2H, m), 1.12–1.19 (2H, m), 2.11–2.22 (1H, m), 3.59 (1H, d, J 1.8 Hz), 4.04 (1H, d, J 1.8 Hz) 5.08 (2H, s), 6.97 (2H, d, J=8.8 Hz), 7.23 (2H, d, J=8.8 Hz), 7.35–7.43 (5H, m)

Preparation 58

To a solution of 4-[3-methoxy-1-(4-methoxyphenyl)-1H-pyrazol-5- yl]phenol (501 mg) in CH2Cl2 (5 ml) was added trifluoromethanesulfonic anhydride (300 µl) and diisopropylethylamine (324 µl) under ice-bath cooling. The mixture was stirred at same temperature for 2 hours. Additional trifluoromethanesulfonic anhydride (57 µl) and diisopropylethylamine (147 µl) were added and stirring at same temperature was continued for 1 hour. The mixture was washed with 1M HCl, saturated aqueous sodium bicarbonate solution and saturated aqueous sodium chloride solution, dried over magnesium sulfate, and concentrated in vacuo. The residue was purified by silica gel column chromatography eluted with AcOEt/n-hexane=20% to give 4-[3-methoxy-1-(4-methoxyphenyl)-1H-pyrazol-5-yl]-phenyl trifluoromethanesulfonate (712.3 mg) as an oil.

MS (ESI+): m/z 429 (M+H)
1HNMR (200 MHz, CDCl3): 3.81 (3H, s), 3.98 (3H, s), 5.97 (1H, s), 6.85 (2H, d, J=9.0 Hz), 7.11–7.32 (6H, m)

The following compound(s) was(were) obtained in a similar manner to that of Preparation 58.

Preparation 59

4-[3-isopropoxy-1-(4-methoxyphenyl)-1H-pyrazol-5-yl]-phenyl trifluoromethanesulfonate oil
MS ESI+): m/z 457 (M+H)

1HNMR (200 MHz, CDC13): 1.40 (6H, d, J=6.2 Hz), 3.81 (3H, s), 4.89 (1H, m), 5.94 (1H, s), 6.84 (2H, d, J=9.0 Hz) 7.14 (2H, d, J=9.0 Hz), 7.20–7.32 (4H, m)

Preparation 60

4-[3-chloro-1-(4-methoxyphenyl)-1H-pyrazol-5-yl]-phenyl trifluoromethanesulfonate oil MS (ESI+): m/z 433 (M+H)

1HNMR (200 MHz, CDCl3): 3.82 (3H, s), 6.46 (1H, s), 6.86 (2H, d, J=9.0 Hz), 7.17 (2H, d, J=9.0 Hz), 7.23–7.32 (4H, m)

Preparation 61

A mixture of 4-[3-methoxy-1-(4-methoxyphenyl)-1H-pyrazol-5-yl]phenyl trifluoromethanesulfonate (679 mg), zinc cyanide (279 mg), and tetrakis(triphenylphosphine)-palladium(0) (183 mg) in DMF (4 ml) was stirred at 85° C. for 5 hours. The reaction mixture was cooled to ambient temperature and AcOEt and H2O were added. Unsoluble matter was filtered off through a celite pad. The filtrate was partitioned, and the organic layer was washed with saturated aqueous sodium chloride solution, dried over magnesium sulfate, and concentrated invacuo. The residue was purified by silica gel column chromatography eluted with AcOEt/n-hexane=20%. The pure fractions were collected and concentrated in vacuo to give 4-[3-methoxy-1-(4-methoxy-phenyl) -1H-pyrazol-5-yl]benzonitrile (326 mg) as a powder.

mp.112–113° C.

MS (ESI+): m/z 306 (M+H), 328 (M+Na)

IR (KBr): 2929, 2227, 1568, 1552, 1541, 1518 cm−1

1HNMR (200 MHz, CDCl3): 3.81 (3H, s), 3.98 (3H, s), 6.01 (1H, s), 6.85 (2H, d, J=8.9 Hz), 7.15 (2H, d, J=8.9 Hz), 7.30 (2H, d, J=8.5 Hz), 7.57 (2H, d, J=8.5 Hz)

The following compound(s) was(were) obtained in a similar manner to that of Preparation 61.

Preparation 62

4-[3-isopropoxy-1-(4-methoxyphenyl)-1H-pyrazol-5-yl]-benzonitrile mp. 96–97° C.

MS (ESI+): m/z 334 (M+H), 356 (M+Na)

1HNMR (200 MHz, CDCl3): 1.40 (6H, d, J=6.1 Hz), 3.81 (3H, s), 4.89 (1H, m), 5.98 (1H, s), 6.84 (2H, d, J=9.0 Hz), 7.14 (2H, d, J=9.0 Hz), 7.30 (2H, d, J=8.6 Hz), 7.56 (2H, d, J=8.6 Hz)

Preparation 63

4-[1-(6-methoxy-3-pyridinyl)-3-(2,2,2-trifluoroethoxy)-1H-pyrazol-5-yl]benzonitrile oil MS (ESI+): m/z 375 (M+H)

1HNMR (200 MHz, CDCl3): 3.94 (3H, s), 4.62 (1H, d, J=8.4 Hz), 4.71 (1H, d, J=8.4 Hz), 6.12 (1H, s), 6.76 (1H, d, J=8.7 Hz), 7.33 (2H, d, J 8.4 Hz), 7.5 (1H, dd, J=2.7, 8.7 Hz), 7.62 (2H, d, J=8.4 Hz), 7.97 (1H, d, J=2.7 Hz)

Preparation 64

4-[3-chloro-1-(4-methoxyphenyl)-1H-pyrazol-5-yl]-benzonitrile

Powder

MS (ESI+): m/z 310 (M+H), 332 (M+Na)

1HNMR (200 MHz, CDCl3): 3.83 (3H, s), 6.50 (1H, s), 6.87 (2H, d, J=9.0 Hz), 7.16 (2H, d, J=9.0 Hz), 7.30 (2H, d, J=8.5 Hz), 7.60 (2H, d, J=8.5 Hz)

Preparation 65

4-[3-chloro-1-(6-methoxy-3-pyridinyl)-1H-pyrazol-5-yl]-benzonitrile

Powder

MS (ESI+): m/z 311 (M+H), 333 (M+Na)

1HNMR (200 MHz, CDCl3): 3.94 (3H, s), 6.53 (1H, s), 6.78 (1H, d, J=8.9 Hz), 7.33 (2H, d, J=8.4 Hz), 7.54 (1H, dd, J=2.7, 8.9 Hz), 7.64 (2H, d, J=8.4 Hz), 7.99 (1H, d, J=2.7 Hz)

Preparation 66

A solution of trifluoromethanesulfonic anhydride (207 μl) in CH2Cl2 (1 mg) was added to a solution of 4-[1-(6-methoxy-3-pyridinyl)-3-(2,2,2-trifluoroethoxy)-1H-pyrazol-5-yl]phenol (300 mg) and pyridine (199 μl) in CH2Cl2 (3 ml) under ice-bath cooling. The mixture was stirred at same temperature for 1 hour. The reaction was quenched by adding saturated aqueous ammonium chloride solution (5 ml) The mixture was partitioned between AcOEt and 1M HCl. The mixture was washed with saturated aqueous sodiumbicarbonate solution and saturated aqueous sodium chloride solution, dried over magnesium sulfate, and concentrated in vacuo to give 4-[l-(6-methoxy-3-pyridinyl)-3-(2,2,2-trifluoro-ethoxy)-1H-pyrazol-5-yl]phenyl trifluoromethane-sulfonate (439 mg) as an oil.

MS (ESI+): m/z 498 (M+H)

1HNMR (200 MHz, CDCl3): 3.94 (3H, s), 4.62 (1H, d, J=8.4 Hz), 4.71 (1H, d, J=8.4 Hz), 6.08 (1H, s), 6.74 (1H, d, J=8.7 Hz), 7.22–7.38 (4H, m), 7.47 (1H, dd, J=2.7, 8.7 Hz), 8.01 (1H, d, J=2.7 Hz)

The following compound(s) was (were) obtained in a similar manner to that of Preparation 66.

Preparation 67

4-[3-chloro-1-(6-methoxy-3-pyridinyl)-1H-pyrazol-5-yl]-phenyl trifluoromethanesulfonate oil MS (ESI+): m/z 434 (M+H)

1HNMR (200 MHz, CDCl3): 3.94 (3H, s), 6.49 (1H, s), 6.76 (1H, d, J=8.9 Hz), 7.23–7.34 (4H, m), 7.52 (1H, dd, J=2.8, 8.9 Hz), 8.02 (1H, d, J=2.8 Hz)

Preparation 68

A solution of 4-[3-chloro-1-(4-methoxyphenyl)-1H-pyrazol-5-yl]phenyl benzyl ether (2.79 g) and thioanisole (3.56 g) intrifluoroacetic acid (25 ml) was stirred at ambient temperature overnight. The mixture was concentrated in vacuo. The residue was recrystallized from AcOEt (15 ml) and n-hexane (12 ml) to give 1st crop of FR282117 (1.48 g). The mother liqour was washed with H2O, saturated aqueous sodium chloride solution, dried over magnesium sulfate, and concentrated in vacuo. The residue was purified by silica gel column chromatography eluted with AcOEt/n-hexane=30%. The pure fractions were collected and concentrated in vacuo.

The residual crystals were collected and washed with IPE to give 2nd crop of 4-[3-chloro-1-(4-methoxyphenyl)-1H-pyrazol-5-yl]phenol(457.2 mg) white powder Mass (ESI+): m/z 301 (M+H)

200 MHz 1HNMR(DMSO-d6, d): 3.78 (3H, s), 6.62 (1H, s), 6.71 (2H, d, J=8.7 Hz), 6.96 (2H, d, J=9.0 Hz), 7.03 (2H, d, J=8.7 Hz), 7.19 (2H, d, J=9.0 Hz), 9.80 (1H, s)

The following compound(s) was(were) obtained in a similar manner to that of Preparation 68.

Preparation 69

4-[1-(4-methoxyphenyl)-3-(methylthio)-1H-pyrazol-5-yl]-phenol

Powder
MS (ESI+): m/z 313 (M+H)
1HNMR (200 MHz, DMSOd6): 2.50 (3H, s), 3.77 (3H, s), 6.49 (1H, s), 6.70 (2H, d, J=8.6 Hz), 6.94 (2H, d, J=9.0 Hz), 7.02 (2H, d, J=8.6 Hz), 7.16 (2H, d, J=9.0 Hz), 9.71 (1H, brs)

The following compound(s) was(were) obtained in a similar manner to that of Example 596.

Preparation 70

4-[1-[4-(methylthio)phenyl]-3-(trifluoromethyl)-1H-pyrazol-5-yl]phenol

MASS (ESI+): m/z=373.1 (M+Na).
1HNMR (400 MHz, CDCl3): 2.49 (3H, s), 5.13 (1H, b.s), 6.67 (1H, s), 6.79 (2H, d, J=8.7 Hz), 7.1 (2H, d, J=8.7 Hz), 7.2 (2H, d, J=9.1 Hz), 7.23 (2H, d, J=9.1 Hz).

Preparation 71

4-{3-(difluoromethyl)-1-[4-(methylthio)phenyl]-1H-pyrazol-5-yl}phenol

MASS (ESI+) m/z=355.1 (M+Na)
1HNMR (400 MHz, CDCl3): 2.49 (3H, s), 5.17 (1H, b.s), 6.65 (1H, s), 6.76 (1H, t, J=55 Hz), 6.78 (2H, d, J=8.7 Hz), 7.1 (2H, d, J=8.7 Hz), 7.2 (4H, s).

Preparation 72

4-[1-(6-methoxy-3-pyridinyl)-3-(trifluoromethyl)-1H-pyrazol-5-yl]benzonitrile

MASS (ESI+): m/z=345.1, 367.1 (m+H, m+Na).
1HNMR (400 MHz, CDC13): 3.96 (3H, s), 6.8 (1H, d, J=8.8 Hz) 6.85 (1H, s), 7.36 (2H, d, J=8.4 Hz), 7.57 (1H, dd, J=2.7, 8.8 Hz), 7.66 (2H, d, J=8.4 Hz), 8.04 (1H, d, J=2.7 Hz).

Preparation 73

4-[3-(difluoromethyl)-1-(6-methoxy-3-pyridinyl)-1H-pyrazol-5-yl]benzonitrile

MASS (ESI+): m/z=327.1 (m+1).
1HNMR (400 MHz, CDCl3): 3.95 (3H, s), 6.77 (1H, t, J=54.8 Hz), 6.79 (1H, d, J=8.8 Hz), 6.82 (1H, s), 7.36 (2H, d, J=8.4 Hz), 7.54 (1H, dd, J=2.8, 8.8 Hz), 7.65 (2H, d, J=8.4 Hz), 8.04 (1H, d, J=2.8 Hz).

EXAMPLE 415

4M HCl in dioxane (3 ml) was added to a solution of tert-butyl (2–14-[3-(1-hydroxy-1-methylethyl)-1-(6-methoxy-3-pyridinyl)-1H-pyrazol-5-yl]phenoxylethyl)-carbamate (236 mg) in CH2Cl2 (3 ml). The reaction mixture was stirred at ambient temperature for 3 hours. 2-Propanol (2 ml) was added to dissolve unsoluble oil, and stirred at ambient temperature for 4 hours. The mixture was concentrated in vacuo. The residue was suspended in CH2Cl2 (3 ml). Methanesulfonyl chloride (127 mg) was added and then Et3N was added to adjust pH of the reaction mixture to neutral. After stirring for 1 hour, the reaction mixture was concentrated in vacuo. The residue was partitioned between ethyl acetate and water. The mixture was extracted with ethyl acetate. The organic layer was washed with saturated aqueous sodium bicarbonate solution and saturated aqueous sodium chloride solution, dried over magnesium sulfate, and concentrated in vacuo. The residue was purified by silica gel column chromatography eluted with 50% AcOEt/n-hexane to give N-(2-{4-[3-isopropenyl-1-(6-methoxy-3-pyridinyl)-1H-pyrazol-5-yl]phenoxy}ethyl)methane-sulfonamide (118 mg) as an oil.

1H NMR (CDCl3) δ 2.20 (3H, s), 3.03 (3H, s), 3.51–3.60 (2H, m), 3.93 (3H, s), 4.07–4.13 (2H, m), 4.77 (1H, t, J=6.0 Hz), 5.15 (1H, brs), 5.60 (1H, brs), 6.59 (1H, s), 6.73 (1H, d, J=8.9 Hz), 6.83 (2H, d, J=8.8 Hz), 7.17 (2H, d, J=8.8 Hz), 7.55 (1H, dd, J=2.6, 8.8 Hz), 8.09 (1H, d, J=2.6 Hz)

EXAMPLE 416

A mixture of 10% Pd-C 50% wet (20 mg) and N-(2-{4-[3-isopropenyl-1-(6-methoxy-3-pyridinyl)-1H-pyrazol-5-yl]phenoxy}ethyl)methanesulfonamide (118 mg) in THF (1 ml) and MeOH (1 ml) was hydrogenated under H2 1atm at ambient temperature for 1 day. The catalyst was removed by filtration. The filtrate and combined washings were concentrated in vacuo. The residue was purified by preparative thin layer silica gel chromatography developed by AcOEt/n-hexane=70%. The separated silica gel was extracted with 10% MeOH/CHCl3 and the solvent was evaporated in vacuo. The residue was recrystallized from AcOEt-IPE to give N-(2-{4-[3-isopropyl-1-(6-methoxy-3-pyridinyl)-1H-pyrazol-5-yl]phenoxy}ethyl)methanesulfonamide (68.6 mg) as white powder.

White Powder
mp. 96–97° C.
IR (KBr): 3269, 2970, 1612, 1512 cm−1
MS (ESI+): m/z 431 (M+H)
1H NMR (DMSO-d6) δ 1.27 (6H, d, J=6.9 Hz), 2.88–2.99 (1H, m), 2.92 (3H, s), 3.92–3.35 (2H, m), 3.85 (3H, s), 3.99–4.06 (2H, m), 6.46 (1H, s), 6.88 (1H, d, J=8.7 Hz), 6.94 (2H, d, J=8.8 Hz), 7.17 (2H, d, J=8.8 Hz), 7.28 (1H, s), 7.60 (1H, dd, J=2.7, 8.7 Hz), 8.02 (1H, d, J=2.7 Hz)

The following compound(s) was(were) obtained in a similar manner to that of Example 416.

EXAMPLE 417 tert-butyl {4-[3-isopropyl-1-(4-methoxyphenyl)-1H-pyrazol-5-yl]benzyl}carbamate oil
MS (ESI+): m/z 422 (M+H)
1HNMR (200 MHz, ): 1.34 (6H, d, J=7.0 Hz), 1.46 (9H, s), 3.08 (1H, m), 3.80 (3H, s), 4.30 (2H, d, J=5.9 Hz), 4.81 (1H, brs), 6.31 (1H, s), 6.83 (2H, d, J=9.0 Hz), 7.15–7.26 (6H, m)

EXAMPLE 418 tert-butyl {4-[3-isopropyl-1-(6-methoxy-3-pyridinyl)-1H-pyrazol-5-yl]benzyl}carbamate oil MS (ESI+): m/z 423 (M+H)

1HNMR (200 MHz, CDCl3) 1.34 (6H, d, J=7 Hz), 1.46 (9H, s), 3.07 (1H, m), 3.92 (3H, s), 4.30 (2H, d, J=6.0 Hz), 4.84 (1H, brs), 6.33 (1H, s), 6.72 (1H, d, J=8.8 Hz), 7.15–7.26 (4H, m), 7.56 (1H, dd, J=2.7, 8.8 Hz), 8.04 (1H, d, J=2.7 Hz)

EXAMPLE 419

A 4M solution of HCl in dioxane (2 ml) was added to a solution of ter-butyl (2-{4-[3-isopropenyl-1-(6-methoxy-3-pyridinyl)-1H-pyrazol-5-yl]phenoxy}ethyl)carbamate (269.7 mg) in CH2Cl2 (2 ml). The reaction mixture was stirred at ambient temperature for 2 hours, then, was concentrated in vacuo to give (2-{4-[3-isopropenyl-1-(6-methoxy-3-pyridinyl)-1H-pyrazol-5-yl]phenoxy}ethyl)amine dihydrochloride (259 mg) as an amorphous powder.

MS (ESI+): m/z 351 (M+H)

1H NMR (DMSO-d6) δ 2.10 (3H, s), 3.15–3.23 (2H, m), 3.86 (3H, s), 4.16–4.24 (2H, m), 5.15 (1H,brs), 5.63 (1H, brs), 6.85 (1H, s), 6.86–7.00 (3H, m), 7.18–7.25 (2H, m), 7.66 (1H, dd, J=2.8, 8.7 Hz), 8.06 (1H, d, J=2.8 Hz), 8.24 (2H, brs)

The following compound(s) was(were) obtained in a similar manner to that of Example 419.

EXAMPLE 420

(2-{4-[3-methoxy-1-(4-methoxyphenyl)-1H-pyrazol-5-yl]-phenoxy}ethyl)amine hydrochloride White Powder Mass (ESI+): 340 (M+H)+

200 MHz 1HNMR (DMSO-d6, d): 3.16–3.23 (2H, m), 3.76 (3H, s), 3.84 (3H, s), 4.14–4.20 (2H, m), 6.06 (1H,s), 6.93 (2H, d, J=8.9 Hz), 6.94 (2H, d, J=8.7 Hz), 7.14 (2H, d, J=8.9 Hz), 7.17 (2H, d, J=8.7 Hz), 8.16 (2H, brs)

EXAMPLE 421

(2-{4-[3-ethoxy-1-(4-methoxyphenyl)-1H-pyrazol-5-yl]-phenoxy}ethyl)amine hydrochloride White Powder Mass (ESI+): 354 (M+H)+

200 MHz 1H NMR (DMSO-d6, d): 1.33 (3H, t, J=7.0 Hz), 3.14–3.23 (2H, m), 3.76 (3H, s), 4.12–4.23 (4H, m), 6.04 (1H, s), 6.92 (2H, d, J=9.0 Hz), 6.94 (2H, d, J=8.8 Hz), 7.12 (2H, d, J=9.0 Hz), 7.16 (2H, d, J=8.8 Hz), 8.24 (2H, brs)

EXAMPLE 422

(2-{4-[3-isobutoxy-1-(4-methoxyphenyl)-1H-pyrazol-5-yl]phenoxy}ethyl)amine hydrochloride amorphous Mass (ESI+): 382 (M+H)+

200 MHz 1H NMR (DMSO-d6, d): 0.97 (6H, d, J=6.7 Hz), 2.03 (1H, m), 3.14–3.23 (2H, m), 3.76 (3H, s), 3.90 (2H, d, J=6.6 Hz), 4.14–4.20 (2H, m), 6.06 (1H,s), 6.92 (2H, d, J=9.0 Hz), 6.94 (2H, d, J=8.8 Hz), 7.08–7.19 (4H, m), 8.23 (2H, brs)

EXAMPLE 423

(2-{4-[3-(2-methoxyethoxy)-1-(4-methoxyphenyl)-1H-pyrazol-5-yl]phenoxy}ethyl)amine hydrochloride amorphous Mass (ESI+): 384 (M+H)+

200 MHz 1H NMR (DMSO-d6, d): 3.15–3.23 (2H, m), 3.31 (3H, s), 3.62–3.67 (2H, m), 3.75 (3H, s), 4.14–4.27 (4H, m), 6.06 (1H, s), 6.92 (2H, d, J=8.9 Hz), 6.95 (2H, d, J=8.8 Hz), 7.13 (2H, d, J=8.9 Hz), 7.17 (2H, d, J=8.8 Hz), 8.20 (2H, brs)

EXAMPLE 424

(2-{4-[3-(2-ethoxyethoxy)-1-(4-methoxyphenyl)-1H-pyrazol-5-yl]phenoxy}ethyl)amine hydrochloride amorphous Mass (ESI+): 398 (M+H)+

200 MHz 1H NMR (DMSO-d6, d): 1.13 (3H, t, J=7.0 Hz), 3.15–3.24 (2H, m), 3.50 (2H, q, J=7.0 Hz), 3.66–3.71 (2H, m), 3.76 (3H, s), 4.13–4.27 (4H, m), 6.07 (1H, s), 6.93 (2H, d, J=8.9 Hz), 6.95 (2H, d, J=8.7 Hz), 7.13 (2H, d, J=8.9 Hz), 7.17 (2H, d, J=8.7 Hz), 8.13 (2H, brs)

EXAMPLE 425

(2-{4-[3-methoxy-1-(6-methoxy-3-pyridinyl)-1H-pyrazol-5-yl]phenoxy}ethyl)amine dihydrochloride amorphous MS (ESI+): m/z 341 (M+H)+

200 MHz 1HNMR (DMSO-d6, d): 3.16–3.23 (2H, m), 3.84 (3H, s), 3.85 (3H, s), 4.16–4.21 (2H, m), 6.12 (1H, s), 6.86 (1H, d, J=8.7 Hz), 6.98 (2H, d, J=8.7 Hz), 7.21 (2H, d, J=8.7 Hz), 7.62 (1H, dd, J=2.5, 8.7 Hz), 7.99 (1H, d, J=2.5 Hz), 8.24 (2H, brs)

EXAMPLE 426

(2-{4-[3-ethoxy-1-(6-methoxy-3-pyridinyl)-1H-pyrazol-5-yl]phenoxy}ethyl)amine dihydrochloride amorphous MS (ESI+): m/z 355 (M+H)+

200 MHz 1H NMR (DMSO-d6, d): 1.33 (3H, t, J=7.0 Hz), 3.15–3.24 (2H, m), 3.84 (3H, s), 4.13–4.24 (2H, m), 4.19 (2H, q, J=7.0 Hz), 6.10 (1H, s), 6.86 (1H, d, J=8.9 Hz), 6.98 (2H, d, J=8.8 Hz), 7.21 (2H, d, J=8.8 Hz), 7.60 (1H, dd, J=2.7, 8.9 Hz), 7.98 (1H, d, J=2.7 Hz), 8.19 (2H, brs)

EXAMPLE 427

(2-{4-[1-(4-methoxyphenyl)-4-methyl-3-(trifluoromethyl)-1H-pyrazol-5-yl]phenoxy}ethyl)amine hydrochloride MASS (ESI+): m/z=392.2 (M+H).

1HNMR (400 MHz, DMSOd6): 2.09 (3H, s), 3.1–3.3 (2H, m), 3.36 (2H, b.s), 3.57 (3H, s), 4.20 (2H, t, J=5 Hz), 6.94 (2H, d, J=8.9 Hz), 7.01 (2H, d, J=8.8 Hz), 7.2 (2H, d, J=8.9 Hz), 7.21 (2H, d, J=8.8 Hz), 8.29 (2H, br.s).

EXAMPLE 428

(2-{4-[1-[4-(methylthio)phenyl]-3-(trifluoromethyl)-1H-pyrazol-5-yl]phenoxy}ethyl)amine hydrochloride MASS (ESI+): m/z=394.1 (M(Free)+1, HCl salt).
1HNMR (200 MHz, DMSOd6): 2.5 (3H, s), 3.15–3.25 (2H, m), 4.22 (2H, t, J=5 Hz), 7 (2H, d, J=8.7 Hz), 7.1 (1H, s), 7.26 (2H, d, J=8.7 Hz), 7.27 (2H, d, J=9.8 Hz) 7.33 (2H, d, J=9.8 Hz), 8.35 (2H, b.s).

EXAMPLE 429

[2-(4-{3-(difluoromethyl)-1-[4-(methylthio)phenyl]-1H-pyrazol-5-yl}phenoxy)ethyl]amine hydrochloride MASS (ESI-): m/z=410.0 (M-1).
1HNMR (400 MHz, DMSOd6): 2.49 (3H, s), 3.2 (2H, t, J=5 Hz), 4.19 (2H, t, J=5 Hz), 6.87 (1H, s), 6.99 (1H, d, J=8.7 Hz), 7.09 (1H, t, J=53.5 Hz), 7.24 (4H, d, J=9.6 Hz), 7.3 (2H, d, J=8.7 Hz), 8.17 (2H, b.s).

EXAMPLE 430

(2-{4-[3-cyclopropyl-1-(6-methoxy-3-pyridinyl)-1H-pyrazol-5-yl]phenoxy}ethyl)amine dihydrochloride amorphous powder
MS (ESI+): m/z 351 (M+H)
1HNMR (200 MHz, DMSOd6): 0.70–0.78 (2H, m), 0.86–1.02 (2H, m), 1.88–1.99 (1H, m), 3.10–3.20 (2H, m), 3.85 (3H, s), 4.15–4.21 (2H, m), 6.31 (1H, s), 6.86 (1H, d, J=8.9 Hz), 6.96 (2H, d, J=8.8 Hz), 7.17 (2H, d, J=8.8 Hz), 7.60 (1H, dd, J=2.7, 8.9 Hz), 8.00 (1H, d, J=2.7 Hz), 8.24 (2H, brs)

EXAMPLE 431

(2-{4-[1-(4-methoxyphenyl)-3-(1-piperidinylcarbonyl)-1H-pyrazol-5-yl]phenoxy}ethyl)amine hydrochloride amorphous powder
MS (ESI+): m/z 421 (M+H)
1HNMR (200 MHz, DMSOd6): 1.43–1.72 (6H, m), 3.14–3.24 (2H, m), 3.52–3.70 (2H, m), 3.77–3.95 (2H, m), 3.78 (3H, s), 4.15–4.20 (2H, m), 6.79 (1H, s), 6.96 (2H, d, J=8.8 Hz), 6.99 (2H, d, J=8.9 Hz), 7.21 (2H, d, J=8.8 Hz), 7.24 (2H, d, J=8.9 Hz), 8.14 (2H, brs)

EXAMPLE 432

(2-{4-[1-(6-methoxy-3-pyridinyl)-3-(1-piperidinylcarbonyl)-1H-pyrazol-5-yl]phenoxy}ethyl)amine dihydrochloride amorphous powder
MS (ESI+): m/z 422 (M+H)
1HNMR (200 MHz, CDCl3): 1.42–1.75 (6H, m), 3.14–3.24 (2H, m), 3.52–3.70 (2H, m), 3.73–3.94 (2H, m), 3.87 (3H, s), 4.16–4.22 (2H, m), 6.83 (1H, s), 6.91 (1H, d, J=8.9 Hz), 6.99 (2H, d, J=8.8 Hz), 7.25 (2H, d, J=8.8 Hz), 7.69 (1H, dd, J=2.7, 8.9 Hz), 8.14 (1H, d, J=2.7 Hz), 8.21 (2H, brs)

EXAMPLE 433

5-[4-(2-aminoethoxy)phenyl]-N-ethyl-1-(6-methoxy-3-pyridinyl)-N-methyl-1H-pyrazole-3-carboxamide dihydrochloride amorphous powder
Mass (ESI+): m/z 396 (M+H)
1HNMR (200 MHz, DMSOd6): 1.09–1.23 (3H, m), 2.98, 3.29 (3H, s), 3.13–3.25 (2H, m), 3.43–3.78 (4H, m), 3.87 (3H, s), 4.16–4.22 (2H, m), 6.84, 6.86 (1H, s), 6.91 (1H, d, J=8.7 Hz), 7.00 (2H, d, J=8.7 Hz), 7.25 (2H, d, J=8.7 Hz), 7.61–7.74 (1H, m), 8.13–8.20 (3H, m)

EXAMPLE 434

(2-{4-[3-(cyclopentyloxy)-1-(6-methoxy-3-pyridinyl)-1H-pyrazol-5-yl]phenoxy}ethyl)amine dihydrochloride amorphous powder
MS (ESI+): m/z 395 (M+H)
1HNMR (400 MHz, DMSOd6): 1.57–1.91 (8H, m), 3.16–3.21 (2H, m), 3.84 (3H, s), 4.17–4.21 (2H, m), 4.95–5 (1H, m), 6.08 (1H, s), 6.85 (1H, d, J=8.8 Hz), 6.98 (2H, d, J=8.8 Hz), 7.2 (2H, d, J=8.8 Hz), 7.59 (1H, dd, J=2.8, 8.8 Hz), 7.98 (1H, d, J=2.8 Hz), 8.24 (2H, brs)

EXAMPLE 435

(2-{4-[1-(4-methoxyphenyl)-3-(2,2,2-trifluoroethoxy)-1H-pyrazol-5-yl]phenoxy}ethyl)amine hydrochloride oil
MS (ESI+): m/z 408 (M+H)
1HNMR (200 MHz, DMSOd6): 3.13–3.24 (2H, m), 3.76 (3H, s), 4.15–4.21 (2H, m), 4.82 (1H, d, J=9.0 Hz), 4.91 (1H, d, J=9.0 Hz), 6.23 (1H, s), 6.92–6.99 (4H, m), 7.13–7.21 (4H, m), 8.20 (2H, brs)

EXAMPLE 436

(2-{4-[3-(2,2-difluoroethoxy)-1-(4-methoxyphenyl)-1H-pyrazol-5-yl]phenoxy}ethyl)amine hydrochloride amorphous powder
MS (ESI+): m/z 390 (M+H)
1HNMR (200 MHz, DMSOd6): 3.13–3.23 (2H, m), 3.76 (3H, s), 4.14–4.20 (2H, m), 4.44 (2H, dt, J=3.5, 14.9 Hz), 6.16 (1H, s), 6.41 (1H, tt, J=3.5, 54.6 Hz), 6.94 (2H, d, J=8.9 Hz), 6.95 (2H, d, J=8.9 Hz), 7.16 (2H, d, J=8.9 Hz), 7.18 (2H, d, J=8.9 Hz), 8.17 (2H, brs)

EXAMPLE 437

(2-{4-[1-(6-methoxy-3-pyridinyl)-3-(2,2,2-trifluoroethoxy)-1H-pyrazol-5-yl]phenoxy}ethyl)amine dihydrochloride amorphous powder
MS (ESI+): m/z 409 (M+H)

1HNMR (200 MHz, DMSOd6): 3.16–3.21 (2H, m), 3.85 (3H, s), 4.16–4.22 (2H, m), 4.83 (1H, d, J=9.0 Hz), 4.92 (1H, d, J=9.0 Hz), 6.29 (1H, s), 6.88 (1H, d, J=8.8 Hz), 6.99 (2H, d, J=8.8 Hz), 7.22 (2H, d, J=8.8 Hz), 7.63 (1H, dd, J=2.7, 8.8 Hz), 8.03 (1H, d, J=2.7 Hz), 8.19 (2H, brs)

EXAMPLE 438

(2-{4-[3-(2,2-difluoroethoxy)-1-(6-methoxy-3-pyridinyl)-1H-pyrazol-5-yl]phenoxy}ethyl)amine dihydrochloride Powder MS (ESI+): m/z 391 (M+H)

1HNMR (200 MHz, DMSOd6): 3.15–3.24 (2H, m), 3.85 (3H, s), 4.16–4.22 (2H, m), 4.46 (2H, dt, J=3.5, 14.9 Hz), 6.22 (1H, s), 6.42 (1H, tt, J=3.5, 54.5 Hz), 6.87 (1H, d, J=8.9 Hz), 6.99 (2H, d, J=8.7 Hz), 7.22 (2H, d, J=8.7 Hz), 7.62 (1H, dd, J=2.7, 8.9 Hz), 8.02 (1H, d, J=2.7 Hz), 8.20 (2H, brs)

EXAMPLE 439

{4-[1-(4-methoxyphenyl)-3-(1-piperidinylcarbonyl)-1H-pyrazol-5-yl]benzyl}amine hydrochloride amorphous powder MS (ESI+): m/z 391 (M+H)

1HNMR (200 MHz, DMSOd6): 1.43–1.74 (6H, m), 3.51–3.72 (2H, m), 3.77–3.93 (2H, m), 3.79 (3H, s), 3.97–4.06 (2H, m), 6.90 (1H, s), 6.99 (2H, d, J=8.9 Hz), 7.26 (2H, d, J=8.9 Hz), 7.30 (2H, d, J=8.2 Hz), 7.46 (2H, d, J=8.2 Hz), 8.38 (2H, brs)

EXAMPLE 440

5-[4-(aminomethyl)phenyl]-N-ethyl-1-(4-methoxyphenyl)-N-methyl-1H-pyrazole-3-carboxamide hydrochloride Powder MS (ESI+): m/z 365 (M+H)

1HNMR (200 MHz, DMSOd6): 1.09–1.22 (3H, m), 2.98, 3.29 (3H, s), 3.35–3.80 (2H, m), 3.79 (3H, s), 3.97–4.08 (2H, m), 6.91, 6.93 (1H, s), 6.99 (2H, d, J=8.9 Hz), 7.26 (2H, d, J=8.9 Hz), 7.30 (2H, d, J=8.3 Hz), 7.46 (2H, d, J=8.3 Hz), 8.37 (2H, brs)

EXAMPLE 441

{4-[3-isopropyl-1-(4-methoxyphenyl)-1H-pyrazol-5-yl]-benzyl}amine hydrochloride oil MS (ESI+): m/z 322 (M+H)

1HNMR (200 MHz, DMSOd6): 1.27 (6H, d, J=6.8 Hz), 2.96 (1H, m), 3.77 (3H, s), 3.95–4.03 (2H, m), 6.51 (1H, s), 6.94 (2H, d, J=8.9 Hz), 7.17 (2H, d, J=8.9 Hz), 7.25 (2H, d, J=8.2 Hz), 7.45 (2H, d, J=8.2 Hz), 8.45 (2H, brs)

EXAMPLE 442

1-[5-[4-(aminomethyl)phenyl]-1-(4-methoxyphenyl)-1H-pyrazol-3-yl]-2-methyl-1-propanone hydrochloride amorphous powder MS (ESI+): m/z 350 (M+H)

1HNMR (200 MHz, DMSOd6): 1.16 (6H, d, J=6.9 Hz), 3.68 (1H, m), 3.80 (3H, s), 4.01 (2H, s), 7.01 (2H, d, J=8.9 Hz), 7.10 (1H, s), 7.26 7.34 (4H, m), 7.46 (2H, d, J=8.2 Hz), 8.33 (2H, brs)

EXAMPLE 443

{4-[1-(6-methoxy-3-pyridinyl)-3-(1-piperidinylcarbonyl)-1H-pyrazol-5-yl]benzyl}amine dihydrochloride oil MS (ESI+): m/z 392 (M+H)

1HNMR (200 MHz, DMSO-d6): 1.45–1.73 (6H, m), 3.53–3.70 (2H, m), 3.70–3.98 (2H, m), 3.98–4.08 (2H, m), 6.92 (1H, d, J=8.8 Hz), 6.93 (1H, s), 7.32–7.55 (4H, m), 7.74 (1H, dd, J=2.7, 8.8 Hz), 8.15 (1H, d, J=2.7 Hz), 8.38 (2H, brs)

EXAMPLE 444

5-[4-(aminomethyl)phenyl]-N-ethyl-1-(6-methoxy-3-pyridinyl)-N-methyl-1H-pyrazole-3-carboxamide dihydrochloride oil MS (ESI+): m/z 366 (M+H)

1HNMR (200 MHz, DMSOd6): 1.09–1.23 (3H, m), 2.98, 3.29 (3H, s), 3.43–3.77 (2H, m), 3.88 (3H, s), 3.97–4.06 (2H, m), 6.89–6.96 (2H, m), 7.32–7.80 (5H, m), 8.14–8.16 (1H, m), 8.52 (2H, brs)

EXAMPLE 445

{4-[3-isopropyl-1-(6-methoxy-3-pyridinyl)-1H-pyrazol-5-yl]benzyl}amine dihydrochloride amorphous powder MS (ESI+): m/z 323 (M+H)

1HNMR (200 MHz, DMSOd6): 1.28 (6H, d, J=6.9 Hz), 2.86–3.05 (1H, m), 3.85 (3H, s), 3.96–4.06 (2H, m), 6.57 (1H, s), 6.88 (1H, d, J=8.8 Hz), 7.26–7.53 (4H, m), 7.66 (1H, dd, J=2.7, 8.8 Hz), 8.02 (1H, d, J=2.7 Hz), 8.48 (2H, brs)

EXAMPLE 446

1-[5-[4-(aminomethyl)phenyl]-1-(6-methoxy-3-pyridinyl)-1H-pyrazol-3-yl]-2-methyl-1-propanone dihydrochloride oil MS (ESI+): m/z 351 (M+H)

1HNMR (200 MHz, DMSOd6): 1.17 (6H, d, J=6.8 Hz), 3.68 (1H, m), 3.89 (3H, s), 3.98–4.06 (2H, m), 6.95 (1H, d, J=8.8 Hz), 7.13 (1H, s), 7.36 (2H, d, J=8.2 Hz), 7.51 (2H, d, J=8.2 Hz), 7.80 (1H, dd, J=2.7, 8.8 Hz), 8.19 (1H, d, J=2.7 Hz), 8.43 (2H, brs)

EXAMPLE 447

(2-{4-[1-(4-methoxyphenyl)-4-methyl-1H-pyrazol-5-yl]-phenoxy}ethyl)amine hydrochloride Powder
MS (ESI+): m/z 324 (M+H)
200 MHz 1H NMR (DMSO-d6, d): 2.02 (3H, s), 3.17–3.26 (2H, m), 3.74 (3H,s),4.13–4.19 (2H, m), 6.89 (2H, d, J=9.0 Hz), 6.98 (2H, d, J=8.7 Hz), 7.10 (2H, d, J=8.9 Hz), 7.13 (2H, d, J=8.7 Hz), 7.57 (1H, s), 8.05 (2H, brs)

EXAMPLE 448

(2-{4-[1-(6-methoxy-3-pyridinyl)-4-methyl-1H-pyrazol-5-yl]phenoxy}ethyl)amine dihydrochloride oil
MS(ESI+): m/z 325 (M+H)
1HNMR (200 MHz, DMSOd6): 2.03 (3H, s), 3.16–3.24 (2H, m), 3.83 (3H, s), 4.18–4.24 (2H, m), 6.84 (1H, d, J=8.7 Hz), 7.01 (2H, d, J=8.8 Hz), 7.17 (2H, d, J=8.8 Hz), 7.56 (1H, dd, J=2.7, 8.7 Hz), 7.64 (1H, s), 7.98 (1H, d, J=2.7 Hz), 8.28 (2H, brs)

EXAMPLE 449

(2-{4-[1-(4-methoxyphenyl)-3-(methylthio)-1H-pyrazol-5-yl]phenoxy}ethyl)amine hydrochloride amorphous powder
MS (ESI+): m/z 356 (M+H)
1HNMR (200 MHz, DMSOd6): 2.52 (3H, s), 3.14–3.23 (2H, m), 3.77 (3H, s), 4.15–4.21 (2H, m), 6.57 (1H, s), 6.95 (4H, d, J=8.9 Hz), 7.17 (4H, d, J=8.9 Hz), 8.22 (2H, brs)

The following compound(s) was(were) obtained in a similar manner to that of Example 428.

EXAMPLE 450

5-[4-(aminomethyl)phenyl]-1-(4-methoxyphenyl)-1H-pyrazole-3-carbonitrile hydrochloride MASS (ESI+): m/z=304.2 (M+1).

EXAMPLE 451

To a solution of (2-{4-[3-isopropenyl-1-(6-methoxy-3-pyridinyl)-1H-pyrazol-5-yl]phenoxy}ethyl)amine dihydrochloride (126.4 mg) and Et3N (125 μl) in CH2Cl2 (2 ml) was added methanesulfonyl chloride (34.7 μl ) under ice bath cooling. The mixture was stirred at ambient temperature for 1 hour. Additional methanesulfonyl chloride (6.9 μl) and Et3N (41.6 μl) were added and the reaction mixture was stirred at ambient temperature for 30 minutes. The mixture was concentrated in vacuo, and the residue was partitioned between AcOEt and 1M HCl. The aqueous layer was reextracted with AcOEt. The combined organic layers were washed with saturated aqueous sodiumbicarbonate solution and saturated aqueous sodium chloride solution, dried over magnesium sulfate, and concentrated in vacuo. The residue was purified by preparative thin layer silica gel chromatography developed by AcOEt/n-hexane=70%. The seaparated silica gel was extracted with 10% MeOH/CDCl3 and the solvent was evaporated in vacuo. The residue was crystallized from AcOEt-IPE to give N-(2-{4-[3-isopropenyl-1-(6-methoxy-3-pyridinyl)-1H-pyrazol-5-yl]phenoxy}ethyl) methane-sulfonamide (48.0 mg) as white powder.
mp. 96–99° C.
IR (KBr): 3205, 3140, 1612, 1502 cm−1
MS (ESI+) m/z 429 (M+H)
1H NMR (CDCl3) δ 2.20 (3H, s), 3.03 (3H, s), 3.51–3.60 (2H, m), 3.93 (3H, s), 4.07–4.13 (2H, m), 4.75 (1H, t, J=5.8 Hz), 5.15 (1H, brs), 5.60 (1H, brs), 6.59 (1H, s), 6.73 (1H, d, J=8.9 Hz), 6.83 (2H, d, J=8.8 Hz), 7.17 (2H, d, J=8.8 Hz), 7.55 (1H, dd, J=2.6, 8.8 Hz), 8.09 (1H, d, J=2.6 Hz)

The following compound(s) was (were) obtained in a similar manner to that of Example 451.

EXAMPLE 452

N-(2-{4-[3-{[(dimethylamino)carbonyl]amino}-1-(4-methoxyphenyl)-1H-pyrazol-5-yl]phenoxy}ethyl) methane-sulfonamide powder: mp. 166–167° C.
IR (KBr): 3309, 3188, 3182, 3174, 1657, 1651, 1643, 1568, 1514 cm−1
Mass (ESI+): 474 (M+H)+
200 MHz 1H NMR (CDCl3, d): 3.02 (3H, s), 3.04 (6H, s), 3.49–3.57 (2H, m), 3.81 (3H, s), 4.07 (2H, t, J=5.0 Hz), 4.84 (1H, t, J=5.5 Hz), 6.78 (2H, d, J=8.9 Hz), 6.85 (2H, d, J=9.0 Hz), 6.85 (1H, s), 7.05 (1H, s), 7.15 (2H, d, J=9.0 Hz), 7.18 (2H, d, J=8.9 Hz)

EXAMPLE 453

N-(2-{4-[3-[[(dimethylamino)carbonyl](methyl)amino]-1-(4-methoxyphenyl)-1H-pyrazol-5-yl]phenoxy}ethyl)-methanesulfonamide amorphous
IR (neat): 1658, 1649, 1641, 1631, 1620, 1612, 1518, 1502 cm−1
Mass (ESI+): 488 (M+H)+
200 MHz 1HNMR (DMSO-d6, d): 2.79 (6H, s), 2.94 (3H, s), 3.12 (3H, s), 3.30–3.34 (2H, m), 3.76 (3H, s), 4.02 (2H, t, J=5.4 Hz), 6.26 (1H, s), 6.92 (2H, d, J=8.7 Hz), 6.94 (2H, d, J=8.9 Hz), 7.16 (2H, d, J=8.7 Hz), 7.16 (2H, d, J=8.9 Hz), 7.29 (1H, s)

EXAMPLE 454

N-(2-{4-[3-chloro-1-(6-methoxy-3-pyridinyl)-1H-pyrazol-5-yl]phenoxy}ethyl)methanesulfonamide white powder: mp. 112–114° C.
IR (KBr): 3280, 1612 cm−1
Mass (ESI+): 423 (M+H)+
200 MHz 1H NMR (DMSO-d6, d): 2.94 (3H, s), 3.29–3.34 (2H, m), 3.87 (3H, s), 4.03 (2H, t, J=5.4 Hz), 6.75 (1H, s), 6.89 (1H, d, J=8.8 Hz), 6.96 (2H, d, J=8.7 Hz), 7.20 (2H, d, J=8.7 Hz), 7.29 (1H, brs), 7.67 (1H, dd, J=2.7, 8.8 Hz), 8.11 (1H, d, J=2.7 Hz)

EXAMPLE 455

N-(2-{4-[3-methoxy-1-(4-methoxyphenyl)-1H-pyrazol-5-yl]phenoxy}ethyl)methanesulfonamide mp. 103–104° C.
IR (KBr): 3271, 1612, 1579, 1560, 1520, 1514 cm−1
Mass (ESI+): 418 (M+H)+

200 MHz 1H NMR (DMSO-d6, d): 2.94 (3H, s), 3.28–3.33 (2H, m), 3.76 (3H, s), 3.83 (3H, s), 3.98–4.05 (2H, m), 6.05 (1H, s), 6.88–6.96 (4H, m), 7.09–7.17 (4H, m), 7.27 (1H, s)

EXAMPLE 456

N-(2-{4-[3-methoxy-1-(4-methoxyphenyl)-1H-pyrazol-5-yl]phenoxy}ethyl)ethanesulfonamide white powder: mp. 117.8–118.0° C.

IR (KBr): 3269, 1612, 1552, 1520 cm−1

Mass (ESI+): 432 (M+H)+

200 MHz 1H NMR (DMSO-d6, d): 1.18 (3H, t, J=7.3 Hz), 3.04 (2H, q, J=7.3 Hz), 3.26–3.34 (2H, m), 3.75 (3H, s), 3.83 (3H, s), 3.96–4.03 (2H, m), 6.05 (1H, s), 6.91 (2H, d, J=8.9 Hz), 6.92 (2H, d, J=9.0 Hz), 7.09–7.17 (4H, m), 7.32 (1H, brs)

EXAMPLE 457

N-(2-{4-[3-ethoxy-1-(4-methoxyphenyl)-1H-pyrazol-5-yl]-phenoxy}ethyl)methanesulfonamide white powder: mp. 146–147° C.

IR (KBr): 3130, 1612, 1518 cm−1

Mass (ESI+): 432 (M+H)+

200 MHz 1H NMR (DMSO-d6, d): 1.33 (3H, t, J=7.0 Hz), 2.94 (3H, s), 3.27–3.36 (2H, m), 3.75 (3H, s), 3.98–4.05 (2H, m), 4.17 (2H, q, J=7.0 Hz), 6.03 (1H, s), 6.91 (2H, d, J=8.8 Hz), 6.92 (2H, d, J=9.0 Hz), 7.12 (2H, d, J=9.0 Hz), 7.14 (2H, d, J=8.8 Hz), 7.29 (1H, t, J=5.8 Hz)

EXAMPLE 458

N-(2-{4-[3-isobutoxy-1-(4-methoxyphenyl)-1H-pyrazol-5-yl]phenoxy}ethyl)methanesulfonamide white powder: mp. 164.3–165.2° C.

IR (KBr): 3140, 2952, 2933, 2870, 1614, 1518 cm−1

Mass (ESI+): 460 (M+H)+

200 MHz 1HNMR (DMSO-d6, d): 0.97 (6H, d, J=6.8 Hz), 2.03 (1H, m), 2.94 (3H, s), 3.27–3.36 (2H, m), 3.75 (3H, s), 3.90 (2H, d, J=6.6 Hz), 3.99–4.05 (2H, m), 6.05 (1H, s), 6.88–6.96 (4H, m), 7.12 (2H, d, J=9.0 Hz), 7.14 (2H, d, J=8.8 Hz), 7.28 (1H, t, J=5.8 Hz)

EXAMPLE 459

N-(2-{4-[3-(2-methoxyethoxy)-1-(4-methoxyphenyl)-1H-pyrazol-5-yl]phenoxy}ethyl)methanesulfonamide white powder: mp. 94.5–94.7° C.

IR (KBr): 3319, 2933, 2891, 1612, 1520 cm−1

Mass (ESI+): 462 (M+H)+

200 MHz 1HNMR (DMSO-d6, d): 2.94 (3H, s), 3.29–3.35 (2H, m), 3.30 (3H, s), 3.62–3.67 (2H, m), 3.75 (3H, s), 3.98–4.05 (2H, m), 4.22–4.27 (2H, m), 6.05 (1H, s), 6.89–6.95 (4H, m), 7.10–7.17 (4H, m), 7.28 (1H, s)

EXAMPLE 460

N-(2-{4-[3-(2-ethoxyethoxy)-1-(4-methoxyphenyl)-1H-pyrazol-5-yl]phenoxy}ethyl)methanesulfonamide white powder: mp. 116.3–116.4° C.

IR (KBr): 3141, 2873, 1612, 1518 cm−1

Mass (ESI+): 476 (M+H)+

200 MHz 1H NMR (DMSO-d6, d): 1.13 (3H, t, J=7.0 Hz), 2.94 (3H, s), 3.28–3.40 (2H, m), 3.49 (2H, q, J=7.0 Hz), 3.66–3.71 (2H, m), 3.75 (3H, s), 3.98–4.05 (2H, m), 4.21–4.26 (2H, m), 6.06 (1H, s), 6.89–6.95 (4H, m), 7.09–7.17 (4H, m), 7.29 (1H, brs)

EXAMPLE 461

N-(2-{4-[3-methoxy-1-(6-methoxy-3-pyridinyl)-1H-pyrazol-5-yl]phenoxy}ethyl)methanesulfonamide mp. 116–117.5° C.

IR (KBr) 3126, 1614, 1520, 1500 cm−1

MS (ESI+): m/z 419 (M+H)+

200 MHz 1H NMR (DMSO-d6, d): 2.94 (3H, s), 3.28–3.36 (2H, m), 3.85 (3H, s), 4.00–4.06 (2H, m), 6.11 (1H, s), 6.85 (1H, d, J=8.9 Hz), 6.94 (2H, d, J=8.8 Hz), 7.18 (2H, d, J=8.8 Hz), 7.29 (1H, s), 7.60 (1H, dd, J=2.6, 8.9 Hz), 8.00 (1H, d, J=2.6 Hz)

EXAMPLE 462

N-(2-{4-[3-ethoxy-1-(6-methoxy-3-pyridinyl)-1H-pyrazol-5-yl]phenoxy}ethyl)methanesulfonamide white powder: mp. 122.0–122.6° C.

IR (KBr): 3242, 1614, 1518, 1502 cm−1

MS (ESI+): m/z 433 (M+H)+

200 MHz 1H NMR (DMSO-d6, d): 1.33 (3H, t, J=7.0 Hz), 2.94 (3H, s), 3.29–3.35 (2H, m), 3.84 (3H, s), 4.00–4.06 (2H, m), 4.19 (2H, q, J=7.0 Hz), 6.10 (1H, s), 6.85 (1H, d, J=8.8 Hz), 6.94 (2H, d, J=8.7 Hz), 7.18 (2H, d, J=8.7 Hz), 7.29 (1H, brs), 7.59 (1H, dd, J=2.7, 8.8 Hz), 7.99 (1H, d, J=2.7 Hz)

EXAMPLE 463

N-(2-{4-[1-(4-methoxyphenyl)-4-methyl-3-(trifluoro-methyl)-1H-pyrazol-5-yl]phenoxy}ethyl)methane-sulfonamide MASS (ESI+): m/z=492.1 (M+Na).

1HNMR (400 MHz, CDCl3): 2.15 (3H, s), 3.03 (3H, s), 3.53–3.57 (2H, m), 3.79 (3H, s), 4.11 (2H, t, J=5.0 Hz), 4.78 (1H, t, J=6.0 Hz), 6.81 (2H, d, J=9.0 Hz), 6.86 (2H, d, J=8.8 Hz), 7.08 (2H, d, J=8.8 Hz), 7.13 (2H, d, J=9.0 Hz)

EXAMPLE 464

N-[2-(4-{3-(difluoromethyl)-1-[4-(methylthio)phenyl]1H-pyrazol-5-yl}phenoxy)ethyl]methane-sulfonamide mp: 122.7–122.8° C.

MASS (ESI+): m/z=476.1 (M+Na).

1HNMR (400 MHz, CDCl3): 2.49 (3H, s), 3.03 (3H, s), 3.55 (2H, dt, J=4.9, 6 Hz), 4.1 (2H, t, J=4.9 Hz), 4.8 (1H, t,

J=6 Hz), 6.66 (1H, s), 6.76 (1H, t, J=55 Hz), 6.83 (2H, d, J=8.8 Hz), 7.16 (2H, d, J=8.8 Hz), 7.22 (4H, s).

EXAMPLE 465

N-{4-[1-(6-methoxy-3-pyridinyl)-3-(trifluoromethyl)-1H-pyrazol-5-yl]benzyl}methanesulfonamide Crystal. mp: 125–126° C.
MASS (ESI+): 449.0 (M+Na).
1HNMR (400 MHz, CDCl3): 2.91 (3H, s), 3.94 (3H, s), 4.34 (2H, d, J=6.2 Hz), 4.74 (1H, t, J=6.2 Hz), 6.74 (1H, s), 6.77 (1H, d, J=8.8 Hz), 7.24 (2H, d, J=8.3 Hz), 7.35 (2H, d, J=8.3 Hz), 7.58 (1H, dd, J=2.7, 8.8 Hz), 8.03 (1H, d, J=2.7 Hz)

EXAMPLE 466

N-{4-[3-(difluoromethyl)-1-(6-methoxy-3-pyridinyl)-1H-pyrazol-5-yl]benzyl}methanesulfonamide mp: 125.7–126.1° C.
MASS (ESI+): m/z=431.0 (M+Na).
1HNMR (400 MHz, CDCl3): 2.92 (3H, s), 3.94 (3H, s), 4.33 (2H, d, J=6.1 Hz), 4.73 (1H, b.s), 6.74 (1H, s), 6.77 (1H, t, J=55 Hz), 7.24 (2H, d, J=8.8 Hz), 7.25 (1H, d, J=7.9 Hz), 7.34 (2H, d, J=7.9 Hz), 7.55 (1H, dd, J=2.3, 8.8 Hz), 8.03 (1H, d, J=2.3 Hz)

EXAMPLE 467

N-(2-{4-[3-cyclopropyl-1-(6-methoxy-3-pyridinyl)-1H-pyrazol-5-yl]phenoxy}ethyl)methanesulfonamide mp. 95–97° C.
MS (ESI+): m/z 429 (M+H)
1HNMR (200 MHz,): 0.70–0.78 (2H, m), 0.87–0.98 (2H, m), 1.87–1.99 (1H, m), 2.94 (3H, s), 3.20–3.52 (2H, m), 3.85 (3H, s), 3.99–4.05 (2H, m), 6.30 (1H, s), 6.85 (1H, d, J=8.8 Hz), 6.93 (2H, d, J=8.7 Hz), 7.15 (2H, d, J=8.7 Hz), 7.27 (1H, brs), 7.59 (1H, dd, J=2.7, 8.8 Hz), 8.00 (1H, d, J=2.7 Hz)

EXAMPLE 468

N-(2-{4-[1-(4-methoxyphenyl)-3-(l-piperidinylcarbonyl)-1H-pyrazol-5-yl]phenoxy}ethyl)methanesulfonamide mp. 149.1–150.3° C.
Mass (ESI+): 499 (M+H)
1HNMR (200 MHz, DMSOd6): 1.43–1.74 (6H, m), 2.94 (3H, s), 3.25–3.39 (2H, m), 3.52–3.70 (2H, m), 3.77–3.92 (2H, m), 3.78 (3H, s), 3.99–4.06 (2H, m), 6.78 (1H, s), 6.93 (2H, d, J=8.9 Hz), 6.98 (2H, d, J=8.9 Hz), 7.18 (2H, d, J=8.9 Hz), 7.23 (2H, d, J=8.9 Hz), 7.27 (1H, brs)

EXAMPLE 469

N-(2-{4-[1-(6-methoxy-3-pyridinyl)-3-(1-piperidinyl-carbonyl)-1H-pyrazol-5-yl]phenoxy}ethyl)methane-sulfonamide mp. 158.8–159.1° C.
Mass (ESI+): m/z 500 (M+H)
1HNMR (200 MHz, DMSOd6): 1.43–1.74 (6H, m), 2.94 (3H, s), 3.22–3.40 (2H, m), 3.52–3.69 (2H, m), 3.75–3.91 (2H, m), 3.87 (3H, s), 4.00–4.07 (2H, m), 6.82 (1H, s), 6.90 (1H, d, J=8.8 Hz), 6.96 (2H, d, J=8.8 Hz), 7.22 (2H, d, J=8.8 Hz), 7.28 (1H, brs), 7.68 (1H, dd, J=2.7, 8.8 Hz), 8.14 (1H, d, J=2.7 Hz)

EXAMPLE 470

N-ethyl-1-(4-methoxyphenyl)-N-methyl-5-(4-{2-[(methyl-sulfonyl)amino]ethoxy}phenyl)-1H-pyrazole-3-carboxamide mp. 106.0–106.3° C.
Mass (ESI+): m/z 473 (M+H)
1HNMR (200 MHz, DMSOd6): 1.08–1.22 (3H, m), 2.94 (3H, s), 2.97, 3.29 (3H, s), 3.28–3.35 (2H, m), 3.42–3.53, 3.67–3.79 (2H, m), 3.78 (3H, s), 3.99–4.06 (2H, m), 6.79, 6.81 (1H, s), 6.93 (2H, d, J=8.9 Hz), 6.98 (2H, d, J=9 Hz), 7.15–7.26 (4H, m), 7.28 (1H, brs)

EXAMPLE 471

N-ethyl-1-(6-methoxy-3-pyridinyl)-N-methyl-5-(4-{2-[(methylsulfonyl)amino]ethoxy}phenyl)-1H-pyrazole-3-carboxamide mp. 110–111° C.
Mass (ESI+): m/z 474 (M+H)
1HNMR (200 MHz, DMSOd6): 1.09–1.23 (3H, m), 2.94 (3H, s), 2.98, 3.28 (3H, s), 3.28–3.36 (2H, m), 3.42–3.55, 3.66–3.78 (2H, m), 3.87 (3H, s), 4.01–4.07 (2H, m), 6.83, 6.85 (1H, s), 6.90 (1H, d, J=9.0 Hz), 6.96 (2H, d, J=8.7 Hz), 7.22 (2H, d, J=8.7 Hz), 7.28 (1H, brs), 7.61–7.75 (1H, m), 8.14–8.16 (1H, m)

EXAMPLE 472

N-(2-{4-[3-isobutyryl-1-(6-methoxy-3-pyridinyl)-1H-pyrazol-5-yl]phenoxy}ethyl)methanesulfonamide mp. 155.6–155.8° C.
MS (ESI+): m/z 459 (M+H)
1HNMR (200 MHz, DMSOd6): 1.16 (6H, d, J=6.9 Hz), 2.94 (3H, s), 3.25–3.40 (2H, m), 3.68 (1H, m), 3.88 (3H, s), 4.01–4.07 (2H, m), 6.93 (1H, d, J=8.7 Hz), 6.96 (2H, d, J=8.7 Hz), 7.02 (1H, s), 7.23 (2H, d, J=8.7 Hz), 7.28 (1H, brs), 7.74 (1H, dd, J=2.7, 8.7 Hz), 8.18 (1H, d, J=2.7 Hz)

EXAMPLE 473

N-(2-{4-[3-(cyclopentyloxy)-1-(6-methoxy-3-pyridinyl)-1H-pyrazol-5-yl]phenoxy}ethyl)methane-sulfonamide oil
MS (ESI+): m/z 473 (M+H)
1HNMR (200 MHz, DMSOd6): 1.51–2.00 (8H, m), 2.94 (3H, s), 3.24–3.39 (2H, m), 3.84 (3H, s), 4–4.06 (2H, m), 4.98 (1H, m), 6.07 (1H, s), 6.84 (1H, d, J=8.8 Hz), 6.94 (2H, d, J=8.8 Hz), 7.18 (2H, d, J=8.8 Hz), 7.28 (1H, brs), 7.58 (1H, dd, J=2.7, 8.8 Hz), 7.99 (1H, d, J=2.7 Hz)

EXAMPLE 474

N-(2-{4-[1-(4-methoxyphenyl)-3-(2,2,2-trifluoroethoxy)-1H-pyrazol-5-yl]phenoxy}ethyl)methanesulfonamide mp. 131.3–131.4° C.

MS (ESI+): m/z 486 (M+H)

1HNMR (200 MHz, DMSOd6): 2.94 (3H, s), 3.25–3.39 (2H, m), 3.76 (3H, s), 3.99–4.05 (2H, m), 4.81 (1H, d, J=9.0 Hz), 4.90 (1H, d, J=9.0 Hz), 6.22 (1H, s), 6.90–6.98 (4H, m), 7.11–7.18 (4H, m), 7.28 (1H, brs)

EXAMPLE 475

N-(2-{4-[3-(2,2-difluoroethoxy)-1-(4-methoxyphenyl)-1H-pyrazol-5-yl]phenoxy}ethyl)methanesulfonamide mp. 145.0–145.1° C.

MS (ESI+): m/z 468 (M+H)

1HNMR (200 MHz, DMSOd6): 2.93 (3H, s), 3.28–3.34 (2H, m), 3.76 (3H, s), 3.99–4.05 (2H, m), 4.44 (2H, dt, J=3.5, 14.9 Hz), 6.15 (1H, s), 6.41 (1H, tt, J=3.5, 54.6 Hz), 6.92 (2H, d, J=9.0 Hz), 6.93 (2H, d, J=9.0 Hz), 7.11–7.18 (4H, m), 7.27 (1H, brs)

EXAMPLE 476

N-(2-{4-[1-(6-methoxy-3-pyridinyl)-3-(2,2,2-trifluoro-ethoxy)-1H-pyrazol-5-yl]phenoxy}ethyl)methane-sulfonamide oil MS (ESI+): m/z 487 (M+H)

1HNMR (200 MHz, DMSOd6): 2.94 (3H, s), 3.29–3.35 (2H, m), 3.85 (3H, s), 4.00–4.06 (2H, m), 4.83 (1H, d, J=9.0 Hz), 4.92 (1H, d, J=9.0 Hz), 6.28 (1H, s), 6.87 (1H, d, J=8.8 Hz), 6.95 (2H, d, J=8.8 Hz), 7.19 (2H, d, J=8.8 Hz), 7.28 (1H, brs), 7.61 (1H, dd, J=2.7, 8.9 Hz), 8.03 (1H, d, J=2.7 Hz)

EXAMPLE 477

N-(2-{4-[3-(2,2-difluoroethoxy)-1-(6-methoxy-3-pyridinyl)-1H-pyrazol-5-yl]phenoxy}ethyl)methanesulfonamide solid MS (ESI+): m/z 469 (M+H)

1HNMR (200 MHz, CDCl3): 3.03 (3H, s), 3.51–3.60 (2H, m), 3.92 (3H, s), 4.07–4.13 (2H, m), 4.46 (2H, dt, J=4.2, 13.4 Hz), 4.76 (1H, t, J=6 Hz), 5.95 (1H, s), 6.17 (1H, tt, J=4.2, 55.4 Hz), 6.72 (1H, d, J=8.8 Hz), 6.83 (2H, d, J=8.8 Hz), 7.15 (2H, d, J=8.8 Hz), 7.49 (1H, dd, J=2.8, 8.8 Hz), 8.01 (1H, d, J=2.8 Hz)

EXAMPLE 478

N-(2-{4-[3-chloro-1-(4-methoxyphenyl)-1H-pyrazol-5-yl]-phenoxy}ethyl)-2-hydroxyethanesulfonamide mp. 139.1–139.4° C.

MS (ESI+): m/z 452 (M+H)

1HNMR (200 MHz, DMSOd6): 3.18–3.35 (4H, m), 3.69–3.77 (2H, m), 3.78 (3H, s), 3.97–4.04 (2H, m), 4.90 (1H, t, J=5.6 Hz), 6.69 (1H, s), 6.90–7.01 (4H, m), 7.14–7.26 (5H, m)

EXAMPLE 479

N-(2-{4-[3-(difluoromethyl)-1-(6-methoxy-3-pyridinyl)-1H-pyrazol-5-yl]phenoxy}ethyl)methanesulfonamide oil Mass (ESI+): m/z 439 (M+H)

1HNMR (200 MHz, CDCl3): 3.03 (3H, s), 3.51–3.60 (2H, m), 3.94 (3H, s), 4.08–4.14 (2H, m), 4.75 (1H, t, J=5.6 Hz), 6.68 (1H, s), 6.75 (1H, d, J=8.9 Hz), 6.76 (1H, t, J=55 Hz), 6.85 (2H, d, J=8.8 Hz), 7.17 (2H, d, J=8.8 Hz), 7.53 (1H, dd, J=2.7, 8.9 Hz), 8.08 (1H, d, J=2.7 Hz)

EXAMPLE 480

N-{4-[1-(4-methoxyphenyl)-3-(1-piperidinylcarbonyl)-1H-pyrazol-5-yl]benzyl}methanesulfonamide mp. 179.3–179.6° C.

MS (ESI+): m/z 469 (M+H)

1HNMR (200 MHz, DMSOd6): 1.42–1.72 (6H, m), 2.85 (3H, s), 3.52–3.69 (2H, m), 3.75–3.92 (2H, m), 3.78 (3H, s), 4.15 (2H, s), 6.85 (1H, s), 6.98 (2H, d, J=9 Hz), 7.21–7.35 (6H, m), 7.58 (1H, brs)

EXAMPLE 481

N-ethyl-1-(4-methoxyphenyl)-N-methyl-5-(4-{[(methyl-sulfonyl)amino]methyl}phenyl)-1H-pyrazole-3-carboxamide mp. 149.8–150.8° C.

MS (ESI+): m/z 443 (M+H)

1HNMR (200 MHz, DMSOd6): 1.09–1.21 (3H, m), 2.86 (3H, s), 2.98, 3.29 (3H, s), 3.40–3.78 (2H, m), 3.78 (3H, s), 4.13–4.17 (2H, m), 6.86, 6.88 (1H, s), 6.98 (2H, d, J=9 Hz), 7.21–7.35 (6H, m), 7.58 (1H, brs)

EXAMPLE 482

N-{4-[3-isopropyl-1-(4-methoxyphenyl)-1H-pyrazol-5-yl]-benzyl}methanesulfonamide mp. 130.9–131.0° C.

MS (ESI+): m/z 400 (M+H)

1HNMR (200 MHz, DMSOd6): 1.27 (6H, d, J=6.9 Hz), 2.84 (3H, s), 2.96 (1H, m), 3.76 (3H, s), 4.14 (2H, s), 6.47 (1H, s), 6.93 (2H, d, J=8.9 Hz), 7.11–7.21 (4H, m), 7.30 (2H, d, J=8.2 Hz), 7.56 (1H, brs)

EXAMPLE 483

N-{4-[3-isobutyryl-1-(4-methoxyphenyl)-1H-pyrazol-5-yl]benzyl}methanesulfonamide mp. 155.8–155.9° C.

MS (ESI+): m/z 428 (M+H)

1HNMR (200 MHz,): 1.16 (6H, d, J=6.9 Hz), 2.86 (3H, s), 3.68 (1H, m), 3.79 (3H, s), 4.15 (2H, s), 7.00 (2H, d, J=8.9 Hz), 7.06 (1H, s), 7.22–7.35 (6H, m), 7.58 (1H, s)

EXAMPLE 484

N-{4-[1-(6-methoxy-3-pyridinyl)-3-(1-piperidinyl-carbonyl)-1H-pyrazol-5-yl]benzyl)methanesulfonamide mp. 182.6–182.9° C.
MS (ESI+): m/z 470 (M+H)
1HNMR (200 MHz, DMSOd6): 1.42–1.72 (6H, m), 2.86 (3H, s), 3.53–3.69 (2H, m), 3.75–3.9 (2H, m), 3.87 (3H, s), 4.16 (2H, s), 6.89 (1H, s), 6.90 (1H, d, J=8.8 Hz), 7.28 (2H, d, J=8.4 Hz), 7.36 (2H, d, J=8.4 Hz), 7.59 (1H, s), 7.70 (1H, dd, J=2.7, 8.8 Hz), 8.14 (1H, d, J=2.7 Hz)

EXAMPLE 485

N-ethyl-1-(6-methoxy-3-pyridinyl)-N-methyl-5-(4-{[(methylsulfonyl)amino]methyl}phenyl)-1H-pyrazole-3-carboxamide white powder
MS (ESI+): m/z 444 (M+H)
1HNMR (200 MHz, DMSOd6): 1.09–1.23 (3H, m), 2.86 (3H, s), 2.98, 3.29 (3H, s), 3.49, 3.72 (2H, q, J=7.1 Hz), 3.87 (3H, s), 4.16 (2H, s), 6.88–6.93 (2H, m), 7.28 (2H, d, J=8.3 Hz), 7.36 (2H, d, J=8.3 Hz), 7.56 (1H, brs), 7.65–7.74 (1H, m), 8.13–8.14 (1H, m)

EXAMPLE 486

N-{4-[3-isopropyl-1-(6-methoxy-3-pyridinyl)-1H-pyrazol-5-yl]benzyl}methanesulfonamide oil
MS (ESI+): m/z 401 (M+H)
1HNMR (200 MHz, CDCl3): 1.34 (6H, d, J=6.9 Hz), 2.86 (3H, s), 3.03 (1H, m), 3.90 (3H, s), 4.28 (2H, d, J=6.1 Hz), 5.19 (1H, t, J=6.1 Hz), 6.34 (1H, s), 6.72 (1H, d, J=8.8 Hz), 7.21 (2H, d, J=8.2 Hz), 7.29 (2H, d, J=8.2 Hz), 7.56 (1H, dd, J=2.7, 8.8 Hz), 7.98 (1H, d, J=2.7 Hz)

EXAMPLE 487

N-{4-[3-isobutyryl-1-(6-methoxy-3-pyridinyl)-1H-pyrazol-5-yl]benzyl}methanesulfonamide mp. 160.8–161.2° C.
MS (ESI+): m/z 429 (M+H)
1HNMR (200 MHz, DMSOd6): 1.16 (6H, d, J=6.8 Hz), 2.86 (3H, s), 3.68 (1H, m), 3.88 (3H, s), 4.16 (2H, d, J=5.5 Hz), 6.93 (1H, d, J=8.8 Hz), 7.09 (1H, s), 7.29 (2H, d, J=8.3 Hz), 7.36 (2H, d, J=8.3 Hz), 7.59 (1H, t, J=5.5 Hz), 7.76 (1H, dd, J=2.8, 8.8 Hz), 8.18 (1H, d, J=2.7 Hz)

EXAMPLE 488

N-{4-[3-methoxy-1-(4-methoxyphenyl)-1H-pyrazol-5-yl]benzyl}methanesulfonamide mp. 94.0–94.3° C.
MS (ESI+): m/z 388 (M+H)
1HNMR (200 MHz, DMSOd6): 2.85 (3H, s), 3.76 (3H, s), 3.84 (3H, s), 4.14 (2H, s), 6.12 (1H, s), 6.92 (2H, d, J=8.9 Hz), 7.14 (2H, d, J=8.9 Hz), 7.20 (2H, d, J=8.2 Hz), 7.30 (2H, d, J=8.2 Hz), 7.57 (1H, s)

EXAMPLE 489

N-{4-[3-isopropoxy-1-(4-methoxyphenyl)-1H-pyrazol-5-yl]benzyl}methanesulfonamide amorphous
MS (ESI+): m/z 416 (M+H)
1HNMR (200 MHz, DMSOd6): 1.32 (6H, d, J=6.1 Hz), 2.85 (3H, s), 3.75 (3H, s), 4.14 (2H, s), 4.77 (1H, m), 6.07 (1H, s), 6.91 (2H, d, J=8.9 Hz), 7.13 (2H, d, J=8.9 Hz), 7.19 (2H, d, J=8.2 Hz), 7.30 (2H, d, J=8.2 Hz), 7.57 (1H, brs)

EXAMPLE 490

N-{4-[1-(6-methoxy-3-pyridinyl)-3-(2,2,2-trifluoro-ethoxy)-1H-pyrazol-5-yl]benzyl}methanesulfonamide mp. 130–131° C.
Mass (ESI+): 457 (M+H)
1HNMR (200 MHz, CDCl3): 2.92 (3H, s), 3.93 (3H, s), 4.33 (2H, d, J=6.0 Hz), 4.54–4.71 (1H, m), 4.62 (1H, d, J=8.4 Hz), 4.70 (1H, d, J=8.4 Hz), 6.04 (1H, s), 6.73 (1H, d, J=8.8 Hz), 7.22 (2H, d, J=8.3 Hz), 7.33 (2H, d, J=8.3 Hz), 7.52 (1H, dd, J=2.7, 8.8 Hz), 7.95 (1H, d, J=2.7 Hz)

EXAMPLE 491

N-{4-[3-chloro-1-(4-methoxyphenyl)-1H-pyrazol-5-yl]benzyl}methanesulfonamide mp. 68.3–69.3° C.
Mass (ESI+): 392 (M+H)
1HNMR (200 MHz, DMSOd6): 2.85 (3H, s), 3.77 (3H, s), 4.14 (2H, s), 6.76 (1H, s), 6.96 (2H, d, J=8.9 Hz), 7.17–7.24 (4H, m), 7.32 (2H, d, J=8.2 Hz), 7.58 (1H, s)

EXAMPLE 492

N-{4-[3-chloro-1-(6-methoxy-3-pyridinyl)-1H-pyrazol-5-yl]benzyl}methanesulfonamide oil
Mass (ESI+): 393 (M+H)
1HNMR (200 MHz, DMSOd6): 2.86 (3H, s), 3.86 (3H, s), 4.16 (2H, s), 6.82 (1H, s), 6.89 (1H, d, J=8.8 Hz), 7.26 (2H, d, J=8.3 Hz), 7.35 (2H, d, J=8.3 Hz), 7.59 (1H, brs), 7.69 (1H, dd, J=2.7, 8.8 Hz), 8.1 (1H, d, J=2.7 Hz)

EXAMPLE 493

N-(2-{4-[1-(4-methoxyphenyl)-3-(methylthio)-1H-pyrazol-5-yl]phenoxy}ethyl)methanesulfonamide mp. 165.0–166.0° C.
MS (ESI+): m/z 434 (M+H)
1HNMR (200 MHz, DMSOd6): 2.51 (3H, s), 2.94 (3H, s), 3.27–3.36 (2H, m), 3.77 (3H, s), 3.99–4.05 (2H, m), 6.56 (1H, s), 6.92 (2H, d, J=8.8 Hz), 6.95 (2H, d, J=8.9 Hz), 7.15 (2H, d, J=8.8 Hz), 7.17 (2H, d, J=8.9 Hz), 7.27 (1H, t, J=5.8 Hz)

EXAMPLE 494

N-(2-{4-[1-(6-methoxy-3-pyridinyl)-3-(trifluoromethyl)-1H-pyrazol-5-yl]phenyl}ethyl)benzenesulfonamide amorphous powder
Mass (ESI+): 503 (M+H)+
200 MHz 1HNMR (DMSO-d6, d): 2.64–2.72 (2H, m), 2.91–3.02 (2H, m), 3.88 (3H, s), 6.91 (1H, d, J=9.0 Hz), 7.03–7.21 (5H, m), 7.56–7.80 (7H, m), 8.18 (1H, d, J=2.6 Hz)

EXAMPLE 495

N-methoxy-1-(4-methoxyphenyl)-N-methyl-5-(4-{2-[(methylsulfonyl)amino]ethyl}phenyl)-1H-pyrazole-3-carboxamide oil
Mass (ESI+): m/z 459 (M+H)
1HNMR (200 MHz, CDCl3): 2.84–2.91 (2H, m), 2.87 (3H, s), 3.35–3.46 (2H, m), 3.51 (3H, s), 3.83 (3H, s), 3.85 (3H, s), 4.26 (1H, t, J=6.2 Hz), 6.86 (2H, d, J=9.0 Hz), 6.97 (1H, s), 7.12–7.29 (6H, m)

EXAMPLE 496

N-methoxy-1-(6-methoxy-3-pyridinyl)-N-methyl-5-(4-{2-[(methylsulfonyl)amino]ethyl}phenyl)-1H-pyrazole-3-carboxamide oil
Mass (ESI+): m/z 460 (M+H)
1HNMR (200 MHz, CDCl3): 2.80 2.93 (2H, m), 2.88 (3H, s), 3.36–3.47 (2H, m), 3.50 (3H, s), 3.85 (3H, s), 3.94 (3H, s), 4.28 (1H, t, J=6.2 Hz), 6.75 (1H, d, J=8.8 Hz), 6.98 (1H, s), 7.20 (4H, s), 7.56 (1H, dd, J=2.7, 8.8 Hz), 8.10 (1H, d, J=2.7 Hz)

EXAMPLE 497

Trimethylsilyl isocyanate (73.8 vl) was added to a solution of (2-{4-[3-isopropenyl-1-(6-methoxy-3-pyridinyl)-1H-pyrazol-5-yl]phenoxy}ethyl)amine dihydrochloride (115.4 mg) and Et3N (114 μl) and the mixture was stirred at ambient temperature for 1.5 hours. The mixture was concentrated in vacuo and the residue was partitioned between AcOEt and 1M HCl. The aqueous layer was reextracted with AcOEt. The combined organic layers were washed with saturated aqueous sodium bicarbonate solution and saturated aqueous sodium chloride solution, dried over magnesium sulfate, and concentrated in vacuo. The residue was purified by preparative thin layer silica gel chromatography developed by 10% MeOH/CHCl3. The seaparated silica gel was extracted with 10% MeOH/CHCl3 and the solvent was evaporated in vacuo.

The residue was crystallized from AcOEt-IPE to give N-(2-{4-[3-isopropenyl-1-(6-methoxy-3-pyridinyl)-1H-pyrazol-5-yl]phenoxy}ethyl)urea (40.1 mg) as a white powder.

white powder: mp. 94–98° C.
IR (KBr): 3435, 3388, 3344, 3333, 1657, 1631, 1610, 1577, 1572, 1562, 1552, 1502 cm−1
1H NMR (DMSO-d6) δ 2.10 (3H, s), 3.28–3.27 (2H, m), 3.86 (3H, s), 3.91–3.97 (2H, m), 5.15 (1H, brs), 5.53 (2H, s), 5.62 (1H, brs), 6.16 (1H, t, J=5.5 Hz), 6.84 (1H, s), 6.88 (1H, d, J=8.8 Hz), 6.95 (2H, d, J=8.8 Hz), 7.19 (2H, d, J=8.8 Hz), 7.64 (1H, dd, J=2.7, 8.8 Hz), 8.07 (1H, d, J=2.7 Hz)

The following compound(s) was (were) obtained in a similar manner to that of Example 497.

EXAMPLE 498

N-(2-{4-[3-methoxy-1-(4-methoxyphenyl)-1H-pyrazol-5-yl]phenoxy}ethyl)urea mp. 108–111° C.
IR (KBr): 3388, 3342, 1657, 1631, 1612, 1593, 1577, 1562, 1522 cm−1
Mass (ESI+): 383 (M+H)+
200 MHz 1H NMR (CDCl3, d): 3.54–3.62 (2H, m), 3.79 (3H, s), 3.96 (3H, s), 3.98–4.04 (2H, m), 4.44 (2H, s), 5.03 (1H, t, J=5.5 Hz), 5.88 (1H, s), 6.78 (2H, d, J=8.8 Hz), 6.82 (2H, d, J=8.9 Hz), 7.12 (2H, d, J=8.8 Hz), 7.16 (2H, d, J=8.9 Hz)

EXAMPLE 499

N-(2-{4-[3-ethoxy-1-(4-methoxyphenyl)-1H-pyrazol-5-yl]phenoxy)ethyl)urea white powder: mp. 154.2–154.4° C.
IR (KBr): 3398, 3332, 1658, 1631, 1612, 1566, 1518 cm−1
Mass (ESI+): 397 (M+H)+
200 MHz 1H NMR (DMSO-d6, d): 1.33 (3H, t, J=7.0 Hz), 3.27–3.34 (2H, m), 3.75 (3H, s), 3.89–3.96 (2H, m), 4.17 (2H, q, J=7.0 Hz), 5.53 (2H, s), 6.03 (1H, s), 6.15 (1H, t, J=5.6 Hz), 6.90 (2H, d, J=8.9 Hz), 6.92 (2H, d, J=9.0 Hz), 7.10–7.15 (4H, m)

EXAMPLE 500

Imidazole (680 mg) and t-butyldimethylsilyl chloride (903 mg) was added successively to a solution of ethyl 5-[4-{2-(hydroxy)ethoxy}phenyl]-1-(4-methoxyphenyl)-1H-pyrazole-3-carboxylate (1.91 g) in DMF (15 ml) under cooling in an ice bath. After stirring at ambient temperature for 2 hours, the mixture was partitioned between AcOEt and H2O. The oreganic layer was washed with H2O, saturated aqueous sodium chloride solution, dried over MgSO4, concentrated in vacuo. The residual crystals were collected and washed with n-hexane to give ethyl 5-[4-(2-{[tert-butyl(dimethyl)silyl]oxy}ethoxy)-phenyl]-1-(4-methoxyphenyl)-1H-pyrazole-3-carboxylate (2.34 g).

powder
mp. 86–87° C.
MS (ESI+): m/z 497 (M+H)
1HNMR (CDCl3) δ 0.09 (6H, s), 0.90 (9H, s), 1.42 (3H, t, J=7.1 Hz), 3.82 (3H, s), 3.94–3.97 (2H, m), 4.01–4.04 (2H, m), 4.44 (2H, q, J=7.1 Hz), 6.83 (2H, d, J=8.7 Hz), 6.85 (2H, d, J=8.9 Hz), 6.96 (1H, s), 7.11 (2H, d, J=8.7 Hz), 7.24 (2H, d, J=8.9 Hz)

EXAMPLE 501

A solution of ethyl 5-[4-(2-{[tert-butyl(dimethyl)silyl]oxy}ethoxy)phenyl]-1-(4-methoxyphenyl)-1H-pyrazole-3-carboxylate (0.3 g) in THF (3 ml) was added dropwise to a 1M solution of methylmagnesium bromide (3 ml) at ambient temperature. The reaction mixture was stirred at ambient temperature for 1 hour, then was poured into a mixture of crushed ice and saturated aqueous ammonium chloride solution. The mixture was extracted with AcOEt. The oreganic layer was washed with saturated aqueous sodium bicarbonate solution and saturated aqueous sodium chloride solution, dried over magnesium sulfate, and concentrated in vacuo to give 2-[5-[4-(2-{[tert-butyl(dimethyl)silyl]oxy}-ethoxy)phenyl]-1-(4-methoxyphenyl)-1H-pyrazol-3-yl]-2-propanol (0.27 g) as an oil.

oil

MS (ESI+): m/z 483 (M+H)

1H NMR (CDCl3) δ 0.09 (6H, s), 0.90 (9H, s), 1.65 (6H, s), 3.81 (3H, s), 3.94–3.97 (2H, m), 4.01–4.04 (2H, m), 6.35 (1H, s), 6.82 (2H, d, J=8.8 Hz), 6.85 (2H, d, J=8.9 Hz), 7.12 (2H, d, J=8.8 Hz), 7.21 (2H, d, J=8.9 Hz)

The following compound(s) was (were) obtained in a similar manner to that of Example 501.

EXAMPLE 502

N-(2-{4-[3-(1-hydroxy-1-methylethyl)-1-(4-methoxy-phenyl)-1H-pyrazol-5-yl]phenoxy}ethyl)urea white powder: mp. 147–152° C.

IR (KBr): 3333, 3271, 2976, 1676, 1664, 1658, 1612, 1547, 1537, 1516, 1502 cm−1

MS (ESI+): m/z 411 (M+H)

1H NMR (DMSO-d6) δ 1.48 (6H, s), 3.22–3.40 (2H, m), 3.76 (3H, s), 3.90–3.96 (2H, m), 4.98 (1H, s), 5.52 (2H, s), 6.14 (1H, t, J=5.6 Hz), 6.49 (1H, s), 6.90 (2H, d, J=8.7 Hz), 6.94 (2H, d, J=8.8 Hz), 7.12 (2H, d, J=8.7 Hz), 7.15 (2H, d, J=8.8 Hz)

EXAMPLE 503 tert-butyl {4-[3-(1-hydroxy-1-methylethyl)-1-(4-methoxyphenyl)-1H-pyrazol-5-yl]benzyl}carbamate powder MS (ESI+): m/z 438 (M+H)

1HNMR (200 MHz, DMSOd6): 1.39 (9H, s), 1.49 (6H, s), 3.76 (3H, s), 4.11 (2H, d, J=6.1 Hz), 5.01 (1H, s), 6.54 (1H, s), 6.94 (2H, d, J=8.9 Hz), 7.15 (2H, d, J=8.9 Hz), 7.17 (4H, brs), 7.4 (1H, t, J=6.1 Hz)

EXAMPLE 504 tert-butyl {4-[3-(1-hydroxy-1-methylethyl)-1-(6-methoxy-3-pyridinyl)-1H-pyrazol-5-yl]benzyl}-carbamate powder MS (ESI+): m/z 439 (M+H)

1HNMR (200 MHz, DMSOd6) 1.39 (9H, s), 1.49 (6H, s), 3.85 (3H, s), 4.12 (2H, d, J=6.1 Hz), 5.05 (1H, s), 6.59 (1H, s), 6.86 (1H, d, J=8.8 Hz), 7.20 (4H, s), 7.40 (1H, t, J=6.1 Hz), 7.62 (1H, dd, J=2.7, 8.8 Hz), 8.00 (1H, d, J=2.7 Hz)

EXAMPLE 505

A solution of 2-[5-[4-(2-{[tert-butyl(dimethyl)silyl]-oxy-ethoxy)phenyl]-1-(4-methoxyphenyl)-1H-pyrazol-3-yl]-2-propanol (180 mg) in DMF (2 mg) was added dropwise to a suspension of sodium hydride 60% dispersion in mineral oil (17 mg) in DMF (1 ml) under cooling in an ice bath. After 10 minutes, iodemethane (63.5 mg) was added and the reaction mixture was stirred at same temperature for 1 hour and at ambient temperature for 1 hour. Additional iodomethane was added until all starting material was consumed. The reaction was quenched by adding saturated ammonium chloride. The mixture was extracted with ethyl acetate. The organic layer was washed with H2O and saturated aqueous sodium chloride solution, dried over magnesium sulfate, and concentrated in vacuo. The residue was purified by silica gel column chromatography eluted with AcOEt/n-hexane, which polarity was gradually changed from 20% to 80%, to give 5-[4-(2-{[tert-butyl (dimethyl)silyl]oxy}ethoxy)phenyl]-3-(1-methoxy-1-methylethyl)-1-(4-methoxyphenyl)-1H-pyrazole (32.2 mg) as an oil.

Mass (ESI+): 497 (M+H)

1H NMR (CDCl3) δ 0.09 (6H, s), 0.90 (9H, s), 1.58 (3H, s), 1.63 (3H, s), 3.22 (3H, s), 3.81 (3H, s), 3.93–4.04 (4H, m), 6.42 (1H, s), 6.82 (2H, d, J=8.8 Hz), 6.84 (2H, d, J=9.0 Hz), 7.13 (2H, d, J=8.8 Hz), 7.22 (2H, d, J=9.0 Hz)

EXAMPLE 506

A 1M solution of tetra-n-butylammonium fluoride in THF (0.24 mg) was added to a solution of 5-[4-(2-{ [tert-butyl-(dimethyl)silyl]oxy}ethoxy)phenyl]-3-(1-methoxy-1-methylethyl)-1-(4-methoxyphenyl)-1H-pyrazole (98 mg) in THF (2 ml) under ice bath cooling. The reaction mixture was stirred at same temperature for 1 hour. The mixture was partitioned between ethyl acetate and H2O. The organic layer was washed with saturated aqueous sodium chloride solution, dried over magnesium sulfate, and concentrated in vacuo. The residue was purified by preparative thin layer silica gel chromatography developed by 50% AcOEt/n-hexane. The seaparated silica gel was extracted with 10% MeOH/CHCl3 and the solvent was evaporated in vacuo to give 2-{4-[3-(1-methoxy-1-methylethyl)-1-(4-methoxyphenyl)-1H-pyrazol-5-yl]phenoxy}ethanol (66 mg) as an oil.

IR (neat): 3423, 3398, 3371, 2976, 2935, 1647, 1612, 1566, 1549, 1512 cm−1

MS (ESI+): m/z 383 (M+H)

1H NMR (CDCl3) δ 1.60 (3H, s), 1.63 (3H, s), 2.03 (1H, t, J=6.1 Hz), 3.22 (3H, s), 3.81 (3H, s), 3.91–4.00 (2H, m), 4.05–4.10 (2H, m), 6.43 (1H, s), 6.83 (2H, d, J=8.9 Hz), 6.84 (2H, d, J=8.9 Hz), 7.15 (2H, d, J=8.9 Hz), 7.21 (2H, d, J=8.9 Hz)

EXAMPLE 507

A 4M solution of HCl in dioxane (2 ml) was added to a solution of ethyl 5-(4-{2-[(tert-butoxycarbonyl)amino] ethoxy}-phenyl)-1-(4- methoxyphenyl)-1H-pyrazole-3-carboxylate (300 mg) in CH2Cl2 (3 ml) under cooling in an ice bath. After stirring at ambient temperature for 1 hour, the reaction mixture was concentrated in vacuo. The residue was dissolved in CH2Cl2 (3 ml), Et3N (189 mg) and trimethylsilyl isocyanate (108 mg) were added, and the mixture was stirred at ambient temperature overnight. The stirring was continued for more 4 hours, adding more trimethylsilyl isocyanate and Et3N to consume all starting material. The mixture was concentrated in vacuo and the residue was partitioned between ethyl acetate and 1M HCl. The organic layer was washed with saturated aqueous sodium bicarbonate solution and saturated aqueous sodium chloride solution, dried over magnesium sulfate, and concentrated in vacuo. The residual crystals were suspended in hot ethyl acetate, cooled with stirring, collected and washed with ethyl acetate to give ethyl 5-(4-{2-[(aminocarbonyl)amino] ethoxy}phenyl)-1-(4-methoxyphenyl)-1H-pyrazole-3-carboxylate (217 mg) as a white powder.

MS (ESI+): m/z 425 (M+H)

1H NMR (DMSO-d6) δ 1.31 (3H, t, J=7.1 Hz), 3.27–3.36 (2H, m), 3.79 (3H, s), 3.90–3.96 (2H, m), 4.32 (2H, q, J=7.1 Hz), 5.52 (2H, s), 6.14 (1H, t, J=5.7 Hz), 6.92 (2H, d, J=8.8 Hz), 6.99 (2H, d, J=8.8 Hz), 7.01 (1H, s), 7.17 (2H, d, J=8.8 Hz), 7.25 (2H, d, J=8.8 Hz)

EXAMPLE 508

1M NaOH (5 ml) was added to a solution of ethyl 5-(4-{2-[(aminocarbonyl)amino]ethoxy}phenyl)-1-(4-methoxyphenyl)-1H-pyrazole-3-carboxylate (1.75 g) in THF (15 ml) and MeOH (10 ml). The reaction mixture was stirred at ambient temperature and concentrated in vacuo. The residue was dissolved in H2O and acidified by 1M HCl. white precipitates were collected and washed successively with H2O and IPE to give 5-(4–12-[(aminocarbonyl)amino]-ethoxy}phenyl)-1-(4-methoxyphenyl)-1H-pyrazole-3-carboxylic acid (1.58 g) as a white powder.

MS (ESI+): m/z 397 (M+H)

1H NMR (DMSO-d6) 6 3.15–3.55 (2H, m), 3.90–3.97 (2H, m), 5.52 (2H, s), 6.14 (1H, t, J=5.7 Hz), 6.89–7.03 (5H, m), 7.17 (2H, d, J=8.8 Hz), 7.24 (2H, d, J=8.9 Hz)

The following compound(s) was (were) obtained in a similar manner to that of Example 508.

EXAMPLE 509

5-(4-{[(tert-butoxycarbonyl)amino]methyl}phenyl)-1-(4-methoxyphenyl)-1H-pyrazole-3-carboxylic acid white powder MS (ESI+): m/z 424 (M+H)

1HNMR (200 MHz, DMSOd6): 1.38 (9H, s), 3.79 (3H, s), 4.11 (2H, d, J=6.1 Hz), 6.99 (2H, d, J=8.9 Hz), 7.01 (1H, s), 7.20 (4H, brs), 7.25 (2H, d, J=8.9 Hz), 7.41 (1H, t, J=6.1 Hz), 12.92 (1H, brs)

EXAMPLE 510

5-(4-{[(tert-butoxycarbonyl)amino]methyl}phenyl)-1-(6-methoxy-3-pyridinyl)-1H-pyrazole-3-carboxylic acid powder MS (ESI+): m/z 425 (M+H)

1HNMR (200 MHz, CDCl3): 1.46 (9H, s), 3.95 (3H, s), 4.33 (2H, d, J=5.9 Hz), 4.9 (1H, brs), 6.76 (1H, d, J=8.8 Hz), 7.07 (1H, s), 7.19 (2H, d, J=8.4 Hz), 7.27 (2H, d, J=8.4 Hz), 7.58 (1H, dd, J=2.7,8.8 Hz), 8.11 (1H, d, J=2.7 Hz)

EXAMPLE 511

A mixture of 5-(4-{2-[(aminocarbonyl)amino]ethoxy}-phenyl)-1-(4-methoxyphenyl)-1H-pyrazole-3-carboxylic acid (1.56 g), diphenylphosphoryl azide (1.62 g), and Et3N (597 mg) in t-butanol (5 ml) was refluxed for 3 hours. The mixture was concentrated in vacuo, and the residue was partitioned between ethyl acetate and H2O. The combined organic layer was washed twice with 1M HCl. and washed with saturated aqueous sodium bicarbonate solution and saturated aqueous sodium chloride solution, dried over magnesium sulfate, and concentrated in vacuo. The residue was purified by silica gel column chromatography eluted-with ethyl acetate to give tert-butyl [5-(4-{2-[(aminocarbonyl)amino]-ethoxy}phenyl)-1-(4-methoxyphenyl)-1H-pyrazol-3-yl]carbamate (519 mg) as an amorphous powder.

MS (ESI+): m/z 468 (M+H)

1H NMR (DMSO-d6) δ 1.46 (9H, s), 3.27–3.36 (2H, m), 3.76 (3H, s), 3.90–3.96 (2H, m), 5.52 (2H, s), 6.15 (1H, t, J=5.6 Hz), 6.55 (1H, s), 6.90 (2H, d, J=8.9 Hz), 6.93 (2H, d, J=8.9 Hz), 7.13 (4H, d, J=8.9 Hz), 9.74 (1H, s)

EXAMPLE 512

A 4M solution of HCl in dioxane (3 ml) was added to a solution of tert-butyl [5-(4-{2-[(aminocarbonyl)amino]ethoxy}-phenyl)-1-(4-methoxyphenyl)-1H-pyrazol-3-yl]carbamate (478 mg) in CH2Cl2 (3 ml) The reaction mixture was stirred at ambient temperature for 5 hours and concentrated in vacuo. The residue was partitioned between CDCl3 and saturated aqueous sodium bicarbonate solution. The aq layer was reextrated with CHCl3. The combined organic layer was dried over magnesium sulfate, and concentrated in vacuo. The residue was purified by silica gel column chromatography eluted with CHCl3:MeOH:28% aqueous NH4OH=10:1:0.1 to give N-(2-{4-[3-amino-1-(4-methoxyphenyl)-1H-pyrazol-5-yl]phenoxy}ethyl)urea (244.6 mg) as an amorphous powder.

MS (ESI+): m/z 368 (M+H)

IR (neat): 3400, 3388, 3342, 3330, 1658, 1651, 1643, 1612, 1579, 1562, 1554, 1520 cm−1

1H NMR (DMSO-d6) δ 3.27–3.37 (2H, m), 3.73 (3H, s), 3.89–3.95 (2H, m), 4.83 (2H, s), 5.52 (2H, s), 5.73 (1H, s), 6.15 (1H, t, J=5.5 Hz), 6.85–6.92 (4H, m), 7.03–7.12 (4H, m)

EXAMPLE 513

37% aqueous solution of formaldehyde (0.23 ml) and sodium cyanoborohydride (53 mg) were added to a solution of N-(2-{4-[3-amino-1-(4-methoxyphenyl)-1H-pyrazol-5-yl]-phenoxy}ethyl)urea (103.1 mg) in MeOH (2 ml). The reaction mixture was stirred at ambient temperature for 3 hours. 37% aqueous solution of formaldehyde (0.23 ml) and sodium cyanoborohydride (53 mg) were added to the mixture and the reaction mixture was stirred at ambient temperature for 4 days. The mixture was concentrated in vacuo, and the residue was partitioned between ethyl acetate and H2O. The organic layer was washed with saturated aqueous sodium chloride solution, dried over magnesium sulfate, and concentrated in vacuo. The residue was purified by preparative thin layer silica gel chromatography developed by CHCl3:MeOH:28% aqueous NH4OH=100:10:1. The separated silica gel was extracted with same solvent and the solvent was evaporated in vacuo to give N-(2-{4-[3-(dimethylamino)-1-(4-methoxyphenyl)-1-H-pyrazol-5-yl]phenoxy}ethyl)urea (59.9 mg) as an amorphous powder.

MS (ESI+): m/z 396 (M+H)

1H NMR (DMSO-d6) δ 2.81 (6H, s), 3.27–3.36 (2H, m), 3.74 (3H, s), 3.89–3.96 (2H, m), 5.52 (2H, s), 5.78 (1H, s), 6.15 (1H, t, J=5.7 Hz), 6.87–6.92 (4H, m), 7.05–7.15 (4H, m)

EXAMPLE 514

To a solution of 4-[3-(dimethylamino)-1-(4-methoxyphenyl)-1-H-pyrazol-5-yl]phenol (98.7 mg) in DMF (2 ml) was added sodium hydride 60% dispersion in mineral oil (15.3 mg). The mixture was stirred at ambient temperature for 1 hour. To the reaction mixture was added (2-bromoethoxy)-tert-butyldimethylsilane (153 mg) in DMF (1 ml) dropwise and the mixture was stirred at ambient temperature overnight. The mixture was poured into ice water, extracted with AcOEt, washed with H2O and saturated aqueous sodium chloride solution. The aqueous layer was reextracted with AcOEt. The combined organic layers were dried over magnesium sulfate, and concentrated in vacuo. The residue was dissolved in EtOH (2 ml). To this solution was added concentrated hydrochloric acid (100 μl) and the mixture was stirred at ambient temperature for 3 hours. The mixture was concentrated invacuo, and the residue was partitioned between AcOEt and saturated aqueous sodium bicarbonate solution, washed with saturated aqueous sodium chloride solution, dried over magnesium sulfate, and concentrated in vacuo. The residue was purified by preparative thin layer silica gel chromatography developed by AcOEt/n-hexane=60%. The residual crystals were collected and washed with IPE to give 2-{4-[3-(dimethylamino)-1-(4-methoxyphenyl)-1-H-pyrazol-5-yl]phenoxy}ethanol (97 mg) as a white powder.

mp. 120–122° C.

IR (KBr): 3292, 2924, 1612, 1577, 1562, 1531, 1514 cm−1

Mass (ESI+): 354 (M+H)+

200 MHz 1H NMR (DMSO-d6, d): 2.81 (6H, s), 3.66–3.72 (2H, m), 3.74 (3H, s), 3.94–4.00 (2H, m), 4.86 (1H, br), 6.02 (1H, s), 6.86–6.94 (4H, m), 7.10 (2H, d, J=8.9 Hz), 7.12 (2H, d, J=8.7 Hz)

The following compound(s) was(were) obtained in a similar manner to that of Example 514.

EXAMPLE 515

N-[5-[4-(2-hydroxyethoxy)phenyl]-1-(4-methoxyphenyl)-1-H-pyrazol-3-yl]-N, N',N'-trimethylurea oil IR (neat): 3410, 2931, 1658, 1649, 1641, 1631, 1612, 1518, 1502 cm−1

Mass (ESI+): 411 (M+H)+

200 MHz 1H NMR (CDCl3, d): 2.08 (1H, t, J=5.9 Hz), 2.89 (6H, s), 3.33 (3H, s), 3.81 (3H, s), 3.92–4.00 (2H,m), 4.05–4.10 (2H, m), 6.15 (1H, s), 6.84 (4H, d, J=9.1 Hz), 7.14 (2H, d, J=9.1 Hz), 7.19 (2H, d, J=9.1 Hz)

EXAMPLE 516

2-{4-[3-ethoxy-1-(4-methoxyphenyl)-1H-pyrazol-5-yl]-phenoxy}ethanol white powder: mp. 67.7–69.2° C.

IR (ATR): 3363, 2993, 2956, 2925, 2837, 1610, 1577, 1552, 1508 cm−1

Mass (ESI+): 355 (M+H)+

200 MHz 1H NMR (CDCl3, d): 1.42 (3H, t, J=7.1 Hz), 2.01 (1H, t, J=6.0 Hz), 3.79 (3H, s), 3.92–4.00 (2H, m), 4.04–4.10 (2H, m), 4.29 (2H, q, J=7.1 Hz), 5.87 (1H, s), 6.77–6.85 (4H, m), 7.14 (2H, d, J=8.8 Hz), 7.17 (2H, d, J=8.9 Hz)

EXAMPLE 517

2-{4-[3-isobutoxy-1-(4-methoxyphenyl)-1H-pyrazol-5-yl]-phenoxy}ethanol oil

Mass (ESI+): m/z 383 (M+H)+

200 MHz 1H NMR (CDCl3, d): 1.03 (6H, d, J=6.8 Hz), 2.02 (1H, t, J=6.1 Hz), 2.11 (1H, m), 3.79 (3H, s), 3.91–4.09 (4H, m), 3.99 (2H, d, J=6.8 Hz), 5.88 (1H, s), 6.77–6.86 (4H, m), 7.09–7.21 (4H, m)

EXAMPLE 518

2-{4-[3-(2-methoxyethoxy)-1-(4-methoxyphenyl)-1H-pyrazol-5-yl]phenoxy}ethanol oil Mass (ESI+): 385 (M+H)+

IR (neat): 3400, 3390, 3369, 2935, 1612, 1517 cm−1

200 MHz 1H NMR (DMSO-d6, d): 3.31 (3H, s), 3.62–3.73 (4H, m), 3.75 (3H, s), 3.94–3.99 (2H, m), 4.22–4.27 (2H, m), 4.85 (1H, t, J=5.5 Hz), 6.04 (1H, s), 6.89 (2H, d, J=8.8 Hz), 6.92 (2H, d, J=8.9 Hz), 7.08–7.15 (4H, m)

EXAMPLE 519

2-{4-[3-(2-ethoxyethoxy)-1-(4-methoxyphenyl)-1H-pyrazol-5-yl]phenoxy}ethanol oil IR(neat): 2972, 2933, 2873, 1612, 1554, 1518, 1510 cm−1

Mass (ESI+): 399 (M+H)+

200 MHz 1H NMR (CDCl3, d): 1.25 (3H, t, J=7.0 Hz), 2.04 (1H, t, J=6.1 Hz), 3.61 (2H, q, J=7.0 Hz), 3.78–3.83 (2H, m), 3.79 (3H, s), 3.93–4.00 (2H, m), 4.04–4.07 (2H, m), 4.38–4.44 (2H, m), 5. 92 (1H, s), 6.82 (4H, d, J=8.8 Hz), 7.13 (2H, d, J=8.8 Hz), 7.16 (2H, d, J=8.8 Hz)

EXAMPLE 520

2-{[5-[4-(2-hydroxyethoxy)phenyl]-1-(4-methoxyphenyl)-1H-pyrazol-3-yl]oxy}-N,N-dimethylacetamide white powder: mp. 106.6–107.1° C.

IR (KBr): 3321, 2939, 1658, 1643, 1608, 1518 cm−1

MS (ESI+): m/z 412 (M+H)+

200 MHz 1H NMR (DMSO-d6, d): 2.84 (3H, s), 2.97 (3H, s), 3.65–3.73 (2H, m), 3.75 (3H, s), 3.94–4.00 (2H, m), 4.87 (1H, t, J=5.1 Hz), 4.87 (2H, s), 6.07 (1H, s), 6.90 (2H, d, J=8.8 Hz), 6.92 (2H, d, J=9.0 Hz), 7.11 (2H, d, J=9.0 Hz), 7.12 (2H, d, J=8.8 Hz)

EXAMPLE 521

2-{4-[3-methoxy-1-(6-methoxy-3-pyridinyl)-1H-pyrazol-5-yl]phenoxy}ethanol white power: mp. 92.2–92.5° C.

IR (KBr): 3325, 1614, 1525, 1504 cm−1

MS (ESI+): m/z 342 (M+H)+

200 MHz 1H NMR (CDCl3, d): 2.01 (1H, t, J=6.1 Hz), 3.92–4.10 (4H, m), 3.92 (3H, s), 3.97 (3H, s), 5.91 (1H, s), 6.70 (1H, d, J=8.5 Hz), 6.85 (2H, d, J=8.8 Hz), 7.15 (2H, d, J=8.8 Hz), 7.52 (1H, dd, J=2.5, 8.5 Hz), 8.04 (1H, d, J=2.5 Hz)

EXAMPLE 522

2-{4-[3-ethoxy-1-(6-methoxy-3-pyridinyl)-1H-pyrazol-5-yl]phenoxy}ethanol white power: mp. 81–82° C.

IR (KBr): 3303, 3298, 1612, 1516 cm−1

Mass (sample ID cox022145) (ESI+): 356 (M+H)+

200 MHz 1H NMR (DMSO-d6, d): 1.33 (3H, t, J=7.0 Hz), 3.65–3.74 (2H, m), 3.84 (3H, s), 3.95–4.01 (2H, m), 4.19 (2H, q, J=7.0 Hz), 4.87 (1H, t, J=5.4 Hz), 6.09 (1H, s), 6.85

(1H, d, J=8.8 Hz), 6.93 (2H, d, J=8.8 Hz), 7.16 (2H, d, J=8.8 Hz), 7.58 (1H, d, J=2.6, 8.8 Hz), 7.99 (1H, d, J=2.6 Hz)

EXAMPLE 523

To a solution of 5-(hydroxyl)phenyl-1-(4-methoxyphenyl)-4-methyl-3-(trifluoromethyl)-1H-pyrazole (5.0 g) and 2-bromoethoxy-tert-butyldimethylsilane (6.87 g) in DMF (100 ml) was added portionwise NaH (919 mg, 50% in oil) at room temperature. The reacion mixture was stirred overnight. The reaction mixture was quenched with water. Aqueouslayer was extracted twice with EtOAc. Combined organic layer was washed twice with water, and brine. Dried, filtered and evaporated under reduced pressure to give 5.29 g (73%) of 5-[4-(2-{[tert-butyl(dimethyl)silyl]oxy}-ethoxy)phenyl]-1-(4-methoxyphenyl)-4-methyl-3-(trifluoromethyl)-1-H-pyrazole.

MASS (ESI+): m/z =507.1 (M+1), 529.0 (M+Na).

1HNMR (400 MHz, CDCl3): 0.07 (3H, s), 0.09 (3H, s), 0.9 (9H, s), 2.15 (3H, s), 3.78 (3H, s), 3.62–4.13 (4H, m), 6.79 (2H, d, J=8.5 Hz), 6.88 (2H, d, J=8.7 Hz), 7.05 (2H, d, J=8.7 Hz), 7.13 (2H, d, J=8.5 Hz).

EXAMPLE 524

2-{4-[1-(4-methoxyphenyl)-3-(2,2,2-trifluoroethoxy)-1H-pyrazol-5-yl]phenoxy}ethanol mp 50.7–51.7° C.

Mass (ESI+): 409 (M+H)+

1HNMR (200 MHz, CDCl3): 1.99 (1H, t, J=6.0Hz), 3.80 (3H, s), 3.92–4.00 (2H, m), 4.05–4.10 (2H, m), 4.62 (1H, d, J=8.5 Hz), 4.70 (1H, d, J=8.5 Hz), 5.95 (1H, s), 6.79–6.92 (4H, m), 7.07–7.18 (4H, m)

EXAMPLE 525

2-{4-[3-(2,2-difluoroethoxy)-1-(4-methoxyphenyl)-1H-pyrazol-5-yl]phenoxy}ethanol oil Mass (ESI+): 391 (M+H)

1HNMR (200 MHz, CDCl3): 1.99 (1H, t, J=6.1 Hz), 3.80 (3H, s), 3.92–4.00 (2H, m), 4.05–4.09 (2H, m), 4.47 (2H, dt, J=4.2, 13.5 Hz), 5.92 (1H, s), 6.17 (1H, tt, J=4.2, 55.5 Hz), 6.79–6.87 (4H, m), 7.09–7.20 (4H, m)

EXAMPLE 526

2-{4-[1-(6-methoxy-3-pyridinyl)-3-(2,2,2-trifluoroethoxy)-1H-pyrazol-5-yl]phenoxy}ethanol mp. 91.2–91.3° C.

Mass (sample ID cox031168) (ESI+): 410 (M+H)+

1HNMR (200 MHz, CDCl3): 1.99 (1H, t, J=6.1 Hz), 3.91 (3H, s), 3.92–4.01 (2H, m), 4.06–4.11 (2H, m), 4.61 (1H, d, J=8.4 Hz), 4.70 (1H, d, J=8.4 Hz), 5.98 (1H, s), 6.71 (1H, d, J=8.8 Hz), 6.86 (2H, d, J=8.8 Hz), 7.14 (2H, d, J=8.8 Hz), 7.48 (1H, dd, J=2.7, 8.8 Hz), 8.02 (1H, d, J=2.7 Hz)

EXAMPLE 527

2-{4-[3-(2,2-difluoroethoxy)-1-(6-methoxy-3-pyridinyl)-1H-pyrazol-5-yl]phenoxy}ethanol oil Mass (ESI+): 392 (M+H)

1HNMR (200 MHz, CDCl3): 3.92 (3H, s), 3.93–4.00 (2H, m), 4.06–4.11 (2H, m), 4.46 (2H, dt, J=4.2, 13.2 Hz), 5.94 (1H, s), 6.17 (1H, tt, J=4.2, 55.5 Hz), 6.71 (1H, d, J=9.0 Hz), 6.86 (2H, d, J=8.9 Hz), 7.14 (2H, d, J=8.9 Hz), 7.48 (1H, dd, J=2.7, 9.0 Hz), 8.02 (1H, d, J=2.7 Hz)

EXAMPLE 528

Carbonyldiimidazole (1.26 g) was added to a solution of 5-[4-(benzyloxy)phenyl]-1-(4-methoxyphenyl)-3-amino-1H-pyrazole (2.4 g) in 1-methyl-2-pyrrolidinone (22 ml). After stirring at ambient temperature for 2 hour, 2M solution of dimethylamine in THF (7.4 ml) was added and the mixture was stirred ambient temperature for 2 hour. The reaction mixture was partitioned between ethyl acetate and H2O. The organic layer was washed with saturated aqueous sodium chloride solution, dried over magnesium sulfate, and concentrated in vacuo. The residue was purified by silica gel column chromatography eluted with AcOEt/n-hexane=80% to give N'-[5-[4-(benzyloxy)phenyl]-1-(4-methoxyphenyl)-1H-pyrazol-3-yl]-N,N-dimethylurea (2.35 g) as amorphous powder.

Mass (ESI+): 443 (M+H)+

200 MHz 1H NMR (DMSO-d6, d): 2.91 (6H, s), 3.76 (3H, s), 5.09 (2H, s), 6.63 (1H, s), 6.93 (2H, d, J=9.0 Hz), 6.98 (2H, d, J=9.0 Hz), 7.14 (2H, d, J=9.0 Hz), 7.15 (2H, d, J=9.0 Hz), 7.34–7.44 (5H, m), 9.02 (1H, s)

EXAMPLE 529

A mixture of N'-[5-[4-(hydroxy)phenyl]-1-(4-methoxyphenyl)-1H-pyrazol-3-yl]-N,N-dimethylurea (121.9 mg), 2-(tert-butyl-dimethylsilyloxy)ethyl bromide (166 mg), and K2CO3 (95.6 mg) in DMF (1.5 ml) was stirred at 75° C. for 7 hours. 2-(tert-butyldimethylsilyloxy)ethyl bromide (83 mg) and KI (57.4 mg) was added to the reaction mixture, and the mixture was stirred at 75° C. overnight. The mixture was allowed to cool to ambient temperature, and was partitioned between ethyl acetate and H2O. The aqueous layer was reextracted with ethyl acetate. The combined organic layer was washed with saturated aqueous sodium chloride solution, dried over magnesium sulfate, and concentrated in vacuo. The residue was purified by preparative thin layer silica gel chromatography developed by 5% MeOH/CHCl3. The separated silica gel was extracted with 10% MeOH/CHCl3 and the solvent was evaporated in vacuo to give N'-[5-[4-(2-hydroxyethoxy)phenyl]-1-(4-methoxyphenyl)-1H-pyrazol-3-yl]-N,N-dimethylurea (115 mg) as an amorphous powder. 84.3 mg of amorphous powder was crystallized from AcOEt-IPE to give N'-[5-[4-(2-hydroxyethoxy)phenyl]-1-(4-methoxyphenyl)-1H-pyrazol-3-yl]-N,N-dimethylurea (79.5 mg) as a white powder.

mp. 167.4–167.6° C.

IR (KBr): 3317, 1670, 1612, 1587, 1572, 1510 cm−1

Mass (ESI+): 397 (M+H)+

200 MHz 1H NMR (DMSO-d6, d): 2.91 (6H, s), 3.65–3.74 (2H, m), 3.76 (3H, s), 3.94–4.00 (2H, m), 4.87 (1H, t, J=5.5 Hz), 6.62 (1H, s), 6.90 (2H, d, J=8.7 Hz), 6.93 (2H, d, J=8.9 Hz), 7.12 (2H, d, J=8.7 Hz), 7.15 (2H, d, J=8.9 Hz), 9.02 (1H, s)

EXAMPLE 530

Diethylazodicarboxylate 308 mg was added to a solution of N'-[5-[4-(hydroxy)-phenyl]-1-(4-methoxyphenyl)-1H-pyrazol-3-yl]-N,N-dimethylurea 415 mg, tert-butyl N-(2-hydroxyethyl)carbamate 380 mg, and triphenylphosphine 463 mg in THF 5 ml. After stirring at ambient temperature for overnight, the reaction mixture was concentrated in vacuo. To a solution of the residue in CH2Cl2 5 ml, was added 4M aolution of HCl in dioxane 5 ml. After stirring at ambient temperature for 1.5 hours, the reaction mixture was concentrated in vacuo. The residue was partitioned between AcOEt and 1M HCl. The aqueous layer was reextracted with AcOEt and concentrated in vacuo. The remained H2O was evaporated azeotropically with toluene to give N'-[5-[4-(2-aminoethoxy)phenyl]-1-(4-methoxyphenyl)-1H-pyrazol-3-yl]-N,N-dimethylurea hydrochloride 580 mg as an amorphous powder.

Mass (ESI+): 396 (M+H)+

200 MHz 1H NMR (DMSO-d6, d): 2.91 (6H, s), 3.15–3.24 (2H, m), 3.76 (3H, s), 4.14–4.21 (2H, m), 6.64 (1H, s), 6.94 (2H, d, J=8.9 Hz), 6.95 (2H, d, J=8.7 Hz), 7.15 (2H, d, J=8.9 Hz), 7.17 (2H, d, J=8.7 Hz), 8.20 (2H, brs), 9.04 (1H, s)

The following compound(s) was(were) obtained in a similar manner to that of Example 530.

EXAMPLE 531

N-[5-[4-(2-aminoethoxy)phenyl]-1-(4-methoxyphenyl)-1H-pyrazol-3-yl]-N,N',N'-trimethylurea hydrochloride amorphous Mass (ESI+): 410 (M+H)+

200 MHz 1H NMR (DMSO-d6, d): 2.79 (6H, s), 3.13 (3H, s), 3.14–3.24 (2H, m), 3.80 (3H, s), 4.15–4.20 (2H, m), 6.27 (1H, s), 6.94 (2H, d, J=8.6 Hz), 6.94 (2H, d, J=8.9 Hz), 7.16 (2H, d, J=8.9 Hz), 7.19 (2H, d, J=8.6 Hz), 8.24 (2H, brs)

EXAMPLE 532

2-{[5-[4-(2-aminoethoxy)phenyl]-1-(4-methoxyphenyl)-1H-pyrazol-3-yl]oxy}-N,N-dimethylacetamide hydrochloride amorphous MS (ESI+): m/z 411 (M+H)+

200 MHz 1H NMR (DMSO-d6, d): 2.84 (3H, s), 2.97 (3H, s), 3.14–3.24 (2H, m), 3.76 (3H, s), 4.14–4.20 (2H, m), 4.88 (2H, s), 6.09 (1H, s), 6.93 (2H, d, J=9.0 Hz), 6.95 (2H, d, J=8.8 Hz), 7.07–7.29 (4H, m), 8.21 (2H, brs)

EXAMPLE 533

A solution of potassium cyanate (64.9 mg) in H2O (0.5 ml) was added to a solution of N'-[5-[4-(2-aminoethoxy)phenyl]-1-(4-methoxy-phenyl)-1H-pyrazol-3-yl]-N,N-dimethylurea hydrochloride (172.8 mg) and sodium acetate (65.6 mg) in a mixture of DMF (1.5 ml) and H2O (0.5 ml). The reaction mixture was stirred at ambient temperature overnight. The mixture was diluted with H2O, partitioned between AcOEt and H2O. The aqueous layer was reextracted with AcOEt. saturated aqueous sodium chloride solution, dried over magnesium sulfate, and concentrated in vacuo. The residue was purified by preparative thin layer silica gel chromatography developed by 10% MeOH/CHCl3. The separated silica gel was extracted with 10% MeOH/CHCl3 and the solvent was evaporated in vacuo. The residue was crystallized from AcOEt-IPE to give N'-[5-(4-{2-[(aminocarbonyl) -amino]ethoxy}phenyl)-1-(4-methoxyphenyl)-1H-pyrazol-3-yl]-N,N-dimethylurea (87.0 mg) as a powder.

mp. 193–196° C.

IR (KBr): 3437, 3421, 1660, 1649, 1620, 1612, 1581, 1562, 1554, 1529, 1512 cm−1

Mass (ESI+): 439 (M+H)+

200 MHz 1H NMR (DMSO-d6, d): 2.91 (6H, s), 3.27–3.34 (2H, m), 3.76 (3H, s), 3.93 (2H, t, J=5.5 Hz), 5.53 (2H, s), 6.16 (1H, t, J=5.7 Hz), 6.62 (1H, s), 6.91 (2H, d, J=8.7 Hz), 6.93 (2H, d, J=8.9 Hz), 7.13 (2H, d, J=8.7 Hz), 7.15 (2H, d, J=8.9 Hz), 9.02 (1H, s)

The following compound(s) was (were) obtained in a similar manner to that of Example 533.

EXAMPLE 534

N-[5-(4-{2-[(aminocarbonyl)amino]ethoxy}phenyl)-1-(4-methoxyphenyl)-1H-pyrazol-3-yl]-N,N',N'-trimethylurea power: mp. 158.6–159.0° C.

IR (KBr): 3433, 3369, 1687, 1658, 1643, 1612, 1514, 1500 cm−1

Mass (ESI+): 453 (M+H)+

200 MHz 1H NMR (DMSO-d6, d): 2.79 (6H, s), 3.12 (3H, s), 3.27–3.34 (2H, m), 3.76 (3H, s), 3.93 (2H, t, J=5.5 Hz), 5.53 (2H, s), 6.15 (1H, t, J=5.6 Hz), 6.25 (1H, s), 6.91 (2H, d, J=8.7 Hz), 6.94 (2H, d, J=8.9 Hz), 7.15 (2H, d, J=8.7 Hz), 7.15 (2H, d, J=8.9 Hz)

EXAMPLE 535

N-(2-{4-[3-(2-methoxyethoxy)-1-(4-methoxyphenyl)-1H-pyrazol-5-yl]phenoxy}ethyl)urea white power: mp. 131–132° C.

IR (KBr): 3435, 3429, 3388, 3350, 1658, 1612, 1562, 1554, 1518 cm−1

Mass (sample ID cox022116) (ESI+): 427 (M+H)+

200 MHz 1H NMR (DMSO-d6, d): 3.28–3.38 (2H, m), 3.30 (3H, s), 3.62–3.68 (2H, m), 3.75 (3H, s), 3.89–3.96 (2H, m), 4.21–4.27 (2H, m), 5.53 (2H, s), 6.05 (1H, s), 6.15 (1H, t, J=5.7 Hz), 6.91 (2H, d, J=8.9 Hz), 6.92 (2H, d, J=9.0 Hz), 7.10–7.15 (4H, m)

EXAMPLE 536

N-(2-{4-[3-(2-ethoxyethoxy)-1-(4-methoxyphenyl)-1H-pyrazol-5-yl]phenoxy}ethyl)urea white power: mp. 124.1–124.2° C.

IR (KBr): 3388, 3379, 3340, 1657, 1643, 1612, 1562, 1554, 1518 cm−1

Mass (ESI+): 441 (M+H)+

200 MHz 1H NMR (DMSO-d6, d): 1.13 (3H, t, J=7.0 Hz), 3.27–3.36 (2H, m), 3.49 (2H, q, J=7.0 Hz), 3.66–3.71 (2H, m), 3.75 (3H, s), 3.89–3.96 (2H, m), 4.21–4.26 (2H, m), 5.53 (2H, s), 6.06 (1H, s), 6.15 (1H, t, J=5.7 Hz), 6.91 (2H, d, J=8.8 Hz), 6.92 (2H, d, J=9.0 Hz), 7.10–7.15 (4H, m)

EXAMPLE 537

2-{[5-(4-{2-[(aminocarbonyl)amino]ethoxy}phenyl)-1-(4-methoxyphenyl)-1H-pyrazol-3-yl]oxy}-N,N-dimethyl-acetamide white power: mp. 223–227° C.

IR (KBr): 3402, 3332, 3201, 3194, 2925, 1664, 1612, 1518, 1502 cm−1

MS (ESI+): m/z 454 (M+H)+

200 MHz 1H NMR (DMSO-d6, d): 2.84 (3H, s), 2.97 (3H, s), 3.27–3.35 (2H, m), 3.75 (3H, s), 3.89–3.96 (2H, m), 4.87 (2H, s), 5.53 (2H, s), 6.07 (1H, s), 6.15 (1H, t, J=5.5 Hz), 6.91 (2H, d, J=8.9 Hz), 6.93 (2H, d, J=9.0 Hz), 7.11 (2H, d, J=9.0 Hz), 7.13 (2H, d, J=8.9 Hz)

EXAMPLE 538

N-(2-{4-[3-methoxy-1-(6-methoxy-3-pyridinyl)-1H-pyrazol-5-yl]phenoxy}ethyl)urea white power: mp. 192.6–192.7° C.

IR (KBr): 3390, 3352, 3311, 3305, 1657, 1610, 1583, 1568, 1525, 1502 cm−1

MS (ESI+): m/z 384 (M+H)+

200 MHz 1H NMR (DMSO-d6, d): 3.27–3.36 (2H, m), 3.34 (3H, s), 3.85 (3H, s), 3.91–3.97 (2H, m), 5.53 (2H, s), 6.11 (1H, s), 6.15 (1H, t, J=5.7 Hz), 6.85 (1H, d, J=8.7 Hz), 6.94 (2H, d, J=8.8 Hz), 7.17 (2H, d, J=8.8 Hz), 7.59 (1H, dd, J=2.6, 8.7 Hz), 8.00 (1H, d, J=2.6 Hz)

EXAMPLE 539

N-(2-{4-[3-ethoxy-1-(6-methoxy-3-pyridinyl)-1H-pyrazol-5-yl]phenoxy}ethyl)urea white power: mp. 133–138° C.

IR (KBr): 3350, 1657, 1643, 1612, 1579, 1562, 1554, 1518, 1500 cm−1; MS (ESI+): m/z 398 (M+H)+

200 MHz 1H NMR (DMSO-d6, d): 1.33 (3H, t, J=7.0 Hz), 3.28–3.35 (2H, m), 3.84 (3H, s), 3.91–3.97 (2H, m), 4.19 (2H, q, J=7.0 Hz), 5.53 (2H, s), 6.09 (1H, s), 6.16 (1H, t, J=5.6 Hz), 6.85 (1H, d, J=8.8 Hz), 6.94 (2H, d, J=8.8 Hz), 7.17 (2H, d, J=8.8 Hz), 7.58 (1H, dd, J=2.7,8.8 Hz), 8.00 (1H, d, J=2.7 Hz)

EXAMPLE 540

N-(2-{4-[3-cyclopropyl-1-(6-methoxy-3-pyridinyl)-1H-pyrazol-5-yl]phenoxy}ethyl)urea mp. 94–96° C.

MS (ESI+): m/z 394 (M+H)

1HNMR (200 MHz, DMSOd6): 0.72–0.78 (2H, m), 0.87–0.95 (2H, m), 1.87–2.01 (1H, m), 3.23–3.42 (2H, m), 3.85 (3H, s), 3.90–3.97 (2H, m), 5.52 (2H, s), 6.12 (1H, t, J=5.6 Hz), 6.30 (1H, s), 6.85 (1H, d, J=8.8 Hz), 6.92 (2H, d, J=8.7 Hz), 7.13 (2H, d, J=8.8 Hz), 7.58 (1H, dd, J=2.7, 8.8 Hz), 8.01 (1H, d, J=2.7 Hz)

EXAMPLE 541

N-(2-{4-[1-(4-methoxyphenyl)-3-(1-piperidinylcarbonyl)-1H-pyrazol-5-yl]phenoxy}ethyl)urea mp. 152.0–152.2° C.

Mass (ESI+): 464 (M+H)

1HNMR (200 MHz, DMSOd6): 1.42–1.73 (6H, m), 3.27–3.36 (2H, m), 3.53–3.67 (2H, m), 3.73–3.96 (2H, m), 3.78 (3H, s), 3.90–3.97 (2H, m), 5.51 (2H, s), 6.14 (1H, t, J=5.7 Hz), 6.77 (1H, s), 6.92 (2H, d, J=8.8 Hz), 6.98 (2H, d, J=9,0 Hz), 7.17 (2H, d, J=8.8 Hz), 7.23 (2H, d, J=9.0 Hz)

EXAMPLE 542

N-(2-{4-[1-(6-methoxy-3-pyridinyl)-3-(1-piperidinyl-carbonyl)-1H-pyrazol-5-yl]phenoxy}ethyl)urea mp.164–167° C.

Mass (ESI+): 465 (M+H)

1HNMR (200 MHz, DMSOd6): 1.42–1.73 (6H, m), 3.22–3.40 (2H, m), 3.52–3.70 (2H, m), 3.75–3.95 (2H, m), 3.87 (3H, s), 3.92–3.98 (2H, m), 5.52 (2H, s), 6.15 (1H, t, J=5.6 Hz), 6.81 (1H, s), 6.90 (1H, d, J=8.9 Hz), 6.95 (2H, d, J=8.8 Hz), 7.21 (2H, d, J=8.8 Hz), 7.67 (1H, dd, J=2.7, 8.9 Hz), 8.14 (1H, d, J=2.7 Hz)

EXAMPLE 543

5-(4-{2-[(aminocarbonyl)amino]ethoxy}phenyl)-N-ethyl-1-(6-methoxy-3-pyridinyl)-N-methyl-1H-pyrazole-3-carboxamide mp. 146.3–146.7° C.

MS (ESI+): m/z 439 (M+H)

1HNMR (200 MHz, DMSOd6): 1.09–1.23 (3H, m), 2.98, 3.28 (3H, s), 3.28–3.37 (2H, m), 3.40–3.53, 3.63–3.77 (2H, m), 3.87 (3H, s), 3.92–3.98 (2H, m), 5.52 (2H, s), 6.15 (1H, t, J=5.5 Hz), 6.82, 6.85 (1H, s), 6.90 (1H, d, J=9.0 Hz), 6.95 (2H, d, J=8.7 Hz), 7.21 (2H, d, J=8.7 Hz), 7.60–7.73 (1H, m), 8.14–8.16 (1H, m)

EXAMPLE 544

N-(2-{4-[1-(4-methoxyphenyl)-3-(2,2,2-trifluoroethoxy)-1H-pyrazol-5-yl]phenoxy}ethyl)urea mp. 130–132° C.

MS (ESI+): m/z 451 (M+H)

1HNMR (200 MHz, DMSOd6): 3.27–3.33 (2H, m), 3.76 (3H, s), 3.90–3.96 (2H, m), 4.81 (1H, d, J=9.0 Hz), 4.90 (1H, d, J=9.0 Hz), 5.52 (2H, s), 6.14 (1H, t, J=5.6 Hz), 6.21 (1H, s), 6.89–6.98 (4H, m), 7.12–7.18 (4H, m)

EXAMPLE 545

N-(2-{4-[3-(2,2-difluoroethoxy)-1-(4-methoxyphenyl)-1H-pyrazol-5-yl]phenoxy}ethyl)urea mp. 138.6–139.1° C.

MS (ESI+): m/z 432 (M+H)

1HNMR (200 MHz, DMSOd6): 3.27–3.36 (2H, m), 3.76 (3H, s), 3.90–3.96 (2H, m), 4.44 (2H, dt, J=3.5, 14.9 Hz), 5.52 (2H, s), 6.11–6.17 (1H, m), 6.15 (1H, s), 6.41 (1H, tt, J=3.5, 54.6 Hz), 6.91 (2H, d, J=8.9 Hz), 6.93 (2H, d, J 8.9 Hz), 7.14 (2H, d, J=8.9 Hz), 7.15 (2H, d, J=8.9 Hz)

EXAMPLE 546

N-(2-{4-[1-(6-methoxy-3-pyridinyl)-3-(2,2,2-trifluoro-ethoxy)-1H-pyrazol-5-yl]phenoxy}ethyl)urea mp. 134.8–134.9° C.

MS (ESI+): m/z 452 (M+H)

1HNMR (200 MHz, ): 3.24–3.39 (2H, m), 3.85 (3H, s), 3.91–3.98 (2H, m), 4.83 (1H, d, J=9 Hz), 4.92 (1H, d, J=9 Hz), 5.52 (2H, s), 6.15 (1H, t, J=5.6 Hz), 6.27 (1H, s), 6.87 (1H, d, J=8.8 Hz), 6.95 (2H, d, J=8.8 Hz), 7.18 (2H, d, J=8.8 Hz), 7.61 (1H, dd, J=2.7, 8.8 Hz), 8.04 (1H, d, J=2.7 Hz)

EXAMPLE 547

N-(2-{4-[3-(2,2-difluoroethoxy)-1-(6-methoxy-3-pyridinyl)-1H-pyrazol-5-yl]phenoxy}ethyl)urea mp. 146.9–147.3° C.

MS (ESI+): m/z 434 (M+H)

1HNMR (200 MHz, DMSOd6): 3.23–3.40 (2H, m), 3.85 (3H, s), 3.91–3.97 (2H, m), 4.45 (2H, dt, J=3.5, 14.9 Hz), 5.52 (2H, s), 6.15 (1H, t, J=5.7 Hz), 6.21 (1H, s), 6.42 (1H, tt, J=3.5, 54.6 Hz), 6.86 (1H, d, J=8.8 Hz), 6.94 (2H, d, J=8.8 Hz), 6.94 (2H, d, J=8.8 Hz), 7.60 (1H, dd, J=2.8, 8.8 Hz), 8.03 (1H, d, J=2.8 Hz)

EXAMPLE 548

5-(4-{[(aminocarbonyl)amino]methyl}phenyl)-N-ethyl-1-(4-methoxyphenyl)-N-methyl-1H-pyrazole-3-carboxamide mp. 184.7–185.1° C.

MS (ESI+): m/z 408 (M+H)

1HNMR (200 MHz, DMSOd6): 1.09–1.22 (3H, m), 2.98, 3.29 (3H, s), 3.41–3.78 (2H, m), 3.78 (3H, s), 4.16 (2H, d, J=6.0Hz ), 5.54 (2H, s), 6.44 (1H, t, J=6 Hz), 6.84, 6.86 (1H, s), 6.99 (2H, d, J=8.9 Hz), 7.2–7.27 (6H, m)

EXAMPLE 549

N-{4-[3-isopropyl-1-(4-methoxyphenyl)-1H-pyrazol-5-yl]benzyl}urea amorphous powder MS (ESI+): m/z 365 (M+H)

1HNMR (200 MHz, DMSOd6): 1.27 (6H, d, J=7.0Hz ), 2.95 (1H, m), 3.76 (3H, s), 4.15 (2H, d, J=6.0 Hz), 5.53 (2H, s), 6.42 (1H, t, J=6.0 Hz), 6.44 (2H, d, J=8.9 Hz), 7.11–7.22 (6H, m)

EXAMPLE 550

N-{4-[1-(6-methoxy-3-pyridinyl)-3-(1-piperidinyl-carbonyl)-1H-pyrazol-5-yl]benzyl}urea mp. 178.9–178.9° C.

MS (ESI+): m/z 435 (M+H)

1HNMR (400 MHz, DMSOd6): 1.47–1.70 (6H, m), 3.55–3.66 (2H, m), 3.78–3.89 (2H, m), 3.87 (3H, s), 4.17 (2H, d, J=6.0 Hz ), 5.55 (2H, s), 6.45 (1H, t, J=6.0 Hz), 6.86 (1H, s), 6.91 (1H, d, J=8.8 Hz), 7.24 (4H, s), 7.70 (1H, dd, J=2.7, 8.8 Hz), 8.14 (1H, d, J=2.7 Hz)

EXAMPLE 551

5-(4-{[(aminocarbonyl)amino]methyl}phenyl)-N-ethyl-1-(6-methoxy-3-pyridinyl)-N-methyl-1H-pyrazole-3-carboxamide mp. 172.6–172.8° C.

MS (ESI+): m/z 409 (M+H)

1HNMR (400 MHz, DMSOd6): 1.13, 1.19 (3H, t, J=7.0 Hz) 2.98, 3.29 (3H, s), 3.48, 3.72 (2H, q, J=7.0 Hz), 3.87 (3H, s), 4.18 (2H, d, J=6.0 Hz), 5.55 (2H, s), 4.45 (1H, t, J=6.0Hz ), 6.87–6.93 (2H, m), 7.24 (4H, s), 7.67–7.73 (1H, m), 8.14–8.16 (1H, m)

EXAMPLE 552

N-{4-[3-isopropyl-1-(6-methoxy-3-pyridinyl)-1H-pyrazol-5-yl]benzyl}urea mp. 139–144° C.

MS (ESI+): m/z 366 (M+H)

1HNMR (200 MHz, DMSOd6): 1.27 (6H, d, J=7.0 Hz), 2.97 (1H, m), 3.85 (3H, s), 4.17 (2H, d, J=6.OHz ), 5.53 (2H, s), 6.43 (1H, t, J=6.0 Hz ), 6.5 0 (1H, s), 6.86 (1H, d, J=8.8 Hz), 7.15–7.26 (4H, m), 7.62 (1H, dd, J=2.8, 8.8 Hz), 8.02 (1H, d, J=2.7 Hz)

EXAMPLE 553

N-{4-[3-isobutyryl-1-(6-methoxy-3-pyridinyl)-1H-pyrazol-5-yl]benzyl}urea mp. 157.0–157.3° C.

MS (ESI+): m/z 394 (M+H)

1HNMR (200 MHz, DMSOd6): 1.16 (6H, d, J=6.8 Hz), 3.68 (1H, m), 3.88 (3H, s), 4.17 (2H, d, J=6.0Hz ), 5.54 (2H, s), 6.45 (1H, t, J=6.0 Hz), 6.93 (1H, d, J=8.8 Hz), 7.06 (1H, s), 7.25 (4H, s), 7.76 (1H, dd, J=2.7, 8.8 Hz), 8.18 (1H, d, J=2.7 Hz)

EXAMPLE 554

N-{4-[3-methoxy-1-(4-methoxyphenyl)-1H-pyrazol-5-yl]benzyl}urea mp. 206.0–260.9° C.

MS (ESI+): m/z 353 (M+H)

1HNMR (200 MHz, DMSOd6): 3.76 (3H, s), 3.84 (3H, s), 4.15 (2H, d, J=6.0 Hz), 5.53 (2H, s), 6.09 (1H, s), 6.42 (1H, t, J=6.0 Hz ), 6.93 (2H, d, J=9 Hz), 7.12–7.23 (6H, m)

EXAMPLE 555

N-{4-[3-isopropoxy-1-(4-methoxyphenyl)-1H-pyrazol-5-yl]benzyl}urea solid

MS (ESI+): m/z 381 (M+H)

1HNMR (200 MHz, DMSOd6): 1.31 (6H, d, J=6.1 Hz), 3.76 (3H, s), 4.15 (2H, d, J=6.0 Hz ), 4.76 (1H, m), 5.53 (2H, s), 6.04 (1H, s), 6.43 (1H, t, J=6.0 Hz), 6.92 (2H, d, J=8.9 Hz), 7.10–7.22 (6H, m)

EXAMPLE 556

N-{4-[3-chloro-1-(4-methoxyphenyl)-1H-pyrazol-5-yl]-benzyl}urea mp. 125.5–126.2° C.
Mass (ESI+): 357 (M+H)
1HNMR (200 MHz, DMSOd6): 3.78 (3H, s), 4.15 (2H, d, J=6.1 Hz), 5.54 (2H, s), 6.43 (1H, t, J=6.1 Hz), 6.73 (1H, s), 6.97 (2H, d, J=8.9 Hz), 7.14–7.24 (6H, m)

EXAMPLE 557

N-{4-[3-chloro-1-(6-methoxy-3-pyridinyl)-1H-pyrazol-5-yl]benzyl}urea mp. 111–115° C.
Mass (ESI+): 358 (M+H)
1HNMR (200 MHz, DMSOd6): 3.87 (3H, s), 4.17 (2H, d, J=6.0 Hz), 5.54 (2H, s), 6.44 (1H, t, J=6.0 Hz), 6.79 (1H, s), 6.89 (1H, d, J=0.8 Hz), 7.23 (4H, s), 7.69 (1H, dd, J=2.7, 8.8 Hz), 8.11 (1H, d, J=2.7 Hz)

EXAMPLE 558

N-(2-{4-[1-(4-methoxyphenyl)-4-methyl-1H-pyrazol-5-yl]-phenoxy}ethyl)urea amorphous powder
MS (ESI+): m/z 367 (M+H)
1HNMR (400 MHz, DMSOd6): 2.02 (3H, s), 3.32–3.36 (2H, m), 3.74 (3H, s), 3.92–3.96 (2H, m), 5.51 (2H, s), 6.15 (1H, t, J=5.6 Hz), 6.89 (2H, d, J=8.9 Hz), 6.94 (2H, d, J=8.8 Hz), 7.08 (2H, d, J=8.8 Hz), 7.09 (2H, d, J=8.9 Hz), 7.55 (1H, s)

EXAMPLE 559

N-(2-{4-[1-(6-methoxy-3-pyridinyl)-4-methyl-1H-pyrazol-5-yl]phenoxy}ethyl)urea powder
MS (ESI+): m/z 368 (M+H)
1HNMR (400 MHz, DMSOd6): 2.03 (3H, s), 3.31–3.36 (2H, m), 3.83 (3H, s), 3.94–3.98 (2H, m), 5.51 (2H, s), 6.15 (1H, t, J=5.6 Hz), 6.82 (1H, d, J=8.8 Hz), 6.97 (2H, d, J=8.8 Hz), 7.13 (2H, d, J=8.8 Hz), 7.53 (1H, dd, J=2.7, 8.8 Hz), 7.62 (1H, s), 7.98 (1H, d, J=2.7 Hz)

EXAMPLE 560

N-(2-{4-[1-(4-methoxyphenyl)-3-(methylthio)-1H-pyrazol-5-yl]phenoxy}ethyl)urea mp. 141.2–142.2° C.
MS (ESI+): m/z 399 (M+H)
1HNMR (200 MHz, DMSOd6) 2.50 (3H, s), 3.27–3.36 (2H, m), 3.77 (3H, s), 3.90–3.96 (2H, m), 5.52 (2H, s), 6.14 (1H, t, J=5.6 Hz), 6.56 (1H, s), 6.91 (2H, d, J=8.8 Hz), 6.95 (2H, d, J=8.8 Hz), 7.14 (2H, d, J=8.8 Hz), 7.17 (2H, d, J=8.8 Hz)

EXAMPLE 561

N-(2-{4-[1-(6-methoxy-3-pyridinyl)-3-(trifluoromethyl)-1H-pyrazol-5-yl]phenyl}ethyl)urea mp. 205–206° C.
MS (ESI+): m/z 406 (M+H)
1HNMR (200 MHz, DMSOd6): 2.64–2.72 (2H, m), 3.13–3.24 (2H, m), 3.88 (3H, s), 5.42 (2H, s), 5.95 (1H, t, J=5.6 Hz), 6.92 (1H, d, J=8.9 Hz), 7.17 (1H, s), 7.24 (4H, s), 7.75 (1H, dd, J=2.8, 8.9 Hz), 8.19 (1H, d, J=2.8 Hz)

EXAMPLE 562

5-(4-{2-[(aminocarbonyl)amino]ethyl}phenyl)-N-methoxy-1-(4-methoxyphenyl)-N-methyl-1H-pyrazole-3-carboxamide oil
MS (ESI+): m/z 243 (M+H)
1HNMR (200 MHz, CDCl3): 2.75–2.82 (2H, m), 3.34–3.45 (2H, m), 3.51 (3H, s), 3.82 (3H, s), 3.83 (3H, s), 4.46 (2H, s), 4.92 (1H, t, J=5.5 Hz), 6.84 (2H, d, J=9.0 Hz), 6.92 (1H, s), 7.11 (4H, s), 7.15 (2H, d, J=9.0 Hz)

EXAMPLE 563

5-(4-{2-[(aminocarbonyl)amino]ethyl}phenyl)-N-methoxy-1-(6-methoxy-3-pyridinyl)-N-methyl-1H-pyrazole-3-carboxamide oil
MS (ESI+): m/z 425 (M+H)
1HNMR (200 MHz, CDCl3): 2.78–2.86 (2H, m), 3.39–3.49 (2H, m), 3.49 (3H, s), 3.85 (3H, s), 3.94 (3H, s), 4.39 (2H, s), 4.70 (1H, t, J=5.8 Hz), 6.75 (1H, d, J=8.9 Hz), 6.80 (1H, s), 7.12–7.23 (4H, m), 7.56 (1H, dd, J=2.7, 8.9 Hz), 8.05 (1H, d, J=2.7 Hz)

EXAMPLE 564

Sodium hydride 60% dispersion in mineral oil 93.1 mg was added in one portion to a solution of N-[5-[4-(benzyloxy)phenyl]-1-(4-methoxyphenyl)-1H-pyrazol-3-yl]-N',N'-dimethylurea 1.43 g in DMF 10 ml under ice bath cooling. The reaction mixture was stirred at ambient temperature for 1 hour. MeI 688 mg was added the reaction mixture was stirred at ambient temperature overnight. The mixture was partitioned between ethyl acetate and H2O. The organic layer was washed with saturated aqueous sodium chloride solution, dried over magnesium sulfate, and concentrated in vacuo. The residue was purified by silica gel column chromatography eluted with AcOEt-n-hexane=75%, 80% to give N-[5-[4-(benzyloxy)phenyl]-1-(4-methoxy-phenyl)-1H-pyrazol-3-yl]-N,N',N'-trimethylurea 1.45 g as an oil.
Mass (ESI+): 457 (M+H)+
200 MHz 1H NMR (DMSO-d6, d): 2.79 (6H, s), 3.12 (3H, s), 3.77 (3H, s), 5.09 (2H, s), 6.25 (1H, s), 6.91–7.00 (4H, m), 7.14–7.19 (4H, m), 7.32–7.46 (5H, m)

EXAMPLE 565

A mixture of N-(2-{4-[3-amino-1-(4-methoxyphenyl)-1H-pyrazol-5-yl]phenoxy}ethyl)urea 111 mg, lithium chloride 64 mg, and copper (II) chloride 81.2 mg in acetonitrile 2 ml was stirred at ambient temperature for 10 minutes. To this mixture was added isoamyl nitrite 62.3 mg, and the mixture was stirred at ambient temperature for 3 hours. The mixture was partitioned between ethyl acetate and saturated aqueous ammonium chloride solution. The organic layer was washed with saturated aqueous ammonium chloride solution, H2O, and saturated aqueous sodium chloride solution, dried over magnesium sulfate, and concentrated in vacuo. The residue was purified by preparative thin layer silica gel chromatography developed by MeOH/CHCl3=10%. The separated silica gel was extracted with 10% MeOH/CHCl3 and the solvent was evaporated in vacuo. The residue was crystallized from AcOEt/IPE to give N-(2-{4-[3-chloro-1-(4-methoxyphenyl)-1H-pyrazol-5-yl]phenoxy}ethyl)urea 31.1 mg as a white powder.

mp. 140–142° C.
Mass (ESI+): 386 (M+H)+
200 MHz 1H NMR (DMSO-d6, d): 3.27–3.34 (2H, m), 3.77 (3H, s), 3.93 (2H, t, J=5.5 Hz), 5.52 (2H, s), 6.15 (1H, t, J=5.7 Hz), 6.68 (1H, s), 6.92 (2H, d, J=9.0 Hz), 6.97 (2H, d, J=9.0 Hz), 7.15 (2H, d, J=9.0 Hz), 7.20 (2H, d, J=9.0 Hz)

EXAMPLE 566

Diethyl azodicarboxylate (0.17 ml) was added dropwise to a suspension of 3-methoxy-1-(4-methoxyphenyl)-5-(4-hydroxyphenyl)-1H-pyrazole (215.6 mg), tert-butyl N-(2-hydroxyethyl)carbamate (352 mg), and triphenylphosphine (286 mg) in THF (3 ml). The mixture was stirred at ambient temperature for 7 hours. Triphenylphosphine (19.1 mg) and diethyl azodicarboxylate (11.5 µl) were added and the mixture stirred at ambient temperature overnight. The mixture was concentrated in vacuo. The residue was purified by silica gel column chromatography eluted with AcOEt/n-hexane=30% to give tert-butyl (2-{4-[3-methoxy-1-(4-methoxyphenyl)-1H-pyrazol-5-yl]phenoxy}ethyl)carbamate (319 mg) as an oil.

Mass (ESI+): 440 (M+H)+
200 MHz 1H NMR (CDCl3, d): 1.45 (9H, s), 3.47–3.56 (2H, m), 3.80 (3H, s), 3.96–4.03 (2H, m), 3.97 (3H, s), 4.96 (1H, brs), 5.87 (1H, s), 6.79 (2H, d, J=8.8 Hz), 6.82 (2H, d, J=8.9 Hz), 7.09–7.20 (4H, m)

The following compound(s) was(were) obtained in a similar manner to that of Example 566.

EXAMPLE 567 tert-butyl (2-{4-[3-isobutoxy-1-(4-methoxyphenyl)-1H-pyrazol-5-yl]phenoxy}ethyl)carbamate white powder
Mass (ESI+): 482 (M+H)+
200 MHz 1H NMR (CDCl3, d): 1.03 (6H, d, J=6.7 Hz), 1.45 (9H, s), 2.11 (1H, m), 3.48–3.57 (2H, m), 3.79 (3H, s), 3.97–4.03 (2H, m), 4.97 (1H, br), 5.88 (1H, s), 6.79 (2H, d, J=8.7 Hz), 6.82 (2H, d, J=8.9 Hz), 7.09–7.19 (4H, m)

EXAMPLE 568 tert-butyl (2-{4-[3-(2-methoxyethoxy)-1-(4-methoxy-phenyl)-1H-pyrazol-5-yl]phenoxy}ethyl)carbamate solid
Mass (ESI+): 484 (M+H)+
200 MHz 1H NMR (DMSO-d6, d): 1.37 (9H, s), 3.22–3.32 (2H, m), 3.31 (3H, s), 3.62–3.67 (2H, m), 3.75 (3H, s), 3.91–3.97 (2H, m), 4.21–4.27 (2H, m), 6.04 (1H, s), 6.86–6.99 (5H, m), 7.10–7.15 (4H, m)

EXAMPLE 569 tert-butyl (2-{4-[3-(2-ethoxyethoxy)-1-(4-methoxy-phenyl)-1H-pyrazol-5-yl]phenoxy}ethyl)carbamate oil
Mass (ESI+): 498 (M+H)+
200 MHz 1H NMR (DMSO-d6, d) : 1.09–1.21 (3H, overlapping), 1.37 (9H, s), 3.25–3.34 (2H, m), 3.66–3.71 (2H, m), 3.75 (3H, s), 3.90–4.15 (4H, m), 4.21–4.26 (2H, m), 6.06 (1H, s), 6.86–6.96 (4H, m), 7.01 (1H, m), 7.12 (4H, d, J=8.9 Hz),

EXAMPLE 570 tert-butyl (2-{4-[3-methoxy-1-(6-methoxy-3-pyridi-nyl)-1H-pyrazol-5-yl]phenoxy}ethyl)carbamate powder
MS (ESI+): m/z 441 (M+H)+
200 MHz 1H NMR (CDCl3, d): 1.45 (9H, s), 3.48–3.57 (2H, m), 3.92 (3H, s), 3.97 (3H, s), 3.98–4.03 (2H, m), 4.99 (1H, br), 5.90 (1H, s), 6.70 (1H, d, J=8.5 Hz), 6.82 (2H, d, J=8.9 Hz), 7.14 (2H, d, J=8.9 Hz), 7.52 (1H, dd, J=2.5, 8.5 Hz), 8.03 (1H, d, J=2.5 Hz)

EXAMPLE 571 tert-butyl (2-{4-[3-ethoxy-1-(6-methoxy-3-pyridi-nyl)-1H-pyrazol-5-yl]phenoxy}ethyl)carbamate white powder
MS (ESI+): m/z 455 (M+H)+
200 MHz 1H NMR (DMSO-d6, d): 1.33 (3H, t, J=7.0 Hz), 1.37 (9H, s), 3.22–3.33 (2H, m), 3.84 (3H, s), 3.92–3.98 (2H, m), 4.19 (2H, q), 6.08 (1H, s), 6.85 (1H, d, J=8.8 Hz), 6.92 (2H, d, J=8.8 Hz), 7.02 (1H, t, J=5.5 Hz), 7.16 (2H, d, J=8.8 Hz), 7.58 (1H, dd, J=2.7, 8.8 Hz), 7.99 (1H, d, J=2.7 Hz)

EXAMPLE 572 tert-butyl [2-(4-{3-(difluoromethyl)-1-[4-(methyl-thio)phenyl]-1H-pyrazol-5-yl}phenoxy)ethyl]car-bamate MASS (ESI+): m/z=498.2 (M+Na).
1HNMR (400 MHz, CDCl3): 1.45 (9H, s), 2.49 (3H, s), 3.54 (2H, q, J=5.1 Hz), 4.02 (2H, t, J=5.1 Hz), 4.98 (1H, b.s), 6.66 (1H, s), 6.76 (1H, t, J=55.1 Hz), 6.84 (2H, d, J=8.8 Hz), 7.15 (2H, d, J=8.8 Hz), 7.2 (4H, s).

EXAMPLE 573 tert-butyl (2-{4-[3-cyclopropyl-1-(6-methoxy-3-pyridinyl)-1H-pyrazol-5-yl]phenoxy}ethyl)carbamate oil
MS ESI+): m/z 451 (M+H)
1HNMR (200 MHz, CDCl3): 0.77–0.86 (2H, m), 0.93–1.04 (2H, m), 1.45 (9H, s), 1.96–2.09 (1H, m), 3.48–3.57 (2H, m), 3.92 (3H, s), 3.97–4.03 (2H, m), 4.97

(1H, brs), 6.10 (1H, s), 6.71 (1H, d, J=8.8 Hz), 6.81 (2H, d, J=8.8 Hz), 7.11 (2H, d, J=8.8 Hz), 7.53 (1H, dd, J=2.7, 8.8 Hz), 8.03 (1H, d, J=2.7 Hz)

EXAMPLE 574 tert-butyl (2-{4-[3-(cyclopentyloxy)-1-(6-methoxy-3-pyridinyl)-1H-pyrazol-5-yl]phenoxy}ethyl)carbamate oil MS (ESI+): m/z 494 (M+H)

1HNMR (200 MHz, CDCl3): 1.45 (9H, s), 1.5–1.99 (8H, m), 3.48–3.57 (2H, m), 3.91 (3H, s), 3.98–4.04 (2H, m), 4.92–5.05 (2H, m), 5.88 (1H, s), 6.69 (1H, d, J=8.9 Hz), 6.82 (2H, d, J=8.8 Hz), 7.14 (2H, d, J=8.8 Hz), 7.52 (1H, dd, J=2.7, 8.9 Hz), 8.02 (1H, d, J=2.7 Hz)

EXAMPLE 575 tert-butyl (2-{4-[1-(4-methoxyphenyl)-3-(2,2,2-trifluoroethoxy)-1H-pyrazol-5-yl]phenoxy}ethyl)carbamate oil MS (ESI+): m/z 508 (M+H)

1HNMR (200 MHz, CDCl3): 1.45 (9H, s), 3.48–3.57 (2H, m), 3.81 (3H, s), 3.97–4.03 (2H, m), 4.62 (1H, d, J=8.5 Hz), 4.70 (1H, d, J=8.5 Hz), 4.95 (1H, brs), 5.95 (1H, s), 6.77–6.86 (4H, m), 7.08–7.18 (4H, m)

EXAMPLE 576 tert-butyl (2-{4-[3-(2,2-difluoroethoxy)-1-(4-methoxyphenyl)-1H-pyrazol-5-yl]phenoxy}ethyl)carbamate oil MS (ESI+): m/z 490 (M+H)

1HNMR (200 MHz, CDCl3): 1.45 (9H, s), 3.48–3.57 (2H, m), 3.80 (3H, s), 3.97–4.03 (2H, m), 4.46 (2H, dt, J=4.3, 13.4 Hz), 4.96 (1H, brs), 5.91 (1H, s), 6.17 (1H, tt, J=4.3, 55.5 Hz), 6.77–6.88 (4H, m), 7.09–7.18 (4H, m)

EXAMPLE 577 tert-butyl (2-{4-[1-(6-methoxy-3-pyridinyl)-3-(2,2,2-trifluoroethoxy)-1H-pyrazol-5-yl]phenoxy}ethyl)-carbamate oil MS (ESI+): m/z 509 (M+H)

1HNMR (200 MHz, CDCl3): 1.45 (9H, s), 3.48–3.57 (2H, m), 3.92 (3H, s), 3.98–4.04 (2H, m), 4.61 (1H, d, J=8.4 Hz), 4.70 (1H, d, J=8.4 Hz), 4.96 (1H, brs), 5.97 (1H, s), 6.71 (1H, d, J=8.8 Hz), 6.83 (2H, d, J=8.8 Hz), 7.13 (2H, d, J=8.8 Hz), 7.48 (1H, dd, J=2.7, 8.8 Hz), 8.02 (1H, d, J=2.7 Hz)

EXAMPLE 578 tert-butyl (2-{4-[3-(2,2-difluoroethoxy)-1-(6-methoxy-3-pyridinyl)-1H-pyrazol-5-yl]phenoxy}ethyl)-carbamate solid MS (ESI+): m/z 513 (M+Na)

1HNMR (200 MHz, CDCl3): 1.45 (9H, s), 3.48–3.57 (2H, m), 3.92 (3H, s), 3.98–4.04 (2H, m), 4.46 (2H, dt, J=4.2, 13.4 Hz), 4.96 (1H, brs), 5.94 (1H, s), 6.16 (1H, tt, J=4.2, 55.5 Hz), 6.71 (1H, d, J=8.8 Hz), 6.83 (2H, d, J=8.9 Hz), 7.13 (2H, d, J=8.9 Hz), 7.48 (1H, dd, J=2.7, 8.8 Hz), 8.02 (1H, d, J=2.7 Hz)

EXAMPLE 579 tert-butyl (2-{4-[1-(4-methoxyphenyl)-4-methyl-1H-pyrazol-5-yl]phenoxy}ethyl)carbamate oil MS (ESI+): m/z 424 (M+H)

200 MHz 1H NMR (DMSO-d6, d): 1.37 (9H, s), 2.01 (3H, s), 3.23–3.33 (2H, m), 3.74 (3H, s), 3.92–3.98 (2H, m), 6.86–6.95 (4H, m), 7.05–7.12 (4H, m), 7.55 (1H, s)

EXAMPLE 580 tert-butyl (2-{4-[1-(6-methoxy-3-pyridinyl)-4-methyl-1H-pyrazol-5-yl]phenoxy}ethyl)carbamate oil MS (ESI+): m/z 425 (M+H)

1HNMR (400 MHz, CDCl3): 1.42 (9H, s), 2.09 (3H, s), 3.52–3.57 (2H, m), 3.91 (3H, s), 4.01–4.04 (2H, m), 4.98 (1H, brs), 6.68 (1H, d, J=8.8 Hz), 6.87 (2H, d, J=8.8 Hz), 7.08 (2H, d, J=8.8 Hz), 7.48 (1H, dd, J=2.7, 8.8 Hz), 7.58 (1H, s), 8.00 (1H, d, J=2.7 Hz)

EXAMPLE 581 tert-butyl (2-{4-[1-(4-methoxyphenyl)-3-(methylthio)-1H-pyrazol-5-yl]phenoxy}ethyl)carbamate oil Mass (ESI+): m/z 456 (M+H)

1HNMR (200 MHz, CDCl3): 1.45 (9H, s), 2.58 (3H, s), 3.48–3.57 (2H, m), 3.81 (3H, s), 3.97–4.03 (2H, m), 4.96 (1H, m), 6.36 (1H, s), 6.77–6.86 (4H, m), 7.12 (2H, d, J=8.9 Hz), 7.2 (2H, d, J=9.0 Hz)

EXAMPLE 582

To a solution of (2-{4-[3-methoxy-1-(4-methoxyphenyl)-1H-pyrazol-5-yl]phenoxy}ethyl)amine hydrochloride (150 mg) and triethylamine (121 mg) in CH2Cl2 (3 ml) was added trifluoromethanesulfonic anhydride (113 mg). The mixture was stirred at ambient temperature for 2 hours. Additional triethylamine (92 mg) was added and stirring at ambient temperature was continued for 4 hours. The mixture was concentrated in vacuo. The residue was partitioned between AcOEt and 1M HCl. The organic layer was washed with saturated aqueous sodium bicarbonate solution and saturated aqueous sodium chloride solution, dried over magnesium sulfate, and concentrated in vacuo. The residue was purified by silica gel column chromatography eluted with AcOEt/n-hexane=50% to give 1,1,1-trifluoro-N-(2-{4-[3-methoxy-1-(4-methoxy-phenyl)-1H-pyrazol-5-yl]phenoxy}ethyl)methane-sulfonamide (109 mg) as an oil.

IR (neat): 2960, 1612, 1522 cm−1

Mass (ESI+): 472 (M+H)+

200 MHz 1H NMR (CDCl3, d): 3.60–3.73 (2H, m), 3.80 (3H, s), 3.97 (3H, s), 4.06–4.12 (2H, m), 5.45 (1H, brs), 5.89 (1H, s), 6.70–6.87 (4H, m), 7.15 (2H, d, J=8.9 Hz), 7.17 (2H, d, J=9.0 Hz)

EXAMPLE 583

To a suspension of 5-[4-(benzyloxy)phenyl]-3-hydroxy-1-(4-methoxyphenyl)-1H-pyrazole 2.0 g and K2CO3 2.23 g in DMSO 20 ml was added diethylsulfate 1.24 g. After stirring at ambient temperature for 2 hours, the reaction was quenched by adding 28% aqueous ammonium hydroxide solution and ice. The mixture was partitioned between AcOEt and H2O. The organic layer was washed with H2O and saturated aqueous sodium chloride solution, dried over magnesium sulfate, and concentrated in vacuo. The residue was purified by silica gel column chromatography eluted with AcOEt/n-hexane=40% and the solvent was evaporated in vacuo. The reisual solid was recrystallized from IPE to give 5-[4-(benzyloxy)phenyl]-3-ethoxy-1-(4-methoxy-phenyl)-1H-pyrazole 1.44 g as a powder.

Mass (ESI+): 401 (M+H)+

200 MHz 1H NMR (DMSO-d6, d): 1.32 (3H, t, J=7.0 Hz), 3.76 (3H, s), 4.17 (2H, q, J=7.0 Hz), 5.08 (2H, s), 6.03 (1H, s), 6.92 (2H, d, J=9.0 Hz), 6.97 (2H, d, J=8.8 Hz), 7.09–7.16 (4H, m), 7.32–7.46 (5H, m)

The following compound(s) was(were) obtained in a similar manner to that of Example 583.

EXAMPLE 584

5-{5-[4-(benzyloxy)phenyl]-3-ethoxy-1H-pyrazol-1-yl}-2-methoxypyridine oil; MS (ESI+): m/z 402 (M+H)+

200 MHz 1H NMR (CDCl3, d): 1.43 (3H, t, J=7.1 Hz), 3.92 (3H, s), 4.28 (2H, q, J=7.1 Hz), 5.05 (2H, s), 5.90 (1H, s), 6.70 (1H, d, J=8.7 Hz), 6.91 (2H, d, J=8.8 Hz), 7.14 (2H, d, J=8.8 Hz), 7.35–7.43 (5H, m), 7.51 (1H, dd, J=2.6, 8.7 Hz), 8.04 (1H, d, J=2.6 Hz)

EXAMPLE 585

To a solution of 4-[3-ethoxy-1-(4-methoxyphenyl)-1H-pyrazol-5-yl]phenol (515.5 mg) in DMF (5 ml) was added sodium hydride 60% dispersion in mineral oil (79.7 mg) at 3° C. The mixture was stirred at ambient temperature for 40 minutes. To the reaction mixture was added a solution of tert-butyl (2-bromoethyl)carbamate (558 mg) in DMF (2 ml). The mixture was stirred at 60° C. for 24 hours. The reaction mixture was poured into ice water and was extracted with AcOEt. The organic layer was washed with saturated aqueous sodium chloride solution, dried over magnesium sulfate, and concentrated in vacuo. The residue was crystallized from AcOEt, collected and washed with IPE to give 1st crop of tert-butyl (2-{4-[3-ethoxy-1-(4-methoxyphenyl)-1H-pyrazol-5-yl]phenoxy}ethyl)carbamate (344 mg) as a white powder. The mother liqour was concentrated in vacuo and purified by silica gel column chromatography eluted with AcOEt/CHCl3=10% to give 2nd crop of tert-butyl (2-{4-[3-ethoxy-1-(4-methoxyphenyl)-1H-pyrazol-5-yl]phenoxy}ethyl)carbamate (218 mg ) as a powder.

Mass (ESI+): 454 (M+H)+

200 MHz 1H NMR (CDCl3, d): 1.42 (3H, t, J=7.1 Hz), 1.45 (9H, s), 3.48–3.57 (2H, m), 3.80 (3H, s), 3.97–4.03 (2H, m), 4.29 (2H, q, J=7.1 Hz), 5.87 (1H, s), 6.79 (2H, d, J=9.0 Hz), 6.82 (2H, d, J=8.9 Hz), 7.00–7.19 (4H, m)

EXAMPLE 586

A suspension of 5-[4-(benzyloxy)phenyl]-3-hydroxy-1-(4-methoxyphenyl)-1H-pyrazole (1.5 g), 1-bromo-2-methylpropane (2.76 g) and anhydrous potassium carbonate (1.67 g) in DMF (10 ml) was added stirred at 100° C. for 1 hour. The mixture was poured into ice water and extracted with AcOEt. The organic layer was washed with H2O, saturated aqueous sodium chloride solution, dried over magnesium sulfate, and concentrated invacuo. The residue was purified by silica gel column chromatography eluted with AcOEt/n-hexane=30% to give 5-[4-(benzyloxy)phenyl]-3-isobutoxy-1-(4-methoxyphenyl)-1H-pyrazole (1.64 g) as a solid.

powder

Mass (ESI+): 429 (M+H)+

200 MHz 1H NMR (CDCl3, d): 1.03 (6H, d, J=6.6 Hz), 2.11 (1H, m), 3.80 (3H, s), 3.99 (2H, d, J=6.6 Hz), 5.04 (2H, s), 5.88 (1H, s), 6.82 (2H, d, J=9.0 Hz), 6.88 (2H, d, J=8.8 Hz), 7.11–7.20 (4H, m), 7.35–7.43 (5H, m)

The following compound(s) was(were) obtained in a similar manner to that of Example 586.

EXAMPLE 587

5-[4-(benzyloxy)phenyl]-3-(2-methoxyethoxy)-1-(4-methoxyphenyl)-1H-pyrazole powder Mass (ESI+): 431 (M+H)+

200 MHz 1H NMR (CDCl3, d): 3.46 (3H, s), 3.73–3.80 (2H, m), 3.79 (3H, s), 4.39–4.44 (2H, m), 5.04 (2H, s), 5.91 (1H, s), 6.83 (2H, d, J=8.9 Hz), 6.87 (2H, d, J=9.0 Hz), 7.10–7.20 (4H, m), 7.34–7.42 (5H, m)

EXAMPLE 588

5-[4-(benzyloxy)phenyl]-3-(2-ethoxyethoxy)-1-(4-methoxyphenyl)-1H-pyrazole oil

Mass (ESI+): 445 (M+H)+

400 MHz 1H NMR (CDCl3, d): 1.25 (3H, t, J=7.0 Hz), 3.61 (2H, q, J=7.0 Hz), 3.79–3.82 (2H, m), 3.80 (3H, s), 4.39–4.42 (2H, m), 5.04 (2H, s), 5.91 (1H, s), 6.82 (2H, d, J=8.9 Hz), 6.88 (2H, d, J=8.7 Hz), 7.12 (2H, d, J=8.7 Hz), 7.17 (2H, d, J=8.9 Hz), 7.36–7.41 (5H, m)

EXAMPLE 589

2-{[5-[4-(benzyloxy)phenyl]-1-(4-methoxyphenyl)-1H-pyrazol-3-yl]oxy}-N,N-dimethylacetamide powder Mass (ESI+): 458 (M+H)+

200 MHz 1 HNMR (DMSO-d6, d): 2.84 (3H, s), 2.97 (3H, s), 3.76 (3H, s), 4.87 (2H, s), 5.09 (2H, s), 6.08 (1H, s), 6.92 (2H, d, J=9.0 Hz), 6.98 (2H, d, J=8.8 Hz), 7.09–7.17 (4H, m), 7.34–7.43 (5H, m)

EXAMPLE 590

5-[5-[4-(benzyloxy)phenyl]-3-(cyclopentyloxy)-1H-pyrazol-1-yl]-2-methoxypyridine solid
MS (ESI+): m/z 442 (M+H)
1HNMR (200 MHz, CDCl3): 1.52–1.98 (8H, m), 3.92 (3H, s), 4.98–5.05 (1H, m), 5.05 (2H, s), 5.88 (1H, s), 6.69 (1H, d, J=8.7 Hz), 6.91 (2H, d, J=8.8 Hz), 7.15 (2H, d, J=8.8 Hz), 7.35–7.43 (5H, m), 7.52 (1H, dd, J=2.7, 8.7 Hz), 8.04 (1H, d, J=2.7 Hz)

EXAMPLE 591

5-[4-(benzyloxy)phenyl]-1-(4-methoxyphenyl)-3-(2,2,2-trifluoroethoxy)-1H-pyrazole oil
MS (ESI+): m/z 455 (M+H)
1HNMR (200 MHz, DMSOd6): 3.76 (3H, s), 4.81 (1H, d, J=9.0 Hz), 4.90 (1H, d, J=9.0 Hz), 5.09 (2H, s), 6.21 (1H, s), 6.91–7.01 (4H, m), 7.13–7.19 (4H, m), 7.34–7.46 (5H, m)

EXAMPLE 592

5-[4-(benzyloxy)phenyl]-3-(2,2-difluoroethoxy)l-1-(4-methoxyphenyl)-1H-pyrazole oil
MS (ESI+): m/z 437 (M+H)
1HNMR (200 MHz, CDCl3): 3.80 (3H, s), 4.46 (2H, dt, J=4.2, 13.5 Hz), 5.04 (2H, s), 5.91 (1H, s), 6.17 (1H, tt, J=4.2, 55.5 Hz), 6.81–6.91 (4H, m), 7.10–7.19 (4H, m), 7.34–7.43 (5H, m)

EXAMPLE 593

5-[5-[4-(benzyloxy)phenyl]-3-(2,2,2-trifluoroethoxy)-1H-pyrazol-1-yl]-2-methoxypyridine oil
Mass (ESI+): 456 (M+H)
1HNMR (200 MHz, CDCl3): 3.93 (3H, s), 4.61 (1H, d, J=8.4 Hz), 4.69 (1H, d, J=8.4 Hz), 5.05 (2H, s), 5.97 (1H, s), 6.71 (1H, d, J=9 Hz), 6.91 (2H, d, J=8.9 Hz), 7.14 (2H, d, J=8.9 Hz), 7.36–7.43 (5H, m), 7.48 (1H, dd, J=2.7, 9 Hz), 8.04 (1H, d, J=2.7 Hz)

EXAMPLE 594

5-[5-[4-(benzyloxy)phenyl]-3-(2,2-difluoroethoxy)-1H-pyrazol-1-yl]-2-methoxypyridine oil
MS (ESI+): m/z 438 (M+H)
1HNMR (200 MHz, CDCl3): 3.93 (3H, s), 4.46 (2H, dt, J=4.2, 13.3 Hz), 5.05 (2H, s), 5.94 (1H, s), 6.16 (1H, tt, J=4.2, 55.4 Hz), 6.71 (1H, d, J=8.8 Hz), 6.91 (2H, d, J=8.8 Hz), 7.14 (2H, d, J=8.8 Hz), 7.35–7.43 (5H, m), 7.48 (1H, dd, J=2.8, 8.8 Hz), 8.04 (1H, d, J=2.8 Hz)

EXAMPLE 595

A suspension of 5-{5-[4-(benzyloxy)phenyl]-3-hydroxy-1H-pyrazol-1-yl}-2-methoxypyridine (800 mg), dimethyl carbonate (0.9 mg) and potassium carbonate (888 mg) in DMF (8 ml) was stirred at 120° C. for 5 hours. The mixture was poured into ice water and extracted with AcOEt. The organic layer was washed with H2O, saturated aqueous sodium chloride solution, dried over magnesium sulfate, and concentrated in vacuo. The residue was purified by silica gel column chromatography eluted with AcOEt/n-hexane=30% to give 5-{5-[4-(benzyloxy)phenyl]-3-methoxy-1H-pyrazol-1-yl}-2-methoxy-pyridine (1.069 g) as a solid.
powder
MS (ESI+): m/z 388 (M+H)+
200 MHz 1H NMR (CDCl3, d): 3.92 (3H, s), 3.97 (3H, s), 5.05 (2H, s), 5.90 (1H, s), 6.71 (1H, d, J=8.7 Hz), 6.91 (2H, d, J=8.9 Hz), 7.14 (2H, d, J=8.9 Hz), 7.35–7.43 (5H, m), 7.52 (1H, dd, J=2.6, 8.7 Hz), 8.05 (1H, d, J=2.6 Hz)

EXAMPLE 596

A solution of 4,4,4-trifluoro-1-[4-(2-hydroxy-ethyl)phenyl]-1,3-butanedione (670 mg) and (4-nitrophenyl)hydrazine hydrochloride (439 mg) in AcOH (5 ml) and H2O (0.5 ml) was stirred at ambient temperature overnight. The mixture was concentrated in vacuo, and the residue was partitioned between AcOEt and 1M HCl. The organic layer was washed with 1M HCl for two times, saturated aqueous sodium bicarbonate solution for three times, and saturated aqueous sodium chloride solution, dried over magnesium sulfate, and concentrated in vacuo. The residue was purified by silica gel column chromatography eluted with AcOEt/n-hexane=10% and 15% to give 2-{4-[1-(4-nitrophenyl)-3-(trifluoromethyl)-1H-pyrazol-5-yl]phenyl}ethyl acetate (501 mg) as an oil.
MS (ESI+): m/z 420 (M+H)+, 442 (M+Na)+
200 MHz 1H NMR (DMSO-d6, d): 1.96 (3H, s), 2.91 (2H, t, J=6.8 Hz), 4.22 (2H, t, J=6.8 Hz), 7.22–7.37 (5H, m), 7.61 (2H, d, J=9.0 Hz), 8.30 (2H, d, J=9.0 Hz)
The following compound(s) was(were) obtained in a similar manner to that of Example 596.

EXAMPLE 597

5-[4-(benzyloxy)phenyl]-1-(4-methoxyphenyl)-4-methyl-3-(trifluoromethyl)-1H-pyrazole
MASS (ESI+): m/z=439.1 (M+1), 461.2 (M+Na).
1HNMR (400 MHz, CDCl3): 2.15 (3H, s), 3.79 (3H, s), 5.06 (2H, s), 6.8 (2H, d, J=8.9 Hz), 6.95 (2H, d, J=8.7 Hz), 7.07 (2H, d, J=8.7 Hz), 7.14 (2H, d, J=8.9 Hz), 7.342–7.44 (5H, m).

EXAMPLE 598

2-{4-[3-(difluoromethyl)-1-(6-methoxy-3-pyridinyl)-1H-pyrazol-5-yl]phenyl}ethyl acetate
MASS (ESI+): m/z=346.1 (M-Ac+2), 388.1 (M+1).
1HNMR (400 MHz, CDCl3): 2.04 (3H, s), 2.94 (2H, t, J=7 Hz), 3.94 (3H, s), 4.28 (2H, t, J=7 Hz), 6.72 (1H, s), 6.77 (1H, t, J=55 Hz), 6.75 (1H, d, J=8.8 Hz), 7.17 (2H, d, J=8.5 Hz), 7.22 (2H, d, J=8.5 Hz), 7.54 (1H, dd, J=3.9, 8.8 Hz), 8.08 (1H, d, J=3.9 Hz)

EXAMPLE 599

To a solution of ammonium chloride 58.8 mg in H2O 0.5 ml was added iron powder 368 mg and EtOH 2 ml. The reaction mixture was warmed in oil bath, and a solution of 2-{4-[1-(4-nitrophenyl)-3-(trifluoromethyl)-1H-pyrazol-5-yl]phenyl}ethyl acetate 460.7 mg in EtOH 3 ml was added. After being refluxed for 3 hours, the reaction mixture was cooled to ambient temperature and unsoluble matter was removed by filtration. The filtrate was concentrated in vacuo. The residue was dissolved in AcOEt, and washed with saturated aqueous sodium bicarbonate solution and saturated aqueous sodium chloride solution, dried over magnesium sulfate, and concentrated in vacuo. The residue was recrystallized from IPE to give 2-{4-[1-(4-aminophenyl)-3-(trifluoro-methyl)-1H-pyrazol-5-yl]phenyl}ethyl acetate 182.3 mg as a powder.

MS (ESI+): m/z 390 (M+H)+

200 MHz 1H NMR (DMSO-d6, d): 1.96 (3H, s), 2.87 (2H, t, J=6.8 Hz), 4.20 (2H, t, J=6.8 Hz), 5.46 (2H, s), 6.54 (2H, d, J=8.7 Hz), 6.95 (2H, d, J=8.7 Hz), 7.07 (1H, s), 7.18–7.28 (4H, m)

EXAMPLE 600

A mixture of 2-{4-[1-(4-aminophenyl)-3-(trifluoromethyl)-1H-pyrazol-5-yl]phenyl}ethyl acetate 165.6 mg and 2,5-dimethoxytetrahydrofuran 112 mg in AcOH 3 ml was stirred at 50° C. for 3 hours. 2,5-Dimethoxytetrahydrofuran 0.22 ml was added and the mixture was stirred at 50° C. for 2 hours. The mixture was partitioned between ethyl acetate and H2O. The organic layer was washed with saturated aqueous sodium bicarbonate solution and saturated aqueous sodium chloride solution, dried over magnesium sulfate, and concentrated in vacuo. The residue was purified by preparative thin layer silica gel chromatography developed by AcOEt/n-hexane=20%. The separated silica gel was extracted with 10% MeOH/CHCl3 and the solvent was evaporated in vacuo to give 2-{4-[1-[4-(1H-pyrrol-1-yl)phenyl]-3-(trifluoromethyl)-1H-pyrazol-5-yl]phenyl}ethyl acetate 136.1 mg as an oil.

MS (ESI+): m/z 440 (M+H)+

200 MHz 1H NMR (DMSO-d6, d): 1.95 (3H, s), 2.88 (2H, t, J=6.8 Hz), 4.20 (2H, t, J=6.8 Hz), 6.29 (2H, t, J=2.0 Hz), 7.18 (1H, s), 7.23–7.32 (4H, m), 7.39–7.47 (4H, m), 7.69 (2H, d, J=8.8 Hz)

EXAMPLE 601

1M NaOH (436 µl) was added to a solution of 2-{4-[1-[4-(1H-pyrrol-1-yl)phenyl]-3-(trifluoromethyl)-1H-pyrazol-5-yl]phenyl}ethyl acetate (128 mg) in THF (1.5 ml) and MeOH (0.3 ml) under ice bath cooling. The mixture was stirred at 0° C.~ambient temperature for 2 hours. The mixture was neutralized with 1M HCl (436 µl), and was partitioned between AcOEt and H2O. The organic layer was washed with saturated aqueous sodium chloride solution, dried over magnesium sulfate, and concentrated in vacuo. The residue was purified by preparative thin layer silica gel chromatography developed by AcOEt/n-hexane=50%. The separated silica gel was extracted with 10% MeOH/CHCl3 and the solvent was evaporated in vacuo to give 2-{4-[1-[4-(1H-pyrrol-1-yl)phenyl]-3-(trifluoromethyl)-1H-pyrazol-5-yl]phenyl}ethanol (96.5 mg) as an amorphous powder.

IR (KBr): 3404, 2924, 2883, 1612, 1522 cm−1

MS (ESI+): m/z 398 (M+H)+

200 MHz 1H NMR (DMSO-d6, d): 2.67–2.75 (2H, m), 3.55–3.65 (2H, m), 4.64 (1H, t, J=5.1 Hz), 6.30 (2H, t, J=2.0 Hz), 7.16 (1H, s), 7.19–7.28 (4H, m), 7.40–7.48 (4H, m), 7.70 (2H, d, J=8.9 Hz)

EXAMPLE 602

A mixture of 10% Pd-C 50% wet (100 mg) and ethyl 5-(4-cyanophenyl)-1-(4-methoxyphenyl)-1H-pyrazol-3-carboxylate (1 g) in THF (10 ml), MeOH (5 ml), and 1M HCl (2.9 ml) was hydrogenated under H2 latmat ambient temperature for 6.5 hours. The catalyst was filtered off through a celite pad and the pad was washed with MeOH. The filtrate and combined washings were concentrated in vacuo. The residue was dissolved in EtOH and concentrated in vacuo. The residue was crystallized from AcOEt to give ethyl 5-[4-(aminomethyl)phenyl]-1-(4-methoxyphenyl)-1H-pyrazole-3-carboxylate hydrochloride (984 mg) as a powder.

MS (ESI+): m/z 352 (M+H)+

1HNMR (DMSO-d6) δ 1.32 (3H, t, J=7.1 Hz), 3.80 (3H, s), 4.01 (2H, s), 4.33 (2H, q, J=7.1 Hz), 7.00 (2H, d, J=9.0 Hz), 7.14 (1H, s), 7.28 (2H, d, J=9.0 Hz), 7.31 (2H, d, J=8.3 Hz), 7.47 (2H, d, J=8.3 Hz), 8.30 (2H, brs)

The following compound(s) was(were) obtained in a similar manner to that of Example 602.

EXAMPLE 603 ethyl 5-[4-(aminomethyl)phenyl]-1-(6-methoxy-3-pyridinyl)-1H-pyrazole-3-carboxylate dihydrochloride powder MS (ESI+): m/z 353 (M+H)

1HNMR (200 MHz, DMSOd6): 1.32 (3H, t, J=7.1 Hz), 3.88 (3H, s), 3.97–4.06 (2H, m), 4.34 (2H, q, J=7.1 Hz), 6.94 (1H, d, J=8.7 Hz), 7.17 (1H, s), 7.35 (2H, d, J=8.2 Hz), 7.51 (2H, d, J=8.2 Hz), 7.78 (1H, dd, J=2.7, 8.7 Hz), 8.15 (1H, d, J=2.7 Hz), 8.47 (2H, brs)

EXAMPLE 604

{4-[3-methoxy-1-(4-methoxyphenyl)-1H-pyrazol-5-yl]-benzyl}amine hydrochloride oil MS (ESI+): m/z 310 (M+H)

1HNMR (200 MHz, DMSOd6): 3.76 (3H, s), 3.85 (3H, s), 3.91–4.26 (2H, m), 6.16 (1H, s), 6.93 (2H, d, J=8.9 Hz), 7.16 (2H, d, J=8.9 Hz), 7.26 (2H, d, J=8.2 Hz), 7.45 (2H, d, J=8.2 Hz), 8.41 (2H, brs)

EXAMPLE 605

{4-[3-isopropoxy-1-(4-methoxyphenyl)-1H-pyrazol-5-yl]benzyl}amine hydrochloride powder MS (ESI+): m/z 338 (M+H)

1HNMR (200 MHz, DMSOd6): 1.32 (6H, d, J=6.2 Hz), 3.76 (3H, s), 4.00 (2H, s), 4.77 (1H, m), 6.11 (1H, s), 6.93 (2H, d, J=8.9 Hz), 7.15 (2H, d, J=8.9 Hz), 7.25 (2H, d, J=8.2 Hz), 7.44 (2H, d, J=8.2 Hz), 8.31 (2H, brs)

EXAMPLE 606

Et3N (326 mg) and then a solution of di-tert-butyl dicarbonate (594 mg) in CH2Cl2 (3 ml) was added successively to a suspension of ethyl 5-[4-(aminomethyl)phenyl]-1-(4-methoxyphenyl)-1H-pyrazole-3-carboxylate hydrochloride (960 mg) in CH2Cl2 (9 ml). After stirring at ambient temperature for 1 hour, the reaction mixture was concentrated in vacuo. The residue was partitioned between ethyl acetate and 1M HCl. The organic layer was washed with saturated aqueous sodium bicarbonate solution and saturated aqueous sodium chloride solution, dried over magnesium sulfate, and concentrated in vacuo. The residue was recrystallized from AcOEt/n-hexane to give ethyl 5-(4-{[(tert-butoxy-carbonyl)amino]methyl}phenyl)-1-(4-methoxyphenyl)-1H-pyrazole-3-carboxylate (1.045 g) as a powder.

MS (ESI+): m/z 452 (M+H)+

1H NMR (DMSO-d6) δ 1.31 (3H, t, J=7.1 Hz), 1.38 (9H, s), 3.79 (3H, s), 4.11 (2H, d, J=6.2 Hz), 4.32 (2H, q, J=7.1 Hz), 6.99 (2H, d, J=8.9 Hz), 7.07 (1H, s), 7.20 (4H, s), 7.26 (2H, d, J=8.9 Hz), 7.40 (1H, t, J=6.2 Hz)

The following compound(s) was(were) obtained in a similar manner to that of Example 606.

EXAMPLE 607 ethyl 5-(4-{[(tert-butoxycarbonyl)amino]methyl}phenyl)-1-(6-methoxy-3-pyridinyl)-1H-pyrazole-3-carboxylate powder Mass (ESI+): m/z 453 (M+H)

1HNMR (200 MHz, DMSOd6): 1.32 (3H, t, J=7.1 Hz), 1.38 (9H, s), 3.88 (3H, s), 4.12 (2H, d, J=6.1 Hz), 4.33 (2H, q, J=7.1 Hz), 6.92 (1H, d, J=8.9 Hz), 7.10 (1H, s), 7.19–7.28 (4H, m), 7.41 (1H, t, J=6.0 Hz), 7.74 (1H, dd, J=2.7, 8.9 Hz), 8.14 (1H, d, J=2.7 Hz)

EXAMPLE 608

A mixture of ethyl 5-(4-{[(tert-butoxycarbonyl)amino]methyl}phenyl)-1-(4-methoxyphenyl)-1H-pyrazole-3-carboxylate (500 mg) and sodium methoxide (239 mg) in formamide 5 ml was stirred at 70° C. for 2 hours. The mixture was cooled to ambient temperature and partitioned between AcOEt and brine. The organic layer was washed with saturated aqueous sodium chloride solution, dried over magnesium sulfate, and concentrated in vacuo to give tert-butyl {4-[3-(aminocarbonyl)-1-(4-methoxyphenyl)-1H-pyrazol-5-yl]benzyl}carbamate (512 mg) as an oil.

MS (ESI+): m/z 423 (M+H)+

1H NMR (DMSO-d6) δ 1.38 (9H, s), 3.78 (3H, s), 4.11 (2H, d, J=6.1 Hz), 6.93 (1H, s), 6.98 (2H, d, J=8.9 Hz), 7.19–7.43 (8H, m), 7.64 (1H, brs)

EXAMPLE 609

Phosphorous oxychloride (0.22 ml) was added to DMF (2 ml) under ice bath cooling. To this solution was added a solution of tert-butyl {4-[3-(aminocarbonyl)-1-(4-methoxyphenyl)-1H-pyrazol-5-yl]benzyl}carbamate (499 mg) in DMF (3 ml) dropwise. The reaction mixture was stirred at 4° C. for 1 hour. Phosphorous oxychloride (0.15 ml) was added and the reaction mixture was stirred at 4° C. for 1 hour. The reaction was quenched by adding saturated aqueous sodium bicarbonate solution. The mixture was extracted with ethyl acetate. The organic layer was washed with saturated aqueous sodium chloride solution, dried over magnesium sulfate, and concentrated in vacuo. The residue was purified by preparative thin layer silica gel chromatography developed by AcOEt/n-hexane=40%. The separated silica gel was extracted with 10% MeOH/CHCl3 and the solvent was evaporated in vacuo to give tert-butyl {4-[3-cyano-1-(4-methoxy-phenyl)-1H-pyrazol-5-yl]benzylcarbamate (136 mg) as an oil.

MS (ESI+): m/z 427 (M+Na)+, (ESI−): m/z 403 (M−H)+

200 MHz 1H NMR (CDCl3, d): 1.46 (9H, s), 3.83 (3H, s), 4.32 (2H, d, J=5.9 Hz), 4.75 (1H, br), 6.83 (1H, s), 6.87 (2H, d, J=9.0 Hz), 7.11–7.26 (6H, m)

EXAMPLE 610

To a solution of 5-[4-(2-{[tert-butyl(dimethyl)-silyl]oxy}ethoxy)phenyl]-1-(4-methoxyphenyl)-4-methyl-3-(trifluoromethyl)-1H-pyrazole (5.2 g) in EtOH (200 ml) was added conc.HCl (20 ml) at room temperature. After stirring for 2 hrs, the reaction mixture was partitioned between EtOAc and water. Organic layer was separated and washed with water, dried over MgSO4, filtered and evaporated. The residue was chromatographed on silica gel (Hex/EtOAc=2:1–1:1) to give 2.05 g (51%) of 2-{4-[1-(4-methoxyphenyl)-4-methyl-3-(trifluoromethyl)-1H-pyrazol-5-yl]phenoxy}ethanol as a crystal.

MASS (ESI+): e/z=415.1 (M+Na).

1HNMR (400 MHz, CDCl3): 2.15 (3H, s), 1.99 (1H, t, J=6.2 Hz), 2.15 (3H, s), 3.95–4.00 (2H, m), 4.08–4.10 (2H, m), 6.80 (2H, d, J=9 Hz), 6.90 (2H, d, J=8.8 Hz), 7.08 (2H, d, J=8.8 Hz), 7.13 (2H, d, J=9 Hz).

EXAMPLE 611

To solution of 4-[1-[4-(methylthio)phenyl]-3-(trifluoromethyl)-1H-pyrazol-5yl]phenol (5.0 g) in DMF (20 ml) was added NaH (0.75 g) over 25 min under ice cooling (5~20° C.) (gas), stir at 3° C. for 10 min. tert-Butyl N-(2-bromoethyl)carbamate (4.48 g) in DMF (5 ml) was added to the mixture over 10 min stir at 60° C. (bath 70° C.) for 6 h and allowed to stand for overnight.

The mixture was poured into water (50 ml) and EtOAc (30 ml), separation and extracted with EtOAc (10 ml). The organic layer was washed with water (25×3) and brine (25 ml), dried MgSO4, evaporated. The residue was column chromatographed on silica gel (75 ml, 15v/w, AcOEt/Hex (2:1–1:1) and evaporated to give 7.0 g of tert-butyl (2-{4-[1-[4-(methylthio)phenyl]-3-(trifluoromethyl)-1H-pyrazol-5-yl]-phenoxy}ethyl)carbamate as an oil.

MASS (ESI+): m/z=516.1 (M+Na).

1HNMR (400 MHz, CDCl3): 1.45 (9H, s), 2.49 (3H, s), 3.49–3.58 (2H, m), 4.02 (2H, t, J=10.2 Hz), 4.97 (1H, b.s), 6.68 (1H, s), 6.84 (2H, d, J=17.5 Hz), 7.14 (2H, d, J=17.5 Hz), 7.21 (4H, s).

The following compound(s) was(were) obtained in a similar manner to that of Example 611.

EXAMPLE 612 tert-butyl (2-{4-[1-(4-methoxyphenyl)-4-methyl-3-(trifluoromethyl)-1H-pyrazol-5-yl]phenoxy}ethyl)-carbamate MASS (ESI+): m/z=514.2 (M+Na).

1HNMR (400 MHz, CDCl3): 1.45 (9H, s), 2.15 (3H, s), 3.52–3.56 (2H, m), 3.79 (3H, s), 4.02 (2H, t, J=5.1 Hz), 4.99 (1H, b.s), 6.80 (2H, d, J=9.0 Hz), 6.87 (2H, d, J=8.8 Hz), 7.07 (2H, d, J=8.8 Hz), 7.13 (H, d, J=9.0 Hz)

EXAMPLE 613

To a suspension of (2-{4-[1-[4-(methylthio)phenyl]-3-(trifluoromethyl)-1H-pyrazol-5-yl]phenoxy}ethyl)amine hydrochloride (7.5 g) in H2O (150 ml) and EtOH (75 ml) was added NaOCN (2.27 g) at room temperature. pH was adjusted to 6.3 with 1NHCl. The mixture was stirred for 5 hours under the condition of pH 6.0–7.0. The reaction mixture was extracted with EtOAc and washed with dil. NaCl (twice), dried over MgSO4, filtered and evaporated. The residue was column chromatographed on silica gel (CH2Cl2/MeOH) and evaporated. The residue was crytalized from IPE/EtOH. Recrystalized from EtOH/H2O (50 ml–50 ml Final) and dried to give 4.10 g (54%) of N-(2-{4-[1-[4-(methylthio)phenyl]-3-(trifluoromethyl)-1H-pyrazol-5-yl]phenoxy}ethyl)urea.

MASS (ESI+): m/z=459.1 (m+Na)

1HNMR (400 MHz, DMSOd6): 2.05 (3H, s), 3.33 (2H, q, J=5.6 Hz), 3.95 (2H, t, J=5.6 Hz), 5.54 (2H, b.s), 6.16 (1H, t, J=5.6 Hz), 6.96 (2H, d, J=8.8 Hz), 7.09 (1H, s), 7.22 (2H, d, J=8.6 Hz), 7.27 (2H, d, J=8.7 Hz), 7.32 (2H, d, J=8.7 Hz).

HORIBA FT-IR for Windows Ver. 4.08 (cm−1): 3399.89, 3197.40, 1650.77, 1614.13, 1554.34, 1475.28, 1459.85, 1442.49, 1232.29, 1160.94, 1126.22, 1087.66, 1049.09, 970.019, 827.312.

The following compound(s) was(were) obtained in a similar manner to that of Example 613.

EXAMPLE 614

N-(2-{4-[1-(4-methoxyphenyl)-4-methyl-3-(trifluoromethyl)-1H-pyrazol-5-yl]phenoxy}ethyl)urea mp: 150.5–151.1° C.

MASS (ESI+): m/z=457.2 (m+Na).

1HNMR (400 MHz, CDCl3): 2.15 (3H, s), 3.6 (2H, dt, J=5, 5.4 Hz), 3.78 (3H, s), 4.04 (2H, t, J=5 Hz), 4.5 (2H, b.s), 5.08 (1H, t, J=5.4 Hz), 6.8 (2H, d, J=9 Hz), 6.86 (2H, d, J=8.8 Hz), 7.07 (2H, d, J=8.8 Hz), 7.13 (2H, d, J=9 Hz).

EXAMPLE 615

N-[2-(4-{3-(difluoromethyl)-1-[4-(methylthio)phenyl]-1H-pyrazol-5-yl}phenoxy)ethyl]urea mp: 184.3–184.7° C.

MASS (ESI+): m/z=441.1 (M+Na).

1HNMR (400 MHz, DMSOd6): 2.5 (3H, s), 3.33 (2H, dt, J=5.6, 6.3 Hz), 3.95 (2H, t, J=5.6 Hz), 5.53 (2H, b.s), 6.15 (1H, t, J=6.3 Hz), 6.85 (1H, s), 6.95 (2H, d, J=8.7 Hz), 7.09 (1H, t, J=54.1 Hz), 7.2 (2H, d, J=8.7 Hz), 7.23 (2H, d, J=8.7 Hz), 7.3 (2H, d, J=8.7 Hz).

EXAMPLE 616

N-(2-{4-[3-(difluoromethyl)-1-(6-methoxy-3-pyridinyl)-1H-pyrazol-5-yl]phenyl}ethyl)urea mp: 194–196 ° C.

MASS (ESI+): m/z=410.2 (M+Na).

1HNMR (400 MHz, DMSOd6): 2.68 (2H, t, J=7.3 Hz), 3.19 (2H, dt, J=5.6, 7.3 Hz)) 3.88 (3H, s), 5.42 (2H, b.s), 5.95 (1H, t, J=5.6 Hz), 6.91 (1H, d, J=8.8 Hz), 6.93 (1H, s), 7.11 (1H, t, J=54.4 Hz), 7.23 (4H, s), 7.7 (1H, dd, J=2.8, 8.8 Hz), 8.15 (1H, d, J=2.8 Hz) ).

EXAMPLE 617

N-{4-[1-(6-methoxy-3-pyridinyl)-3-(trifluoromethyl)-1H-pyrazol-5-yl]benzyl}urea

Crystal. mp: 147–149° C.

MASS (ESI+): m/z=414.1 (M+Na).

1HNMR (400 MHz, CDCl3): 3.93 (3H, s), 4.37 (2H, d, J=6 Hz), 4.52 (2H, b.s), 5.08 (1H, t, J=6 Hz), 6.73 (1H, s), 6.77 (1H, d, J=8.8 Hz), 7.18 (2H, d, J=8.3 Hz), 7.27 (2H, d, J=8.3 Hz), 7.59 (1H, dd, J=2.7, 8.8 Hz), 8.03 (1H, d, J=2.7 Hz).

EXAMPLE 618

N-{4-[3-(difluoromethyl)-1-(6-methoxy-3-pyridinyl)-1H-pyrazol-5-yl]benzyl}urea

MASS (ESI+): m/z=396.1 (m+Na).

1HNMR (400 MHz, DMSOd6): 3.87 (3H, s), 4.17 (2H, d, J=6 Hz), 5.55 (2H, b.s), 6.45 (1H, t, J=6 Hz), 6.91 (1H, d, J=8.8 Hz), 6.94 (1H, s), 7.11 (1H, t, J=53.2 Hz), 7.27 (4H, s), 7.71 (1H, dd, J=2.7, 8.8 Hz), 8.14 (1H, d, J=2.7 Hz).

EXAMPLE 619

A mixture of N-(2-{4-[1-[4-(methylthio)phenyl]-3-(trifluoromethyl)-1H-pyrazol-5-yl]phenoxy}ethyl)urea (250 mg) and mCPBA (326 mg) in CH2Cl2 (10 ml) was stirred for 18 hrs. sat. NaHCO3 and CH2Cl2 was added. Aqueous layer was separated and extracted. The combined organic layer was washed with sat. NaHCO3 (twice), dried and evaporated to give 207 mg (79.9%) of crude product. The crude product was column chromatographed by preparative TLC to give 207 mg (80%) of N-(2-{4-[1-[4-(methylsulfinyl)phenyl]-3-(trifluoromethyl)-1H-pyrazol-5-yl]phenoxy}ethyl)urea as an amorphous.

MASS (ESI+): 475.1 (m+Na).

1HNMR (400 MHz, DMSOd6): 2.79 (3H, s), 3.3–3.34 (2H, m), 3.95 (2H, t, J=5.6 Hz), 5.53 (2H, b.s), 6.15 (1H, t, J=5.6 Hz), 6.97 (2H, d, J=8.8 Hz), 7.16 (1H, s), 7.23 (2H, d, J=8.8 Hz), 7.55 (2H, d, J=8.6 Hz), 7.77 (2H, d, J=8.6 Hz).

EXAMPLE 620

A mixture of N-(2-{4-[1-[4-(methylthio)phenyl]-3-(trifluoromethyl)-1H-pyrazol-5-yl]phenoxy}ethyl)urea (250 mg) and mCPBA (326 mg) in CH2Cl2 (10 ml) was stirred for 18 hrs. sat. NaHCO3 and CH2Cl2 was added. Aqueous layer was separated and extracted. The combined organic layer was washed with sat. NaHCO3 (twice), dried and evaporated to give 207 mg (79.9%) of crude product. The crude product was column chromatographed by preparative TLC to give 116 mg (43%) of N-(2-{4-[1-[4-(methylsulfonyl)phenyl]-3-(trifluoromethyl)-1H-pyrazol-5-yl]phenoxy}ethyl)urea as a amorphous.

MASS (ESI+): m/z=491.0 (m+Na).

1HNMR (400 MHz, DMSOd6): 3.28 (3H, s), 3.28–3.34 (2H, m), 3.96 (2H, t, J=5.4 Hz), 5.54 (2H, b.s), 6.16 (1H, t, J=5.4 Hz), 6.99 (2H, d, J=8.4 Hz), 7.18 (1H, s), 7.25 (2H, d, J=8.4 Hz), 7.61 (2H, d, J=8.4 Hz), 8.01 (2H, d, J=8.4 Hz).

EXAMPLE 621

To a solution of 2-{4-[3-(difluoromethyl)-1-(6-methoxy-3-pyridinyl)-1H-pyrazol-5-yl]phenyl}ethyl acetate (10 g) in THF (120 ml) and MeOH (30 ml) was added 1NNaOH (60 ml) at room temperature. The reaction mixture was stirred at the same temperature for 4 hrs, and then neutralized with 1NHCl (60 ml), evaporated, and extracted twice with EtOAc. The organic layer was washed with water and brine, dried over MgSO4, filtered and evaporated to give crude product. The residue was column chromatographed on silica gel and crystalized from IPE and filtered to give 3.0 g of 2-{4-[3-(difluoromethyl)-1-(6-methoxy-3-pyridinyl)-1-H-pyrazol-5-yl]phenyl}ethanol. The filtrate was evaporated and filtered to give 4.65 g of second crystal.

MASS (ESI+): m/z=368.2 (M+Na).

1HNMR (400 MHz, CDCl3): 1.49 (1H, t, J=5.8 Hz), 2.87 (2H, t, J=6.5 Hz), 3.88 (2H, dt, J=5.8, 6.5 Hz), 6.71 (1H, s), 6.76 (1H, t, J=55 Hz), 6.75 (1H, d, J=8.8 Hz), 7.17 (2H, d, J=8.4 Hz), 7.21 (2H, d, J=8.4 Hz), 7.55 (1H, dd, J=2.8, 8.8 Hz), 8.08 (1H, d, J=2.8 Hz).

EXAMPLE 622

To a solution of 2-{4-[3-(difluoromethyl)-1-(6-methoxy-3-pyridinyl)-1-H-pyrazol-5-yl]phenyl}ethanol (7.4 g) and Et3N (4.5 ml) in CH2Cl2 (75 ml) was added MsCl (2.5 ml) under ice-cooling. After stirring for 1 hour, the reaction mixture was quenched with water, separated. The aqueous layer was extracted with CH2Cl2 and combined organic layer was washed with water and brine, dried over MgSO4, filtered and evaporated under reduced pressure to give 10.5 g (quant) of 2-{4-[3-(difluoromethyl)-1-(6-methoxy-3-pyridinyl)-1-H-pyrazol-5-yl]phenyl}ethyl methanesulfonate as an oil.

MASS (ESI+): m/z=446.1 (M+Na).

1HNMR (400 MHz, CDCl3): 2.9 (3H, s), 3.06 (2H, t, J=6.8 Hz), 3.94 (3H, s), 4.42 (2H, t, J=6.8 Hz), 6.73 (1H, s), 6.76 (1H, d, J=8.8 Hz), 6.77 (1H, t, J=55 Hz), 7.19 (2H, d, J=8.6 Hz), 7.23 (2H, d, J=8.6 Hz), 7.55 (1H, dd, J=2.6, 8.8 Hz), 8.04 (1H, d, J=2.6 Hz).

EXAMPLE 623

A mixture of 2-{4-[3-(difluoromethyl)-1-(6-methoxy-3-pyridinyl)-1H-pyrazol-5-yl]phenyl}ethyl methanesulfonate (7.4 g) and Ph(CO)2NK (3.88 g) in DMF (50 ml) was stirred at 60° C. for 8 hours. Added water. The organic layer was extracted twice with EtOAc. Aqueous layer was washed with water (twice) and brine, dried over MgSO4, filtered, and evaporated under reduced pressure. The residue was triturated with IPE, filtered and dried to give 7.65 g of 2-(2-{4-[3-(difluoromethyl)-1-(6-methoxy-3-pyridinyl)-1H-pyrazol-5-yl]phenyl}ethyl)-1H-isoindole-1,3 (2H)-dione as a solid.

MASS (ESI+): 475.2 (M+1), 497.2 (M+Na).

1HNMR (400 MHz, CDCl3): 3 (2H, t, J=7.6 Hz), 3.92 (2H, t, J=7.6 Hz), 3.95 (3H, s), 6.7 (1H, s), 6.73 (1H, d, J=8.8 Hz), 6.76 (1H, t, J=55 Hz), 7.14 (2H, d, J=8.1 Hz), 7.22 (2H, d, J=8.1 Hz), 7.46 (1H, dd, J=2.7, 8.8 Hz), 7.71–7.73 (2H, m), 7.83–7.85 (2H, m), 8.1 (1H, d, J=2.7 Hz).

EXAMPLE 624

A mixture of 2- (2-{4-[3-(difluoromethyl)-1-(6-methoxy-3-pyridinyl)-1H-pyrazol-5-yl]phenyl}ethyl)-1H-isoindole-1,3 (2H)-dion (5.0 g) and NH2NH2 (2.8 ml) in CH3CN (50 ml) was stirred at 60° C. for 8 hours. The reaction mixture was filtered. Filtrate was evaporated under reduced pressure. 4N HCl/Dioxane and then IPE was added. The product was triturated, filtered and died under reduced pressure to give 3.94 g (90%) of (2-{4-[3-(difluoromethyl)-1-(6-methoxy-3-pyridinyl)-1H-pyrazol-5-yl]phenyl}ethyl)amine dihydrochloride as a solid.

MASS (ESI+): m/z=345.2 (M(free)+1).

1HNMR (400 MHz, DMSOd6): 2.9–2.95 (2H, m), 3.01–3.06 (2H, m), 3.88 (3H, s), 6.92 (1H, d, J=8.8 Hz), 6.95 (1H, s), 7.13 (1H, t, J=56.1 Hz), 7.27 (2H, d, J=8.4 Hz), 7.3 (2H, d, J=8.4 Hz), 7.72 (1H, dd, J=2.8, 8.8 Hz), 8.15 (1H, d, J=2.8 Hz).

The following compound(s) was(were) obtained in a similar manner to that of Example 602.

EXAMPLE 625

{4-[1-(6-methoxy-3-pyridinyl)-3-(trifluoromethyl)-1H-pyrazol-5-yl]benzyl}amine dihydrochloride MASS (ESI+): m/z=332.2 (M-NH2), 349.1 (M+H).

1HNMR (400 MHz, DMSOd6): 3.88 (3H, s), 6.94 (1H, d, J=9.6 Hz), 7.25 (1H, s), 7.37 (2H, d, J=8 Hz), 7.53 (2H, d, J=8 Hz), 7.8 (1H, dd, J=2.9, 9.6 Hz), 8.45 (1H, d, J=2.8 Hz).

EXAMPLE 626

{4-[3-(difluoromethyl)-1-(6-methoxy-3-pyridinyl)-1H-pyrazol-5-yl]-benzyl}amine hydrochloride MASS (ESI+): m/z=314.2 (M-NH2), 331.1 (M+1).

1HNMR (400 MHz, DMSOd6): 3.88 (3H, s), 6.93 (1H, d, J=8.8 Hz), 7.00 (1H, s), 7.14 (1H, t, J=54 Hz), 7.35 (2H, d, J=8.2 Hz), 7.53 (2H, d, J=8.2 Hz), 7.75 (1H, dd, J=2.7, 8.8 Hz), 8.15 (1H, d, J=2.7 Hz) )

EXAMPLE 627

To a solution of 5-hydrazino-2-methoxypyridine dihydrochloride (4.78 g) and Et3N (7.01 g) in EtOH (50 ml) was added {(2R, 3S)-3-[4-(benzyloxy)phenyl]-2-oxiranyl}-(cyclopropyl)methanone (5.10 g) and refluxed for 9 hours.

THs mixture was concentrated in vacuo. To the residue were added AcOEt and 1M HCl, and unsoluble matter was filtered off through a celit pad. The filtrate was partitioned, and the organic lauer was washed with saturated aqueous sodium bicarbonate solution, dried over magnesium sulfate, and concentrated in vacuo. The residue was dissolved in CH2Cl2 (50 ml). To this solution were added Et3N (5.26 g) and methanesulfonyl chloride (2.98 g) successively under ice-bath cooling. The mixture was stirred at ambient temperature for 2 hours. The mixture was washed with 1M HCl, saturated aqueous sodium bicarbonate solution, and saturated aqueous sodium chloride solution, dried over magnesium sulfate, and concentrated in vacuo. The residue was purified by silica gel column chromatography eluted with AcOEt/n-hexane=20% to give 5-{5-[4-(benzyloxy)phenyl]-3-cyclopropyl-1-H-pyrazol-1-yl}-2-methoxypyridine (4.20 g) as a solid.

MS (ESI+): m/z 398 (M+H)

1HNMR (200 MHz, DMSOd6): 0.69–0.78 (2H, m), 0.87–0.97 (2H, m), 1.89–1.99 (1H, m), 3.85 (3H, s), 5.09 (2H, s), 6.30 (1H, s), 6.85 (1H, d, J=8.8 Hz), 6.99 (2H, d, J=8.8 Hz), 7.15 (2H, d, J=8.8 Hz), 7.34–7.46 (5H, m), 7.60 (1H, dd, J=2.7, 8.8 Hz)), 8.01 (1H, d, J=2.7 Hz)

EXAMPLE 628

To a mixture of tert-butyl (2-{4-[1-(4-methoxyphenyl)-3-carboxy-1-H-pyrazol-5-yl]phenoxy}ethyl)carbamate (313.9 mg), piperidine (88.4 mg), and 1-hydroxybenzotriazole (140 mg) in DMF 3 ml was added water soluble carbodiimide hydrochloride (199 mg) under ice-bath cooling. The mixture was stirred at ambient temperature overnight, then was partitioned between AcOEt and H2O. The organic layer was separated, washed with 1M HCl, saturated aqueous sodium bicarbonate solution and saturated aqueous sodium chloride solution, dried over magnesium sulfate, and concentrated in vacuo. The residue was purified by silica gel column chromatography eluted with AcOEt/n-hexane=70%. The residue was crystallized from IPE to give tert-butyl 2-{4-[1-(4- methoxyphenyl)-3-(1-piperidinyl-carbonyl)-1H-pyrazol-5-yl]phenoxy}ethyl)carbamate (332.5 mg) as a white powder.

MS (ESI+): m/z 521 (M+H)

1HNMR (200 MHz, CDCl3): 1.45 (9H, s), 1.53–1.79 (6H, m), 3.48–3.57 (2H, m), 3.67–3.81 (2H, m), 3.82 (3H, s), 3.88–4.02 (2H, m), 3.98–4.04 (2H, m), 4.96 (1H, brs), 6.77 (1H, s), 6.81 (2H, d, J=8.8 Hz), 6.86 (2H, d, J=9.0 Hz), 7.15 (2H, d, J=8.8 Hz), 7.21 (2H, d, J=9.0 Hz)

The following compound(s) was(were) obtained in a similar manner to that of Example 628.

EXAMPLE 629 tert-butyl (2-{4-[1-(6-methoxy-3-pyridinyl)-3-(1-piperidinylcarbonyl)-1H-pyrazol-5-yl]phenoxy}ethyl)-carbamate powder MS (ESI+): m/z 522 (M+H)

1HNMR (200 MHz, CDCl3): 1.45 (9H, s), 1.54–1.78 (6H, m), 3.49–3.57 (2H, m), 3.69–3.82 (2H, m), 3.86–3.99 (2H, m), 3.94 (3H, s), 3.99–4.05 (2H, m), 4.96 (1H, s), 6.73 (1H, d, J=8.8 Hz), 6.79 (1H, s), 6.84 (2H, d, J=8.8 Hz), 7.16 (2H, d, J=8.8 Hz), 7.50 (1H, dd, J=2.7, 8.8 Hz), 8.12 (1H, d, J=2.7 Hz)

EXAMPLE 630 tert-butyl (2-{4-[3-{[ethyl(methyl)amino]carbonyl}-1-(6-methoxy-3-pyridinyl)-1H-pyrazol-5-yl]phenoxy}-ethyl)carbamate powder Mass (ESI+): m/z 496 (M+H)

1HNMR (200 MHz, DMSOd6): 1.08–1.22 (3H, m), 1.37 (9H, s), 2.98, 3.29 (3H, s), 3.23–3.32 (2H, m), 3.42–3.53, 3.63–3.75 (2H, m), 3.87 (3H, s), 3.93–4.00 (2H, m), 6.82, 6.84 (1H, s), 6.87–7.00 (4H, m), 7.21 (2H, d, J=8.6 Hz), 7.61–7.72 (1H, m), 8.13–8.15 (1H, m)

EXAMPLE 631

2-{4-[1-(4-methoxyphenyl)-3-(1-piperidinylcarbonyl)-1H-pyrazol-5-yl]phenoxy}ethanol mp. 121.9–123.8° C.

Mass (ESI+): m/z 422 (M+H)

1HNMR (200 MHz, DMSOd6): 1.42–1.74 (6H, m), 3.53–3.70 (2H, m), 3.65–3.73 (2H, m), 3.70–3.92 (2H, m), 3.78 (3H, s), 3.95–4.00 (2H, m), 4.86 (1H, t, J=5.4 Hz), 6.77 (1H, s), 6.91 (2H, d, J=8.8 Hz), 6.98 (2H, d, J=8.9 Hz), 7.16 (2H, d, J=8.8 Hz), 7.23 (2H, d, J=8.9 Hz)

EXAMPLE 632

2-{4-[1-(6-methoxy-3-pyridinyl)-3-(1-piperidinyl-carbonyl)-1-H-pyrazol-5-yl]phenoxy}ethanol mp. 123.4–124.0° C.

Mass (ESI+): m/z 423 (M+H)

1HNMR (200 MHz, DMSOd6): 1.45–1.74 (6H, m), 3.50–3.69 (2H, m), 3.65–3.74 (2H, m), 3.71–3.90 (2H, m), 3.87 (3H, s), 3.96–4.02 (2H, m), 4.86 (1H, t, J=5.4 Hz), 6.81 (1H, s), 6.90 (1H, d, J=8.7 Hz), 6.94 (2H, d, J=8.6 Hz), 7.20 (2H, d, J=8.6 Hz), 7.68 (1H, dd, J=2.7, 8.7 Hz), 8.14 (1H, d, J=2.7 Hz)

EXAMPLE 633 tert-butyl {4-[1-(4-methoxyphenyl)-3-(1-piperidinyl-carbonyl)-1-H-pyrazol-5-yl]benzyl}carbamate amorphous powder MS (ESI+): m/z 491 (M+H)

1HNMR (200 MHz, CDCl3): 1.46 (9H, s), 1.55–1.8 (6H, m), 3.68–3.82 (2H, m), 3.82 (3H, s), 3.97–4.00 (2H, m), 4.31 (2H, d, J=6.0 Hz ), 4.84 (1H, brs), 6.82 (1H, s), 6.86 (2H, d, J=9 Hz), 7.15–7.25 (6H, m)

EXAMPLE 634 tert-butyl {4-[3-{[ethyl(methyl)amino]carbonyl}-1-(4-methoxyphenyl)-1-H-pyrazol-5-yl]benzyl}carbamate amorphous powder MS (ESI+): m/z 465 (M+H)

1HNMR (200 MHz, CDCl3): 1.20–1.31 (3H, m), 1.46 (9H, s), 3.11, 3.40 (3H, s), 3.61, 3.85 (2H, q, J=7.1 Hz), 3.82 (3H, s), 4.31 (2H, d, J=5.8 Hz), 4.86 (1H, brs), 6.81–6.90 (3H, m), 7.16–7.25 (6H, m)

EXAMPLE 635 tert-butyl {4-[3-{[methoxy(methyl)amino]carbonyl}-1-(4-methoxyphenyl)-1H-pyrazol-5-yl]benzyl}carbamate solid MS (ESI+): m/z 467 (M+H)

1HNMR (200 MHz, CDCl3): 1.46 (9H, s), 3.51 (3H, s), 3.82 (3H, s), 3.85 (3H, s), 4.31 (2H, d, J=5.9 Hz), 4.87 (1H, brs), 6.86 (2H, d, J=9.0 Hz), 6.96 (1H, s), 7.15–7.26 (6H, m)

EXAMPLE 636 tert-butyl {4-[1-(6-methoxy-3-pyridinyl)-3-(1-piperidinyl-carbonyl)-1-H-pyrazol-5-yl]benzyl}carbamate oil MS (ESI+): m/z 492 (M+H)

1HNMR (200 MHz, DMSOd6): 1.39 (9H, s), 1.46–1.75 (6H, m), 3.52–3.69 (2H, m), 3.75–3.93 (2H, m), 3.87 (3H, s), 4.13 (2H, d, J=6.1 Hz), 6.86 (1H, s), 6.90 (1H, d, J=8.9 Hz), 7.19–7.28 (4H, m), 7.41 (1H, t, J=6.1 Hz) 7.70 (1H, dd, J=2.7, 8.9 Hz), 8.13 (1H, d, J=2.7 Hz)

EXAMPLE 637 tert-butyl {4-[3-{[ethyl(methyl)amino]carbonyl}-1-(6-methoxy-3-pyridinyl)-1H-pyrazol-5-yl]benzyl}-carbamate oil MS (ESI+): m/z 466 (M+H)

1HNMR (200 MHz, DMSOd6): 1.09–1.22 (3H, m), 1.39 (9H, s), 2.98, 3.28 (3H, s), 3.73–3.77 (2H, m), 3.87 (3H, s), 4.13 (2H, d, J=6.0 Hz), 6.87–6.93 (2H, m), 7.18–7.30 (4H, m), 7.41 (1H, t, J=6.0 Hz ), 7.65–7.74 (1H, m), 8.14 (1H, d, J=2.6 Hz)

EXAMPLE 638 tert-butyl {4-[3-{[methoxy(methyl)amino]carbonyl}-1-(6-methoxy-3-pyridinyl)-1H-pyrazol-5-yl]benzyl}carbamate Powder
MS (ESI+): m/z 468 (M+H)
1HNMR (200 MHz, DMSOd6): 1.39 (9H, s), 3.37 (3H, s), 3.77 (3H, s), 3.87 (3H, s), 4.13 (2H, d, J=6.1 Hz), 6.91 (1H, d, J=8.8 Hz), 6.97 (1H, s), 7.25 (4H, s), 7.42 (1H, t, J=6.1 Hz), 7.71 (1H, dd, J=2.7, 8.8 Hz), 8.15 (1H, d, J=2.7 Hz)

EXAMPLE 639

5-[4-(2-hydroxyethyl)phenyl]-N-methoxy-1-(4-methoxy-phenyl)-N-methyl-1-H-pyrazole-3-carboxamide oil
MS (ESI+): m/z 382 (M+H)
1HNMR (200 MHz, CDCl3): 1.44 (1H, t, J=5.8 Hz), 2.83–2.90 (2H, m), 3.51 (3H, s), 3.82 (3H, s), 3.85 (3H, s), 3.84–3.89 (2H, m), 6.86 (2H, d, J=9.0 Hz), 6.96 (1H, s), 7.13–7.26 (6H, m)

EXAMPLE 640

5-[4-(2-hydroxyethyl)phenyl]-N-methoxy-1-(6-methoxy-3-pyridinyl)-N-methyl-1H-pyrazole-3-carboxamide oil
Mass (ESI+): m/z 383 (M+H)
1HNMR (200 MHz, CDCl3): 2.84–2.91 (2H, m), 3.51 (3H, s), 3.85 (3H, s), 3.81–3.92 (2H, m), 3.95 (3H, s), 6.74 (1H, d, J=8.6 Hz), 6.97 (1H, s), 7.20 (4H, s), 7.55 (1H, dd, J=2.8, 8.6 Hz), 8.13 (1H, d, J=2.8 Hz)

EXAMPLE 641

To a solution of tert-butyl{4-[3-(1-hydroxy-1-methylethyl)-1-(4-methoxyphenyl)-1H-pyrazol-5-yl]benzyl}-carbamate (1.1 g) and Et3N (1.02 g) was added methane sulfonyl chloride (576 mg). The mixture was stirred at ambient temperature overnight. The mixture was concentrated in vacuo. The residue was partitioned between AcOEt and 1M HCl. The organic layer was separated, washed with saturated aqueous sodium bicarbonate solution and saturated aqueous sodium chloride solution, dried over magnesium sulfate, and concentrated in vacuo. The residue was purified by silica gel column chromatography eluted with AcOEt/n-hexane=25%. The pure fraction was collected and concentrated in vacuo to give tert-butyl {4-[3-isopropenyl-1-(4-methoxyphenyl)-1-H-pyrazol-5-yl]benzyl}carbamate (857 mg) as a solid.
MS (ESI+): m/z 420 (M+H)
1HNMR (200 MHz, ): 1.46 (9H, s), 2.21 (3H, s), 3.81 (3H, s), 4.30 (2H, d, J=5.9 Hz), 4.84 (1H, brs), 5.13 (1H, brs), 5.60 (1H, brs), 6.60 (1H, s), 6.84 (2H, d, J=8.9 Hz) 7.18–7.26 (6H, m)

The following compound(s) was(were) obtained in a similar manner to that of Example 641.

EXAMPLE 642 tert-butyl {4-[3-isopropenyl-1-(6-methoxy-3-pyridinyl)-1-H-pyrazol-5-yl]benzyl}carbamate oil
MS (ESI+): m/z 421 (M+H)
1HNMR (200 MHz, DMSOd6): 1.39 (9H, s), 2.10 (3H, s), 3.86 (3H, s), 4.12 (2H, d, J=6.2 Hz), 5.15 (1H, brs), 5.63 (1H, brs), 6.88 (1H, s), 6.88 (1H, d, J=8.8 Hz), 7.22 (4H, s), 7.40 (1H, t, J=6.2 Hz), 7.67 (1H, dd, J=2.7, 8.8 Hz), 8.06 (1H, d, J=2.7 Hz)

EXAMPLE 643

A 0.76M solution of isopropyl magnesium bromide in THF (8.5 ml) was added dropwise to a solution of tert-butyl {4-[3-{[methoxy(methyl)amino]carbonyl}-1-(4-methoxyphenyl)-1-H-pyrazol-5-yl]benzyl}carbamate (1 g) in THF (10 ml) at 10–15° C. The mixture was stirred at ambient temperature for 4 hours. The reaction mixture was poured into a mixture of 1M HCl and ice. The mixture was extracted with AcOEt. The organic layer was washed with saturated aqueous sodium bicarbonate solution and saturated aqueous sodium chloride solution, dried over magnesium sulfate, and concentrated in vacuo. The residue was purified by silica gel column chromatography eluted with AcOEt/n-hexane=20%, 25%, then 10% MeOH/CHCl3. The combined pure fraction was concentrated in vacuo to give tert-butyl {4-[3-isobutyryl-1-(4-methoxyphenyl)-1H-pyrazol-5-yl]benzyl}carbamate (318 mg) as an amorphous powder.
MS (ESI+): m/z 450 (M+H)
1HNMR (200 MHz, CDCl3): 1.25 (6H, d, J=6.8 Hz), 1.46 (9H, s), 3.72–3.87 (1H, m), 3.83 (3H, s), 4.31 (2H, d, J=5.9 Hz), 4.75–4.93 (1H, m), 6.88 (2H, d, J=9 Hz), 6.98 (1H, s), 7.14–7.27 (6H, m)

The following compound(s) was(were) obtained in a similar manner to that of Example 643.

EXAMPLE 644 tert-butyl {4-[3-isobutyryl-1-(6-methoxy-3-pyridinyl)-1-H-pyrazol-5-yl]benzyl}carbamate oil
MS (ESI+): m/z 451 (M+H)
1HNMR (200 MHz, DMSOd6): 1.16 (6H, d, J=6.8 Hz), 1.38 (9H, s), 3.68 (1H, m), 3.88 (3H, s), 4.13 (2H, d, J=6.1 Hz), 6.92 (1H, d, J=8.8 Hz), 7.07 (1H, s), 7.19–7.29 (4H, m), 7.41 (1H, t, J=6.1 Hz), 7.75 (1H, dd, J=2.7, 8.8 Hz), 8.17 (1H, d, J=2.7 Hz)

EXAMPLE 645

To a solution of 4-[1-(6-methoxy-3-pyridinyl)-3-(2,2,2-trifluoroethoxy)-1-H-pyrazol-5-yl]benzonitrile (197 mg) in THF (2 ml) was added lithium aluminum hydride (30 mg) under ice-bath cooling. The mixture was stirred at same temperature for 1 hour and then at ambient temperature for 2 hours. The reaction was quenched by adding 5% aqueous solution of potassium sodium tartaric acid (ca. 0.5 ml). The mixture was diluted with AcOEt, dried over MgSO4, and filtered through a celite pad. The filtrate was concentrated in vacuo to give {4-[1-(6-methoxy-3-pyridinyl)-3-(2,2,2-trifluoro-ethoxy)-1-H-pyrazol-5-yl]benzyl}amine (200 mg) as an oil.
MS ((ESI+): m/z 379 (M+H)

1HNMR (200 MHz, DMSOd6) 3.75 (2H, s), 3.85 (3H, s), 4.84 (1H, d, J=9 Hz), 4.93 (1H, d, J=9 Hz), 6.32 (1H, s), 6.87 (1H, d, J=8.9 Hz), 7.19 (2H, d, J=8.2 Hz), 7.33 (2H, d, J=8.2 Hz), 7.64 (1H, dd, J=2.7, 8.9 Hz), 8.03 (1H, d, J=2.7 Hz)

The following compound(s) was(were) obtained in a similar manner to that of Example 645.

EXAMPLE 646

1-{4-[3-chloro-1-(4-methoxyphenyl)-1H-pyrazol-5-yl]-phenyl}methanamine oil
MS: (ESI+): m/z 314 (M+H)
1HNMR (200 MHz, DMSOd6): 3.69 (2H, s), 3.78 (3H, s), 6.72 (1H, s), 6.96 (2H, d, J=9 Hz), 7.16 (2H, d, J=8.2 Hz), 7.22 (2H, d, J=9 Hz), 7.3 (2H, d, J=8.2 Hz)

EXAMPLE 647

1-{4-[3-chloro-1-(6-methoxy-3-pyridinyl)-1H-pyrazol-5-yl]phenyl}methanamine powder
MS (ESI+): m/z 315 (M+H)
1HNMR (200 MHz, DMSOd6): 3.70 (2H, s), 3.86 (3H, s), 6.78 (1H, s), 6.89 (1H, d, J=8.7 Hz), 7.20 (2H, d, J=8.3 Hz), 7.33 (2H, d, J=8.3 Hz), 7.69 (1H, dd, J=2.7, 8.7 Hz), 8.10 (1H, d, J=2.7 Hz)

EXAMPLE 648

A mixture of 5-[4-(benzyloxy)phenyl]-3-amino-1-(4-methoxyphenyl)-1H-pyrazole (4.0 g), lithium chloride (2.28 g), and copper(II) chloride (2.90 g) in acetonitrile (50 ml) was stirred at ambient temperature for 10 minutes. To this mixture was added isoamyl nitrite (2.52 g), and the mixture was stirred at ambient temperature for 1.5 hours. To the reaction mixture was added a mixture of ethyl acetate and saturated aqueous ammonium chloride solution. The mixture was stirred at ambient temperature for a while, and partitioned. The aqueous layer was reextracted with ethyl acetate. The combined organic layers were washed with saturated aqueous ammonium chloride solution and saturated aqueous sodium chloride solution, dried over magnesium sulfate, and concentrated in vacuo. The residue was purified by silica gel column chromatography eluted with 20% AcOEt/n-hexane. The pure fractions were collected and concentrated in vacuo to give 5-[4-(benzyloxy)phenyl]-3-chloro-1-(4-methoxyphenyl)-1H-pyrazole (2.81 g) as a solid.

MS ESI+): m/z 391 (M+H)
1HNMR (200 MHz, CDCl3): 3.81 (3H, s), 5.05 (2H, s), 6.35 (1H, s), 6.84 (2H, d, J 9 Hz), 6.89 (2H, d, J=8.9 Hz), 7.12 (2H, d, J=8.9 Hz), 7.19 (2H, d, J=9 Hz), 7.34–7.43 (5H, m)

EXAMPLE 649

A solution of 4-benzyloxypropiophenone (5 g) in N,N-dimethylformamide dimethyl acetal (20 ml) was refluxed for 24 hours. The mixture was concentrated in vacuo. The residue was dissolved in toluene and concentrated in vacuo. This was repeated one more time. The residue was dissolved in EtOH. To this solution was added 4-methoxyphenylhydrazine hydrochloride (3.63 g), and the mixture was refluxed for 3 hours. The reaction mixture was cooled to ambient temperature and partitioned between AcOEt and 1MHCl. The organic layer was washed with saturated aqueous sodium bicarbonate solution and saturated aqueous sodium chloride solution, dried over magnesium sulfate, and concentrated in vacuo. The residue was purified by silica gel column chromatography eluted with AcOEt/n-hexane=30% to give 5-[4-(benzyloxy)phenyl]-1-(4-methoxyphenyl)-4-methyl-1-H-pyrazole (5.31 g) as a powder.

MS (ESI+): m/z 371 (M+H)
200 MHz 1HNMR (CDCl3, d): 2.10 (3H, s), 3.79 (3H, s), 5.06 (2H, s), 6.80 (2H, d, J=8.9 Hz), 6.94 (2H, d, J=8.8 Hz), 7.09 (2H, d, J=8.8 Hz), 7.14 (2H, d, J=8.9 Hz), 7.31–7.48 (5H, m), 7.55 (2H, s)

The following compound(s) was(were) obtained in a similar manner to that of Example 649.

EXAMPLE 650

5-{5-[4-(benzyloxy)phenyl]-4-methyl-1H-pyrazol-1-yl}-2-methoxypyridine powder
MS (ESI+): m/z 372 (M+H)
200 MHz 1HNMR (CDCl3, d): 2.10 (3H, s), 3.91 (3H, s), 5.06 (2H, s), 6.68 (1H, d, J=8.8 Hz), 6.96 (2H, d, J=8.7 Hz), 7.09 (2H, d, J=8.7 Hz), 7.36–7.52 (6H, m), 7.59 (1H, s), 8.02 (1H, d, J=2.7 Hz)

EXAMPLE 651

A solution of t-butyl nitrite (1.14 ml) in CHCl3 (3 ml) was added dropwise to a solution of 5-[4-(benzyloxy)phenyl]-1-(4-methoxyphenyl)-3-amino-1H-pyrazole (1.5 g) and dimethyldisulfide (1.15 ml) in CHCl3 (10 ml). After all of t-butyl nitrite solution was added, the temperature of reaction mixture began to rise and reached to reflux. After the reflux ceased, the mixture was stirred at ambient temperature for 1 hour. The mixture was concentrated in vacuo and the residue was purified by silica gel column chromatography eluted with AcOEt/n-hexane=25% to give 5-[4-(benzyloxy)phenyl]-1-(4-methoxyphenyl)-3-(methylthio)-1-H-pyrazole (635.2 mg) as an oil.

Mass (ESI+): m/z 403 (M+H)
1HNMR (200 MHz, CDCl3): 2.58 (3H, s), 3.81 (3H, s), 5.04 (2H, s), 6.36 (1H, s), 6.81–6.91 (4H, m), 7.13 (2H, d, J=8.7 Hz), 7.20 (2H, d, J=9 Hz), 7.34–7.43 (5H, m)

EXAMPLE 652

A mixture of 3-cyano-1-(4-methoxyphenyl)-5-[4-(aminometyl)phenyl]-1H-pyrazole (90 mg) trimethylsilylisocyanate (152 mg) and Et3N (0.18 ml) in CH2Cl2 (5 ml) was stirred at room temperature. After stirring for 5 hours (checked by TLC), water and CHCl3 was added. The organic layer was separated. Aqueous layer was extracted with EtOAc. The combined organic layer was washed with water and brine. Dried over MgSO4, filtered and evaporated under reduced pressure to give 48 mg (52%) of N-{4-[3-cyano-1-(4-methoxyphenyl)-1H-pyrazol-5-yl]benzyl}urea.

MASS (ESI+): m/z=370.1 (M+Na).
1HNMR (200 MHz, CDCl3): 3.83 ( H, s), 4.38 (2H, d, J=6 Hz), 4.42 (2H, b.s), 4.902- (1H, m), 6.82 (1H, s), 6.87 (2H, d, J=9 Hz), 7.15 (2H, d, J=8.3 Hz), 7.19 (2H, d, J=9 Hz), 7.26 (2H, d, J=8.3 Hz).

EXAMPLE 653

To a mixture of (2-{4-[3-methoxy-1-(4-methoxyphenyl)-1H-pyrazol-5-yl]phenoxy}ethyl)amine hydrochloride (150 mg) in CHCl3 (2 ml) and saturated aqueous sodium bicarbonate solution (1 ml) was added thiophosgene (68.8 mg) under ice-bath cooling. The mixture was stirred at ambient temperature for 5 hours. To the mixture was added 28% aqueous ammonium hydroxide (1 ml) and the mixture was stirred at ambient temperature overnight. To the mixture were added 28% aqueous ammonium hydroxide (1 ml) and MeOH (1 ml) and the mixture was stirred at r.t. for 7 hours. The reaction mixture was partitioned between AcOEt and H2O. The organic layer was washed with saturated aqueous sodium bicarbonate solution and saturated aqueous sodium chloride solution, dried over magnesium sulfate, and concentrated in vacuo. The residue was crystallized from ACOEt-IPE. The obtained powder was recrystallized from AcOEt-n-hexane to give N-(2-{4-[3-methoxy-1-(4-methoxyphenyl)-1H-pyrazol-5-yl]phenoxy}ethyl)thiourea (116 mg) as a powder.

mp. 141.6–142.3° C.

MS (ESI+): m/z 399 (M+H)

1HNMR (200 MHz, DMSOd6): 3.61–3.89 (2H, m), 3.75 (3H, s), 3.83 (3H, s), 3.98–4.12 (2H, m), 6.04 (1H, s), 6.92 (4H, d, J=8.9 Hz), 7.09 (2H, brs), 7.13 (4H, d, J=8.9 Hz), 7.77 (1H, t, J=5.2 Hz)

EXAMPLE 654

A solution of methanesulfonyl chloride (328 mg) in CH2Cl2 (2 ml) was added to a solution of 5-[4-(2-hydroxyethyl)-phenyl]-N-methoxy-1-(4-methoxyphenyl)-N-methyl-1H-pyrazole-3-carboxamide (840 mg) and Et3N (334 mg) in CH2Cl2 (10 ml) under ice bath cooling. The mixture was stirred at same temperature for 1 hour. The mixture was diluted with CHCl3 and washed with 1M HCl, saturated aqueous sodium bicarbonate solution and saturated aqueous sodium chloride solution, dried over magnesium sulfate, and concentrated in vacuo. The residue was purified by silica gel column chromatography eluted with AcOEt/n-hexane=80%, 90%. The pure fractions were collected and concentrated in vacuo to give 2-{4-[3-{[methoxy(methyl)amino]carbonyl}-1-(4-methoxyphenyl)-1H-pyrazol-5-yl]phenyl}ethyl methanesulfonate (1.01 g) as an oil.

Mass (ESI+): m/z 460 (M+H)

1HNMR (200 MHz, CDCl3): 2.89 (3H, s), 3.05 (2H, t, J=6.8 Hz), 3.51 (3H, s), 3.83 (3H, s), 3.85 (3H, s), 4.41 2H, t, J=6.8 Hz), 6.86 (2H, d, J=9.0 Hz), 6.97 (1H, s), 7.18–7.26 (6H, m)

The following compound(s) was(were) obtained in a similar manner to that of Example 654.

EXAMPLE 655

2-{4-[3-{[methoxy(methyl)amino]carbonyl}-1-(6-methoxy-3-pyridinyl)-1H-pyrazol-5-yl]phenyl}ethyl methanesulfonate oil Mass (ESI+): m/z 461 (M+H)

1HNMR (200 MHz, CDCl3): 2.91 (3H, s), 3.06 (2H, t, J=6.8 Hz), 3.50 (3H, s), 3.85 (3H, s), 3.94 (3H, s), 4.43 (2H, t, J=6.8 Hz), 6.74 (1H, d, J=8.8 Hz), 6.99 (1H, s), 7.32 (4H, s), 7.55 (1H, dd, J=2.7, 8.8 Hz), 8.09 (1H, d, J=2.7 Hz)

EXAMPLE 656

A mixture of 2-{4-[3-{[methoxy(methyl)amino]-carbonyl}-1-(4-methoxyphenyl)-1H-pyrazol-5-yl]phenyl}ethyl methanesulfonate (1.02 g), 15-crown-5 (489 mg), sodium azide (722 mg) in hexamethylphosphoric triamide (6 ml) was stirred at 55° C. for 1 hour. The mixture was poured into ice water, and the mixture was extracted with AcOEt. The organic layer was washed with saturated aqueous sodium chloride solution, dried over magnesium sulfate, and concentrated in vacuo. The residue was dissolved in MeOH (6 ml). To this solution was added a solution of 6M HCl (0.37 ml) in MeOH (2 ml) and 10% palladium on carbon (50% wet) (200 mg). The mixture was hydrogenated under H2 1 atm at ambient temperature for 2 hours. The catalyst was removed by filtration. The filtrate was concentrated in vacuo to give 5-[4-(2-aminoethyl)phenyl]-N-methoxy-1-(4-methoxy-phenyl)-N-methyl-1-H-pyrazole-3-carboxamide hydrochloride (0.93 g) as an oil.

Mass (ESI+): m/z 381 (M+H)

1HNMR (200 MHz, DMSOd6): 2.79–3.16 (4H, m), 3.38 (3H, s), 3.77 (3H, s), 3.79 (3H, s), 6.95 (1H, s), 6.99 (2H, d, J=9.0 Hz), 7.15–7.36 (6H, m), 8.00 (2H, brs)

The following compound(s) was(were) obtained in a similar manner to that of Example 656.

EXAMPLE 657

5-[4-(2-aminoethyl)phenyl]-N-methoxy-1-(6-methoxy-3-pyridinyl)-N-methyl-1-H-pyrazole-3-carboxamide hydrochloride oil Mass (ESI+): m/z 382 (M+H)

1HNMR (200 MHz, DMSOd6): 2.80–3.15 (4H, m), 3.38 (3H, s), 3.77 (3H, s), 3.88 (3H, s), 6.92 (1H, d, J=8.8 Hz), 6.98 (1H, s), 7.22–7.36 (4H, m), 7.72 (1H, dd, J=2.7, 8.8 Hz), 8.02 (2H, brs), 8.17 (1H, d, J=2.7 Hz)

EXAMPLE 658

To a 0.76M solution of isopropylmagnesium bromide in THF (2.0 ml) was added a solution of 5-(4-{2-[(aminocarbonyl)-amino]ethyl}phenyl)-N-methoxy-1-(4-methoxyphenyl)-N-methyl-1H-pyrazole-3-carboxamide (130 mg) in THF (2 ml) dropwise at at 4° C. The mixture was stirred at ambient temperature overnight. Additional 0.76M solution of isopropylmagnesium bromide in THF (2.0 ml) was added and the mixture was stirred at 50° C. for 5 hours. The reaction mixture was cooled to ambient temperature and was quenched by adding saturated aqueous ammonium chloride solution. The mixture was extracted with AcOEt. The organic layer was washed with 1M HCl, saturated aqueous sodium bicarbonate solution, saturated aqueous sodium chloride solution, dried over magnesium sulfate, and concentrated in vacuo. The residue was purified by preparative thin layer silica gel chromatography developed by MeOH/CHC3 10%. The separated silica gel was extracted with 10% MeOH/CHCl3 and the solvent was evaporated in vacuo to give N-(2-{4-[3-isobutyryl-1-(4-methoxyphenyl)-1H-pyrazol-5-yl]phenyl}ethyl)urea (30 mg) as amorphous powder.

MS (ESI+): m/z 407 (M+H)

1HNMR (200 MHz, CDCl3): 1.25 (6H, d, J=6.8 Hz), 2.77–2.85 (2H, m), 3.37–3.48 (2H, m), 3.72–3.87 (1H, m), 3.83 (3H, s), 4.32 (2H, s), 4.57 (1H, t, J=4.9 Hz), 6.89 (2H, d, J=8.9 Hz), 6.96 (1H, s), 7.14 (4H, s), 7.24 (2H, d, J=8.9 Hz)

The following compound(s) was(were) obtained in a similar manner to that of Example 658.

EXAMPLE 659

N-(2-{4-[3-isobutyryl-1-(4-methoxyphenyl)-1H-pyrazol-5-yl]phenyl}ethyl)methanesulfonamide oil MS (ESI+): m/z 442

1HNMR (200 MHz, CDCl3): 1.26 (6H, d, J=6.9 Hz), 2.84–2.91 (2H, m), 2.87 (3H, s), 3.35–3.46 (2H, m), 3.73–3.87 (1H, m), 3.84 (3H, s), 4.21 (1H, t, J=6.1 Hz), 6.89 (2H, d, J=9.0 Hz), 6.99 (1H, s), 7.13–7.29 (6H, m)

EXAMPLE 660

N-(2-{4-[3-isobutyryl-1-(6-methoxy-3-pyridinyl)-1H-pyrazol-5-yl]phenyl}ethyl)urea oil MS (ESI+): m/z 408 (M+H)

1HNMR (200 MHz, CDCl3): 1.26 (6H, d, J=6.9 Hz), 2.79–2.87 (2H, m), 3.39–3.50 (2H, m), 3.77-(1H, m), 3.95 (3H, s), 4.35 (2H, s), 4.57 (1H, t, J=5.4 Hz), 6.78 (1H, d, J=8.9 Hz), 6.98 (1H, s), 7.17 (4H, s), 7.60 (1H, dd, J=2.7, 8.9 Hz), 8.07 (1H, d, J=2.7 Hz)

EXAMPLE 661

N-(2-{4-[3-isobutyryl-1-(6-methoxy-3-pyridinyl)-1H-pyrazol-5-yl]phenyl}ethyl)methanesulfonamide oil MS (ESI+): m/z 443 (M+H)

1HNMR (200 MHz, CDCl3): 1.26 (6H, d, J=6.8 Hz), 2.85–2.93 (2H, m), 2.88 (3H, s), 3.36–3.47 (2H, m), 3.77 (3H, m), 3.95 (3H, s), 4.24 (1H, t, J=6.2 Hz), 6.78 (1H, d, J=8.8 Hz), 7.00 (1H, s), 7.19 (4H, s), 7.57 (1H, dd, J=2.7, 8.8 Hz), 8.11 (1H, d, J=2.7 Hz)

EXAMPLE 662

To a solution of cyclopropylmagnesium bromide, which was prepared from cyclopropyl bromide (257 ml) and magnesium (57 mg) in THF (1 ml) as usual method, was added a solution of 5-(4-{2-[(aminocarbonyl)-amino]ethyl}phenyl)-N-methoxy-1-(4-methoxyphenyl)-N-methyl-1H-pyrazole-3-carboxamide (90 mg) in THF (3 ml) dropwise at ambient temperature. The mixture was stirred at 50° C. for 5 hours. The reaction mixture was cooled to ambient temperature and was quenched by adding saturated aqueous ammonium chloride solution. The mixture was extracted with AcOEt. The organic layer was washed with 1M HCl, saturated aqueous sodium bicarbonate solution, saturated aqueous sodium chloride solution, dried over magnesium sulfate, and concentrated in vacuo. The residue was purified by preparative thin layer silica gel chromatography developed by MeOH/CHC3 10%. The separated silica gel was extracted with 10% MeOH/CHCl3 and the solvent was evaporated in vacuo to give N-(2-{4-[3-(cyclopropylcarbonyl)-1-(4-methoxyphenyl)-1H-pyrazol-5-yl]phenyl}ethyl) urea (23 mg) as a powder.

Mass (ESI+): m/z 405 (M+H)

1HNMR (200 MHz, CDCl3): 0.99–1.09 (2H, m), 1.22–1.30 (2H, m), 2.77–2.84 (2H, m), 3.13 (1H, m), 3.37–3.48 (2H, m), 3.84 (3H, s), 4.33 (2H, s), 4.59 (1H, t, J=5.4 Hz), 6.89 (2H, d, J=8.9 Hz), 6.96 (1H, s), 7.14 (4H, s), 7.26 (2H, d, J=8.9 Hz)

The following compound(s) was(were) obtained in a similar manner to that of Example 662.

EXAMPLE 663

N-(2-{4-[3-(cyclopropylcarbonyl)-1-(4-methoxyphenyl)-1H-pyrazol-5-yl]phenyl}ethyl)methanesulfonamide oil MS (ESI+): m/z 440 (M+H)

1HNMR (200 MHz, CDCl3): 0.99–1.09 (2H, m), 1.22–1.31 (2H, m), 2.80–2.91 (2H, m), 2.87 (3H, s), 3.14 (1H, m), 3.35–3.46 (2H, m), 3.84 (1H, s), 4.22 (1H, t, J=5.7 Hz), 6.90 (2H, d, J=9.0 Hz), 6.99 (1H, s), 7.12 (4H, s), 7.27 (2H, d, J=9.0 Hz)

EXAMPLE 664

N-(2-{4-[3-(cyclopropylcarbonyl)-1-(6-methoxy-3-pyridinyl)-1H-pyrazol-5-yl]phenyl}ethyl)methanesulfonamide oil Mass (ESI+): m/z 441 (M+H)

1HNMR (200 MHz, CDCl3): 1.03–1.11 (2H, m), 1.24–1.32 (2H, m), 2.85–2.93 (2H, m), 2.88 (3H, s), 3.11 (1H, m), 3.36–3.47 (2H, m), 3.96 (3H, s), 4.22 (1H, t, J=6.0 Hz), 6.78 (1H, d, J=8.9 Hz), 7.00 (1H, s), 7.20 (4H, s), 7.60 (1H, dd, J=2.7, 8.9 Hz), 8.13 (1H, d, J=2.7 Hz)

The invention claimed is:

1. A compound of the formula (I):

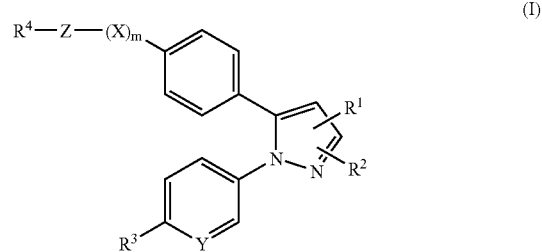

wherein $R^1$ is hydrogen or lower alkyl;

$R^2$ is lower alkyl optionally substituted with halogen, hydroxy, lower alkoxyimino or lower alkoxy; lower alkenyl; cycloalkyl; cyano; lower alkanoyl; cycloalkylcarbonyl; N,N-di(lower)alkylcarbamoyl; carbamoyl; N-lower alkoxy-N-lower alkylcarbamoyl; amino; di(lower)alkylamino; lower alkoxycarbonylamino; N,N-di(lower)alkylcarbamoylamino; N-(N,N-di(lower)alkylcarbamoyl)-N-lower alkylamino; halogen; hydroxy; carboxy; lower alkoxycarbonyl; aroyl; lower alkylsulfonyl; lower alkoxy optionally substituted with lower alkoxy, N,N-di(lower)alkylcarbamoyl or halogen; cycloalkyloxy; lower alkylthio; or lower alkylsufinyl;

$R^3$ is lower alkyl optionally substituted with amino, carbamoylamino or lower alkylsulfonylamino; halogen; cyano; hydroxy; lower alkanoyloxy; lower alkylenedioxy;lower alkoxy optionally substituted with aryl, hydroxy, cyano, amino, lower alkoxycarbonylamino, lower alkylsulfonylamino or carbamoylamino; nitro; amino; lower alkylthio; lower alkylsulfinyl; or lower alkylsufonyl;

$R^4$ is a group of the formula:

$R^5$—G—J— in which G is —CO—;

J is —N ($R^6$)—

(wherein $R^6$ is hydrogen or lower alkyl); and
$R^5$ is amino optionally substituted with lower alkoxycarbonyl or lower alkyl; lower alkyl optionally substituted with hydroxy, lower alkoxycarbonylamino, lower alkanoyloxy, amino or halogen; lower alkoxy; hydrogen; or aryl;

X is O, S, SO or $SO_2$;
Y is CH;
Z is lower alkylene or lower alkenylene; and
m is 0 or 1;

or a salt thereof.

2. The compound of claim 1, wherein
$R^1$ is hydrogen;
$R^2$ is lower alkyl optionally substituted with halogen, hydroxy, lower alkyoxyimino or lower alkoxy; cycloalkyl; halogen; lower alkoxy optionally substituted with halogen; or lower alkylthio;
$R^3$ is lower alkoxy optionally substituted with aryl, hydroxy, cyano, amino, lower alkoxyxcarbonylamino, lower alkylsulfonylamino or carbamoylamino;
X is O or S; and
Z is lower alkylene.

3. The compound of claim 2, wherein
$R^2$ is lower alkyl optionally substituted with halogen; cycloalkyl; halogen; or lower alkoxy optionally substituted with halogen;
$R^3$ is lower alkoxy;
J is —NH— and
$R^5$ is amino or lower alkyl; and
X is O.

4. The compound of claim 3, which is
N-(2-(4-[3-chloro-1-(4-methoxyphenyl)-1H-pyrazol-5-yl]-phenoxy)ethyl)urea,
N-(4-[3-(difluoromethyl)-1-(4-methoxyphenyl)-1H-pyrazol-5-yl]benzyl)methanesulfonamide,
N-(4-[3-(difluoromethyl)-1-(4-methoxyphenyl)-1H-pyrazol-5-yl]benzyl)urea,
N-(2-(4-[3-(difluoromethyl)-1-(4-methoxyphenyl)-1H-pyrazol-5-yl]phenoxy)ethyl)urea,
N-(2-(4-[1-(4-methoxyphenyl)-3-(trifluoromethyl)-1H-pyrazol-5-yl]phenoxy)ethyl)urea,
N-(2-(4-[3-cyclopropyl-1-(4-methoxyphenyl)-1H-pyrazol-5-yl]phenoxy)ethyl)urea, or
N-(2-(4-[1-(4-methoxyphenyl)-3-(trifluoromethyl)-1H-pyrazol-5-yl]phenoxylethyl)acetamide.

5. A pharmaceutical composition comprising the compound of claim 1, as an active ingredient, in association with a pharmaceutically non-toxic carrier or excipient.

6. The compound of claim 4, which is N-(2-(4-[1-(4-methoxyphenyl)-3-(trifluoromethyl)-1H-pyrazol-5-yl]phenoxy)ethyl)urea.

* * * * *